US012606528B2

(12) United States Patent
Chen et al.

(10) Patent No.: US 12,606,528 B2
(45) Date of Patent: Apr. 21, 2026

(54) METHODS AND MATERIALS FOR INHIBITING NF-kB ACTIVITY

(71) Applicant: University of Pittsburgh - Of the Commonwealth System of Higher Education, Pittsburgh, PA (US)

(72) Inventors: Beibei Chen, Sewickley, PA (US); Toren Finkel, Pittsburgh, PA (US); Yuan Liu, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 827 days.

(21) Appl. No.: 17/778,492

(22) PCT Filed: Nov. 20, 2020

(86) PCT No.: PCT/US2020/061670

§ 371 (c)(1),
(2) Date: May 20, 2022

(87) PCT Pub. No.: WO2021/102370

PCT Pub. Date: May 27, 2021

(65) Prior Publication Data

US 2023/0041576 A1 Feb. 9, 2023

Related U.S. Application Data

(60) Provisional application No. 63/059,488, filed on Jul. 31, 2020, provisional application No. 62/938,820, filed on Nov. 21, 2019.

(51) Int. Cl.

| | |
|---|---|
| ***A61K 31/421*** | (2006.01) |
| ***A61K 31/4164*** | (2006.01) |
| ***A61K 31/426*** | (2006.01) |
| ***C07D 213/71*** | (2006.01) |
| ***C07D 215/36*** | (2006.01) |
| ***C07D 215/40*** | (2006.01) |
| ***C07D 217/24*** | (2006.01) |
| ***C07D 241/42*** | (2006.01) |
| ***C07D 263/46*** | (2006.01) |
| ***C07D 265/36*** | (2006.01) |
| ***C07D 267/14*** | (2006.01) |
| ***C07D 277/36*** | (2006.01) |
| ***C07D 311/12*** | (2006.01) |
| ***C07D 401/12*** | (2006.01) |
| ***C07D 403/04*** | (2006.01) |
| ***C07D 403/12*** | (2006.01) |
| ***C07D 471/04*** | (2006.01) |
| ***C07D 487/04*** | (2006.01) |

(52) U.S. Cl.
CPC ........ *C07D 215/36* (2013.01); *A61K 31/4164* (2013.01); *A61K 31/421* (2013.01); *A61K 31/426* (2013.01); *C07D 213/71* (2013.01); *C07D 215/40* (2013.01); *C07D 217/24* (2013.01); *C07D 241/42* (2013.01); *C07D 263/46* (2013.01); *C07D 265/36* (2013.01); *C07D 267/14* (2013.01); *C07D 277/36* (2013.01); *C07D 311/12* (2013.01); *C07D 401/12* (2013.01); *C07D 403/04* (2013.01); *C07D 403/12* (2013.01); *C07D 471/04* (2013.01); *C07D 487/04* (2013.01)

(58) Field of Classification Search
CPC ................ A61K 31/421; A61K 31/426; A61K 31/4164; A61P 29/00; A61P 35/00; A61P 37/00
See application file for complete search history.

(56) References Cited

U.S. PATENT DOCUMENTS

| | | | | |
|---|---|---|---|---|
| 5,304,121 | A | 4/1994 | Sahatjian | |
| 5,886,026 | A | 3/1999 | Hunter et al. | |
| 6,099,562 | A | 8/2000 | Ding et al. | |
| 6,803,031 | B2 | 10/2004 | Rabinowitz et al. | |
| 7,557,213 | B2 | 7/2009 | Melikian et al. | |
| 9,316,633 | B2 * | 4/2016 | Verkman ................ | G01N 33/80 |
| 2014/0018384 | A1 | 1/2014 | Wallner et al. | |
| 2014/0073668 | A1 | 3/2014 | Landry et al. | |
| 2017/0174704 | A1 | 6/2017 | Gigstad et al. | |
| 2023/0103444 | A1 * | 4/2023 | LaBarbera ........... | C07D 403/04 514/238.8 |

FOREIGN PATENT DOCUMENTS

WO WO-2018012769 A1 * 1/2018 ........... A61K 31/421

OTHER PUBLICATIONS

A machine generated English translation of WO 2018/012769 A1 (Lee et al.) (Year: 2018).*
Giovannini et al., "Interleukin-6, C-reactive protein, and tumor necrosis factor-alpha as predictors of mortality in frail, community-living elderly individuals," J. Am. Geriatr. Society, Sep. 2011, 59(9):1679-1685.
He et al., "Senescence in Health and Disease," Cell, Jun. 1, 2017, 169(6):1000-1011.
Illum, "Is nose-to-brain transport of drugs in man a reality?," J. Pharm. Pharmacology, Jan. 2004, 56(1):3-17.
Illum, "Transport of drugs from the nasal cavity to the central nervous system," Eur. J. Pharm. Sciences, Jul. 2000, 11(1):1-18.
PCT International Preliminary Report on Patentability in International Appln. No. PCT/US2020/061670, mailed on Jun. 2, 2022, 7 pages.
PCT International Search Report and Written Opinion in International Appln. No. PCT/US2020/061670, mailed on Mar. 25, 2021, 10 pages.
Ridker et al., "Antiinflammatory Therapy with Canakinumab for Atherosclerotic Disease," N. Engl. J. Medicine, Sep. 21, 2017, 377(12):1119-1131.

* cited by examiner

*Primary Examiner* — Laura L Stockton
(74) *Attorney, Agent, or Firm* — Fish & Richardson P.C.

(57) ABSTRACT

This document provides compounds that are inhibitors of NF-κB activity, as well as the methods of using such compounds for treating diseases and conditions such as cancer, inflammatory conditions, or autoimmune diseases.

33 Claims, 5 Drawing Sheets

| Cpds concentration | BC18S-01 | BC18S-02 | BC18S-03 | BC18S-04 | BC18S-05 | BC18S-06 | BC18S-07 | BC18S-08 |
|---|---|---|---|---|---|---|---|---|
| | 380.2 | 4508 | 365.2 | 687.9667 | 394.5 | 10583.33 | 3613.667 | 5890.333 |
| | 1631.333 | 6748.333 | 517.5667 | 767.2 | 2625.667 | 12163.33 | 5306.667 | 8615.333 |
| | 1256.667 | 8244.667 | 1091.067 | 2667 | 14376.67 | 9715.667 | 7404.333 | 10808.67 |
| | 3584 | 11317.67 | 5898.333 | 8408.667 | 25716.67 | 12876.67 | 15716.67 | 12246.67 |
| | 5549.333 | 15303.33 | 11638.33 | 16393.33 | 27190 | 16413.33 | 20283.33 | 14683.33 |
| | 10681.67 | 20126.67 | 19506.67 | 23930 | 26110 | 24850 | 26813.33 | 19886.67 |
| | 16643.33 | 25463.33 | 18013.33 | 25840 | 28060 | 26420 | 26380 | 26123.33 |
| LPS | 28140 | 28140 | 28140 | 28140 | 28140 | 28140 | 28140 | 28140 |

| Cpds concentration | BC18S-09 | BC18S-10 | BC18S-11 | BC18S-12 | BC18S-13 | BC18S-14 | BC18S-15 | BC18S-16 |
|---|---|---|---|---|---|---|---|---|
| | 2370 | 4335.333 | 1264.633 | 1830.333 | 537.1333 | 615.5 | 825.5333 | 10361.67 |
| | 6953.667 | 11766.67 | 4368.333 | 8077.333 | 501.4667 | 685.1333 | 550.2667 | 14003.33 |
| | 8030.667 | 12216.67 | 4896.667 | 10145.67 | 639.6667 | 1018.967 | 749.0667 | 14953.33 |
| | 16983.33 | 24210 | 12313.33 | 15906.67 | 2249 | 1866.333 | 1693.667 | 20900 |
| | 16556.67 | 23976.67 | 14390 | 20113.33 | 3542.667 | 2442.333 | 3712.333 | 21103.33 |
| | 22293.33 | 27350 | 24460 | 23406.67 | 8206 | 4579.333 | 8709.667 | 22190 |
| | 26613.33 | 26306.67 | 26956.67 | 24766.67 | 14206.67 | 4493 | 10306 | 20803.33 |
| LPS | 28140 | 28140 | 28140 | 28140 | 28140 | 28140 | 28140 | 28140 |

| Cpds concentration | BC18S-01 | BC18S-02 | BC18S-03 | BC18S-04 | BC18S-05 | BC18S-06 | BC18S-07 | BC18S-08 |
|---|---|---|---|---|---|---|---|---|
| |  |  |  |  |  |  |  |  |
| | 311.5333 | 776.7667 | 147.5367 | 1077.567 | 333.7333 | 1013.867 | 627.4 | 1348.667 |
| | 484 | 819.6333 | 399.5 | 1168 | 2052.333 | 1151.667 | 1114.3 | 1621 |
| | 373.7333 | 1019.6 | 1127.1 | 1998 | 2271.333 | 1376.333 | 2223.667 | 1357 |
| | 616.5 | 1674.667 | 2450.667 | 2135.667 | 2577 | 2202.667 | 2371.667 | 2633 |
| | 1094.433 | 1914 | 2615.333 | 2659 | 2781.333 | 2259.333 | 2639.667 | 2440 |
| | 1484 | 3229.667 | 2296 | 2828.667 | 3008 | 2674.333 | 2880.667 | 2675.667 |
| | 2370.333 | 3102.667 | 2645 | 2812.333 | 2815.333 | 2817 | 2909 | 2902.333 |
| PAM | 3022.917 | 3022.917 | 3022.917 | 3022.917 | 3022.917 | 3022.917 | 3022.917 | 3022.917 |

| Cpds concentration | BC18S-09 | BC18S-10 | BC18S-11 | BC18S-12 | BC18S-13 | BC18S-14 | BC18S-15 | BC18S-16 |
|---|---|---|---|---|---|---|---|---|
| | 234.7667 | 911.6667 | 501.9333 | 537.4667 | 119.01 | 223.9 | 242.3533 | 1611 |
| | 714.4667 | 1350.667 | 764.8667 | 1026.933 | 153.5367 | 246.9667 | 104.6667 | 1381.333 |
| | 1001.567 | 2175.667 | 942.2667 | 1307.067 | 338.8667 | 260.0333 | 265.5 | 1382.667 |
| | 1256.967 | 2522 | 1495.667 | 1492.667 | 557.4 | 515.7 | 451.8 | 1680.333 |
| | 1904 | 2692.667 | 2242.667 | 2156.667 | 1053.967 | 357.2667 | 734.1667 | 2213.333 |
| | 2362.333 | 3107.333 | 2700 | 3167 | 1612.667 | 877.9333 | 1082.033 | 2900 |
| | 2769.667 | 3025.667 | 2932 | 3036.667 | 1898 | 831.9667 | 1565 | 2969.667 |
| PAM | 3022.917 | 3022.917 | 3022.917 | 3022.917 | 3022.917 | 3022.917 | 3022.917 | 3022.917 |
| |  |  |  |  |  |  |  |  |

Cpds concentration

| BC18S-01 | BC18S-02 | BC18S-03 | BC18S-04 | BC18S-05 | BC18S-06 | BC18S-07 | BC18S-08 | R848 |
|---|---|---|---|---|---|---|---|---|
| 296.6333 | 1853.667 | 467.8667 | 564.1 | 328.7667 | 5624 | 1119.833 | 4146.333 | |
| 454.8333 | 1699.033 | 351.5333 | 394.5 | 997.1333 | 5429 | 3748.333 | 3391 | |
| 534.6333 | 2014.667 | 461.9333 | 1127.467 | 3719.667 | 5349.333 | 5075 | 5113 | |
| 966.8667 | 3354 | 1984 | 4951.333 | 10077 | 5923.667 | 7395.667 | 8053.333 | |
| 2095 | 3524 | 2586.333 | 8541.333 | 11120 | 10350 | 11273.33 | 9081.333 | |
| 7771.667 | 6858.333 | 3955 | 8770.667 | 9106.667 | 10435 | 9512.667 | 10187.67 | |
| 8007.333 | 10800 | 6912 | 10063.67 | 10746.67 | 10418.33 | 10723 | 9175 | |
| 10535.02 | 10535.02 | 10535.02 | 10535.02 | 10535.02 | 10535.02 | 10535.02 | 10535.02 | |

Cpds concentration

| BC18S-09 | BC18S-10 | BC18S-11 | BC18S-12 | BC18S-13 | BC18S-14 | BC18S-15 | BC18S-16 | R848 |
|---|---|---|---|---|---|---|---|---|
| 735.3333 | 2264 | 874.5 | 610.5333 | 438.2 | 342.7667 | 243.6667 | 1113.333 | |
| 1057.7 | 4054.667 | 1979.667 | 982.1667 | 313.0667 | 330.9 | 274.9667 | 2713 | |
| 2142 | 5468.333 | 2802 | 2818 | 431.2667 | 269.7667 | 297.2667 | 3226 | |
| 4447.667 | 10309.67 | 3907.667 | 4350 | 854.9333 | 623.1 | 741 | 6565.667 | |
| 5921.333 | 12280 | 4516.333 | 5483.667 | 2996.333 | 990.7 | 1762 | 7538.333 | |
| 6679.667 | 9486.667 | 6227.667 | 8244.333 | 2998.667 | 1146.333 | 4824.667 | 10581.33 | |
| 7975 | 10523.33 | 7532.667 | 8096.333 | 4354.667 | 1499.067 | 6062.667 | 12070 | |
| 10535.02 | 10535.02 | 10535.02 | 10535.02 | 10535.02 | 10535.02 | 10535.02 | 10535.02 | |

METHODS AND MATERIALS FOR INHIBITING NF-kB ACTIVITY

CLAIM OF PRIORITY

This application is a National Stage application under 35 U.S.C. § 371 of International Application No. PCT/US2020/061670, having an International Filing Date of Nov. 20, 2020 which claims priority to U.S. Provisional Patent Application Ser. No. 63/059,488, filed on Jul. 31, 2020, and U.S. Provisional Patent Application Ser. No. 62/938,820, filed on Nov. 21, 2019, the entire contents of which are hereby incorporated by reference.

FEDERALLY SPONSORED RESEARCH AND DEVELOPMENT

This invention was made with government support under grant numbers HL139860, HL142777, HL142663, and HL142589 awarded by National Institutes of Health (NIH). The government has certain rights in the invention.

TECHNICAL FIELD

This document relates to methods and materials for inhibiting nuclear factor kappa-light-chain-enhancer of activated B cells (NF-κB) activity. For example, this document provides compounds (e.g., organic compounds) having the ability to inhibit NF-κB activity within cells, formulations containing one or more compounds having the ability to inhibit NF-κB activity within cells, methods for making one or more compounds having the ability to inhibit NF-κB activity within cells, methods for inhibiting NF-κB activity within cells, and methods for treating mammals (e.g., humans) having a condition responsive to inhibition of NF-κB activity.

BACKGROUND

The transcription factor NF-κB is a key regulator of both the innate and adaptive immune response to various pathogens. Activated by an array of stressors, NF-κB protein complexes initiate expression of a wide array of cytokines and other inflammatory mediators. Inappropriate or excessive activation of an NF-κB regulatory pathway can lead to excessive inflammation, which may be harmful to an individual and may lead to numerous disease states. Reducing excessive inflammation, acute or chronic, may be beneficial, for example, in a number of auto-immune conditions.

SUMMARY

This document provides methods and materials for inhibiting NF-κB activity. For example, the document provides compounds (e.g., organic compounds) having the ability to inhibit NF-κB activity within cells, formulations containing one or more compounds having the ability to inhibit NF-κB activity within cells, methods for making one or more compounds having the ability to inhibit NF-κB activity within cells, methods for making formulations containing one or more compounds having the ability to inhibit NF-κB activity within cells, methods for inhibiting NF-κB activity within cells, and methods for treating mammals (e.g., humans) having a condition responsive to inhibition of NF-κB activity. Suitable examples of conditions responsive to inhibition of NF-κB activity within cells include autoimmune conditions, such as Crohn's disease, ulcerative colitis, colitis, psoriatic arthritis, systemic lupus, erythematosis (SLE), and psoriasis.

As described herein, the methods and materials provided herein can be used to inhibit NF-κB activity within cells in vitro, in vivo, or ex vivo. In some cases, the compounds provided herein can be used to treat mammals (e.g., humans) having a disease, disorder, or condition associated with activation of an NF-κB polypeptide complex within cells. In some cases, one or more compounds provided herein can be used to treat mammals (e.g., humans) having a disease, disorder, or condition that is responsive to inhibition of NF-κB activity.

In one general aspect, the present disclosure provides a method for inhibiting NF-κB activity within a cell within a mammal, wherein said method comprises administering, to said mammal, an effective amount of a compound of Formula (Ia):

(Ia)

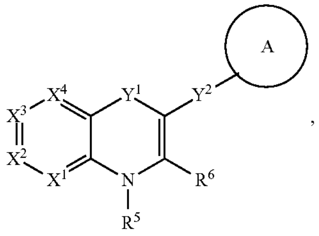

or a pharmaceutically acceptable salt thereof, wherein $X^1$, $X^2$, $X^3$, $X^4$, $Y^1$, $Y^2$, $R^5$, $R^6$, and ring A are as described herein.

In another general aspect, the present disclosure provides a compound of Formula (Ib):

(Ib)

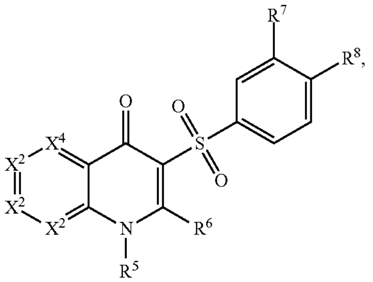

or a pharmaceutically acceptable salt thereof, wherein $X^1$, $X^2$, $X^3$, $X^4$, $R^5$, $R^6$, $R^7$, and $R^8$ are as described herein.

In yet another general aspect, the present disclosure provides a pharmaceutical composition comprising a compound of Formula (Ib), or a pharmaceutically acceptable salt thereof, and a pharmaceutically available carrier.

In yet another general aspect, the present disclosure provides a method for inhibiting NF-κB activity within a cell within a mammal, wherein said method comprises administering, to said mammal, an effective amount of a compound of Formula (Ic):

(Ic)

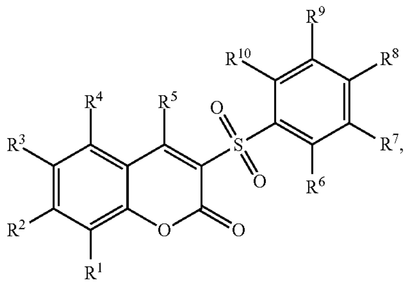

or a pharmaceutically acceptable salt thereof, wherein $R^1$, $R^2$, $R^3$, $R^4$, $R^5$, $R^6$, $R^7$, $R^8$, $R^9$, and $R^{10}$ are as described herein.

In yet another general aspect, the present disclosure provides a method for inhibiting NF-κB activity within a cell within a mammal, wherein said method comprises administering, to said mammal, an effective amount of a compound of Formula (Id):

(Id)

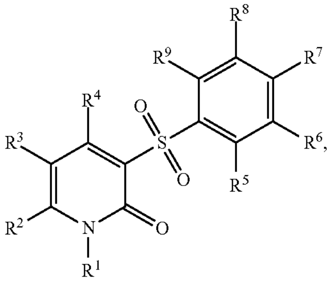

or a pharmaceutically acceptable salt thereof, wherein $R^1$, $R^2$, $R^3$, $R^4$, $R^5$, $R^6$, $R^7$, $R^8$, and $R^9$ are as described herein.

In yet another general aspect, the present disclosure provides a compound of Formula (Ie):

(Ie)

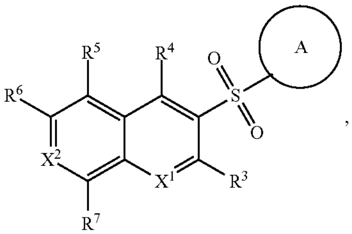

, or a pharmaceutically acceptable salt thereof, wherein $X^1$, $X^2$, ring A, $R^3$, $R^4$, $R^5$, $R^6$, and $R^7$ are as described herein.

In yet another general aspect, the present disclosure provides a pharmaceutical composition comprising a compound of Formula (Ie), or a pharmaceutically acceptable salt thereof, and a pharmaceutically acceptable carrier.

In yet another general aspect, the present disclosure provides a compound of Formula (If):

(If)

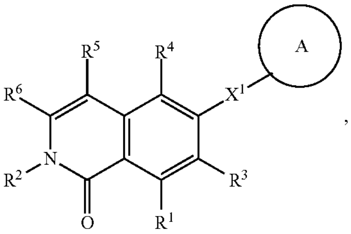

, or a pharmaceutically acceptable salt thereof, wherein $X^1$, ring A, $R^1$, $R^2$, $R^3$, $R^4$, $R^5$, and $R^6$ are as described herein.

In yet another general aspect, the present disclosure provides a pharmaceutical composition comprising a compound of Formula (If), or a pharmaceutically acceptable salt thereof, and a pharmaceutically acceptable carrier.

In yet another general aspect, the present disclosure provides a compound of Formula (Ig):

(Ig)

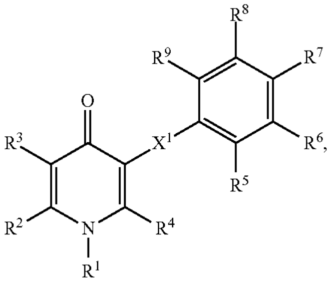

or a pharmaceutically acceptable salt thereof, wherein $X^1$, $R^1$, $R^2$, $R^3$, $R^4$, $R^5$, $R^6$, $R^7$, $R^8$, and $R^9$ are as described herein.

In yet another general aspect, the present disclosure provides a pharmaceutical composition comprising a compound of Formula (Ig), or a pharmaceutically acceptable salt thereof, and a pharmaceutically acceptable carrier.

In yet another general aspect, the present disclosure provides a method of inhibiting activation of an NF-κB pathway within a cell within a mammal, wherein said method comprises administering, to said mammal, an effective amount of a compound of Formula (IIa):

(IIa)

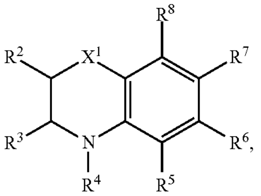

or a pharmaceutically acceptable salt thereof, wherein $X^1$, $R^2$, $R^3$, $R^4$, $R^5$, $R^6$, $R^7$, and $R^8$ are as described herein.

In yet another general aspect, the present disclosure provides a compound of Formula (IIb):

(IIb)

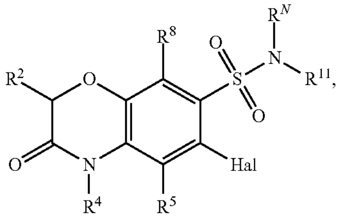

or a pharmaceutically acceptable salt thereof, wherein $R^N$, Hal, $R^2$, $R^4$, $R^5$, $R^8$ and $R^{11}$ are as described herein.

In yet another general aspect, the present disclosure provides a pharmaceutical composition comprising a compound of Formula (IIb), or a pharmaceutically acceptable salt thereof, and a pharmaceutically acceptable carrier.

In yet another general aspect, the present disclosure provides a compound of Formula (IIc):

(IIc)

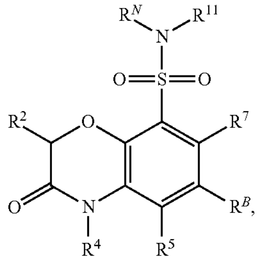

or a pharmaceutically acceptable salt thereof, wherein $R^N$, $R^B$, $R^2$, $R^4$, $R^5$, $R^7$ and $R^{11}$ are as described herein.

In yet another general aspect, the present disclosure provides a pharmaceutical composition comprising a compound of Formula (IIc), or a pharmaceutically acceptable salt thereof, and a pharmaceutically acceptable carrier.

In yet another general aspect, the present disclosure provides a compound of Formula (IId):

(IId)

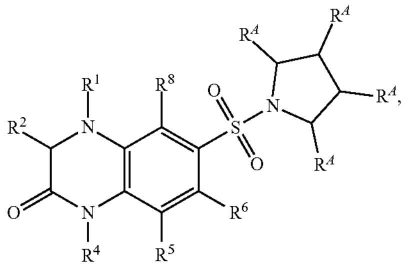

or a pharmaceutically acceptable salt thereof, wherein $R^A$, $R^1$, $R^2$, $R^4$, $R^5$, $R^6$, and $R^8$ are as described herein.

In yet another general aspect, the present disclosure provides a pharmaceutical composition comprising a compound of Formula (IId), or a pharmaceutically acceptable salt thereof, and a pharmaceutically acceptable carrier.

In yet another general aspect, the present disclosure provides a compound of Formula (IIe):

(IIe)

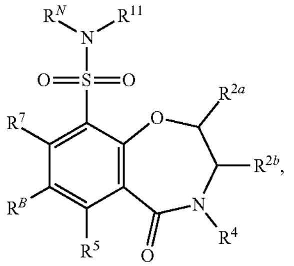

or a pharmaceutically acceptable salt thereof, wherein $R^N$, $R^{2a}$, $R^{2b}$, $R^4$, $R^5$, $R^B$, $R^7$, and $R^{11}$ are as described herein.

In yet another general aspect, the present disclosure provides a pharmaceutical composition comprising a compound of Formula (IIe), or a pharmaceutically acceptable salt thereof, and a pharmaceutically acceptable carrier.

In yet another general aspect, the present disclosure provides a compound of Formula (IIf):

(IIf)

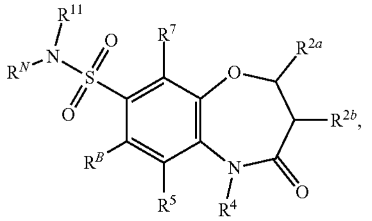

or a pharmaceutically acceptable salt thereof, wherein $R^N$, $R^{2a}$, $R^{2b}$, $R^4$, $R^5$, $R^B$, $R^7$, and $R^{11}$ are as described herein.

In yet another general aspect, the present disclosure provides a pharmaceutical composition comprising a compound of Formula (IIf), or a pharmaceutically acceptable salt thereof, and a pharmaceutically acceptable carrier.

In yet another general aspect, the present disclosure provides a compound of Formula (IIg):

(IIg)

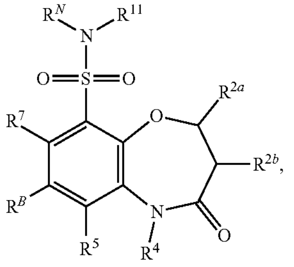

or a pharmaceutically acceptable salt thereof, wherein $R^N$, $R^{2a}$, $R^{2b}$, $R^4$, $R^5$, $R^B$, $R^7$, and $R^{11}$ are as described herein.

In yet another general aspect, the present disclosure provides a pharmaceutical composition comprising a compound of Formula (IIg), or a pharmaceutically acceptable salt thereof, and a pharmaceutically acceptable carrier.

In yet another general aspect, the present disclosure provides a method for inhibiting NF-κB activity within a cell within a mammal, wherein said method comprises administering, to said mammal, an effective amount of a compound of Formula (IIIa):

(IIIa)

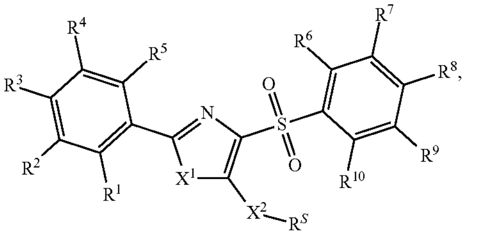

or a pharmaceutically acceptable salt thereof, wherein $X^1$, $X^2$, $R^S$, $R^1$, $R^2$, $R^3$, $R^4$, $R^5$, $R^6$, $R^7$, $R^8$, $R^9$, and $R^{10}$ are as described herein.

In yet another general aspect, the present disclosure provides a compound selected from any one of the compounds of Table 3b, or a pharmaceutically acceptable salt thereof.

In yet another general aspect, the present disclosure provides a pharmaceutical composition comprising any one of the compound of Table 3b, or a pharmaceutically acceptable salt thereof, and a pharmaceutically acceptable carrier.

In yet another general aspect, the present disclosure provides a compound of Formula (IIIc):

(IIIc)

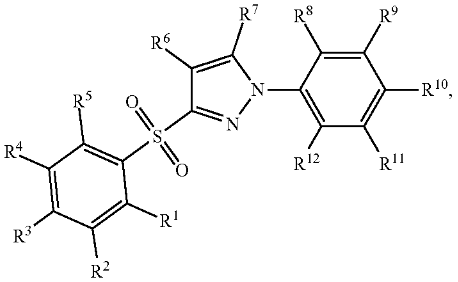

or a pharmaceutically acceptable salt thereof, wherein $R^1$, $R^2$, $R^3$, $R^4$, $R^5$, $R^6$, $R^7$, $R^8$, $R^9$, $R^{10}$, $R^{11}$, and $R^{12}$ are as described herein.

In yet another general aspect, the present disclosure provides a pharmaceutical composition comprising a compound of Formula (IIIc), or a pharmaceutically acceptable salt thereof, and a pharmaceutically acceptable carrier.

In yet another general aspect, the present disclosure provides a compound of Formula (IIId):

(IIId)

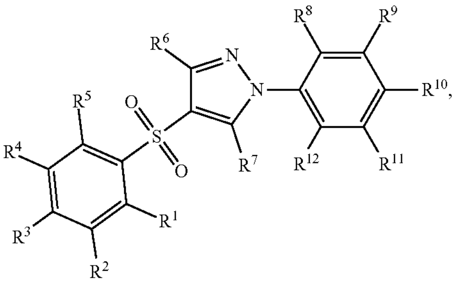

or a pharmaceutically acceptable salt thereof, wherein $R^1$, $R^2$, $R^3$, $R^4$, $R^5$, $R^6$, $R^7$, $R^8$, $R^9$, $R^{10}$, $R^{11}$, and $R^{12}$ are as described herein.

In yet another general aspect, the present disclosure provides a pharmaceutical composition comprising a compound of Formula (IIId), or a pharmaceutically acceptable salt thereof, and a pharmaceutically acceptable carrier.

In yet another general aspect, the present disclosure provides a compound of Formula (IIIe):

(IIIe)

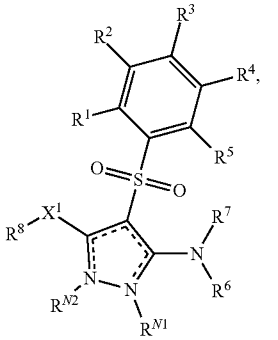

or a pharmaceutically acceptable salt thereof, wherein $X^1$, $R^{N2}$, $R^{N1}$, $R^1$, $R^2$, $R^3$, $R^4$, $R^5$, $R^6$, $R^7$, and $R^8$ are as described herein.

In yet another general aspect, the present disclosure provides a pharmaceutical composition comprising a compound of Formula (IIIe), or a pharmaceutically acceptable salt thereof, and a pharmaceutically acceptable carrier.

In yet another general aspect, the present disclosure provides a compound of Formula (IIIf):

(IIIf)

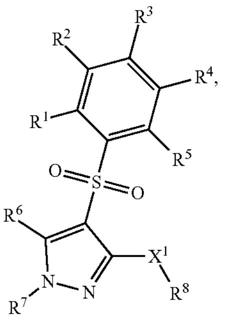

or a pharmaceutically acceptable salt thereof, wherein $X^1$, $R^1$, $R^2$, $R^3$, $R^4$, $R^5$, $R^6$, $R^7$, and $R^8$ are as described herein.

In yet another general aspect, the present disclosure provides a pharmaceutical composition comprising a compound of Formula (IIIf), or a pharmaceutically acceptable salt thereof, and a pharmaceutically acceptable carrier.

In yet another general aspect, the present disclosure provides a compound of Formula (IIIg-2):

(IIIg-2)

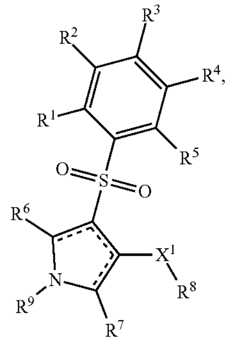

or a pharmaceutically acceptable salt thereof, wherein $X^1$, $R^1$, $R^2$, $R^3$, $R^4$, $R^5$, $R^6$, $R^7$, $R^8$ and $R^9$ are as described herein.

In yet another general aspect, the present disclosure provides a pharmaceutical composition comprising a compound of Formula (IIIg-2), or a pharmaceutically acceptable salt thereof, and a pharmaceutically acceptable carrier.

In yet another general aspect, the present disclosure provides a compound of Formula (IIIg):

(IIIg)

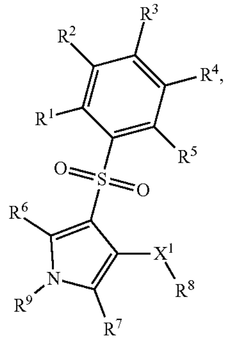

or a pharmaceutically acceptable salt thereof, wherein $X^1$, $R^1$, $R^2$, $R^3$, $R^4$, $R^5$, $R^6$, $R^7$, $R^8$ and $R^9$ are as described herein.

In yet another general aspect, the present disclosure provides a pharmaceutical composition comprising a compound of Formula (IIIg), or a pharmaceutically acceptable salt thereof, and a pharmaceutically acceptable carrier.

In yet another general aspect, the present disclosure provides a compound of Formula (IIIh):

(IIIh)

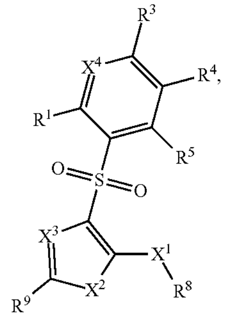

or a pharmaceutically acceptable salt thereof, wherein $X^1$, $X^2$, $X^3$, $X^4$, $R^3$, $R^4$, $R^5$, $R^8$ and $R^9$ are as described herein.

In yet another general aspect, the present disclosure provides a pharmaceutical composition comprising a compound of Formula (IIIh), or a pharmaceutically acceptable salt thereof, and a pharmaceutically acceptable carrier.

In yet another general aspect, the present disclosure provides a compound of Formula (IIIi):

(IIIi)

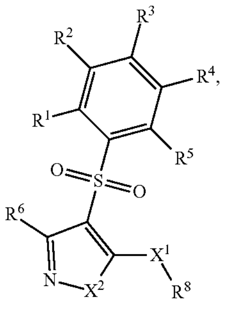

or a pharmaceutically acceptable salt thereof, wherein $X^1$, $X^2$, $R^1$, $R^2$, $R^3$, $R^4$, $R^5$, $R^6$ and $R^8$ are as described herein.

In yet another general aspect, the present disclosure provides a pharmaceutical composition comprising a compound of Formula (IIIi), or a pharmaceutically acceptable salt thereof, and a pharmaceutically acceptable carrier.

In yet another general aspect, the present disclosure provides a method for inhibiting NF-κB activity within a cell within a mammal, wherein said method comprises administering, to said mammal, an effective amount of a compound of Formula (IVa):

(IVa)

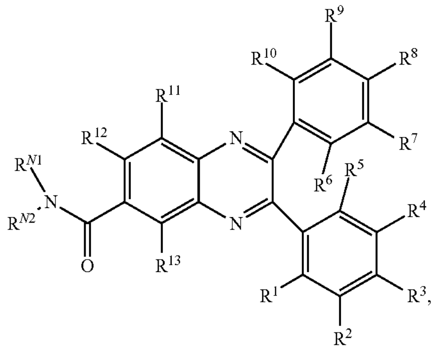

or a pharmaceutically acceptable salt thereof, wherein $R^{N1}$, $R^{N2}$, $R^1$, $R^2$, $R^3$, $R^4$, $R^5$, $R^6$, $R^7$, $R^8$, $R^9$, $R^{10}$, $R^{11}$, $R^{12}$, and $R^{13}$ are as described herein.

In yet another general aspect, the present disclosure provides a compound selected from any one of the compounds of Table 4b, or a pharmaceutically acceptable salt thereof.

In yet another general aspect, the present disclosure provides a pharmaceutical composition comprising any one of the compounds of Table 4b, or a pharmaceutically acceptable salt thereof, and a pharmaceutically acceptable carrier.

In yet another general aspect, the present disclosure provides a compound of Formula (IVb):

(IVb)

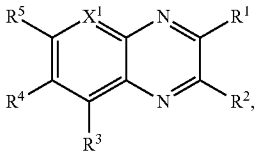

or a pharmaceutically acceptable salt thereof, wherein $X^1$, $R^1$, $R^2$, $R^3$, $R^4$, and $R^5$ are as described herein.

In yet another general aspect, the present disclosure provides a pharmaceutical composition comprising a compound of Formula (IVb), or a pharmaceutically acceptable salt thereof, and a pharmaceutically acceptable carrier.

In yet another general aspect, the present disclosure provides a compound of Formula (IVc):

(IVc)

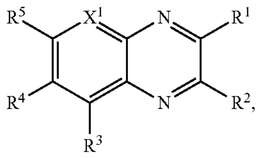

or a pharmaceutically acceptable salt thereof, wherein $X^1$, $R^1$, $R^2$, $R^3$, $R^4$, and $R^5$ are as described herein.

In yet another general aspect, the present disclosure provides a pharmaceutical composition comprising a compound of Formula (IVc), or a pharmaceutically acceptable salt thereof, and a pharmaceutically acceptable carrier.

In yet another general aspect, the present disclosure provides a compound of Formula (IVd):

(IVd)

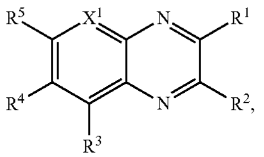

or a pharmaceutically acceptable salt thereof, wherein $X^1$, $R^1$, $R^2$, $R^3$, $R^4$, and $R^5$ are as described herein.

In yet another general aspect, the present disclosure provides a pharmaceutical composition comprising a compound of Formula (IVd), or a pharmaceutically acceptable salt thereof, and a pharmaceutically acceptable carrier.

In yet another general aspect, the present disclosure provides a compound of Formula (IVe):

(IVe)

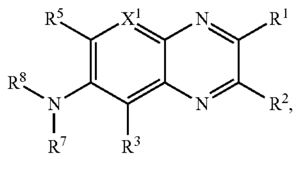

or a pharmaceutically acceptable salt thereof, wherein $X^1$, $R^1$, $R^2$, $R^3$, $R^5$, $R^7$, and $R^8$ are as described herein.

In yet another general aspect, the present disclosure provides a pharmaceutical composition comprising a compound of Formula (IVe), or a pharmaceutically acceptable salt thereof, and a pharmaceutically acceptable carrier.

In yet another general aspect, the present disclosure provides a compound of Formula (IVf):

(IVf)

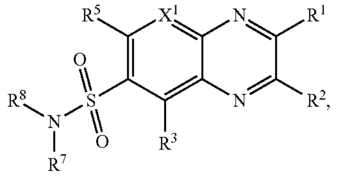

or a pharmaceutically acceptable salt thereof, wherein $X^1$, $R^1$, $R^2$, $R^3$, $R^5$, $R^7$, and $R^8$ are as described herein.

In yet another general aspect, the present disclosure provides a pharmaceutical composition comprising a compound of Formula (IVf), or a pharmaceutically acceptable salt thereof, and a pharmaceutically acceptable carrier.

In yet another general aspect, the present disclosure provides a compound of Formula (IVg):

(IVg)

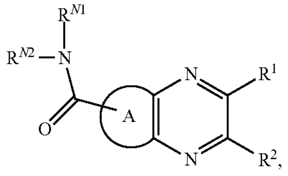

or a pharmaceutically acceptable salt thereof, wherein $R^1$, $R^2$, ring A, $R^{N1}$, and $R^{N2}$ are as described herein.

In yet another general aspect, the present disclosure provides a pharmaceutical composition comprising a compound of Formula (IVg), or a pharmaceutically acceptable salt thereof, and a pharmaceutically acceptable carrier.

In yet another general aspect, the present disclosure provides a method of treating a mammal having a disease, disorder, or condition responsive to inhibiting NF-κB activity within a cell, wherein said method comprises administering, to said mammal, any one of the compounds described herein, or a pharmaceutical composition comprising same. In some embodiments, the mammal is a human. In some embodiments, the method comprises treating a mammal having a cancer. In some embodiments, the method comprises treating a mammal having an inflammation. In some embodiments, the inflammation is an autoimmune disease.

In yet another general aspect, the present disclosure provides a method for inhibiting NF-κB activity within cells of a mammal, wherein said method comprises administering, to said mammal, any one of the compounds described herein or a pharmaceutical composition comprising same.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the present application will be apparent from the following detailed description and figures, and from the claims.

DETAILED DESCRIPTION

Figure 1:
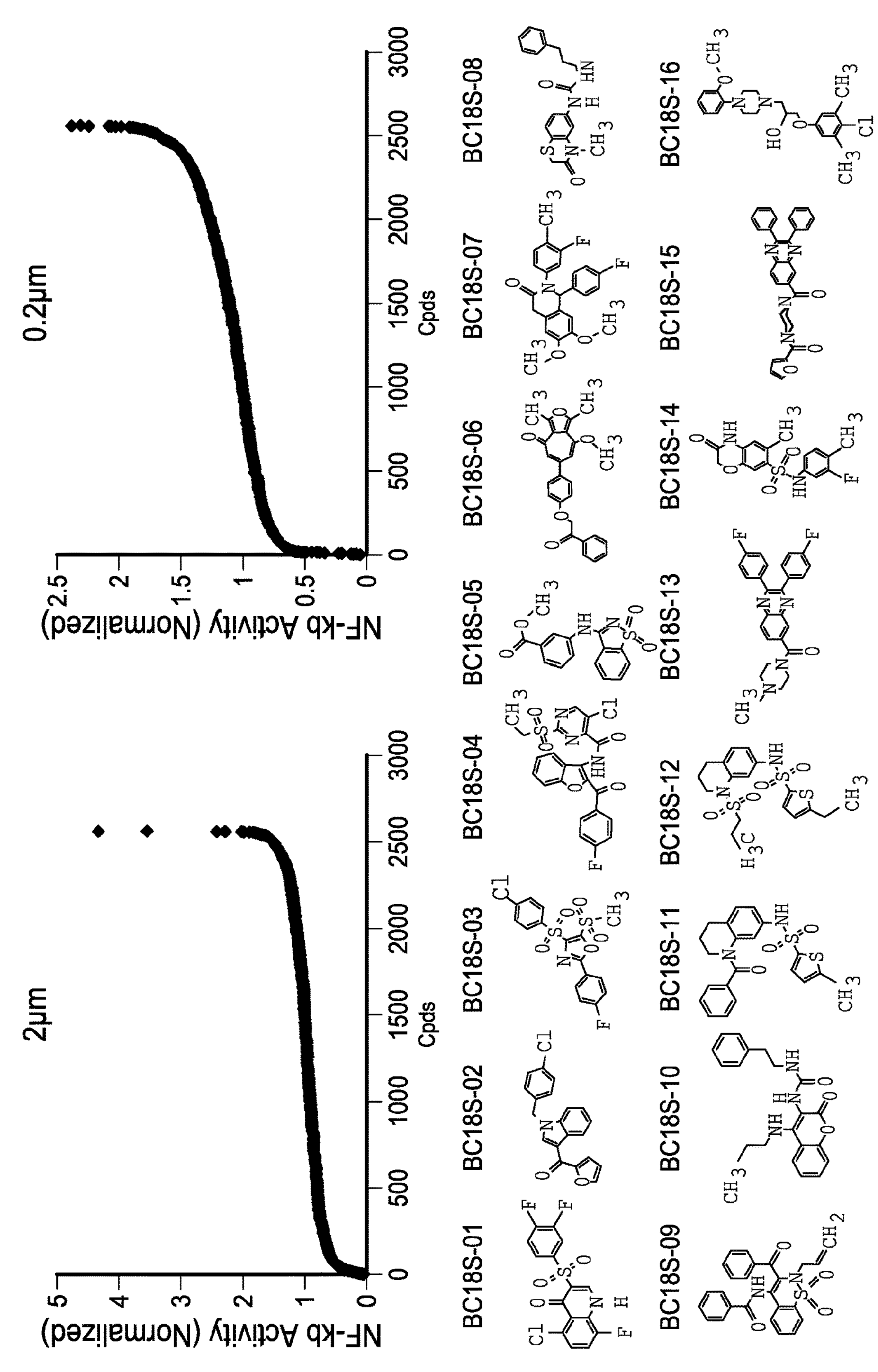
FIG. 1 contains line plots showing NF-κB activity of exemplified compounds. 25k THP1-NF-κB-LUC cells were dispensed into 384 well plate (per well). Cells were treated with compounds (2 μM and 0.2 μM) for 2 hours before addition of LPS (10 ng/mL) for 18 hours. Secreted luciferase activity were measured using quant-luc reagents (1 bag of luc reagent dilute to 40 mL, use 10 μL per well). Data were normalized to vehicle control and graphed. Structures of selected exemplified compounds are shown.
Figure 2:
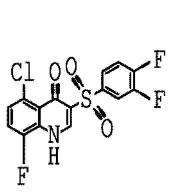
FIG. 2 contains heat charts showing NF-κB activity of exemplified compounds as a function of concentration. 25k THP1-NF-κB-LUC cells were dispensed into 384 well plate (per well). Cells were treated with compounds (with serial dilution) for 2 hours before addition of LPS (10 ng/ml) for 18 hours. Secreted luciferase activity were measured using quant-luc reagents (1 bag of luc reagent dilute to 40 mL, use 10 μL per well). Structures of selected exemplified compounds are shown.
Figure 2:
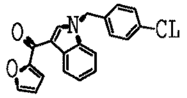
Figure 2:
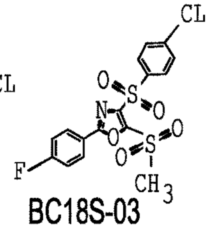
Figure 2:
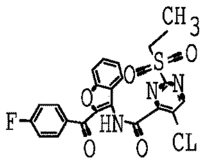
Figure 2:
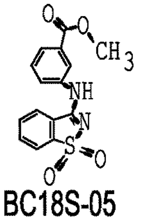
Figure 2:
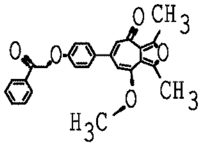
Figure 2:
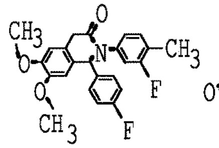
Figure 2:
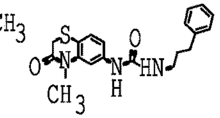
Figure 2:
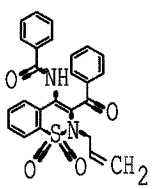
Figure 2:
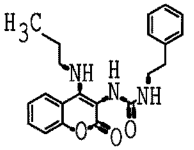
Figure 2:
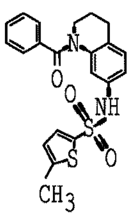
Figure 2:
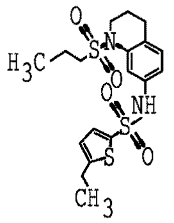
Figure 2:
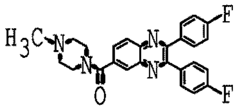
Figure 2:
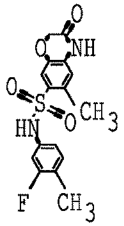
Figure 2:
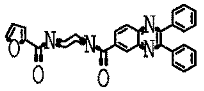
Figure 2:
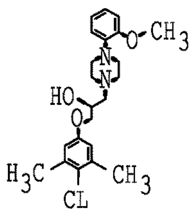
Figure 3:
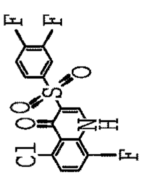
FIG. 3 contains heat charts showing NF-κB activity of exemplified compounds as a function of concentration. 25k THP1-NF-κB-LUC cells were dispensed into 384 well plate (per well). Cells were treated with compounds (with serial dilution) for 2 hours before addition of Pam3CSK4 (1 g/mL) for 18 hours. Secreted luciferase activity were measured using quant-luc reagents (1 bag of luc reagent dilute to 40 mL, use 10 μL per well). Structures of selected exemplified compounds are shown.
Figure 3:
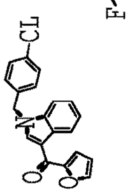
Figure 3:
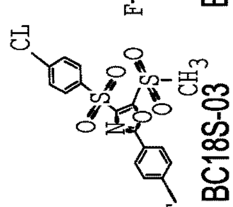
Figure 3:
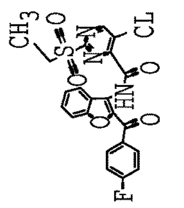
Figure 3:
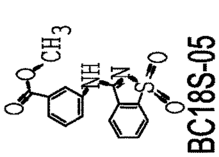
Figure 3:
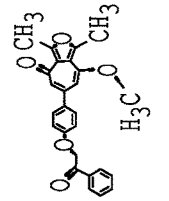
Figure 3:
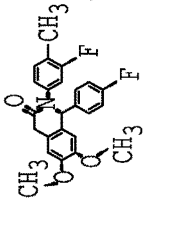
Figure 3:
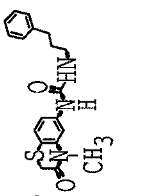
Figure 3:
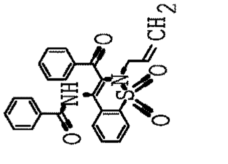
Figure 3:
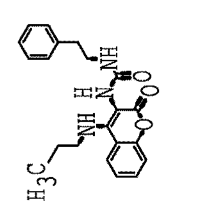
Figure 3:
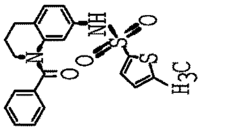
Figure 3:
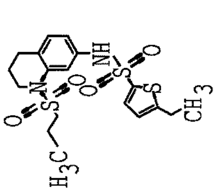
Figure 3:
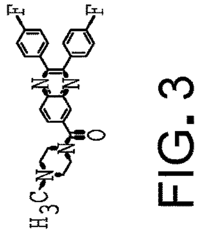
Figure 3:
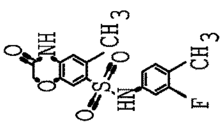
Figure 3:
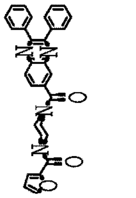
Figure 3:
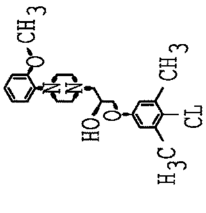
Figure 4:
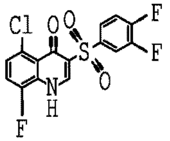
FIG. 4 contains heat charts showing NF-κB activity of exemplified compounds as a function of concentration. 25k THP1-NF-κB-LUC cells were dispensed into 384 well plate (per well). Cells were treated with compounds (with serial dilution) for 2 hours before addition of R848 (1 μg/mL) for 18 hours. Secreted luciferase activity were measured using quant-luc reagents (1 bag of luc reagent dilute to 40 mL, use 10 μL per well). Structures of selected exemplified compounds are shown.
Figure 4:
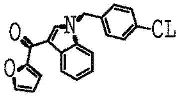
Figure 4:
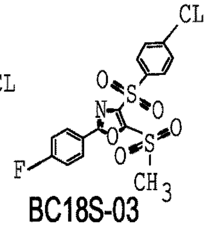
Figure 4:
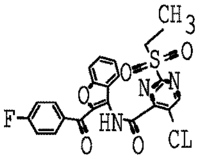
Figure 4:
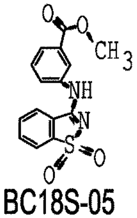
Figure 4:
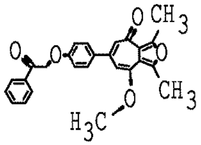
Figure 4:
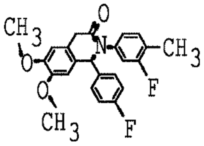
Figure 4:
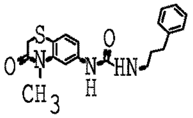
Figure 4:
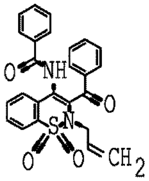
Figure 4:
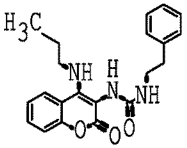
Figure 4:
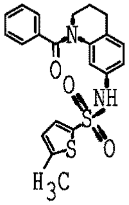
Figure 4:
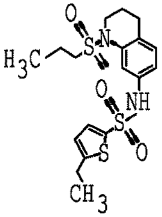
Figure 4:
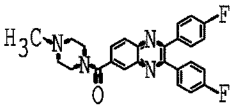
Figure 4:
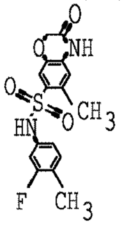
Figure 4:
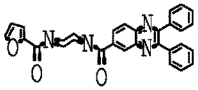
Figure 4:
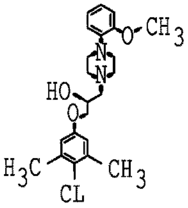
Figure 5:
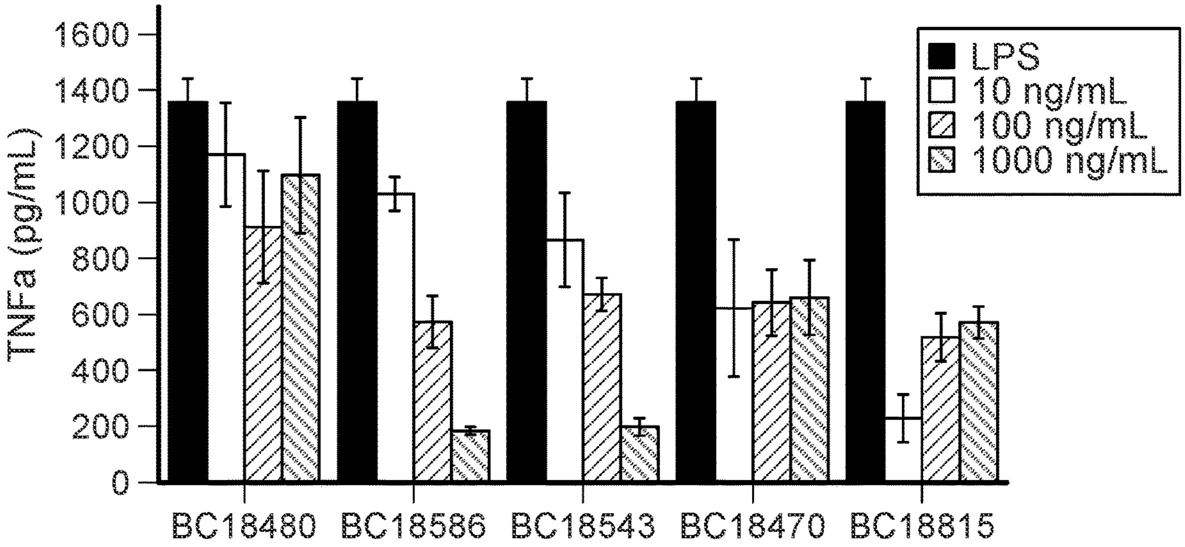
FIG. 5 contains a bar graph showing TNFα inhibitory activity for selected exemplified compounds. Mouse bone marrow macrophages were cultured in 96 well and differentiated before compound treatment at various concentrations for 2 hours. Cells were further treated with LPS (10 ng/mL) for 2 hours, and supernatants were collected and assayed for TNF.

This document provides methods and materials for inhibiting NF-κB activity. For example, the document provides compounds (e.g., organic compounds) having the ability to inhibit NF-κB activity within cells, formulations containing one or more compounds having the ability to inhibit NF-κB activity within cells, methods for making one or more compounds having the ability to inhibit NF-κB activity within cells, methods for making formulations containing one or more compounds having the ability to inhibit NF-κB activity within cells, methods for inhibiting NF-κB activity within cells, and methods for treating mammals (e.g., humans) having a condition responsive to inhibition of NF-κB activity. Suitable examples of conditions responsive to inhibition of NF-κB activity within cells include autoimmune conditions, such as Crohn's disease, ulcerative colitis, colitis, psoriatic arthritis, systemic lupus, erythematosis (SLE), and psoriasis.

Methods of Treatment Using One or More Inhibitors of NF-κB Activity

In some cases, this document provides methods for inhibiting NF-κB activity within a cell by contacting the cell with one or more compounds provided herein (e.g., a compound set forth in any one of the Formulae (I)-(IV), or a pharmaceutically acceptable salt thereof).

In some cases, methods for inhibiting NF-κB activity within cells can be performed in vivo. For example, one or more compounds provided herein (e.g., a compound set forth in any one of the Formulae (I)-(IV), or a pharmaceutically acceptable salt thereof) can be administered to a mammal (e.g., a human) to inhibit NF-κB activity within cells within that mammal. In some cases, methods for inhibiting NF-κB activity within cells can be performed in vitro. For example, one or more compounds provided herein (e.g., a compound set forth in any one of the Formulae (I)-(IV), or a pharmaceutically acceptable salt thereof) can be added to a cell culture containing cells (e.g., human cells) to inhibit NF-κB activity within those cells. In some cases, such intervention can improve the quality of the cell while in culture or subsequently.

This document also provides methods for treating diseases, disorders, and conditions in a mammal by administering one or more compounds provided herein (e.g., a compound set forth in any one of the Formulae (I)-(IV), or a pharmaceutically acceptable salt thereof) to a mammal in need thereof. In some cases, the disease, disorder, or condition being treated can be a disease, disorder, or condition that is responsive to inhibiting NF-κB activity within cells within the mammal. In some cases, the disease, disorder, or condition being treated can be a disease, disorder, or condition that is associated with enhanced NF-κB activity within the mammal.

Examples of diseases, disorders, and conditions that can be treated with one or more compounds provided herein include, without limitation, cancer and inflammation disorders (e.g., acute or chronic inflammation, or viral or influenza-induced inflammation such as HIV-related inflammation).

Suitable examples of disorders associated with inflammation include asthma, chronic obstructive lung disease, pulmonary fibrosis, pneumonitis (e.g., hypersensitivity pneumonitis and radiation pneumonitis), pneumonia, cystic fibrosis, psoriasis, arthritis, rheumatoid arthritis, rhinitis, pharyngitis, cystitis, prostatitis, dermatitis, allergy (e.g., hay fever), nephritis, conjunctivitis, encephalitis, meningitis, opthalmitis, uveitis, pleuritis, pericarditis, myocarditis, atherosclerosis, diabetes, osteoarthritis, psoriatic arthritis, autoimmune diseases or conditions, inflammatory bowel disease (e.g., Crohn's disease or ulcerative colitis), colitis, sepsis, vasculitis, bursitis, connective tissue disease, systemic lupus erythematosis (SLE), polymyalgia rheumatica, scleroderma, Wegener's granulomatosis, temporal arteritis, vasculitis, cryoglobulinemia, multiple sclerosis, and edema.

Suitable examples of cancers include prostate cancer, pancreatic cancer, ovarian cancer, breast cancer, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastroesophageal cancer, gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma, hepatobiliary cancer); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasmlungrectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

In some cases, provided herein are methods for treating a cancer (e.g., any one of the cancers described herein) in a mammal (e.g., human) by administering one or more compounds provided herein (e.g., a compound set forth in any one of the Formulae (I)-(IV), or a pharmaceutically acceptable salt thereof) to a mammal in need thereof.

In some cases, provided herein are methods for treating inflammation (e.g., any one of the inflammation disorders described herein) in a mammal (e.g., human) by administering one or more compounds provided herein (e.g., a compound set forth in any one of the Formulae (I)-(IV), or a pharmaceutically acceptable salt thereof) to a mammal in need thereof.

In some cases, provided herein are methods for treating autoimmune disease (e.g., any one of the autoimmune diseases described herein) in a mammal (e.g., human) by administering one or more compounds provided herein (e.g., a compound set forth in any one of the Formulae (I)-(IV), or a pharmaceutically acceptable salt thereof) to a mammal in need thereof.

In some cases, one or more compounds provided herein (e.g., a compound set forth in any one of the Formulae (I)-(IV), or a pharmaceutically acceptable salt thereof) can be used as described herein (e.g., to inhibit NF-κB activity within cells and/or to treat a disease, disorder, or condition as described herein) as the sole active ingredient(s). For example, a composition containing a compound set forth in any one of the Formulae (I)-(IV), or a pharmaceutically acceptable salt thereof, can lack any other active ingredients that inhibit NF-κB activity within cells. In some cases, a composition containing a compound set forth in any one of the Formulae (I)-(IV), or a pharmaceutically acceptable salt thereof, can lack any other active ingredients that are effective to treat a disease, disorder, or condition as described herein.

Therapeutic Compounds

As described herein, any one or more of the compounds provided herein can be used to inhibit NF-κB activity within cells and/or can be used to treat (or prevent) a disease, disorder, and condition in a mammal (e.g., a human) as described herein.

Formula (Ia)

In one general aspect, the present disclosure provides a compound of Formula (Ia):

(Ia)

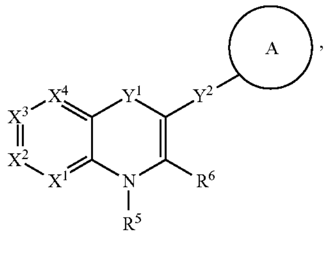

or a pharmaceutically acceptable salt thereof, wherein:

$Y^1$ is selected from C(O) and $S(O)_2$;

$Y^2$ is selected from C(O) and $S(O)_2$;

$X^1$ is selected from N and $CR^1$;

$X^2$ is selected from N and $CR^2$;

$X^3$ is selected from N and $CR^3$;

$X^4$ is selected from N and $CR^4$;

provided that no more than two of $X^1$, $X^2$, $X^3$, and $X^4$ are N;

each of $R^1$, $R^2$, $R^3$, $R^4$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^5$ is selected from H, $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $R^8$;

each $R^8$ is independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$ wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $Y^1$ is C(O). In some embodiments, $Y^1$ is $S(O)_2$.

In some embodiments, $Y^2$ is C(O). In some embodiments, $Y^2$ is $S(O)_2$.

In some embodiments, $Y^1$ is C(O) and $Y^2$ is $S(O)_2$. In some embodiments, $Y^1$ is C(O) and $Y^2$ is C(O). In some embodiments, $Y^1$ is $S(O)_2$ and $Y^2$ is $S(O)_2$. In some embodiments, $Y^1$ is $S(O)_2$ and $Y^2$ is C(O).

In some embodiments, $X^1$ is N. In some embodiments, $X^1$ is $CR^1$. In some embodiments, $X^2$ is N. In some embodiments, $X^2$ is $CR^2$. In some embodiments, $X^3$ is N. In some embodiments, $X^3$ is $CR^3$. In some embodiments, $X^4$ is N. In some embodiments, $X^4$ is $CR^1$. In some embodiments, one of $X^1$, $X^2$, $X^3$, and $X^4$ is N. In some embodiments, two of $X^1$, $X^2$, $X^3$, and $X^4$ are N.

In some embodiments, the compound of Formula (Ia) has formula:

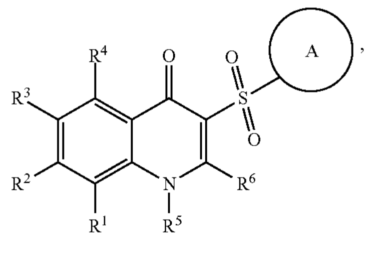

or a pharmaceutically acceptable salt thereof.

In some embodiments, the compound of Formula (Ia) has formula:

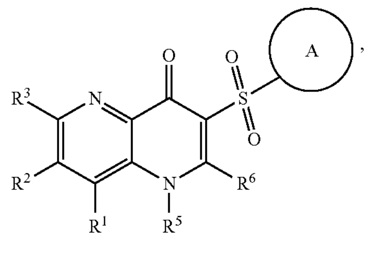

or a pharmaceutically acceptable salt thereof.

In some embodiments, the compound of Formula (Ia) has formula:

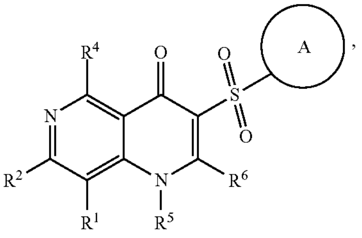

or a pharmaceutically acceptable salt thereof.

In some embodiments, the compound of Formula (Ia) has formula:

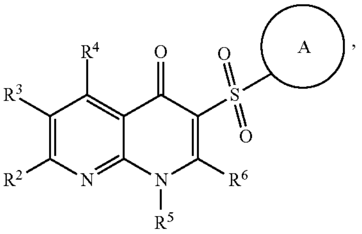

or a pharmaceutically acceptable salt thereof.

In some embodiments, ring A is selected from $C_{6-10}$ aryl and 5-10 membered heteroaryl, each of which is substituted with 1-6 substituents independently selected from $R^A$.

In some embodiments, ring A is $C_{6-10}$ aryl, substituted with 1-5 substituents independently selected from $R^A$. In some embodiments, ring A is phenyl, optionally substituted with 1-5 substituents independently selected from $R^A$. In some embodiments, ring A is naphthyl, optionally substituted with 1-5 substituents independently selected from $R^A$.

In some embodiments, ring A is 5-10 membered heteroaryl, substituted with 1-6 substituents independently selected from $R^A$. In some embodiments, ring A is selected from pyridin-2-yl, pyridin-3-yl, pyridin-4-yl, thiophen-2-yl, thiophen-3-yl, pyrazol-3-yl, pyrazlol-4-yl, pyrazol-5-yl, quinolin-6-yl, quinolin-7-yl, thiazolyl, 1,3,4-thiadiazolyl, and quinoxaline-6-yl, each of which is optionally substituted with 1-6 substituents independently selected from $R^A$.

In some embodiments, ring A is selected from any one of the following moieties:

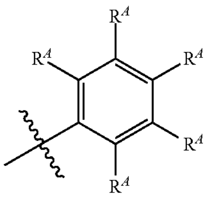
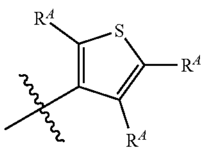
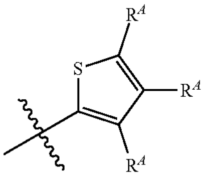
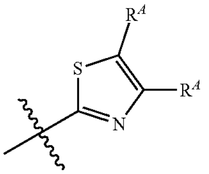

-continued

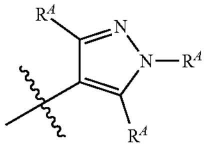
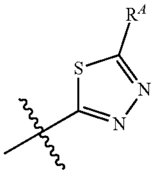
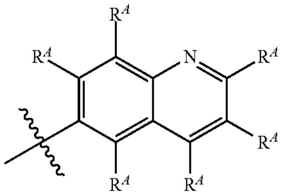
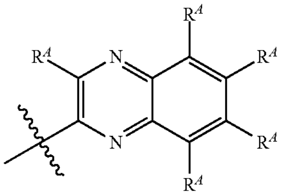
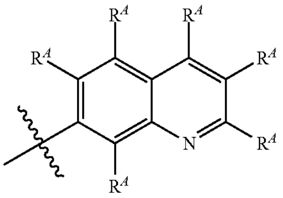
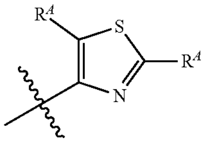

In some embodiments, ring A is:

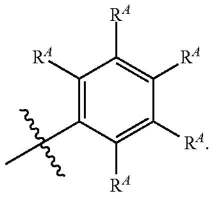

In some embodiments, ring A is:

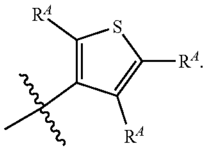

In some embodiments, ring A is:

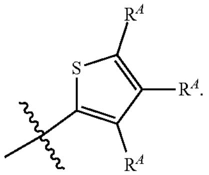

In some embodiments, ring A is:

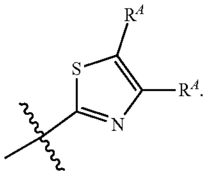

In some embodiments, ring A is:
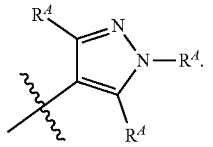
In some embodiments, ring A is:
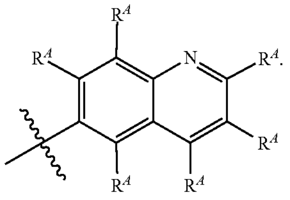
In some embodiments, ring A is:
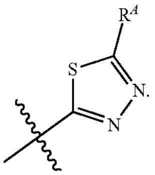
In some embodiments, ring A is:
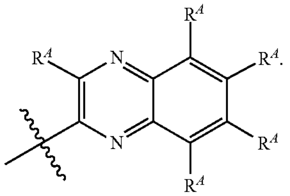
In some embodiments, ring A is:
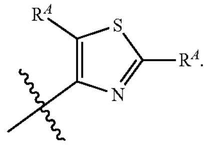
In some embodiments, ring A is:
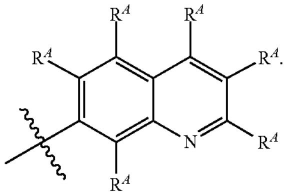
In some embodiments, the compound of Formula (Ia) is selected from any one of the following compounds:
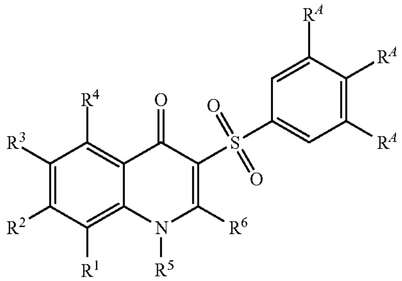
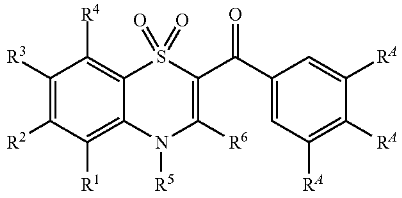
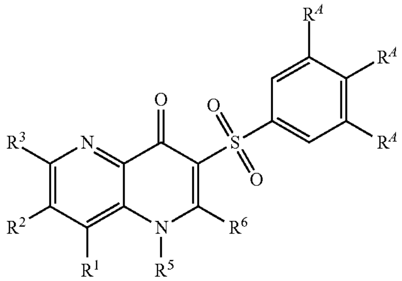
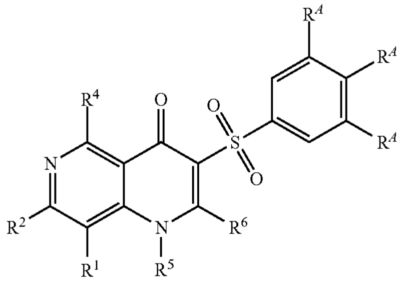
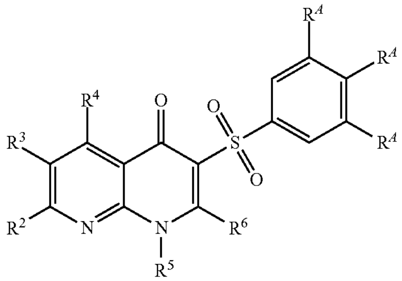
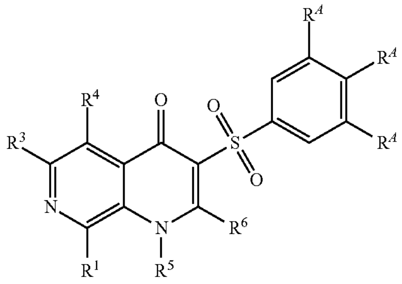
or a pharmaceutically acceptable salt thereof.

In some embodiments, the compound of Formula (Ia) has formula:

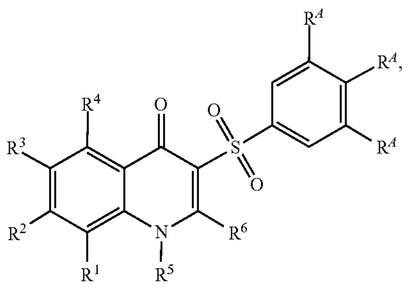

or a pharmaceutically acceptable salt thereof.

In some embodiments, the compound of Formula (Ia) has formula:

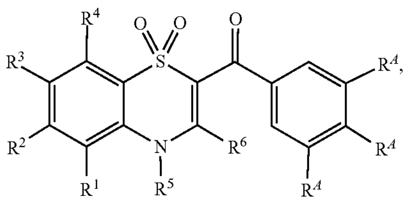

or a pharmaceutically acceptable salt thereof.

In some embodiments, the compound of Formula (Ia) has formula:

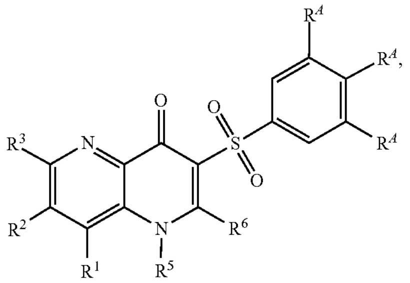

or a pharmaceutically acceptable salt thereof.

In some embodiments, the compound of Formula (Ia) has formula:

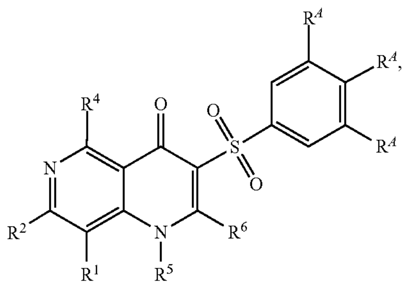

or a pharmaceutically acceptable salt thereof.

In some embodiments, the compound of Formula (Ia) has formula:

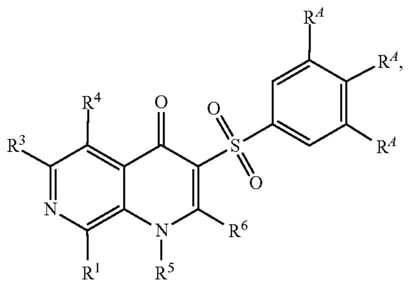

or a pharmaceutically acceptable salt thereof.

In some embodiments, the compound of Formula (Ia) has formula:

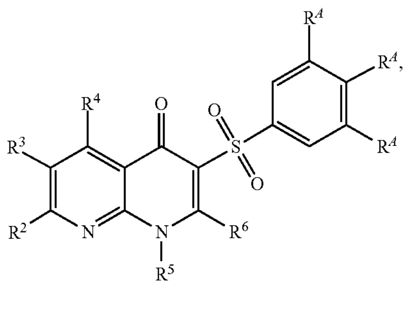

or a pharmaceutically acceptable salt thereof.

In some embodiments, each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$.

In some embodiments, each $R^9$ is independently selected from CN, $NO_2$, OH, $C_{1-6}$ alkoxy, $C(O)NH_2$, C(O)OH, $NH_2$, and $S(O)_2NH_2$.

In some embodiments, each $R^A$ is independently selected from H, halo, CN, $C_{1-6}$ alkyl, and $C_{1-6}$ alkoxy. In some embodiments, $R^A$ is H. In some embodiments, $R^A$ is halo. In some embodiments, $R^A$ is CN. In some embodiments, $R^A$ is $C_{1-6}$ alkyl. In some embodiments, $R^A$ is $C_{1-6}$ alkoxy.

In some embodiments, each of $R^1$, $R^2$, $R^3$, $R^4$, and $R^6$, if present in the compound of Formula (Ia), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; wherein said $C_{1-6}$ alkyl is optionally substituted with 1, 2, or 3 substituents independently selected from $R^7$.

In some embodiments, each of $R^1$, $R^2$, $R^3$, $R^4$, and $R^6$, if present in the compound of Formula (Ia), is independently selected from H, halo, CN, $C_{1-6}$ alkyl, and $OR^{a1}$. In some embodiments, at least one of $R^1$, $R^2$, $R^3$, $R^4$, and $R^6$ is H. In some embodiments, at least one of $R^1$, $R^2$, $R^3$, $R^4$, and $R^6$ is halo. In some embodiments, at least one of $R^1$, $R^2$, $R^3$, $R^4$, and $R^6$ is CN. In some embodiments, at least one of $R^1$, $R^2$, $R^3$, $R^4$, and $R^6$ is $C_{1-6}$ alkyl. In some embodiments, at least one of $R^1$, $R^2$, $R^3$, $R^4$, and $R^6$ is $OR^{a1}$.

In some embodiments, $R^1$, if present in the compound of Formula (Ia), is selected from H, halo, $C_{1-6}$ alkyl, and $C_{1-6}$ alkoxy; $R^2$, if present in the compound of Formula (Ia), is selected from H, CN, halo, $C_{1-6}$ alkoxy, and $C_{1-6}$ alkyl; $R^3$, if present in the compound of Formula (Ia), is selected from H, CN, halo, $C_{1-6}$ alkoxy, and $C_{1-6}$ alkyl; $R^4$, if present in the compound of Formula (Ia), is selected from H, halo, $C_{1-6}$ alkyl, and $C_{1-6}$ alkoxy; and $R^6$, if present in the compound of Formula (Ia), is selected from H and OH. In some embodiments, $R^6$ is OH.

In some embodiments, $R^7$ is selected from CN, $NO_2$, OH, $C_{1-6}$ alkoxy, $C(O)NH_2$, C(O)OH, $NH_2$, and $S(O)_2NH_2$.

In some embodiments, $R^5$ is selected from H, $C_{1-6}$ alkyl, and $Cy^1$, wherein said $C_{1-6}$ alkyl is optionally substituted with 1, 2, or 3 substituents independently selected from $R^8$.

In some embodiments, $R^8$ is selected from $Cy^1$, CN, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$.

In some embodiments, $R^8$ is selected from $Cy^1$ and $C(O)NR^{c1}R^{d1}$. In some embodiments, $R^8$ is $Cy^1$. In some embodiments, $R^8$ is $C(O)NR^{c1}R^{d1}$.

In some embodiments, $R^5$ is H.

In some embodiments, $R^5$ is $Cy^1$.

In some embodiments, $R^5$ is $C_{1-6}$ alkyl, optionally substituted with $Cy^1$. In some embodiments, $R^5$ is $C_{1-6}$ alkyl substituted with $Cy^1$. I In some embodiments, $R^5$ is $C_{1-6}$ alkyl, optionally substituted with $C(O)NR^{c1}R^{d1}$. In some embodiments, $R^5$ is $C_{1-6}$ alkyl substituted with $C(O)NR^{c1}R^{d1}$.

In some embodiments, $Cy^1$ is selected from $C_{6-10}$ aryl and 5-10 membered heteroaryl, each of which is optionally substituted with 1, 2, or 3 substituents independently selected from $R^{Cy1}$.

In some embodiments, $Cy^1$ is $C_{6-10}$ aryl, optionally substituted with $R^{Cy1}$. In some embodiments, $R^{Cy1}$ is selected from halo, CN, $NO_2$, $C_{1-6}$ alkyl, $C_{1-6}$ alkoxy, and $C_{1-6}$ haloalkyl. In some embodiments, $R^{Cy1}$ is halo.

In some embodiments, $Cy^1$ is $C_{6-10}$ aryl, optionally substituted with halo.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^g$.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, each $R^8$ is independently selected from halo and $C_{1-6}$ alkyl.

In some embodiments of Formula (Ia):

each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

each $R^9$ is independently selected from CN, $NO_2$, OH, $C_{1-6}$ alkoxy, $C(O)NH_2$, C(O)OH, $NH_2$, and $S(O)_2NH_2$;

each of $R^1$, $R^2$, $R^3$, $R^4$, and $R^6$, if present in the compound of Formula (Ia), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^7$;

$R^7$ is selected from CN, $NO_2$, OH, $C_{1-6}$ alkoxy, $C(O)NH_2$, C(O)OH, $NH_2$, and $S(O)_2NH_2$;

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$, CN, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$;

each $Cy^1$ is independently selected from $C_{6-10}$ aryl and 5-10 membered heteroaryl, each of which is optionally substituted with 1, 2, or 3 substituents independently selected from $R^{Cy1}$;

each $R^{Cy1}$ is independently selected from halo, CN, $NO_2$, $C_{1-6}$ alkyl, $C_{1-6}$ alkoxy, and $C_{1-6}$ haloalkyl;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$; and each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of Formula (Ia):

each $R^A$ is independently selected from H, halo, CN, $C_{1-6}$ alkyl, and $C_{1-6}$ alkoxy;

each of $R^1$, $R^2$, $R^3$, $R^4$, and $R^6$, if present in the compound of Formula (Ia), is independently selected from H, halo, CN, $C_{1-6}$ alkyl, and $OR^{a1}$;

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$ and $C(O)NR^{c1}R^{d1}$;

$Cy^1$ is $C_{6-10}$ aryl, optionally substituted with $R^{Cy1}$;

$R^{Cy1}$ is selected from halo, CN, $NO_2$, $C_{1-6}$ alkyl, $C_{1-6}$ alkoxy, and $C_{1-6}$ haloalkyl;

each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$; and wherein each $R^g$ is independently selected from halo and $C_{1-6}$ alkyl.

In some embodiments:

each $R^A$ is independently selected from H, halo, CN, $C_{1-6}$ alkyl, and $C_{1-6}$ alkoxy;

$R^1$, if present in the compound of Formula (Ia), is selected from H, halo, $C_{1-6}$ alkyl, and $C_{1-6}$ alkoxy;

$R^2$, if present in the compound of Formula (Ia), is selected from H, CN, halo, $C_{1-6}$ alkoxy, and $C_{1-6}$ alkyl;

$R^3$, if present in the compound of Formula (Ia), is selected from H, CN, halo, $C_{1-6}$ alkoxy, and $C_{1-6}$ alkyl;

$R^4$, if present in the compound of Formula (Ia), is selected from H, halo, $C_{1-6}$ alkyl, and $C_{1-6}$ alkoxy; and $R^6$, if present in the compound of Formula (Ia), is selected from H and OH.

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$ and $C(O)NR^{c1}R^{d1}$;

$Cy^1$ is $C_{6-10}$ aryl, optionally substituted with halo;

each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$; and each $R^8$ is independently selected from halo and $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ia) is selected from any one of the compounds of Table 1a, Table 1d, or Table 1e, or a pharmaceutically acceptable salt thereof. In some embodiments, the compound of Formula (Ia) is selected from any one of the compounds of Table 1a, or a pharmaceutically acceptable salt thereof.

In some embodiments, the compound of Formula (Ia) is selected from any one of the compounds of Table 1d, or a pharmaceutically acceptable salt thereof. In some embodiments, the compound of Formula (Ia) is selected from any one of the compounds of Table 1e, or a pharmaceutically acceptable salt thereof. In some embodiments, the compound of Formula (Ia) has Formula (Ib), or a pharmaceutically acceptable salt thereof.

Formula (Ib):

In one general aspect, the present disclosure provides a compound of Formula (Ib):

(Ib)

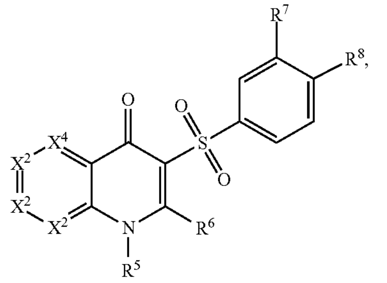

or a pharmaceutically acceptable salt thereof, wherein:

$X^1$ is selected from N and $CR^1$;

$X^2$ is selected from N and $CR^2$;

$X^3$ is selected from N and $CR^3$;

$X^4$ is selected from N and $CR^4$;

provided that at least one of $X^1$, $X^2$, $X^3$, and $X^4$ is N;

each of $R^1$, $R^2$, $R^3$, $R^4$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^5$ is selected from H, $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is N. In some embodiments, $X^1$ is $CR^1$. In some embodiments, $X^2$ is N. In some embodiments, $X^2$ is $CR^2$. In some embodiments, $X^3$ is N. In some embodiments, $X^3$ is $CR^3$. In some embodiments, $X^4$ is N. In some embodiments, $X^4$ is $CR^1$. In some embodiments, one of $X^1$, $X^2$, $X^3$, and $X^4$ is N. In some embodiments, two of $X^1$, $X^2$, $X^3$, and $X^4$ are N.

In some embodiments, the compound of Formula (Ib) has formula:

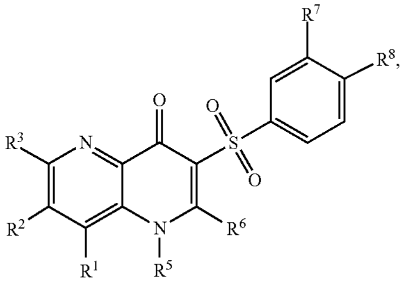

or a pharmaceutically acceptable salt thereof.

In some embodiments, the compound of Formula (Ib) has formula:

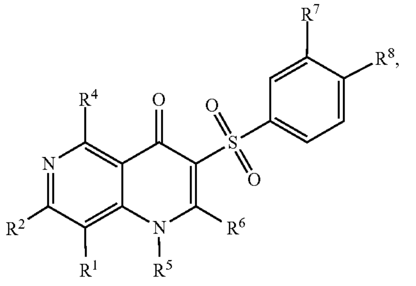

or a pharmaceutically acceptable salt thereof.

In some embodiments, the compound of Formula (Ib) has formula:

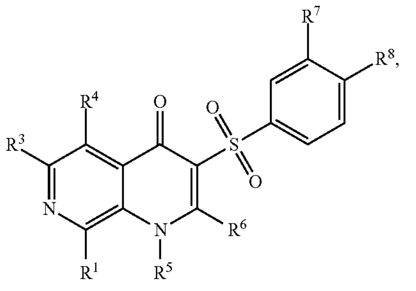

or a pharmaceutically acceptable salt thereof.

In some embodiments, the compound of Formula (Ib) has formula:

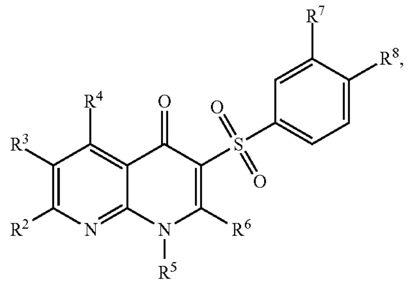

or a pharmaceutically acceptable salt thereof.

In some embodiments, $R^7$ and $R^8$ are each independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$.

In some embodiments, $R^7$ and $R^8$ are each independently selected from H, halo, and $C_{1-6}$ alkyl. In some embodiments, $R^7$ is H and $R^8$ is halo. In some embodiments, $R^7$ is halo and $R^8$ is H. In some embodiments, $R^7$ is $C_{1-6}$ alkyl and $R^8$ is halo. In some embodiments, $R^7$ is halo and $R^8$ is $C_{1-6}$ alkyl. In some embodiments, $R^7$ and $R^8$ are each halo. In some embodiments, $R^8$ is F.

In some embodiments, each of $R^1$, $R^2$, $R^3$, $R^4$, and $R^6$, if present in the compound of Formula (Ib), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

In some embodiments, each of $R^1$, $R^2$, $R^3$, $R^4$, and $R^6$, if present in the compound of Formula (Ib), is independently selected from H, halo, and $OR^{a1}$. In some embodiments, at least one of $R^1$, $R^2$, $R^3$, and $R^4$ is selected from halo and $C_{1-6}$ alkoxy. In some embodiments, $R^6$ is H. In some embodiments, $R^6$ is OH.

In some embodiments:

each of $R^1$, $R^2$, $R^3$, and $R^4$, if present in the compound of Formula (Ib), is independently selected from H, halo, and $C_{1-6}$ alkoxy; and $R^6$ is selected from H and OH.

In some embodiments, $R^5$ is selected from H, $C_{1-6}$ alkyl, and $Cy^1$, wherein said $C_{1-6}$ alkyl is optionally substituted with 1, 2, or 3 substituents independently selected from $R^{10}$.

In some embodiments, $R^5$ is selected from H and $C_{1-6}$ alkyl.

In some embodiments, $R^5$ is H.

In some embodiments, $R^5$ is $Cy^1$.

In some embodiments, $R^5$ is $C_{1-6}$ alkyl, optionally substituted with $R^{10}$.

In some embodiments, $R^{10}$ is selected from $Cy^1$, $OR^{a1}$, $C(O)NR^{c1}R^{d1}$, $C(O)OR^{a1}$, and $NR^{c1}R^{d1}$. In some embodiments, $R^{10}$ is $OR^{a1}$. In some embodiments, $R^{10}$ is $C(O)NR^{c1}R^{d1}$. In some embodiments, $R^{10}$ is $C(O)OR^{a1}$. In some embodiments, $R^{10}$ is $NR^{c1}R^{d1}$.

In some embodiments, each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$.

In some embodiments, each $R^{a1}$, $R^{b1}$, $R^{c1}$, and $R^{d1}$ is independently selected from H and $C_{1-6}$ alkyl.

In some embodiments:

$R^7$ and $R^8$ are each independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$;

each of $R^1$, $R^2$, $R^3$, $R^4$, and $R^6$, if present in the compound of Formula (Ib), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

$R^5$ is selected from H, $C_{1-6}$ alkyl, and $Cy^1$, wherein said $C_{1-6}$ alkyl is optionally substituted with 1, 2, or 3 substituents independently selected from $R^{10}$, and $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^g$.

In some embodiments:

$R^7$ and $R^8$ are each independently selected from H, halo, and $C_{1-6}$ alkyl;

each of $R^1$, $R^2$, $R^3$, and $R^4$, if present in the compound of Formula (Ib), is independently selected from H, halo, and $C_{1-6}$ alkoxy;

$R^6$ is selected from H and OH;

$R^5$ is selected from H and $C_{1-6}$ alkyl; and each $R^{a1}$, $R^{b1}$, $R^{c1}$, and $R^{d1}$ is independently selected from H and $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ib) is selected from any one of the compounds of Table 1d, or a pharmaceutically acceptable salt thereof.

In one general aspect, the present disclosure provides a compound selected from any one of the compounds of Table 1e, or a pharmaceutically acceptable salt thereof.

Formula (Ic):

In a general aspect, the present disclosure provides a compound of Formula (Ic):

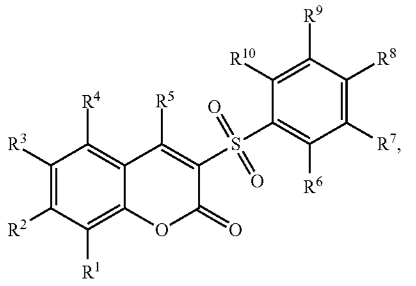

(Ic)

or a pharmaceutically acceptable salt thereof, wherein:

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^B$, each $R^B$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^B$.

In some embodiments, each $R^B$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$.

In some embodiments, each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)NR^{c1}R^{d1}$, and $C(O)OR^{a1}$.

In some embodiments, at least one of $R^1$, $R^2$, $R^3$, $R^4$, and $R^5$ is halo. In some embodiments, at least one of $R^1$, $R^2$, $R^3$, $R^4$, and $R^5$ is $OR^{a1}$. In some embodiments, at least one of $R^1$, $R^2$, $R^3$, $R^4$, and $R^5$ is $C_{1-6}$ alkoxy.

In some embodiments, each of $R^1$, $R^2$, $R^3$, $R^4$, and $R^5$ is independently selected from H, halo, and $C_{1-6}$ alkoxy.

In some embodiments, each of $R^6$, $R^7$, $R^8$, $R^9$, and $R^{10}$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^C$.

In some embodiments, each $R^C$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$.

In some embodiments, each of $R^6$, $R^7$, $R^8$, $R^9$, and $R^{10}$ is independently selected from H, halo, CN, and $C_{1-6}$ alkyl. In some embodiments, at least one of $R^6$, $R^7$, $R^8$, $R^9$, and $R^{10}$ is halo. In some embodiments, at least one of $R^6$, $R^7$, $R^8$, $R^9$, and $R^{10}$ is CN. In some embodiments, at least one of $R^6$, $R^7$, $R^8$, $R^9$, and $R^{10}$ is $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, each of which is optionally substituted with 1, 2, 3, 4, or 5 substituents independently selected from $R^g$.

In some embodiments, each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are each optionally substituted with 1, 2, 3, 4, or 5 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each $R^{a1}$, $R^{b1}$, $R^{c1}$, and $R^{d1}$ is independently selected from H and $C_{1-6}$ alkyl.

In some embodiments:

each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^B$;

each $R^B$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$;

each of $R^6$, $R^7$, $R^8$, $R^9$, and $R^{10}$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^C$;

each $R^C$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, each of which is optionally substituted with 1, 2, 3, 4, or 5 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each of $R^1$, $R^2$, $R^3$, $R^4$, and $R^5$ is independently selected from H, halo, and $C_{1-6}$ alkoxy; and each of $R^6$, $R^7$, $R^8$, $R^9$, and $R^{10}$ is independently selected from H, halo, CN, and $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ic) is selected from any one of the compound of Table 1b, or a pharmaceutically acceptable salt thereof.

Formula (Id):

In one general aspect, the present disclosure provides a compound of Formula (Id)

(Id)

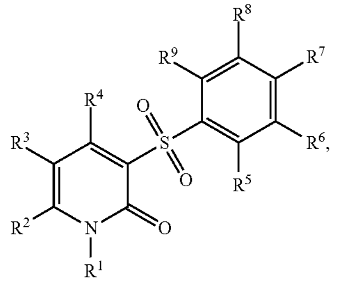

or a pharmaceutically acceptable salt thereof, wherein:

$R^1$ is selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^2$, $R^3$, and $R^4$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^B$;

each $R^B$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^5$, $R^6$, $R^7$, $R^8$, and $R^9$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is H. In some embodiments, $R^1$ is $C_{1-6}$ alkyl. In some embodiments, $R^1$ is selected from H, $C_{1-6}$ alkyl, and $C_{1-6}$ haloalkyl. In some embodiments, $R^1$ is selected from H and $C_{1-6}$ alkyl. In some embodiments, $R^1$ is $C_{1-6}$ alkyl, optionally substituted with 1, 2, or 3 substituents independently selected from $R^{10}$.

In some embodiments, each $R^{10}$ is independently selected from $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, and $S(O)_2NR^{c1}R^{d1}$. In some embodiments, each $R^{10}$ is independently selected from OH, $C_{1-6}$ alkoxy, $C(O)NH_2$, $C(O)OH$, $NH_2$, and $S(O)_2NH_2$.

In some embodiments, each of $R^2$, $R^3$, and $R^4$ is independently selected from H, halo, $C_{1-6}$ alkyl, $C_{1-6}$ haloalkyl, and $OR^{a1}$; wherein said $C_{1-6}$ alkyl is each optionally substituted with 1, 2, or 3 substituents independently selected from $R^B$.

In some embodiments, each $R^B$ is independently selected from $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, and $S(O)_2NR^{c1}R^{d1}$. In some embodiments, each $R^B$ is independently selected from OH, $C_{1-6}$ alkoxy, $C(O)NH_2$, $C(O)OH$, $NH_2$, and $S(O)_2NH_2$.

In some embodiments, each of $R^2$, $R^3$, and $R^4$ is independently selected from H and $C_{1-6}$ alkyl. In some embodiments, $R^3$ is H, and $R^2$ and $R^4$ are each $C_{1-6}$ alkyl.

In some embodiments, each of $R^5$, $R^6$, $R^7$, $R^8$, and $R^9$ is independently selected from H, halo, $C_{1-6}$ alkyl, $C_{1-6}$ haloalkyl, and $OR^{a1}$, wherein said $C_{1-6}$ alkyl is optionally substituted with 1, 2, or 3 substituents independently selected from $R^C$.

In some embodiments, each $R^C$ is independently selected from $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, and $S(O)_2NR^{c1}R^{d1}$. In some embodiments, each $R^C$ is independently selected from OH, $C_{1-6}$ alkoxy, $C(O)NH_2$, $C(O)OH$, $NH_2$, and $S(O)_2NH_2$. In some embodiments, each of $R^5$, $R^6$, $R^7$, $R^8$, and $R^9$ is independently selected from H and halo. In some embodiments, at least one of $R^5$, $R^6$, $R^7$, $R^8$, and $R^9$ is halo.

In some embodiments, each of $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, each of which is optionally substituted with 1, 2, 3, 4, or 5 substituents independently selected from $R^g$.

In some embodiments, each of $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are each optionally substituted with 1, 2, 3, 4, or 5 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each $R^{a1}$, $R^{b1}$, $R^{c1}$, and $R^{d1}$ is independently selected from H and $C_{1-6}$ alkyl.

In some embodiments:

$R^1$ is H;

each of $R^2$, $R^3$, and $R^4$ is independently selected from H and $C_{1-6}$ alkyl; and each of $R^5$, $R^6$, $R^7$, $R^8$, and $R^9$ is independently selected from H and halo.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Id) is selected from any one of the compounds of Table 1c, or a pharmaceutically acceptable salt thereof.

Formula (Ie)

In one general aspect, the present disclosure provides a compound of Formula (Ie):

(Ie)

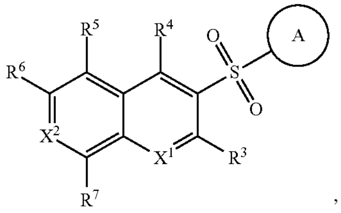

or a pharmaceutically acceptable salt thereof, wherein:

$X^1$ is selected from N and $CR^1$;

$X^2$ is selected from N and $CR^2$;

each $R^1$, $R^2$, $R^3$, $R^4$, $R^5$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^8$, each $R^8$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^7$ is selected from $OR^{a2}$ and $NR^{c2}R^{d2}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (Ie) has formula:

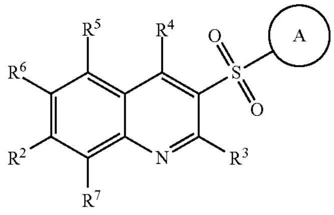

or a pharmaceutically acceptable salt thereof.

In some embodiments, the compound of Formula (Ie) has formula:

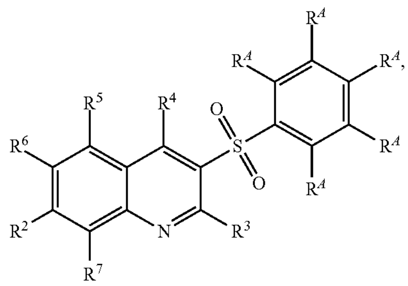

or a pharmaceutically acceptable salt thereof.

In some embodiments, the compound of Formula (Ie) has formula:

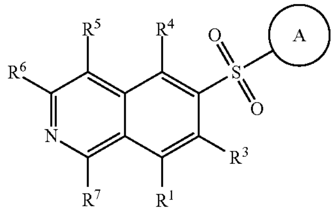

or a pharmaceutically acceptable salt thereof.

In some embodiments, the compound of Formula (Ie) has formula:

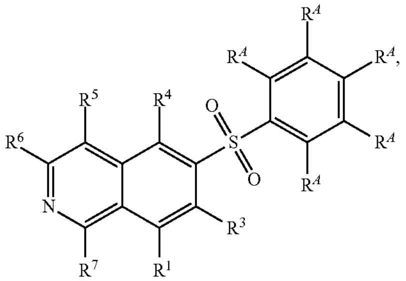

or a pharmaceutically acceptable salt thereof.

In some embodiments, the compound of Formula (Ie) has formula:

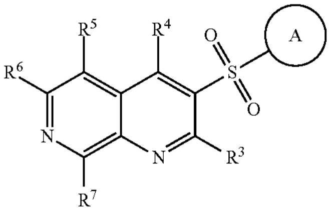

, or a pharmaceutically acceptable salt thereof.

In some embodiments, the compound of Formula (Ie) has formula:

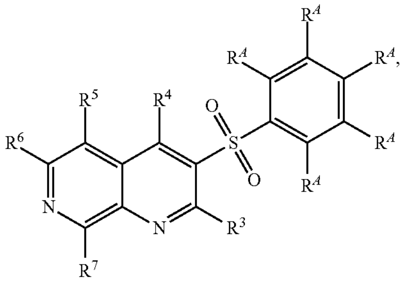

or a pharmaceutically acceptable salt thereof.

In some embodiments, each of $R^1$, $R^2$, $R^3$, $R^4$, and $R^6$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; wherein said $C_{1-6}$ alkyl is optionally substituted with 1, 2, or 3 substituents independently selected from $R^8$.

In some embodiments, each $R^8$ is independently selected from CN, $NO_2$, OH, $C_{1-6}$ alkoxy, $C(O)NH_2$, C(O)OH, $NH_2$, and $S(O)_2NH_2$.

In some embodiments, each of $R^1$, $R^2$, $R^3$, $R^4$, and $R^6$, if present in the compound of Formula (Ia), is independently selected from H, halo, CN, OH, $C_{1-6}$ alkyl, and $C_{1-6}$ alkoxy. In some embodiments, each of $R^1$, $R^2$, $R^3$, $R^4$, and $R^6$, if present in the compound of Formula (Ia), is independently selected from H, halo, $C_{1-6}$ alkyl, and $C_{1-6}$ alkoxy. In some embodiments, each of $R^1$, $R^2$, $R^3$, $R^4$, and $R^6$, if present in the compound of Formula (Ia), is independently selected from H and $C_{1-6}$ alkyl.

In some embodiments, $R^7$ is $OR^{a2}$. In some embodiments, $R^7$ is OH. In some embodiments, $R^7$ is $C_{1-6}$ alkoxy. In some embodiments, $R^7$ is $NR^{c2}R^{d2}$. In some embodiments, $R^7$ is amino. In some embodiments, $R^7$ is $C_{1-6}$ alkylamino. In some embodiments, $R^7$ is di($C_{1-6}$ alkyl)amino.

In some embodiments, ring A is selected from $C_{6-10}$ aryl and 5-10 membered heteroaryl, each of which is optionally substituted with 1-6 substituents independently selected from $R^A$.

In some embodiments, ring A is $C_{6-10}$ aryl, substituted with 1-5 substituents independently selected from $R^A$. In some embodiments, ring A is phenyl, optionally substituted with 1-5 substituents independently selected from $R^A$. In some embodiments, ring A is naphthyl, optionally substituted with 1-5 substituents independently selected from $R^A$.

In some embodiments, ring A is 5-10 membered heteroaryl, substituted with 1-6 substituents independently selected from $R^A$. In some embodiments, ring A is selected from pyridin-2-yl, pyridin-3-yl, pyridin-4-yl, thiophen-2-yl, thiophen-3-yl, pyrazol-3-yl, pyrazlol-4-yl, pyrazol-5-yl, quinolin-6-yl, quinolin-7-yl, thiazolyl, 1,3,4-thiadiazolyl, and quinoxaline-6-yl, each of which is optionally substituted with 1-6 substituents independently selected from $R^A$.

In some embodiments, ring A is selected from any one of the following moieties:

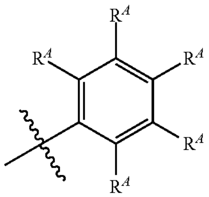
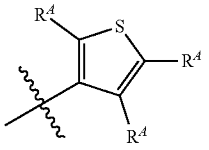
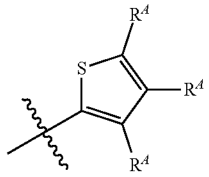
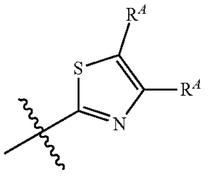
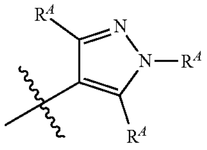
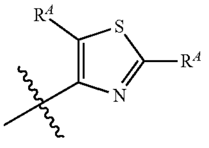
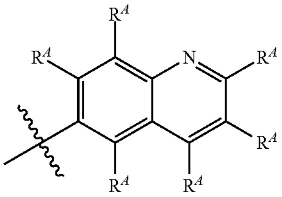
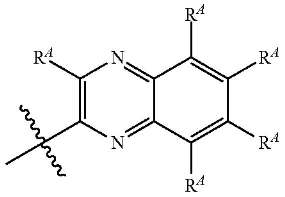
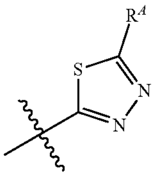
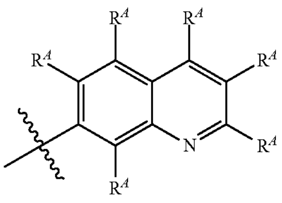

In some embodiments, the compound of Formula (Ie) has formula:

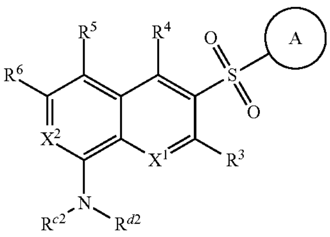

, or a pharmaceutically acceptable salt thereof.

In some embodiments, the compound of Formula (Ie) has formula:

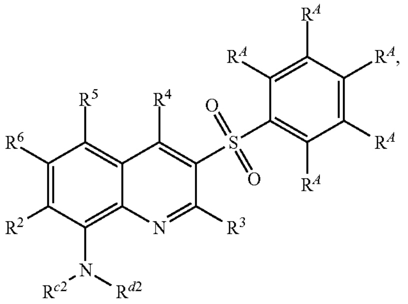

or a pharmaceutically acceptable salt thereof.

In some embodiments, the compound of Formula (Ie) has formula:

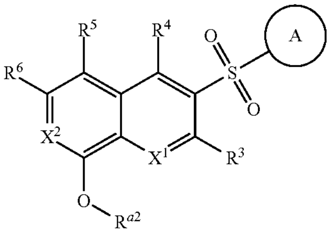

, or a pharmaceutically acceptable salt thereof.

In some embodiments, the compound of Formula (Ie) has formula:

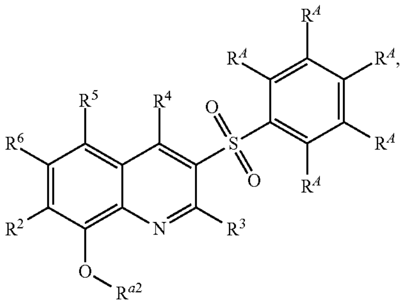

or a pharmaceutically acceptable salt thereof.

In some embodiments, each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$.

In some embodiments, each $R^9$ is independently selected from CN, $NO_2$, OH, $C_{1-6}$ alkoxy, $C(O)NH_2$, C(O)OH, $NH_2$, and $S(O)_2NH_2$.

In some embodiments, each $R^A$ is independently selected from H, halo, CN, $C_{1-6}$ alkyl, and $C_{1-6}$ alkoxy. In some embodiments, $R^A$ is H. In some embodiments, at least one $R^A$ is halo. In some embodiments, at least one $R^A$ is CN. In some embodiments, at least one $R^A$ is $C_{1-6}$ alkyl. In some embodiments, at least one $R^A$ is $C_{1-6}$ alkoxy.

In some embodiments, each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, each $R^{a1}$, $R^{a2}$, $R^{b1}$, $R^{c1}$, $R^{c2}$, $R^{d1}$, and $R^{d2}$ is independently selected from H and $C_{1-6}$ alkyl. In some embodiments, $R^{c2}$ is H and $R^{d2}$ is $C_{1-6}$ alkyl. In some embodiments, $R^{c2}$ and $R^{d2}$ are both H. In some embodiments, $R^{c2}$ and $R^{d2}$ are both $C_{1-6}$ alkyl.

In some embodiments:

$R^1$, $R^2$, $R^3$, $R^4$, and $R^6$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; wherein said $C_{1-6}$ alkyl is optionally substituted with 1, 2, or 3 substituents independently selected from $R^8$;

each $R^8$ is independently selected from CN, $NO_2$, OH, $C_{1-6}$ alkoxy, $C(O)NH_2$, C(O)OH, $NH_2$, and $S(O)_2NH_2$;

ring A is selected from $C_{6-10}$ aryl and 5-10 membered heteroaryl, each of which is optionally substituted with 1-6 substituents independently selected from $R^A$;

each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$ and $S(O)_2NR^{c1}R^{d1}$; wherein said $C_{1-6}$ alkyl is optionally substituted with 1, 2, or 3 substituents independently selected from $R^9$;

each $R^9$ is independently selected from CN, $NO_2$, OH, $C_{1-6}$ alkoxy, $C(O)NH_2$, C(O)OH, $NH_2$, and $S(O)_2NH_2$;

each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments:

each of $R^1$, $R^2$, $R^3$, $R^4$, and $R^6$, if present in the compound of Formula (Ia), is independently selected from H, halo, CN, OH, $C_{1-6}$ alkyl, and $C_{1-6}$ alkoxy;

ring A is selected from $C_{6-10}$ aryl and 5-10 membered heteroaryl, each of which is optionally substituted with 1-6 substituents independently selected from $R^A$;

each $R^A$ is independently selected from H, halo, CN, $C_{1-6}$ alkyl, and $C_{1-6}$ alkoxy; and each $R^{a1}$, $R^{a2}$, $R^{b1}$, $R^{c1}$, $R^{c2}$, $R^{d1}$, and $R^{d2}$ is independently selected from H and $C_{1-6}$ alkyl.

In some embodiments, each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (Ie) is selected from any one of the compounds of Table If, or a pharmaceutically acceptable salt thereof.

Formula (If)

In one general aspect, the present disclosure provides a compound of Formula (If):

(If)

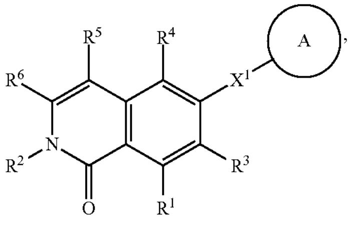

or a pharmaceutically acceptable salt thereof, wherein:

$X^1$ is selected from S, S(O), and $S(O)_2$;

$R^1$, $R^3$, $R^4$, $R^5$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

$R^2$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^4$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is S.

In some embodiments, $X^1$ is S(O).

In some embodiments, $X^1$ is $S(O)_2$.

In some embodiments, $R^1$, $R^3$, $R^4$, $R^5$, and $R^6$ is independently selected from H, halo, OH, CN, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^1$, $R^3$, $R^4$, $R^5$, and $R^6$ are each H.

In some embodiments, $R^2$ is selected from H, $C_{1-6}$ alkyl, and $C_{1-6}$ haloalkyl.

In some embodiments, ring A is $C_{6-10}$ aryl, optionally substituted with 1 or 2 substituents independently selected from halo and $C_{1-6}$ alkyl.

In some embodiments:

$R^1$, $R^3$, $R^4$, $R^5$, and $R^6$ is independently selected from H, halo, OH, CN, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$R^2$ is selected from H, $C_{1-6}$ alkyl, and $C_{1-6}$ haloalkyl; and ring A is $C_{6-10}$ aryl, optionally substituted with 1 or 2 substituents independently selected from halo and $C_{1-6}$ alkyl.

In some embodiments, the compound of Formula (If) is selected from any one of the compound of Table 1g, or a pharmaceutically acceptable salt thereof.

Formula (Ig)

In one general aspect, the present disclosure provides a compound of Formula (Ig):

(Ig)

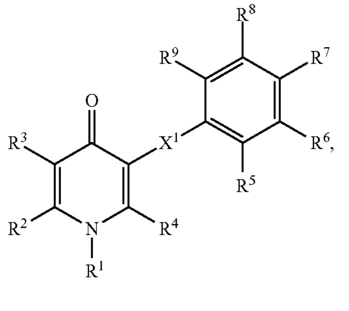

or a pharmaceutically acceptable salt thereof, wherein:

$X^1$ is selected from S, S(O), and $S(O)_2$;

$R^1$ is selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^2$, $R^3$, and $R^4$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^B$;

each $R^B$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

each of $R^5$, $R^6$, $R^7$, $R^8$, and $R^9$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from S(O) and $S(O)_2$.

In some embodiments, $R^1$ is H.

In some embodiments, each of $R^2$, $R^3$, and $R^4$ is independently selected from H and $C_{1-6}$ alkyl.

In some embodiments, each of $R^5$, $R^6$, $R^7$, $R^8$, and $R^9$ is independently selected from H, halo, and $C_{1-6}$ alkyl.

In some embodiments:

$X^1$ is S(O) or $S(O)_2$;

$R^1$ is H;

each of $R^2$, $R^3$, and $R^4$ is independently selected from H and $C_{1-6}$ alkyl; and each of $R^5$, $R^6$, $R^7$, $R^8$, and $R^9$ is independently selected from H, $C_{1-6}$ alkyl and halo.

In some embodiments, the compound of Formula (Ig) is selected from any one of the compounds of Table 1h, or a pharmaceutically acceptable salt thereof.

Formula (IIa)

In one general aspect, the present disclosure provides a compound of Formula (IIa):

(IIa)

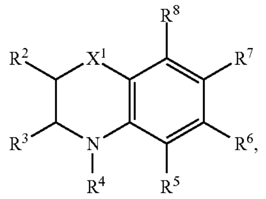

or a pharmaceutically acceptable salt thereof, wherein:

$X^1$ is selected from O and $NR^1$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^3$ is selected from H, $C_{1-6}$ alkyl, $C_{1-6}$ haloalkyl, $C_{2-6}$ alkenyl, $C_{2-6}$ alkynyl, oxo, wherein said $C_{1-6}$ alkyl, $C_{2-6}$ alkenyl, and $C_{2-6}$ alkynyl are each optionally substituted with 1, 2, or 3 substituents independently selected from $R^9$;

$R^1$ and $R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^5$ and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, $S(O)_2NR^{c1}R^{d1}$; and a group of formula (i):

(i)

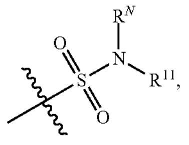

wherein said $C_{1-6}$ alkyl, $C_{2-6}$ alkenyl, and $C_{2-6}$ alkynyl are each optionally substituted with 1, 2, or 3 substituents independently selected from $R^9$;

provided that at least one of $R^7$ and $R^8$ is a group of formula (i);

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^8$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (IIa) has formula:

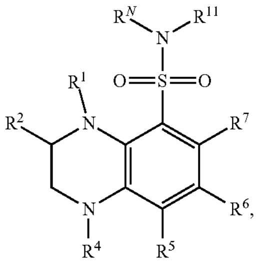

or a pharmaceutically acceptable salt thereof.

In some embodiments, the compound of Formula (IIa) has formula:

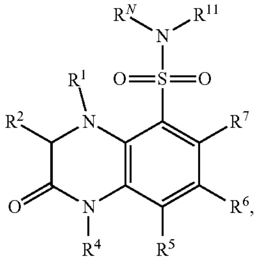

or a pharmaceutically acceptable salt thereof.

In some embodiments, the compound of Formula (IIa) has formula:

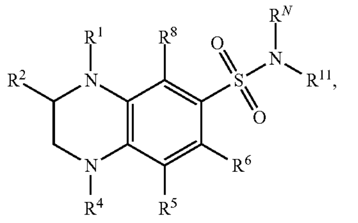

or a pharmaceutically acceptable salt thereof.

In some embodiments, the compound of Formula (IIa) has formula:

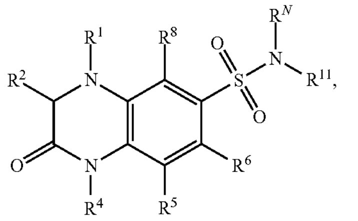

or a pharmaceutically acceptable salt thereof.

In some embodiments:

$R^2$ is selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$.

In some embodiments:

$R^2$ is selected from H and $C_{1-6}$ alkyl;

$R^1$ is selected from $C_{1-6}$ alkyl, $C(O)R^{b1}$, and $C(O)NR^{c1}R^{d1}$.

In some embodiments, the compound of Formula (Ia) has formula:

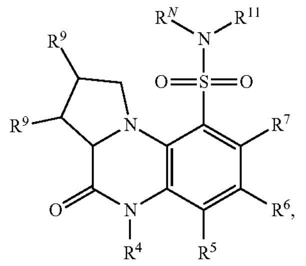

or a pharmaceutically acceptable salt thereof.

In some embodiments, the compound of Formula (IIa) has formula:

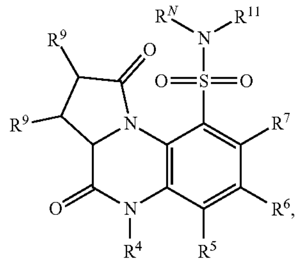

or a pharmaceutically acceptable salt thereof.

In some embodiments, the compound of Formula (Ia) has formula:

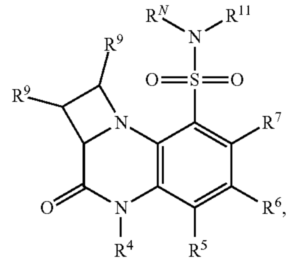

or a pharmaceutically acceptable salt thereof.

In some embodiments, the compound of Formula (IIa) has formula:

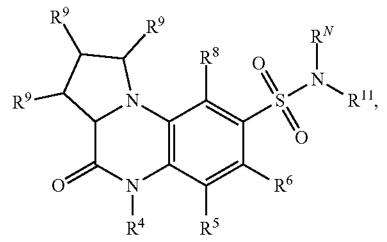

or a pharmaceutically acceptable salt thereof.

In some embodiments, the compound of Formula (Ia) has formula:

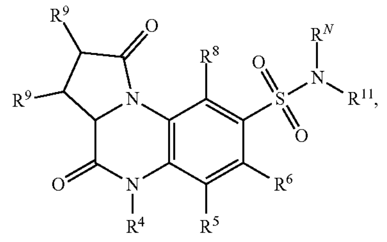

or a pharmaceutically acceptable salt thereof.

In some embodiments, the compound of Formula (Ia) has formula:

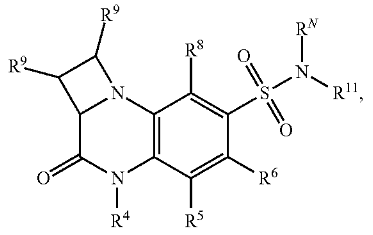

or a pharmaceutically acceptable salt thereof.

In some embodiments, the compound of Formula (IIa) has formula:

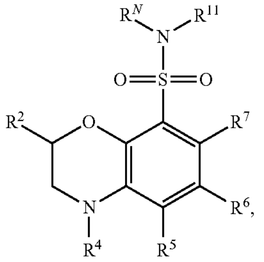

or a pharmaceutically acceptable salt thereof.

In some embodiments, the compound of Formula (Ia) has formula:

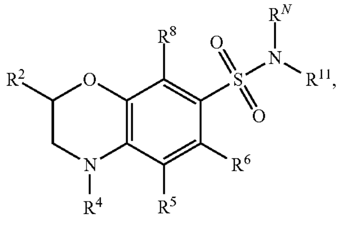

or a pharmaceutically acceptable salt thereof.

In some embodiments, the compound of Formula (Ia) has formula:

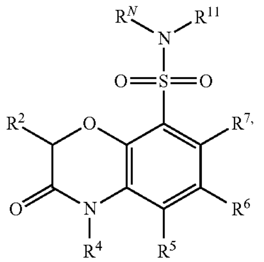

or a pharmaceutically acceptable salt thereof.

In some embodiments, the compound of Formula (IIa) has formula:

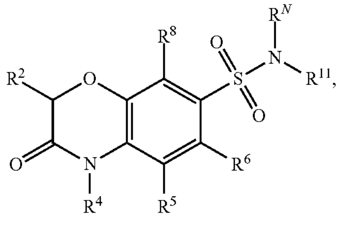

or a pharmaceutically acceptable salt thereof.

In some embodiments, $R^2$ is selected from H and $C_{1-6}$ alkyl. In some embodiments, $R^2$ is H. In some embodiments, $R^2$ is $C_{1-6}$ alkyl.

In some embodiments, $R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$. In some embodiments, $R^4$ is H. In some embodiments, $R^4$ is $C_{1-6}$ alkyl.

In some embodiments, $R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

In some embodiments, $R^5$ and $R^6$ are each independently selected from H, halo, $C_{1-6}$ alkyl, and $S(O)_2R^{b1}$, wherein said $C_{1-6}$ alkyl is optionally substituted with $R^9$.

In some embodiments, $R^5$ is H and $R^6$ is $C_{1-6}$ alkyl, optionally substituted with $NR^{c1}R^{d1}$. In some embodiments, $R^5$ is H and $R^6$ is halo. In some embodiments, $R^5$ is Hand $R^6$ is $S(O)_2R^{b1}$.

In some embodiments, $R^7$ is selected from H and $C_{1-6}$ alkyl (and $R^8$ is a moiety of formula (i)). In some embodiments, $R^8$ is selected from H and $C_{1-6}$ alkyl (and $R^7$ is a moiety of formula (i)).

In some embodiments, $R^N$ is selected from H and $C_{1-6}$ alkyl. In some embodiments, $R^N$ is H. In some embodiments, $R^N$ is $C_{1-6}$ alkyl.

In some embodiments, $R^{11}$ is ring A.

In some embodiments, $R^{11}$ is $C_{1-6}$ alkyl, optionally substituted with ring A.

In some embodiments, $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$.

In some embodiments, ring A is selected from any one of the following moieties:

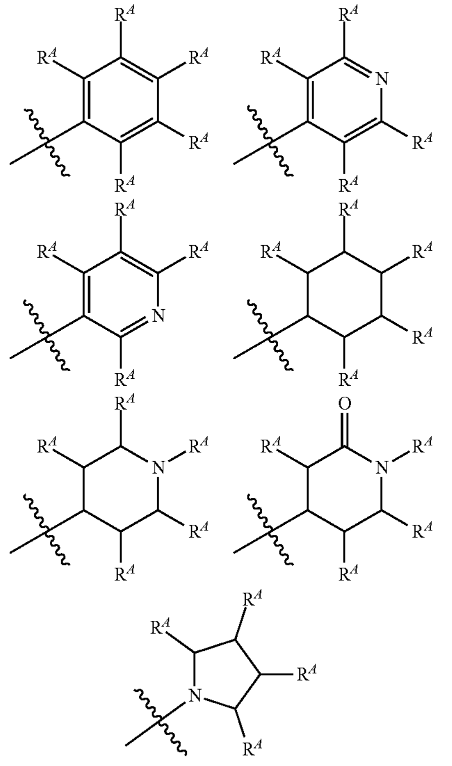

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$.

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with 1, 2, or 3 substituents independently selected from $R^{11}$.

In some embodiments, each $R^{11}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$.

In some embodiments, each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with $C(O)OR^{a1}$.

In some embodiments, each $R^9$ is independently selected from H, $C_{1-6}$ alkyl, $C_{1-6}$ haloalkyl, halo, CN, OH, $C_{1-6}$ alkoxy, carboxy, amino, $C(O)NH_2$, $C_{1-6}$ alkylamino, di($C_{1-6}$ alkyl)amino, and $C_{1-6}$ haloalkoxy. In some embodiments, each $R^9$ is independently selected from OH, $C_{1-6}$ alkoxy, carboxy, $C(O)NH_2$, amino, $C_{1-6}$ alkylamino, and di($C_{1-6}$ alkyl)amino.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, $C(O)NH_2$, and carboxy.

In some embodiments, each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^8$; and In some embodiments, each $R^g$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

In some embodiments:

$R^2$ is selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^3$ is selected from H and oxo;

$R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$;

$R^5$ and $R^6$ are each independently selected from H, halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{11}$;

$R^{11}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$; and each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments:

$R^2$ is selected from H and $C_{1-6}$ alkyl;

$R^1$ is selected from $C_{1-6}$ alkyl, $C(O)R^{b1}$, and $C(O)NR^{c1}R^{d1}$ $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^3$ is selected from H and oxo;

$R^4$ is H;

$R^5$ and $R^6$ are each independently selected from H, halo, $C_{1-6}$ alkyl, and $S(O)_2R^{b1}$, wherein said $C_{1-6}$ alkyl is optionally substituted with $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with $C(O)OR^{a1}$;

each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^8$; and each $R^8$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIa) is selected from any one of the compounds of Table 2a, Table 2c, Table 2c-2, Table 2d, Table 2d-2, Table 2e, or Table 16, or a pharmaceutically acceptable salt thereof.

In some embodiments, the compound of Formula (IIa) is selected from any one of the compounds of Table 2a, Table 2c, Table 2d, or Table 2e, or a pharmaceutically acceptable salt thereof. In some embodiments, the compound of Formula (IIa) is selected from any one of the compounds of Table 2a, or a pharmaceutically acceptable salt thereof. In some embodiments, the compound of Formula (IIa) is selected from any one of the compounds of Table 2c, or a pharmaceutically acceptable salt thereof. In some embodiments, the compound of Formula (IIa) is selected from any one of the compounds of Table 2d, or a pharmaceutically acceptable salt thereof. In some embodiments, the compound of Formula (IIa) is selected from any one of the compounds of Table 2e, or a pharmaceutically acceptable salt thereof. In some embodiments, the compound of Formula (IIa) is selected from any one of the compounds of Table 2c-2, or a pharmaceutically acceptable salt thereof. In some embodiments, the compound of Formula (IIa) is selected from any one of the compounds of Table 2d-2, or a pharmaceutically acceptable salt thereof. In some embodiments, the compound of Formula (IIa) is selected from any one of the compounds of Table 16, or a pharmaceutically acceptable salt thereof. In some embodiments, the present disclosure provides a compound selected from any one of the compounds of Table 16, or a pharmaceutically acceptable salt thereof.

In some embodiments, the compound of Formula (IIa) has Formula (IIb), or a pharmaceutically acceptable salt thereof.

In some embodiments, the compound of Formula (IIa) has Formula (IIc), or a pharmaceutically acceptable salt thereof.

In some embodiments, the compound of Formula (IIa) has Formula (IId), or a pharmaceutically acceptable salt thereof.

Formula (IIb)

In one general aspect, the present disclosure provides a compound of Formula (IIb):

(IIb)

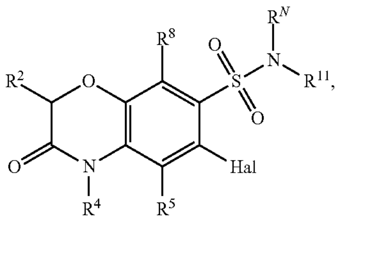

or a pharmaceutically acceptable salt thereof, wherein:

Hal is a halogen, and $R^2$, $R^4$, $R^5$, $R^8$, $R^N$, and $R^{11}$ are as described herein for Formula (IIa).

In some embodiments:

Hal is a halogen;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ is selected from H, $C_{1-6}$ alkyl, $C_{1-6}$ haloalkyl, $C_{2-6}$ alkenyl, $C_{2-6}$ alkynyl, C(O)$R^{b1}$, C(O)N$R^{c1}R^{d1}$, C(O)O$R^{a1}$, S(O)$_2R^{b1}$, and S(O)$_2$N$R^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^4$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, O$R^{a1}$, S$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, O$R^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^2$ is H or $C_{1-6}$ alkyl.

In some embodiments, $R^4$ is H or $C_{1-6}$ alkyl.

In some embodiments, $R^5$ is H or $C_{1-6}$ alkyl.

In some embodiments, $R^8$ is H or $C_{1-6}$ alkyl.

In some embodiments, $R^4$, $R^5$, and $R^8$ are each H.

In some embodiments, $R^N$ is H.

In some embodiments, $R^N$ and $R^{11}$, together with the N atom to which they are attached, form a ring selected from pyrrolidinyl, morpholinyl, piperidinyl, and piperazinyl, each of which is optionally substituted with 1, 2, or 3 substituents independently selected from $R^9$.

In some embodiments, $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$.

In some embodiments, $R^{11}$ is ring A. In some embodiments, $R^{11}$ is $C_{1-6}$ alkyl, optionally substituted with ring A.

In some embodiments, ring A is selected from $C_{6-10}$ aryl and $C_{3-10}$ cycloalkyl, each of which is optionally substituted with 1-10 substituents independently selected from $R^A$.

In some embodiments, ring A is $C_{6-10}$ aryl, optionally substituted with 1-10 substituents independently selected from $R^A$.

In some embodiments, ring A is $C_{3-10}$ cycloalkyl, optionally substituted with 1-10 substituents independently selected from $R^A$.

In some embodiments, each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{11}$.

In some embodiments, each $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{11}$.

In some embodiments:

$R^2$ is selected from H and $C_{1-6}$ alkyl;

$R^4$, $R^5$, and $R^8$ are each H;

$R^N$ is H; or $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$; ring A is selected from $C_{6-10}$ aryl and $C_{3-10}$ cycloalkyl, each of which is optionally substituted with 1-10 substituents independently selected from $R^A$; and each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{11}$.

In some embodiments, $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{11}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIb) is selected from any one of the compounds of Table 2c or Table 2c-2, or a pharmaceutically acceptable salt thereof.

In some embodiments, the compound of Formula (IIb) is selected from any one of the compounds of Table 2c, or a pharmaceutically acceptable salt thereof. In some embodiments, the compound of Formula (IIb) is selected from any one of the compounds of Table 2c-2, or a pharmaceutically acceptable salt thereof.

Formula (IIc)

In one general aspect, the present disclosure provides a compound of Formula (IIc):

(IIc)

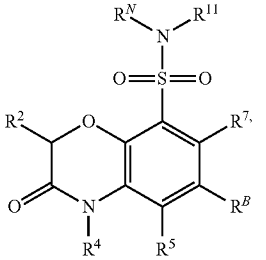

or a pharmaceutically acceptable salt thereof, wherein:

$R^B$ is selected from halogen and $S(O)_2R^{b1}$; and $R^2$, $R^4$, $R^5$, $R^7$, $R^N$, and $R^{11}$ are as described herein for Formula (IIa).

In some embodiments:

$R^B$ is selected from halogen and $S(O)_2R^{b1}$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and RY, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^4$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^8$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen (e.g., $C_1$, F, or Br). In some embodiments, $R^B$ is $C_1$. In some embodiments, $R^B$ is $S(O)_2R^{b1}$ (e.g., $R^{b1}$ is $C_{1-6}$ alkyl). In some embodiments, $R^B$ is ethylsulfonyl.

In some embodiments, $R^2$ is selected H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, $R^N$ and $R^{11}$, together with the N atom to which they are attached, form a ring selected from morpholinyl and piperazinyl, each of which is optionally substituted with 1, 2, or 3 substituents independently selected from $R^9$.

In some embodiments, $R^{11}$ is ring A. In some embodiments, $R^{11}$ is $C_{1-6}$ alkyl, optionally substituted with ring A.

In some embodiments, ring A is selected from $C_{6-10}$ aryl and $C_{3-10}$ cycloalkyl, optionally substituted with 1-10 substituents independently selected from $R^A$.

In some embodiments, ring A is $C_{6-10}$ aryl, optionally substituted with 1-10 substituents independently selected from $R^A$.

In some embodiments, ring A is $C_{3-10}$ cycloalkyl, optionally substituted with 1-10 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{11}$.

In some embodiments:

$R^2$ is selected H and $C_{1-6}$ alkyl;

$R^4$ is H;

$R^5$ is H;

$R^7$ is selected H and $C_{1-6}$ alkyl;

$R^N$ is H; or $R^N$ and $R^{11}$, together with the N atom to which they are attached, form a ring selected from morpholinyl and piperazinyl, each of which is optionally substituted with 1, 2, or 3 substituents independently selected from $R^9$;

ring A is selected from $C_{6-10}$ aryl and $C_{3-10}$ cycloalkyl, optionally substituted with 1-10 substituents independently selected from $R^A$; and each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{11}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIc) is selected from any one of the compounds of Table 2d or Table 2d-2, or a pharmaceutically acceptable salt thereof.

In some embodiments, the compound of Formula (IIc) is selected from any one of the compounds of Table 2d, or a pharmaceutically acceptable salt thereof. In some embodiments, the compound of Formula (IIc) is selected from any one of the compounds of Table 2d-2, or a pharmaceutically acceptable salt thereof.

Formula (IId)

In one general aspect, the present disclosure provides a compound of Formula (IId):

(IId)

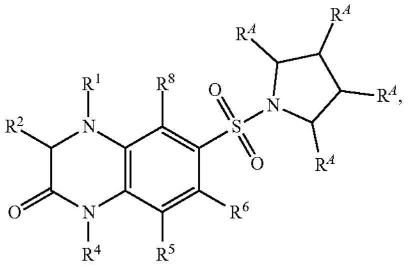

or a pharmaceutically acceptable salt thereof, wherein $R^1$, $R^2$, $R^4$, $R^5$, $R^6$, $R^8$, and $R^A$ are as described herein for Formula (IIa).

In some embodiments:

$R^1$ and $R^4$ are each independently selected from H, $C_{1-6}$ alkyl, $C_{1-6}$ haloalkyl, $C_{2-6}$ alkenyl, $C_{2-6}$ alkynyl, C(O)$R^{b1}$, C(O)$NR^{c1}R^{d1}$, C(O)$OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^5$, $R^6$, and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$; each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, C(O)$R^{b1}$, C(O)$NR^{c1}R^{d1}$, C(O)$OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, C(O)$R^{b1}$, C(O)$NR^{c1}R^{d1}$, C(O)$OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^8$; and each $R^8$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^2$ is selected from H and $C_{1-6}$ alkyl.

In some embodiments, $R^4$ is H.

In some embodiments, $R^1$ is selected from H, $C_{1-6}$ alkyl, C(O)$R^{b1}$, and C(O)$NR^{c1}R^{d1}$, wherein said $C_{1-6}$ alkyl is optionally substituted with 1, 2, or 3 substituents independently selected from $R^9$.

In some embodiments, each $R^9$ is independently selected from OH, $C_{1-6}$ alkoxy, carboxy, C(O)$NH_2$, amino, $C_{1-6}$ alkylamino, and di($C_{1-6}$ alkyl)amino.

In some embodiments, $R^5$, $R^6$, and $R^8$ are each independently selected from H, halo, $C_{1-6}$ alkyl, $C_{1-6}$ haloalkyl, and $C_{1-6}$ alkoxy. In some embodiments, $R^5$, $R^6$, and $R^8$ are each H.

In some embodiments, each $R^A$ is independently selected from H, halo, CN, $C_{1-6}$ alkyl, $C_{1-6}$ haloalkyl, $OR^{a1}$, $SR^{a1}$, C(O)$R^{b1}$, C(O)$OR^{a1}$, $NR^{c1}R^{d1}$, and $NR^{c1}C(O)R^{b1}$, wherein said $C_{1-6}$ alkyl is optionally substituted with 1, 2, or 3 substituents independently selected from $R^{11}$.

In some embodiments, each $R^A$ is independently selected from H, $C_{1-6}$ alkyl, $C_{1-6}$ haloalkyl, halo, CN, OH, $C_{1-6}$ alkoxy, carboxy, amino, C(O)$NH_2$, $C_{1-6}$ alkylamino, di($C_{1-6}$ alkyl)amino, and $C_{1-6}$ haloalkoxy. In some embodiments, each $R^A$ is independently selected from H, $C_{1-6}$ alkyl, $C_{1-6}$ haloalkyl, halo, and $C_{1-6}$ alkoxy. In some embodiments, each $R^A$ is independently selected from H and $C_{1-6}$ alkyl. In some embodiments, each $R^A$ is H.

In some embodiments:

$R^2$ is selected from H and $C_{1-6}$ alkyl;

$R^4$ is H;

$R^5$, $R^6$, and $R^8$ are each H;

$R^1$ is selected from H, $C_{1-6}$ alkyl, C(O)$R^{b1}$, and C(O)$NR^{c1}R^{d1}$, wherein said $C_{1-6}$ alkyl is optionally substituted with 1, 2, or 3 substituents independently selected from $R^9$;

each $R^9$ is independently selected from OH, $C_{1-6}$ alkoxy, carboxy, C(O)$NH_2$, amino, $C_{1-6}$ alkylamino, and di($C_{1-6}$ alkyl)amino; and each $R^A$ is H.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IId) is selected from any one of the compounds of Table 2e, or a pharmaceutically acceptable salt thereof.

Formula (IIe)

In one general aspect, the present disclosure provides a compound of Formula (IIe):

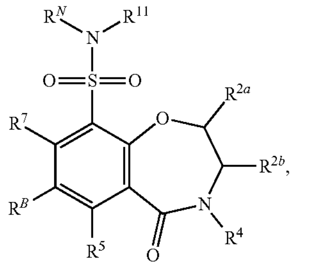

(IIe)

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is $S(O)_2R^{b1}$.

In some embodiments, $R^{2a}$ and $R^{2b}$ are each independently selected from H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{11}$.

In some embodiments:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (IIe) is selected from any one of the compounds of Table 2f, or a pharmaceutically acceptable salt thereof.

Formula (IIf)

In one general aspect, the present disclosure provides a compound of Formula (IIf):

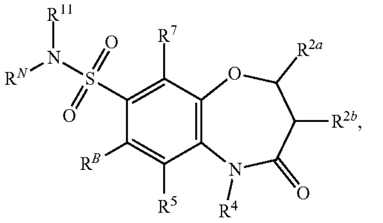

(IIf)

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen.

In some embodiments, $R^B$ is $S(O)_2R^{b1}$.

In some embodiments, $R^{2a}$ and $R^{2b}$ are each independently selected from H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{11}$.

In some embodiments:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (IIf) is selected from any one of the compounds of Table 2g, or a pharmaceutically acceptable salt thereof.

Formula (IIg)

In one general aspect, the present disclosure provides a compound of Formula (IIg):

(IIg)

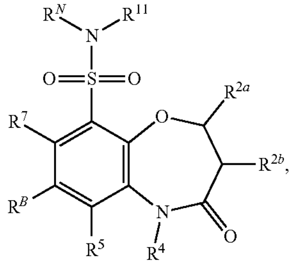

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^B$ is a halogen.

In some embodiments, $R^B$ is $S(O)_2R^{b1}$.

In some embodiments, $R^{2a}$ and $R^{2b}$ are each independently selected from H and $C_{1-6}$ alkyl.

In some embodiments, $R^4$ is H.

In some embodiments, $R^5$ is H.

In some embodiments, $R^7$ is selected H and $C_{1-6}$ alkyl.

In some embodiments, $R^N$ is H.

In some embodiments, ring A is $C_{6-10}$ aryl, optionally substituted with 1-5 substituents independently selected from $R^A$.

In some embodiments, each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{11}$.

In some embodiments:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$, and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

In some embodiments, the compound of Formula (IIg) is selected from any one of the compounds of Table 2h, or a pharmaceutically acceptable salt thereof.

Formula (IIIa)

In one general aspect, the present disclosure provides a compound of Formula (IIIa):

(IIIa)

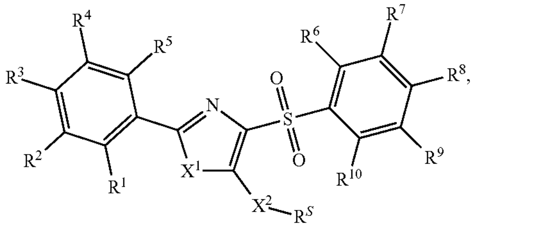

or a pharmaceutically acceptable salt thereof, wherein:

$X^1$ is selected from O, S, and NRN, $R^N$ is selected from H and $C_{1-6}$ alkyl;

$X^2$ is selected from S, S(O), and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

or any two adjacent $R^1$, $R^2$, $R^3$, $R^4$, and $R^5$ groups, together with the carbon atoms to which they are attached, form a $C_{6-10}$ aryl ring, which is optionally substituted with 1, 2, or 3 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments:

$X^1$ is selected from O, S, and NRN;

$R^N$ is selected from H and $C_{1-6}$ alkyl;

$X^2$ is selected from S, S(O), and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is O. In some embodiments, $X^1$ is S. In some embodiments, $X^1$ is NRN. In some embodiments, $X^2$ is S. In some embodiments, $X^2$ is S(O). In some embodiments, $X^2$ is $S(O)_2$.

In some embodiments, $X^1$ is O and $X^2$ is S. In some embodiments, $X^1$ is O and $X^2$ is S(O). In some embodiments, $X^1$ is O and $X^2$ is $S(O)_2$. In some embodiments, $X^1$ is S and $X^2$ is S. In some embodiments, $X^1$ is S and $X^2$ is S(O). In some embodiments, $X^1$ is S and $X^2$ is $S(O)_2$. In some embodiments, $X^1$ is NRN and $X^2$ is S. In some embodiments, $X^1$ is NRN and $X^2$ is S(O). In some embodiments, $X^1$ is NRN and $X^2$ is $S(O)_2$.

In some embodiments, the compound of Formula (IIIa) has formula:

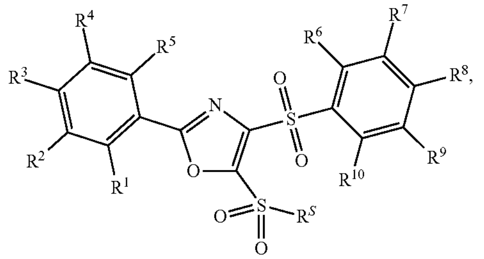

or a pharmaceutically acceptable salt thereof.

In some embodiments, the compound of Formula (IIIa) has formula:

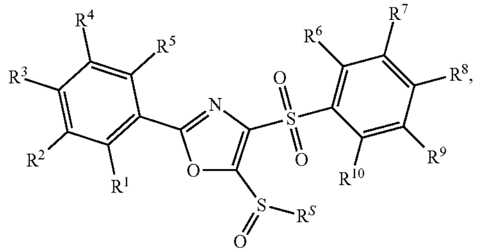

or a pharmaceutically acceptable salt thereof.

In some embodiments, $R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$.

In some embodiments, $R^S$ is $C_{1-6}$ alkyl, optionally substituted with $Cy^1$, $OR^{a1}$, $C(O)R^{b1}$, $NR^{c1}R^{d1}$, and $C(O)NR^{c1}R^{d1}$.

In some embodiments, $R^S$ is $C_{1-6}$ alkyl, optionally substituted with $Cy^1$, $OR^{a1}$, $C(O)R^{b1}$, and $C(O)NR^{c1}R^{d1}$. In some embodiments, $R^S$ is $C_{1-6}$ alkyl. In some embodiments, $R^S$ is $C_{1-6}$ alkyl, optionally substituted with $Cy^1$. In some embodiments, $R^S$ is $C_{1-6}$ alkyl, optionally substituted with $OR^{a1}$. In some embodiments, $R^S$ is $C_{1-6}$ alkyl, optionally substituted with $C_{1-6}$ alkoxy. In some embodiments, $R^S$ is $C_{1-6}$ alkyl, optionally substituted with $C(O)R^{b1}$. In some embodiments, $R^S$ is $C_{1-6}$ alkyl, optionally substituted with $C(O)NR^{c1}R^{d1}$.

In some embodiments, $R^S$ is selected from $C_{6-10}$ aryl and $C_{3-10}$ cycloalkyl, each of which is optionally substituted with 1, 2, or 3 substituents independently selected from $R^{11}$. In some embodiments, $R^S$ is $C_{6-10}$ aryl, optionally substituted with 1, 2, or 3 substituents independently selected from $R^{11}$. In some embodiments, $R^S$ is $C_{3-10}$ cycloalkyl, optionally substituted with 1, 2, or 3 substituents independently selected from $R^{11}$.

In some embodiments, $R^S$ is selected from $C_{6-10}$ aryl and $C_{3-10}$ cycloalkyl, each of which is optionally substituted with 1, 2, or 3 substituents independently selected from halo and $C_{1-6}$ alkyl. In some embodiments, $R^S$ is $C_{6-10}$ aryl, optionally substituted with 1, 2, or 3 substituents independently selected from halo and $C_{1-6}$ alkyl. In some embodiments, $R^S$ is $C_{3-10}$ cycloalkyl, optionally substituted with 1, 2, or 3 substituents independently selected from halo and $C_{1-6}$ alkyl.

In some embodiments, each $R^{11}$ independently selected from $Cy^1$, halo, $C_{1-6}$ alkyl, $OR^{a1}$, $C(O)R^{b1}$, and $C(O)NR^{c1}R^{d1}$. In some embodiments, $R^{11}$ is $Cy^1$. In some embodiments, $R^{11}$ is halo. In some embodiments, $R^{11}$ is $C_{1-6}$ alkyl. In some embodiments, $R^{11}$ is $OR^{a1}$. In some embodiments, $R^{11}$ is $C_{1-6}$ alkoxy. In some embodiments, $R^{11}$ is $C(O)R^{b1}$. In some embodiments, $R^{11}$ is $C(O)NR^{c1}R^{d1}$.

In some embodiments, each $Cy^1$ is independently selected from $C_{6-10}$ aryl and $C_{3-10}$ cycloalkyl, each of which is optionally substituted with 1, 2, or 3 substituents independently selected from $R^{Cy1}$. In some embodiments, $Cy^1$ is $C_{6-10}$ aryl, optionally substituted with 1, 2, or 3 substituents independently selected from $R^{Cy1}$. In some embodiments, $Cy^1$ is $C_{3-10}$ cycloalkyl, optionally substituted with 1, 2, or 3 substituents independently selected from $R^{Cy1}$. In some embodiments, each $R^{Cy1}$ is independently selected from halo, $C_{1-6}$ alkyl, $C_{1-6}$ haloalkyl, $OR^{a1}$, $C(O)R^{b1}$, $(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$. In some embodiments, $R^{Cy1}$ is halo. In some embodiments, $R^{Cy1}$ is $C_{1-6}$ alkyl. In some embodiments, $R^{Cy1}$ is $C_{1-6}$ haloalkyl. In some embodiments, $R^{Cy1}$ is $OR^{a1}$. In some embodiments, $R^{Cy1}$ is $C_{1-6}$ alkoxy. In some embodiments, $R^{Cy1}$ is $C(O)R^{b1}$. In some embodiments, $R^{Cy1}$ is $NR^{c1}R^{d1}$. In some embodiments, each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, and $C_{6-10}$ aryl, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy. In some embodiments, $R^8$ is halo. In some embodiments, $R^g$ is $C_{1-6}$ alkyl.

In some embodiments:

$R^S$ is selected from $C_{1-6}$ alkyl, $C_{6-10}$ aryl, and $C_{3-10}$ cycloalkyl, each of which is optionally substituted with 1, 2, or 3, 4, or 5 substituents independently selected from $R^{11}$;

$R^{11}$ independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, $C_{1-6}$ alkyl, $C_{1-6}$ haloalkyl, $OR^{a1}$, $C(O)R^{b1}$, $(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$;

each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy. In some aspects of these embodiments, $R^{11}$ independently selected from $Cy^1$, halo, $C_{1-6}$ alkyl, $OR^{a1}$, $C(O)R^{b1}$, and $C(O)NR^{c1}R^{d1}$.

In some embodiments:

$R^S$ is selected from $C_{1-6}$ alkyl, $C_{6-10}$ aryl, and $C_{3-10}$ cycloalkyl, each of which is optionally substituted with 1, 2, or 3, 4, or 5 substituents independently selected from $R^{11}$;

$R^{11}$ independently selected from $Cy^1$, halo, $C_{1-6}$ alkyl, $OR^{a1}$, $C(O)R^{b1}$ $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$;

each $R^{a1}$, $R^{b1}$, $R^{c1}$, and $R^{d1}$ is independently selected from H, $C_{1-6}$ alkyl, and $C_{6-10}$ aryl, each of which is optionally substituted with 1, 2, or 3 substituents independently selected from $R^g$; and $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy. In some aspects of these embodiments, $R^{11}$ independently selected from $Cy^1$, halo, $C_{1-6}$ alkyl, $OR^{a1}$, $C(O)R^{b1}$, and $C(O)NR^{c1}R^{d1}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIIa) is selected from any one of the compounds of Table 3a, Table 3b, Table 3b-2, Table 10, or Table 11.

In some embodiments, the compound of Formula (IIIa) is selected from any one of the compounds of Table 3a or Table 3b, or a pharmaceutically acceptable salt thereof. In some embodiments, the compound of Formula (IIIa) is selected from any one of the compounds of Table 3a, or a pharmaceutically acceptable salt thereof. In some embodiments, the compound of Formula (IIIa) is selected from any one of the compounds of Table 3b, or a pharmaceutically acceptable salt thereof.

In some embodiments, the present disclosure provides a compound selected from any one of the compounds of Table 3b or Table 3b-2, or a pharmaceutically acceptable salt thereof. In some embodiments, the present disclosure provides a compound selected from any one of the compounds of Table 3b, or a pharmaceutically acceptable salt thereof. In some embodiments, the present disclosure provides a compound selected from any one of the compounds of Table 3b-2, or a pharmaceutically acceptable salt thereof.

Formula (IIIc)

In a general aspect, the present disclosure provides a compound of Formula (IIIc):

(IIIc)

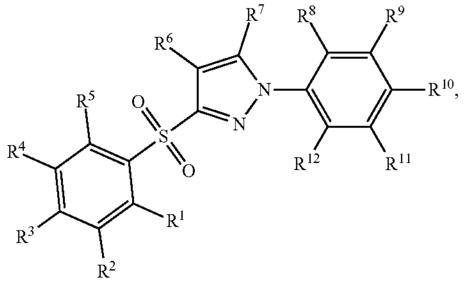

or a pharmaceutically acceptable salt thereof, wherein $R^1$, $R^2$, $R^3$, $R^4$, $R^5$, $R^6$, $R^7$, $R^8$, $R^9$, $R^{10}$, $R^{11}$, and $R^{12}$ are as described herein.

In some embodiments:

each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{13}$;

each $R^{13}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, OH, $C_{1-6}$ alkyl, $C_{1-6}$ haloalkyl, $C_{1-6}$ alkoxy, $C_{1-6}$ haloalkoxy.

In some embodiments, each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, OH, $C_{1-6}$ alkyl, and $C_{1-6}$ alkoxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIIc) is:

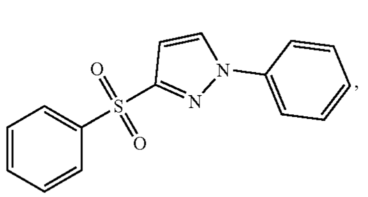 [SMILES: O=S(=O)(c1ccccc1)c1ccn(-c2ccccc2)n1]

or a pharmaceutically acceptable salt thereof.

Formula (IIId)

In some embodiments, the present disclosure provides a compound of Formula (IIId):

(IIId)

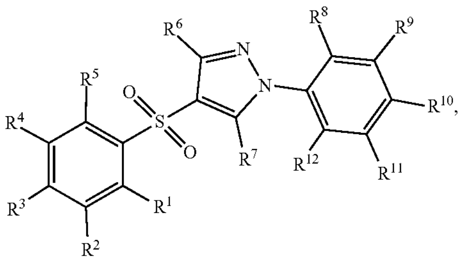

or a pharmaceutically acceptable salt thereof, wherein $R^1$, $R^2$, $R^3$, $R^4$, $R^5$, $R^6$, $R^7$, $R^8$, $R^9$, $R^{10}$, $R^{11}$, and $R^{12}$ are as described herein.

In some embodiments:

each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{13}$;

each $R^{13}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, OH, $C_{1-6}$ alkyl, $C_{1-6}$ haloalkyl, $C_{1-6}$ alkoxy, $C_{1-6}$ haloalkoxy.

In some embodiments, each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, OH, $C_{1-6}$ alkyl, and $C_{1-6}$ alkoxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIId) is:

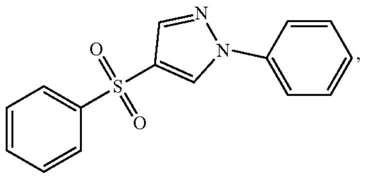 [SMILES: O=S(=O)(c1ccccc1)c1cnn(-c2ccccc2)c1], or a pharmaceutically acceptable salt thereof.

Formula (IIIe)

In one general aspect, the present disclosure provides a compound of Formula (IIIe):

(IIIe)

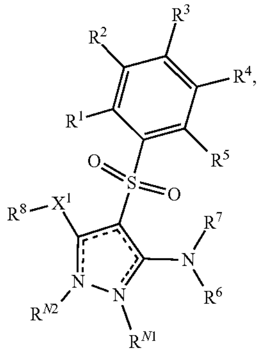

or a pharmaceutically acceptable salt thereof, wherein:

$X^1$ is selected from S, S(O), and $S(O)_2$;

each  represents a single bond or a double bond, provided that not more than two of  are double bonds;

$R^{N2}$ is absent if  between the N atom to which $R^{N2}$ is attached and the C atom to which $X^1$ is attached is a double bond; or $R^{N2}$ is selected from the group consisting of H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^{N1}$ is absent if  between the N atom to which $R^{N1}$ is attached and the C atom to which $NR^6R^7$ is attached is a double bond; or $R^{N1}$ is selected from the group consisting of H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^{N1}$ together with the N atoms to which they are attached from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, C(O)$R^{b1}$, C(O)N$R^{c1}R^{d1}$, C(O)O$R^{a1}$, N$R^{c1}R^{d1}$, N$R^{c1}$C(O)$R^{b1}$, N$R^{c1}$C(O)O$R^{a1}$, N$R^{c1}$S(O)$_2R^{b1}$, S(O)$_2R^{b1}$, and S(O)$_2$N$R^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, O$R^{a1}$, C(O)$R^{b1}$, C(O)N$R^{c1}R^{d1}$, C(O)O$R^{a1}$, N$R^{c1}R^{d1}$ N$R^{c1}$C(O)$R^{b1}$, N$R^{c1}$C(O)O$R^{a1}$, N$R^{c1}$S(O)$_2R^{b1}$, S(O)$_2$ $R^{b1}$, and S(O)$_2$N$R^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^8$; and each $R^8$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from S(O) and S(O)$_2$. In some embodiments, $X^1$ is S(O). In some embodiments, $X^1$ is S(O)$_2$. In some embodiments, $X^1$ is S.

In some embodiments, the compound of Formula (IIIe) has formula:

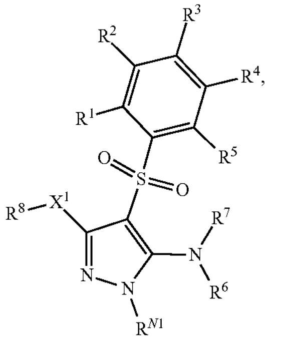

or a pharmaceutically acceptable salt thereof.

In some embodiments, $R^{N1}$ is selected from H and $C_{1-6}$ alkyl. In some embodiments, $R^{N1}$ is H. In some embodiments, $R^{N1}$ is $C_{1-6}$ alkyl, which is optionally substituted with 1, 2, or 3 substituents independently selected from $R^9$.

In some embodiments, the compound of Formula (IIIe) has formula:

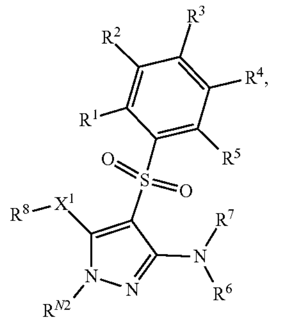

or a pharmaceutically acceptable salt thereof.

In some embodiments, $R^6$ is H. In some embodiments, $R^7$ is H. In some embodiments, $R^6$ and $R^7$ are each independently selected from H and $C_{1-6}$ alkyl. In some embodiments, $R^6$ and $R^7$ are both H. In some embodiments, $R^6$ is H and $R^7$ is $C_{1-6}$ alkyl, optionally substituted with 1, 2, or 3 substituents independently selected from $R^9$.

In some embodiments, $R^6$ and $R^7$ are each independently selected from H and $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$. In some embodiments, $R^6$ is H and $R^7$ is $C_{6-10}$ aryl (e.g., phenyl, naphthyl), optionally substituted with 1, 2, or 3 substituents independently selected from $R^9$. In some embodiments, $R^6$ is H and $R^7$ is $C_{3-10}$ cycloalkyl (e.g., cyclohexyl, cyclopropyl), optionally substituted with 1, 2, or 3 substituents independently selected from $R^9$. In some embodiments, $R^6$ is H and $R^7$ is 5-10 membered heteroaryl (e.g., pyridine), optionally substituted with 1, 2, or 3 substituents independently selected from $R^9$. In some embodiments, $R^6$ is H and $R^7$ is 4-10 membered heterocycloalkyl (e.g., piperidine, tetrahydropyran), optionally substituted with 1, 2, or 3 substituents independently selected from $R^9$.

In some embodiments, $R^6$ and $R^{N1}$ together with the N atoms to which they are attached from a 5-10 membered heteroaryl, substituted with 1, 2, or 3 substituents independently selected from $R^{10}$ (e.g., pyrimidine, triazine).

In some embodiments, $R^6$ and $R^{N1}$ together with the N atoms to which they are attached from a 4-10 membered heterocycloalkyl, substituted with 1, 2, or 3 substituents independently selected from $R^{10}$ (e.g., hexahydropyrimidine).

In some embodiments, the compound of Formula (IIIe) has formula:

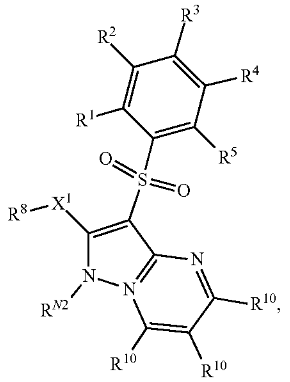

or a pharmaceutically acceptable salt thereof.

In some embodiments, each $R^{10}$ independently selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, and $NR^{c1}R^{d1}$ In some embodiments, each $R^{10}$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, each $R^{10}$ is independently selected from H, halo, OH, $C_{1-6}$ alkyl, and $C_{1-6}$ alkoxy. In some embodiments, each $R^{10}$ is independently selected from H, OH, and $C_{1-6}$ alkyl.

In some embodiments, $R^{N2}$ is selected from H and $C_{1-6}$ alkyl. In some embodiments, $R^{N2}$ is $C_{1-6}$ alkyl, optionally substituted with 1, 2, or 3 substituents independently selected from $R^9$. In some embodiments, $R^{N2}$ is H.

In some embodiments, each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^9$. In some embodiments, each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, each of $R^1$, $R^2$, $R^3$, $R^4$, and $R^5$ is independently selected from H, halo, $C_{1-6}$ alkyl, and $C_{1-6}$ alkoxy. In some embodiments, each of $R^1$, $R^2$, $R^3$, $R^4$, and $R^5$ is independently selected from H and $C_{1-6}$ alkyl. In some embodiments, $R^1$, $R^2$, $R^3$, $R^4$, and $R^5$ are all H.

In some embodiments, $R^8$ is $C_{1-6}$ alkyl. In some embodiments, $R^8$ is $C_{1-6}$ alkyl, optionally substituted with 1, 2, or 3 substituents independently selected from $R^9$. In some embodiments, $R^8$ is selected from $C_{1-6}$ alkyl and $C_{1-6}$ haloalkyl. In some embodiments, $R^8$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$. In some embodiments, $R^8$ is $C_{6-10}$ aryl, optionally substituted with 1, 2, or 3 substituents independently selected from $R^9$. In some embodiments, $R^8$ is $C_{3-10}$ cycloalkyl (e.g., cyclopentyl, cyclohexyl), optionally substituted with 1, 2, or 3 substituents independently selected from $R^9$. In some embodiments, $R^8$ is 5-10 membered heteroaryl, optionally substituted with 1, 2, or 3 substituents independently selected from $R^9$. In some embodiments, $R^8$ is 4-10 membered heterocycloalkyl (e.g., tetrahydrofuran), optionally substituted with 1, 2, or 3 substituents independently selected from $R^9$.

In some embodiments, $R^8$ is $C_{1-6}$ alkyl, optionally substituted with $OR^{a1}$. In some embodiments, $R^8$ is $C_{1-6}$ alkyl, optionally substituted with $C_{1-6}$ alkoxy. In some embodiments, $R^8$ is $C_{1-6}$ alkyl, optionally substituted with $NR^{c1}R^{d1}$.

In some embodiments, each $R^9$ independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, and $NR^{c1}R^{d1}$ In some embodiments, each $R^9$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, each $R^9$ is independently selected from H, halo, OH, $C_{1-6}$ alkyl, and $C_{1-6}$ alkoxy. In some embodiments, each $R^9$ is independently selected from H and $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments (when $R^6$ and $R^{N1}$ together with the N atoms to which they are attached form a ring):

$X^1$ is selected from S(O) and $S(O)_2$;

each $R^{10}$ is independently selected from H, halo, CN, $NO_2$, OH, $C_{1-6}$ alkyl, $C_{1-6}$ haloalkyl, $C_{1-6}$ alkoxy, $C_{1-6}$ haloalkoxy;

$R^{N2}$ is selected from H and $C_{1-6}$ alkyl;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy; and $R^8$ is $C_{1-6}$ alkyl.

In some embodiments (when $R^6$ and $R^{N1}$ together with the N atoms to which they are attached form a ring):

$X^1$ is selected from S(O) and $S(O)_2$;

each $R^{10}$ is independently selected from H, OH, and $C_{1-6}$ alkyl;

$R^{N2}$ is H;

$R^1$, $R^2$, $R^3$, $R^4$, and $R^5$ are each independently selected from H, halo, $C_{1-6}$ alkyl, and $C_{1-6}$ alkoxy; and $R^8$ is $C_{1-6}$ alkyl.

In some embodiments:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl;

$R^{N1}$ is selected from H and $C_{1-6}$ alkyl; and $R^6$ and $R^7$ are each independently selected from H and $C_{1-6}$ alkyl.

In some embodiments, the compound of Formula (IIIe) has formula:

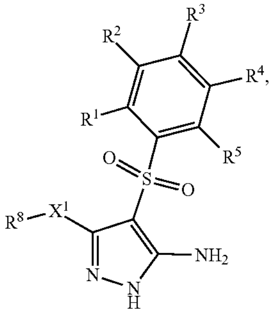

or a pharmaceutically acceptable salt thereof.

In some embodiments:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl;

$R^{N2}$ is selected from H and $C_{1-6}$ alkyl; and $R^6$ and $R^7$ are each independently selected from H and $C_{1-6}$ alkyl.

In some embodiments, the compound of Formula (IIIe) has formula:

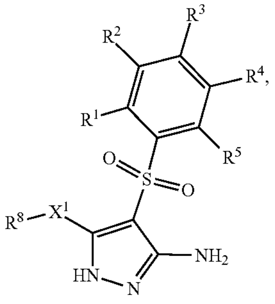

or a pharmaceutically acceptable salt thereof.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIIe) is selected from any one of the following compounds:

| | | |
|---|---|---|
| BC19338 | ZE23-0091 | 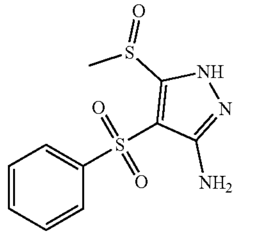 [SMILES: CS(=O)c1[nH]nc(N)c1S(=O)(=O)c1ccccc1] |
| BC19339 | ZE23-0092 | 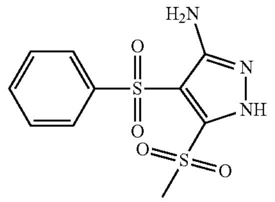 [SMILES: CS(=O)(=O)c1[nH]nc(N)c1S(=O)(=O)c1ccccc1] |
| BC19340 | ZE23-0096 | 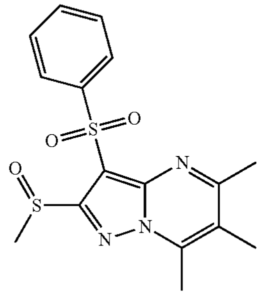 |
| BC19341 | ZE23-0098 | 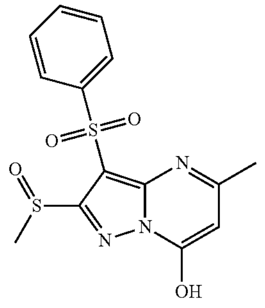 |

or a pharmaceutically acceptable salt thereof.

Formula (IIIf)

In one general aspect, the present disclosure provides a compound of Formula (IIIf):

(IIIf)

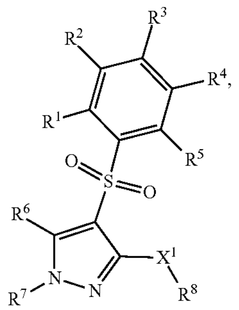

or a pharmaceutically acceptable salt thereof, wherein:

$X^1$ is selected from S, S(O), and S(O);

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

provided that at least one of $R^6$ and $R^7$ is selected from $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^7$, together with the C atom to which $R^6$ is attached and N atom to which $R^7$ is attached, from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from S(O) and $S(O)_2$.

In some embodiments, $X^1$ is S.

In some embodiments, $X^1$ is S(O).

In some embodiments, $X^1$ is $S(O)_2$.

In some embodiments, each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

In some embodiments, each of $R^1$, $R^2$, $R^3$, $R^4$, and $R^5$ is independently selected from H, halo, $C_{1-6}$ alkyl, and $C_{1-6}$ alkoxy.

In some embodiments, $R^8$ is $C_{1-6}$ alkyl, optionally substituted with $OR^{a1}$ or $NR^{c1}R^{d1}$. In some embodiments, $R^8$ is $C_{1-6}$ alkyl, optionally substituted with OH. In some embodiments, $R^8$ is $C_{1-6}$ alkyl, optionally substituted with $C_{1-6}$ alkoxy. In some embodiments, $R^8$ is $C_{1-6}$ alkyl, optionally substituted with $NR^{c1}R^{d1}$.

In some embodiments, $R^8$ is selected from $C_{3-10}$ cycloalkyl and 4-10 membered heterocycloalkyl, each of which is optionally substituted with 1, 2, or 3 substituents independently selected from $R^9$. In some embodiments, $R^8$ is $C_{3-10}$ cycloalkyl, optionally substituted with 1, 2, or 3 substituents independently selected from $R^9$. In some embodiments, $R^8$ is 4-10 membered heterocycloalkyl, optionally substituted with 1, 2, or 3 substituents independently selected from $R^9$.

In some embodiments:

$R^6$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$; and $R^7$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$.

In some embodiments:

$R^6$ is selected from H, $C_{1-6}$ alkyl, and $C_{1-6}$ haloalkyl; and $R^7$ is selected from phenyl, naphthyl, pyridinyl, cyclohexyl, tetrahydropyranyl, and piperidinyl, each of which is optionally substituted with 1, 2, or 3 substituents independently selected from $R^9$.

In some embodiments:

$R^7$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$; and $R^6$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$.

In some embodiments:

$R^7$ is selected from H, $C_{1-6}$ alkyl, and $C_{1-6}$ haloalkyl; and $R^6$ is selected from phenyl, naphthyl, pyridinyl, cyclohexyl, tetrahydropyranyl, and piperidinyl, each of which is optionally substituted with 1, 2, or 3 substituents independently selected from $R^9$.

In some embodiments, the compound of Formula (IIIf) has formula:

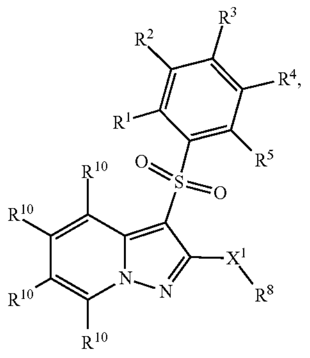

or a pharmaceutically acceptable salt thereof.

In some embodiments, the compound of Formula (IIIf) has formula:

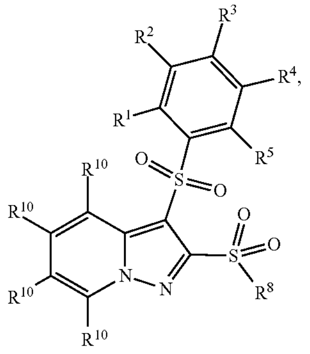

or a pharmaceutically acceptable salt thereof.

In some embodiments, the compound of Formula (IIIf) has formula:

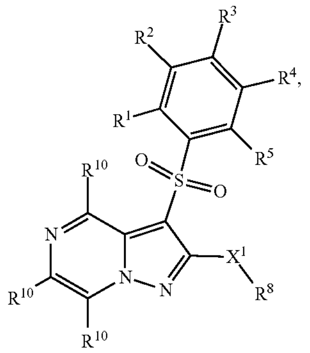

or a pharmaceutically acceptable salt thereof.

In some embodiments, the compound of Formula (IIIf) has formula:

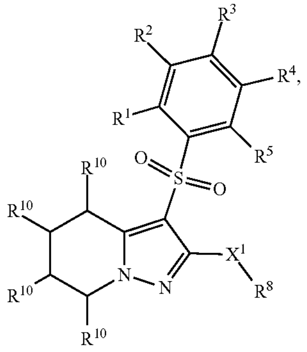

or a pharmaceutically acceptable salt thereof.

In some embodiments, the compound of Formula (IIIf) has formula:

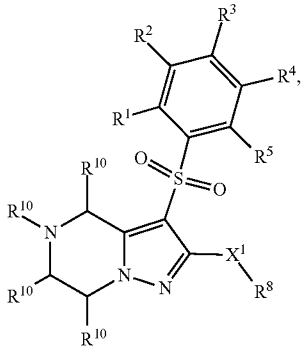

or a pharmaceutically acceptable salt thereof.

In some embodiments, each $R^9$ is independently selected from halo, OH, $C_{1-6}$ alkyl, $C_{1-6}$ haloalkyl, $C_{1-6}$ alkoxy, and $C_{1-6}$ haloalkoxy.

In some embodiments, each $R^{10}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments, each $R^{a1}$, $R^{b1}$, $R^{c1}$, and $R^{d1}$ is independently selected from H, $C_{1-6}$ alkyl, and $C_{6-10}$ aryl, each of which is optionally substituted with 1, 2, or 3 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of the compound of Formula (IIIf):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^6$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$;

$R^7$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIf):

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^6$ is selected from H, $C_{1-6}$ alkyl, and $C_{1-6}$ haloalkyl; and $R^7$ is selected from phenyl, naphthyl, pyridinyl, cyclohexyl, tetrahydropyranyl, and piperidinyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIf):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^7$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$;

$R^6$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIf):

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^7$ is selected from H, $C_{1-6}$ alkyl, and $C_{1-6}$ haloalkyl; and $R^6$ is selected from phenyl, naphthyl, pyridinyl, cyclohexyl, tetrahydropyranyl, and piperidinyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IVf):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^9$;

each $R^9$ is independently selected from halo, OH, $C_{1-6}$ alkyl, $C_{1-6}$ haloalkyl, $C_{1-6}$ alkoxy, and $C_{1-6}$ haloalkoxy; and each $R^{10}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

Formula (IIIg-2)

In one general aspect, the present disclosure provides a compound of Formula (IIIg):

(IIIg-2)

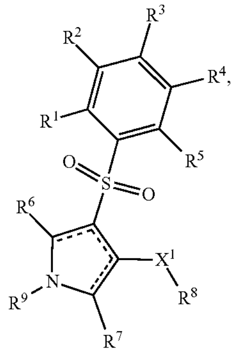

or a pharmaceutically acceptable salt thereof, wherein:

$X^1$ is selected from S, S(O), and $S(O)_2$;

each  represents a single bond or a double bond, provided that not more than two of  are double bonds;

each of $R^1$, $R^2$, $R^3$, $R^4$, $R^5$, $R^6$, and $R^7$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$.

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$R^9$ is selected from $C(O)R^{b1}$, $C(O)NR^{c1}R^{d1}$, $S(O)_2R^{b1}$, $S(O)_2NR^{c1}R^{d1}$, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein each of said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl is optionally substituted with 1, 2, 3, 4, or 5 substituents independently selected from $R^{10}$; or $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^9$, together with the N atom to which $R^9$ is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$;

each $R^{10}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{11}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$; or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (IIIg-2) has formula (IIIg):

(IIIg)

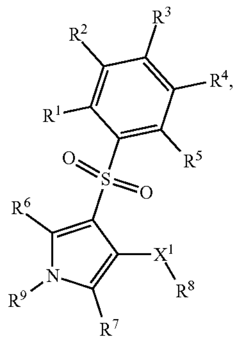

or a pharmaceutically acceptable salt thereof, wherein:

$X^1$ is selected from S, S(O), and $S(O)_2$;

each of $R^1$, $R^2$, $R^3$, $R^4$, $R^5$, $R^6$, and $R^7$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$R^9$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^9$, together with the N atom to which $R^9$ is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$;

each $R^{10}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (IIIg-2) has formula:

(IIIg)

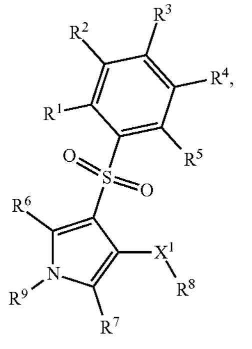

or a pharmaceutically acceptable salt thereof.

In some embodiments, the compound of Formula (IIIg-2) has formula:

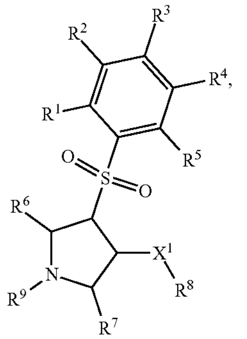

or a pharmaceutically acceptable salt thereof.

In some embodiments, $X^1$ is selected from S(O) and $S(O)_2$.

In some embodiments, $X^1$ is S(O).

In some embodiments, $X^1$ is $S(O)_2$.

In some embodiments, $X^1$ is S.

In some embodiments, each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{10}$.

In some embodiments, each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

In some embodiments, each of $R^1$, $R^2$, $R^3$, $R^4$, and $R^5$ is independently selected from H, halo, $C_{1-6}$ alkyl, and $C_{1-6}$ alkoxy. In some embodiments, at least one of $R^1$, $R^2$, $R^3$, $R^4$, and $R^5$ is H.

In some embodiments, $R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

In some embodiments, $R^6$ and $R^7$ are each independently selected from H, halo, $C_{1-6}$ alkyl, $C_{1-6}$ haloalkyl, $C_{1-6}$ alkoxy, and $C_{1-6}$ haloalkoxy.

In some embodiments, $R^6$ is H or $C_{1-6}$ alkyl, and $R^7$ is H or $C_{1-6}$ alkyl.

In some embodiments, $R^6$ and $R^7$ are each independently selected from H and $C_{1-6}$ alkyl. In some embodiments, $R^6$ is H. In some embodiments, $R^7$ is H.

In some embodiments, $R^6$ is H or $C_{1-6}$ alkyl; and $R^7$ is selected from halo, CN, $NO_2$, OH, $C_{1-6}$ alkyl, $C_{1-6}$ haloalkyl, $C_{1-6}$ alkoxy, and $C_{1-6}$ haloalkoxy. In some aspects of these embodiments, $R^6$ is H.

In some embodiments, $R^7$ is H or $C_{1-6}$ alkyl; and $R^6$ is selected from halo, CN, $NO_2$, OH, $C_{1-6}$ alkyl, $C_{1-6}$ haloalkyl, $C_{1-6}$ alkoxy, and $C_{1-6}$ haloalkoxy. In some aspects of these embodiments, $R^7$ is H.

In some embodiments, $R^6$ is H or $C_{1-6}$ alkyl; and $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$. In some aspects of these embodiments, $R^6$ is H.

In some embodiments, the compound of Formula (IIIg) has formula:

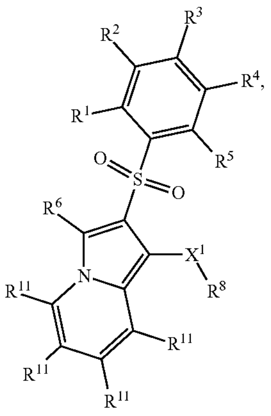

or a pharmaceutically acceptable salt thereof.

In some embodiments, the compound has formula:

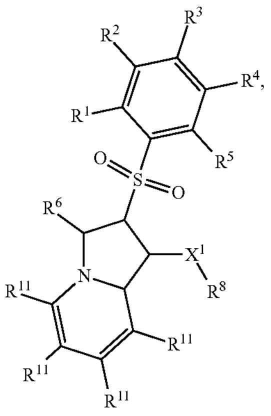

or a pharmaceutically acceptable salt thereof.

In some embodiments, the compound of Formula (IIIg) has formula:

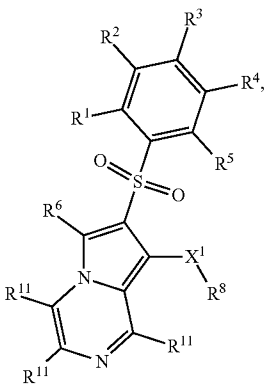

or a pharmaceutically acceptable salt thereof.

In some embodiments, the compound has formula:

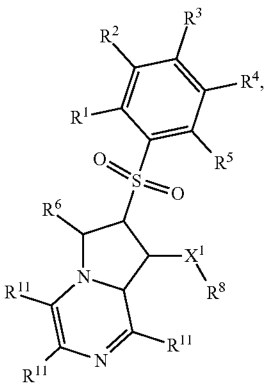

or a pharmaceutically acceptable salt thereof.

In some embodiments, the compound of Formula (IIIg) has formula:

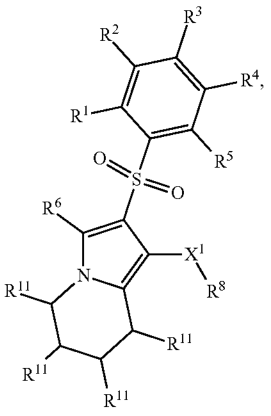

or a pharmaceutically acceptable salt thereof.

In some embodiments, the compound has formula:

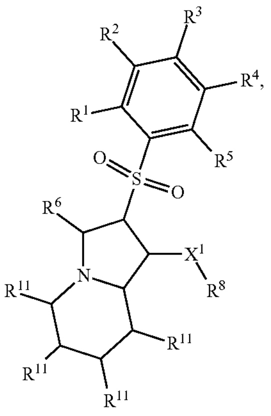

or a pharmaceutically acceptable salt thereof.

In some embodiments, the compound of Formula (IIIg) has formula:

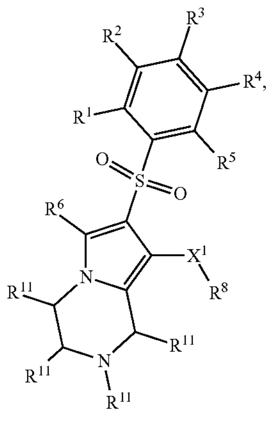

or a pharmaceutically acceptable salt thereof.

In some embodiments, the compound has formula:

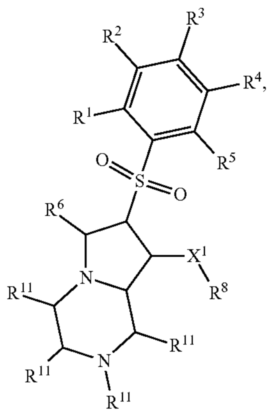

or a pharmaceutically acceptable salt thereof.

In some embodiments:

$R^7$ is H or $C_{1-6}$ alkyl; and $R^6$ and $R^9$, together with the N atom to which R' is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$.

In some embodiments, the compound of Formula (IIIg) has formula:

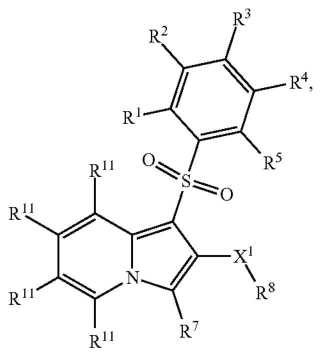

or a pharmaceutically acceptable salt thereof.

In some embodiments, the compound has formula:

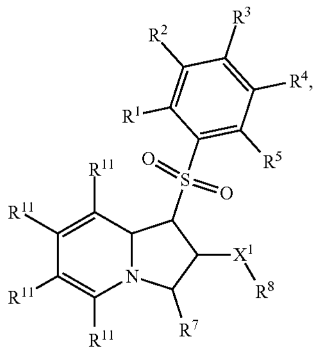

or a pharmaceutically acceptable salt thereof.

In some embodiments, the compound of Formula (IIIg) has formula:

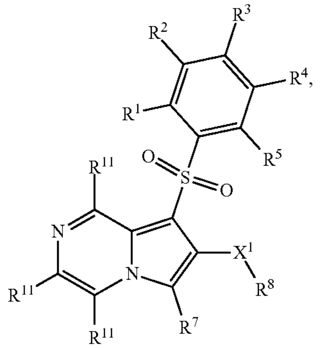

or a pharmaceutically acceptable salt thereof.

In some embodiments, the compound has formula:

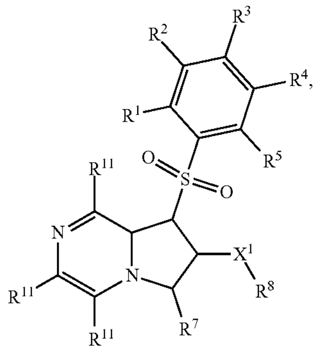

or a pharmaceutically acceptable salt thereof.

In some embodiments, the compound of Formula (IIIg) has formula:

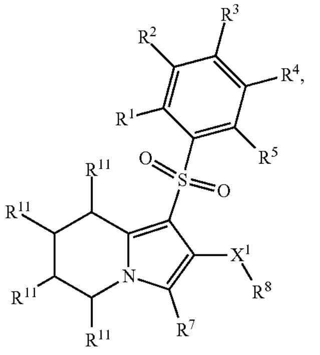

or a pharmaceutically acceptable salt thereof.

In some embodiments, the compound has formula:

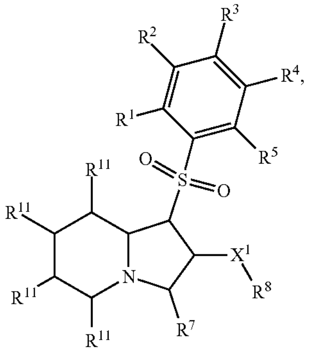

or a pharmaceutically acceptable salt thereof.

In some embodiments, the compound of Formula (IIIg) has formula:

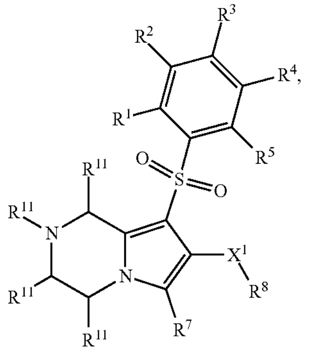

or a pharmaceutically acceptable salt thereof.

In some embodiments, the compound has formula:

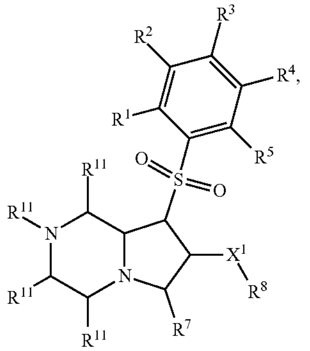

or a pharmaceutically acceptable salt thereof.

In some embodiments, $R^9$ is $C_{1-6}$ alkyl, optionally substituted with 1, 2, or 3 substituents independently selected from $R^{10}$.

In some embodiments, $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

In some embodiments, $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$.

In some embodiments, $R^9$ is $C(O)R^{b1}$. In some embodiments, $R^9$ is 4-10 membered heterocycloalkyl, which is optionally substituted with 1, 2, or 3 substituents independently selected from $R^{10}$.

In some embodiments, $R^8$ is $C_{1-6}$ alkyl, optionally substituted with $OR^{a1}$ or $NR^{c1}R^{d1}$.

In some embodiments, $R^8$ is selected from $C_{3-10}$ cycloalkyl and 4-10 membered heterocycloalkyl, each of which is optionally substituted with 1, 2, or 3 substituents independently selected from $R^{10}$.

In some embodiments, $R^{10}$ is selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^{10}$ is selected from halo, OH, $C_{1-6}$ alkyl, $C_{1-6}$ haloalkyl, $C_{1-6}$ alkoxy, and $C_{1-6}$ haloalkoxy.

In some embodiments, $R^{10}$ is independently selected from $C_{6-12}$ aryl, halo, OH, $C_{1-6}$ alkyl, $C_{1-6}$ haloalkyl, $C_{1-6}$ alkoxy, and $C_{1-6}$ haloalkoxy.

In some embodiments, $R^{11}$ is selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, $R^{11}$ is selected from H, halo, OH, $C_{1-6}$ alkyl, $C_{1-6}$ haloalkyl, $C_{1-6}$ alkoxy, and $C_{1-6}$ haloalkoxy.

In some embodiments:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$;

$R^9$ is selected from $C(O)R^{b1}$, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^{10}$; and each $R^{10}$ is independently selected from $C_{6-12}$ aryl, halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIg):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$, and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIg):

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^6$ is H or $C_{1-6}$ alkyl;

$R^7$ is selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$, and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIg):

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^7$ is H or $C_{1-6}$ alkyl;

$R^6$ is selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$; and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIg):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is H or $C_{1-6}$ alkyl;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIg):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is H or $C_{1-6}$ alkyl;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound is selected from any one of the compounds of Table 12, or a pharmaceutically acceptable salt thereof.

Formula (IIIh)

In one general aspect, the present disclosure provides a compound of Formula (IIIh)

(IIIh)

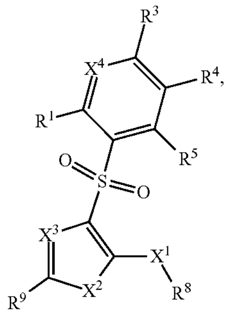

or a pharmaceutically acceptable salt thereof, wherein:

$X^1$ is selected from S, S(O), and $S(O)_2$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$, $X^4$ is selected from N and $CR^2$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^2$ is selected from O, S, and $NR^6$;

$R^6$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^3$ is selected from N and $CR^7$;

$R^7$ is selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^9$ is selected from $S(O)_2R^{b1}$, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^9$ and $R^6$, together with the carbon atom to which $R^9$ is attached and the N atom to which $R^6$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^8$, together with N atom to which $R^6$ is attached and S atom to which $R^8$ is attached, form 4-10 membered heterocycloalkyl substituted with 1, 2, 3, 4, or 5 substituents independently selected from $R^{11}$;

each $R^{10}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{11}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino. In some embodiments, if $X^3$ is N and $X^2$ is O, then $R^9$ is selected from $S(O)_2R^{b1}$, $C_{1-6}$ alkyl, $C_{1-6}$ haloalkyl, $C_{2-6}$ alkenyl, $C_{2-6}$ alkynyl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$.

In some embodiments, the present disclosure provides a compound of Formula (IIIh):

(IIIh)

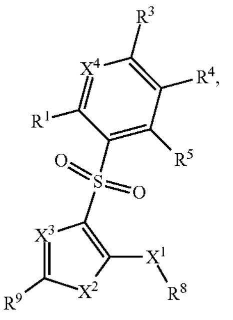

or a pharmaceutically acceptable salt thereof, wherein:

$X^1$ is selected from S, S(O), and $S(O)_2$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$X^4$ is selected from N and $CR^2$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^2$ is selected from O, S, and $NR^6$;

$R^6$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^3$ is selected from N and $CR^7$;

$R^7$ is selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$, $R^9$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^9$ and $R^6$, together with the carbon atom to which $R^9$ is attached and the N atom to which $R^6$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^8$, together with N atom to which $R^6$ is attached and S atom to which $R^8$ is attached, form 4-10 membered heterocycloalkyl substituted with 1, 2, 3, 4, or 5 substituents independently selected from $R^{11}$;

each $R^{10}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is selected from S(O) and $S(O)_2$. In some embodiments, $X^1$ is S(O). In some embodiments, $X^1$ is $S(O)_2$. In some embodiments, $X^1$ is S.

In some embodiments, $X^4$ is $CR^2$. In some embodiments, $X^4$ is N.

In some embodiments, $X^1$ is $S(O)_2$ and $X^4$ is $CR^2$. In some embodiments, $X^1$ is $S(O)_2$ and $X^4$ is N.

In some embodiments, each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{10}$.

In some embodiments, each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

In some embodiments, each of $R^1$, $R^2$, $R^3$, $R^4$, and $R^5$ is independently selected from H, halo, $C_{1-6}$ alkyl, and $C_{1-6}$ alkoxy. In some embodiments, at least one of $R^1$, $R^2$, $R^3$, $R^4$, and $R^5$ is H.

In some embodiments, $R^8$ is selected from $C_{1-6}$ alkyl, $C_{1-6}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

In some embodiments, $R^8$ is $C_{6-10}$ aryl, optionally substituted with 1, 2, or 3 substituents independently selected from $R^{10}$. In some embodiments, $R^8$ is $C_{3-10}$ cycloalkyl, optionally substituted with 1, 2, or 3 substituents independently selected from $R^{10}$. In some embodiments, $R^8$ is 5-10 membered heteroaryl, optionally substituted with 1, 2, or 3 substituents independently selected from $R^{10}$. In some embodiments, $R^8$ is 4-10 membered heterocycloalkyl, optionally substituted with 1, 2, or 3 substituents independently selected from $R^{10}$. In some embodiments, $R^8$ is $C_{1-6}$ alkyl, optionally substituted with 1, 2, or 3 substituents independently selected from $R^{10}$.

In some embodiments, $R^8$ is $C_{1-6}$ alkyl, optionally substituted with $OR^{a1}$ or $NR^{c1}R^{d1}$.

In some embodiments, $R^8$ is selected from $C_{3-10}$ cycloalkyl and 4-10 membered heterocycloalkyl, each of which is optionally substituted with 1, 2, or 3 substituents independently selected from $R^{10}$.

In some embodiments, the compound of Formula (IIIh) has formula:

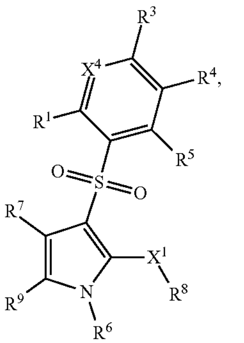

or a pharmaceutically acceptable salt thereof.

In some embodiments, $R^7$ is selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{10}$.

In some embodiments, $R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^7$ is selected from H, halo, $C_{1-6}$ alkyl, and $C_{1-6}$ alkoxy.

In some embodiments, the compound of Formula (IIIh) has formula:

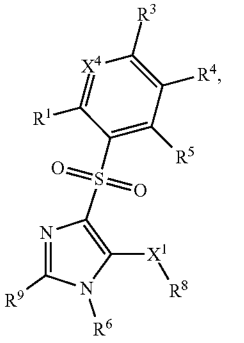

or a pharmaceutically acceptable salt thereof.

In some embodiments, $R^6$ is selected from H, $C_{1-6}$ alkyl, $C_{1-6}$ haloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{10}$. In some embodiments, $R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$. In some embodiments, $R^6$ is selected from H and $C_{1-6}$ alkyl.

In some embodiments, the compound of Formula (IIIh) has formula:

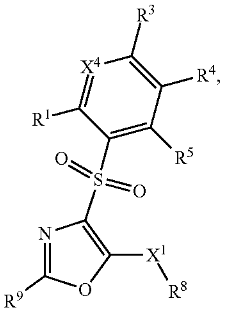

or a pharmaceutically acceptable salt thereof.

In some embodiments, the compound of Formula (IIIh) has formula:

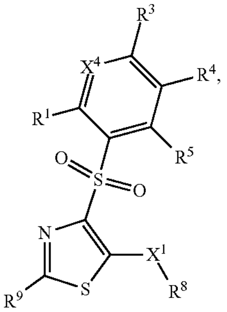

or a pharmaceutically acceptable salt thereof.

In some embodiments, $R^9$ is selected from $C_{1-6}$ alkyl, $C_{1-6}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

In some embodiments, $R^9$ is $S(O)_2R^{b1}$.

In some embodiments, $R^9$ is $C_{1-6}$ alkyl, optionally substituted with 1, 2, or 3 substituents independently selected from $R^{10}$.

In some embodiments, $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

In some embodiments, $R^9$ is selected from $C_{3-10}$ cycloalkyl and 5-10 membered heteroaryl, each of which is optionally substituted with 1, 2, or 3 substituents independently selected from $R^{10}$.

In some embodiments, $R^9$ is $C_{6-10}$ aryl, optionally substituted with 1, 2, or 3 substituents independently selected from $R^{10}$.

In some embodiments, $R^9$ is $C_{3-10}$ cycloalkyl, optionally substituted with 1, 2, or 3 substituents independently selected from $R^{10}$.

In some embodiments, $R^9$ is selected from 5-10 membered heteroaryl, optionally substituted with 1, 2, or 3 substituents independently selected from $R^{10}$.

In some embodiments, $R^9$ is 4-10 membered heterocycloalkyl, optionally substituted with 1, 2, or 3 substituents independently selected from $R^{10}$.

In some embodiments, $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$.

In some embodiments, the compound of Formula (IIIh) has formula:

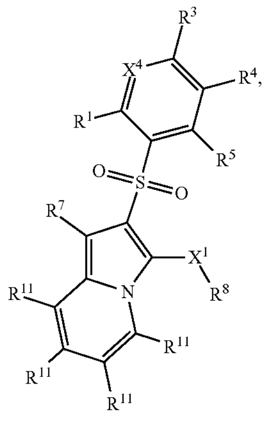

or a pharmaceutically acceptable salt thereof.

In some embodiments, the compound of Formula (IIIh) has formula:

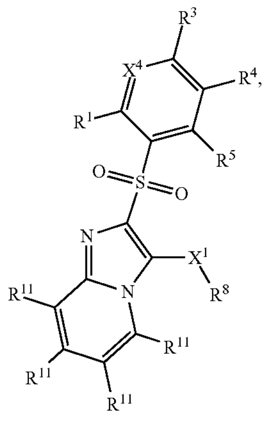

or a pharmaceutically acceptable salt thereof.

In some embodiments, the compound of Formula (IIIh) has formula:

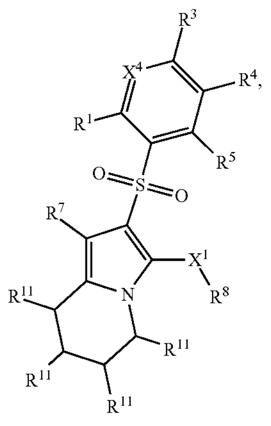

or a pharmaceutically acceptable salt thereof.

In some embodiments, the compound of Formula (IIIh) has formula:

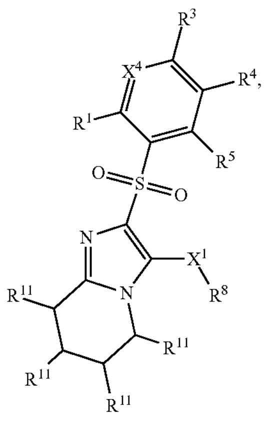

or a pharmaceutically acceptable salt thereof.

In some embodiments, the compound of Formula (IIIh) has formula:

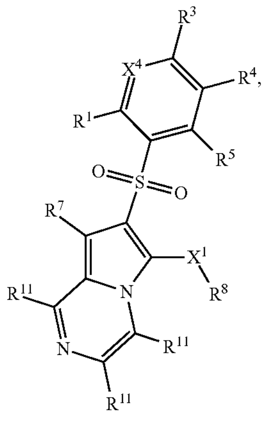

or a pharmaceutically acceptable salt thereof.

In some embodiments, the compound of Formula (IIIh) has formula:

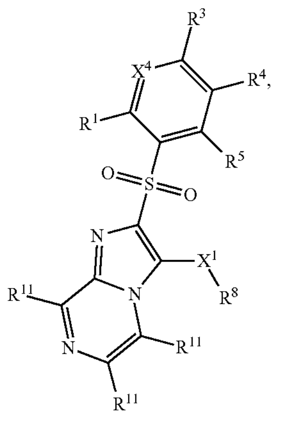

or a pharmaceutically acceptable salt thereof.

In some embodiments, the compound of Formula (IIIh) has formula:

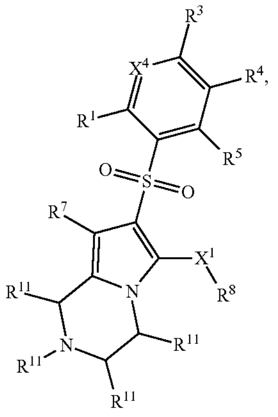

or a pharmaceutically acceptable salt thereof.

In some embodiments, the compound of Formula (IIIh) has formula:

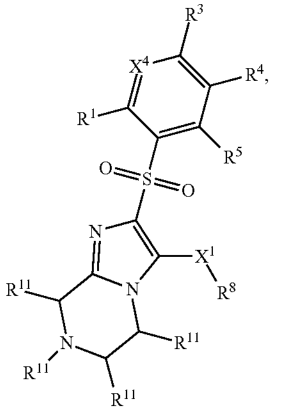

or a pharmaceutically acceptable salt thereof.

In some embodiments, the compound of Formula (IIIh) has formula:

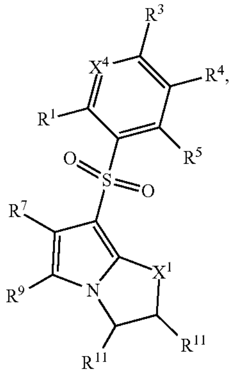

or a pharmaceutically acceptable salt thereof.

In some embodiments, the compound of Formula (IIIh) has formula:

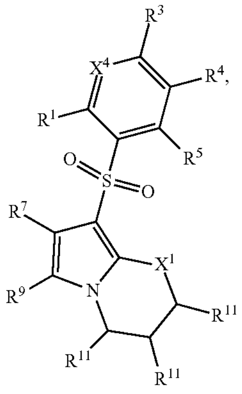

or a pharmaceutically acceptable salt thereof.

In some embodiments, the compound of Formula (IIIh) has formula:

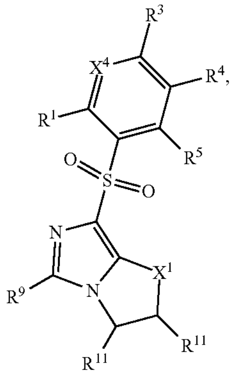

or a pharmaceutically acceptable salt thereof.

In some embodiments, the compound of Formula (IIIh) has formula:

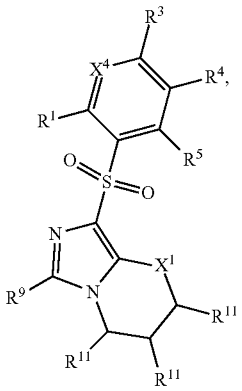

or a pharmaceutically acceptable salt thereof.

In some embodiments, each $R^{10}$ is independently selected from $Cy^1$, halo, $C_{1-6}$ alkyl, $C_{1-6}$ haloalkyl, $OR^{a1}$, C(O)$NR^{c1}R^{d1}$, and $NR^{c1}R^{d1}$.

In some embodiments, $Cy^1$ is $C_{3-10}$ cycloalkyl, optionally substituted with 1, 2, or 3 substituents independently selected from $R^{11}$.

In some embodiments, each $R^{10}$ is independently selected from halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, each $R^{10}$ is independently selected from halo, OH, $C_{1-6}$ alkyl, $C_{1-6}$ haloalkyl, $C_{1-6}$ alkoxy, and $C_{1-6}$ haloalkoxy.

In some embodiments, each $R^{11}$ is independently selected from H, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$;

$R^9$ is selected from $S(O)_2R^{b1}$ and $C_{1-6}$ alkyl, optionally substituted with 1, 2, or 3 substituents independently selected from $R^{10}$; or $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

each $R^{10}$ is independently selected from $Cy^1$, halo, $C_{1-6}$ alkyl, $C_{1-6}$ haloalkyl, $OR^{a1}$, $C(O)NR^{c1}R^{d1}$, and $NR^{c1}R^{d1}$, and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIh):

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$;

$R^9$ is selected from $R^9$ is $C_{1-6}$ alkyl, optionally substituted with 1, 2, or 3 substituents independently selected from $R^{10}$; or $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments of the compound of Formula (IIIh):

$X^1$ is selected from S(O) and $S(O)_2$;

$R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, $C_{1-6}$ alkyl, and $C_{1-6}$ alkoxy;

$R^6$ is selected from H and $C_{1-6}$ alkyl;

$R^9$ is $C_{1-6}$ alkyl, optionally substituted with 1, 2, or 3 substituents independently selected from $R^{10}$; or $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, the compound of Formula (IIIh) is selected from any one of the compounds of Table 8, Table 9, Table 10, and Table 11, or a pharmaceutically acceptable salt thereof. In some embodiments, the compound of Formula (IIIh) is selected from any one of the compounds of Table 8, or a pharmaceutically acceptable salt thereof. In some embodiments, the compound of Formula (IIIh) is selected from any one of the compounds of Table 9, or a pharmaceutically acceptable salt thereof. In some embodiments, the compound of Formula (IIIh) is selected from any one of the compounds of Table 10, or a pharmaceutically acceptable salt thereof. In some embodiments, the compound of Formula (IIIh) is selected from any one of the compounds of Table 11, or a pharmaceutically acceptable salt thereof.

Formula (IIIi)

In one general aspect, the present disclosure provides a compound of Formula (IIIi):

(IIIi)

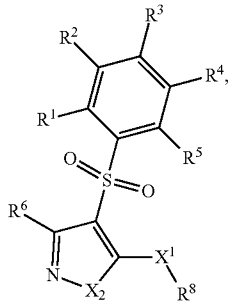

or a pharmaceutically acceptable salt thereof, wherein:

$X^1$ is selected from S, S(O), and $S(O)_2$;

$X^2$ is selected from S and $NR^7$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

provided that at least one of $R^6$ and $R^7$ is selected from $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^7$, together with the C atom to which $R^6$ is attached and N atom to which $R^7$ is attached, from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^8$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, the compound of Formula (IIIi) has formula:

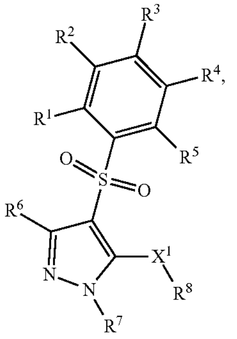

or a pharmaceutically acceptable salt thereof.

In some embodiments, the compound of Formula (IIIi) has formula:

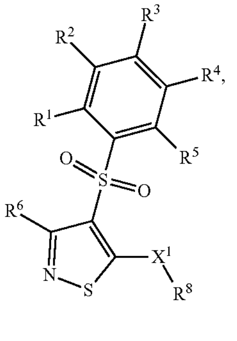

or a pharmaceutically acceptable salt thereof.

In some embodiments, each of $R^1$, $R^2$, $R^3$, $R^4$, and $R^5$ is independently selected from H and halo.

In some embodiments, $R^6$ is $C_{6-10}$ aryl, optionally substituted with 1, 2, or 3 substituents independently selected from $R^9$.

In some embodiments, $R^8$ is $C_{1-6}$ alkyl, optionally substituted with 1, 2, or 3 substituents independently selected from $R^9$.

In some embodiments:

each of $R^1$, $R^2$, $R^3$, $R^4$, and $R^5$ is independently selected from H and halo;

$R^6$ is $C_{6-10}$ aryl, optionally substituted with 1, 2, or 3 substituents independently selected from $R^9$; and $R^8$ is $C_{1-6}$ alkyl, optionally substituted with 1, 2, or 3 substituents independently selected from $R^9$.

In some embodiments, the compound is selected from any one of the compounds of Table 15, or a pharmaceutically acceptable salt thereof.

Formula (IVa)

In one general aspect, the present disclosure provides a compound of Formula (IVa):

(IVa)

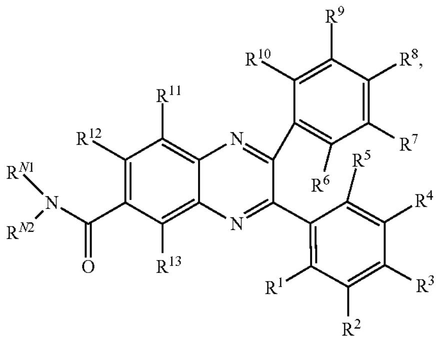

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{14}$, each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$;

or $R^{N1}$ and $R^{N2}$ together with the N atom to which they are attached from a 4-10 membered heterocycloalkyl, each of which is optionally substituted with 1, 2, 3, 4, or 5 substituents independently selected from $R^{14}$, each $R^{14}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{14}$.

In some embodiments, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, $C_{1-6}$ haloalkyl, $OR^{a1}$, $C(O)NR^{c1}R^{d1}$, $C(O)OR^{a1}$, and $NR^{c1}R^{d1}$; wherein said $C_{1-6}$ alkyl is optionally substituted with 1, 2, or 3 substituents independently selected from $R^{14}$.

In some embodiments, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, and $C_{1-6}$ alkoxy. In some embodiments, at least one of $R^1$, $R^2$, $R^3$, $R^4$, $R^5$, $R^6$, $R^7$, $R^8$, $R^9$, $R^{10}$, $R^{11}$, $R^{12}$, and $R^{13}$ is H.

In some embodiments, $R^{N1}$ is selected from H, $C_{1-6}$ alkyl, and $C_{2-6}$ alkenyl. In some embodiments, $R^{N1}$ is H. In some embodiments, $R^{N1}$ is $C_{1-6}$ alkyl. In some embodiments, $R^{N1}$ is $C_{2-6}$ alkenyl.

In some embodiments, $R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$.

In some embodiments, $R^{N2}$ is H.

In some embodiments, $R^{N2}$ is $C_{1-6}$ alkyl, optionally substituted with 1, 2, or 3 substituents independently selected from $R^{14}$. In some embodiments, $R^{N2}$ is $C_{2-6}$ alkenyl, optionally substituted with 1, 2, or 3 substituents independently selected from $R^{14}$. In some embodiments, $R^{N2}$ is $C_{3-10}$ cycloalkyl, optionally substituted with 1, 2, or 3 substituents independently selected from $R^{14}$.

In some embodiments, $R^{N1}$ and $R^{N2}$ together with the N atom to which they are attached from a 4-10 membered heterocycloalkyl, each of which is optionally substituted with 1, 2, or 3 substituents independently selected from $R^{14}$. In some aspects of these embodiments, the 4-10 membered heterocycloalkyl is selected from pyrrolidine, piperazine, morpholine, and piperidine.

In some embodiments, each $R^{14}$ independently selected from $Cy^1$, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, each $R^{14}$ independently selected from $Cy^1$, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$.

In some embodiments, each $R^{14}$ independently selected from $Cy^1$, $C_{1-6}$ alkyl, $OR^{a1}$, $C(O)R^{b1}$, $C(O)NR^{c1}R^{d1}$, $C(O)OR^{a1}$, and $NR^{c1}R^{d1}$. In some embodiments, $R^{14}$ is $Cy^1$. In some embodiments, $R^{14}$ is $C_{1-6}$ alkyl. In some embodiments, $R^{14}$ is $OR^{a1}$ In some embodiments, $R^{14}$ is $C(O)R^{b1}$. In some embodiments, $R^{14}$ is $C(O)NR^{c1}R^{d1}$ In some embodiments, $R^{14}$ is $C(O)OR^{a1}$. In some embodiments, $R^{14}$ is $NR^{c1}R^{d1}$ In some embodiments, each $Cy^1$ is independently selected from $C_{6-10}$ aryl, 5-10 membered heteroaryl, and 4-10 membered heterocycloalkyl, each of which is optionally substituted with 1, 2, or 3, substituents independently selected from $R^{Cy1}$.

In some embodiments, $Cy^1$ is $C_{6-10}$ aryl, optionally substituted with 1, 2, or 3, substituents independently selected from $R^{Cy1}$. In some embodiments, $Cy^1$ is 5-10 membered heteroaryl, optionally substituted with 1, 2, or 3, substituents independently selected from $R^{Cy1}$. In some embodiments, $Cy^1$ is 4-10 membered heterocycloalkyl, optionally substituted with 1, 2, or 3, substituents independently selected from $R^{Cy1}$.

In some embodiments, each $Cy^1$ is independently selected from phenyl, piperidine, thiophene, pyridine, piperazine, morpholine, azepane, pyrrolidone, pyrrolidine, and pyrimidine, each of which is optionally substituted with 1, 2, or 3, substituents independently selected from $R^{Cy1}$.

In some embodiments, each $R^{Cy1}$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{15}$.

In some embodiments, each $R^{Cy1}$ is independently selected from halo, $C_{1-6}$ alkyl, $C_{1-6}$ haloalkyl, $OR^{a1}$, $SR^{a1}$, $C(O)NR^{c1}R^{d1}$, $C(O)OR^{a1}$, and $NR^{c1}R^{d1}$.

In some embodiments, each $R^{Cy1}$ is independently selected from halo, $C_{1-6}$ alkyl, $OR^{a1}$, $SR^{a1}$, and $NR^{c1}R^{d1}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of the compound of Formula (IVa):

each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, $C_{1-6}$ haloalkyl, $OR^{a1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{14}$, $R^{N1}$ is selected from H, $C_{1-6}$ alkyl, and $C_{2-6}$ alkenyl;

$R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$; or $R^{N1}$ and $R^{N2}$ together with the N atom to which they are attached from a 4-10 membered heterocycloalkyl, each of which is optionally substituted with 1, 2, or 3 substituents independently selected from $R^{14}$, $R^{14}$ independently selected from $Cy^1$, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$;

$Cy^1$ is independently selected from $C_{6-10}$ aryl, 5-10 membered heteroaryl, and 4-10 membered heterocycloalkyl, each of which is optionally substituted with 1, 2, or 3, substituents independently selected from $R^{Cy1}$;

$R^{Cy1}$ is independently selected from halo, $C_{1-6}$ alkyl, $C_{1-6}$ haloalkyl, $OR^{a1}$, $SR^{a1}$, $C(O)NR^{c1}R^{d1}$, $C(O)OR^{a1}$, and $NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of the compound of Formula (IVa):

each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, and $C_{1-6}$ alkoxy; $R^{N1}$ is selected from H, $C_{1-6}$ alkyl, and $C_{2-6}$ alkenyl;

$R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$; or $R^{N1}$ and $R^{N2}$ together with the N atom to which they are attached from pyrrolidine, piperazine, morpholine, or piperidine, each of which is optionally substituted with 1, 2, or 3 substituents independently selected from $R^{14}$, each $R^{14}$ independently selected from $Cy^1$, $C_{1-6}$ alkyl, $OR^{a1}$, $C(O)R^{b1}$, $C(O)NR^{c1}R^{d1}$, $C(O)OR^{a1}$, and $NR^{c1}R^{d1}$, each $Cy^1$ is independently selected from phenyl, piperidine, thiophene, pyridine, piperazine, morpholine, azepane, pyrrolidone, pyrrolidine, and pyrimidine, each of which is optionally substituted with 1, 2, or 3, substituents independently selected from $R^{Cy1}$;

each $R^{Cy1}$ is independently selected from halo, $C_{1-6}$ alkyl, $OR^{a1}$, $SR^{a1}$, and $NR^{c1}R^{d1}$;

each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$; and each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

In some embodiments, the compound of Formula (IVa) is selected from any one of the compounds of Table 4a or Table 4b, or a pharmaceutically acceptable salt thereof. In some embodiments, the compound of Formula (IVa) is selected from any one of the compounds of Table 4a, or a pharmaceutically acceptable salt thereof. In some embodiments, the compound of Formula (IVa) is selected from any one of the compounds of Table 4b, or a pharmaceutically acceptable salt thereof. In some embodiments, the present disclosure provides a compound selected from any one of the compounds of Table 4b or Table 4b-2, or a pharmaceutically acceptable salt thereof. In some embodiments, the present disclosure provides a compound selected from any one of the compounds of Table 4b, or a pharmaceutically acceptable salt thereof. In some embodiments, the present disclosure provides a compound selected from any one of the compounds of Table 4b-2, or a pharmaceutically acceptable salt thereof.

Formula (IVb)

In one general aspect, the present disclosure provides a compound of Formula (IVb)

(IVb)

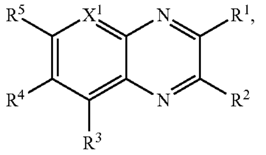

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^4$ is 5-10 membered heteroaryl, optionally substituted with 1, 2, 3, 4, or 5 substituents independently selected from $R^8$;

each $R^8$ is independently selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^9$;

each $R^9$ is independently selected from $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, 3, 4, or 5 substituents independently selected from $R^8$;

$R^1$ and $R^2$ are each independently selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is $CR^6$.

In some embodiments, $X^1$ is N.

In some embodiments, $R^3$, $R^5$, and $R^6$ are each independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^7$.

In some embodiments, $R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

In some embodiments, $R^3$, $R^5$, and $R^6$ are each independently selected from H, halo, $C_{1-6}$ alkyl, and $C_{1-6}$ alkoxy.

In some embodiments, $R^4$ is 5-10 membered heteroaryl, optionally substituted with 1, 2, or 3 substituents independently selected from $R^8$. In some embodiments, $R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$.

In some embodiments, each $R^8$ is independently selected from halo, CN, $NO_2$, $C_{1-6}$ alkyl, $C_{1-6}$ haloalkyl, $C_{3-10}$ cycloalkyl, $C_{6-10}$ aryl, 5-10 membered heteroaryl, 4-10 membered heterocycloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^9$.

In some embodiments, each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$. In some embodiments, $R^8$ is $C_{1-6}$ alkyl, optionally substituted with 1, 2, or 3 substituents independently selected from $R^9$.

In some embodiments, each $R^9$ is independently selected from $C_{1-6}$ alkyl, $C_{3-10}$ cycloalkyl, $C_{6-10}$ aryl, 5-10 membered heteroaryl, 4-10 membered heterocycloalkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^g$.

In some embodiments, each $R^9$ is independently selected from $C_{1-6}$ alkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$. In some embodiments, each $R^9$ is independently selected from $C_{1-6}$ alkyl, halo, CN, $NO_2$, $OR^{a1}$, $C(O)R^{b1}$, $C(O)NR^{c1}R^{d1}$, $C(O)OR^{a1}$, $NR^{c1}R^{d1}$. In some embodiments, each $R^9$ is independently selected from $OR^{a1}$ and $NR^{c1}R^{d1}$. In some embodiments, $R^9$ is $OR^{a1}$. In some embodiments, $R^9$ is $NR^{c1}R^{d1}$.

In some embodiments, $R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments, $R^1$ is $C_{1-6}$ haloalkyl; and $R^2$ is $C_{6-10}$ aryl, optionally substituted with 1, 2, or 3 substituents independently selected from $R^{10}$.

In some embodiments, $R^1$ is $C_{6-10}$ aryl, optionally substituted with 1, 2, or 3 substituents independently selected from $R^{10}$; and $R^2$ is $C_{1-6}$ haloalkyl.

In some embodiments, $R^1$ is 5-10 membered heteroaryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

In some embodiments, $R^1$ is $C_{6-10}$ aryl, optionally substituted with 1, 2, or 3 substituents independently selected from $R^{10}$; and $R^2$ is 5-10 membered heteroaryl, optionally substituted with 1, 2, or 3 substituents independently selected from $R^{10}$.

In some of the above embodiments, the 5-10 membered heteroaryl is thiophene. In some of the above embodiments, the $C_{6-10}$ aryl is phenyl.

In some embodiments, each $R^{10}$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$. In some embodiments, each $R^{10}$ is independently selected from halo and $S(O)_2R^{b1}$. In some embodiments, $R^{10}$ is halo. In some embodiments, $R^{10}$ is $S(O)_2R^{b1}$.

In some embodiments, each $R^{11}$ is independently selected from $OR^{a1}$, $C(O)R^{b1}$, $C(O)NR^{c1}R^{d1}$, $C(O)OR^{a1}$, and $NR^{c1}R^{d1}$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of the compound of Formula (IVb):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$.

$R^1$ is $C_{6-10}$ aryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments, of the compound of Formula (IVb):

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$, $R^1$ is phenyl, optionally substituted with 1, 2, or 3 substituents independently selected from $R^{10}$, $R^2$ is phenyl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$.

$R^1$ is $C_{1-6}$ haloalkyl;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is trifluoromethyl;

$R^2$ is phenyl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$.

$R^1$ is $C_{6-10}$ aryl, optionally substituted with 1, 2, or 3 substituents independently selected from $R^{10}$; and $R^2$ is $C_{1-6}$ haloalkyl;

each $R^{10}$ is independently selected from halo and $S(O)_2R^{b1}$.

In some embodiments of a compound of Formula (IVb):

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is phenyl, optionally substituted with 1, 2, or 3 substituents independently selected from $R^{10}$; and $R^2$ is trifluoromethyl;

each $R^{10}$ is independently selected from halo and $S(O)_2R^{b1}$.

In some embodiments of a compound of Formula (IVb):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$ wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is 5-10 membered heteroaryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$.

$R^1$ is thiophenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is 5-10 membered heteroaryl, optionally substituted with 1, 2, or 3 substituents independently selected from $R^{10}$; and each $R^{10}$ is independently selected from halo and $S(O)_2R^{b1}$.

In some embodiments of a compound of Formula (IVb):

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$, $R^1$ is phenyl, optionally substituted with 1, 2, or 3 substituents independently selected from $R^{10}$;

$R^2$ is thiophenyl, optionally substituted with 1, 2, or 3 substituents independently selected from $R^{10}$; and each $R^{10}$ is independently selected from halo and $S(O)_2R^{b1}$.

In some embodiments, the compound of Formula (IVb) is selected from any one of the compounds of Table 4c, or a pharmaceutically acceptable salt thereof. In some embodiments, the compound of Formula (IVb) is selected from any one of the compounds of Table 4c or Table 4c-2, or a pharmaceutically acceptable salt thereof.

Formula (IVc)

In one general aspect, the present disclosure provides a compound of Formula (IVc)

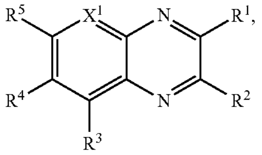

(IVc)

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^4$ is selected from $C(O)NR^{N1}R^{N2}$, $C(O)OR^{a1}$, and CN;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-10 membered heterocycloalkyl, which is substituted with 1, 2, or 3 substituents independently selected from $R^{14}$;

each $R^{14}$ independently selected from H, $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^8$ and $S(O)_2R^8$;

$R^8$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

provided that $R^1$ and $R^2$ are not both $C_{6-10}$ aryl;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is $CR^6$.

In some embodiments, $X^1$ is N.

In some embodiments, $R^3$, $R^5$, and $R^6$ are each independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^7$.

In some embodiments, $R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^3$, $R^5$, and $R^6$ are each independently selected from H, halo, $C_{1-6}$ alkyl, and $C_{1-6}$ alkoxy.

In some embodiments, $R^4$ is selected from $C(O)NR^{N1}R^{N2}$ and $C(O)OR^{a1}$. In some embodiments, $R^4$ is selected from $C(O)NR^{N1}R^{N2}$ and CN. In some embodiments, $R^4$ is selected from $C(O)OR^{a1}$ and CN. In some embodiments, $R^4$ is $C(O)NR^{N1}R^{N2}$. In some embodiments, $R^4$ is $C(O)OR^{a1}$. In some embodiments, $R^4$ is CN.

In some embodiments, each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N1}$ is selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N1}$ is H. In some embodiments, $R^{N1}$ is $C_{1-6}$ alkyl, optionally substituted with 1, 2, or 3 substituents independently selected from $R^{14}$. In some embodiments, $R^{N1}$ is $C_{2-6}$ alkynyl, optionally substituted with 1, 2, or 3 substituents independently selected from $R^{14}$. In some embodiments, $R^{N1}$ is 4-10 membered heterocycloalkyl, optionally substituted with 1, 2, or 3 substituents independently selected from $R^{14}$.

In some embodiments, $R^{N2}$ is selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N2}$ is H. In some embodiments, $R^{N2}$ is $C_{1-6}$ alkyl, optionally substituted with 1, 2, or 3 substituents independently selected from $R^{14}$. In some embodiments, $R^{N2}$ is $C_{2-6}$ alkynyl, optionally substituted with 1, 2, or 3 substituents independently selected from $R^{14}$. In some embodiments, $R^{N2}$ is 4-10 membered heterocycloalkyl, optionally substituted with 1, 2, or 3 substituents independently selected from $R^{14}$.

In some embodiments, $R^{N1}$ and $R^{N2}$, together with the N atom to which they are attached, form a 4-6 membered heterocycloalkyl, which is substituted with 1, 2, or 3 substituents independently selected from $R^{14}$.

In some embodiments, each $R^{14}$ is independently selected from H, $Cy^1$, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

In some embodiments, each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$. In some embodiments, each $R^{14}$ is independently selected from $C_{1-6}$ alkyl and $NR^{c1}R^{d1}$. In some embodiments, $R^{14}$ is $C_{1-6}$ alkyl. In some embodiments, $NR^{c1}R^{d1}$.

In some embodiments, the compound of Formula (IVc) has formula:

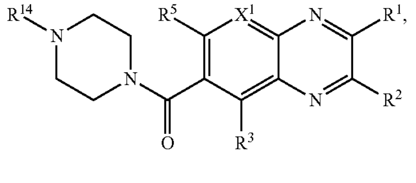

or a pharmaceutically acceptable salt thereof.

In some embodiments, $R^1$ is $C_{1-6}$ haloalkyl; and $R^2$ is selected from $C_{6-10}$ aryl and 5-10 membered heteroaryl, each of which is optionally substituted with 1, 2, or 3 independently selected $R^{10}$.

In some embodiments, $R^1$ is selected from $C_{6-10}$ aryl and 5-10 membered heteroaryl, each of which is optionally substituted with 1, 2, or 3 independently selected $R^{10}$; and $R^2$ is $C_{1-6}$ haloalkyl.

In some embodiments, $R^1$ is $C_{6-10}$ aryl, optionally substituted with 1, 2, or 3 independently selected $R^{10}$, and $R^2$ is 5-10 membered heteroaryl, optionally substituted with 1, 2, or 3 independently selected $R^{10}$.

In some embodiments, $R^1$ is 5-10 membered heteroaryl, optionally substituted with 1, 2, or 3 independently selected $R^{10}$; and $R^1$ is $C_{6-10}$ aryl, optionally substituted with 1, 2, or 3 independently selected $R^{10}$.

In some embodiments, the compound of Formula (IVc) has formula:

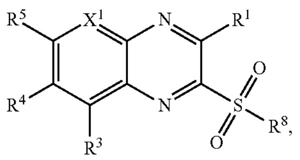

or a pharmaceutically acceptable salt thereof.

In some embodiments, the compound of Formula (IVc) has formula:

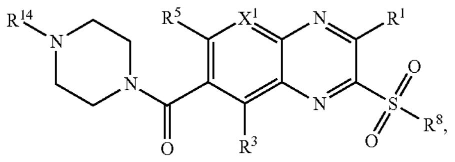

or a pharmaceutically acceptable salt thereof.

In some embodiments, $R^1$ is $C_{1-6}$ haloalkyl; and $R^8$ is selected from $C_{6-10}$ aryl and 5-10 membered heteroaryl, each of which is optionally substituted with 1, 2, or 3 independently selected $R^{10}$.

In some embodiments, $R^1$ is selected from $C_{6-10}$ aryl and 5-10 membered heteroaryl, each of which is optionally substituted with 1, 2, or 3 independently selected $R^{10}$; and $R^8$ is $C_{1-6}$ haloalkyl.

In some embodiments, $R^1$ is $C_{6-10}$ aryl, optionally substituted with 1, 2, or 3 independently selected $R^{10}$, and $R^8$ is 5-10 membered heteroaryl, optionally substituted with 1, 2, or 3 independently selected $R^{10}$.

In some embodiments, $R^1$ is 5-10 membered heteroaryl, optionally substituted with 1, 2, or 3 independently selected $R^{10}$; and $R^8$ is $C_{6-10}$ aryl, optionally substituted with 1, 2, or 3 independently selected $R^{10}$.

In some embodiments, $R^1$ is $C_{6-10}$ aryl, optionally substituted with 1, 2, or 3 independently selected $R^{10}$; and $R^8$ is $C_{6-10}$ aryl, optionally substituted with 1, 2, or 3 independently selected $R^{10}$.

In some embodiments, $R^1$ is 5-10 membered heteroaryl, optionally substituted with 1, 2, or 3 independently selected $R^{10}$; and $R^8$ is 5-10 membered heteroaryl, optionally substituted with 1, 2, or 3 independently selected $R^{10}$.

In some aspects of the above embodiments, the 5-10 membered heteroaryl is selected from thiophenyl and pyridinyl; and the $C_{6-10}$ aryl is phenyl.

In some embodiments, $R^1$ is $C_{1-6}$ haloalkyl; and $R^8$ is $C_{1-6}$ haloalkyl. In some embodiments, each $R^{10}$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$. In some embodiments, each $R^{10}$ is independently selected from halo and $C_{1-6}$ alkyl. In some embodiments, $R^{10}$ is halo. In some embodiments, $R^{10}$ is $C_{1-6}$ alkyl.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of a compound of Formula (IVc):

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-6 membered heterocycloalkyl, which is substituted with 1, 2, or 3 substituents independently selected from $R^{14}$;

each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; and each $R^{10}$ is independently selected from halo and $C_{1-6}$ alkyl.

In some aspects of the above embodiments, $R^3$, $R^5$, and $R^6$ are each independently selected from H, halo, $C_{1-6}$ alkyl, and $C_{1-6}$ alkoxy; and $R^{14}$ is independently selected from $C_{1-6}$ alkyl and $NR^{c1}R^{d1}$.

In some embodiments, the compound of Formula (IVc) is selected from any one of the compounds of Table 4d, or a pharmaceutically acceptable salt thereof.

Formula (IVd)

In one general aspect, the present disclosure provides a compound of Formula (IVd):

(IVd)

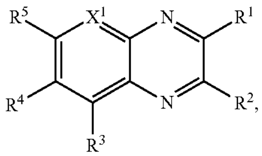

or a pharmaceutically acceptable salt thereof, wherein:

$X^1$ is selected from N and $CR^6$;

$R^4$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^3$ is selected from $C(O)NR^{N1}R^{N2}$ and $C(O)OR^{a1}$;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-10 membered heterocycloalkyl, which is substituted with 1, 2, or 3 substituents independently selected from $R^{14}$;

each $R^{14}$ independently selected from H, $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^8$ and $S(O)_2R^8$;

$R^8$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is $CR^6$.

In some embodiments, $X^1$ is N.

In some embodiments, $R^4$, $R^5$, and $R^6$ are each independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$.

In some embodiments, $R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^4$, $R^5$, and $R^6$ are each independently selected from H, halo, $C_{1-6}$ alkyl, and $C_{1-6}$ alkoxy.

In some embodiments, $R^3$ is $C(O)NR^{N1}R^{N2}$.

In some embodiments, $R^3$ is $C(O)OR^{a1}$.

In some embodiments, each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N1}$ is selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N1}$ is H. In some embodiments, $R^{N1}$ is $C_{1-6}$ alkyl, optionally substituted with 1, 2, or 3 substituents independently selected from $R^{14}$. In some embodiments, $R^{N1}$ is $C_{2-6}$ alkynyl, optionally substituted with 1, 2, or 3 substituents independently selected from $R^{14}$. In some embodiments, $R^{N1}$ is 4-10 membered heterocycloalkyl, optionally substituted with 1, 2, or 3 substituents independently selected from $R^{14}$.

In some embodiments, $R^{N2}$ is selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

In some embodiments, $R^{N2}$ is H. In some embodiments, $R^{N2}$ is $C_{1-6}$ alkyl, optionally substituted with 1, 2, or 3 substituents independently selected from $R^{14}$. In some embodiments, $R^{N2}$ is $C_{2-6}$ alkynyl, optionally substituted with 1, 2, or 3 substituents independently selected from $R^{14}$. In some embodiments, $R^{N2}$ is 4-10 membered heterocycloalkyl, optionally substituted with 1, 2, or 3 substituents independently selected from $R^{14}$.

In some embodiments, $R^{N1}$ and $R^{N2}$, together with the N atom to which they are attached, form a 4-6 membered heterocycloalkyl, which is substituted with 1, 2, or 3 substituents independently selected from $R^{14}$.

In some embodiments, the compound of Formula (IVd) has formula:

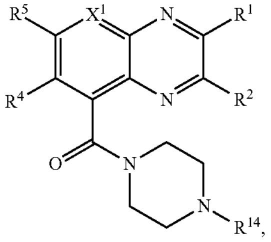

or a pharmaceutically acceptable salt thereof.

In some embodiments, each $R^{14}$ is independently selected from H, $Cy^1$, halo, $C_{1-6}$ alkyl, $C_{1-6}$ haloalkyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$. In some embodiments, each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$ In some embodiments, each $R^{14}$ is independently selected from $C_{1-6}$ alkyl and $NR^{c1}R^{d1}$. In some embodiments, $R^{14}$ is $C_{1-6}$ alkyl. In some embodiments, $R^{14}$ is $NR^{c1}R^{d1}$.

In some embodiments, $R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

In some embodiments, each $R^{10}$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^{11}$. In some embodiments, each $R^{10}$ is independently selected from halo and $C_{1-6}$ alkyl.

In some embodiments, each $R^{11}$ is independently selected from $OR^{a1}$, $C(O)R^{b1}$, $C(O)NR^{c1}R^{d1}$, $C(O)OR^{a1}$, and $NR^{c1}R^{d1}$;

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments of a compound of Formula (IVd):

- $R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;
- each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$, or
- $R^{N1}$ and $R^{N2}$, together with the N atom to which they are attached, form a 4-6 membered heterocycloalkyl, which is substituted with 1, 2, or 3 substituents independently selected from $R^{14}$;
- wherein each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; and
- each $R^{10}$ is independently selected from halo and $C_{1-6}$ alkyl.

In some aspects of the above embodiments:

- $R^4$, $R^5$, and $R^6$ are each independently selected from H, halo, $C_{1-6}$ alkyl, and $C_{1-6}$ alkoxy;
- each $R^{14}$ is independently selected from $C_{1-6}$ alkyl and $NR^{c1}R^{d1}$.

In some embodiments, the compound of Formula (IVd) is selected from any one of the compound of Table 4e, or a pharmaceutically acceptable salt thereof.

Formula (IVe)

In one general aspect, the present disclosure provides a compound of Formula (IVe)

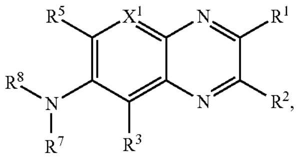

(IVe)

or a pharmaceutically acceptable salt thereof, wherein:

- $X^1$ is selected from N and $CR^6$;
- $R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;
- $R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

or $R^7$ and $R^8$ together with the N atom to which they are attached form a 4-10 membered heterocycloalkyl ring, which is optionally substituted with 1, 2, or 3 substituents independently selected from $R^8$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^8$ and $S(O)_2R^8$;

$R^8$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^{8a}$ and $S(O)_2R^{8a}$;

$R^{8a}$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $X^1$ is $CR^6$.

In some embodiments, $X^1$ is N.

In some embodiments, $R^4$, $R^5$, and $R^6$ are each independently selected from H, halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

In some embodiments, $R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy. In some embodiments, $R^4$, $R^5$, and $R^6$ are each independently selected from H, halo, $C_{1-6}$ alkyl, and $C_{1-6}$ alkoxy.

In some embodiments, $R^7$ is selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$.

In some embodiments, $R^8$ is selected from H, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$.

In some embodiments, each $R^9$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$.

In some embodiments, $R^7$ is selected from H and $C_{1-6}$ alkyl; and $R^8$ is selected from $C(O)R^{b1}$ and $C(O)OR^{a1}$. In some embodiments, $R^7$ is selected from H and $C_{1-6}$ alkyl; and $R^8$ is $C(O)NR^{c1}R^{d1}$.

In some embodiments, each $R^{c1}$ and $R^{d1}$ is independently selected from H, $C_{1-6}$ alkyl, and $C_{3-10}$ cycloalkyl, wherein said $C_{1-6}$ alkyl and $C_{3-10}$ cycloalkyl are each optionally substituted with 1 or 2 independently selected $R^g$.

In some embodiments, each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$.

In some embodiments, each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$.

In some embodiments, each $R^{a1}$ and $R^{b1}$ is independently selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1, 2, or 3 substituents independently selected from $R^g$.

In some embodiments, each $R^g$ is independently selected from OH, halo, $C_{1-6}$ alkyl, $C_{1-6}$ alkoxy, 4-10 membered heterocycloalkyl, amino, $C_{1-6}$ alkylamino, di($C_{1-6}$ alkyl) amino, $C_{1-6}$ alkylsulfonyl, $C_{1-6}$ alkylcarbamyl, and $C_{1-6}$ alkylcarbonyl, and any $C_{1-6}$ alkyl, $C_{1-6}$ alkoxy, or 4-10 membered heterocycloalkyl of $R^8$ is optionally substituted with 1 or 2 substituents independently selected from $C_{1-6}$ alkyl and $C_{1-6}$ alkoxy.

In some embodiments, each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

In some embodiments, each $R^8$ is independently selected from halo, $C_{1-6}$ alkyl, 4-10 membered heterocycloalkyl, amino, $C_{1-6}$ alkylsulfonyl, $C_{1-6}$ alkylcarbamyl, and $C_{1-6}$ alkylcarbonyl.

In some embodiments, $R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

In some embodiments, each $R^{10}$ is independently selected from halo, CN, $NO_2$, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$. In some embodiments, each $R^{10}$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$; wherein said $C_{1-6}$ alkyl is optionally substituted with 1, 2, or 3 substituents independently selected from $R^{11}$. In some embodiments, each $R^{10}$ is independently selected from halo and $C_{1-6}$ alkyl.

In some embodiments of a compound of Formula (IVe):

$R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is selected from H and $C_{1-6}$ alkyl;

$R^8$ is selected from $C(O)R^{b1}$ and $C(O)OR^{a1}$;

each $R^{a1}$ and $R^{b1}$ is independently selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1, 2, or 3 substituents independently selected from $R^g$;

each $R^g$ is independently selected from halo, $C_{1-6}$ alkyl, 4-10 membered heterocycloalkyl, amino, $C_{1-6}$ alkylsulfonyl, $C_{1-6}$ alkylcarbamyl, and $C_{1-6}$ alkylcarbonyl;

$R^1$ is $C_{6-10}$ aryl, optionally substituted with 1, 2, or 3 independently selected $R^{10}$.

$R^2$ is $C_{6-10}$ aryl, optionally substituted with 1, 2, or 3 independently selected $R^{10}$; and each $R^{10}$ is independently selected from halo and $C_{1-6}$ alkyl.

In some embodiments:

$R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is selected from H and $C_{1-6}$ alkyl;

$R^8$ is $C(O)NR^{c1}R^{d1}$;

each $R^{c1}$ and $R^{d1}$ is independently selected from H, $C_{1-6}$ alkyl, and $C_{3-10}$ cycloalkyl, wherein said $C_{1-6}$ alkyl and $C_{3-10}$ cycloalkyl are each optionally substituted with 1 or 2 independently selected $R^g$;

each $R^g$ is independently selected from OH, halo, $C_{1-6}$ alkyl, $C_{1-6}$ alkoxy, 4-10 membered heterocycloalkyl, amino, $C_{1-6}$ alkylamino, di($C_{1-6}$ alkyl)amino, $C_{1-6}$ alkylsulfonyl, $C_{1-6}$ alkylcarbamyl, and $C_{1-6}$ alkylcarbonyl, and any $C_{1-6}$ alkyl, $C_{1-6}$ alkoxy, or 4-10 membered heterocycloalkyl of $R^g$ is optionally substituted with 1 or 2 substituents independently selected from $C_{1-6}$ alkyl and $C_{1-6}$ alkoxy;

$R^1$ is $C_{6-10}$ aryl, optionally substituted with 1, 2, or 3 independently selected $R^{10}$;

$R^2$ is $C_{6-10}$ aryl, optionally substituted with 1, 2, or 3 independently selected $R^{10}$; and each $R^{10}$ is independently selected from halo and $C_{1-6}$ alkyl.

In some embodiments, the compound of Formula (IVe) is selected from any one of the compounds of Table 4f, or a pharmaceutically acceptable salt thereof.

In some embodiments, the compound of Formula (IVe) is selected from any one of the compounds of Table 4f or Table 4f-2, or a pharmaceutically acceptable salt thereof. In some embodiments, the compound of Formula (IVe) is selected from any one of the compounds of Table 4f-2, or a pharmaceutically acceptable salt thereof.

Formula (IVf)

In one general aspect, the present disclosure provides a compound of Formula (IVf)

(IVf)

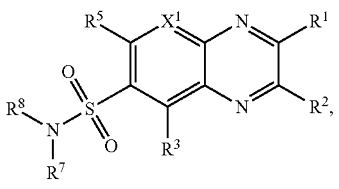

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

or $R^7$ and $R^8$ together with the N atom to which they are attached form a 4-10 membered heterocycloalkyl ring, which is optionally substituted with 1, 2, or 3 substituents independently selected from $R^g$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, X is N.

In some embodiments, X is $CR^6$.

In some embodiments, $R^3$, $R^5$, and $R^6$ are each independently selected from H, halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, $R^3$, $R^5$, and $R^6$ are each H.

In some embodiments:

$R^7$ is H; and $R^8$ is selected from $C_{1-6}$ alkyl and $C_{3-10}$ cycloalkyl, each of which is independently selected from 1 or 2 substituents independently selected from $R^9$. In some embodiments, $R^9$ is independently selected from $C_{3-10}$ cycloalkyl, 5-10 membered heteroaryl, 4-10 membered heterocycloalkyl, halo, $C_{1-6}$ alkyl, $C_{1-6}$ haloalkyl, CN, $OR^{a1}$, $C(O)NR^{c1}R^{d1}$, $C(O)OR^{a1}$, and $NR^{c1}R^{d1}$, wherein said $C_{3-10}$ cycloalkyl, 5-10 membered heteroaryl, and 4-10 membered heterocycloalkyl are each optionally substituted with 1 or 2 substituents independently selected from $R^{10}$.

In some embodiments:

$R^1$ is $C_{6-10}$ aryl, optionally substituted with 1 or 2 independently selected $R^{10}$; and $R^2$ is $C_{6-10}$ aryl, optionally substituted with 1 or 2 independently selected $R^{10}$.

In some embodiments, each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments:

$R^1$ is $C_{6-10}$ aryl, optionally substituted with 1 or 2 independently selected $R^{10}$;

$R^2$ is $C_{6-10}$ aryl, optionally substituted with 1 or 2 independently selected $R^{10}$;

X is $CR^6$;

$R^3$, $R^5$, and $R^6$ are each independently selected from H, halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$R^7$ is H;

$R^8$ is selected from $C_{1-6}$ alkyl and $C_{3-10}$ cycloalkyl, each of which is independently selected from 1 or 2 substituents independently selected from $R^9$;

each $R^9$ is independently selected from $C_{3-10}$ cycloalkyl, 5-10 membered heteroaryl, 4-10 membered heterocycloalkyl, halo, $C_{1-6}$ alkyl, $C_{1-6}$ haloalkyl, CN, $OR^{a1}$, $C(O)NR^{c1}R^{d1}$, $C(O)OR^{a1}$, and $NR^{c1}R^{d1}$; wherein said $C_{3-10}$ cycloalkyl, 5-10 membered heteroaryl, and 4-10 membered heterocycloalkyl are each optionally substituted with 1 or 2 substituents independently selected from $R^{10}$; and each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, the compound is selected from any one of the compounds of Table 4g, or a pharmaceutically acceptable salt thereof.

Formula (IVg)

In one general aspect, the present disclosure provides a compound of Formula (IVg):

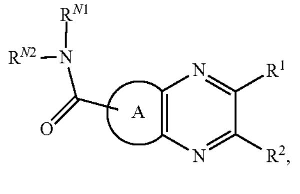

(IVg)

or a pharmaceutically acceptable salt thereof, wherein:

ring A is $C_{3-8}$ cycloalkyl, which is optionally substituted with 1, 2, or 3 substituents independently selected from $R^{14}$, each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$, or $R^{N1}$ and $R^{N2}$ together with the N atom to which they are attached from a 4-10 membered heterocycloalkyl, each of which is optionally substituted with 1, 2, 3, 4, or 5 substituents independently selected from $R^{14}$, each $R^{14}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, $R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^8$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

In some embodiments, the compound of Formula (IVg) has formula:

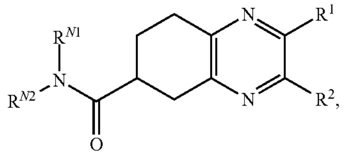

or a pharmaceutically acceptable salt thereof.

In some embodiments, the compound of Formula (IVg) has formula:

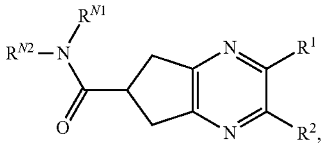

or a pharmaceutically acceptable salt thereof.

In some embodiments:

$R^{N1}$ and $R^{N2}$ together with the N atom to which they are attached from a 4-10 membered heterocycloalkyl, which is optionally substituted with 1, 2, or 3 substituents independently selected from $R^{14}$, $R^1$ is $C_{6-10}$ aryl, optionally substituted with 1, 2, or 3 substituents independently selected from $R^{10}$, and $R^2$ is $C_{6-10}$ aryl, optionally substituted with 1, 2, or 3 substituents independently selected from $R^{10}$.

In some embodiments, the compound is selected from any one of the compounds of Table 17, or a pharmaceutically acceptable salt thereof.

In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and those formed with organic acids such as maleic acid.

In some embodiments, bases commonly employed to form pharmaceutically acceptable salts of the compounds disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, any one of the compounds disclosed herein, or a pharmaceutically acceptable salt thereof, is substantially isolated.

Methods of Making Therapeutic Compounds

Compounds as set forth in any one of the Formulae disclosed herein, including salts thereof, can be prepared using organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates, and products can be identified by reference to the literature, including reference sources such as: *Advances in Heterocyclic Chemistry*, Vols. 1-107 (Elsevier, 1963-2012); *Journal of Heterocyclic Chemistry* Vols. 1-49 (*J. Heterocyclic Chemistry,* 1964-2012); Carreira et al., (Ed.) *Science of Synthesis*, Vols. 1-48 (2001-2010) and Knowledge Updates KU2010/1-4; 2011/1-4; 2012/1-2 (Thieme, 2001-2012); Katritzky et al., (Ed.) *Comprehensive Organic Functional Group Transformations*, (Pergamon Press, 1996); Katritzky et al., (Ed.) *Comprehensive Organic Functional Group Transformations II* (Elsevier, $2^{nd}$ Edition, 2004); Katritzky et al., (Ed.) *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure,* 6th Ed. (Wiley, 2007); Trost et al. (Ed.) *Comprehensive Organic Synthesis* (Pergamon Press, 1991).

The reactions for preparing the compounds provided herein can be carried out in suitable solvents that can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis,* 4th Ed., Wiley & Sons, Inc., New York (2006).

Pharmaceutical Compositions and Formulations

This document also provides pharmaceutical compositions comprising an effective amount of a compound disclosed herein, or a pharmaceutically acceptable salt thereof; and a pharmaceutically acceptable carrier. The pharmaceutical composition also can comprise any one of the additional therapeutic agents and/or therapeutic molecules described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that can be used in the pharmaceutical compositions provided herein include, without limitation, ion exchangers, alumina, aluminum stearate, lecithin, serum proteins (e.g., human serum albumin), buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms can contain any one or more of the compounds or therapeutic agents described herein in the range of 0.005 percent to 100 percent with the balance made up from the suitable pharmaceutically acceptable carriers or excipients. The contemplated compositions can contain from about 0.001 percent to about 100 percent (e.g., from about 0.1 percent to about 95 percent, from about 75 percent to about 85 percent, or from about 20 percent to about 80 percent) of any one or more of the compounds or therapeutic agents provided herein, wherein the balance can be made up of any pharmaceutically acceptable carrier or excipient described herein, or any combination of these carriers or excipients.

Routes of Administration and Dosage Forms

The therapeutic compounds and/or pharmaceutical compositions provided herein (e.g., a composition containing one or more compounds disclosed herein, or a pharmaceutically acceptable salt thereof) can include those suitable for any acceptable route of administration. Acceptable routes of administration include, without limitation, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral, vaginal, intravitreal, subretinal or other intraocular routes of administrations.

Compositions and formulations described herein can conveniently be presented in a unit dosage form, e.g., tablets, sustained release capsules, and in liposomes, and can be prepared by any methods well known in the art of pharmacy. See, for example, Remington: The Science and Practice of Pharmacy, Lippincott Williams & Wilkins, Baltimore, MD (20th ed. 2000). Such preparative methods include, without limitation, the step of bringing into association with the molecule to be administered ingredients such as a carrier that constitutes one or more accessory ingredients. In general, the compositions can be prepared by uniformly and intimately bringing into association the active ingredients with liquid carriers, liposomes, or finely divided solid carriers, or both, and then, if necessary, shaping the product.

In some embodiments, any one or more of the compounds or therapeutic agents described herein can be administered orally. Compositions described herein that are suitable for oral administration can be presented as discrete units such as capsules, sachets, granules, or tablets each containing a predetermined amount (e.g., effective amount) of the active ingredient(s); a powder or granules; a solution or a suspension in an aqueous liquid or a non-aqueous liquid; an oil-in-water liquid emulsion; a water-in-oil liquid emulsion; packed in liposomes; or as a bolus. Soft gelatin capsules can be useful for containing such suspensions, which can beneficially increase the rate of compound absorption. In the case of tablets for oral use, carriers that are commonly used include, without limitation, lactose, sucrose, glucose, mannitol, silicic acid, and starches. Other acceptable excipients can include, without limitation, (a) fillers or extenders such as starches, lactose, sucrose, glucose, mannitol, and silicic acid, (b) binders such as carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. For oral administration in a capsule form, useful diluents include, without limitation, lactose and dried cornstarch. When aqueous suspensions are administered orally, the active ingredient(s) can be combined with emulsifying and suspending agents. If desired, certain sweetening and/or flavoring and/or coloring agents can be added. Compositions suitable for oral administration include, without limitation, lozenges comprising ingredients in a flavored basis, usually sucrose and acacia or tragacanth; and pastilles comprising the active ingredient(s) in an inert basis such as gelatin and glycerin, or sucrose and acacia.

Compositions suitable for parenteral administration include, without limitation, aqueous and non-aqueous sterile injection solutions or infusion solutions that may contain antioxidants, buffers, bacteriostats, and solutes that render the formulation isotonic with the blood of the intended recipient; and aqueous and non-aqueous sterile suspensions that may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water, for injections, saline (e.g., 0.9% saline solution), or 5% dextrose solution, immediately prior to use. Extemporaneous injection solutions and suspensions can be prepared from sterile powders, granules, and tablets. The injection solutions can be in the form of, for example, a sterile injectable aqueous or oleaginous suspension. This suspension can be formulated according to techniques known in the art using suitable dispersing or wetting agents and suspending agents. A sterile injectable preparation also can be a sterile injectable solution or suspension in a non-toxic parenterally-acceptable diluent or solvent, for example, as a solution in 1,3-butanediol. Among the acceptable vehicles and solvents that can be employed are mannitol, water, Ringer's solution, and isotonic sodium chloride solution. In addition, sterile, fixed oils can be used as a solvent or suspending medium. For this purpose, any bland fixed oil can be used including, without limitation, synthetic mono- or diglycerides. Fatty acids such as oleic acid and its glyceride derivatives can be used to prepare injectables. In some cases, natural pharmaceutically acceptable oils such as olive oil or castor oil, especially in their polyoxyethylated versions, can be used to prepare injectables. These oil solutions or suspensions also can contain a long-chain alcohol diluent or dispersant.

In some cases, a therapeutic compound and/or pharmaceutical composition provided herein can be administered in the form of suppository for rectal administration. These compositions can be prepared by mixing a compound described herein (e.g., any one of the compounds disclosed herein, or a pharmaceutically acceptable salt thereof) with a suitable non-irritating excipient that is solid at room temperature but liquid at the rectal temperature and therefore will melt in the rectum to release the active component(s). Such materials include, without limitation, cocoa butter, beeswax, and polyethylene glycols.

In some cases, a therapeutic compounds and/or pharmaceutical composition provided herein can be administered by nasal aerosol or inhalation. Such compositions can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J. Pharm. Pharmacol.,* 56:3-17 (2004); and Ilium, L., *Eur. J. Pharm. Sci.,* 11:1-18 (2000).

In some cases, a therapeutic compounds and/or pharmaceutical composition provided herein can be prepared as a topical composition and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of a therapeutic compounds and/or pharmaceutical composition provided herein can be useful when the desired treatment involves areas or organs readily accessible by topical application. In some cases, a topical composition can include a combination of any one or more of the compounds or therapeutic agents described herein (e.g., a compound set forth in any one of Formulae (I)-(IV), or a pharmaceutically acceptable salt thereof), and one or more additional ingredients, carriers, excipients, or diluents including, without limitation, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

In some cases, one or more compounds or therapeutic agent described herein (e.g., any one of the compounds disclosed herein, or a pharmaceutically acceptable salt thereof) can be incorporated into a composition for coating an implantable medical device such as a prosthesis, artificial valve, vascular graft, stent, or catheter. Suitable coatings and the general preparation of coated implantable devices are known in the art and are exemplified in U.S. Pat. Nos.

6,099,562; 5,886,026; and 5,304,121. The coatings can be biocompatible polymeric materials such as a hydrogel polymer, polymethyldisiloxane, polycaprolactone, polyethylene glycol, polylactic acid, ethylene vinyl acetate, or mixture thereof. In some cases, the coating can optionally be further covered by a suitable topcoat of fluorosilicone, polysaccharides, polyethylene glycol, phospholipids or combinations thereof to impart controlled release characteristics in the composition.

In some cases, this document provides an implantable drug release device impregnated with or containing one or more compounds or therapeutic agents described herein (e.g., any one of the compounds disclosed herein, or a pharmaceutically acceptable salt thereof) such that the compound(s) or therapeutic agent(s) are released from the device and are therapeutically active.

Dosages and Regimens

A composition (e.g., pharmaceutical compositions provided herein) containing a compound provided herein, or a pharmaceutically acceptable salt thereof, can include that compound in an effective amount (e.g., a therapeutically effective amount).

Effective doses can vary, depending on the diseases being treated, the severity of the disease, the route of administration, the sex, age and general health condition of the subject, excipient usage, the possibility of co-usage with other therapeutic treatments such as use of other agents, and the judgment of the treating physician.

In some embodiments, an effective amount of a compound as disclosed herein, or a pharmaceutically acceptable salt thereof, can range, for example, from about 0.1 mg to about 1000 mg. In some cases, the effective amount can be from about 0.5 mg to about 500 mg of a compound disclosed herein, or any amount in between these two values, for example, one of about 0.5 mg, about 1 mg, about 2 mg, about 5 mg, about 10 mg, about 20 mg, about 50 mg, about 100 mg, about 200 mg, about 250 mg, about 300 mg, about 400 mg, or about 500 mg. The effective amount can be an amount sufficient to alleviate or reduce one or more of the symptoms associated with a disease, disorder, or condition being treated as described herein.

In some cases, an effective amount of a compound as disclosed herein, or a pharmaceutically acceptable salt thereof, can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; from about 0.1 mg/kg to about 0.5 mg/kg, or from about 0.5 mg/kg to about 500 mg/kg).

In some cases, an effective amount of a compound as disclosed herein, or a pharmaceutically acceptable salt thereof, can be about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or on a non-daily basis (e.g., every other day, every two days, every three days, once weekly, twice weekly, once every two weeks, or once a month). In some cases, the dosages can be administered every 4 hours, 6 hours, 8 hours, 12 hours, or 24 hours.

Kits

This document also provides pharmaceutical kits useful, for example, to inhibit NF-κB within cells within a mammal (e.g., a human). In some cases, this document provides pharmaceutical kits useful, for example, to treat diseases, disorders, and conditions referred to herein. Such pharmaceutical kits can include one or more containers containing a pharmaceutical composition that includes a therapeutically effective amount of a compound provided herein, or a pharmaceutically acceptable salt thereof. In some cases, such kits can further include, if desired, one or more of various conventional pharmaceutical kit components such as containers with one or more pharmaceutically acceptable carriers. Instructions, either as inserts or as labels, indicating quantities of the components to be administered, guidelines for administration, and/or guidelines for mixing the components also can be included in a kit provided herein.

Combination Therapies

In some cases, one or more compounds provided herein, or a pharmaceutically acceptable salt thereof, can be combined with one or more therapeutic molecules. Examples of therapeutic molecules that can be used in combination with one or more compounds provided herein, or a pharmaceutically acceptable salt thereof, include, without limitation, anti-inflammatory agents (e.g., steroids and antibodies against IL-6 or TNF-alpha), antimicrobial agents (e.g., antibiotics, anti-mycobacterial drugs, and anti-viral agents), anti-cancer agents (e.g., chemotherapeutic agents and cellular products such as engineered T cells), therapies for atherosclerosis (e.g., lipid-lowering agents, platelet inhibitors), agents to treat polycystic kidney disease (e.g. tolvaptan), therapies used for metabolic syndrome (e.g., insulin, glucose-lowering therapies), therapies for polycystic ovarian syndrome (e.g., metformin), treatment for muscular dystrophies (e.g., steroids, gene therapy approaches) and therapies for pain relief (e.g., non-steroidal anti-inflammatory medicines, opioids, regional nerve blocks).

One or more compounds provided herein, or a pharmaceutically acceptable salt thereof, and the one or more therapeutic molecules can be administered in any order or simultaneously. If simultaneously administered, they can be provided in a single, unified, form or in multiple forms (e.g., either as a single pill or as two separate pills). One of the items can be given in multiple doses, or both can be given as multiple doses. If not simultaneous, the timing between the multiple doses can vary from more than zero weeks to less than four weeks.

Definitions

As used herein, the term "about" means "approximately" (e.g., plus or minus approximately 10% of the indicated value).

At various places in this document, substituents of compounds provided herein are disclosed in groups or in ranges. It is specifically intended that these groups and ranges include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in this document various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features described herein, which are, for clarity, described in the context of separate embodiments, can also be provided in combination in a single embodiment. Conversely, various features described herein which are, for brevity, described in the context of a single embodiment, also can be provided separately or in any suitable subcombination.

The term "aromatic" refers to a carbocycle or heterocycle having one or more polyunsaturated rings having aromatic character (i.e., having (4n+2) delocalized π (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution can be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, without limitation, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms that may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, without limitation, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, without limitation, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl-linking group having n to m carbons. Examples of alkylene groups include, without limitation, ethan-1,1-diyl, ethan-1,2-diyl, propan-1,1-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula-O-alkyl, wherein the alkyl group has n to m carbons. Example alkoxy groups include, without limitation, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula-O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula $—NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, without limitation, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula-N(alkyl) 2, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, without limitation, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, without limitation, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula $—NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula $—S(O)_2NH_2$.

As used herein, the term "$C_{n-m}$ alkylaminosulfonyl" refers to a group of formula $—S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N$(alkyl) 2, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula-$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N$(alkyl) 2, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl) 2, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —$C(O)NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —C(O)N(alkyl) 2, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)— group, which may also be written as C(O).

As used herein, the term "carboxy" refers to a —C(O)OH group. In some embodiments, the "carboxy" group also refers to a bioisostere replacement group selected from the group consisting of:

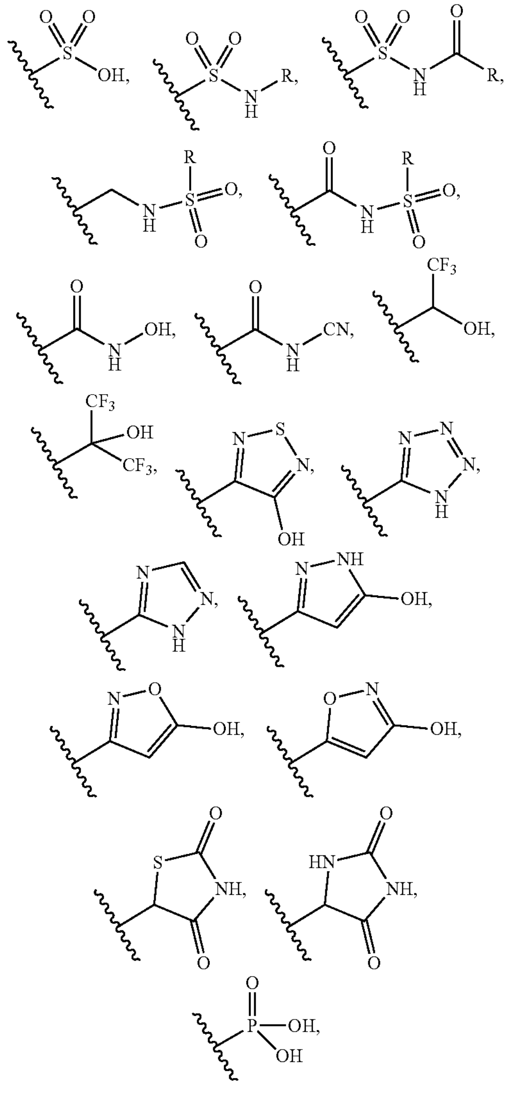

and the like, where R refers to a hydrogen, ($C_1$-$C_8$) alkyl, or $C_6$ aryl.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which can be monocyclic or polycyclic (e.g., having 2, 3, or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups can have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3, or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include, without limitation, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur, and oxygen. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from nitrogen, sulfur, and oxygen. In some embodiments, the heteroaryl is a 5-6 monocyclic heteroaryl having 1 or 2 heteroatom ring members independently selected from nitrogen, sulfur, and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls include, without limitation, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls include, without limitation, pyridyl, pyrazinyl, pyrimidinyl, triazinyl, and pyridazinyl. Ring-forming carbon atoms of a heteroaryl group can be optionally substituted by 1 or 2 independently selected oxo or sulfide groups (e.g., C(O) or C(S)).

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9-, or 10-membered heterocycloalkyl groups. Heterocycloalkyl groups can also include spirocycles. Example heterocycloalkyl groups include, without limitation, pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring can be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C═O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Any appropriate method can be used to prepare optically active forms from, for example, optically inactive starting materials. For example, techniques such as resolution of racemic mixtures or stereoselective synthesis can be used to prepare optically active forms of a compound provided herein. Many geometric isomers of olefins, C═N double bonds, N═N double bonds, and the like also can be present in a compound described herein, and all such stable isomers are contemplated herein. Cis and trans geometric isomers of the compounds provided herein are described and can be isolated as a mixture of isomers or as separated isomeric forms. In some embodiments, a compound provided herein has the (R)-configuration. In some embodiments, a compound provided herein has the (S)-configuration.

Compounds provided herein also include tautomeric forms. Tautomeric forms result from the swapping of a single bond with an adjacent double bond together with the concomitant migration of a proton. Tautomeric forms include prototropic tautomers that are isomeric protonation states having the same empirical formula and total charge. Example prototropic tautomers include, without limitation, ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H-, and 4H-1,2,4-triazole, 1H- and 2H-isoindole, and 1H- and 2H-pyrazole. Tautomeric forms can be in equilibrium or sterically locked into one form by appropriate substitution.

For example, in aqueous solution, pyrazoles can exhibit the following isomeric forms, which are referred to as tautomers of each other:

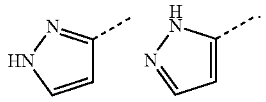

As readily understood by one skilled in the art, a wide variety of functional groups and other structures can exhibit tautomerism, and all tautomers of compounds as described herein are within the scope provided herein.

As used herein, the term "cell" is meant to refer to a cell that is in vitro, ex vivo, or in vivo. In some embodiments, an ex vivo cell can be part of a tissue sample excised from an organism such as a mammal (e.g., a human). In some embodiments, an in vitro cell can be a cell in cell culture. In some embodiments, an in vivo cell is a cell living in an organism such as a mammal (e.g., a human).

As used herein, the term "contacting" refers to the bringing together of indicated moieties or items in an in vitro system, an ex vivo system, or an in vivo system. For example, "contacting" a cell with a compound provided herein includes the act of administering that compound to a mammal (e.g., a human) containing that cell as well as, for example, introducing that compound into a cell culture containing that cell.

As used herein, the term "mammal" includes, without limitation, mice, rats, other rodents, rabbits, dogs, cats, swine, cattle, sheep, horses, elephants, deer, non-human primates (e.g., monkeys and apes), house pets, and humans.

As used herein, the phrase "effective amount" or "therapeutically effective amount" refers to the amount of active compound or pharmaceutical agent that elicits the biological or medicinal response in a tissue, system, mammal, or human that is being sought by a researcher, veterinarian, medical doctor, or other clinician.

As used herein, the term "treating" or "treatment" refers to (a) inhibiting a disease, disorder, or condition, for example, inhibiting a disease, disorder, or condition in a mammal (e.g., human) that is experiencing or displaying the pathology or symptomatology of the disease, disorder, or condition (e.g., arresting further development of the pathology and/or symptomatology), or (b) ameliorating the disease, disorder, or condition, for example, ameliorating a disease, disorder, or condition in a mammal (e.g., a human) that is experiencing or displaying the pathology or symptomatology of the disease, disorder, or condition (e.g., reversing the pathology and/or symptomatology).

As used herein, the term "preventing" or "prevention" of a disease, disorder, or condition refers to decreasing the risk of occurrence of the disease, disorder, or condition in a mammal or group of mammals (e.g., a mammal or group of mammals predisposed to or susceptible to the disease, disorder, or condition). In some embodiments, preventing a disease, disorder, or condition refers to decreasing the possibility of acquiring the disease, disorder, or condition and/or its associated symptoms. In some embodiments, preventing a disease, disorder, or condition refers to completely or almost completely stopping the disease, disorder, or condition from occurring.

REFERENCES

1. Giovannini, S., Onder, G., Liperoti, R., Russo, A., Carter, C., Capoluongo, E., Pahor, M., Bernabei, R., and Landi, F. 2011. Interleukin-6, C-reactive protein, and tumor necrosis factor-alpha as predictors of mortality in frail, community-living elderly individuals. J Am Geriatr Soc 59:1679-1685.
2. He, S., and Sharpless, N. E. 2017. Senescence in Health and Disease. Cell 169:1000-1011.
3. Ridker, P. M., Everett, B. M., Thuren, T., MacFadyen, J. G., Chang, W. H., Ballantyne, C., Fonseca, F., Nicolau, J., Koenig, W., Anker, S. D., et al. 2017. Antiinflammatory Therapy with Canakinumab for Atherosclerotic Disease. N Engl J Med 377:1119-1131.

EXAMPLES

Methods

25k THP1-NF-κB-LUC cells were dispensed into 384 well plate (per well). Cells were treated with compounds with various concentrations for 2 hours before addition of LPS (10 ng/mL) for 18 hours. Secreted luciferase activity were measured using quant-luc reagents (1 bag of luc reagent dilute to 40 mL, use 10 μL per well). Data were normalized to vehicle control and graphed. Compound $IC_{50}$ towards inhibiting NF-κB were determined through Prism. Similarly, 10k human PBMCs cells were cultured in 384 well plate (per well). Cells were treated with compounds with various concentrations for 2 hours before addition of LPS (10 ng/ml) for 18 hours, and supernatants were collected and assayed for TNF ELISA. Compound $IC_{50}$ towards inhibiting TNF release were determined through Prism.

Activity: "+">10 μM, "++">1 μM and <10 μM, "+++">0.1 μM and <1 μM, "++++"<0.1 μM.

Example 1—Bioassay Results for Tested Compounds

TABLE 1a

| No. | Compound | $IC_{50}$ (NF-κB assay) |
|---|---|---|
| BC18300 | 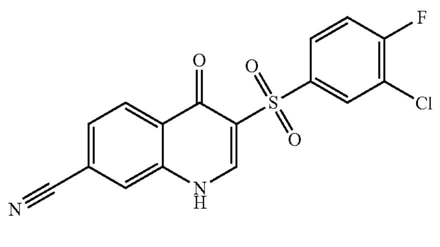 [SMILES: N#Cc1ccc2c(=O)c(S(=O)(=O)c3ccc(F)c(Cl)c3)c[nH]c2c1] | +++ |

TABLE 1a-continued
| No. | Compound | $IC_{50}$ (NF-κB assay) |
|---|---|---|
| BC18301 | 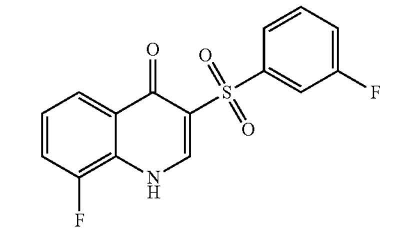 [SMILES: O=c1c(S(=O)(=O)c2cccc(F)c2)c[nH]c2c(F)cccc12] | ++ |
| BC18302 | 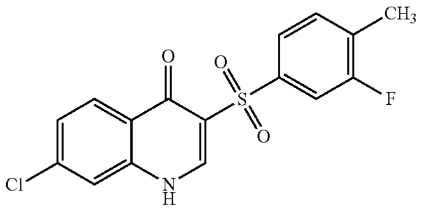 [SMILES: Cc1ccc(S(=O)(=O)c2c[nH]c3cc(Cl)ccc3c2=O)cc1F] | ++++ |
| BC18303 | 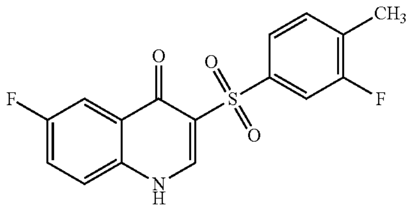 [SMILES: Cc1ccc(S(=O)(=O)c2c[nH]c3ccc(F)cc3c2=O)cc1F] | ++++ |
| BC18304 | 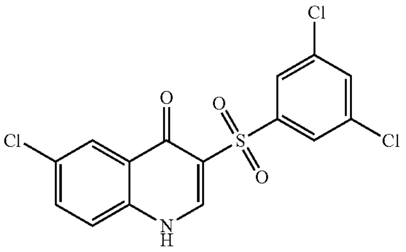 [SMILES: O=c1c(S(=O)(=O)c2cc(Cl)cc(Cl)c2)c[nH]c2ccc(Cl)cc12] | ++ |
| BC18305 | 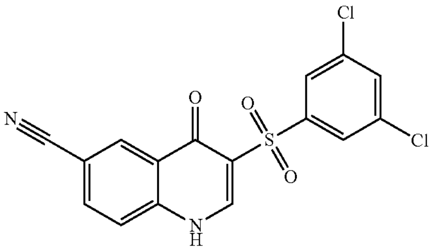 [SMILES: N#Cc1ccc2[nH]cc(S(=O)(=O)c3cc(Cl)cc(Cl)c3)c(=O)c2c1] | +++ |
| BC18306 | 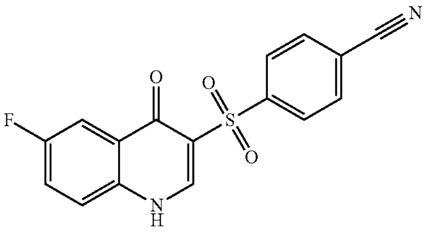 [SMILES: N#Cc1ccc(S(=O)(=O)c2c[nH]c3ccc(F)cc3c2=O)cc1] | + |

TABLE 1a-continued
| No. | Compound | $IC_{50}$ (NF-κB assay) |
|---|---|---|
| BC18307 | 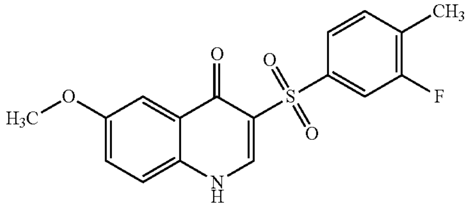 [SMILES: COc1ccc2[nH]cc(S(=O)(=O)c3ccc(C)c(F)c3)c(=O)c2c1] | +++ |
| BC18308 | 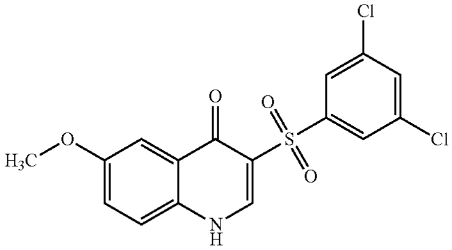 [SMILES: COc1ccc2[nH]cc(S(=O)(=O)c3cc(Cl)cc(Cl)c3)c(=O)c2c1] | + |
| BC18309 | 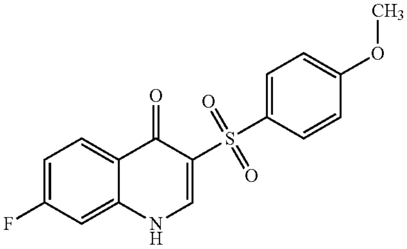 [SMILES: COc1ccc(S(=O)(=O)c2c[nH]c3cc(F)ccc3c2=O)cc1] | ++ |
| BC18310 | 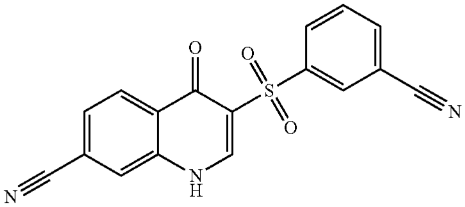 [SMILES: N#Cc1cccc(S(=O)(=O)c2c[nH]c3cc(C#N)ccc3c2=O)c1] | ++++ |
| BC18311 | 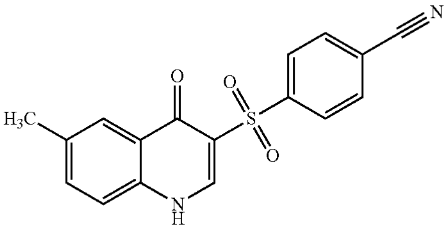 [SMILES: Cc1ccc2[nH]cc(S(=O)(=O)c3ccc(C#N)cc3)c(=O)c2c1] | + |
| BC18312 | 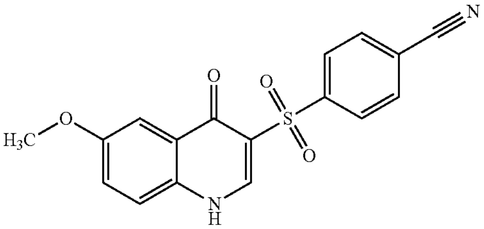 [SMILES: COc1ccc2[nH]cc(S(=O)(=O)c3ccc(C#N)cc3)c(=O)c2c1] | + |

TABLE 1a-continued
| No. | Compound | $IC_{50}$ (NF-κB assay) |
| --- | --- | --- |
| BC18318 | 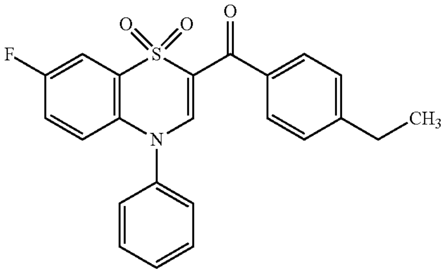 [SMILES: CCc1ccc(C(=O)C2=CN(c3ccccc3)c3ccc(F)cc3S2(=O)=O)cc1] | + |
| BC18320 | 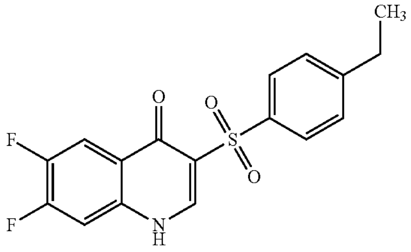 [SMILES: CCc1ccc(S(=O)(=O)c2c[nH]c3cc(F)c(F)cc3c2=O)cc1] | ++++ |
| BC18321 | 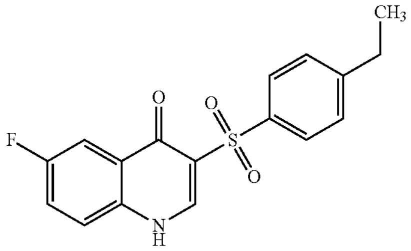 [SMILES: CCc1ccc(S(=O)(=O)c2c[nH]c3ccc(F)cc3c2=O)cc1] | +++ |
| BC18322 | 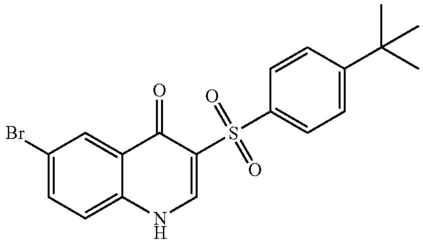 [SMILES: CC(C)(C)c1ccc(S(=O)(=O)c2c[nH]c3ccc(Br)cc3c2=O)cc1] | ++ |
| BC18323 | 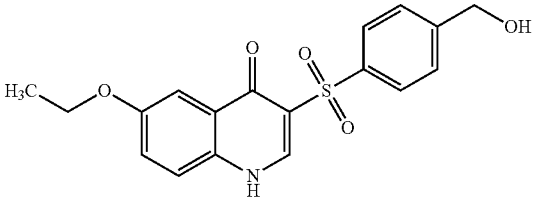 [SMILES: CCOc1ccc2[nH]cc(S(=O)(=O)c3ccc(CO)cc3)c(=O)c2c1] | +++ |
| BC18324 | 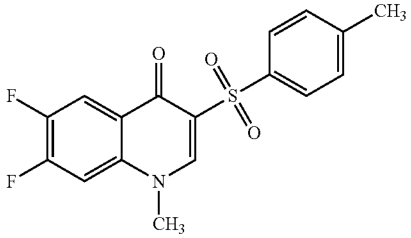 [SMILES: Cc1ccc(S(=O)(=O)c2cn(C)c3cc(F)c(F)cc3c2=O)cc1] | + |

TABLE 1a-continued
| No. | Compound | $IC_{50}$ (NF-κB assay) |
|---|---|---|
| BC18325 | 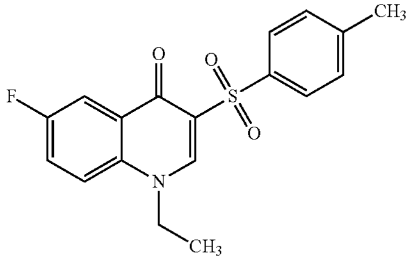 [SMILES: CCn1cc(S(=O)(=O)c2ccc(C)cc2)c(=O)c2cc(F)ccc21] | + |
| BC18326 | 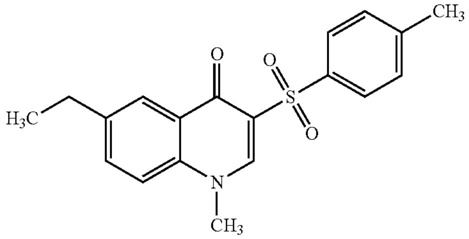 [SMILES: CCc1ccc2c(c1)c(=O)c(S(=O)(=O)c1ccc(C)cc1)cn2C] | + |
| BC18327 | 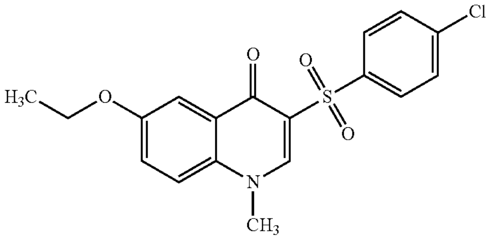 [SMILES: CCOc1ccc2c(c1)c(=O)c(S(=O)(=O)c1ccc(Cl)cc1)cn2C] | + |
| BC18328 | 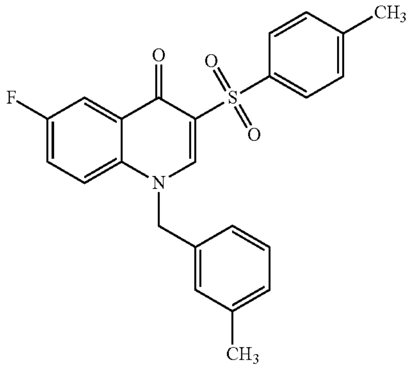 [SMILES: Cc1ccc(S(=O)(=O)c2cn(Cc3cccc(C)c3)c3ccc(F)cc3c2=O)cc1] | ++ |
| BC18329 | 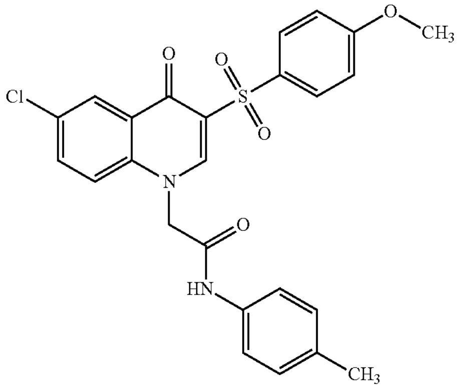 [SMILES: COc1ccc(S(=O)(=O)c2cn(CC(=O)Nc3ccc(C)cc3)c3ccc(Cl)cc3c2=O)cc1] | + |

TABLE 1a-continued
| No. | Compound | IC$_{50}$ (NF-κB assay) |
|---|---|---|
| BC18330 | 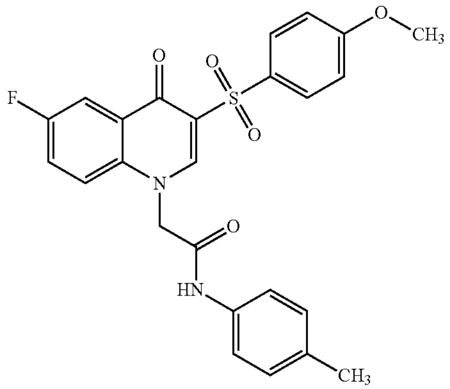 [SMILES: COc1ccc(S(=O)(=O)c2cn(CC(=O)Nc3ccc(C)cc3)c3ccc(F)cc3c2=O)cc1] | + |
| BC18331 | 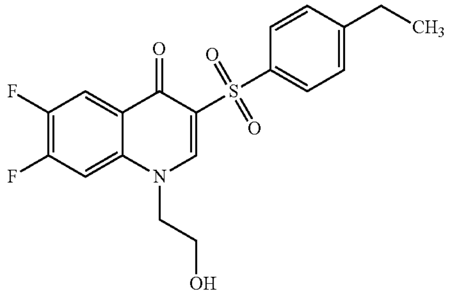 [SMILES: CCc1ccc(S(=O)(=O)c2cn(CCO)c3cc(F)c(F)cc3c2=O)cc1] | + |
| BC18332 | 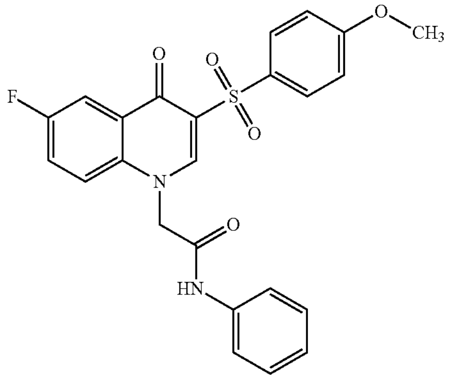 [SMILES: COc1ccc(S(=O)(=O)c2cn(CC(=O)Nc3ccccc3)c3ccc(F)cc3c2=O)cc1] | + |
| BC18333 | 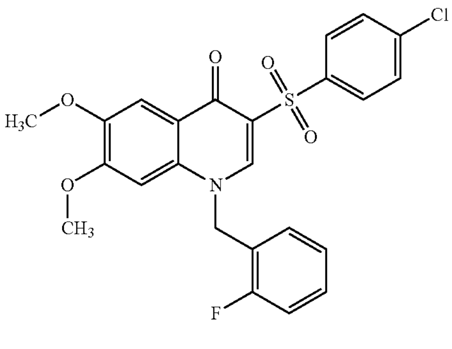 [SMILES: COc1cc2c(=O)c(S(=O)(=O)c3ccc(Cl)cc3)cn(Cc3ccccc3F)c2cc1OC] | + |

TABLE 1a-continued
| No. | Compound | $IC_{50}$ (NF-κB assay) |
|---|---|---|
| BC18334 | 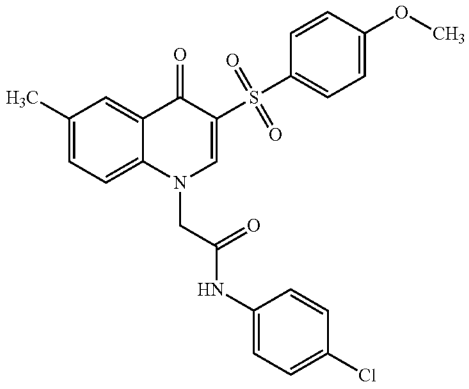 | + |
| BC18335 | 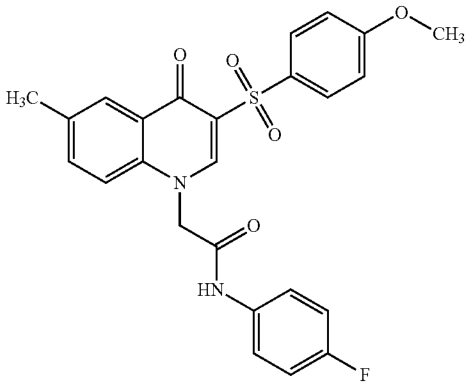 | + |
| BC18336 | 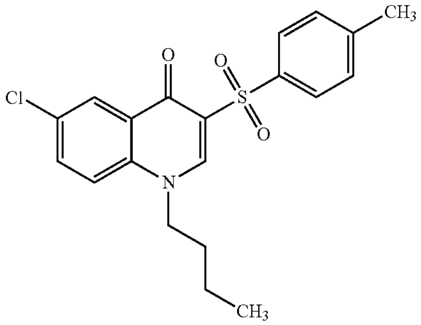 [SMILES: CCCCn1cc(S(=O)(=O)c2ccc(C)cc2)c(=O)c2cc(Cl)ccc21] | + |
| BC18337 | 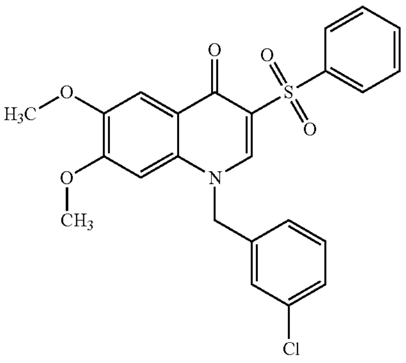 [SMILES: COc1cc2c(=O)c(S(=O)(=O)c3ccccc3)cn(Cc3cccc(Cl)c3)c2cc1OC] | + |

TABLE 1a-continued
| No. | Compound | IC50 (NF-κB assay) |
|---|---|---|
| BC18338 | 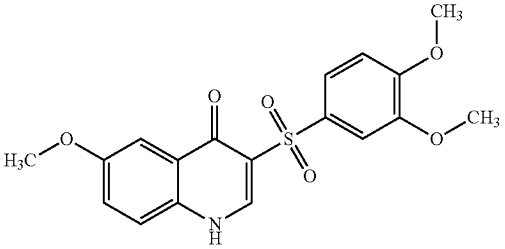 | + |
| BC18339 | 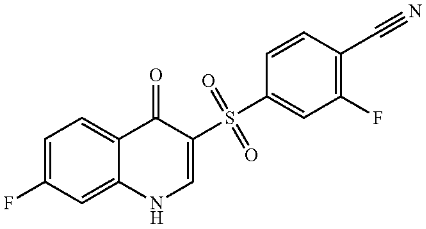 [SMILES: N#Cc1ccc(S(=O)(=O)c2c[nH]c3cc(F)ccc3c2=O)cc1F] | +++ |
| BC18340 | 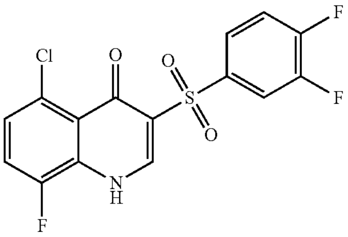 [SMILES: O=c1c(S(=O)(=O)c2ccc(F)c(F)c2)c[nH]c2c(F)ccc(Cl)c12] | ++++ |
| BC19001 | 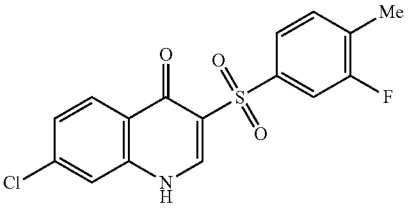 [SMILES: Cc1ccc(S(=O)(=O)c2c[nH]c3cc(Cl)ccc3c2=O)cc1F] | |
| BC19003 | 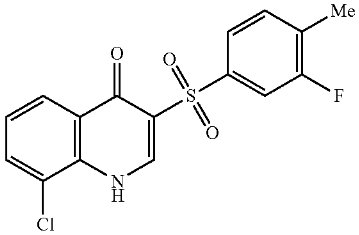 [SMILES: Cc1ccc(S(=O)(=O)c2c[nH]c3c(Cl)cccc3c2=O)cc1F] | |
| BC19004 | 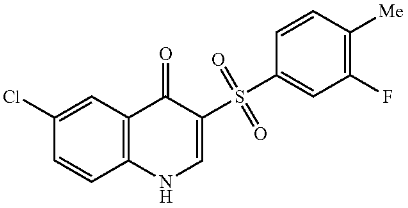 [SMILES: Cc1ccc(S(=O)(=O)c2c[nH]c3ccc(Cl)cc3c2=O)cc1F] | |

TABLE 1a-continued
| No. | Compound | $IC_{50}$ (NF-κB assay) |
|---|---|---|
| BC19005 | 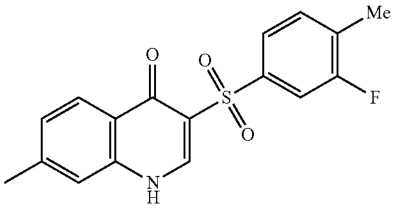 [SMILES: Cc1ccc2c(=O)c(S(=O)(=O)c3ccc(C)c(F)c3)c[nH]c2c1] | |
| BC19006 | 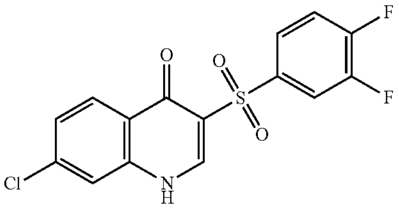 [SMILES: O=c1c(S(=O)(=O)c2ccc(F)c(F)c2)c[nH]c2cc(Cl)ccc12] | |
| BC19007 | 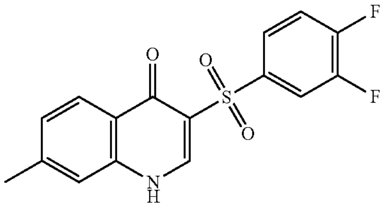 [SMILES: Cc1ccc2c(=O)c(S(=O)(=O)c3ccc(F)c(F)c3)c[nH]c2c1] | |
TABLE 1b
| No. | Compound | $IC_{50}$ (NF-κB assay) |
|---|---|---|
| BC18313 | 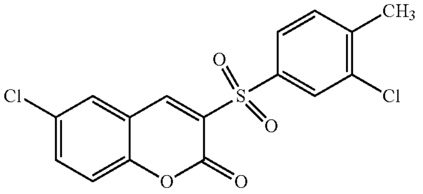 | + |
| BC18314 | 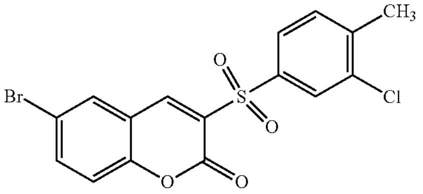 [SMILES: Cc1ccc(S(=O)(=O)c2cc3cc(Cl)ccc3oc2=O)cc1Cl] | + |
| BC18316 | 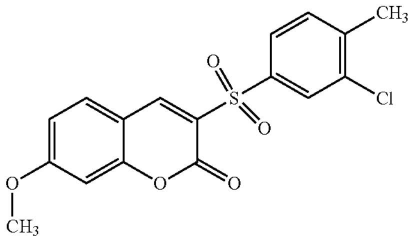 [SMILES: COc1ccc2cc(S(=O)(=O)c3ccc(C)c(Cl)c3)c(=O)oc2c1] | + |

TABLE 1b-continued
| No. | Compound | $IC_{50}$ (NF-κB assay) |
|---|---|---|
| BC18317 | 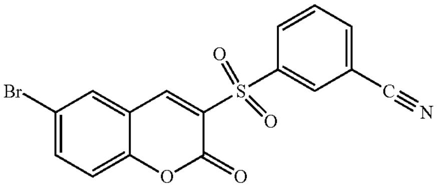 [SMILES: N#Cc1cccc(S(=O)(=O)c2cc3cc(Br)ccc3oc2=O)c1] | + |
| BC18319 | 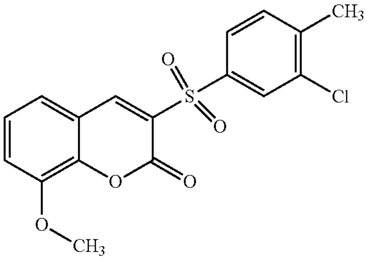 [SMILES: COc1cccc2cc(S(=O)(=O)c3ccc(C)c(Cl)c3)c(=O)oc12] | + |
TABLE 1c
| No. | Compound | $IC_{50}$ (NF-κB assay) |
|---|---|---|
| BC18315 | 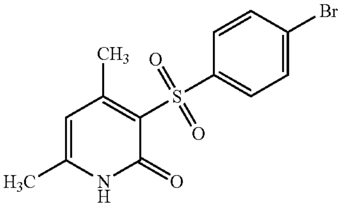 [SMILES: Cc1cc(C)c(S(=O)(=O)c2ccc(Br)cc2)c(=O)[nH]1] | + |
TABLE 1d
| BC No. | ZE No. | Compound | $IC_{50}$ (NF-κB assay) | $IC_{50}$ (TNF assay) |
|---|---|---|---|---|
| BC19121 | ZE22-0017 | 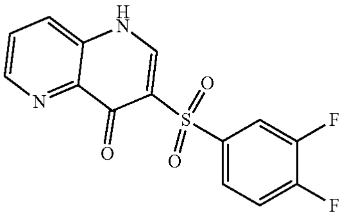 [SMILES: O=c1c(S(=O)(=O)c2ccc(F)c(F)c2)c[nH]c2cccnc12] | + | + |
| BC19122 | ZE22-0018 | 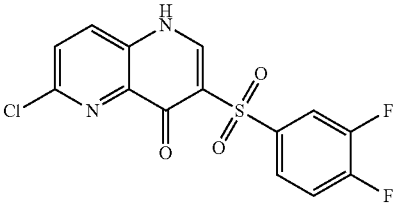 [SMILES: O=c1c(S(=O)(=O)c2ccc(F)c(F)c2)c[nH]c2ccc(Cl)nc12] | + | + |

TABLE 1d-continued
| BC No. | ZE No. | Compound | $IC_{50}$ (NF-κB assay) | $IC_{50}$ (TNF assay) |
|---|---|---|---|---|
| BC19123 | ZE22-0021 | 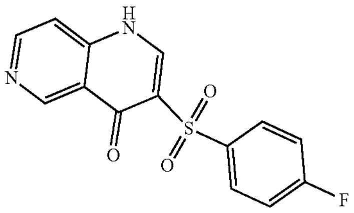 [SMILES: O=c1c(S(=O)(=O)c2ccc(F)cc2)c[nH]c2ccncc12] | ++ | + |
| BC19124 | ZE22-0024 | 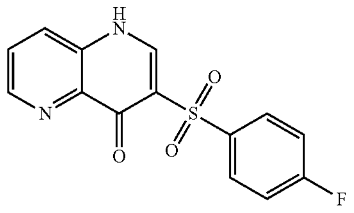 [SMILES: O=c1c(S(=O)(=O)c2ccc(F)cc2)c[nH]c2cccnc12] | + | + |
| BC19160 | ZE22-0019 | 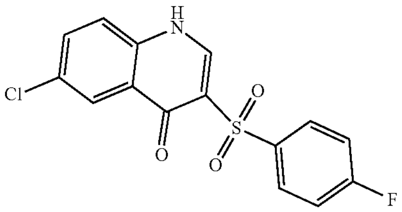 [SMILES: O=c1c(S(=O)(=O)c2ccc(F)cc2)c[nH]c2ccc(Cl)cc12] | + | + |
| BC19201 | ZE22-0020 | 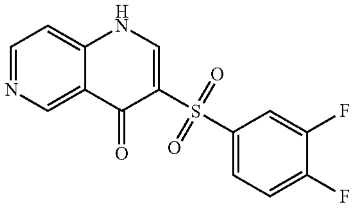 [SMILES: O=c1c(S(=O)(=O)c2ccc(F)c(F)c2)c[nH]c2ccncc12] | + | + |
| BC19202 | ZE22-0022 | 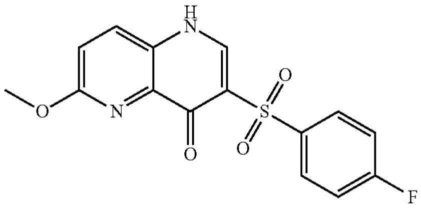 [SMILES: COc1ccc2[nH]cc(S(=O)(=O)c3ccc(F)cc3)c(=O)c2n1] | + | + |
| BC 19203 | ZE22-0023 | 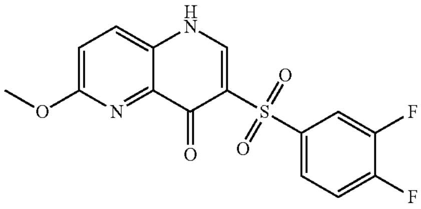 [SMILES: COc1ccc2[nH]cc(S(=O)(=O)c3ccc(F)c(F)c3)c(=O)c2n1] | ++ | + |
| BC19256 | ZE22-0016 | 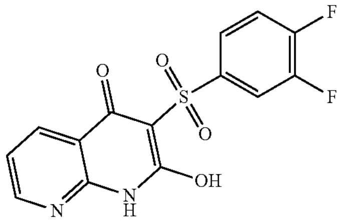 [SMILES: O=c1c(S(=O)(=O)c2ccc(F)c(F)c2)c(O)[nH]c2ncccc12] | ++ | + |

TABLE 1d-continued
| BC No. | ZE No. | Compound | $IC_{50}$ (NF-κB assay) | $IC_{50}$ (TNF assay) |
|---|---|---|---|---|
| BC19257 | ZE22-0025 | 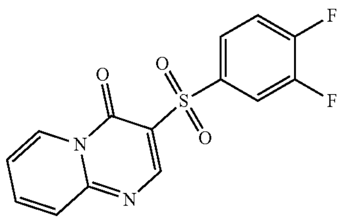 [SMILES: O=c1c(S(=O)(=O)c2ccc(F)c(F)c2)cnc2ccccn12] | + | + |
| BC19258 | ZE22-0027 | 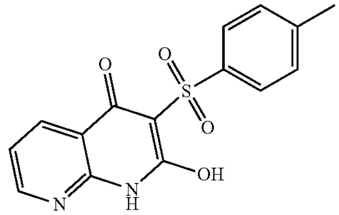 [SMILES: Cc1ccc(S(=O)(=O)c2c(O)[nH]c3ncccc3c2=O)cc1] | ++ | + |
| BC19259 | ZE22-0029 | 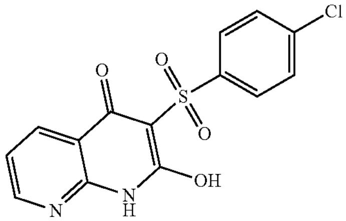 [SMILES: O=c1c(S(=O)(=O)c2ccc(Cl)cc2)c(O)[nH]c2ncccc12] | ++ | + |
| BC19322 | ZE22-0015 | 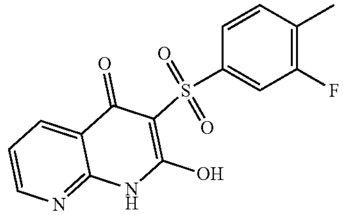 [SMILES: Cc1ccc(S(=O)(=O)c2c(O)[nH]c3ncccc3c2=O)cc1F] | ++ | + |
| BC19323 | ZE22-0028 | 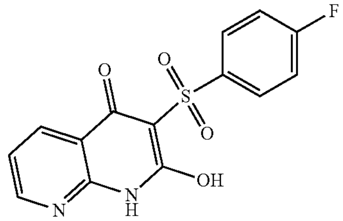 [SMILES: O=c1c(S(=O)(=O)c2ccc(F)cc2)c(O)[nH]c2ncccc12] | + | + |
| BC19409 | ZE22-0013 | 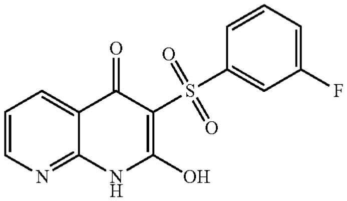 [SMILES: O=c1c(S(=O)(=O)c2cccc(F)c2)c(O)[nH]c2ncccc12] | + | + |

TABLE 1e
| BC No. | ZE No. | Compound | $IC_{50}$ (NF-κB assay) | $IC_{50}$ (TNF assay) |
|---|---|---|---|---|
| BC19196 | ZE22-0004 | 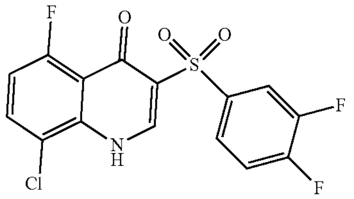 [SMILES: O=c1c(S(=O)(=O)c2ccc(F)c(F)c2)c[nH]c2c(Cl)ccc(F)c12] | +++ | + |
| BC19197 | ZE22-0007 | 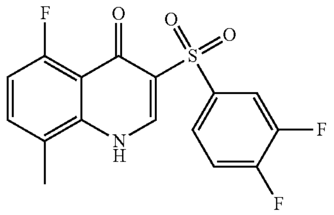 [SMILES: Cc1ccc(C)c2c(=O)c(S(=O)(=O)c3ccc(F)c(F)c3)c[nH]c12] | +++ | + |
| BC19198 | ZE22-0009 | 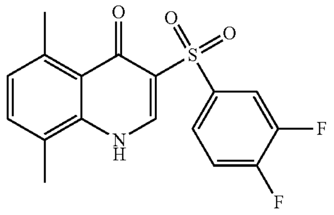 | ++ | + |
| BC19199 | ZE22-0010 | 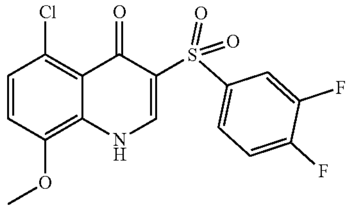 [SMILES: COc1ccc(Cl)c2c(=O)c(S(=O)(=O)c3ccc(F)c(F)c3)c[nH]c12] | +++ | + |
| BC19200 | ZE22-0011 | 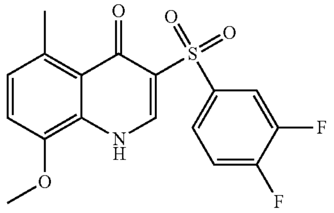 [SMILES: COc1ccc(C)c2c(=O)c(S(=O)(=O)c3ccc(F)c(F)c3)c[nH]c12] | ++ | + |
| BC19252 | ZE22-0001 | 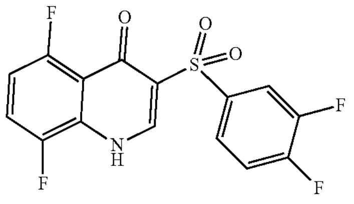 [SMILES: O=c1c(S(=O)(=O)c2ccc(F)c(F)c2)c[nH]c2c(F)ccc(F)c12] | ++++ | + |
| BC19253 | ZE22-0002 | 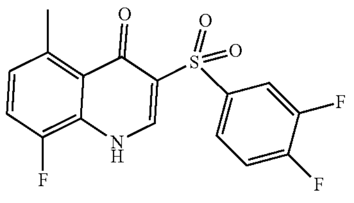 [SMILES: Cc1ccc(F)c2[nH]cc(S(=O)(=O)c3ccc(F)c(F)c3)c(=O)c12] | ++++ | + |

TABLE 1e-continued
| BC No. | ZE No. | Compound | $IC_{50}$ (NF-κB assay) | $IC_{50}$ (TNF assay) |
|---|---|---|---|---|
| BC19254 | ZE22-0008 | 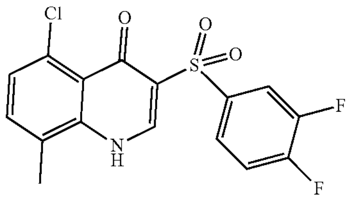 | ++++ | + |
| BC19255 | ZE22-0012 | 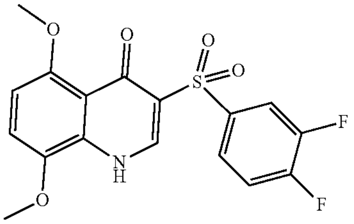 [SMILES: COc1ccc(OC)c2c(=O)c(S(=O)(=O)c3ccc(F)c(F)c3)c[nH]c12] | ++ | + |
TABLE 1f
| BC No. | ZE No. | Compound | $IC_{50}$ (NF-κB assay) | $IC_{50}$ (TNF assay) |
|---|---|---|---|---|
| BC19324 | ZE22-0030 | 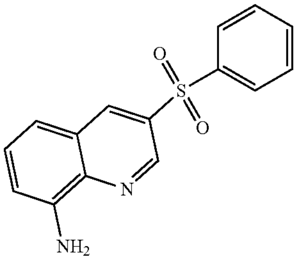 [SMILES: Nc1cccc2cc(S(=O)(=O)c3ccccc3)cnc12] | + | +++ |
| BC19325 | ZE22-0032 | 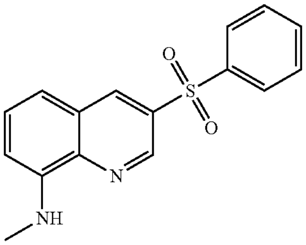 [SMILES: CNc1cccc2cc(S(=O)(=O)c3ccccc3)cnc12] | + | ++ |
| BC19326 | ZE22-0034 | 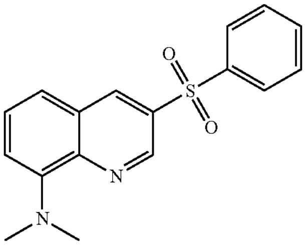 [SMILES: CN(C)c1cccc2cc(S(=O)(=O)c3ccccc3)cnc12] | + | ++ |

TABLE 1g
| BC No. | Structure | $IC_{50}$ (NF-κB assay) | $IC_{50}$ (TNF assay) |
|---|---|---|---|
| BC19454 | 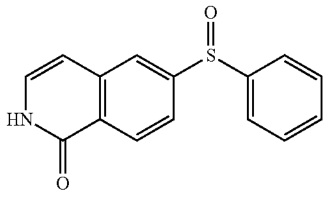 [SMILES: O=c1[nH]ccc2cc(S(=O)c3ccccc3)ccc12] | + | + |
| BC19515 | 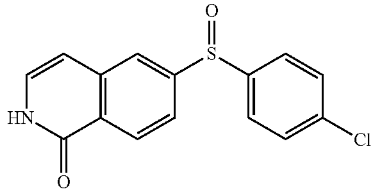 [SMILES: O=c1[nH]ccc2cc(S(=O)c3ccc(Cl)cc3)ccc12] | + | + |
| BC19516 | 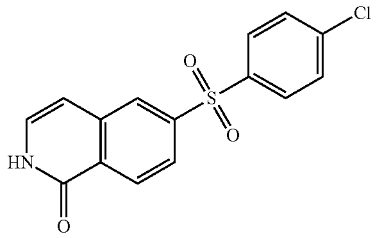 [SMILES: O=c1[nH]ccc2cc(S(=O)(=O)c3ccc(Cl)cc3)ccc12] | + | + |
| BC19517 | 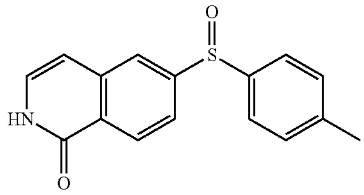 [SMILES: Cc1ccc(S(=O)c2ccc3c(=O)[nH]ccc3c2)cc1] | + | + |
| BC19518 | 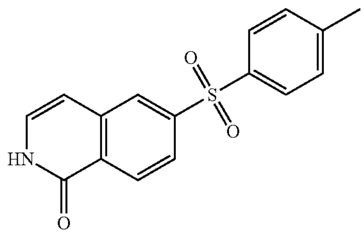 [SMILES: Cc1ccc(S(=O)(=O)c2ccc3c(=O)[nH]ccc3c2)cc1] | + | + |
| BC19519 | 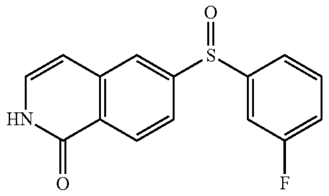 [SMILES: O=c1[nH]ccc2cc(S(=O)c3cccc(F)c3)ccc12] | + | + |
| BC19520 | 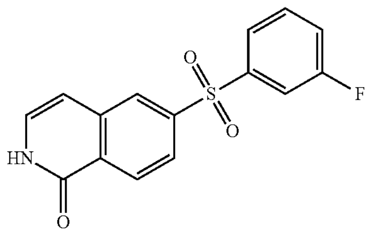 [SMILES: O=c1[nH]ccc2cc(S(=O)(=O)c3cccc(F)c3)ccc12] | + | + |

TABLE 1g-continued
| BC No. | Structure | $IC_{50}$ (NF-κB assay) | $IC_{50}$ (TNF assay) |
|---|---|---|---|
| BC19579 | 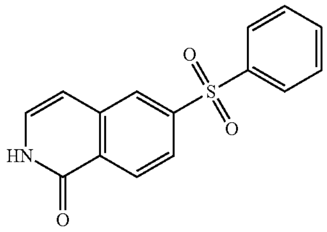 [SMILES: O=c1[nH]ccc2cc(S(=O)(=O)c3ccccc3)ccc12] | + | + |
| BC19580 | 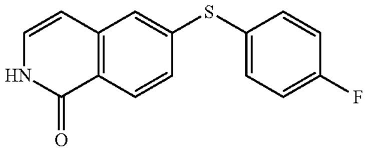 [SMILES: O=c1[nH]ccc2cc(Sc3ccc(F)cc3)ccc12] | + | + |
TABLE 1h
| BC No. | Structure | $IC_{50}$ (NF-κB assay) | $IC_{50}$ (TNF assay) |
|---|---|---|---|
| BC19455 | 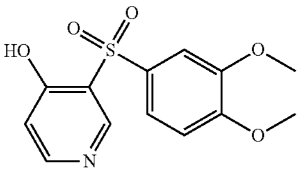 [SMILES: COc1ccc(S(=O)(=O)c2cnccc2O)cc1OC] | + | + |
| BC19456 | 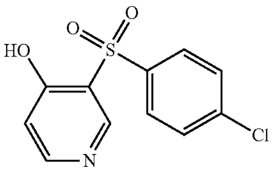 [SMILES: O=S(=O)(c1ccc(Cl)cc1)c1cnccc1O] | + | + |
| BC19457 | 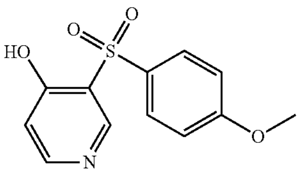 [SMILES: COc1ccc(S(=O)(=O)c2cnccc2O)cc1] | + | + |
| BC19458 | 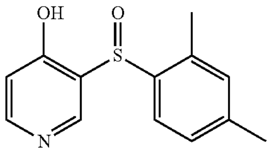 [SMILES: Cc1ccc(S(=O)c2cnccc2O)c(C)c1] | + | + |
TABLE 1h-continued
| BC No. | Structure | $IC_{50}$ (NF-κB assay) | $IC_{50}$ (TNF assay) |
|---|---|---|---|
| BC19459 | 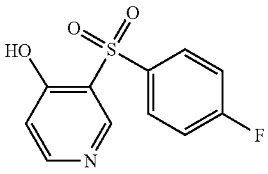 [SMILES: O=S(=O)(c1ccc(F)cc1)c1cnccc1O] | + | + |
| BC 19460 | 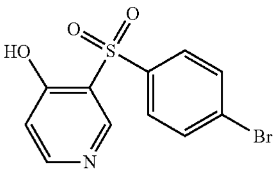 [SMILES: O=S(=O)(c1ccc(Br)cc1)c1cnccc1O] | + | + |
| BC19461 | 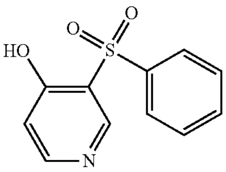 [SMILES: O=S(=O)(c1ccccc1)c1cnccc1O] | + | + |

Example 2—Bioassay Results for Tested Compounds
TABLE 2a
| BC No. | Compound | $IC_{50}$ NF-κB assay |
|---|---|---|
| BC181300 | 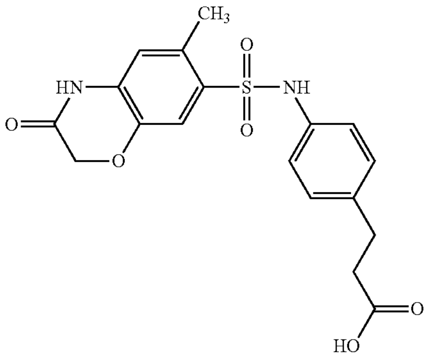 [SMILES: Cc1cc2c(cc1S(=O)(=O)Nc1ccc(CCC(=O)O)cc1)OCC(=O)N2] | + |
| BC181301 | 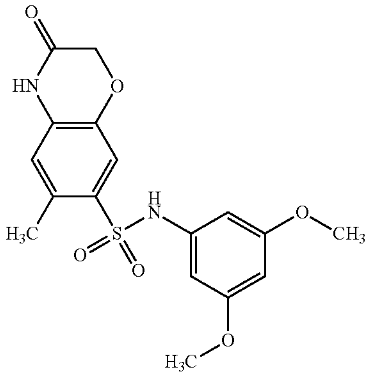 [SMILES: COc1cc(NS(=O)(=O)c2cc3c(cc2C)NC(=O)CO3)cc(OC)c1] | + |
| BC181302 | 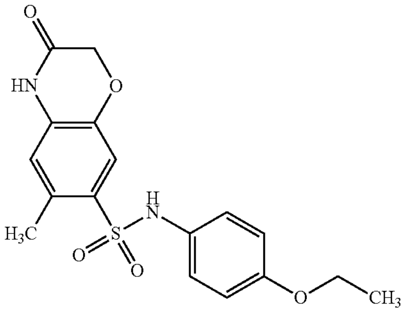 [SMILES: CCOc1ccc(NS(=O)(=O)c2cc3c(cc2C)NC(=O)CO3)cc1] | ++++ |
| BC181303 | 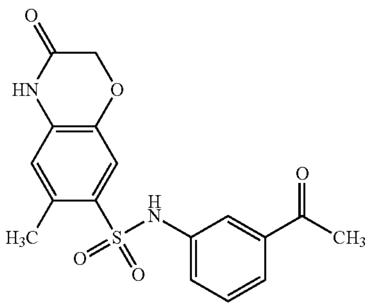 [SMILES: CC(=O)c1cccc(NS(=O)(=O)c2cc3c(cc2C)NC(=O)CO3)c1] | ++++ |

TABLE 2a-continued
| BC No. | Compound | $IC_{50}$ NF-κB assay |
|---|---|---|
| BC181304 | 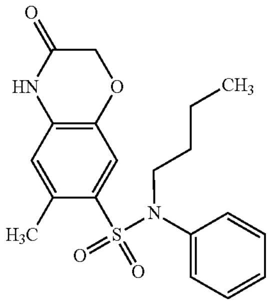 [SMILES: CCCCN(c1ccccc1)S(=O)(=O)c1cc2c(cc1C)NC(=O)CO2] | + |
| BC181305 | 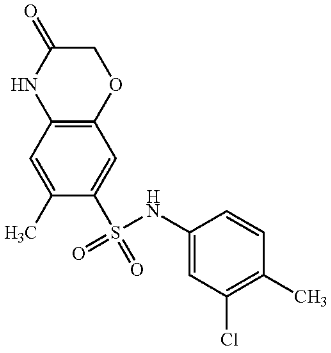 [SMILES: Cc1ccc(NS(=O)(=O)c2cc3c(cc2C)NC(=O)CO3)cc1Cl] | ++++ |
| BC181306 | 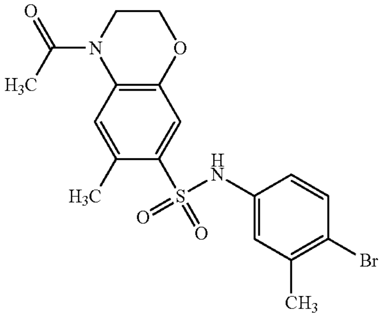 [SMILES: CC(=O)N1CCOc2cc(S(=O)(=O)Nc3ccc(Br)c(C)c3)c(C)cc21] | ++ |
| BC181307 | 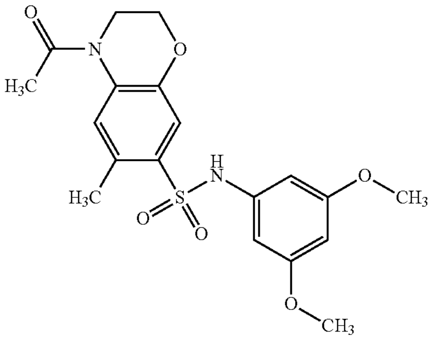 [SMILES: COc1cc(NS(=O)(=O)c2cc3c(cc2C)N(C(C)=O)CCO3)cc(OC)c1] | + |

TABLE 2a-continued
| BC No. | Compound | IC50 NF-κB assay |
|---|---|---|
| BC181308 | 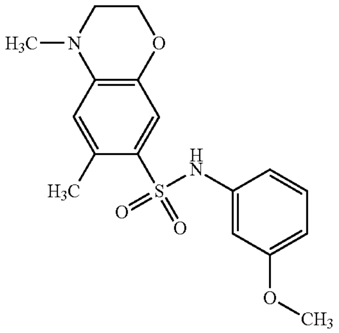 | + |
| BC181309 | 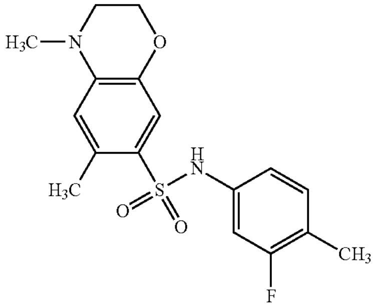 | + |
| BC181310 | 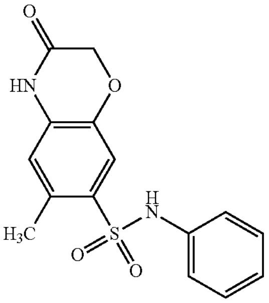 [SMILES: Cc1cc2c(cc1S(=O)(=O)Nc1ccccc1)OCC(=O)N2] | ++++ |
| BC181311 | 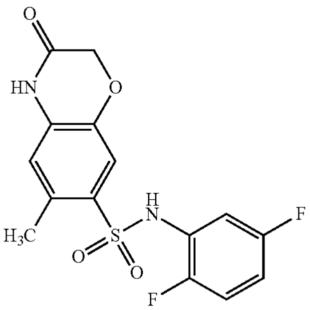 [SMILES: Cc1cc2c(cc1S(=O)(=O)Nc1cc(F)ccc1F)OCC(=O)N2] | ++++ |

TABLE 2a-continued
| BC No. | Compound | IC50 NF-κB assay |
|---|---|---|
| BC181312 | 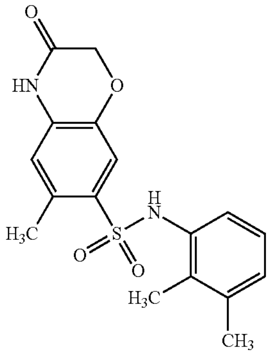 [SMILES: Cc1cc2c(cc1S(=O)(=O)Nc1cccc(C)c1C)OCC(=O)N2] | ++ |
| BC181313 | 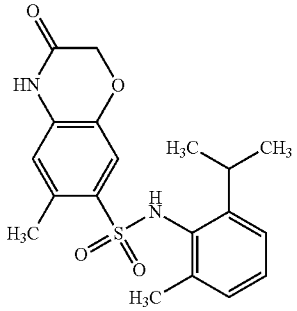 [SMILES: Cc1cc2c(cc1S(=O)(=O)Nc1c(C)cccc1C(C)C)OCC(=O)N2] | + |
| BC181314 | 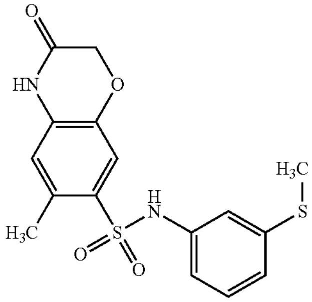 [SMILES: CSc1cccc(NS(=O)(=O)c2cc3c(cc2C)NC(=O)CO3)c1] | ++++ |
| BC181315 | 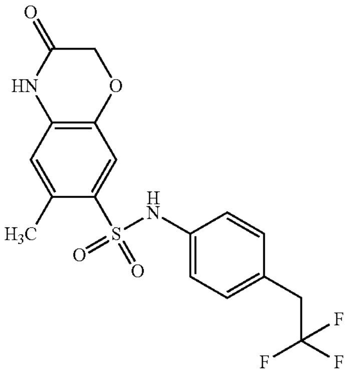 [SMILES: Cc1cc2c(cc1S(=O)(=O)Nc1ccc(CC(F)(F)F)cc1)OCC(=O)N2] | ++++ |

TABLE 2a-continued
| BC No. | Compound | $IC_{50}$ NF-κB assay |
|---|---|---|
| BC181316 | 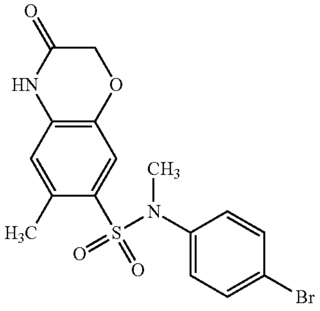 [SMILES: Cc1cc2c(cc1S(=O)(=O)N(C)c1ccc(Br)cc1)OCC(=O)N2] | + |
| BC181317 | 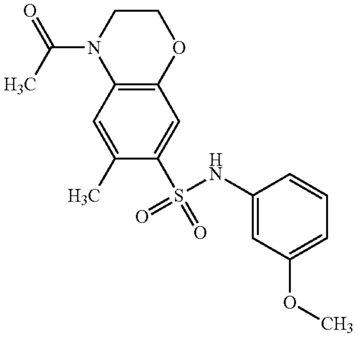 [SMILES: COc1cccc(NS(=O)(=O)c2cc3c(cc2C)N(C(C)=O)CCO3)c1] | + |
| BC181318 | 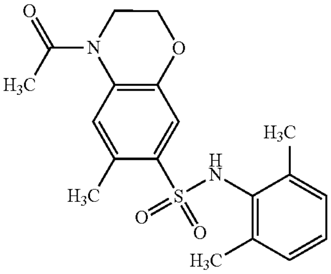 [SMILES: CC(=O)N1CCOc2cc(S(=O)(=O)Nc3c(C)cccc3C)c(C)cc21] | + |
| BC181319 | 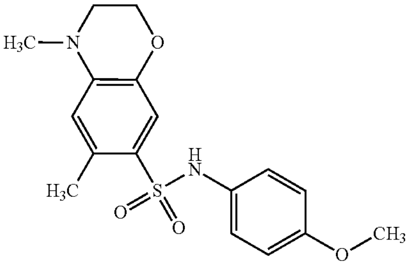 | + |
| BC181320 | 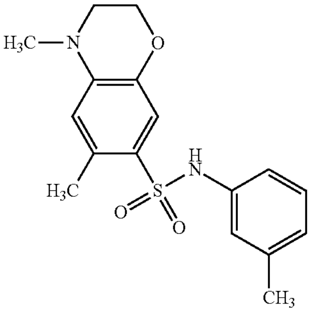 [SMILES: Cc1cccc(NS(=O)(=O)c2cc3c(cc2C)N(C)CCO3)c1] | + |

TABLE 2a-continued
| BC No. | Compound | $IC_{50}$ NF-κB assay |
|---|---|---|
| BC181321 | 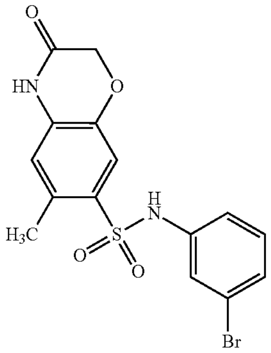 [SMILES: Cc1cc2c(cc1S(=O)(=O)Nc1cccc(Br)c1)OCC(=O)N2] | ++++ |
| BC181322 | 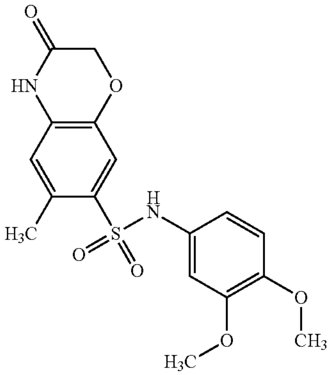 [SMILES: COc1ccc(NS(=O)(=O)c2cc3c(cc2C)NC(=O)CO3)cc1OC] | + |
| BC181323 | 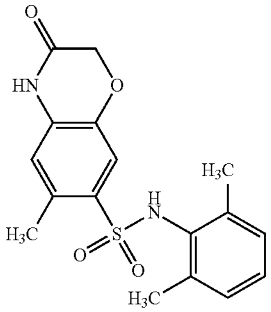 [SMILES: Cc1cc2c(cc1S(=O)(=O)Nc1c(C)cccc1C)OCC(=O)N2] | + |
| BC181324 | 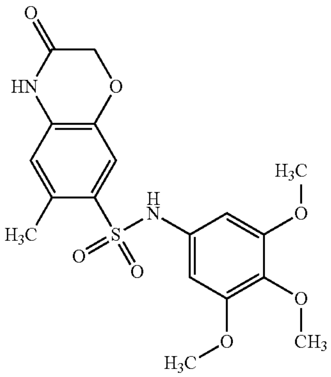 [SMILES: COc1cc(NS(=O)(=O)c2cc3c(cc2C)NC(=O)CO3)cc(OC)c1OC] | + |

TABLE 2a-continued
| BC No. | Compound | $IC_{50}$ NF-κB assay |
|---|---|---|
| BC181325 | 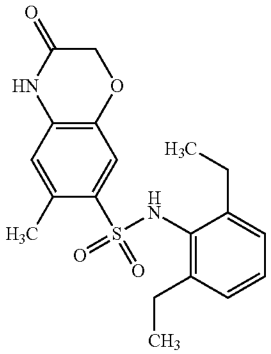 [SMILES: CCc1cccc(CC)c1NS(=O)(=O)c1cc2c(cc1C)NC(=O)CO2] | + |
| BC181326 | 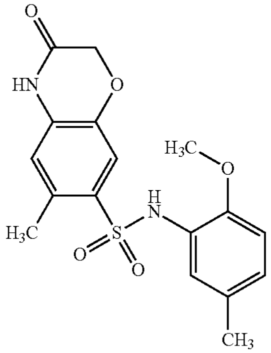 [SMILES: COc1ccc(C)cc1NS(=O)(=O)c1cc2c(cc1C)NC(=O)CO2] | + |
| BC181327 | 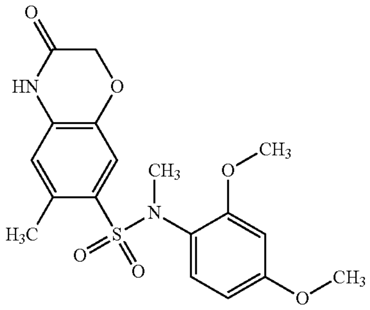 [SMILES: COc1ccc(N(C)S(=O)(=O)c2cc3c(cc2C)NC(=O)CO3)c(OC)c1] | + |
| BC181328 | 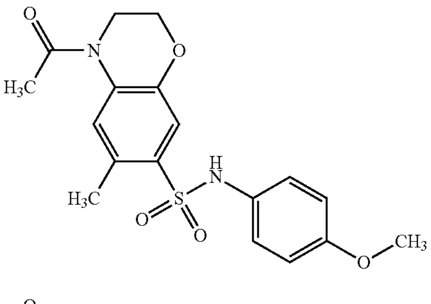 | + |
| BC181329 | 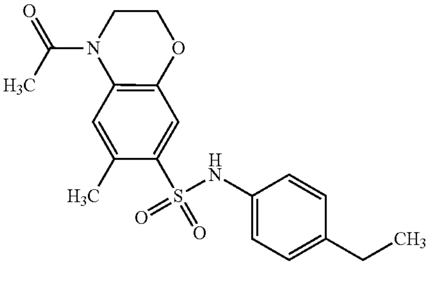 [SMILES: CCc1ccc(NS(=O)(=O)c2cc3c(cc2C)N(C(C)=O)CCO3)cc1] | ++ |

TABLE 2a-continued
| BC No. | Compound | IC50 NF-κB assay |
|---|---|---|
| BC181330 | 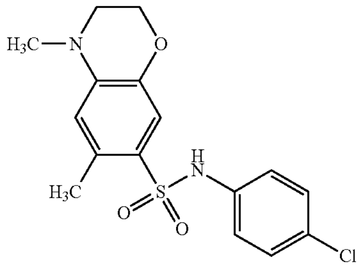 [SMILES: Cc1cc2c(cc1S(=O)(=O)Nc1ccc(Cl)cc1)OCCN2C] | ++ |
| BC181331 | 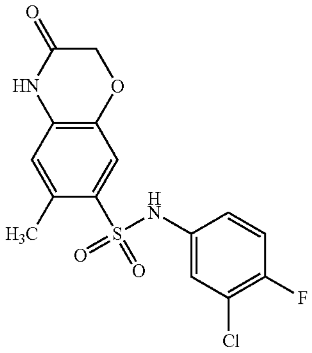 [SMILES: Cc1cc2c(cc1S(=O)(=O)Nc1ccc(F)c(Cl)c1)OCC(=O)N2] | ++++ |
| BC181332 | 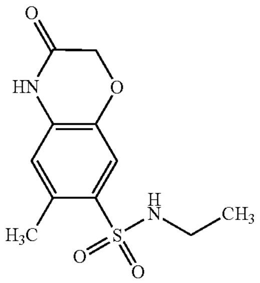 [SMILES: CCNS(=O)(=O)c1cc2c(cc1C)NC(=O)CO2] | + |
| BC181333 | 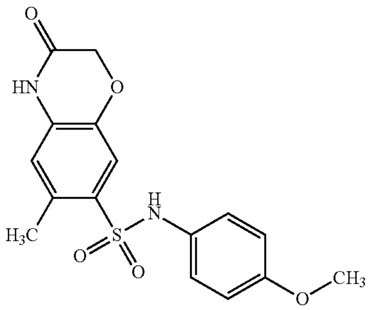 [SMILES: COc1ccc(NS(=O)(=O)c2cc3c(cc2C)NC(=O)CO3)cc1] | ++ |
| BC181334 | 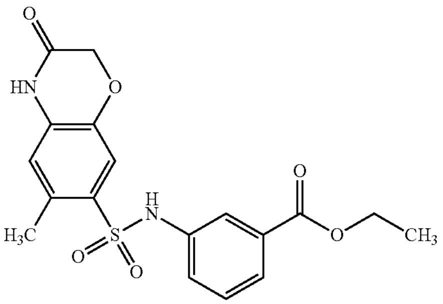 [SMILES: CCOC(=O)c1cccc(NS(=O)(=O)c2cc3c(cc2C)NC(=O)CO3)c1] | ++ |

TABLE 2a-continued
| BC No. | Compound | IC50 NF-κB assay |
|---|---|---|
| BC181335 | 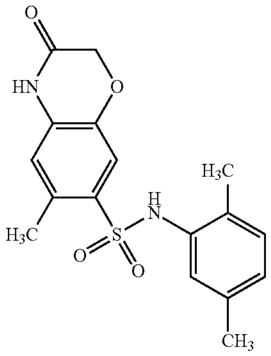 [SMILES: Cc1ccc(C)c(NS(=O)(=O)c2cc3c(cc2C)NC(=O)CO3)c1] | + |
| BC181336 | 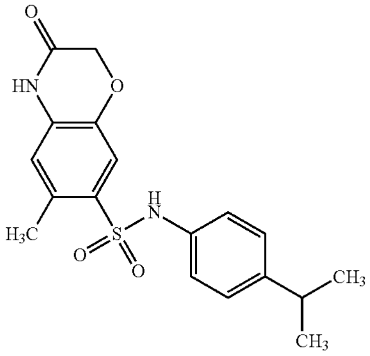 [SMILES: Cc1cc2c(cc1S(=O)(=O)Nc1ccc(C(C)C)cc1)OCC(=O)N2] | ++++ |
| BC181337 | 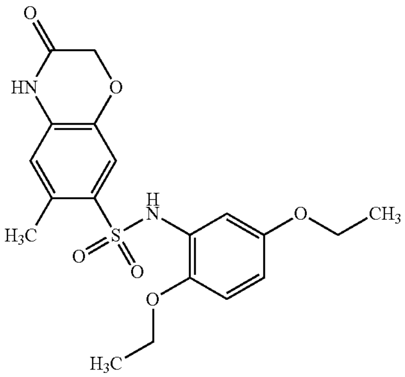 [SMILES: CCOc1ccc(OCC)c(NS(=O)(=O)c2cc3c(cc2C)NC(=O)CO3)c1] | + |
| BC181338 | 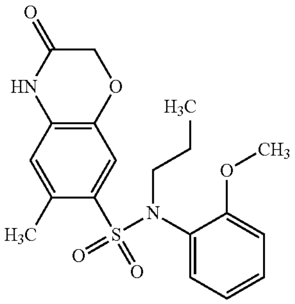 [SMILES: CCCN(c1ccccc1OC)S(=O)(=O)c1cc2c(cc1C)NC(=O)CO2] | ++ |

TABLE 2a-continued
| BC No. | Compound | $IC_{50}$ NF-κB assay |
|---|---|---|
| BC181339 | 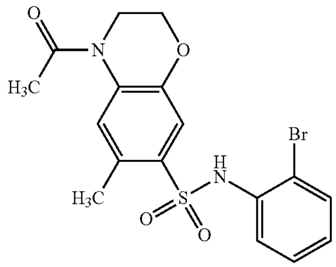 [SMILES: CC(=O)N1CCOc2cc(S(=O)(=O)Nc3ccccc3Br)c(C)cc21] | + |
| BC181340 | 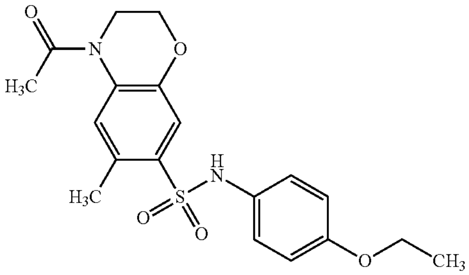 [SMILES: CCOc1ccc(NS(=O)(=O)c2cc3c(cc2C)N(C(C)=O)CCO3)cc1] | + |
| BC181341 | 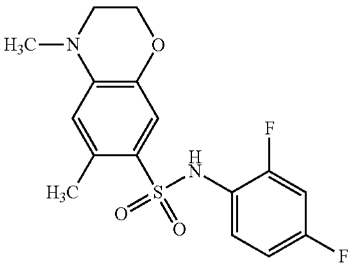 [SMILES: Cc1cc2c(cc1S(=O)(=O)Nc1ccc(F)cc1F)OCCN2C] | ++ |
| BC181342 | 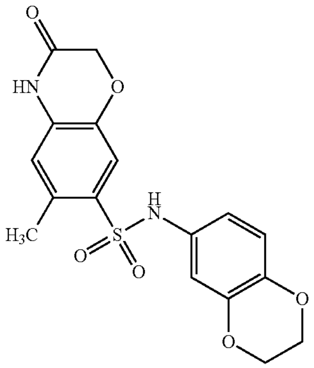 [SMILES: Cc1cc2c(cc1S(=O)(=O)Nc1ccc3c(c1)OCCO3)OCC(=O)N2] | +++ |
| BC181343 | 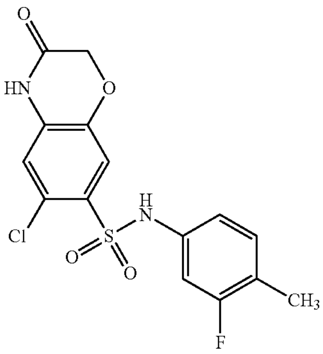 [SMILES: Cc1ccc(NS(=O)(=O)c2cc3c(cc2Cl)NC(=O)CO3)cc1F] | ++++ |

TABLE 2a-continued
| BC No. | Compound | $IC_{50}$ NF-κB assay |
|---|---|---|
| BC181344 | 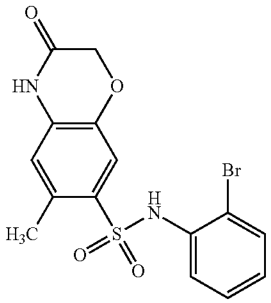 [SMILES: Cc1cc2c(cc1S(=O)(=O)Nc1ccccc1Br)OCC(=O)N2] | +++ |
| BC181345 | 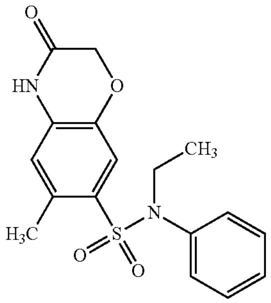 [SMILES: CCN(c1ccccc1)S(=O)(=O)c1cc2c(cc1C)NC(=O)CO2] | + |
| BC181346 | 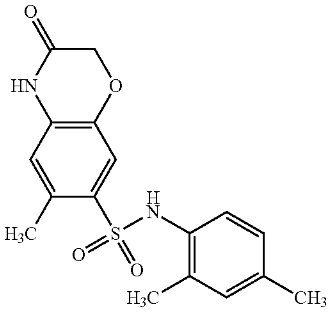 [SMILES: Cc1ccc(NS(=O)(=O)c2cc3c(cc2C)NC(=O)CO3)c(C)c1] | + |
| BC181347 | 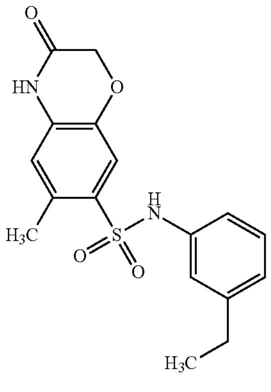 [SMILES: CCc1cccc(NS(=O)(=O)c2cc3c(cc2C)NC(=O)CO3)c1] | ++ |

TABLE 2a-continued
| BC No. | Compound | IC50 NF-κB assay |
|---|---|---|
| BC181348 | 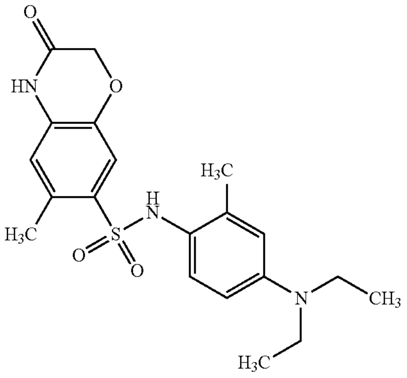 [SMILES: CCN(CC)c1ccc(NS(=O)(=O)c2cc3c(cc2C)NC(=O)CO3)c(C)c1] | + |
| BC181349 | 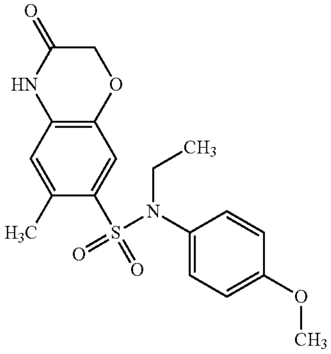 [SMILES: CCN(c1ccc(OC)cc1)S(=O)(=O)c1cc2c(cc1C)NC(=O)CO2] | + |
| BC181350 | 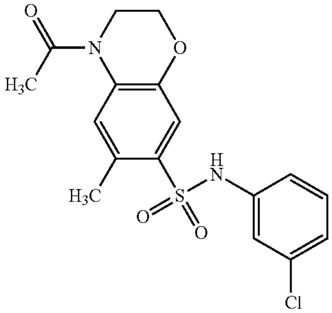 [SMILES: CC(=O)N1CCOc2cc(S(=O)(=O)Nc3cccc(Cl)c3)c(C)cc21] | ++ |
| BC181351 | 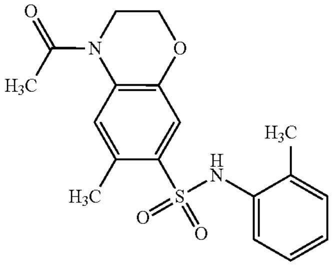 [SMILES: CC(=O)N1CCOc2cc(S(=O)(=O)Nc3ccccc3C)c(C)cc21] | + |

TABLE 2a-continued
| BC No. | Compound | $IC_{50}$ NF-κB assay |
|---|---|---|
| BC181352 | 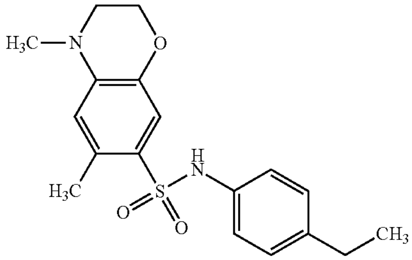 [SMILES: CCc1ccc(NS(=O)(=O)c2cc3c(cc2C)N(C)CCO3)cc1] | + |
| BC181353 | 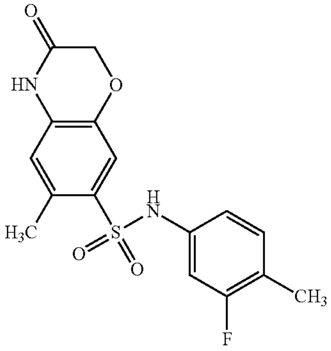 | ++++ |
| BC181354 | 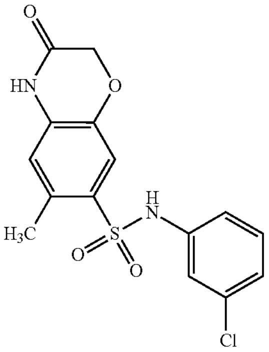 [SMILES: Cc1cc2c(cc1S(=O)(=O)Nc1cccc(Cl)c1)OCC(=O)N2] | ++++ |
| BC181355 | 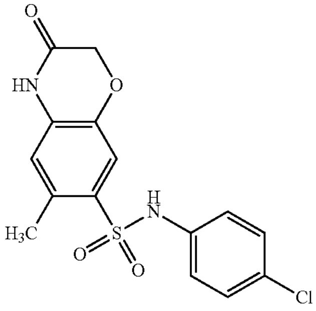 [SMILES: Cc1cc2c(cc1S(=O)(=O)Nc1ccc(Cl)cc1)OCC(=O)N2] | ++++ |

TABLE 2a-continued
| BC No. | Compound | $IC_{50}$ NF-κB assay |
|---|---|---|
| BC181356 | 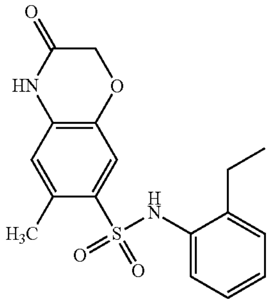 [SMILES: CCc1ccccc1NS(=O)(=O)c1cc2c(cc1C)NC(=O)CO2] | + |
| BC181357 | 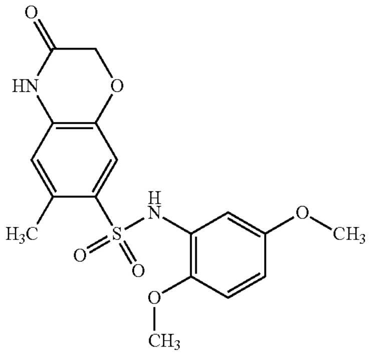 [SMILES: COc1ccc(OC)c(NS(=O)(=O)c2cc3c(cc2C)NC(=O)CO3)c1] | + |
| BC181358 | 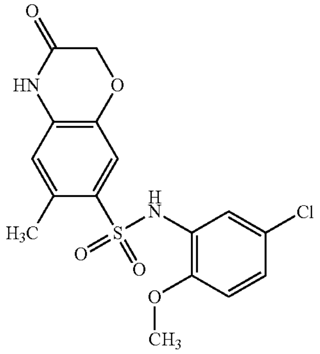 [SMILES: COc1ccc(Cl)cc1NS(=O)(=O)c1cc2c(cc1C)NC(=O)CO2] | + |
| BC181359 | 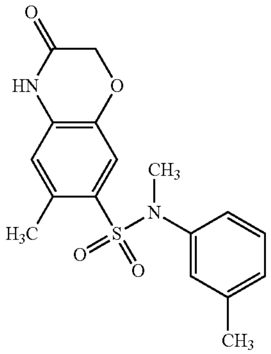 [SMILES: Cc1cccc(N(C)S(=O)(=O)c2cc3c(cc2C)NC(=O)CO3)c1] | + |

TABLE 2a-continued
| BC No. | Compound | $IC_{50}$ NF-κB assay |
|---|---|---|
| BC181360 | 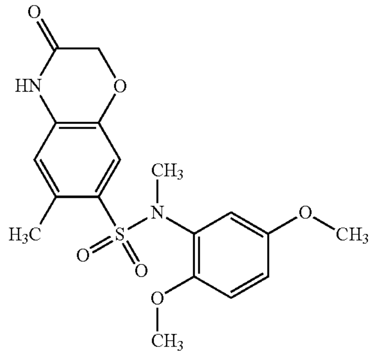 [SMILES: COc1ccc(OC)c(N(C)S(=O)(=O)c2cc3c(cc2C)NC(=O)CO3)c1] | + |
| BC181361 | 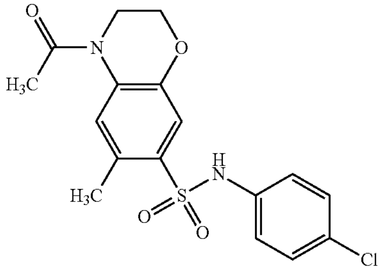 [SMILES: CC(=O)N1CCOc2cc(S(=O)(=O)Nc3ccc(Cl)cc3)c(C)cc21] | +++ |
| BC181362 | 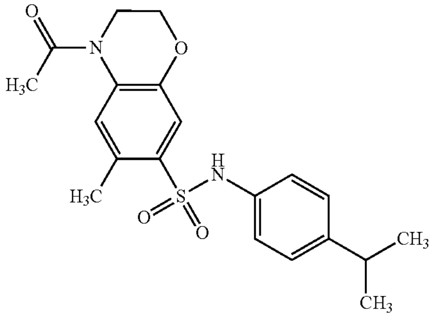 [SMILES: CC(=O)N1CCOc2cc(S(=O)(=O)Nc3ccc(C(C)C)cc3)c(C)cc21] | ++ |
| BC181363 | 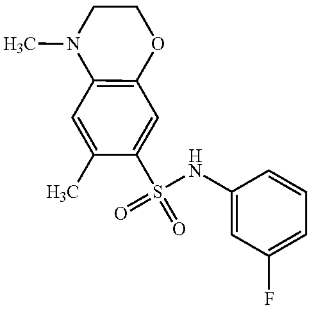 [SMILES: Cc1cc2c(cc1S(=O)(=O)Nc1cccc(F)c1)OCCN2C] | + |

TABLE 2a-continued
| BC No. | Compound | IC50 NF-κB assay |
|---|---|---|
| BC181364 | 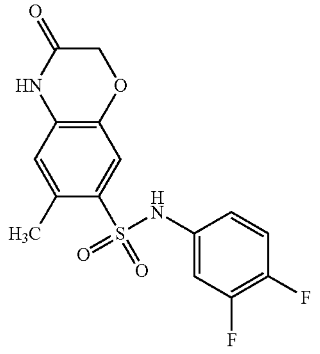 [SMILES: Cc1cc2c(cc1S(=O)(=O)Nc1ccc(F)c(F)c1)OCC(=O)N2] | +++ |
| BC181365 | 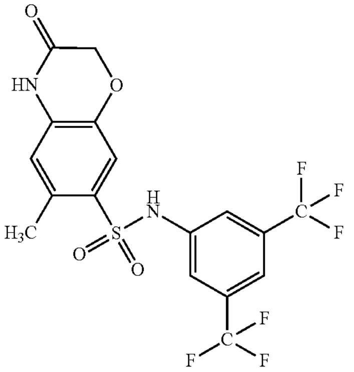 [SMILES: Cc1cc2c(cc1S(=O)(=O)Nc1cc(C(F)(F)F)cc(C(F)(F)F)c1)OCC(=O)N2] | ++ |
| BC181366 | 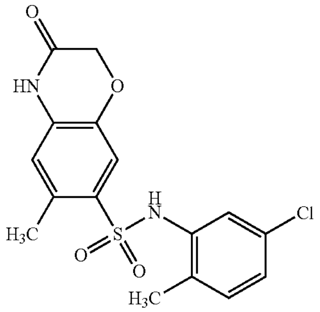 [SMILES: Cc1ccc(Cl)cc1NS(=O)(=O)c1cc2c(cc1C)NC(=O)CO2] | ++ |
| BC181367 | 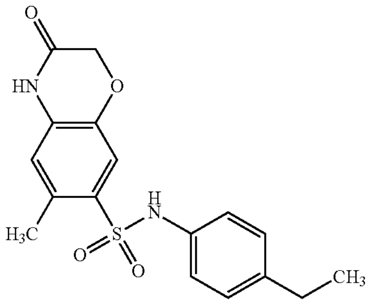 [SMILES: CCc1ccc(NS(=O)(=O)c2cc3c(cc2C)NC(=O)CO3)cc1] | ++++ |

TABLE 2a-continued
| BC No. | Compound | $IC_{50}$ NF-κB assay |
|---|---|---|
| BC181368 | 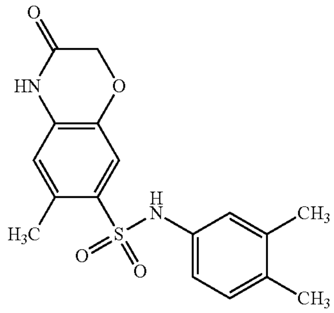 [SMILES: Cc1ccc(NS(=O)(=O)c2cc3c(cc2C)NC(=O)CO3)cc1C] | ++ |
| BC181369 | 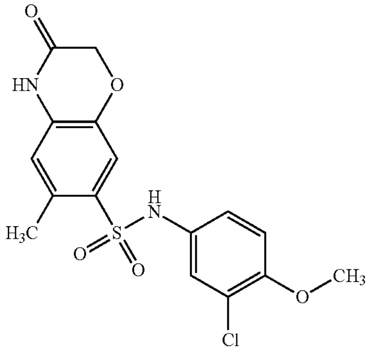 [SMILES: COc1ccc(NS(=O)(=O)c2cc3c(cc2C)NC(=O)CO3)cc1Cl] | ++ |
| BC181370 | 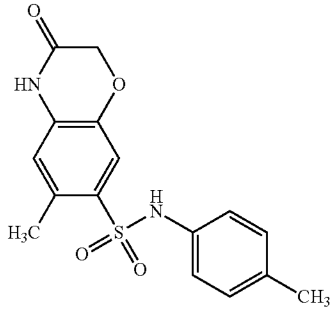 [SMILES: Cc1ccc(NS(=O)(=O)c2cc3c(cc2C)NC(=O)CO3)cc1] | ++++ |
| BC181371 | 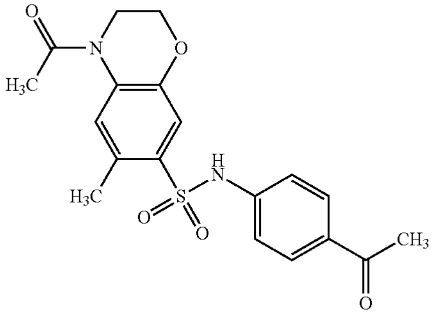 [SMILES: CC(=O)c1ccc(NS(=O)(=O)c2cc3c(cc2C)N(C(C)=O)CCO3)cc1] | + |
| BC181372 | 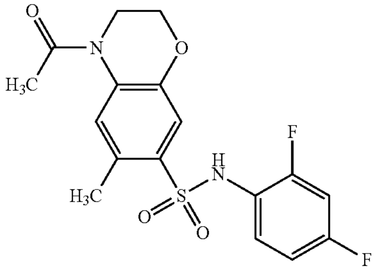 [SMILES: CC(=O)N1CCOc2cc(S(=O)(=O)Nc3ccc(F)cc3F)c(C)cc21] | ++ |

TABLE 2a-continued
| BC No. | Compound | $IC_{50}$ NF-κB assay |
|---|---|---|
| BC181373 | 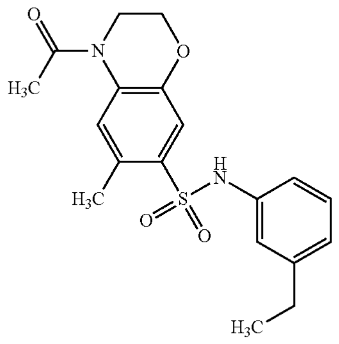 [SMILES: CCc1cccc(NS(=O)(=O)c2cc3c(cc2C)N(C(C)=O)CCO3)c1] | + |
| BC181374 | 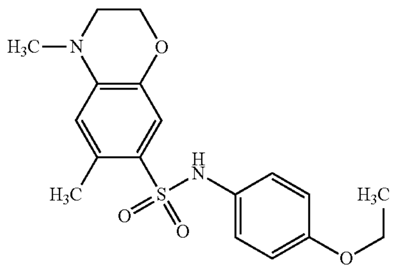 [SMILES: CCOc1ccc(NS(=O)(=O)c2cc3c(cc2C)N(C)CCO3)cc1] | + |
| BC181375 | 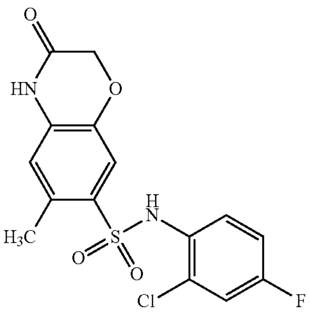 [SMILES: Cc1cc2c(cc1S(=O)(=O)Nc1ccc(F)cc1Cl)OCC(=O)N2] | +++ |
| BC181376 | 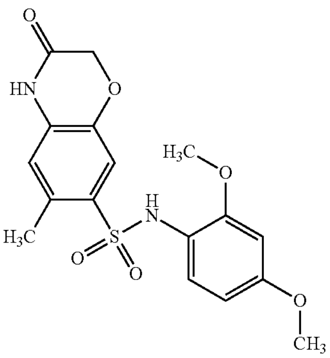 [SMILES: COc1ccc(NS(=O)(=O)c2cc3c(cc2C)NC(=O)CO3)c(OC)c1] | + |

TABLE 2a-continued
| BC No. | Compound | $IC_{50}$ NF-κB assay |
|---|---|---|
| BC181377 | 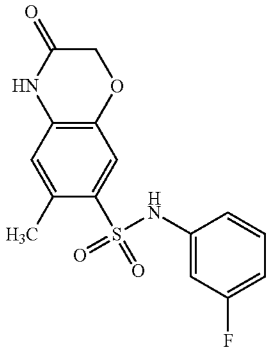 [SMILES: Cc1cc2c(cc1S(=O)(=O)Nc1cccc(F)c1)OCC(=O)N2] | ++++ |
| BC181378 | 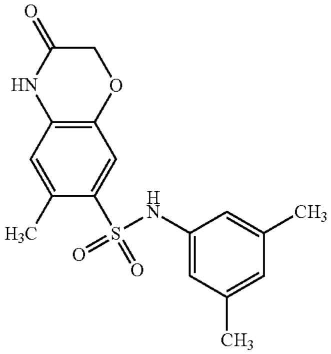 [SMILES: Cc1cc(C)cc(NS(=O)(=O)c2cc3c(cc2C)NC(=O)CO3)c1] | ++ |
| BC181379 | 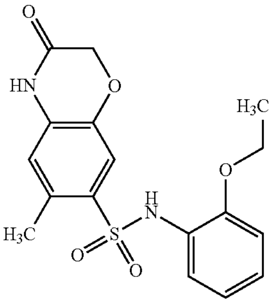 [SMILES: CCOc1ccccc1NS(=O)(=O)c1cc2c(cc1C)NC(=O)CO2] | + |
| BC181380 | 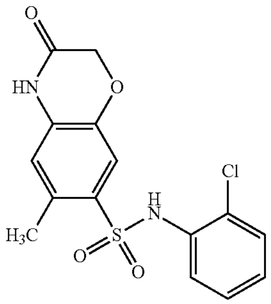 [SMILES: Cc1cc2c(cc1S(=O)(=O)Nc1ccccc1Cl)OCC(=O)N2] | +++ |

TABLE 2a-continued
| BC No. | Compound | $IC_{50}$ NF-κB assay |
|---|---|---|
| BC181381 | 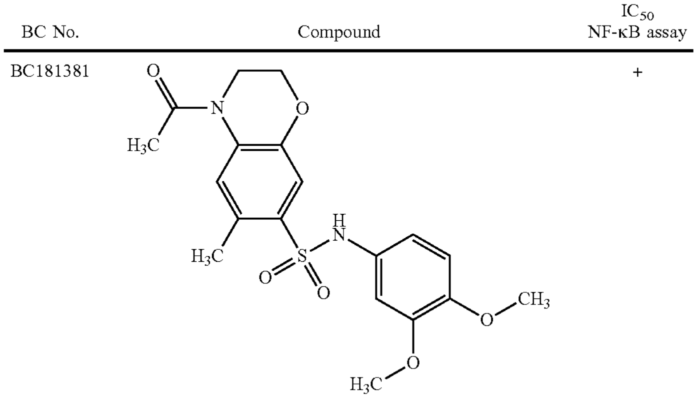 | + |
| BC181382 | 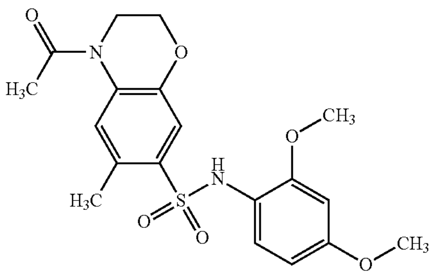 [SMILES: COc1ccc(NS(=O)(=O)c2cc3c(cc2C)N(C(C)=O)CCO3)c(OC)c1] | + |
| BC181383 | 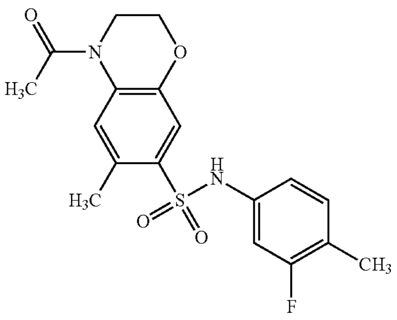 [SMILES: CC(=O)N1CCOc2cc(S(=O)(=O)Nc3ccc(C)c(F)c3)c(C)cc21] | +++ |
| BC181384 | 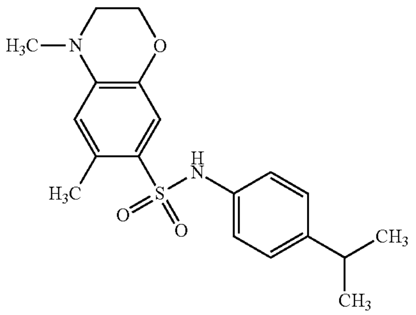 [SMILES: Cc1cc2c(cc1S(=O)(=O)Nc1ccc(C(C)C)cc1)OCCN2C] | ++ |
| BC181385 | 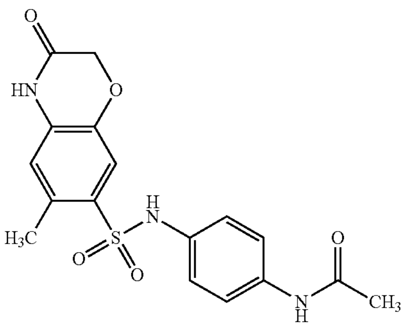 [SMILES: CC(=O)Nc1ccc(NS(=O)(=O)c2cc3c(cc2C)NC(=O)CO3)cc1] | + |

TABLE 2a-continued
| BC No. | Compound | $IC_{50}$ NF-κB assay |
|---|---|---|
TABLE 2c
| BC No. | ZE No. | Structure | $IC_{50}$ (NF-κB assay) | $IC_{50}$ (TNF assay) |
|---|---|---|---|---|
| BC19133 | ZE24-0004 | 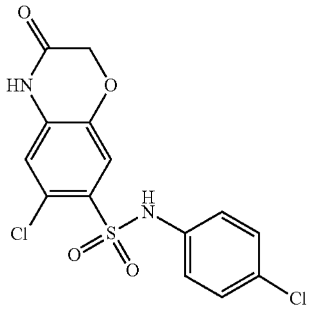 [SMILES: O=C1COc2cc(S(=O)(=O)Nc3ccc(Cl)cc3)c(Cl)cc2N1] | ++++ | + |
| BC19135 | ZE24-0009 | 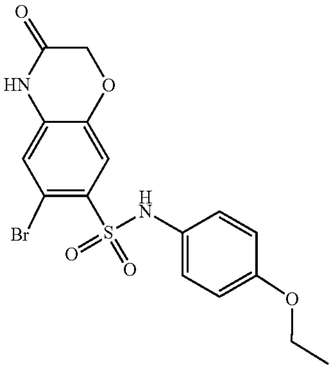 [SMILES: CCOc1ccc(NS(=O)(=O)c2cc3c(cc2Br)NC(=O)CO3)cc1] | + | + |
| BC19136 | ZE24-0010 | 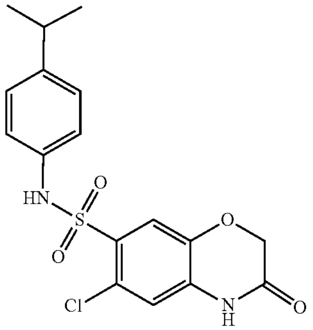 [SMILES: CC(C)c1ccc(NS(=O)(=O)c2cc3c(cc2Cl)NC(=O)CO3)cc1] | + | + |
| BC19137 | ZE24-0011 | 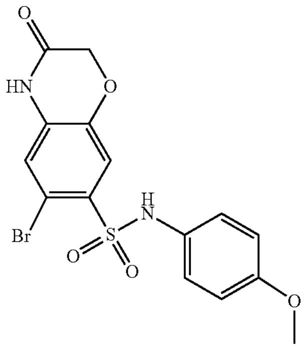 [SMILES: COc1ccc(NS(=O)(=O)c2cc3c(cc2Br)NC(=O)CO3)cc1] | +++ | + |

TABLE 2c-continued
| BC No. | ZE No. | Structure | $IC_{50}$ (NF-κB assay) | $IC_{50}$ (TNF assay) |
| --- | --- | --- | --- | --- |
| BC19138 | ZE24-0015 | 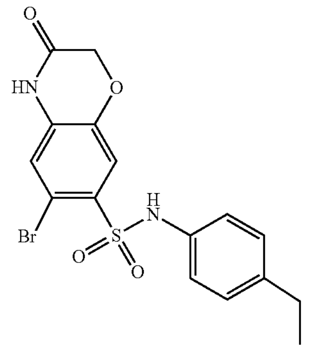 [SMILES: CCc1ccc(NS(=O)(=O)c2cc3c(cc2Br)NC(=O)CO3)cc1] | ++++ | + |
| BC19161 | ZE24-0003 | 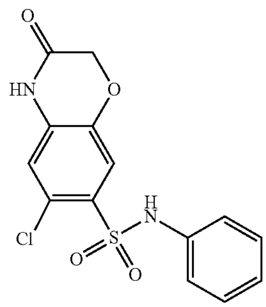 [SMILES: O=C1COc2cc(S(=O)(=O)Nc3ccccc3)c(Cl)cc2N1] | ++ | + |
| BC19162 | ZE24-0005 | 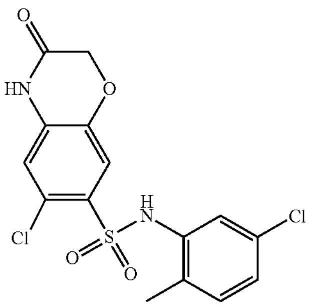 [SMILES: Cc1ccc(Cl)cc1NS(=O)(=O)c1cc2c(cc1Cl)NC(=O)CO2] | + | + |
| BC19163 | ZE24-0007 | 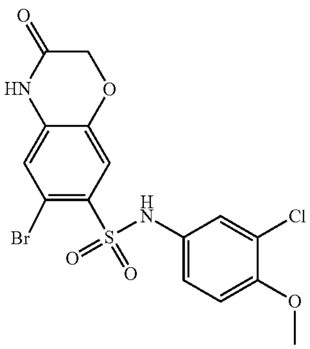 [SMILES: COc1ccc(NS(=O)(=O)c2cc3c(cc2Br)NC(=O)CO3)cc1Cl] | + | + |

TABLE 2c-continued
| BC No. | ZE No. | Structure | $IC_{50}$ (NF-κB assay) | $IC_{50}$ (TNF assay) |
|---|---|---|---|---|
| BC19164 | ZE24-0008 | 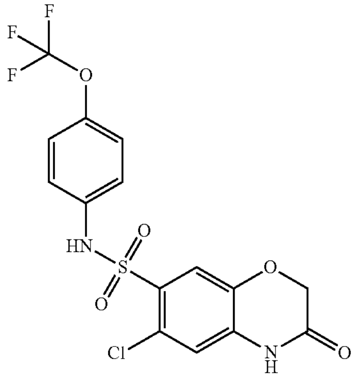 [SMILES: O=C1COc2cc(S(=O)(=O)Nc3ccc(OC(F)(F)F)cc3)c(Cl)cc2N1] | ++++ | + |
| BC19165 | ZE24-0012 | 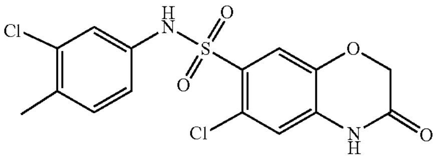 [SMILES: Cc1ccc(NS(=O)(=O)c2cc3c(cc2Cl)NC(=O)CO3)cc1Cl] | +++ | + |
| BC19166 | ZE24-0014 | 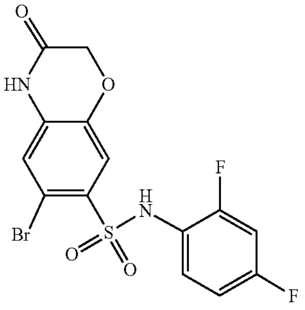 [SMILES: O=C1COc2cc(S(=O)(=O)Nc3ccc(F)cc3F)c(Br)cc2N1] | ++++ | + |
| BC19167 | ZE24-0016 | 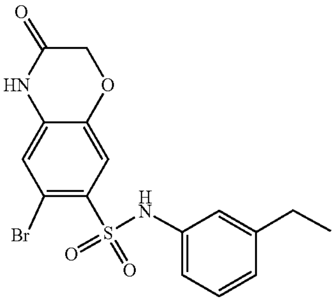 [SMILES: CCc1cccc(NS(=O)(=O)c2cc3c(cc2Br)NC(=O)CO3)c1] | +++ | + |
| BC19206 | ZE24-0018 | 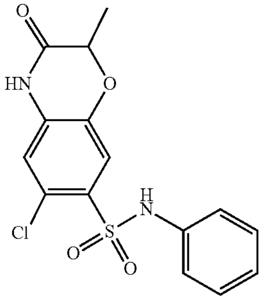 [SMILES: CC1Oc2cc(S(=O)(=O)Nc3ccccc3)c(Cl)cc2NC1=O] | ++ | + |

TABLE 2c-continued
| BC No. | ZE No. | Structure | IC50 (NF-κB assay) | IC50 (TNF assay) |
|---|---|---|---|---|
| BC19207 | ZE24-0023 | 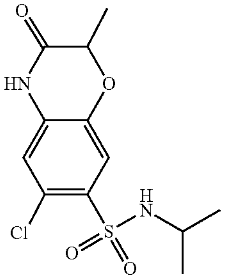 [SMILES: CC(C)NS(=O)(=O)c1cc2c(cc1Cl)NC(=O)C(C)O2] | + | + |
| BC19208 | ZE24-0024 | 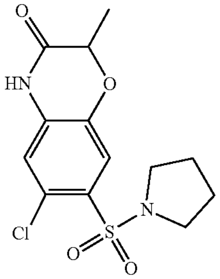 [SMILES: CC1Oc2cc(S(=O)(=O)N3CCCC3)c(Cl)cc2NC1=O] | + | + |
| BC19209 | ZE24-0025 | 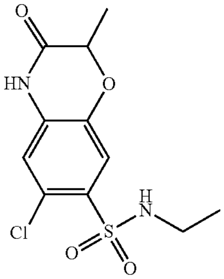 [SMILES: CCNS(=O)(=O)c1cc2c(cc1Cl)NC(=O)C(C)O2] | ++ | + |
| BC19210 | ZE24-0028 | 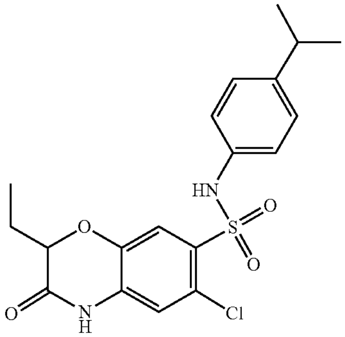 [SMILES: CCC1Oc2cc(S(=O)(=O)Nc3ccc(C(C)C)cc3)c(Cl)cc2NC1=O] | ++++ | + |
| BC19211 | ZE24-0029 | 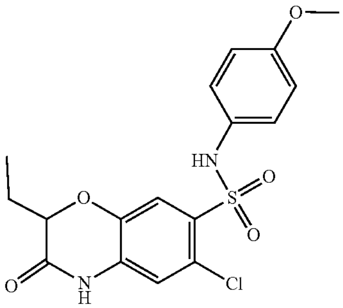 [SMILES: CCC1Oc2cc(S(=O)(=O)Nc3ccc(OC)cc3)c(Cl)cc2NC1=O] | +++ | + |

TABLE 2c-continued
| BC No. | ZE No. | Structure | $IC_{50}$ (NF-κB assay) | $IC_{50}$ (TNF assay) |
|---|---|---|---|---|
| BC19212 | ZE24-0030 | 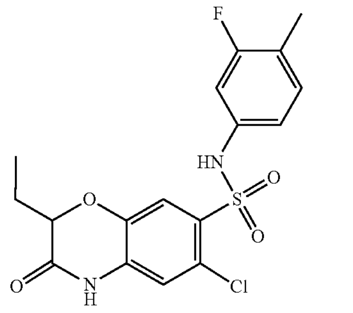 [SMILES: CCC1Oc2cc(S(=O)(=O)Nc3ccc(C)c(F)c3)c(Cl)cc2NC1=O] | ++++ | + |
| BC19213 | ZE24-0031 | 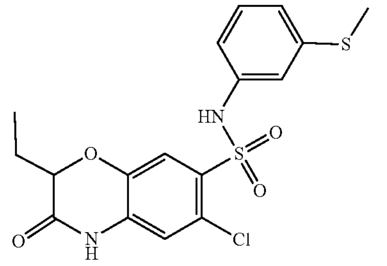 [SMILES: CCC1Oc2cc(S(=O)(=O)Nc3cccc(SC)c3)c(Cl)cc2NC1=O] | +++ | + |
| BC19214 | ZE24-0032 | 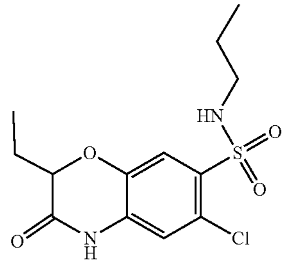 [SMILES: CCCNS(=O)(=O)c1cc2c(cc1Cl)NC(=O)C(CC)O2] | + | + |
| BC19215 | ZE24-0033 | 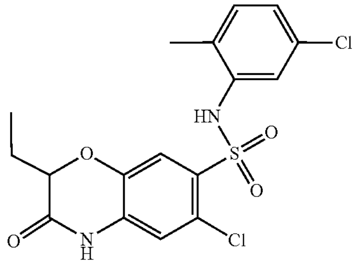 [SMILES: CCC1Oc2cc(S(=O)(=O)Nc3cc(Cl)ccc3C)c(Cl)cc2NC1=O] | ++ | + |
| BC19216 | ZE24-0034 | 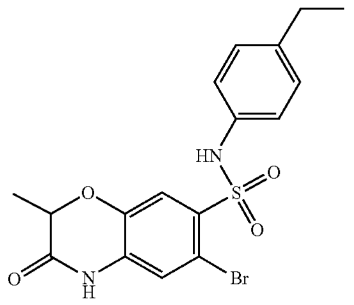 [SMILES: CCc1ccc(NS(=O)(=O)c2cc3c(cc2Br)NC(=O)C(C)O3)cc1] | ++++ | + |

TABLE 2c-continued
| BC No. | ZE No. | Structure | $IC_{50}$ (NF-κB assay) | $IC_{50}$ (TNF assay) |
|---|---|---|---|---|
| BC19217 | ZE24-0039 | 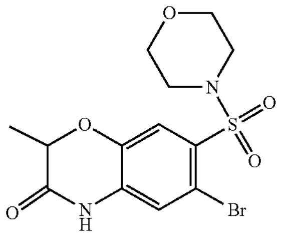 [SMILES: CC1Oc2cc(S(=O)(=O)N3CCOCC3)c(Br)cc2NC1=O] | + | + |
| BC19218 | ZE24-0040 | 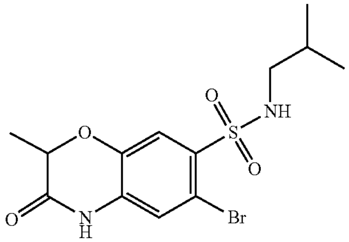 [SMILES: CC(C)CNS(=O)(=O)c1cc2c(cc1Br)NC(=O)C(C)O2] | + | + |
| BC19219 | ZE24-0041 | 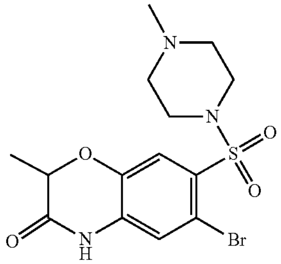 [SMILES: CC1Oc2cc(S(=O)(=O)N3CCN(C)CC3)c(Br)cc2NC1=O] | + | + |
| BC19220 | ZE24-0043 | 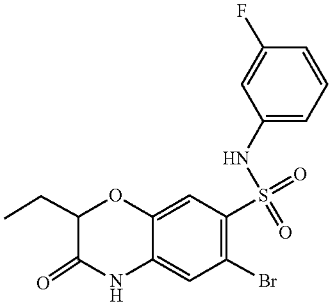 [SMILES: CCC1Oc2cc(S(=O)(=O)Nc3cccc(F)c3)c(Br)cc2NC1=O] | +++ | + |
| BC19221 | ZE24-0044 | 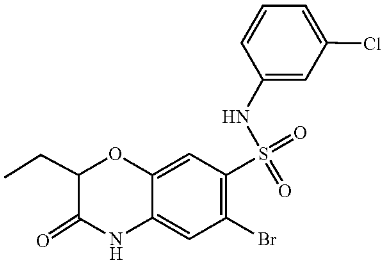 [SMILES: CCC1Oc2cc(S(=O)(=O)Nc3cccc(Cl)c3)c(Br)cc2NC1=O] | +++ | + |

TABLE 2c-continued
| BC No. | ZE No. | Structure | $IC_{50}$ (NF-κB assay) | $IC_{50}$ (TNF assay) |
|---|---|---|---|---|
| BC19222 | ZE24-0045 | 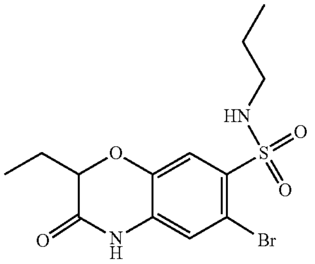 [SMILES: CCCNS(=O)(=O)c1cc2c(cc1Br)NC(=O)C(CC)O2] | + | + |
| BC19223 | ZE24-0047 | 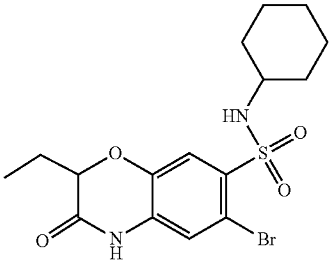 [SMILES: CCC1Oc2cc(S(=O)(=O)NC3CCCCC3)c(Br)cc2NC1=O] | + | + |
| BC19224 | ZE24-0048 | 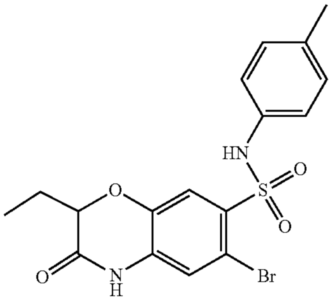 [SMILES: CCC1Oc2cc(S(=O)(=O)Nc3ccc(C)cc3)c(Br)cc2NC1=O] | +++ | + |
| BC19280 | ZE24-0020 | 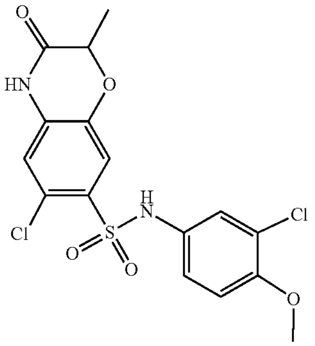 [SMILES: COc1ccc(NS(=O)(=O)c2cc3c(cc2Cl)NC(=O)C(C)O3)cc1Cl] | ++ | + |
| BC19281 | ZE24-0021 | 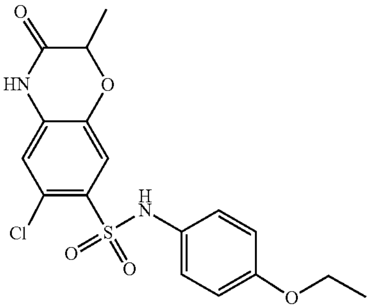 [SMILES: CCOc1ccc(NS(=O)(=O)c2cc3c(cc2Cl)NC(=O)C(C)O3)cc1] | +++ | + |

TABLE 2c-continued
| BC No. | ZE No. | Structure | $IC_{50}$ (NF-κB assay) | $IC_{50}$ (TNF assay) |
|---|---|---|---|---|
| BC19282 | ZE24-0027 | 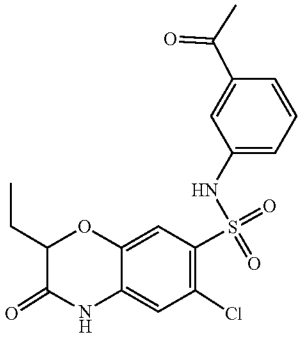 [SMILES: CCC1Oc2cc(S(=O)(=O)Nc3cccc(C(C)=O)c3)c(Cl)cc2NC1=O] | +++ | + |
| BC19283 | ZE24-0036 | 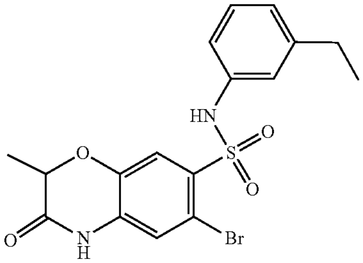 [SMILES: CCc1cccc(NS(=O)(=O)c2cc3c(cc2Br)NC(=O)C(C)O3)c1] | +++ | + |
| BC19284 | ZE24-0037 | 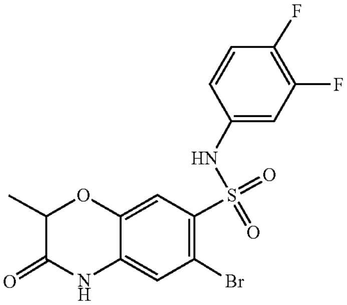 [SMILES: CC1Oc2cc(S(=O)(=O)Nc3ccc(F)c(F)c3)c(Br)cc2NC1=O] | ++++ | + |
| BC19285 | ZE24-0038 | 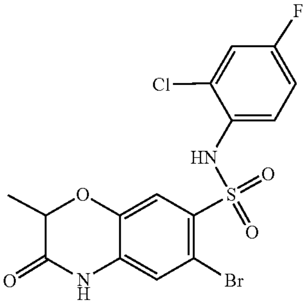 [SMILES: CC1Oc2cc(S(=O)(=O)Nc3ccc(F)cc3Cl)c(Br)cc2NC1=O] | ++ | + |
| BC19286 | ZE24-0042 | 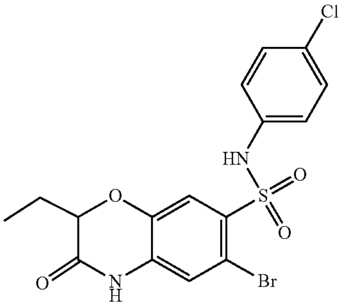 [SMILES: CCC1Oc2cc(S(=O)(=O)Nc3ccc(Cl)cc3)c(Br)cc2NC1=O] | ++++ | + |

TABLE 2c-continued
| BC No. | ZE No. | Structure | $IC_{50}$ (NF-κB assay) | $IC_{50}$ (TNF assay) |
|---|---|---|---|---|
| BC19287 | ZE24-0046 | 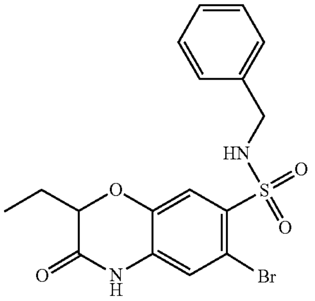 [SMILES: CCC1Oc2cc(S(=O)(=O)NCc3ccccc3)c(Br)cc2NC1=O] | ++ | + |
| BC19354 | ZE24-0019 | 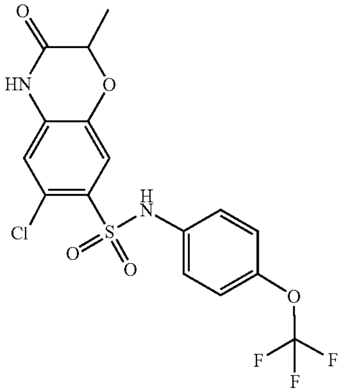 [SMILES: CC1Oc2cc(S(=O)(=O)Nc3ccc(OC(F)(F)F)cc3)c(Cl)cc2NC1=O] | ++++ | + |
| BC19356 | ZE24-0082 | 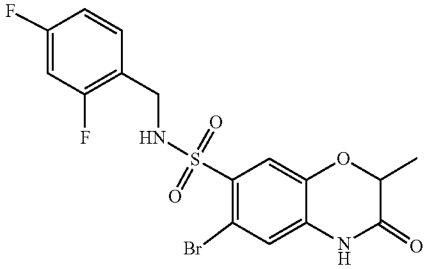 [SMILES: CC1Oc2cc(S(=O)(=O)NCc3ccc(F)cc3F)c(Br)cc2NC1=O] | ++ | + |
| BC19357 | ZE24-0083 | 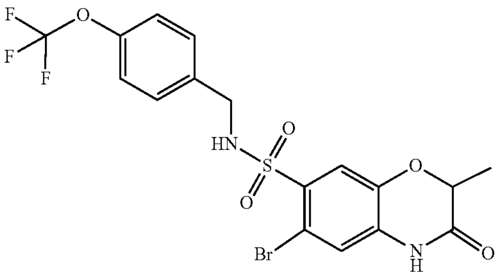 [SMILES: CC1Oc2cc(S(=O)(=O)NCc3ccc(OC(F)(F)F)cc3)c(Br)cc2NC1=O] | + | + |

TABLE 2c-continued
| BC No. | ZE No. | Structure | $IC_{50}$ (NF-κB assay) | $IC_{50}$ (TNF assay) |
|---|---|---|---|---|
| BC19358 | ZE24-0084 | 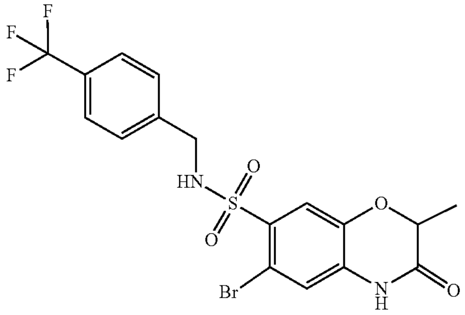 [SMILES: CC1Oc2cc(S(=O)(=O)NCc3ccc(C(F)(F)F)cc3)c(Br)cc2NC1=O] | + | + |
| BC19359 | ZE24-0086 | 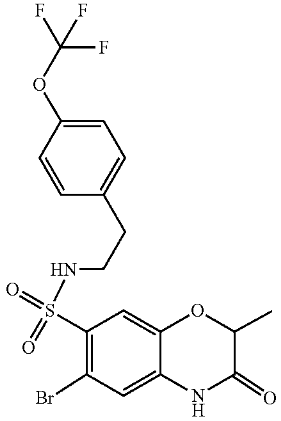 [SMILES: CC1Oc2cc(S(=O)(=O)NCCc3ccc(OC(F)(F)F)cc3)c(Br)cc2NC1=O] | + | + |
| BC19360 | ZE24-0087 | 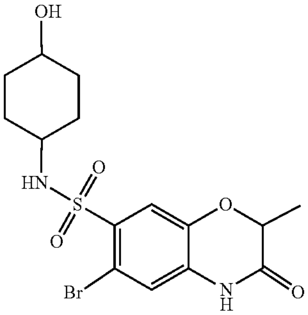 [SMILES: CC1Oc2cc(S(=O)(=O)NC3CCC(O)CC3)c(Br)cc2NC1=O] | + | + |
| BC19361 | ZE24-0088 | 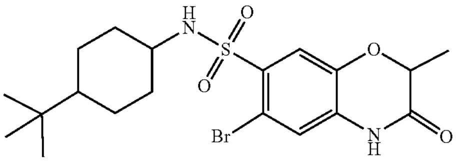 [SMILES: CC1Oc2cc(S(=O)(=O)NC3CCC(C(C)(C)C)CC3)c(Br)cc2NC1=O] | + | + |
| BC19368 | ZE24-0096 | 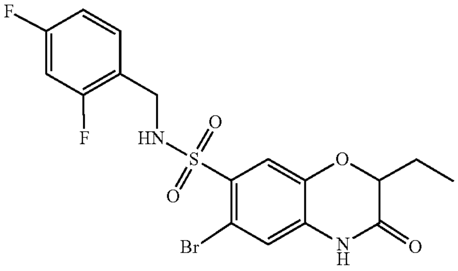 [SMILES: CCC1Oc2cc(S(=O)(=O)NCc3ccc(F)cc3F)c(Br)cc2NC1=O] | + | + |

TABLE 2c-continued
| BC No. | ZE No. | Structure | $IC_{50}$ (NF-κB assay) | $IC_{50}$ (TNF assay) |
|---|---|---|---|---|
| BC19369 | ZE24-0097 | 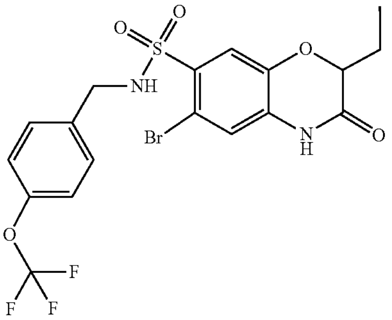 [SMILES: CCC1Oc2cc(S(=O)(=O)NCc3ccc(OC(F)(F)F)cc3)c(Br)cc2NC1=O] | + | + |
| BC19370 | ZE24-0098 | 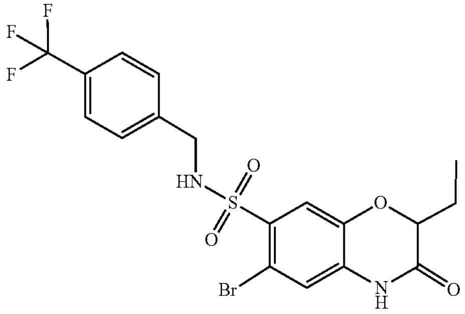 [SMILES: CCC1Oc2cc(S(=O)(=O)NCc3ccc(C(F)(F)F)cc3)c(Br)cc2NC1=O] | + | + |
| BC19371 | ZE24-0099 | 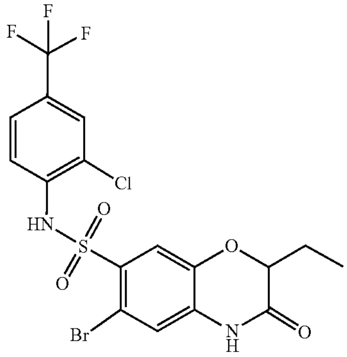 [SMILES: CCC1Oc2cc(S(=O)(=O)Nc3ccc(C(F)(F)F)cc3Cl)c(Br)cc2NC1=O] | ++ | + |
| BC19372 | ZE24-0100 | 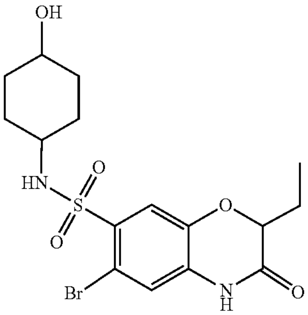 [SMILES: CCC1Oc2cc(S(=O)(=O)NC3CCC(O)CC3)c(Br)cc2NC1=O] | + | + |

TABLE 2c-continued
| BC No. | ZE No. | Structure | $IC_{50}$ (NF-κB assay) | $IC_{50}$ (TNF assay) |
|---|---|---|---|---|
| BC19373 | ZE24-0102 | 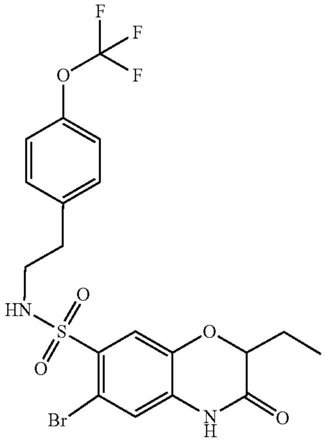 [SMILES: CCC1Oc2cc(S(=O)(=O)NCCc3ccc(OC(F)(F)F)cc3)c(Br)cc2NC1=O] | + | + |
| BC19387 | ZE24-0117 | 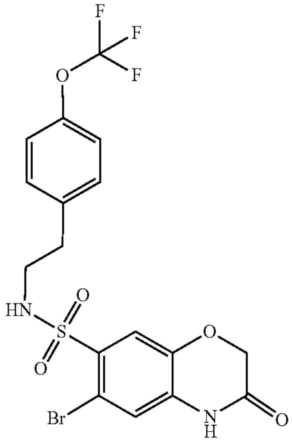 [SMILES: O=C1COc2cc(S(=O)(=O)NCCc3ccc(OC(F)(F)F)cc3)c(Br)cc2N1] | + | + |
| BC19388 | ZE24-0118 | 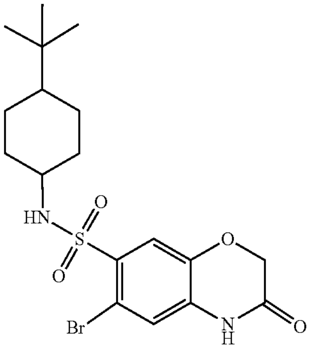 [SMILES: CC(C)(C)C1CCC(NS(=O)(=O)c2cc3c(cc2Br)NC(=O)CO3)CC1] | + | + |
| BC19389 | ZE24-0119 | 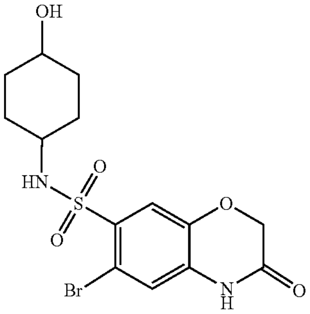 [SMILES: O=C1COc2cc(S(=O)(=O)NC3CCC(O)CC3)c(Br)cc2N1] | + | + |

TABLE 2c-continued
| BC No. | ZE No. | Structure | $IC_{50}$ (NF-κB assay) | $IC_{50}$ (TNF assay) |
|---|---|---|---|---|
| BC19390 | ZE24-0120 | 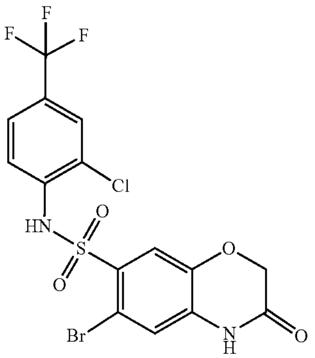 [SMILES: O=C1COc2cc(S(=O)(=O)Nc3ccc(C(F)(F)F)cc3Cl)c(Br)cc2N1] | ++ | + |
| BC19391 | ZE24-0121 | 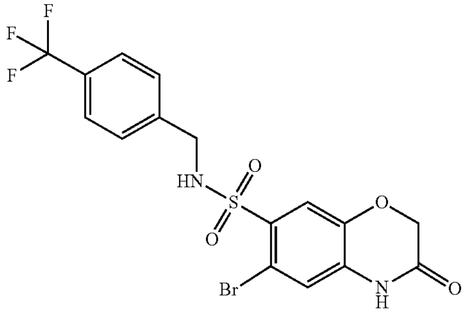 [SMILES: O=C1COc2cc(S(=O)(=O)NCc3ccc(C(F)(F)F)cc3)c(Br)cc2N1] | + | + |
| BC19392 | ZE24-0122 | 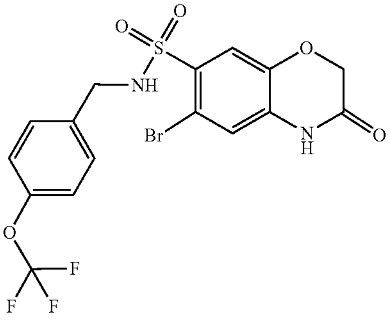 [SMILES: O=C1COc2cc(S(=O)(=O)NCc3ccc(OC(F)(F)F)cc3)c(Br)cc2N1] | + | + |
| BC19393 | ZE24-0123 | 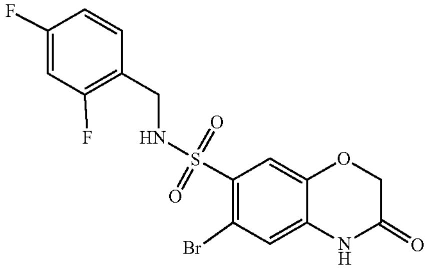 [SMILES: O=C1COc2cc(S(=O)(=O)NCc3ccc(F)cc3F)c(Br)cc2N1] | + | + |

TABLE 2c-2
| BC No. | Structure | $IC_{50}$ (NF-κB assay) | $IC_{50}$ (TNF assay) |
|---|---|---|---|
| BC19696 | 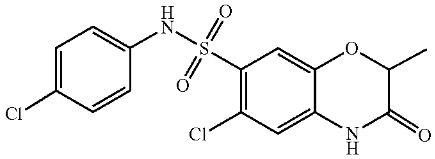 [SMILES: CC1Oc2cc(S(=O)(=O)Nc3ccc(Cl)cc3)c(Cl)cc2NC1=O] | +++ | + |
| BC19698 | 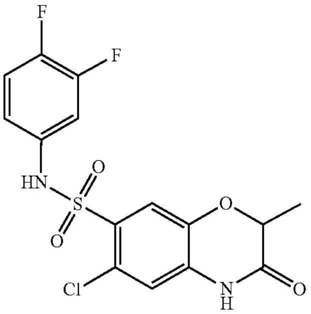 [SMILES: CC1Oc2cc(S(=O)(=O)Nc3ccc(F)c(F)c3)c(Cl)cc2NC1=O] | ++++ | + |
| BC19700 | 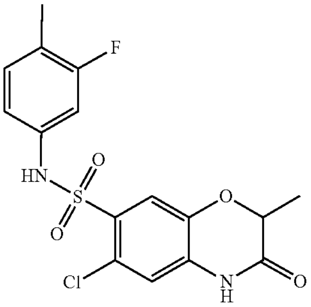 [SMILES: Cc1ccc(NS(=O)(=O)c2cc3c(cc2Cl)NC(=O)C(C)O3)cc1F] | ++++ | + |
| BC19702 | 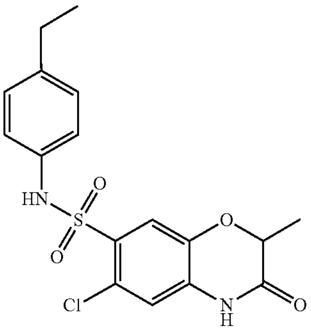 [SMILES: CCc1ccc(NS(=O)(=O)c2cc3c(cc2Cl)NC(=O)C(C)O3)cc1] | ++++ | + |
| BC19704 | 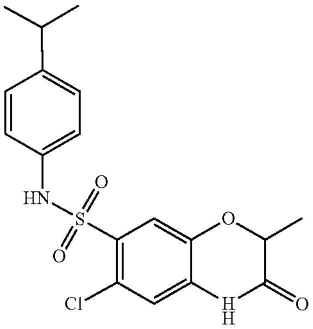 | + | + |

TABLE 2c-2-continued
| BC No. | Structure | $IC_{50}$ (NF-κB assay) | $IC_{50}$ (TNF assay) |
|---|---|---|---|
| BC19706 | 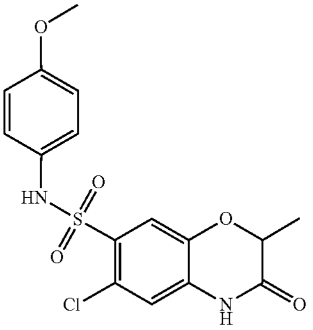 [SMILES: COc1ccc(NS(=O)(=O)c2cc3c(cc2Cl)NC(=O)C(C)O3)cc1] | ++++ | + |
| BC19708 | 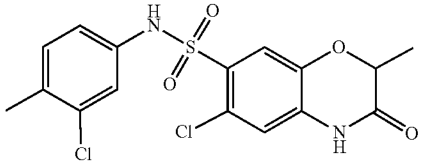 | ++++ | + |
| BC19709 | 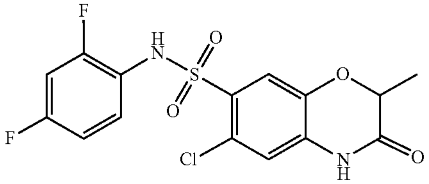 [SMILES: CC1Oc2cc(S(=O)(=O)Nc3ccc(F)cc3F)c(Cl)cc2NC1=O] | ++++ | + |
| BC19711 | 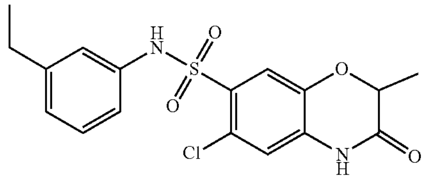 [SMILES: CCc1cccc(NS(=O)(=O)c2cc3c(cc2Cl)NC(=O)C(C)O3)c1] | ++++ | + |
| BC19713 | 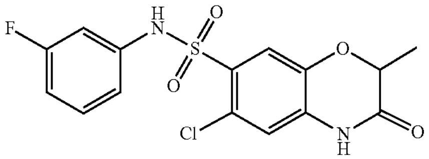 [SMILES: CC1Oc2cc(S(=O)(=O)Nc3cccc(F)c3)c(Cl)cc2NC1=O] | +++ | ++ |
| BC19715 | 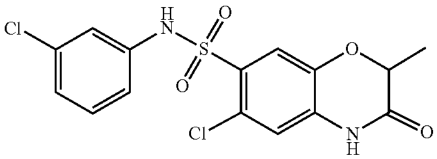 [SMILES: CC1Oc2cc(S(=O)(=O)Nc3cccc(Cl)c3)c(Cl)cc2NC1=O] | ++++ | ++ |
| BC19717 | 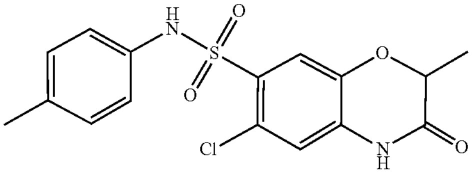 | ++++ | + |

TABLE 2c-2-continued
| BC No. | Structure | $IC_{50}$ (NF-κB assay) | $IC_{50}$ (TNF assay) |
|---|---|---|---|
| BC19719 | 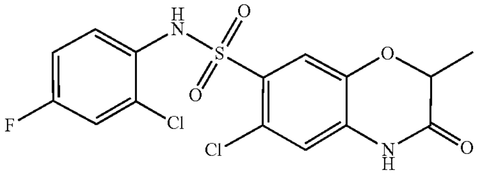 [SMILES: CC1Oc2cc(S(=O)(=O)Nc3ccc(F)cc3Cl)c(Cl)cc2NC1=O] | +++ | + |
| BC19721 | 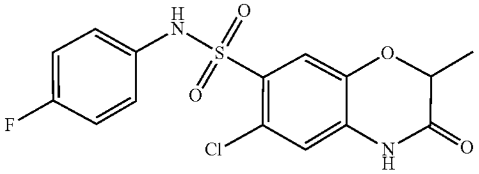 [SMILES: CC1Oc2cc(S(=O)(=O)Nc3ccc(F)cc3)c(Cl)cc2NC1=O] | ++++ | ++ |
| BC19729 | 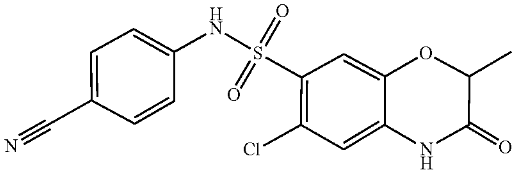 [SMILES: CC1Oc2cc(S(=O)(=O)Nc3ccc(C#N)cc3)c(Cl)cc2NC1=O] | +++ | + |
| BC19731 | 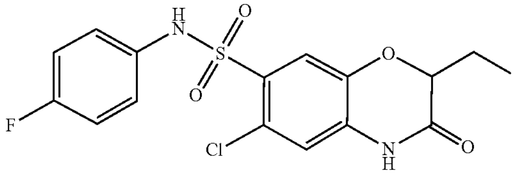 [SMILES: CCC1Oc2cc(S(=O)(=O)Nc3ccc(F)cc3)c(Cl)cc2NC1=O] | +++ | + |
| BC19733 | 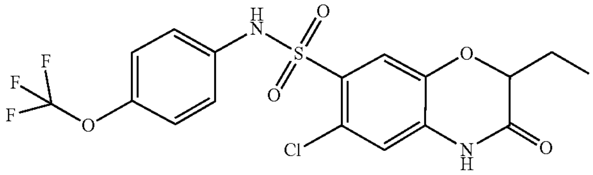 [SMILES: CCC1Oc2cc(S(=O)(=O)Nc3ccc(OC(F)(F)F)cc3)c(Cl)cc2NC1=O] | ++++ | + |
| BC19735 | 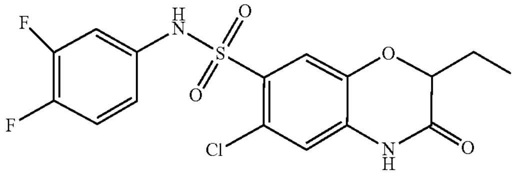 [SMILES: CCC1Oc2cc(S(=O)(=O)Nc3ccc(F)c(F)c3)c(Cl)cc2NC1=O] | ++++ | + |
| BC19737 | 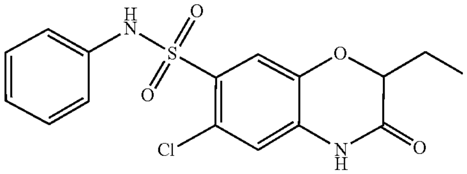 [SMILES: CCC1Oc2cc(S(=O)(=O)Nc3ccccc3)c(Cl)cc2NC1=O] | +++ | + |
| BC19739 | 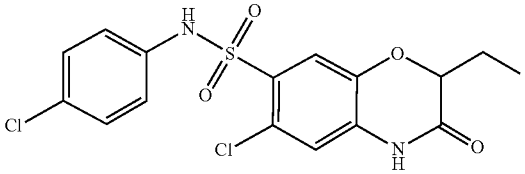 [SMILES: CCC1Oc2cc(S(=O)(=O)Nc3ccc(Cl)cc3)c(Cl)cc2NC1=O] | ++++ | + |

TABLE 2c-2-continued
| BC No. | Structure | $IC_{50}$ (NF-κB assay) | $IC_{50}$ (TNF assay) |
|---|---|---|---|
| BC19741 | 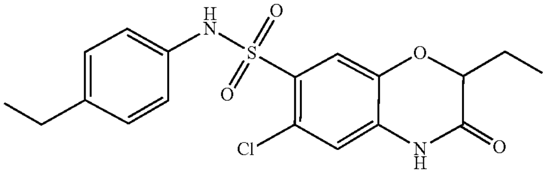 [SMILES: CCc1ccc(NS(=O)(=O)c2cc3c(cc2Cl)NC(=O)C(CC)O3)cc1] | ++++ | + |
| BC19743 | 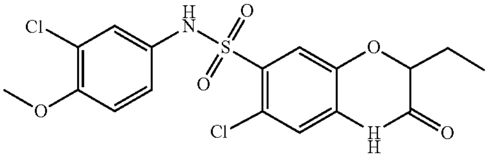 | ++ | + |
| BC19745 | 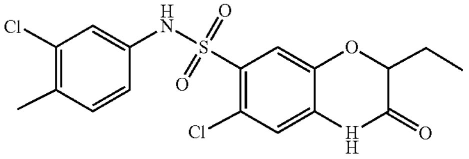 | ++ | + |
| BC19747 | 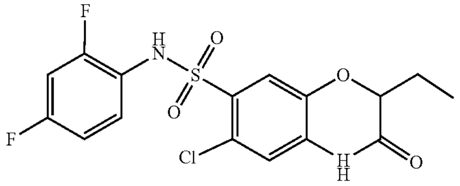 | +++ | + |
| BC19749 | 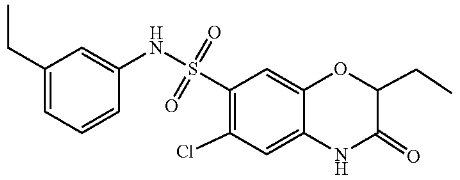 [SMILES: CCc1cccc(NS(=O)(=O)c2cc3c(cc2Cl)NC(=O)C(CC)O3)c1] | +++ | + |
| BC19751 | 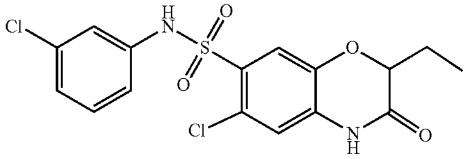 [SMILES: CCC1Oc2cc(S(=O)(=O)Nc3cccc(Cl)c3)c(Cl)cc2NC1=O] | +++ | + |
| BC19753 | 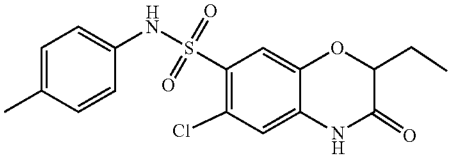 [SMILES: CCC1Oc2cc(S(=O)(=O)Nc3ccc(C)cc3)c(Cl)cc2NC1=O] | ++++ | + |
| BC19755 | 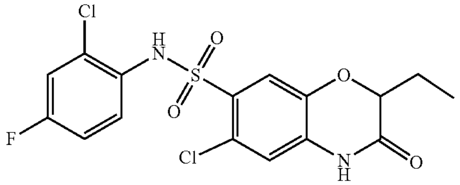 [SMILES: CCC1Oc2cc(S(=O)(=O)Nc3ccc(F)cc3Cl)c(Cl)cc2NC1=O] | ++ | + |

TABLE 2c-2-continued
| BC No. | Structure | IC50 (NF-κB assay) | IC50 (TNF assay) |
|---|---|---|---|
| BC19758 | 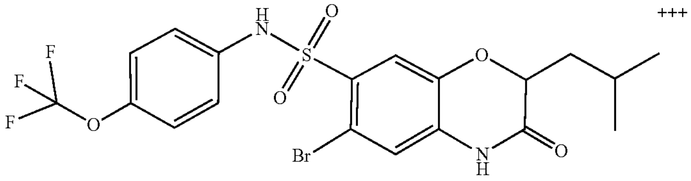 | +++ | + |
| BC19760 | 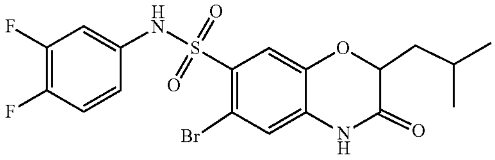 [SMILES: CC(C)CC1Oc2cc(S(=O)(=O)Nc3ccc(F)c(F)c3)c(Br)cc2NC1=O] | ++++ | + |
| BC19762 | 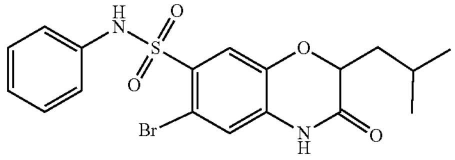 [SMILES: CC(C)CC1Oc2cc(S(=O)(=O)Nc3ccccc3)c(Br)cc2NC1=O] | +++ | + |
| BC19764 | 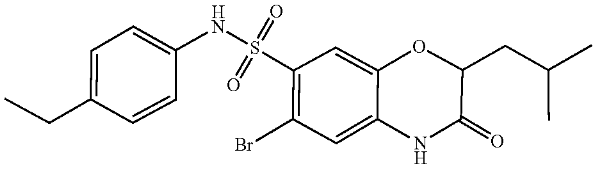 [SMILES: CCc1ccc(NS(=O)(=O)c2cc3c(cc2Br)NC(=O)C(CC(C)C)O3)cc1] | ++ | + |
| BC19766 | 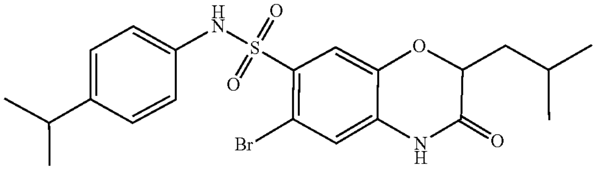 [SMILES: CC(C)CC1Oc2cc(S(=O)(=O)Nc3ccc(C(C)C)cc3)c(Br)cc2NC1=O] | ++ | ++ |
| BC19768 | 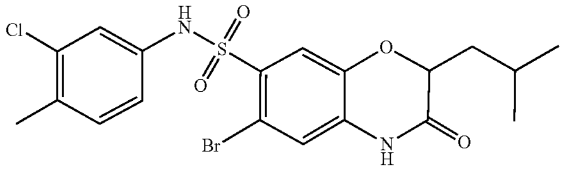 [SMILES: Cc1ccc(NS(=O)(=O)c2cc3c(cc2Br)NC(=O)C(CC(C)C)O3)cc1Cl] | ++ | + |
| BC19770 | 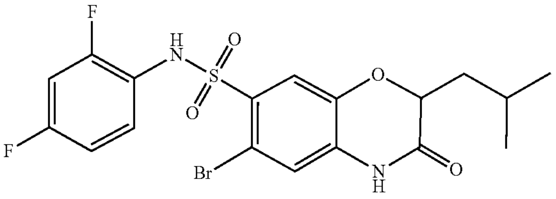 [SMILES: CC(C)CC1Oc2cc(S(=O)(=O)Nc3ccc(F)cc3F)c(Br)cc2NC1=O] | +++ | + |
| BC19772 | 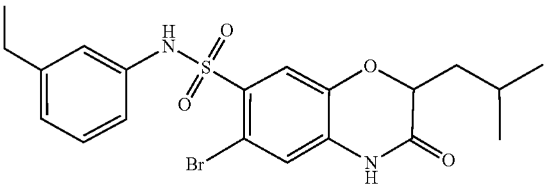 [SMILES: CCc1cccc(NS(=O)(=O)c2cc3c(cc2Br)NC(=O)C(CC(C)C)O3)c1] | +++ | + |

TABLE 2c-2-continued
| BC No. | Structure | IC50 (NF-κB assay) | IC50 (TNF assay) |
|---|---|---|---|
| BC19774 | 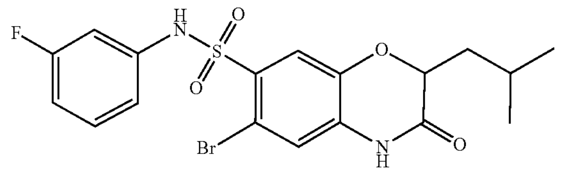 [SMILES: CC(C)CC1Oc2cc(S(=O)(=O)Nc3cccc(F)c3)c(Br)cc2NC1=O] | +++ | + |
| BC19776 | 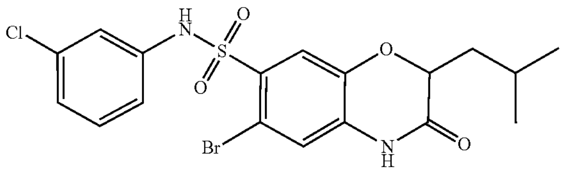 [SMILES: CC(C)CC1Oc2cc(S(=O)(=O)Nc3cccc(Cl)c3)c(Br)cc2NC1=O] | +++ | + |
| BC19778 | 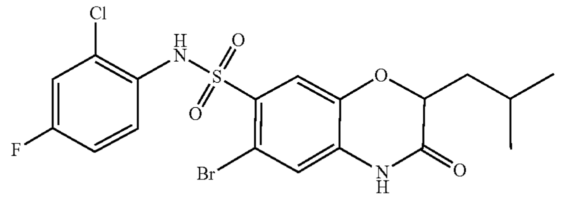 [SMILES: CC(C)CC1Oc2cc(S(=O)(=O)Nc3ccc(F)cc3Cl)c(Br)cc2NC1=O] | + | + |
| BC19778 | 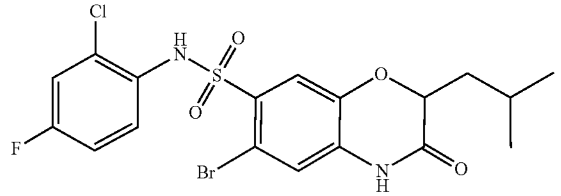 [SMILES: CC(C)CC1Oc2cc(S(=O)(=O)Nc3ccc(F)cc3Cl)c(Br)cc2NC1=O] | + | + |
| BC19780 | 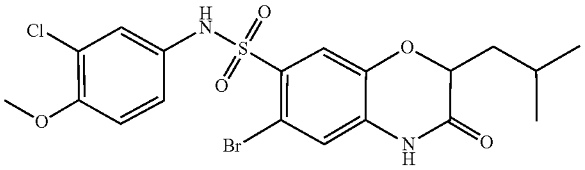 [SMILES: COc1ccc(NS(=O)(=O)c2cc3c(cc2Br)NC(=O)C(CC(C)C)O3)cc1Cl] | ++ | + |
| BC19782 | 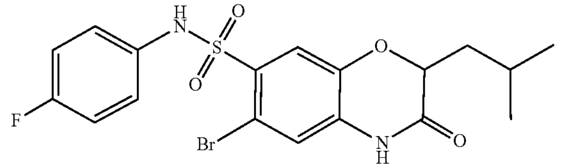 [SMILES: CC(C)CC1Oc2cc(S(=O)(=O)Nc3ccc(F)cc3)c(Br)cc2NC1=O] | ++ | + |
| BC19784 | 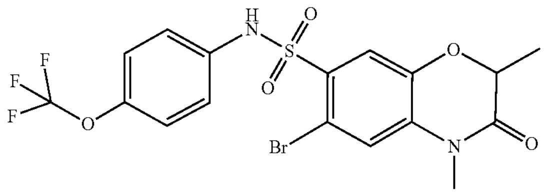 [SMILES: CC1Oc2cc(S(=O)(=O)Nc3ccc(OC(F)(F)F)cc3)c(Br)cc2N(C)C1=O] | ++ | + |
| BC19786 | 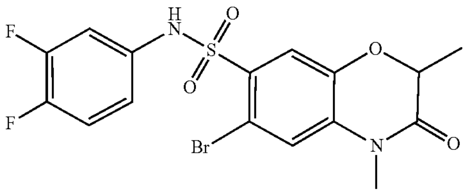 [SMILES: CC1Oc2cc(S(=O)(=O)Nc3ccc(F)c(F)c3)c(Br)cc2N(C)C1=O] | ++ | + |

TABLE 2c-2-continued
| BC No. | Structure | $IC_{50}$ (NF-κB assay) | $IC_{50}$ (TNF assay) |
|---|---|---|---|
| BC19788 | 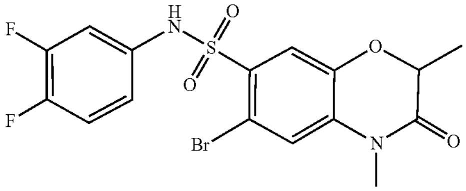 [SMILES: CC1Oc2cc(S(=O)(=O)Nc3ccc(F)c(F)c3)c(Br)cc2N(C)C1=O] | ++++ | + |
| BC19790 | 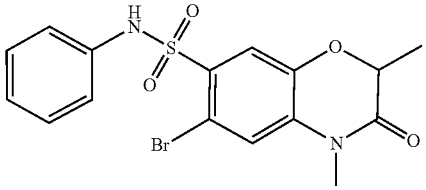 [SMILES: CC1Oc2cc(S(=O)(=O)Nc3ccccc3)c(Br)cc2N(C)C1=O] | ++ | + |
| BC19792 | 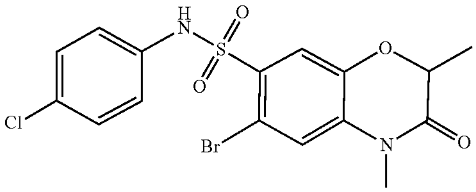 [SMILES: CC1Oc2cc(S(=O)(=O)Nc3ccc(Cl)cc3)c(Br)cc2N(C)C1=O] | ++ | + |
| BC19794 | 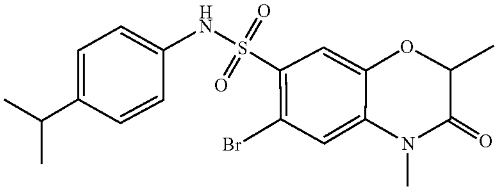 [SMILES: CC1Oc2cc(S(=O)(=O)Nc3ccc(C(C)C)cc3)c(Br)cc2N(C)C1=O] | ++ | + |
| BC19795 | 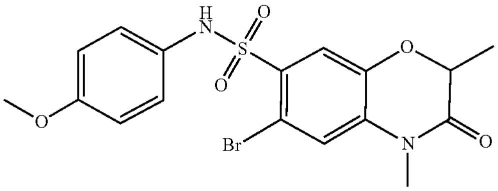 | + | ++ |
| BC19797 | 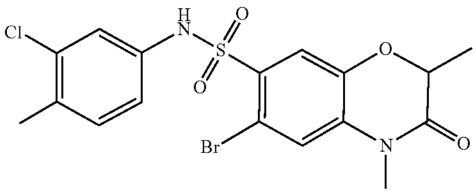 [SMILES: Cc1ccc(NS(=O)(=O)c2cc3c(cc2Br)N(C)C(=O)C(C)O3)cc1Cl] | ++ | ++ |
| BC19799 | 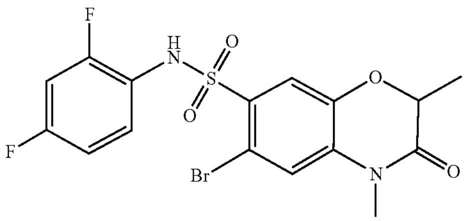 [SMILES: CC1Oc2cc(S(=O)(=O)Nc3ccc(F)cc3F)c(Br)cc2N(C)C1=O] | +++ | ++ |

TABLE 2c-2-continued
| BC No. | Structure | $IC_{50}$ (NF-κB assay) | $IC_{50}$ (TNF assay) |
|---|---|---|---|
| BC19901 | 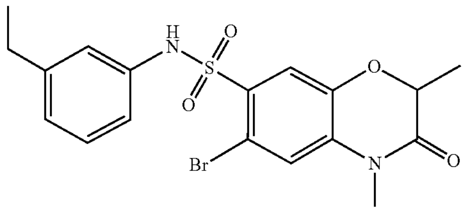 [SMILES: CCc1cccc(NS(=O)(=O)c2cc3c(cc2Br)N(C)C(=O)C(C)O3)c1] | ++ | + |
| BC19903 | 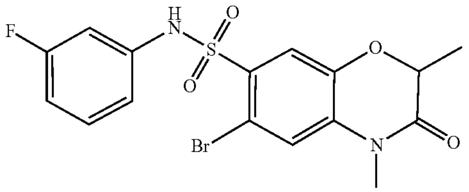 [SMILES: CC1Oc2cc(S(=O)(=O)Nc3cccc(F)c3)c(Br)cc2N(C)C1=O] | +++ | + |
| BC19905 | 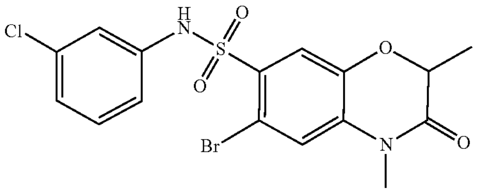 [SMILES: CC1Oc2cc(S(=O)(=O)Nc3cccc(Cl)c3)c(Br)cc2N(C)C1=O] | ++ | + |
| BC19907 | 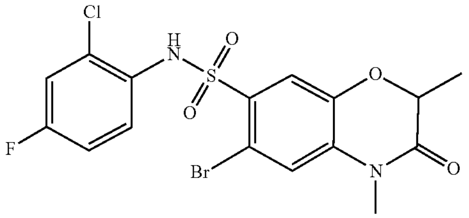 | + | + |
| BC19910 | 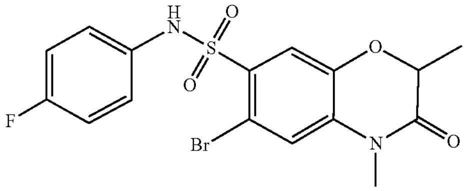 [SMILES: CC1Oc2cc(S(=O)(=O)Nc3ccc(F)cc3)c(Br)cc2N(C)C1=O] | ++ | + |
| BC19912 | 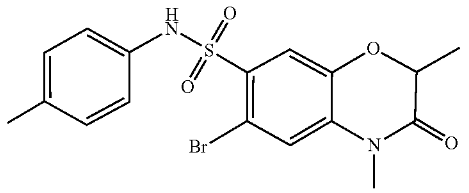 | + | + |
| BC19914 | 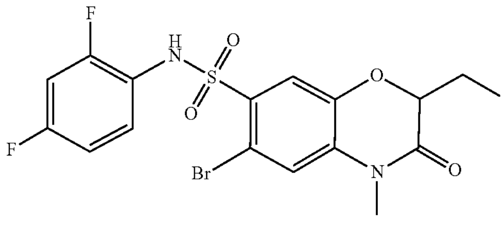 [SMILES: CCC1Oc2cc(S(=O)(=O)Nc3ccc(F)cc3F)c(Br)cc2N(C)C1=O] | +++ | + |

TABLE 2c-2-continued
| BC No. | Structure | IC50 (NF-κB assay) | IC50 (TNF assay) |
|---|---|---|---|
| BC19916 | 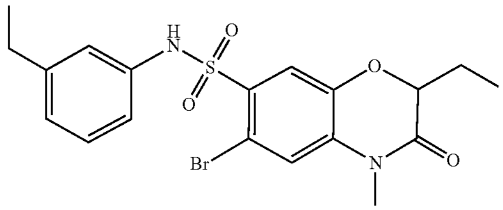 [SMILES: CCc1cccc(NS(=O)(=O)c2cc3c(cc2Br)N(C)C(=O)C(CC)O3)c1] | ++ | + |
| BC19919 | 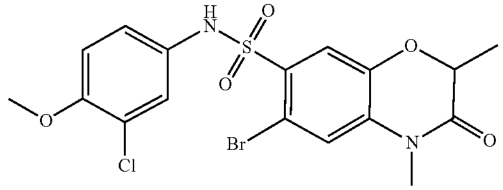 | + | + |
| BC19920 | 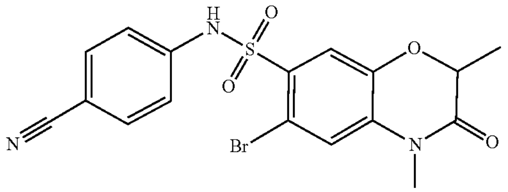 [SMILES: CC1Oc2cc(S(=O)(=O)Nc3ccc(C#N)cc3)c(Br)cc2N(C)C1=O] | +++ | + |
| BC19922 | 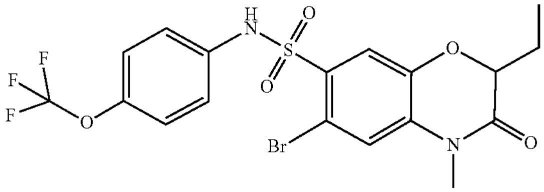 [SMILES: CCC1Oc2cc(S(=O)(=O)Nc3ccc(OC(F)(F)F)cc3)c(Br)cc2N(C)C1=O] | ++++ | + |
| BC19924 | 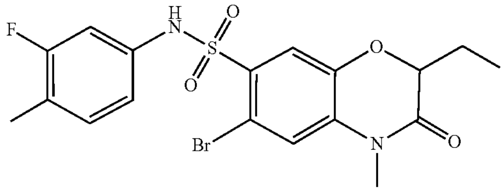 [SMILES: CCC1Oc2cc(S(=O)(=O)Nc3ccc(C)c(F)c3)c(Br)cc2N(C)C1=O] | ++++ | ++ |
| BC19926 | 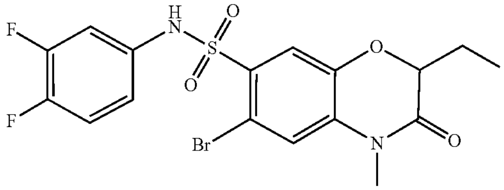 [SMILES: CCC1Oc2cc(S(=O)(=O)Nc3ccc(F)c(F)c3)c(Br)cc2N(C)C1=O] | ++++ | + |
| BC19928 | 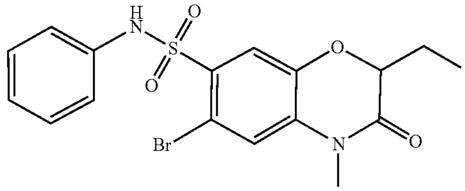 [SMILES: CCC1Oc2cc(S(=O)(=O)Nc3ccccc3)c(Br)cc2N(C)C1=O] | +++ | ++ |

TABLE 2c-2-continued
| BC No. | Structure | $IC_{50}$ (NF-κB assay) | $IC_{50}$ (TNF assay) |
|---|---|---|---|
| BC19930 | 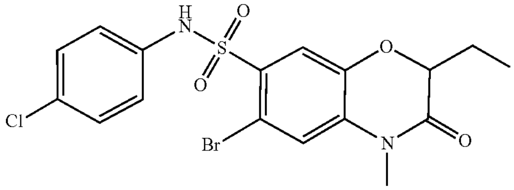 [SMILES: CCC1Oc2cc(S(=O)(=O)Nc3ccc(Cl)cc3)c(Br)cc2N(C)C1=O] | +++ | + |
| BC19932 | 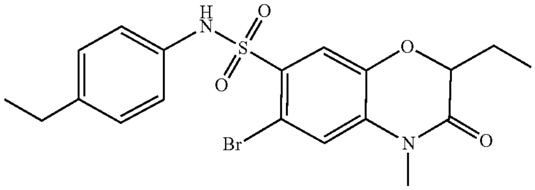 [SMILES: CCc1ccc(NS(=O)(=O)c2cc3c(cc2Br)N(C)C(=O)C(CC)O3)cc1] | ++++ | ++ |
| BC19934 | 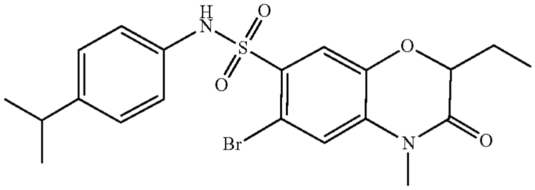 [SMILES: CCC1Oc2cc(S(=O)(=O)Nc3ccc(C(C)C)cc3)c(Br)cc2N(C)C1=O] | +++ | ++ |
| BC19936 | 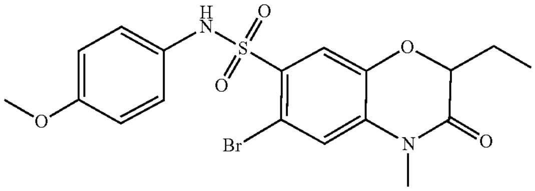 [SMILES: CCC1Oc2cc(S(=O)(=O)Nc3ccc(OC)cc3)c(Br)cc2N(C)C1=O] | ++++ | + |
| BC19938 | 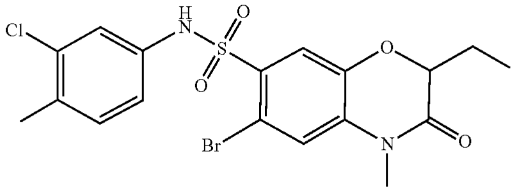 [SMILES: CCC1Oc2cc(S(=O)(=O)Nc3ccc(C)c(Cl)c3)c(Br)cc2N(C)C1=O] | +++ | ++ |
TABLE 2d
| BC No. | ZE No. | Structure | $IC_{50}$ (NF-κB assay) | $IC_{50}$ (TNF assay) |
|---|---|---|---|---|
| BC19168 | ZE24-0050 | 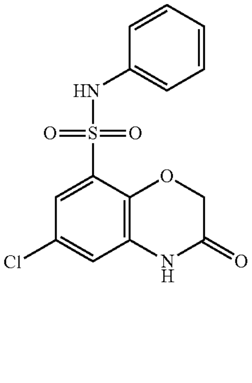 [SMILES: O=C1COc2c(cc(Cl)cc2S(=O)(=O)Nc2ccccc2)N1] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19169 | ZE24-0051 | 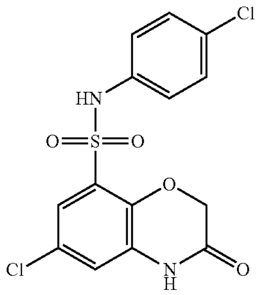 [SMILES: O=C1COc2c(cc(Cl)cc2S(=O)(=O)Nc2ccc(Cl)cc2)N1] | ++++ | + |
| BC19170 | ZE24-0052 | 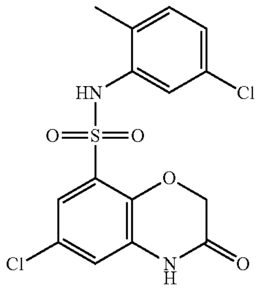 [SMILES: Cc1ccc(Cl)cc1NS(=O)(=O)c1cc(Cl)cc2c1OCC(=O)N2] | ++ | + |
| BC19171 | ZE24-0053 | 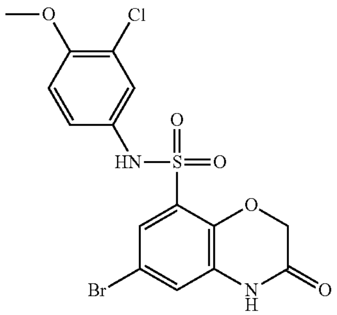 [SMILES: COc1ccc(NS(=O)(=O)c2cc(Br)cc3c2OCC(=O)N3)cc1Cl] | ++++ | + |
| BC19172 | ZE24-0054 | 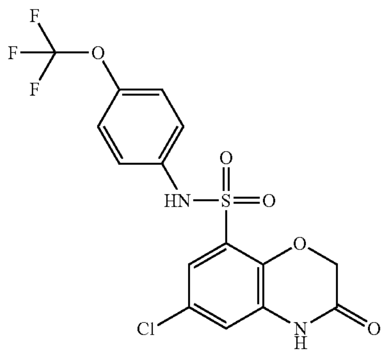 [SMILES: O=C1COc2c(cc(Cl)cc2S(=O)(=O)Nc2ccc(OC(F)(F)F)cc2)N1] | ++++ | + |

TABLE 2d-continued
| BC No. | ZE No. | Structure | IC50 (NF-κB assay) | IC50 (TNF assay) |
|---|---|---|---|---|
| BC19173 | ZE24-0055 | 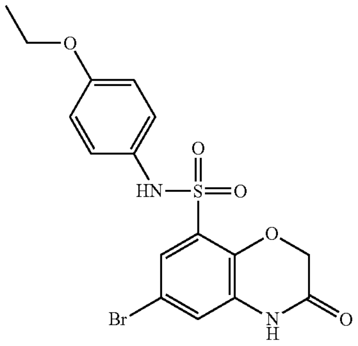 [SMILES: CCOc1ccc(NS(=O)(=O)c2cc(Br)cc3c2OCC(=O)N3)cc1] | ++++ | + |
| BC19174 | ZE24-0056 | 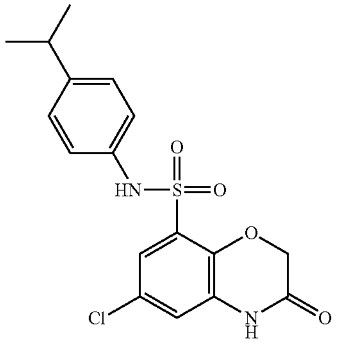 [SMILES: CC(C)c1ccc(NS(=O)(=O)c2cc(Cl)cc3c2OCC(=O)N3)cc1] | ++++ | + |
| BC19175 | ZE24-0057 | 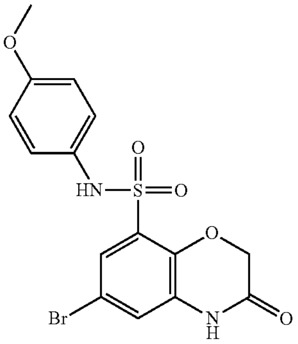 [SMILES: COc1ccc(NS(=O)(=O)c2cc(Br)cc3c2OCC(=O)N3)cc1] | ++++ | + |
| BC19176 | ZE24-0058 | 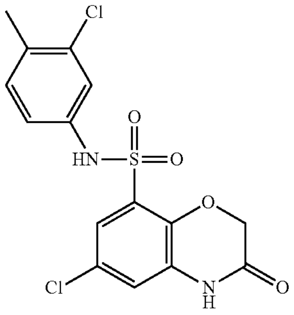 [SMILES: Cc1ccc(NS(=O)(=O)c2cc(Cl)cc3c2OCC(=O)N3)cc1Cl] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19177 | ZE24-0059 | 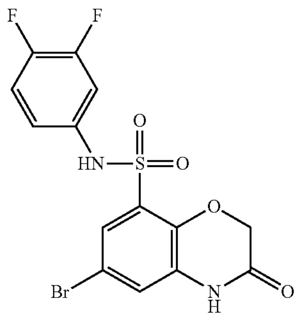 [SMILES: O=C1COc2c(cc(Br)cc2S(=O)(=O)Nc2ccc(F)c(F)c2)N1] | ++++ | + |
| BC19178 | ZE24-0060 | 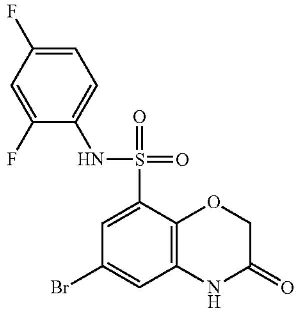 [SMILES: O=C1COc2c(cc(Br)cc2S(=O)(=O)Nc2ccc(F)cc2F)N1] | ++++ | ++ |
| BC19179 | ZE24-0061 | 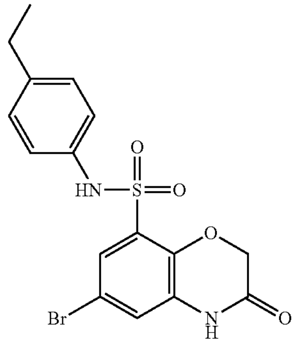 [SMILES: CCc1ccc(NS(=O)(=O)c2cc(Br)cc3c2OCC(=O)N3)cc1] | ++++ | + |
| BC19180 | ZE24-0062 | 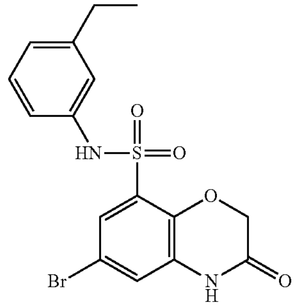 [SMILES: CCc1cccc(NS(=O)(=O)c2cc(Br)cc3c2OCC(=O)N3)c1] | ++++ | + |
| BC19225 | ZE24-0064 | 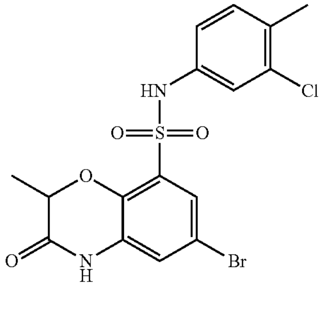 [SMILES: Cc1ccc(NS(=O)(=O)c2cc(Br)cc3c2OC(C)C(=O)N3)cc1Cl] | +++ | + |

TABLE 2d-continued
| BC No. | ZE No. | Structure | $IC_{50}$ (NF-κB assay) | $IC_{50}$ (TNF assay) |
|---|---|---|---|---|
| BC19226 | ZE24-0065 | 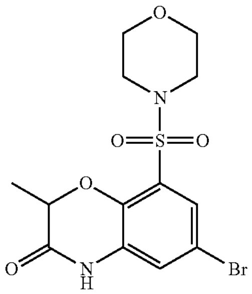 [SMILES: CC1Oc2c(cc(Br)cc2S(=O)(=O)N2CCOCC2)NC1=O] | ++ | + |
| BC19227 | ZE24-0066 | 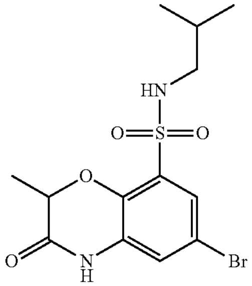 [SMILES: CC(C)CNS(=O)(=O)c1cc(Br)cc2c1OC(C)C(=O)N2] | + | + |
| BC19228 | ZE24-0067 | 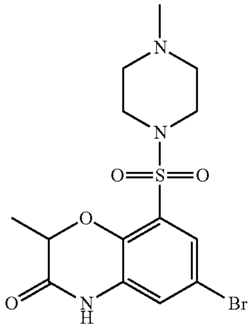 [SMILES: CC1Oc2c(cc(Br)cc2S(=O)(=O)N2CCN(C)CC2)NC1=O] | + | + |
| BC19229 | ZE24-0068 | 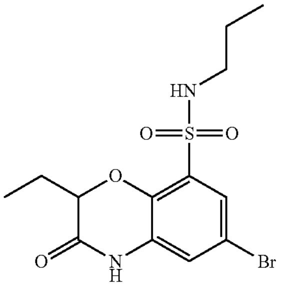 [SMILES: CCCNS(=O)(=O)c1cc(Br)cc2c1OC(CC)C(=O)N2] | ++ | + |
| BC19230 | ZE24-0069 | 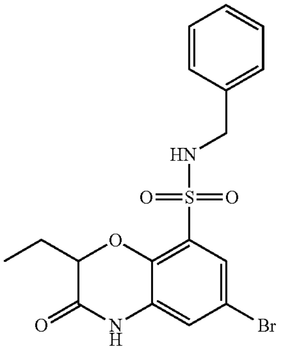 [SMILES: CCC1Oc2c(cc(Br)cc2S(=O)(=O)NCc2ccccc2)NC1=O] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19231 | ZE24-0070 | 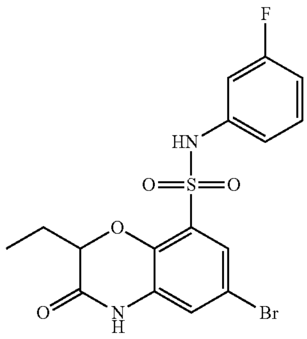 [SMILES: CCC1Oc2c(cc(Br)cc2S(=O)(=O)Nc2cccc(F)c2)NC1=O] | ++++ | + |
| BC19232 | ZE24-0071 | 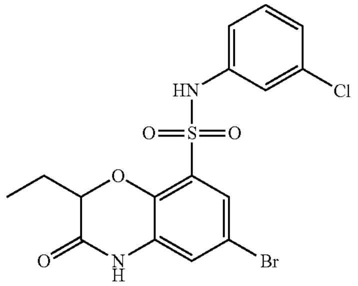 [SMILES: CCC1Oc2c(cc(Br)cc2S(=O)(=O)Nc2cccc(Cl)c2)NC1=O] | ++++ | + |
| BC19233 | ZE24-0072 | 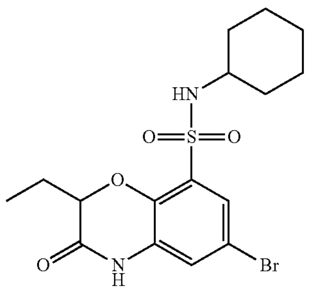 [SMILES: CCC1Oc2c(cc(Br)cc2S(=O)(=O)NC2CCCCC2)NC1=O] | ++ | ++ |
| BC19234 | ZE24-0073 | 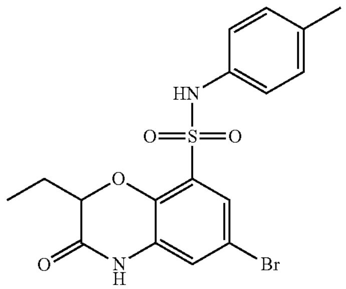 [SMILES: CCC1Oc2c(cc(Br)cc2S(=O)(=O)Nc2ccc(C)cc2)NC1=O] | ++++ | ++ |
| BC19288 | ZE24-0074 | 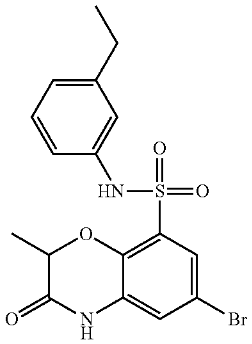 [SMILES: CCc1cccc(NS(=O)(=O)c2cc(Br)cc3c2OC(C)C(=O)N3)c1] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19289 | ZE24-0075 | 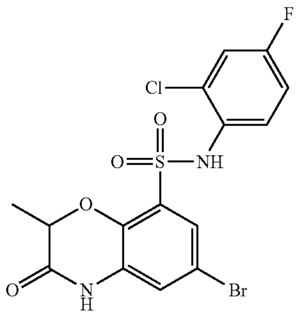 [SMILES: CC1Oc2c(cc(Br)cc2S(=O)(=O)Nc2ccc(F)cc2Cl)NC1=O] | ++++ | + |
| BC19290 | ZE24-0076 | 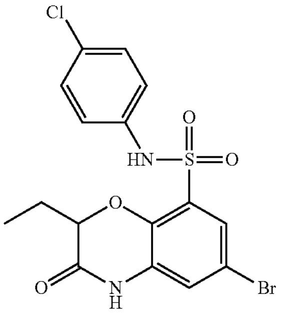 [SMILES: CCC1Oc2c(cc(Br)cc2S(=O)(=O)Nc2ccc(Cl)cc2)NC1=O] | ++++ | + |
| BC19291 | ZE24-0077 | 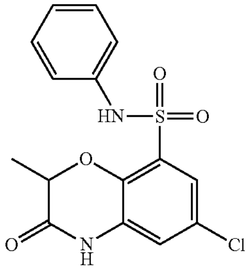 [SMILES: CC1Oc2c(cc(Cl)cc2S(=O)(=O)Nc2ccccc2)NC1=O] | ++++ | + |
| BC19292 | ZE24-0078 | 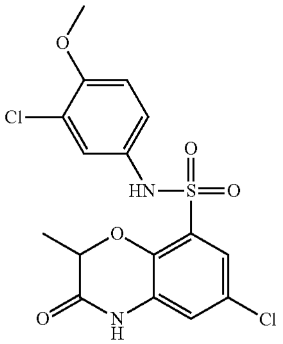 [SMILES: COc1ccc(NS(=O)(=O)c2cc(Cl)cc3c2OC(C)C(=O)N3)cc1Cl] | ++++ | + |
| BC19293 | ZE24-0080 | 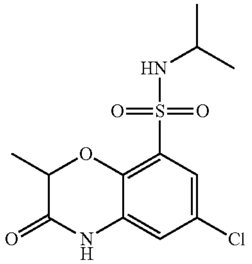 [SMILES: CC(C)NS(=O)(=O)c1cc(Cl)cc2c1OC(C)C(=O)N2] | +++ | + |

TABLE 2d-continued
| BC No. | ZE No. | Structure | $IC_{50}$ (NF-κB assay) | $IC_{50}$ (TNF assay) |
|---|---|---|---|---|
| BC19294 | ZE24-0081 | 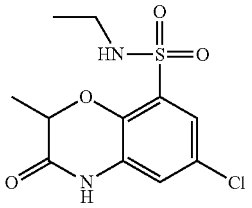 [SMILES: CCNS(=O)(=O)c1cc(Cl)cc2c1OC(C)C(=O)N2] | ++ | + |
| BC19355 | ZE24-0079 | 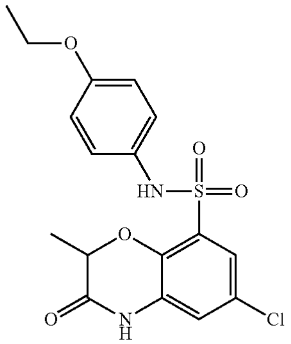 [SMILES: CCOc1ccc(NS(=O)(=O)c2cc(Cl)cc3c2OC(C)C(=O)N3)cc1] | ++++ | + |
| BC19362 | ZE24-0089 | 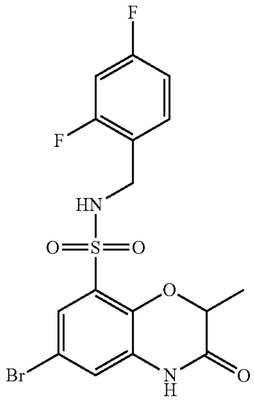 [SMILES: CC1Oc2c(cc(Br)cc2S(=O)(=O)NCc2ccc(F)cc2F)NC1=O] | +++ | + |
| BC19363 | ZE24-0090 | 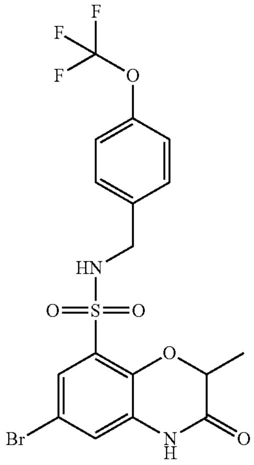 [SMILES: CC1Oc2c(cc(Br)cc2S(=O)(=O)NCc2ccc(OC(F)(F)F)cc2)NC1=O] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19364 | ZE24-0092 | 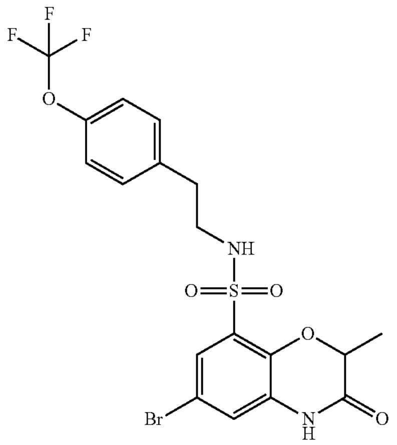 [SMILES: CC1Oc2c(cc(Br)cc2S(=O)(=O)NCCc2ccc(OC(F)(F)F)cc2)NC1=O] | + | + |
| BC19365 | ZE24-0093 | 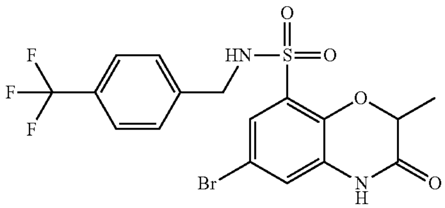 [SMILES: CC1Oc2c(cc(Br)cc2S(=O)(=O)NCc2ccc(C(F)(F)F)cc2)NC1=O] | ++ | + |
| BC19366 | ZE24-0094 | 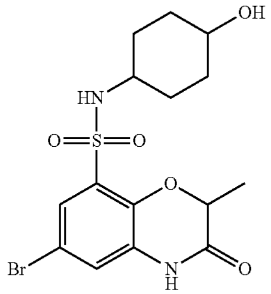 [SMILES: CC1Oc2c(cc(Br)cc2S(=O)(=O)NC2CCC(O)CC2)NC1=O] | + | + |
| BC19367 | ZE24-0095 | 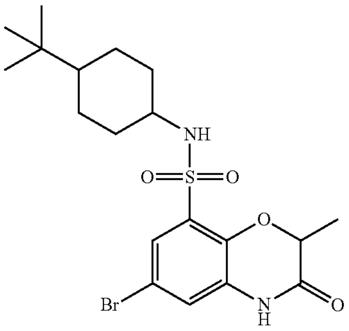 [SMILES: CC1Oc2c(cc(Br)cc2S(=O)(=O)NC2CCC(C(C)(C)C)CC2)NC1=O] | + | + |

TABLE 2d-continued
| BC No. | ZE No. | Structure | $IC_{50}$ (NF-κB assay) | $IC_{50}$ (TNF assay) |
|---|---|---|---|---|
| BC19374 | ZE24-0103 | 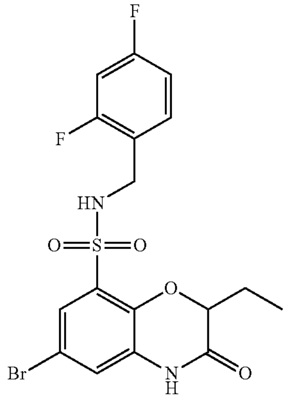 [SMILES: CCC1Oc2c(cc(Br)cc2S(=O)(=O)NCc2ccc(F)cc2F)NC1=O] | ++++ | ++ |
| BC19375 | ZE24-0104 | 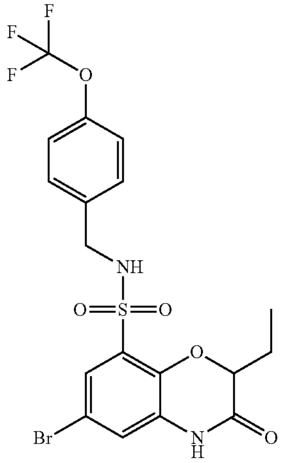 [SMILES: CCC1Oc2c(cc(Br)cc2S(=O)(=O)NCc2ccc(OC(F)(F)F)cc2)NC1=O] | ++++ | + |
| BC19376 | ZE24-0106 | 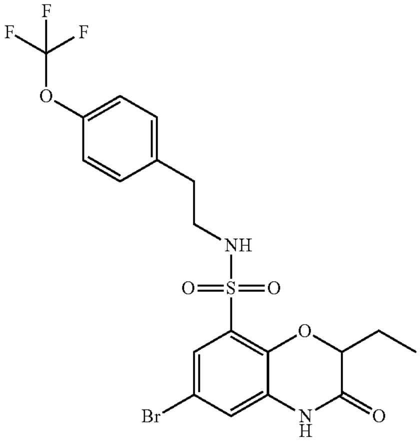 [SMILES: CCC1Oc2c(cc(Br)cc2S(=O)(=O)NCCc2ccc(OC(F)(F)F)cc2)NC1=O] | ++ | + |

TABLE 2d-continued
| BC No. | ZE No. | Structure | $IC_{50}$ (NF-κB assay) | $IC_{50}$ (TNF assay) |
|---|---|---|---|---|
| BC19377 | ZE24-0107 | 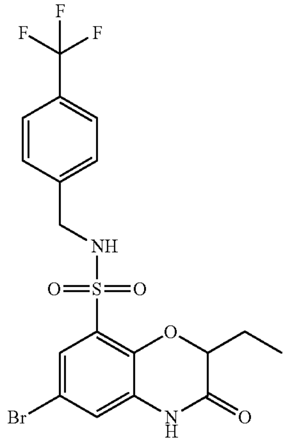 [SMILES: CCC1Oc2c(cc(Br)cc2S(=O)(=O)NCc2ccc(C(F)(F)F)cc2)NC1=O] | ++++ | + |
| BC19378 | ZE24-0108 | 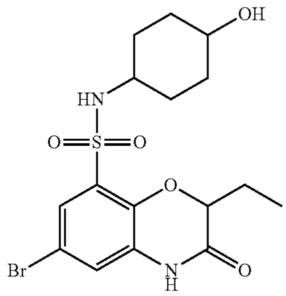 [SMILES: CCC1Oc2c(cc(Br)cc2S(=O)(=O)NC2CCC(O)CC2)NC1=O] | + | + |
| BC19379 | ZE24-0109 | 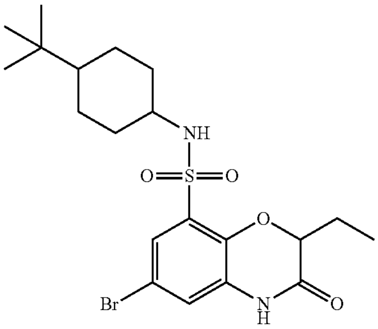 [SMILES: CCC1Oc2c(cc(Br)cc2S(=O)(=O)NC2CCC(C(C)(C)C)CC2)NC1=O] | + | + |
| BC19380 | ZE24-0110 | 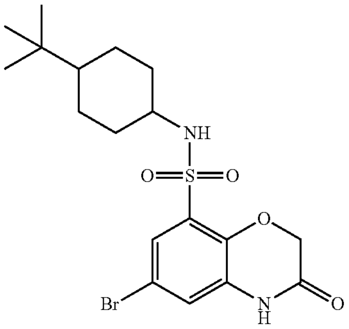 [SMILES: CC(C)(C)C1CCC(NS(=O)(=O)c2cc(Br)cc3c2OCC(=O)N3)CC1] | + | + |

TABLE 2d-continued
| BC No. | ZE No. | Structure | $IC_{50}$ (NF-κB assay) | $IC_{50}$ (TNF assay) |
|---|---|---|---|---|
| BC19381 | ZE24-0111 | 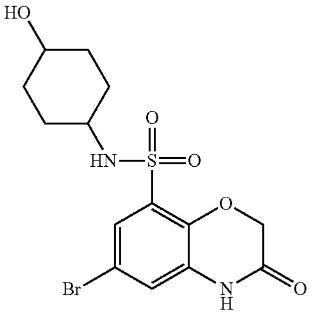 [SMILES: O=C1COc2c(cc(Br)cc2S(=O)(=O)NC2CCC(O)CC2)N1] | + | + |
| BC19382 | ZE24-0112 | 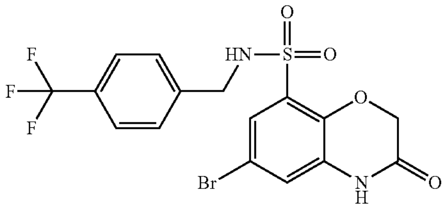 [SMILES: O=C1COc2c(cc(Br)cc2S(=O)(=O)NCc2ccc(C(F)(F)F)cc2)N1] | + | + |
| BC19383 | ZE24-0113 | 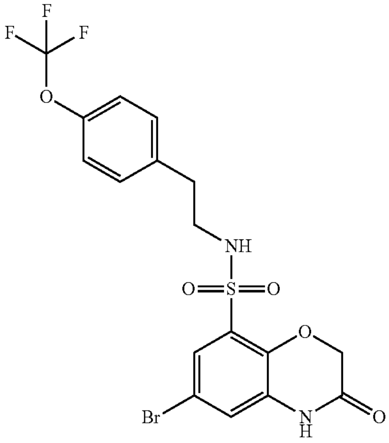 [SMILES: O=C1COc2c(cc(Br)cc2S(=O)(=O)NCCc2ccc(OC(F)(F)F)cc2)N1] | + | + |
| BC19384 | ZE24-0114 | 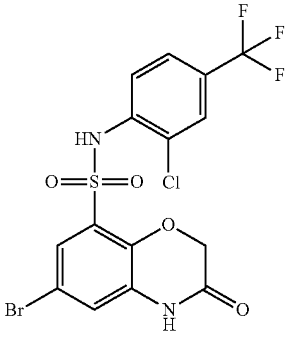 [SMILES: O=C1COc2c(cc(Br)cc2S(=O)(=O)Nc2ccc(C(F)(F)F)cc2Cl)N1] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19385 | ZE24-0115 | 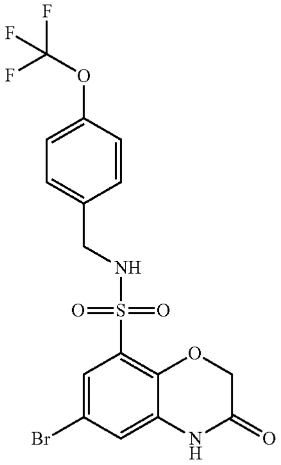 [SMILES: O=C1COc2c(cc(Br)cc2S(=O)(=O)NCc2ccc(OC(F)(F)F)cc2)N1] | + | + |
| BC19386 | ZE24-0116 | 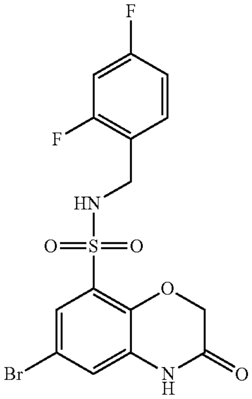 [SMILES: O=C1COc2c(cc(Br)cc2S(=O)(=O)NCc2ccc(F)cc2F)N1] | + | + |
| BC19394 | ZE24-0124 | 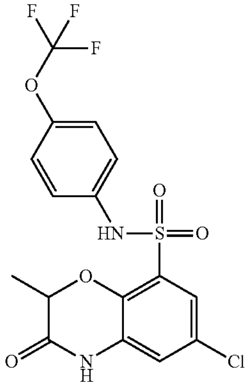 [SMILES: CC1Oc2c(cc(Cl)cc2S(=O)(=O)Nc2ccc(OC(F)(F)F)cc2)NC1=O] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19421 | ZE24-0125 | 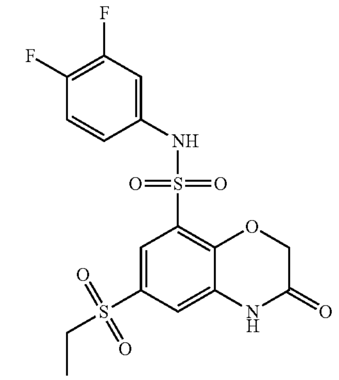 [SMILES: CCS(=O)(=O)c1cc2c(c(S(=O)(=O)Nc3ccc(F)c(F)c3)c1)OCC(=O)N2] | ++++ | + |
| BC19422 | ZE24-0127 | 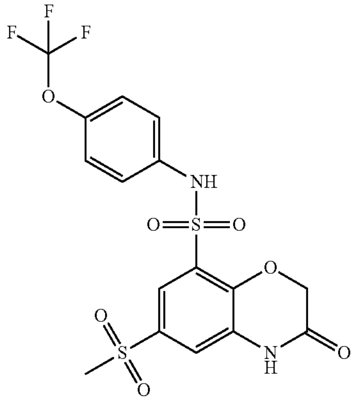 [SMILES: CS(=O)(=O)c1cc2c(c(S(=O)(=O)Nc3ccc(OC(F)(F)F)cc3)c1)OCC(=O)N2] | ++++ | + |
| BC19423 | ZE24-0128 | 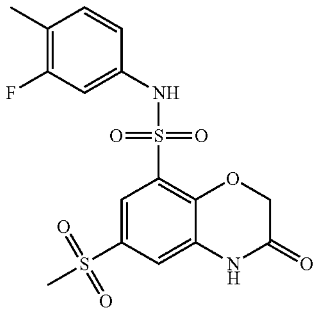 [SMILES: Cc1ccc(NS(=O)(=O)c2cc(S(C)(=O)=O)cc3c2OCC(=O)N3)cc1F] | ++++ | + |
| BC19424 | ZE24-0132 | 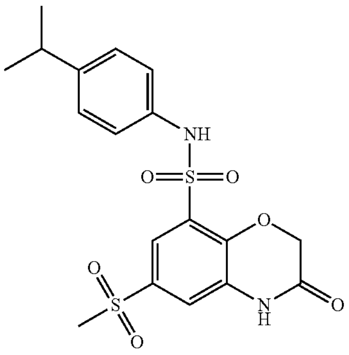 [SMILES: CC(C)c1ccc(NS(=O)(=O)c2cc(S(C)(=O)=O)cc3c2OCC(=O)N3)cc1] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19425 | ZE24-0135 | 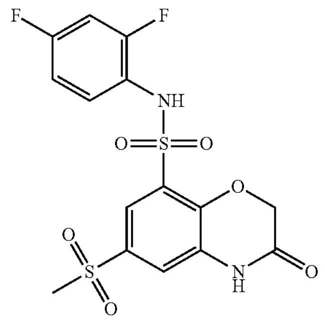 [SMILES: CS(=O)(=O)c1cc2c(c(S(=O)(=O)Nc3ccc(F)cc3F)c1)OCC(=O)N2] | ++++ | + |
| BC19426 | ZE24-0137 | 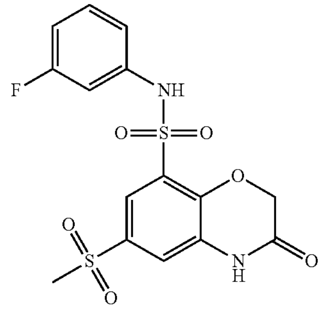 [SMILES: CS(=O)(=O)c1cc2c(c(S(=O)(=O)Nc3cccc(F)c3)c1)OCC(=O)N2] | ++++ | + |
| BC19427 | ZE24-0138 | 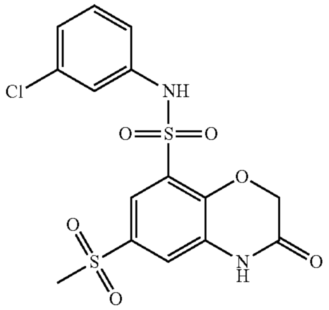 [SMILES: CS(=O)(=O)c1cc2c(c(S(=O)(=O)Nc3cccc(Cl)c3)c1)OCC(=O)N2] | ++++ | + |
| BC19428 | ZE24-0140 | 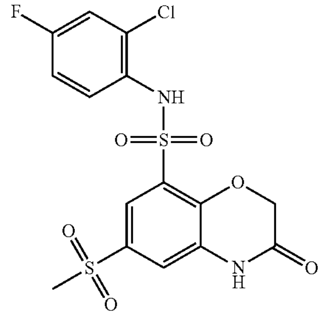 [SMILES: CS(=O)(=O)c1cc2c(c(S(=O)(=O)Nc3ccc(F)cc3Cl)c1)OCC(=O)N2] | +++ | + |
| BC19429 | ZE24-0141 | 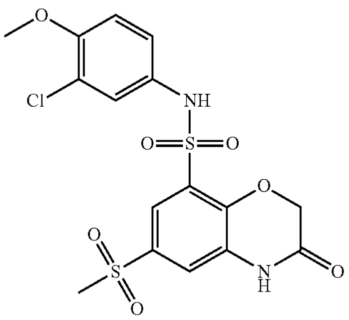 [SMILES: COc1ccc(NS(=O)(=O)c2cc(S(C)(=O)=O)cc3c2OCC(=O)N3)cc1Cl] | + | + |

TABLE 2d-continued
| BC No. | ZE No. | Structure | $IC_{50}$ (NF-κB assay) | $IC_{50}$ (TNF assay) |
|---|---|---|---|---|
| BC19430 | ZE24-0142 | 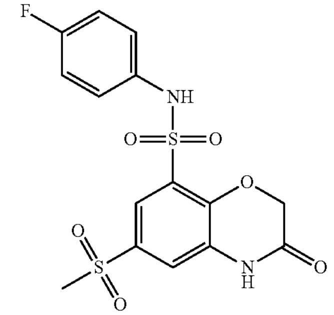 [SMILES: CS(=O)(=O)c1cc2c(c(S(=O)(=O)Nc3ccc(F)cc3)c1)OCC(=O)N2] | ++++ | + |
| BC19431 | ZE24-0144 | 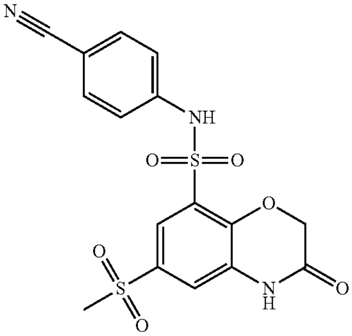 [SMILES: CS(=O)(=O)c1cc2c(c(S(=O)(=O)Nc3ccc(C#N)cc3)c1)OCC(=O)N2] | ++++ | + |
| BC19432 | ZE24-0147 | 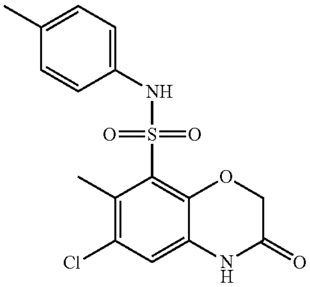 [SMILES: Cc1ccc(NS(=O)(=O)c2c(C)c(Cl)cc3c2OCC(=O)N3)cc1] | +++ | + |
| BC19433 | ZE24-0150 | 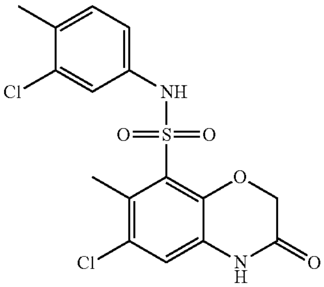 [SMILES: Cc1ccc(NS(=O)(=O)c2c(C)c(Cl)cc3c2OCC(=O)N3)cc1Cl] | ++++ | + |
| BC19434 | ZE24-0151 | 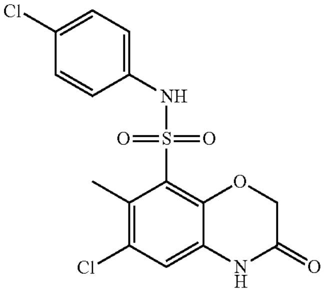 [SMILES: Cc1c(Cl)cc2c(c1S(=O)(=O)Nc1ccc(Cl)cc1)OCC(=O)N2] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19435 | ZE24-0152 | 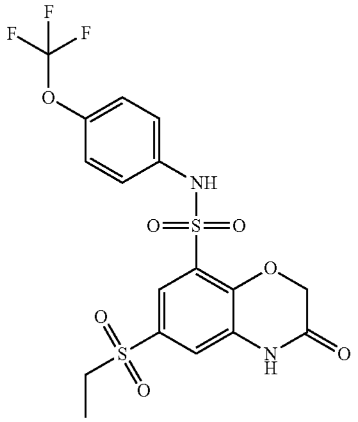 [SMILES: CCS(=O)(=O)c1cc2c(c(S(=O)(=O)Nc3ccc(OC(F)(F)F)cc3)c1)OCC(=O)N2] | ++++ | + |
| BC19436 | ZE24-0153 | 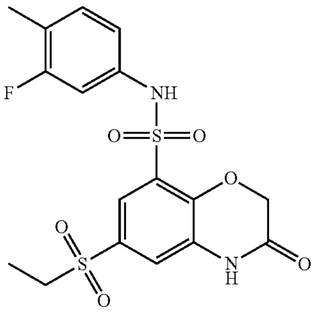 [SMILES: CCS(=O)(=O)c1cc2c(c(S(=O)(=O)Nc3ccc(C)c(F)c3)c1)OCC(=O)N2] | ++++ | + |
| BC19437 | ZE24-0154 | 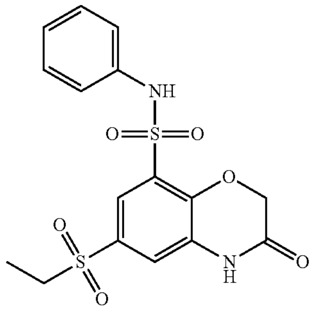 [SMILES: CCS(=O)(=O)c1cc2c(c(S(=O)(=O)Nc3ccccc3)c1)OCC(=O)N2] | ++++ | + |
| BC19438 | ZE24-0158 | 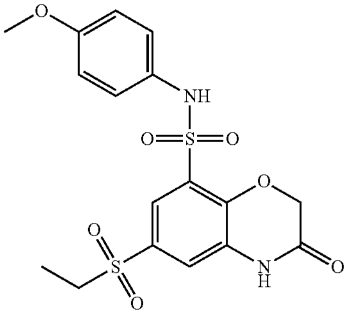 [SMILES: CCS(=O)(=O)c1cc2c(c(S(=O)(=O)Nc3ccc(OC)cc3)c1)OCC(=O)N2] | ++++ | + |

TABLE 2d-continued
| BC No. | ZE No. | Structure | $IC_{50}$ (NF-κB assay) | $IC_{50}$ (TNF assay) |
|---|---|---|---|---|
| BC19439 | ZE24-0161 | 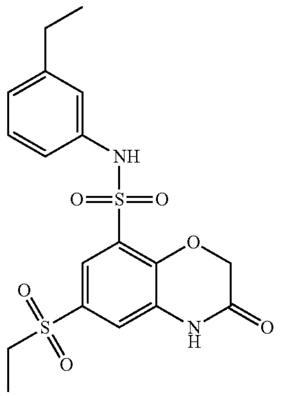 [SMILES: CCc1cccc(NS(=O)(=O)c2cc(S(=O)(=O)CC)cc3c2OCC(=O)N3)c1] | ++++ | + |
| BC19440 | ZE24-0162 | 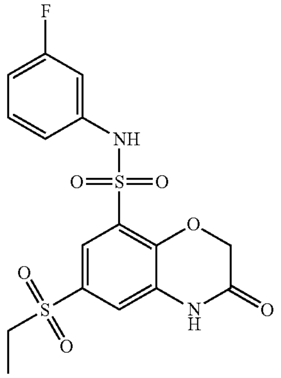 [SMILES: CCS(=O)(=O)c1cc2c(c(S(=O)(=O)Nc3cccc(F)c3)c1)OCC(=O)N2] | ++++ | + |
| BC19441 | ZE24-0163 | 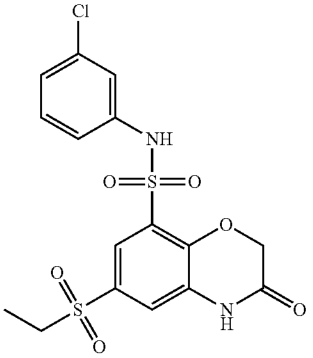 [SMILES: CCS(=O)(=O)c1cc2c(c(S(=O)(=O)Nc3cccc(Cl)c3)c1)OCC(=O)N2] | ++++ | + |
| BC19442 | ZE24-0165 | 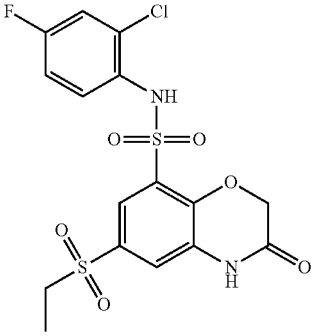 [SMILES: CCS(=O)(=O)c1cc2c(c(S(=O)(=O)Nc3ccc(F)cc3Cl)c1)OCC(=O)N2] | +++ | + |

TABLE 2d-continued
| BC No. | ZE No. | Structure | $IC_{50}$ (NF-κB assay) | $IC_{50}$ (TNF assay) |
|---|---|---|---|---|
| BC19443 | ZE24-0167 | 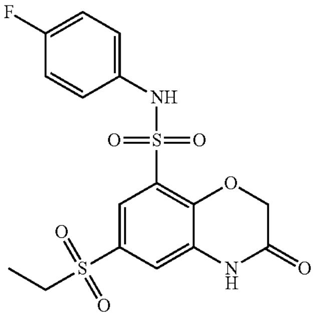 [SMILES: CCS(=O)(=O)c1cc2c(c(S(=O)(=O)Nc3ccc(F)cc3)c1)OCC(=O)N2] | ++++ | + |
TABLE 2d-2
| BC No. | Structure | $IC_{50}$ (NF-κB assay) | $IC_{50}$ (TNF assay) |
|---|---|---|---|
| BC19481 | 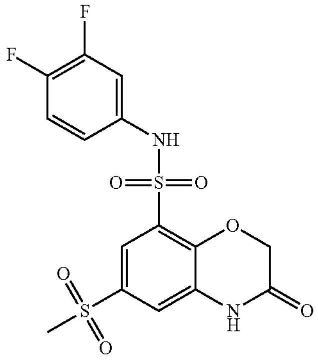 [SMILES: CS(=O)(=O)c1cc2c(c(S(=O)(=O)Nc3ccc(F)c(F)c3)c1)OCC(=O)N2] | ++++ | + |
| BC19482 | 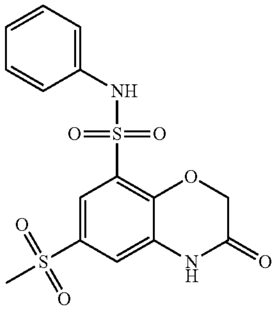 [SMILES: CS(=O)(=O)c1cc2c(c(S(=O)(=O)Nc3ccccc3)c1)OCC(=O)N2] | +++ | + |
| BC19483 | 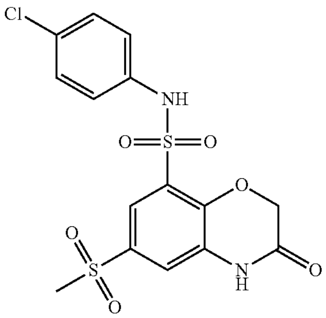 [SMILES: CS(=O)(=O)c1cc2c(c(S(=O)(=O)Nc3ccc(Cl)cc3)c1)OCC(=O)N2] | ++++ | + |

TABLE 2d-2-continued
| BC No. | Structure | $IC_{50}$ (NF-κB assay) | $IC_{50}$ (TNF assay) |
|---|---|---|---|
| BC19484 | 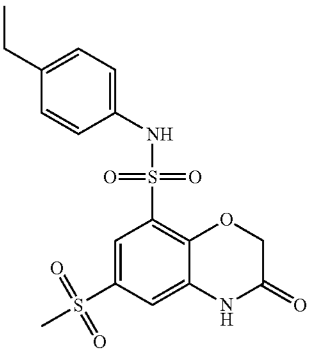 [SMILES: CCc1ccc(NS(=O)(=O)c2cc(S(C)(=O)=O)cc3c2OCC(=O)N3)cc1] | ++++ | + |
| BC19485 | 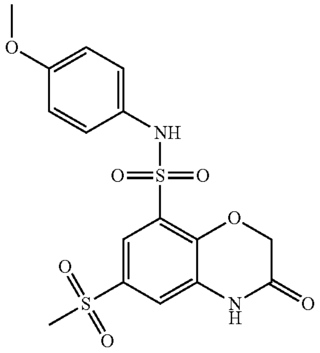 [SMILES: COc1ccc(NS(=O)(=O)c2cc(S(C)(=O)=O)cc3c2OCC(=O)N3)cc1] | ++++ | + |
| BC19486 | 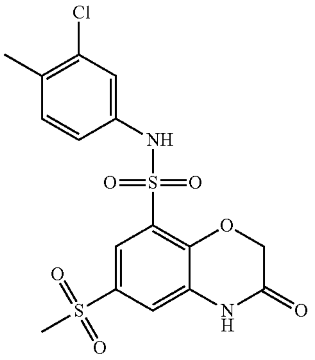 [SMILES: Cc1ccc(NS(=O)(=O)c2cc(S(C)(=O)=O)cc3c2OCC(=O)N3)cc1Cl] | ++++ | + |
| BC19487 | 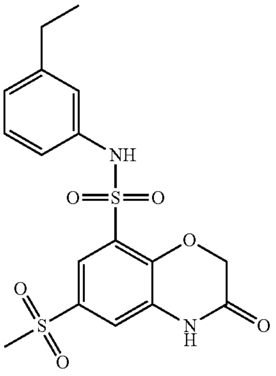 [SMILES: CCc1cccc(NS(=O)(=O)c2cc(S(C)(=O)=O)cc3c2OCC(=O)N3)c1] | +++ | + |

TABLE 2d-2-continued
| BC No. | Structure | $IC_{50}$ (NF-κB assay) | $IC_{50}$ (TNF assay) |
|---|---|---|---|
| BC19488 | 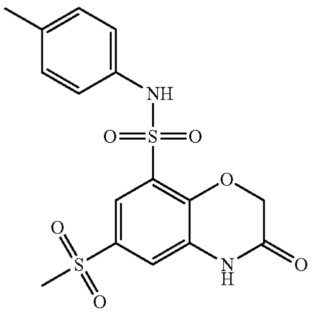 [SMILES: Cc1ccc(NS(=O)(=O)c2cc(S(C)(=O)=O)cc3c2OCC(=O)N3)cc1] | ++++ | + |
| BC19489 | 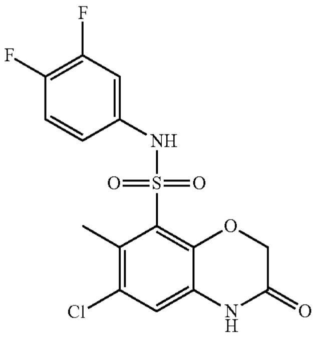 [SMILES: Cc1c(Cl)cc2c(c1S(=O)(=O)Nc1ccc(F)c(F)c1)OCC(=O)N2] | ++++ | + |
| BC19490 | 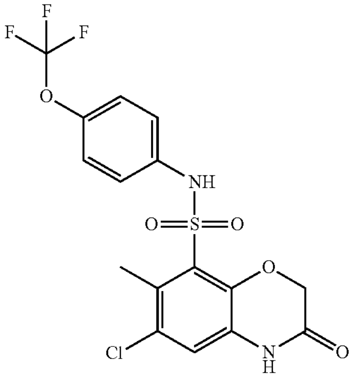 [SMILES: Cc1c(Cl)cc2c(c1S(=O)(=O)Nc1ccc(OC(F)(F)F)cc1)OCC(=O)N2] | ++++ | + |
| BC19491 | 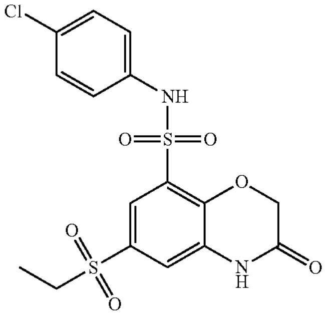 [SMILES: CCS(=O)(=O)c1cc2c(c(S(=O)(=O)Nc3ccc(Cl)cc3)c1)OCC(=O)N2] | ++++ | + |

TABLE 2d-2-continued
| BC No. | Structure | IC50 (NF-κB assay) | IC50 (TNF assay) |
|---|---|---|---|
| BC19492 | 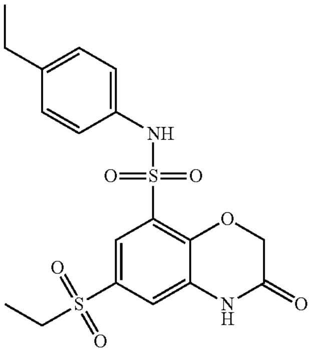 [SMILES: CCc1ccc(NS(=O)(=O)c2cc(S(=O)(=O)CC)cc3c2OCC(=O)N3)cc1] | ++++ | + |
| BC19493 | 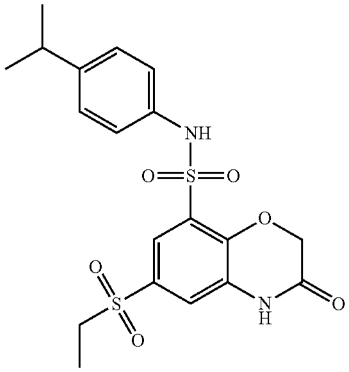 [SMILES: CCS(=O)(=O)c1cc2c(c(S(=O)(=O)Nc3ccc(C(C)C)cc3)c1)OCC(=O)N2] | ++++ | + |
| BC19544 | 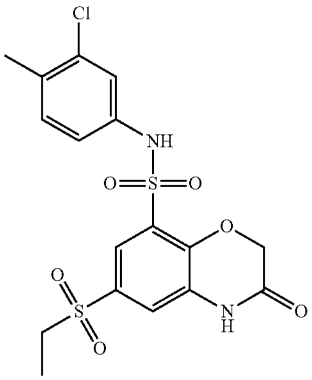 [SMILES: CCS(=O)(=O)c1cc2c(c(S(=O)(=O)Nc3ccc(C)c(Cl)c3)c1)OCC(=O)N2] | ++++ | + |
| BC19545 | 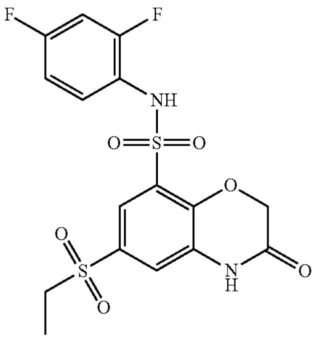 | ++++ | + |

TABLE 2d-2-continued
| BC No. | Structure | $IC_{50}$ (NF-κB assay) | $IC_{50}$ (TNF assay) |
|---|---|---|---|
| BC19546 | 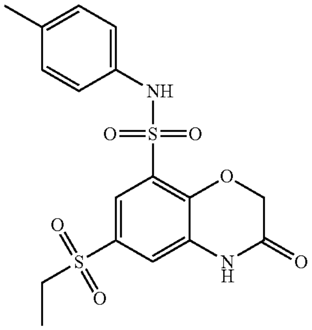 [SMILES: CCS(=O)(=O)c1cc2c(c(S(=O)(=O)Nc3ccc(C)cc3)c1)OCC(=O)N2] | ++++ | + |
| BC19547 | 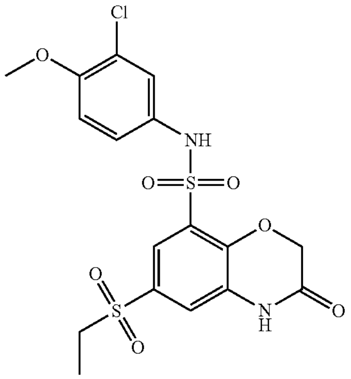 [SMILES: CCS(=O)(=O)c1cc2c(c(S(=O)(=O)Nc3ccc(OC)c(Cl)c3)c1)OCC(=O)N2] | +++ | + |
| BC19548 | 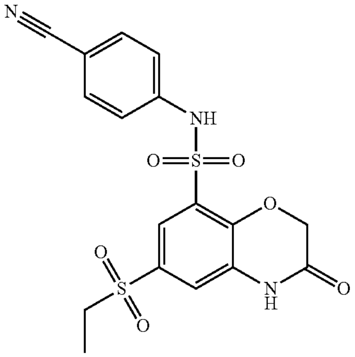 [SMILES: CCS(=O)(=O)c1cc2c(c(S(=O)(=O)Nc3ccc(C#N)cc3)c1)OCC(=O)N2] | ++++ | + |
| BC19697 | 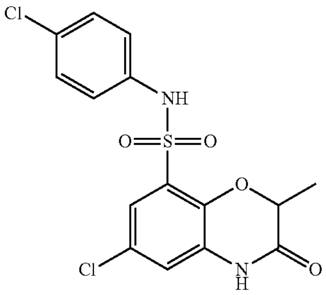 [SMILES: CC1Oc2c(cc(Cl)cc2S(=O)(=O)Nc2ccc(Cl)cc2)NC1=O] | ++++ | + |

TABLE 2d-2-continued
| BC No. | Structure | $IC_{50}$ (NF-κB assay) | $IC_{50}$ (TNF assay) |
|---|---|---|---|
| BC19699 | 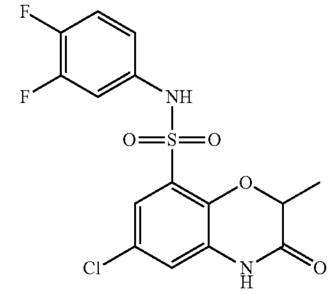 [SMILES: CC1Oc2c(cc(Cl)cc2S(=O)(=O)Nc2ccc(F)c(F)c2)NC1=O] | ++++ | + |
| BC19701 | 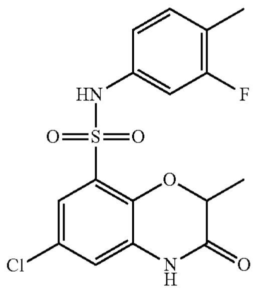 [SMILES: Cc1ccc(NS(=O)(=O)c2cc(Cl)cc3c2OC(C)C(=O)N3)cc1F] | ++++ | + |
| BC19703 | 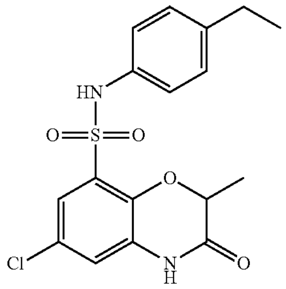 [SMILES: CCc1ccc(NS(=O)(=O)c2cc(Cl)cc3c2OC(C)C(=O)N3)cc1] | ++++ | + |
| BC19705 | 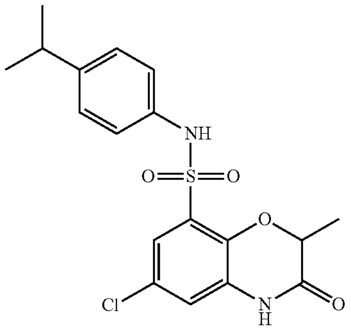 [SMILES: CC1Oc2c(cc(Cl)cc2S(=O)(=O)Nc2ccc(C(C)C)cc2)NC1=O] | ++++ | + |
| BC19707 | 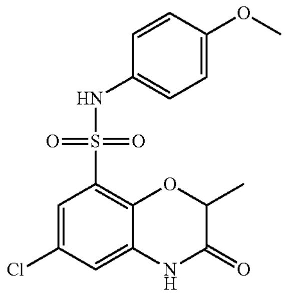 [SMILES: COc1ccc(NS(=O)(=O)c2cc(Cl)cc3c2OC(C)C(=O)N3)cc1] | ++++ | + |

TABLE 2d-2-continued
| BC No. | Structure | $IC_{50}$ (NF-κB assay) | $IC_{50}$ (TNF assay) |
|---|---|---|---|
| BC19710 | 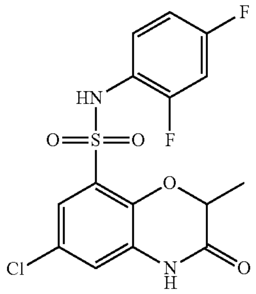 [SMILES: CC1Oc2c(cc(Cl)cc2S(=O)(=O)Nc2ccc(F)cc2F)NC1=O] | ++++ | + |
| BC19712 | 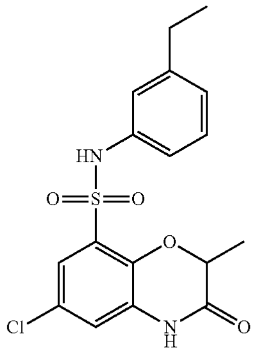 [SMILES: CCc1cccc(NS(=O)(=O)c2cc(Cl)cc3c2OC(C)C(=O)N3)c1] | ++++ | + |
| BC19714 | 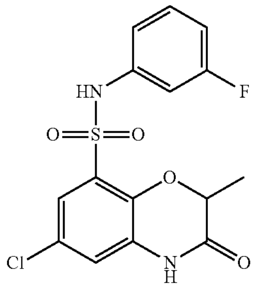 [SMILES: CC1Oc2c(cc(Cl)cc2S(=O)(=O)Nc2cccc(F)c2)NC1=O] | ++++ | ++ |
| BC19716 | 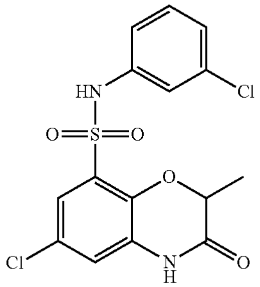 [SMILES: CC1Oc2c(cc(Cl)cc2S(=O)(=O)Nc2cccc(Cl)c2)NC1=O] | ++++ | ++ |
| BC19718 | 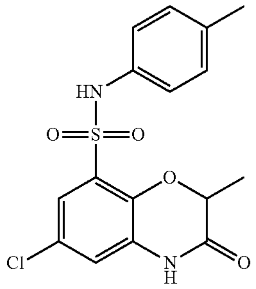 [SMILES: Cc1ccc(NS(=O)(=O)c2cc(Cl)cc3c2OC(C)C(=O)N3)cc1] | ++++ | ++ |

TABLE 2d-2-continued
| BC No. | Structure | $IC_{50}$ (NF-κB assay) | $IC_{50}$ (TNF assay) |
|---|---|---|---|
| BC19720 | 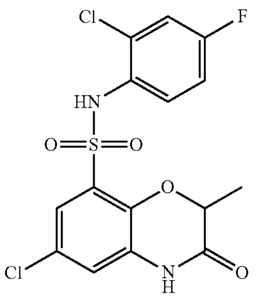 [SMILES: CC1Oc2c(cc(Cl)cc2S(=O)(=O)Nc2ccc(F)cc2Cl)NC1=O] | ++++ | + |
| BC19722 | 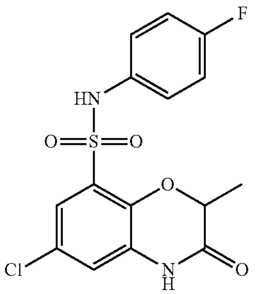 [SMILES: CC1Oc2c(cc(Cl)cc2S(=O)(=O)Nc2ccc(F)cc2)NC1=O] | ++++ | ++ |
| BC19730 | 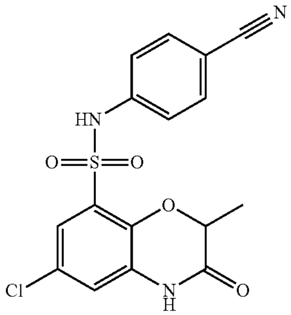 [SMILES: CC1Oc2c(cc(Cl)cc2S(=O)(=O)Nc2ccc(C#N)cc2)NC1=O] | ++++ | + |
| BC19732 | 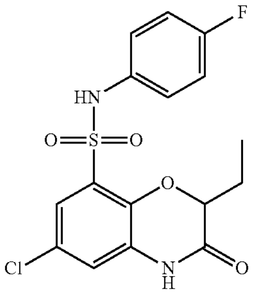 [SMILES: CCC1Oc2c(cc(Cl)cc2S(=O)(=O)Nc2ccc(F)cc2)NC1=O] | ++++ | ++ |
| BC19734 | 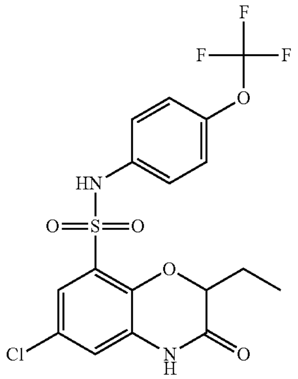 [SMILES: CCC1Oc2c(cc(Cl)cc2S(=O)(=O)Nc2ccc(OC(F)(F)F)cc2)NC1=O] | ++++ | + |

TABLE 2d-2-continued
| BC No. | Structure | $IC_{50}$ (NF-κB assay) | $IC_{50}$ (TNF assay) |
|---|---|---|---|
| BC19736 | 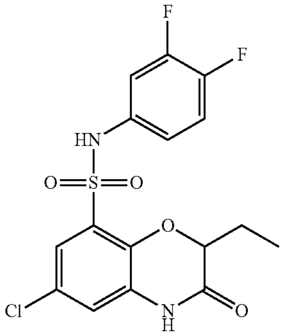 [SMILES: CCC1Oc2c(cc(Cl)cc2S(=O)(=O)Nc2ccc(F)c(F)c2)NC1=O] | ++++ | + |
| BC19738 | 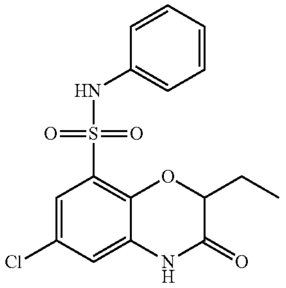 [SMILES: CCC1Oc2c(cc(Cl)cc2S(=O)(=O)Nc2ccccc2)NC1=O] | ++++ | + |
| BC19740 | 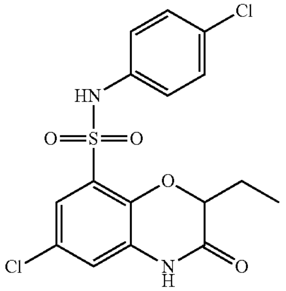 | ++++ | + |
| BC19742 | 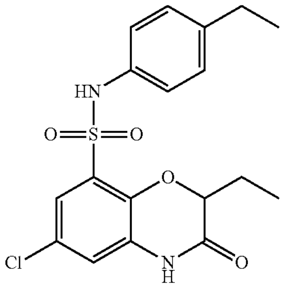 [SMILES: CCc1ccc(NS(=O)(=O)c2cc(Cl)cc3c2OC(CC)C(=O)N3)cc1] | ++++ | ++ |
| BC19744 | 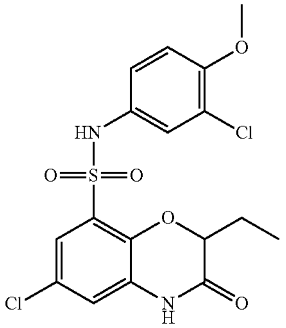 [SMILES: CCC1Oc2c(cc(Cl)cc2S(=O)(=O)Nc2ccc(OC)c(Cl)c2)NC1=O] | ++++ | ++ |

TABLE 2d-2-continued
| BC No. | Structure | $IC_{50}$ (NF-κB assay) | $IC_{50}$ (TNF assay) |
|---|---|---|---|
| BC19746 | 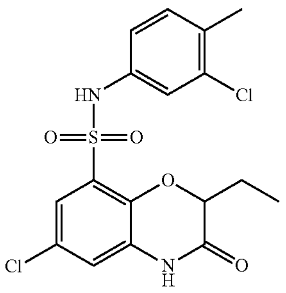 [SMILES: CCC1Oc2c(cc(Cl)cc2S(=O)(=O)Nc2ccc(C)c(Cl)c2)NC1=O] | ++++ | + |
| BC19748 | 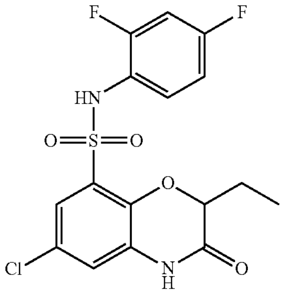 [SMILES: CCC1Oc2c(cc(Cl)cc2S(=O)(=O)Nc2ccc(F)cc2F)NC1=O] | ++++ | + |
| BC19750 | 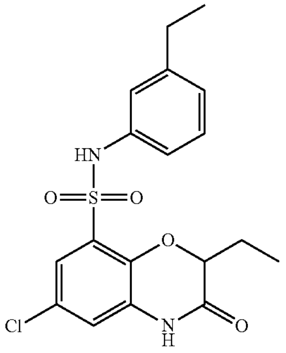 [SMILES: CCc1cccc(NS(=O)(=O)c2cc(Cl)cc3c2OC(CC)C(=O)N3)c1] | ++++ | + |
| BC19752 | 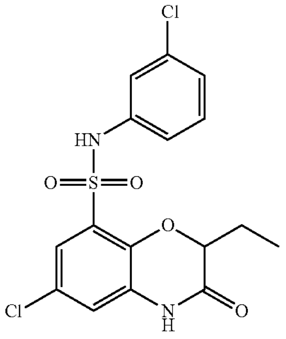 [SMILES: CCC1Oc2c(cc(Cl)cc2S(=O)(=O)Nc2cccc(Cl)c2)NC1=O] | ++++ | + |

TABLE 2d-2-continued
| BC No. | Structure | IC$_{50}$ (NF-κB assay) | IC$_{50}$ (TNF assay) |
|---|---|---|---|
| BC19754 | 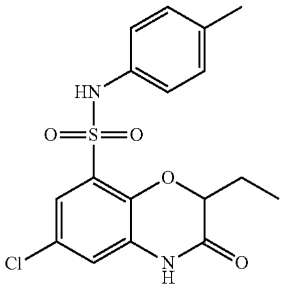 | ++++ | ++ |
| BC19756 | 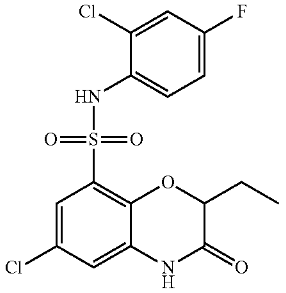 | ++++ | + |
| BC19757 | 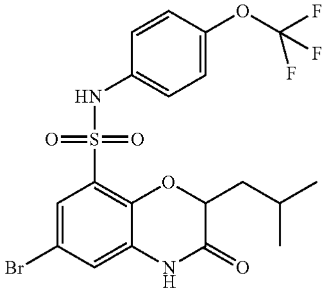 [SMILES: CC(C)CC1Oc2c(cc(Br)cc2S(=O)(=O)Nc2ccc(OC(F)(F)F)cc2)NC1=O] | ++++ | + |
| BC19759 | 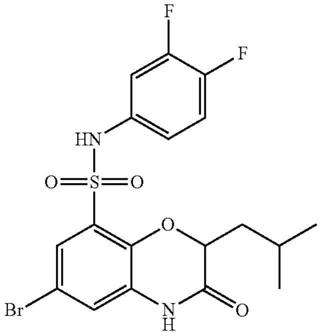 [SMILES: CC(C)CC1Oc2c(cc(Br)cc2S(=O)(=O)Nc2ccc(F)c(F)c2)NC1=O] | ++++ | + |
| BC19761 | 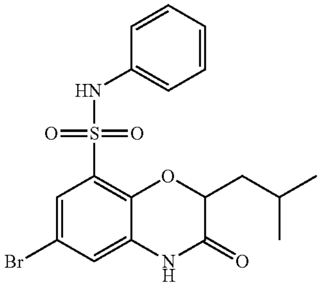 [SMILES: CC(C)CC1Oc2c(cc(Br)cc2S(=O)(=O)Nc2ccccc2)NC1=O] | +++ | + |

TABLE 2d-2-continued
| BC No. | Structure | $IC_{50}$ (NF-κB assay) | $IC_{50}$ (TNF assay) |
|---|---|---|---|
| BC19763 | 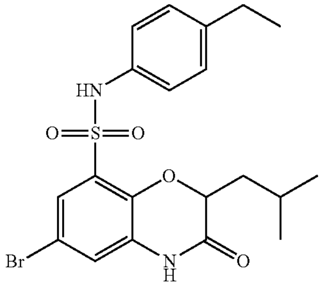 [SMILES: CCc1ccc(NS(=O)(=O)c2cc(Br)cc3c2OC(CC(C)C)C(=O)N3)cc1] | +++ | ++ |
| BC19765 | 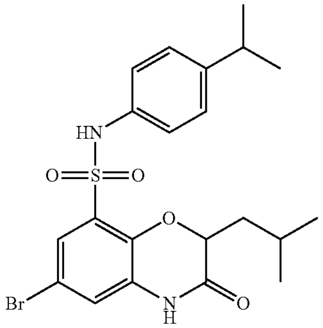 [SMILES: CC(C)CC1Oc2c(cc(Br)cc2S(=O)(=O)Nc2ccc(C(C)C)cc2)NC1=O] | ++++ | + |
| BC19767 | 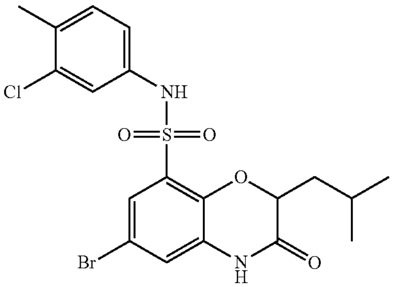 [SMILES: Cc1ccc(NS(=O)(=O)c2cc(Br)cc3c2OC(CC(C)C)C(=O)N3)cc1Cl] | ++++ | + |
| BC19769 | 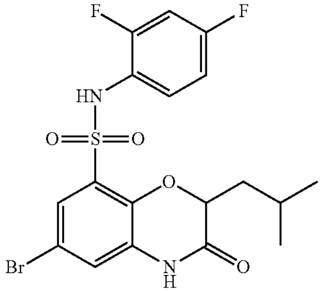 [SMILES: CC(C)CC1Oc2c(cc(Br)cc2S(=O)(=O)Nc2ccc(F)cc2F)NC1=O] | ++++ | + |
| BC19771 | 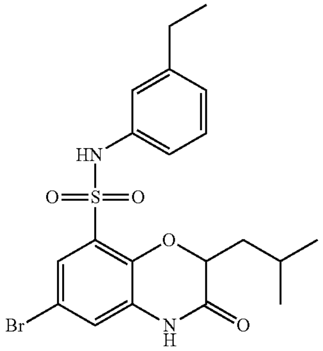 [SMILES: CCc1cccc(NS(=O)(=O)c2cc(Br)cc3c2OC(CC(C)C)C(=O)N3)c1] | ++++ | + |

TABLE 2d-2-continued
| BC No. | Structure | $IC_{50}$ (NF-κB assay) | $IC_{50}$ (TNF assay) |
|---|---|---|---|
| BC19773 | 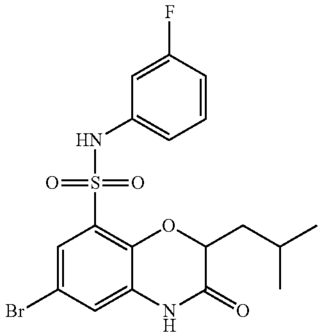 [SMILES: CC(C)CC1Oc2c(cc(Br)cc2S(=O)(=O)Nc2cccc(F)c2)NC1=O] | ++++ | + |
| BC19775 | 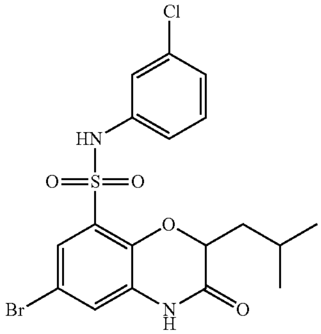 | ++++ | + |
| BC19777 | 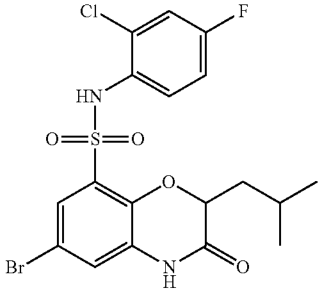 [SMILES: CC(C)CC1Oc2c(cc(Br)cc2S(=O)(=O)Nc2ccc(F)cc2Cl)NC1=O] | ++++ | + |
| BC19779 | 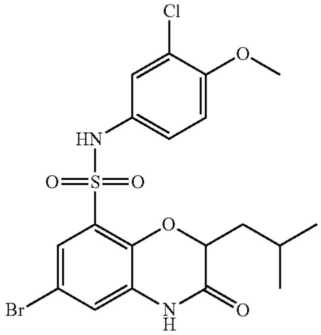 [SMILES: COc1ccc(NS(=O)(=O)c2cc(Br)cc3c2OC(CC(C)C)C(=O)N3)cc1Cl] | +++ | ++ |

TABLE 2d-2-continued
| BC No. | Structure | $IC_{50}$ (NF-κB assay) | $IC_{50}$ (TNF assay) |
|---|---|---|---|
| BC19781 | 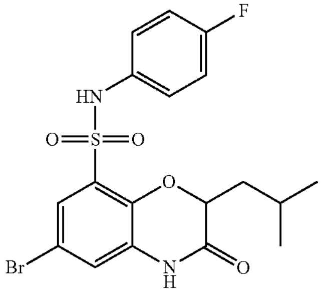 [SMILES: CC(C)CC1Oc2c(cc(Br)cc2S(=O)(=O)Nc2ccc(F)cc2)NC1=O] | ++++ | ++ |
| BC19783 | 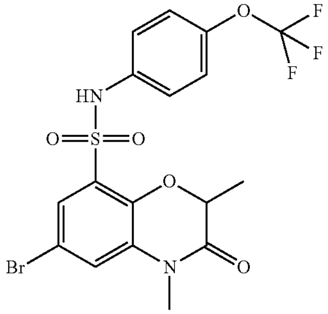 [SMILES: CC1Oc2c(cc(Br)cc2S(=O)(=O)Nc2ccc(OC(F)(F)F)cc2)N(C)C1=O] | ++++ | + |
| BC19785 | 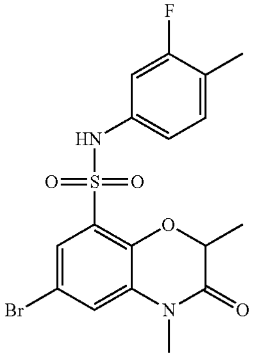 [SMILES: Cc1ccc(NS(=O)(=O)c2cc(Br)cc3c2OC(C)C(=O)N3C)cc1F] | ++++ | + |
| BC19787 | 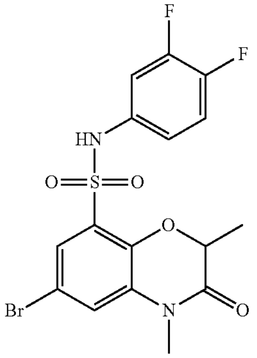 [SMILES: CC1Oc2c(cc(Br)cc2S(=O)(=O)Nc2ccc(F)c(F)c2)N(C)C1=O] | ++++ | + |

TABLE 2d-2-continued
| BC No. | Structure | $IC_{50}$ (NF-κB assay) | $IC_{50}$ (TNF assay) |
|---|---|---|---|
| BC19789 | 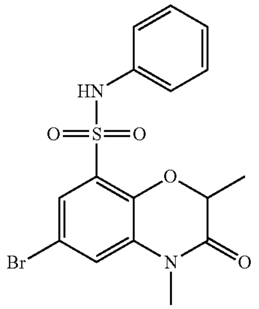 [SMILES: CC1Oc2c(cc(Br)cc2S(=O)(=O)Nc2ccccc2)N(C)C1=O] | ++++ | ++ |
| BC19791 | 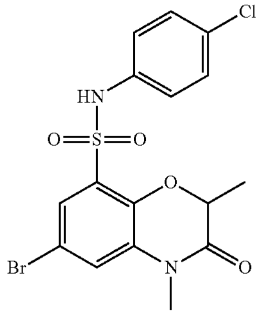 [SMILES: CC1Oc2c(cc(Br)cc2S(=O)(=O)Nc2ccc(Cl)cc2)N(C)C1=O] | ++++ | + |
| BC19793 | 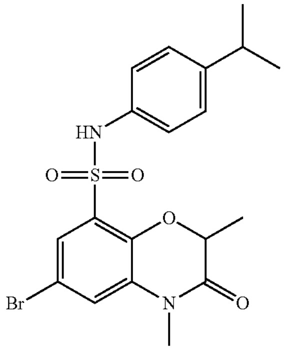 [SMILES: CC1Oc2c(cc(Br)cc2S(=O)(=O)Nc2ccc(C(C)C)cc2)N(C)C1=O] | ++++ | + |
| BC19796 | 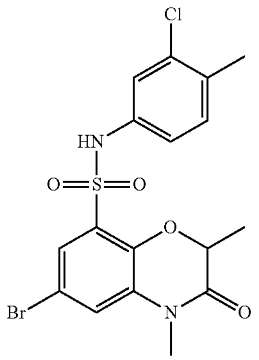 | ++++ | ++ |

TABLE 2d-2-continued
| BC No. | Structure | $IC_{50}$ (NF-κB assay) | $IC_{50}$ (TNF assay) |
|---|---|---|---|
| BC19798 | 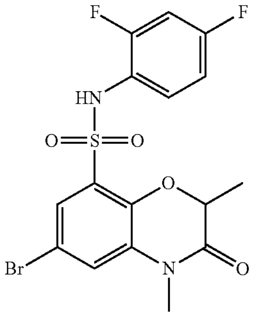 [SMILES: CC1Oc2c(cc(Br)cc2S(=O)(=O)Nc2ccc(F)cc2F)N(C)C1=O] | ++++ | ++ |
| BC19900 | 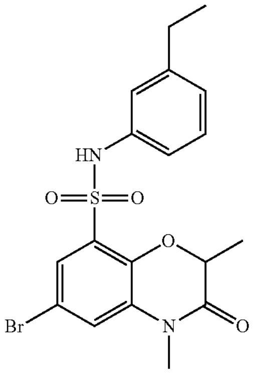 [SMILES: CCc1cccc(NS(=O)(=O)c2cc(Br)cc3c2OC(C)C(=O)N3C)c1] | +++ | + |
| BC19902 | 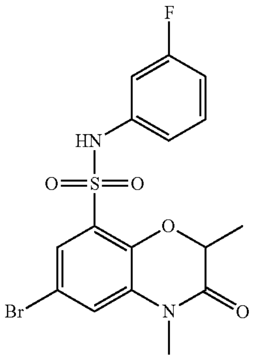 [SMILES: CC1Oc2c(cc(Br)cc2S(=O)(=O)Nc2cccc(F)c2)N(C)C1=O] | ++++ | + |
| BC19904 | 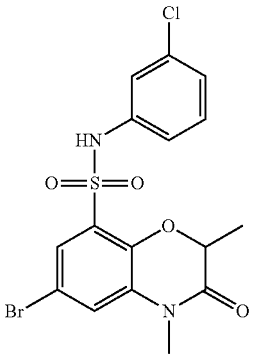 [SMILES: CC1Oc2c(cc(Br)cc2S(=O)(=O)Nc2cccc(Cl)c2)N(C)C1=O] | ++++ | + |

TABLE 2d-2-continued
| BC No. | Structure | $IC_{50}$ (NF-κB assay) | $IC_{50}$ (TNF assay) |
|---|---|---|---|
| BC19906 | 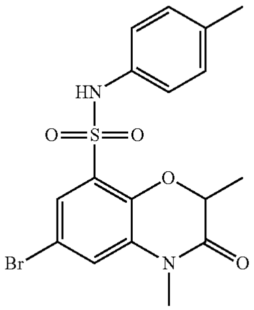 [SMILES: Cc1ccc(NS(=O)(=O)c2cc(Br)cc3c2OC(C)C(=O)N3C)cc1] | ++++ | ++ |
| BC19908 | 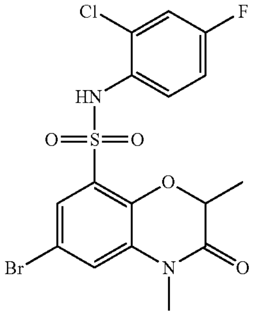 [SMILES: CC1Oc2c(cc(Br)cc2S(=O)(=O)Nc2ccc(F)cc2Cl)N(C)C1=O] | ++++ | + |
| BC19909 | 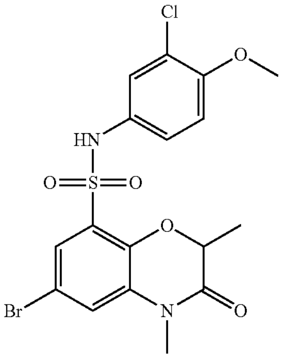 [SMILES: COc1ccc(NS(=O)(=O)c2cc(Br)cc3c2OC(C)C(=O)N3C)cc1Cl] | + | + |
| BC19911 | 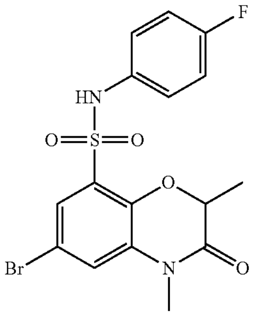 [SMILES: CC1Oc2c(cc(Br)cc2S(=O)(=O)Nc2ccc(F)cc2)N(C)C1=O] | ++++ | + |

TABLE 2d-2-continued
| BC No. | Structure | $IC_{50}$ (NF-κB assay) | $IC_{50}$ (TNF assay) |
|---|---|---|---|
| BC19913 | 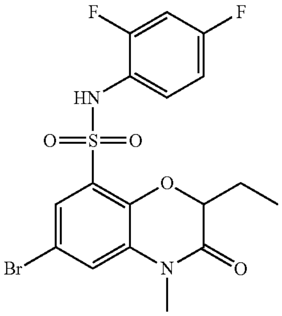 [SMILES: CCC1Oc2c(cc(Br)cc2S(=O)(=O)Nc2ccc(F)cc2F)N(C)C1=O] | ++++ | + |
| BC19915 | 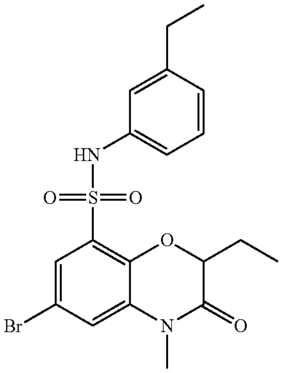 [SMILES: CCc1cccc(NS(=O)(=O)c2cc(Br)cc3c2OC(CC)C(=O)N3C)c1] | ++++ | + |
| BC19921 | 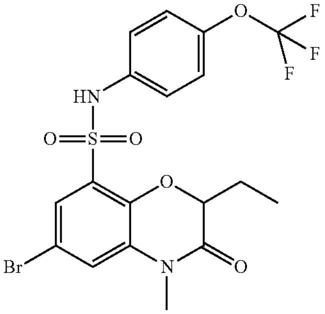 [SMILES: CCC1Oc2c(cc(Br)cc2S(=O)(=O)Nc2ccc(OC(F)(F)F)cc2)N(C)C1=O] | ++++ | ++ |
| BC19923 | 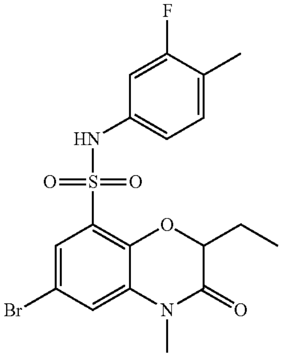 [SMILES: CCC1Oc2c(cc(Br)cc2S(=O)(=O)Nc2ccc(C)c(F)c2)N(C)C1=O] | ++++ | ++ |

TABLE 2d-2-continued
| BC No. | Structure | IC50 (NF-κB assay) | IC50 (TNF assay) |
|---|---|---|---|
| BC19925 | 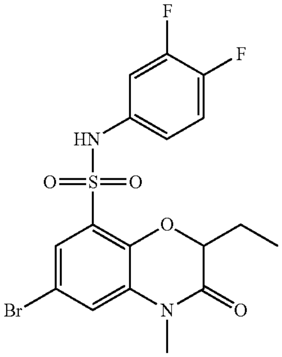 [SMILES: CCC1Oc2c(cc(Br)cc2S(=O)(=O)Nc2ccc(F)c(F)c2)N(C)C1=O] | ++++ | ++ |
| BC19927 | 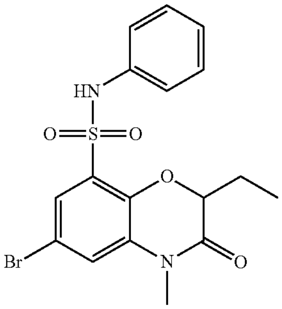 [SMILES: CCC1Oc2c(cc(Br)cc2S(=O)(=O)Nc2ccccc2)N(C)C1=O] | ++++ | ++ |
| BC19929 | 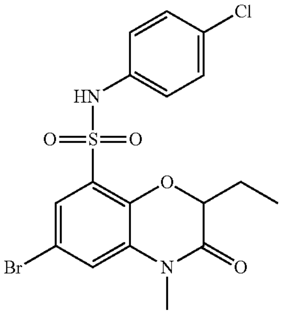 [SMILES: CCC1Oc2c(cc(Br)cc2S(=O)(=O)Nc2ccc(Cl)cc2)N(C)C1=O] | ++++ | ++ |
| BC19931 | 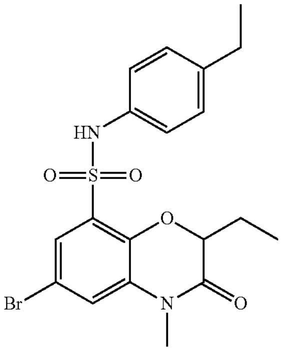 [SMILES: CCc1ccc(NS(=O)(=O)c2cc(Br)cc3c2OC(CC)C(=O)N3C)cc1] | ++++ | ++ |

TABLE 2d-2-continued
| BC No. | Structure | IC50 (NF-κB assay) | IC50 (TNF assay) |
|---|---|---|---|
| BC19933 | 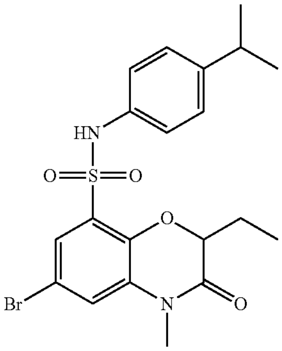 [SMILES: CCC1Oc2c(cc(Br)cc2S(=O)(=O)Nc2ccc(C(C)C)cc2)N(C)C1=O] | ++++ | ++ |
| BC19935 | 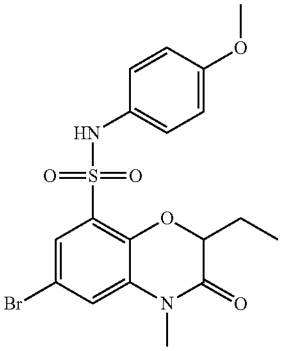 [SMILES: CCC1Oc2c(cc(Br)cc2S(=O)(=O)Nc2ccc(OC)cc2)N(C)C1=O] | ++++ | ++ |
| BC19937 | 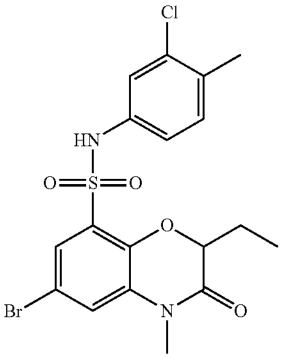 [SMILES: CCC1Oc2c(cc(Br)cc2S(=O)(=O)Nc2ccc(C)c(Cl)c2)N(C)C1=O] | ++++ | ++ |
TABLE 2e
| BC No. | ZE No. | Structure | IC50 (NF-κB assay) | IC50 (TNF assay) |
|---|---|---|---|---|
| BC19181 | ZE25-0002 | 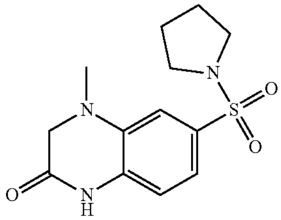 [SMILES: CN1CC(=O)Nc2ccc(S(=O)(=O)N3CCCC3)cc21] | + | + |

TABLE 2e-continued
| BC No. | ZE No. | Structure | $IC_{50}$ (NF-κB assay) | $IC_{50}$ (TNF assay) |
|---|---|---|---|---|
| BC19182 | ZE25-0005 | 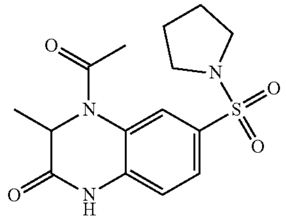 [SMILES: CC(=O)N1c2cc(S(=O)(=O)N3CCCC3)ccc2NC(=O)C1C] | + | + |
| BC19183 | ZE25-0017 | 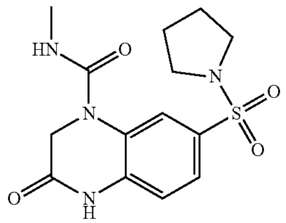 [SMILES: CNC(=O)N1CC(=O)Nc2ccc(S(=O)(=O)N3CCCC3)cc21] | + | + |
| BC19184 | ZE25-0026 | 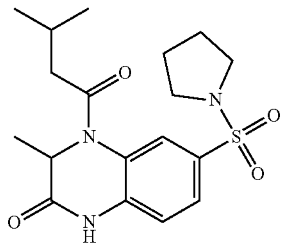 [SMILES: CC(C)CC(=O)N1c2cc(S(=O)(=O)N3CCCC3)ccc2NC(=O)C1C] | + | + |
| BC19235 | ZE25-0015 | 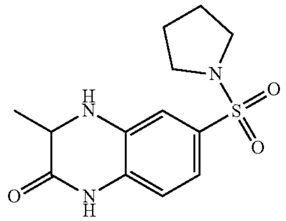 [SMILES: CC1Nc2cc(S(=O)(=O)N3CCCC3)ccc2NC1=O] | + | + |
| BC19236 | ZE25-0028 | 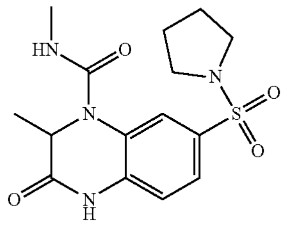 [SMILES: CNC(=O)N1c2cc(S(=O)(=O)N3CCCC3)ccc2NC(=O)C1C] | + | + |
| BC19295 | ZE25-0001 | 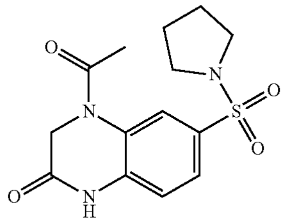 [SMILES: CC(=O)N1CC(=O)Nc2ccc(S(=O)(=O)N3CCCC3)cc21] | ++++ | + |

TABLE 2e-continued
| BC No. | ZE No. | Structure | $IC_{50}$ (NF-κB assay) | $IC_{50}$ (TNF assay) |
|---|---|---|---|---|
| BC19296 | ZE25-0007 | 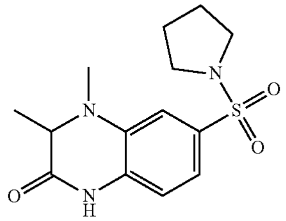 [SMILES: CC1C(=O)Nc2ccc(S(=O)(=O)N3CCCC3)cc2N1C] | ++ | + |
| BC19297 | ZE25-0030 | 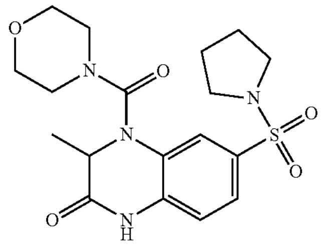 [SMILES: CC1C(=O)Nc2ccc(S(=O)(=O)N3CCCC3)cc2N1C(=O)N1CCOCC1] | ++ | + |
| BC19298 | ZE25-0032 | 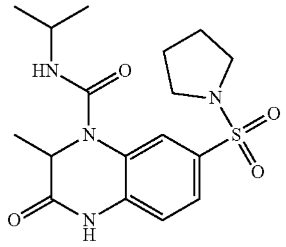 [SMILES: CC(C)NC(=O)N1c2cc(S(=O)(=O)N3CCCC3)ccc2NC(=O)C1C] | ++++ | + |
| BC19299 | ZE25-0033 | 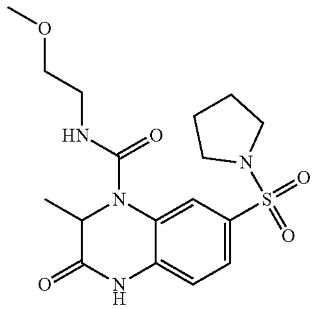 [SMILES: COCCNC(=O)N1c2cc(S(=O)(=O)N3CCCC3)ccc2NC(=O)C1C] | ++ | + |
| BC19300 | ZE25-0039 | 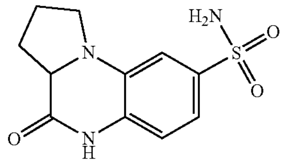 [SMILES: NS(=O)(=O)c1ccc2c(c1)N1CCCC1C(=O)N2] | +++ | + |

TABLE 16
| BC No. | Structure | $IC_{50}$ (NF-κB assay) | $IC_{50}$ (TNF assay) |
|---|---|---|---|
| BC19917 | 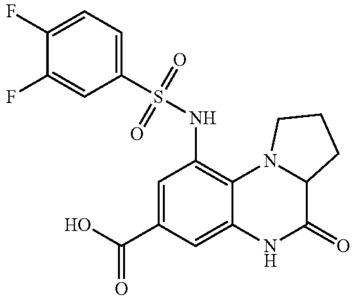 [SMILES: O=C(O)c1cc2c(c(NS(=O)(=O)c3ccc(F)c(F)c3)c1)N1CCCC1C(=O)N2] | + | + |
TABLE 2f
| BC No. | Structure | $IC_{50}$ (NF-κB assay) | $IC_{50}$ (TNF assay) |
|---|---|---|---|
| BC19549 | 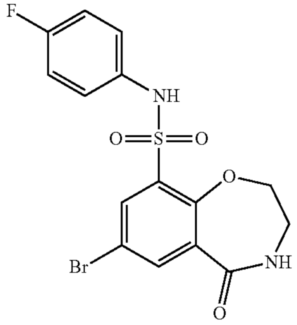 [SMILES: O=C1NCCOc2c1cc(Br)cc2S(=O)(=O)Nc1ccc(F)cc1] | ++ | + |
| BC19550 | 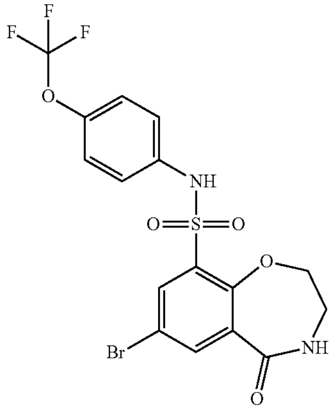 [SMILES: O=C1NCCOc2c1cc(Br)cc2S(=O)(=O)Nc1ccc(OC(F)(F)F)cc1] | ++++ | + |

TABLE 2f-continued
| BC No. | Structure | IC50 (NF-κB assay) | IC50 (TNF assay) |
|---|---|---|---|
| BC19551 | 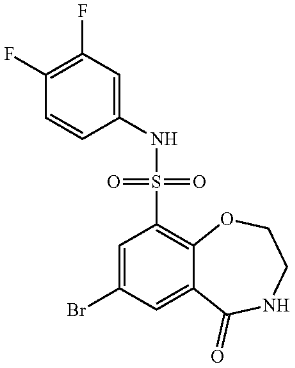 [SMILES: O=C1NCCOc2c1cc(Br)cc2S(=O)(=O)Nc1ccc(F)c(F)c1] | +++ | + |
| BC19552 | 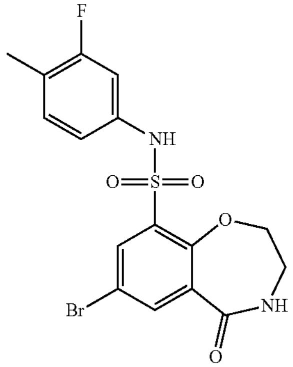 [SMILES: Cc1ccc(NS(=O)(=O)c2cc(Br)cc3c2OCCNC3=O)cc1F] | +++ | + |
| BC19553 | 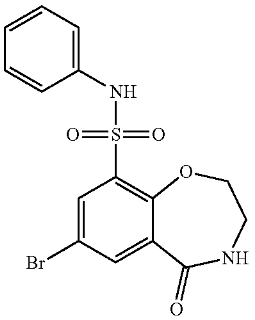 [SMILES: O=C1NCCOc2c1cc(Br)cc2S(=O)(=O)Nc1ccccc1] | ++ | + |
| BC19603 | 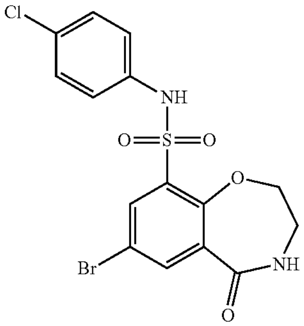 [SMILES: O=C1NCCOc2c1cc(Br)cc2S(=O)(=O)Nc1ccc(Cl)cc1] | +++ | + |

TABLE 2f-continued
| BC No. | Structure | $IC_{50}$ (NF-κB assay) | $IC_{50}$ (TNF assay) |
|---|---|---|---|
| BC19604 | 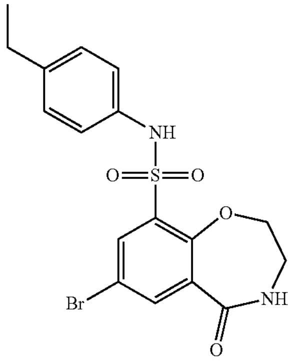 [SMILES: CCc1ccc(NS(=O)(=O)c2cc(Br)cc3c2OCCNC3=O)cc1] | ++ | + |
| BC19605 | 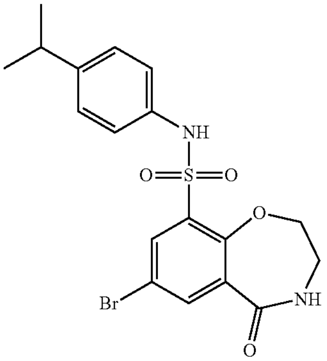 [SMILES: CC(C)c1ccc(NS(=O)(=O)c2cc(Br)cc3c2OCCNC3=O)cc1] | + | + |
| BC19606 | 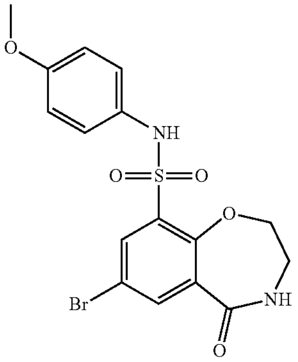 [SMILES: COc1ccc(NS(=O)(=O)c2cc(Br)cc3c2OCCNC3=O)cc1] | ++ | + |
| BC19607 | 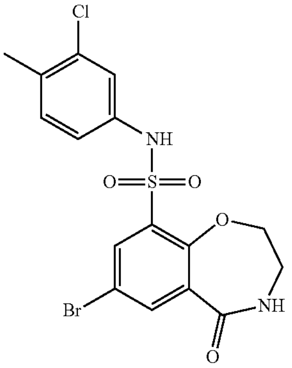 [SMILES: Cc1ccc(NS(=O)(=O)c2cc(Br)cc3c2OCCNC3=O)cc1Cl] | +++ | + |

TABLE 2f-continued
| BC No. | Structure | IC50 (NF-κB assay) | IC50 (TNF assay) |
|---|---|---|---|
| BC19608 | 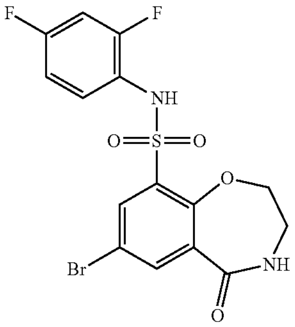 [SMILES: O=C1NCCOc2c1cc(Br)cc2S(=O)(=O)Nc1ccc(F)cc1F] | ++ | + |
| BC19609 | 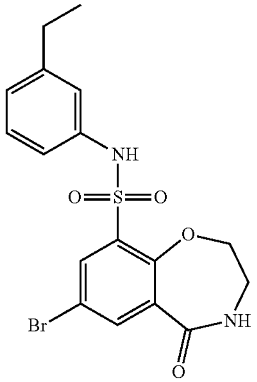 [SMILES: CCc1cccc(NS(=O)(=O)c2cc(Br)cc3c2OCCNC3=O)c1] | ++ | + |
| BC19610 | 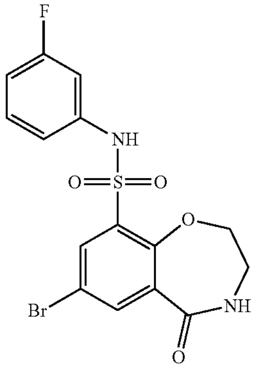 [SMILES: O=C1NCCOc2c1cc(Br)cc2S(=O)(=O)Nc1cccc(F)c1] | +++ | + |
| BC19611 | 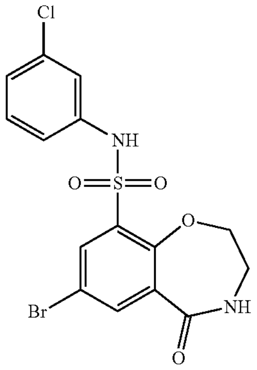 [SMILES: O=C1NCCOc2c1cc(Br)cc2S(=O)(=O)Nc1cccc(Cl)c1] | ++++ | + |

TABLE 2f-continued
| BC No. | Structure | IC50 (NF-κB assay) | IC50 (TNF assay) |
|---|---|---|---|
| BC19612 | 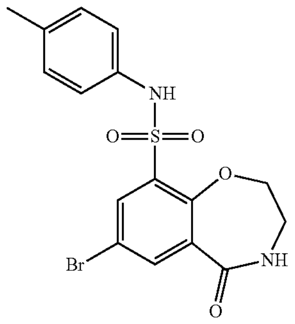 [SMILES: Cc1ccc(NS(=O)(=O)c2cc(Br)cc3c2OCCNC3=O)cc1] | ++ | + |
| BC19613 | 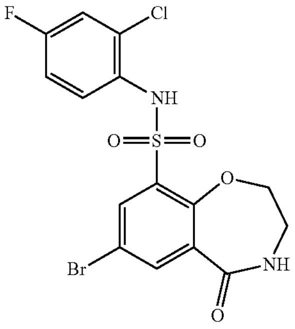 [SMILES: O=C1NCCOc2c1cc(Br)cc2S(=O)(=O)Nc1ccc(F)cc1Cl] | + | + |
| BC19614 | 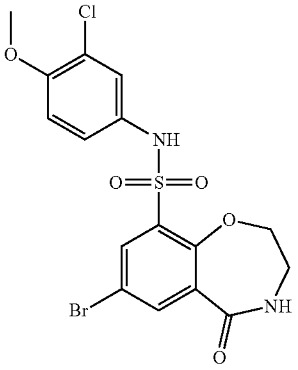 [SMILES: COc1ccc(NS(=O)(=O)c2cc(Br)cc3c2OCCNC3=O)cc1Cl] | + | + |
| BC19615 | 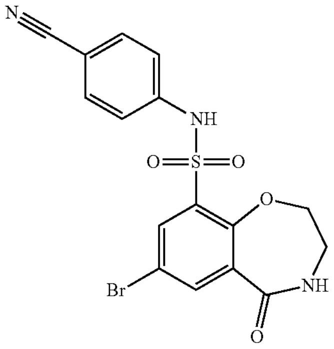 [SMILES: N#Cc1ccc(NS(=O)(=O)c2cc(Br)cc3c2OCCNC3=O)cc1] | +++ | + |

TABLE 2g
| BC No. | Structure | IC50 (NF-κB assay) | IC50 (TNF assay) |
|---|---|---|---|
| BC19652 | 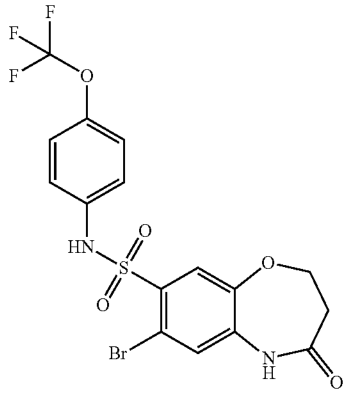 [SMILES: O=C1CCOc2cc(S(=O)(=O)Nc3ccc(OC(F)(F)F)cc3)c(Br)cc2N1] | ++ | + |
| BC19653 | 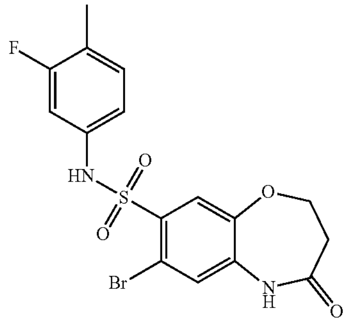 [SMILES: Cc1ccc(NS(=O)(=O)c2cc3c(cc2Br)NC(=O)CCO3)cc1F] | + | + |
| BC19654 | 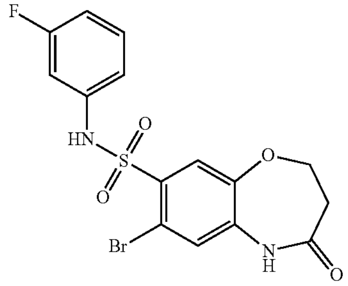 [SMILES: O=C1CCOc2cc(S(=O)(=O)Nc3cccc(F)c3)c(Br)cc2N1] | + | + |
| BC19655 | 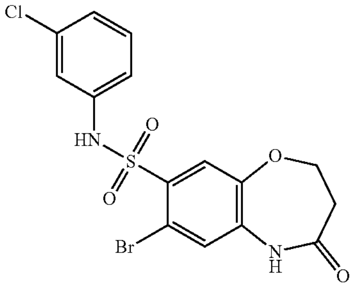 [SMILES: O=C1CCOc2cc(S(=O)(=O)Nc3cccc(Cl)c3)c(Br)cc2N1] | + | + |

TABLE 2g-continued
| BC No. | Structure | $IC_{50}$ (NF-κB assay) | $IC_{50}$ (TNF assay) |
|---|---|---|---|
| BC19656 | 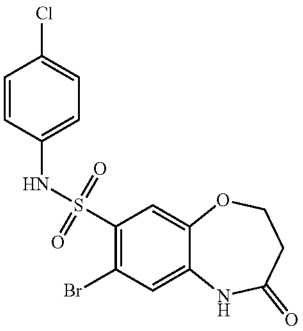 [SMILES: O=C1CCOc2cc(S(=O)(=O)Nc3ccc(Cl)cc3)c(Br)cc2N1] | ++ | + |
| BC19657 | 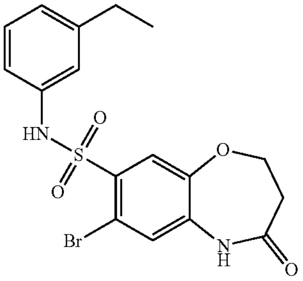 [SMILES: CCc1cccc(NS(=O)(=O)c2cc3c(cc2Br)NC(=O)CCO3)c1] | ++ | + |
| BC19658 | 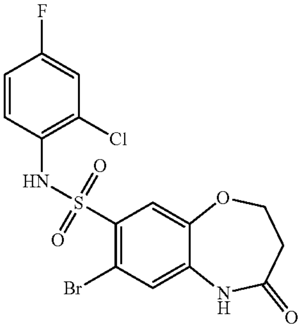 [SMILES: O=C1CCOc2cc(S(=O)(=O)Nc3ccc(F)cc3Cl)c(Br)cc2N1] | + | + |
| BC19659 | 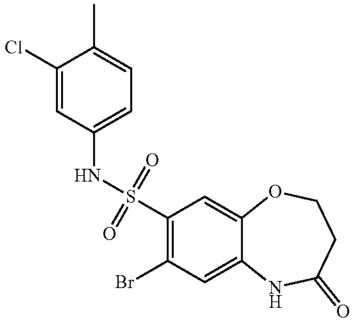 [SMILES: Cc1ccc(NS(=O)(=O)c2cc3c(cc2Br)NC(=O)CCO3)cc1Cl] | + | + |

TABLE 2g-continued
| BC No. | Structure | IC50 (NF-κB assay) | IC50 (TNF assay) |
|---|---|---|---|
| BC19660 | 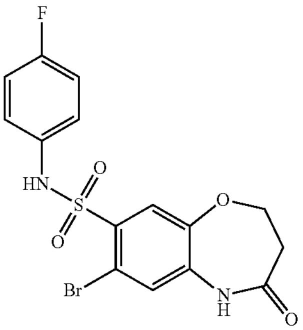 [SMILES: O=C1CCOc2cc(S(=O)(=O)Nc3ccc(F)cc3)c(Br)cc2N1] | + | + |
| BC19661 | 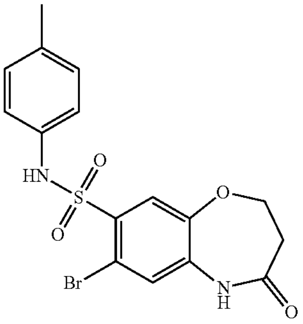 [SMILES: Cc1ccc(NS(=O)(=O)c2cc3c(cc2Br)NC(=O)CCO3)cc1] | + | + |
| BC19689 | 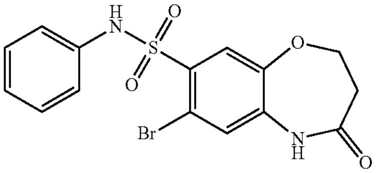 [SMILES: O=C1CCOc2cc(S(=O)(=O)Nc3ccccc3)c(Br)cc2N1] | + | ++ |
| BC19690 | 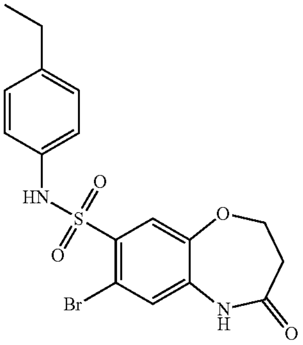 [SMILES: CCc1ccc(NS(=O)(=O)c2cc3c(cc2Br)NC(=O)CCO3)cc1] | + | + |
| BC19691 | 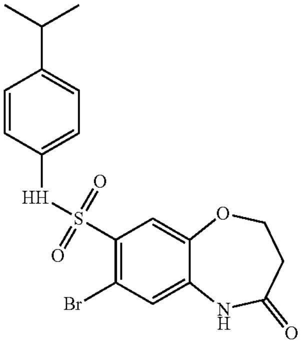 | + | ++ |

TABLE 2g-continued
| BC No. | Structure | $IC_{50}$ (NF-κB assay) | $IC_{50}$ (TNF assay) |
| --- | --- | --- | --- |
| BC19692 | 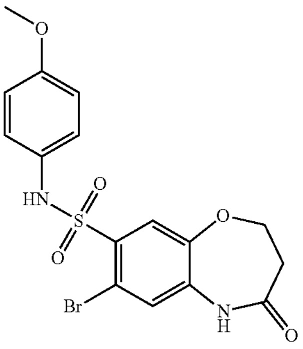 [SMILES: COc1ccc(NS(=O)(=O)c2cc3c(cc2Br)NC(=O)CCO3)cc1] | + | + |
| BC19693 | 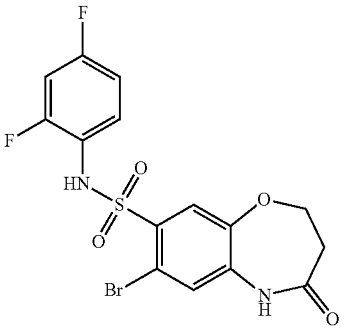 [SMILES: O=C1CCOc2cc(S(=O)(=O)Nc3ccc(F)cc3F)c(Br)cc2N1] | + | + |
| BC19694 | 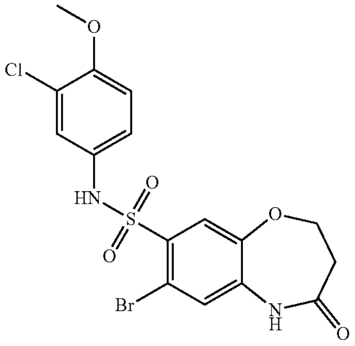 [SMILES: COc1ccc(NS(=O)(=O)c2cc3c(cc2Br)NC(=O)CCO3)cc1Cl] | + | + |
| BC19695 | 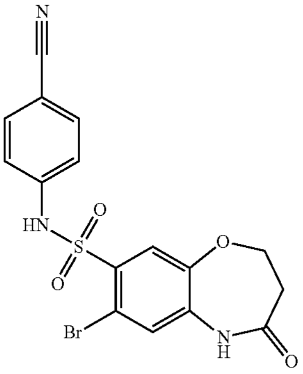 [SMILES: N#Cc1ccc(NS(=O)(=O)c2cc3c(cc2Br)NC(=O)CCO3)cc1] | + | ++ |

TABLE 2h
| BC No. | Structure | IC50 (NF-κB assay) | IC50 (TNF assay) |
|---|---|---|---|
| BC19648 | 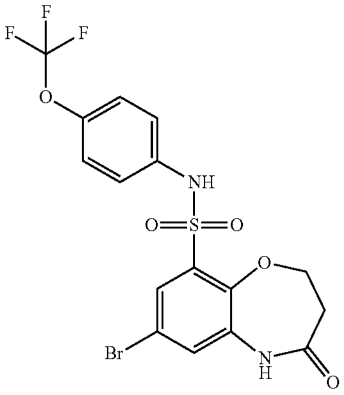 [SMILES: O=C1CCOc2c(cc(Br)cc2S(=O)(=O)Nc2ccc(OC(F)(F)F)cc2)N1] | ++++ | + |
| BC19649 | 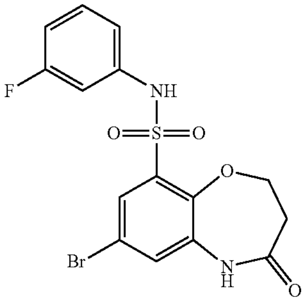 [SMILES: O=C1CCOc2c(cc(Br)cc2S(=O)(=O)Nc2cccc(F)c2)N1] | ++++ | + |
| BC19650 | 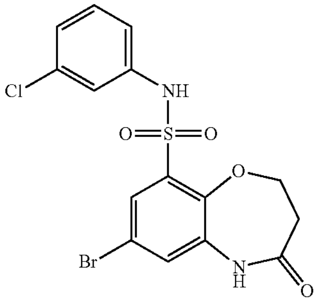 [SMILES: O=C1CCOc2c(cc(Br)cc2S(=O)(=O)Nc2cccc(Cl)c2)N1] | ++++ | + |
| BC19651 | 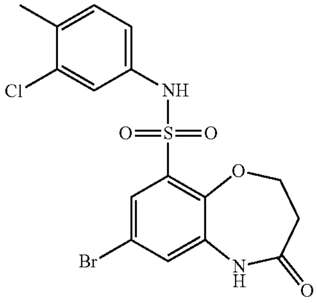 [SMILES: Cc1ccc(NS(=O)(=O)c2cc(Br)cc3c2OCCC(=O)N3)cc1Cl] | +++ | + |

TABLE 2h-continued
| BC No. | Structure | $IC_{50}$ (NF-κB assay) | $IC_{50}$ (TNF assay) |
|---|---|---|---|
| BC19685 | 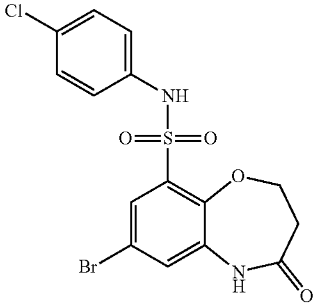 [SMILES: O=C1CCOc2c(cc(Br)cc2S(=O)(=O)Nc2ccc(Cl)cc2)N1] | ++++ | ++ |
| BC19686 | 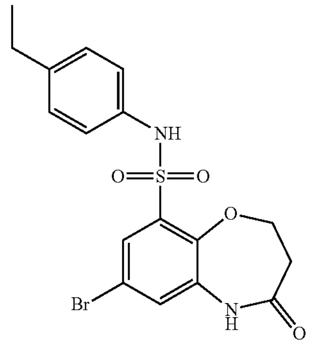 [SMILES: CCc1ccc(NS(=O)(=O)c2cc(Br)cc3c2OCCC(=O)N3)cc1] | ++++ | + |
| BC19687 | 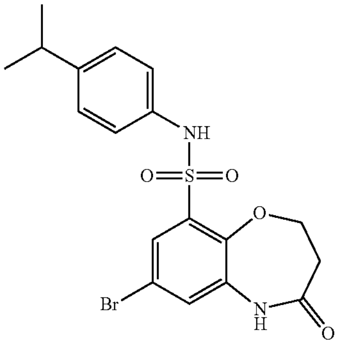 [SMILES: CC(C)c1ccc(NS(=O)(=O)c2cc(Br)cc3c2OCCC(=O)N3)cc1] | ++++ | + |
| BC19688 | 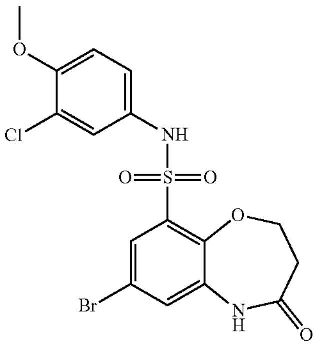 [SMILES: COc1ccc(NS(=O)(=O)c2cc(Br)cc3c2OCCC(=O)N3)cc1Cl] | + | + |

Example 3—Bioassay Results for Tested Compounds
TABLE 3a
| BC No. | Compound | $IC_{50}$ (NF-κB assay) |
|---|---|---|
| BC18500 | 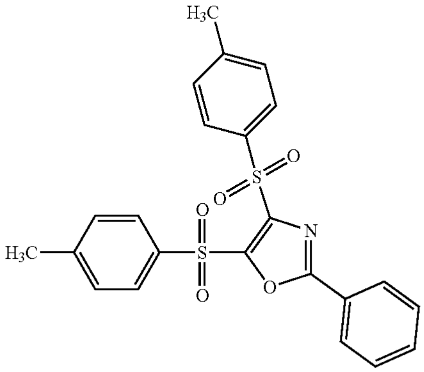 [SMILES: Cc1ccc(S(=O)(=O)c2nc(-c3ccccc3)oc2S(=O)(=O)c2ccc(C)cc2)cc1] | ++++ |
| BC18501 | 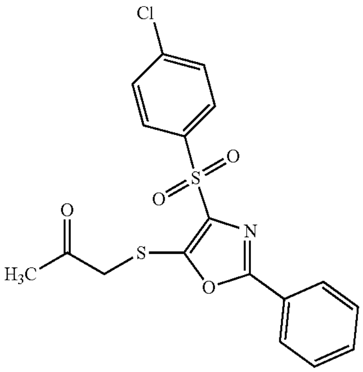 [SMILES: CC(=O)CSc1oc(-c2ccccc2)nc1S(=O)(=O)c1ccc(Cl)cc1] | + |
| BC18502 | 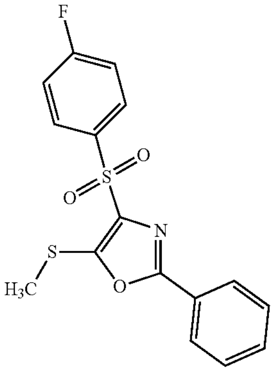 [SMILES: CSc1oc(-c2ccccc2)nc1S(=O)(=O)c1ccc(F)cc1] | + |
| BC18503 | 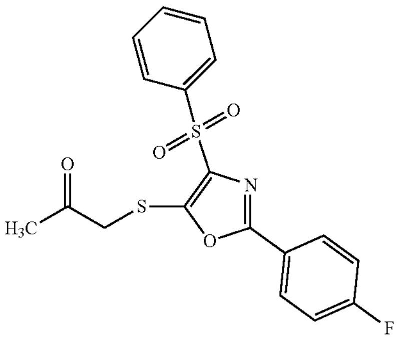 [SMILES: CC(=O)CSc1oc(-c2ccc(F)cc2)nc1S(=O)(=O)c1ccccc1] | ++ |
TABLE 3a-continued
| BC No. | Compound | $IC_{50}$ (NF-κB assay) |
|---|---|---|
| BC18504 | 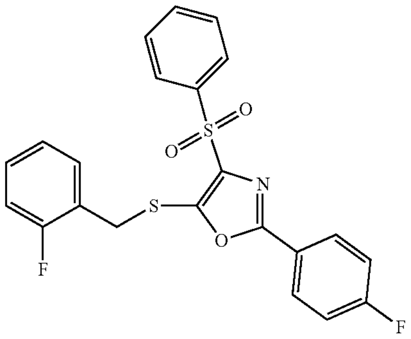 [SMILES: O=S(=O)(c1ccccc1)c1nc(-c2ccc(F)cc2)oc1SCc1ccccc1F] | ++ |
| BC18505 | 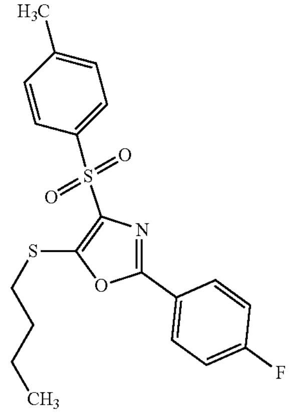 [SMILES: CCCCSc1oc(-c2ccc(F)cc2)nc1S(=O)(=O)c1ccc(C)cc1] | ++ |
| BC18506 | 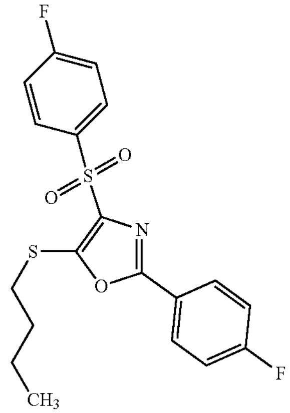 [SMILES: CCCCSc1oc(-c2ccc(F)cc2)nc1S(=O)(=O)c1ccc(F)cc1] | + |
| BC18507 | 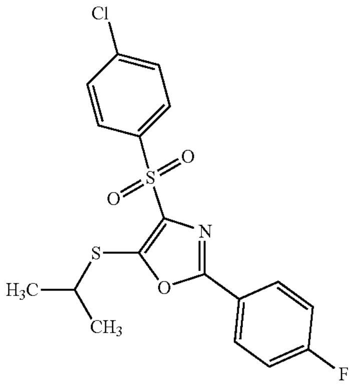 [SMILES: CC(C)Sc1oc(-c2ccc(F)cc2)nc1S(=O)(=O)c1ccc(Cl)cc1] | ++ |

TABLE 3a-continued
| BC No. | Compound | $IC_{50}$ (NF-κB assay) |
|---|---|---|
| BC18508 | 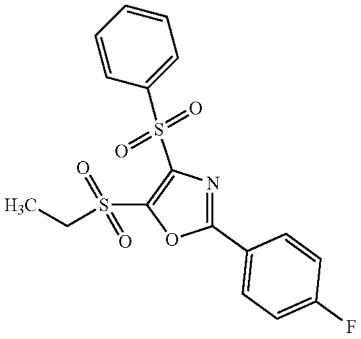 [SMILES: CCS(=O)(=O)c1oc(-c2ccc(F)cc2)nc1S(=O)(=O)c1ccccc1] | ++++ |
| BC18509 | 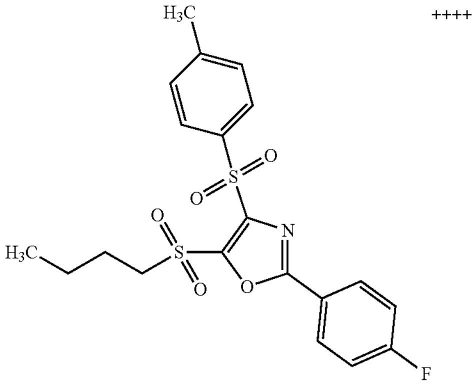 | ++++ |
| BC18510 | 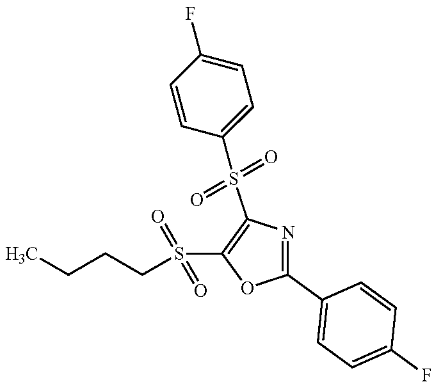 [SMILES: CCCCS(=O)(=O)c1oc(-c2ccc(F)cc2)nc1S(=O)(=O)c1ccc(F)cc1] | +++ |
| BC18511 | 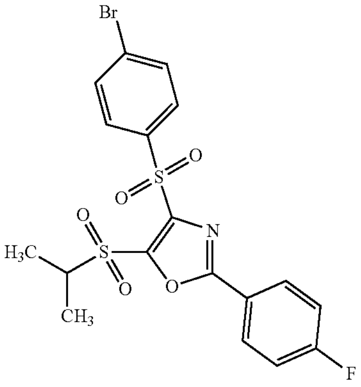 [SMILES: CC(C)S(=O)(=O)c1oc(-c2ccc(F)cc2)nc1S(=O)(=O)c1ccc(Br)cc1] | ++++ |
TABLE 3a-continued
| BC No. | Compound | $IC_{50}$ (NF-κB assay) |
|---|---|---|
| BC18512 | 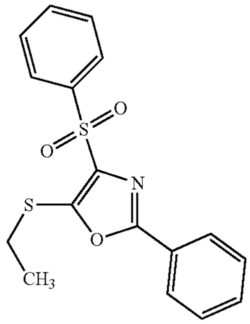 [SMILES: CCSc1oc(-c2ccccc2)nc1S(=O)(=O)c1ccccc1] | ++ |
| BC18513 | 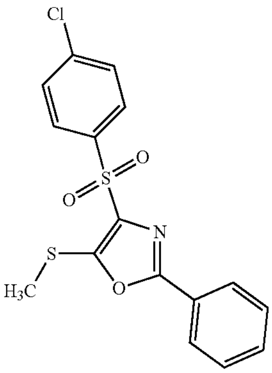 | + |
| BC18514 | 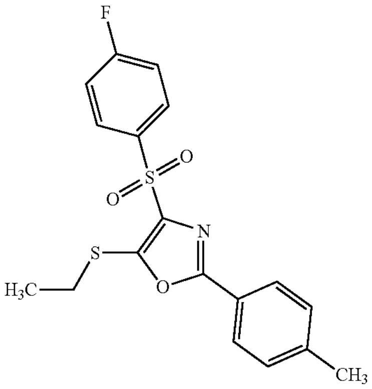 [SMILES: CCSc1oc(-c2ccc(C)cc2)nc1S(=O)(=O)c1ccc(F)cc1] | ++ |
| BC18515 | 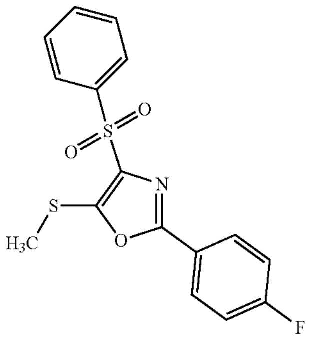 [SMILES: CSc1oc(-c2ccc(F)cc2)nc1S(=O)(=O)c1ccccc1] | + |

TABLE 3a-continued
| BC No. | Compound | $IC_{50}$ (NF-κB assay) |
| --- | --- | --- |
| BC18516 | 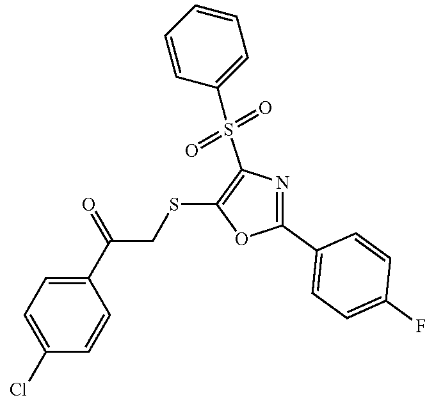 [SMILES: O=C(CSc1oc(-c2ccc(F)cc2)nc1S(=O)(=O)c1ccccc1)c1ccc(Cl)cc1] | ++ |
| BC18517 | 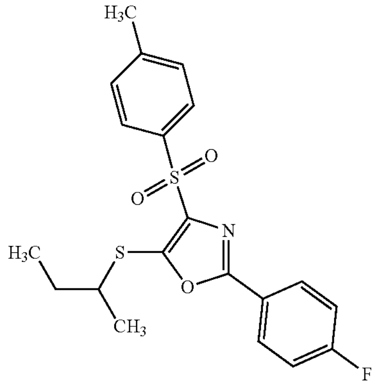 [SMILES: CCC(C)Sc1oc(-c2ccc(F)cc2)nc1S(=O)(=O)c1ccc(C)cc1] | ++ |
| BC18518 | 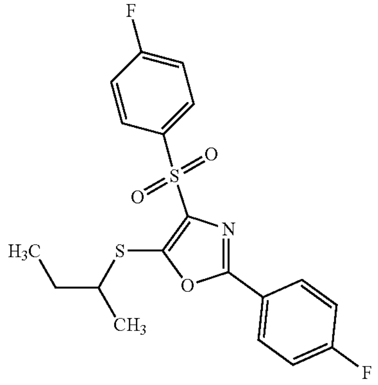 [SMILES: CCC(C)Sc1oc(-c2ccc(F)cc2)nc1S(=O)(=O)c1ccc(F)cc1] | ++ |
| BC18519 | 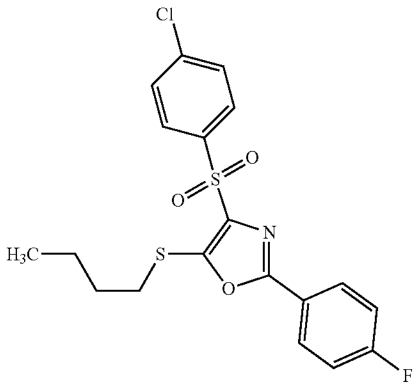 [SMILES: CCCCSc1oc(-c2ccc(F)cc2)nc1S(=O)(=O)c1ccc(Cl)cc1] | + |
TABLE 3a-continued
| BC No. | Compound | $IC_{50}$ (NF-κB assay) |
| --- | --- | --- |
| BC18520 | 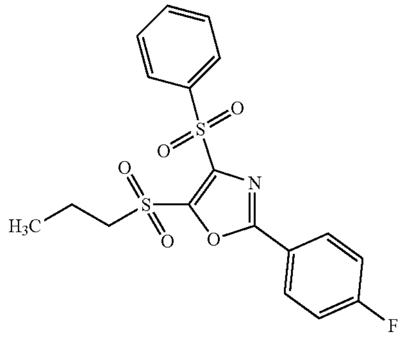 [SMILES: CCCS(=O)(=O)c1oc(-c2ccc(F)cc2)nc1S(=O)(=O)c1ccccc1] | ++++ |
| BC18521 | 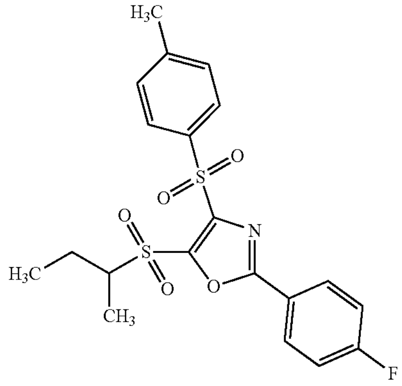 [SMILES: CCC(C)S(=O)(=O)c1oc(-c2ccc(F)cc2)nc1S(=O)(=O)c1ccc(C)cc1] | ++++ |
| BC18522 | 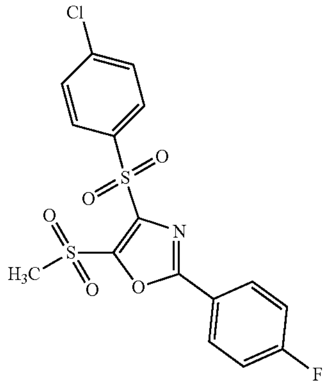 [SMILES: CS(=O)(=O)c1oc(-c2ccc(F)cc2)nc1S(=O)(=O)c1ccc(Cl)cc1] | ++++ |
| BC18523 | 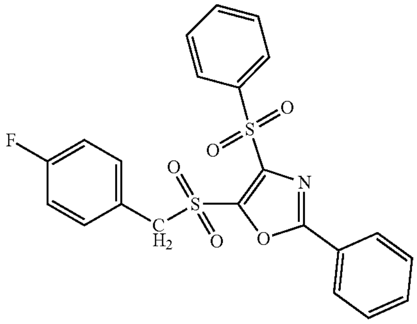 [SMILES: O=S(=O)(Cc1ccc(F)cc1)c1oc(-c2ccccc2)nc1S(=O)(=O)c1ccccc1] | + |

TABLE 3a-continued
| BC No. | Compound | IC50 (NF-κB assay) |
|---|---|---|
| BC18524 | 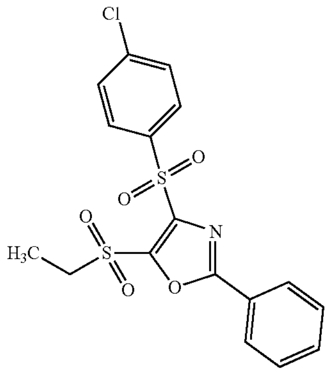 [SMILES: CCS(=O)(=O)c1oc(-c2ccccc2)nc1S(=O)(=O)c1ccc(Cl)cc1] | ++ |
| BC18525 | 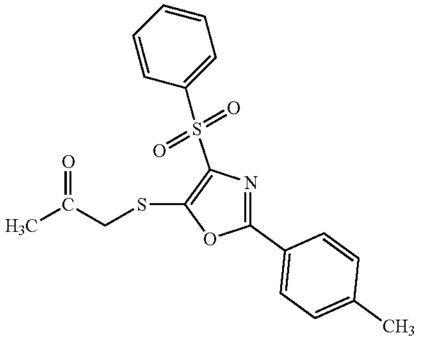 [SMILES: CC(=O)CSc1oc(-c2ccc(C)cc2)nc1S(=O)(=O)c1ccccc1] | + |
| BC18526 | 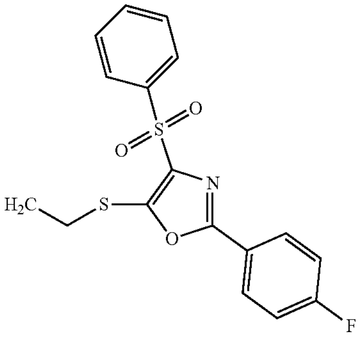 [SMILES: CCSc1oc(-c2ccc(F)cc2)nc1S(=O)(=O)c1ccccc1] | ++ |
| BC18527 | 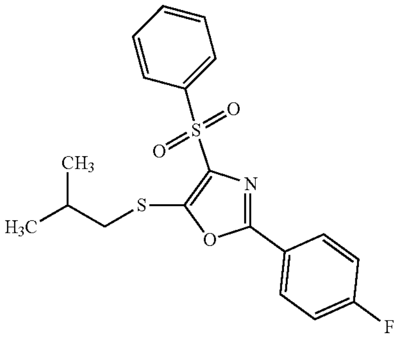 [SMILES: CC(C)CSc1oc(-c2ccc(F)cc2)nc1S(=O)(=O)c1ccccc1] | ++ |
TABLE 3a-continued
| BC No. | Compound | IC50 (NF-κB assay) |
|---|---|---|
| BC18528 | 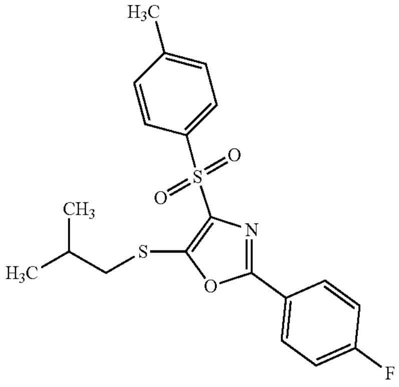 [SMILES: Cc1ccc(S(=O)(=O)c2nc(-c3ccc(F)cc3)oc2SCC(C)C)cc1] | + |
| BC18529 | 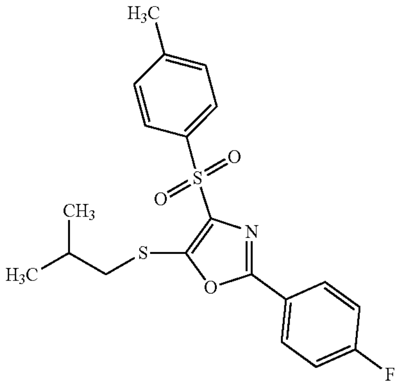 [SMILES: Cc1ccc(S(=O)(=O)c2nc(-c3ccc(F)cc3)oc2SCC(C)C)cc1] | ++ |
| BC18530 | 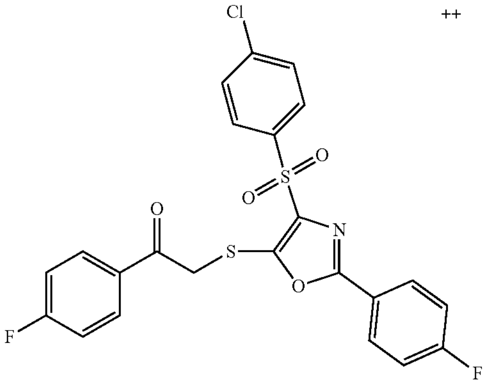 [SMILES: O=C(CSc1oc(-c2ccc(F)cc2)nc1S(=O)(=O)c1ccc(Cl)cc1)c1ccc(F)cc1] | ++ |
| BC18531 | 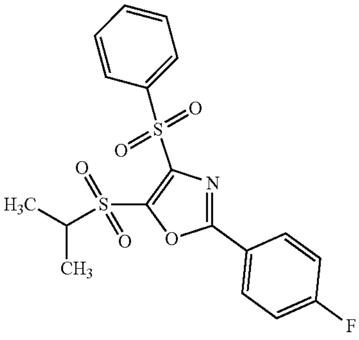 [SMILES: CC(C)S(=O)(=O)c1oc(-c2ccc(F)cc2)nc1S(=O)(=O)c1ccccc1] | ++++ |

TABLE 3a-continued
| BC No. | Compound | IC50 (NF-κB assay) |
|---|---|---|
| BC18532 | 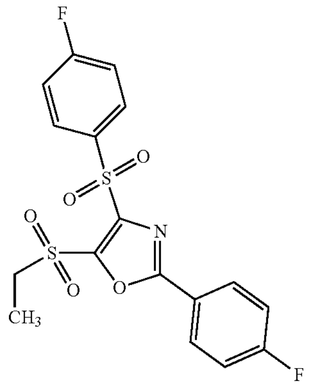 [SMILES: CCS(=O)(=O)c1oc(-c2ccc(F)cc2)nc1S(=O)(=O)c1ccc(F)cc1] | ++++ |
| BC18533 | 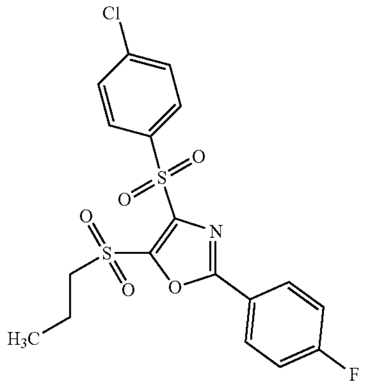 [SMILES: CCCS(=O)(=O)c1oc(-c2ccc(F)cc2)nc1S(=O)(=O)c1ccc(Cl)cc1] | ++++ |
| BC18534 | 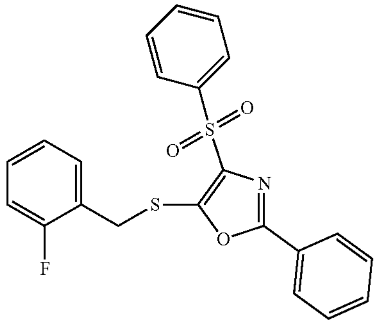 [SMILES: O=S(=O)(c1ccccc1)c1nc(-c2ccccc2)oc1SCc1ccccc1F] | + |
| BC18535 | 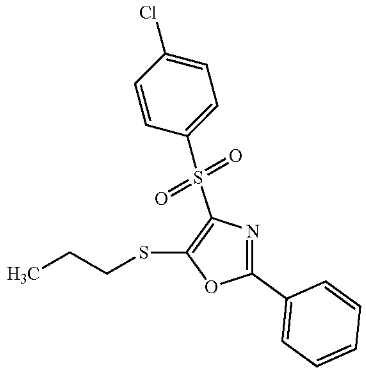 [SMILES: CCCSc1oc(-c2ccccc2)nc1S(=O)(=O)c1ccc(Cl)cc1] | ++ |
| BC18536 | 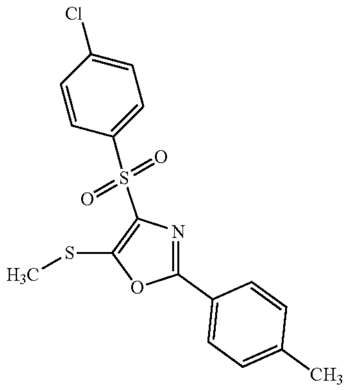 | + |
| BC18537 | 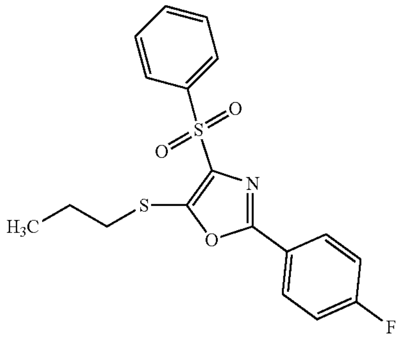 [SMILES: CCCSc1oc(-c2ccc(F)cc2)nc1S(=O)(=O)c1ccccc1] | ++ |
| BC18538 | 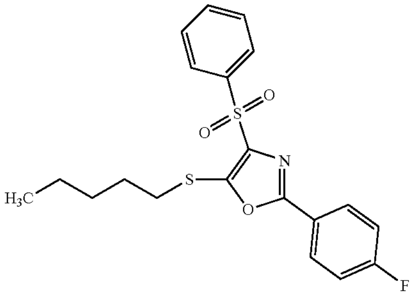 [SMILES: CCCCCSc1oc(-c2ccc(F)cc2)nc1S(=O)(=O)c1ccccc1] | + |
| BC18539 | 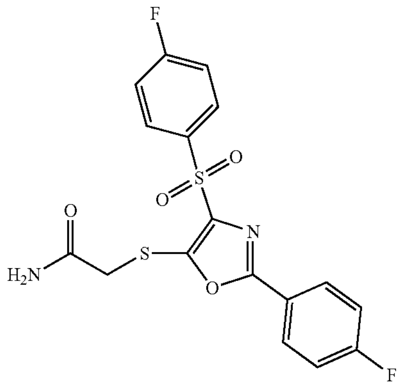 [SMILES: NC(=O)CSc1oc(-c2ccc(F)cc2)nc1S(=O)(=O)c1ccc(F)cc1] | + |

TABLE 3a-continued
| BC No. | Compound | $IC_{50}$ (NF-κB assay) |
|---|---|---|
| BC18540 | 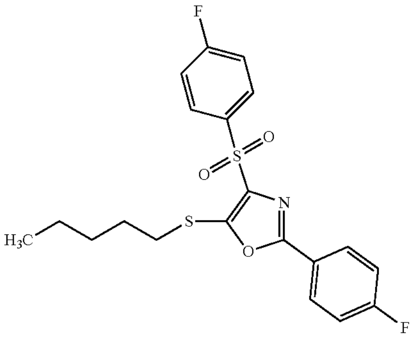 [SMILES: CCCCCSc1oc(-c2ccc(F)cc2)nc1S(=O)(=O)c1ccc(F)cc1] | + |
| BC18541 | 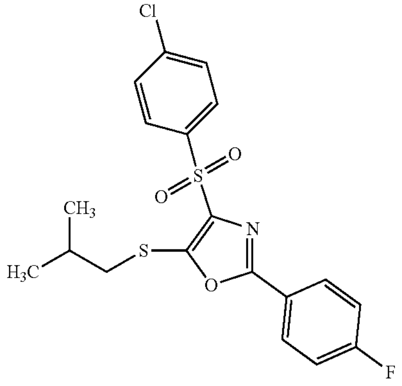 [SMILES: CC(C)CSc1oc(-c2ccc(F)cc2)nc1S(=O)(=O)c1ccc(Cl)cc1] | + |
| BC18542 | 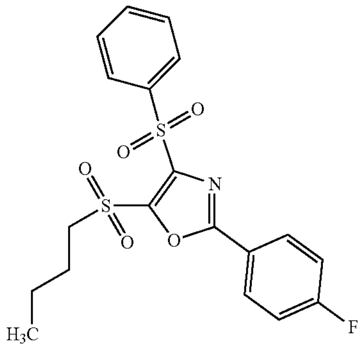 [SMILES: CCCCS(=O)(=O)c1oc(-c2ccc(F)cc2)nc1S(=O)(=O)c1ccccc1] | ++++ |
| BC18543 | 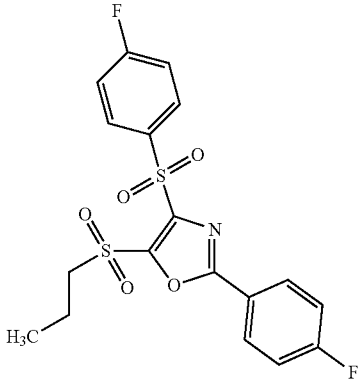 [SMILES: CCCS(=O)(=O)c1oc(-c2ccc(F)cc2)nc1S(=O)(=O)c1ccc(F)cc1] | ++++ |
TABLE 3a-continued
| BC No. | Compound | $IC_{50}$ (NF-κB assay) |
|---|---|---|
| BC18544 | 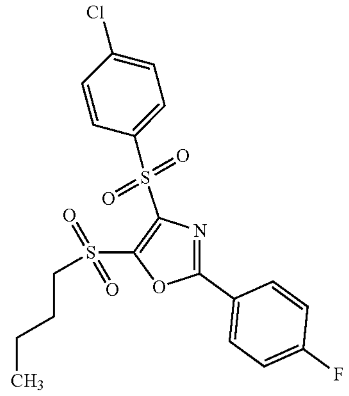 [SMILES: CCCCS(=O)(=O)c1oc(-c2ccc(F)cc2)nc1S(=O)(=O)c1ccc(Cl)cc1] | +++ |
| BC18545 | 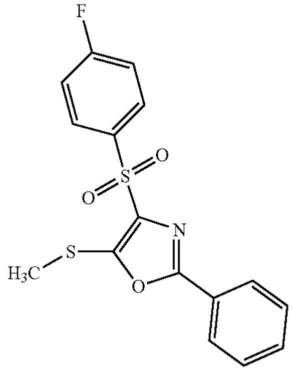 [SMILES: CSc1oc(-c2ccccc2)nc1S(=O)(=O)c1ccc(F)cc1] | ++ |
| BC18546 | 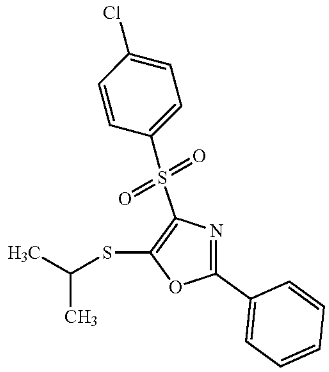 [SMILES: CC(C)Sc1oc(-c2ccccc2)nc1S(=O)(=O)c1ccc(Cl)cc1] | ++ |
| BC18547 | 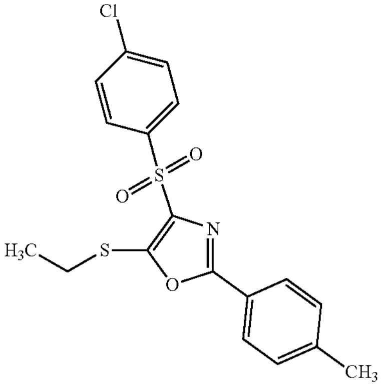 [SMILES: CCSc1oc(-c2ccc(C)cc2)nc1S(=O)(=O)c1ccc(Cl)cc1] | + |

TABLE 3a-continued
| BC No. | Compound | $IC_{50}$ (NF-κB assay) |
|---|---|---|
| BC18548 | 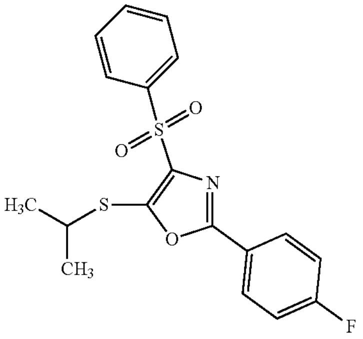 [SMILES: CC(C)Sc1oc(-c2ccc(F)cc2)nc1S(=O)(=O)c1ccccc1] | ++ |
| BC18549 | 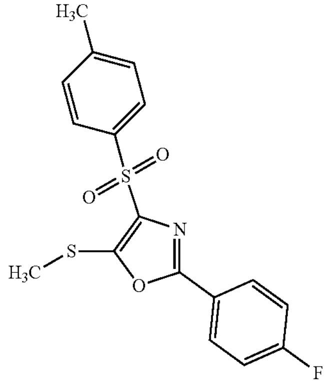 [SMILES: CSc1oc(-c2ccc(F)cc2)nc1S(=O)(=O)c1ccc(C)cc1] | + |
| BC18550 | 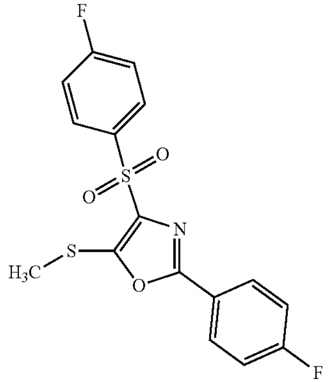 [SMILES: CSc1oc(-c2ccc(F)cc2)nc1S(=O)(=O)c1ccc(F)cc1] | + |
| BC18551 | 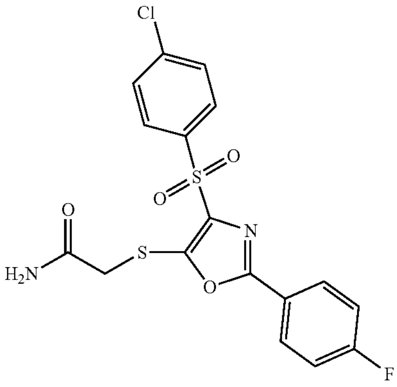 [SMILES: NC(=O)CSc1oc(-c2ccc(F)cc2)nc1S(=O)(=O)c1ccc(Cl)cc1] | + |
TABLE 3a-continued
| BC No. | Compound | $IC_{50}$ (NF-κB assay) |
|---|---|---|
| BC18552 | 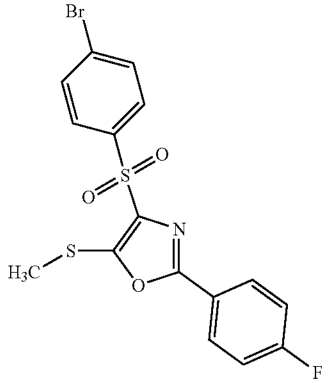 [SMILES: CSc1oc(-c2ccc(F)cc2)nc1S(=O)(=O)c1ccc(Br)cc1] | + |
| BC18553 | 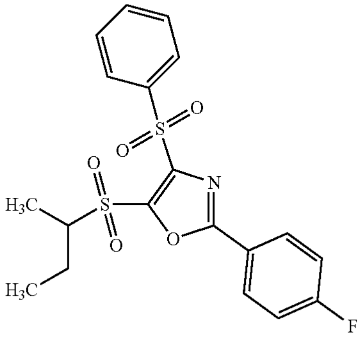 [SMILES: CCC(C)S(=O)(=O)c1oc(-c2ccc(F)cc2)nc1S(=O)(=O)c1ccccc1] | ++++ |
| BC18554 | 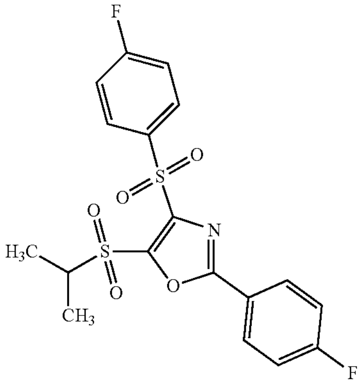 [SMILES: CC(C)S(=O)(=O)c1oc(-c2ccc(F)cc2)nc1S(=O)(=O)c1ccc(F)cc1] | ++++ |
| BC18555 | 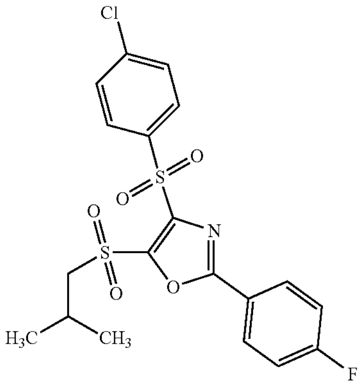 [SMILES: CC(C)CS(=O)(=O)c1oc(-c2ccc(F)cc2)nc1S(=O)(=O)c1ccc(Cl)cc1] | ++++ |

TABLE 3a-continued
| BC No. | Compound | IC50 (NF-κB assay) |
|---|---|---|
| BC18556 | 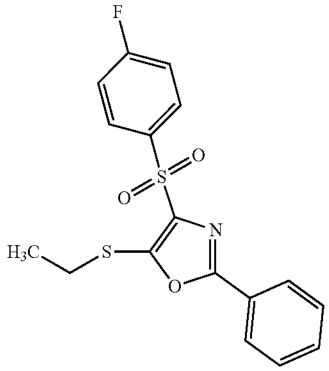 [SMILES: CCSc1oc(-c2ccccc2)nc1S(=O)(=O)c1ccc(F)cc1] | ++ |
| BC18557 | 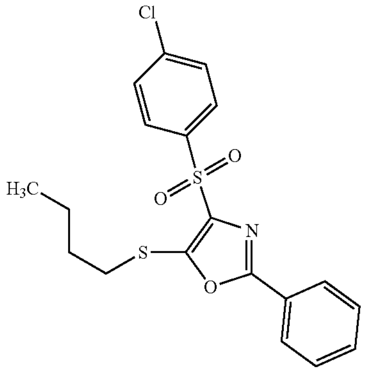 [SMILES: CCCCSc1oc(-c2ccccc2)nc1S(=O)(=O)c1ccc(Cl)cc1] | ++ |
| BC18558 | 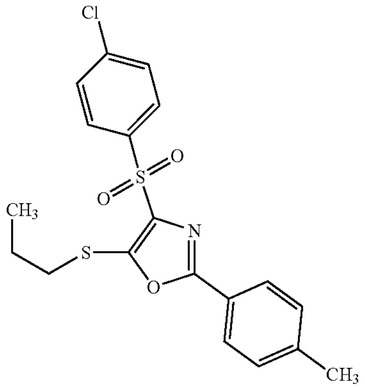 [SMILES: CCCSc1oc(-c2ccc(C)cc2)nc1S(=O)(=O)c1ccc(Cl)cc1] | + |
| BC18559 | 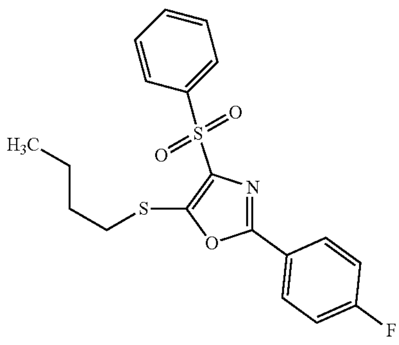 [SMILES: CCCCSc1oc(-c2ccc(F)cc2)nc1S(=O)(=O)c1ccccc1] | ++ |
TABLE 3a-continued
| BC No. | Compound | IC50 (NF-κB assay) |
|---|---|---|
| BC18560 | 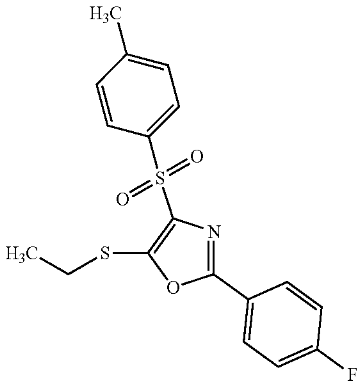 [SMILES: CCSc1oc(-c2ccc(F)cc2)nc1S(=O)(=O)c1ccc(C)cc1] | ++ |
| BC18561 | 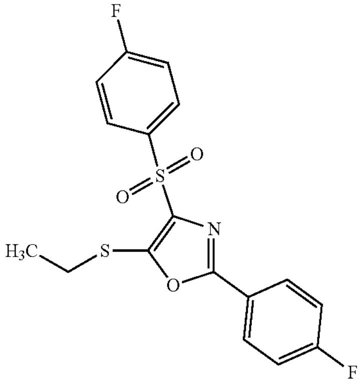 [SMILES: CCSc1oc(-c2ccc(F)cc2)nc1S(=O)(=O)c1ccc(F)cc1] | ++ |
| BC18562 | 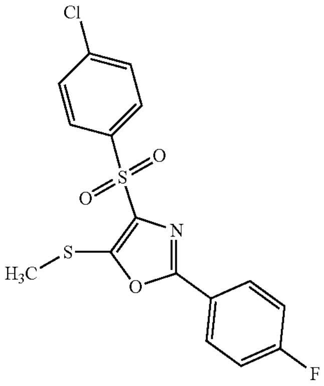 | + |
| BC18563 | 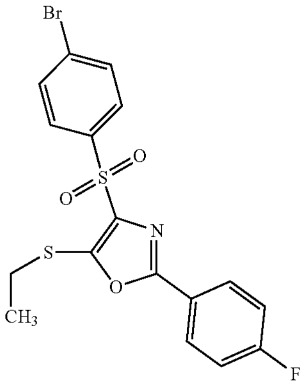 [SMILES: CCSc1oc(-c2ccc(F)cc2)nc1S(=O)(=O)c1ccc(Br)cc1] | + |

TABLE 3a-continued
| BC No. | Compound | IC50 (NF-κB assay) |
|---|---|---|
| BC18564 | 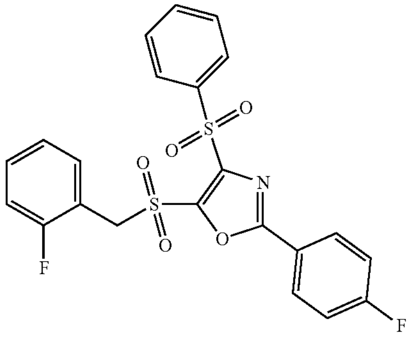 [SMILES: O=S(=O)(Cc1ccccc1F)c1oc(-c2ccc(F)cc2)nc1S(=O)(=O)c1ccccc1] | ++++ |
| BC18565 | 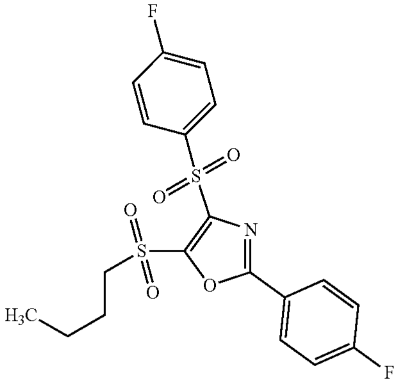 [SMILES: CCCCS(=O)(=O)c1oc(-c2ccc(F)cc2)nc1S(=O)(=O)c1ccc(F)cc1] | ++++ |
| BC18566 | 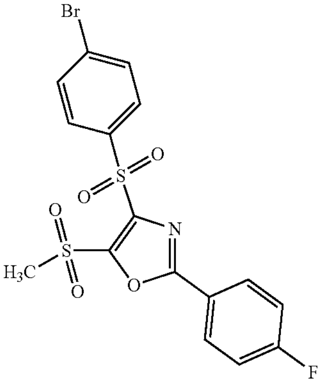 [SMILES: CS(=O)(=O)c1oc(-c2ccc(F)cc2)nc1S(=O)(=O)c1ccc(Br)cc1] | ++++ |
| BC18567 | 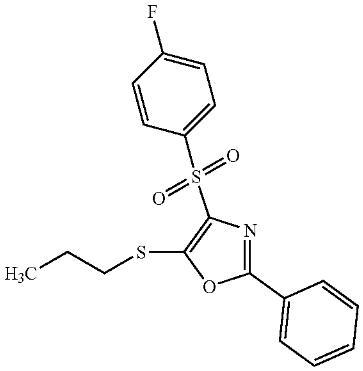 [SMILES: CCCSc1oc(-c2ccccc2)nc1S(=O)(=O)c1ccc(F)cc1] | + |
| BC18568 | 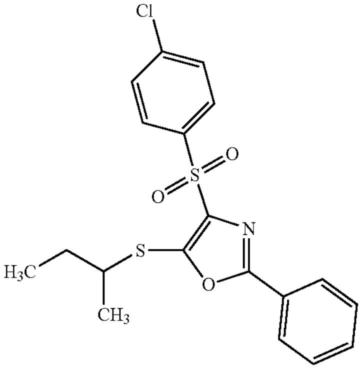 [SMILES: CCC(C)Sc1oc(-c2ccccc2)nc1S(=O)(=O)c1ccc(Cl)cc1] | ++ |
| BC18569 | 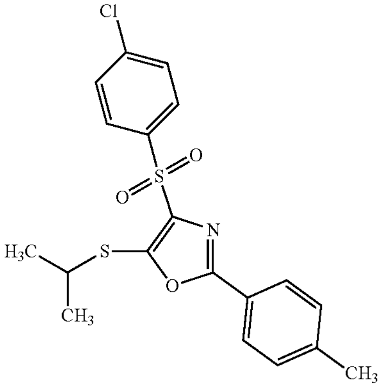 [SMILES: Cc1ccc(-c2nc(S(=O)(=O)c3ccc(Cl)cc3)c(SC(C)C)o2)cc1] | ++ |
| BC18570 | 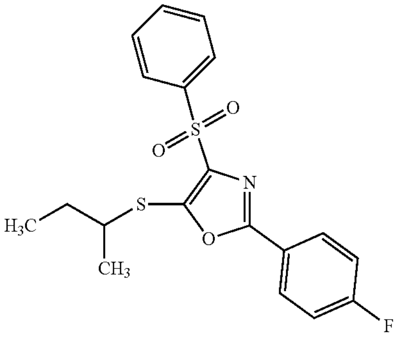 [SMILES: CCC(C)Sc1oc(-c2ccc(F)cc2)nc1S(=O)(=O)c1ccccc1] | ++ |
| BC18571 | 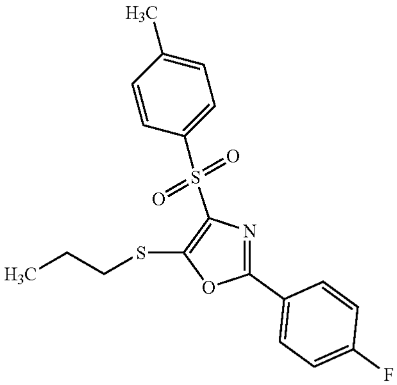 [SMILES: CCCSc1oc(-c2ccc(F)cc2)nc1S(=O)(=O)c1ccc(C)cc1] | ++ |

TABLE 3a-continued
| BC No. | Compound | $IC_{50}$ (NF-κB assay) |
| --- | --- | --- |
| BC18572 | 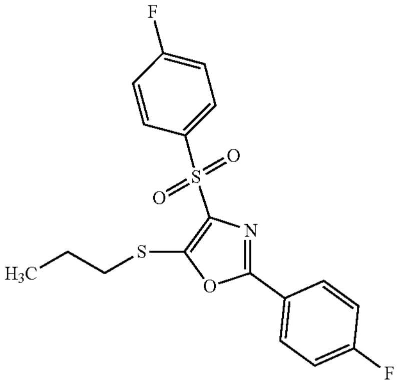 [SMILES: CCCSc1oc(-c2ccc(F)cc2)nc1S(=O)(=O)c1ccc(F)cc1] | + |
| BC18573 | 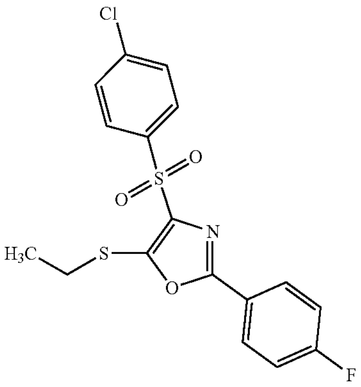 [SMILES: CCSc1oc(-c2ccc(F)cc2)nc1S(=O)(=O)c1ccc(Cl)cc1] | ++ |
| BC18574 | 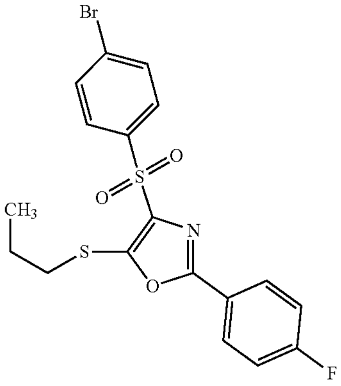 [SMILES: CCCSc1oc(-c2ccc(F)cc2)nc1S(=O)(=O)c1ccc(Br)cc1] | + |
| BC18575 | 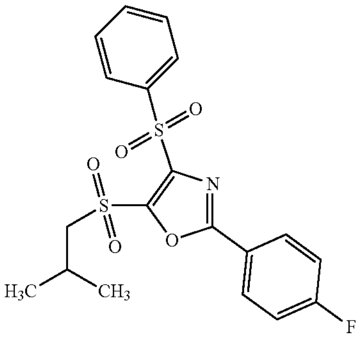 [SMILES: CC(C)CS(=O)(=O)c1oc(-c2ccc(F)cc2)nc1S(=O)(=O)c1ccccc1] | ++++ |
TABLE 3a-continued
| BC No. | Compound | $IC_{50}$ (NF-κB assay) |
| --- | --- | --- |
| BC18576 | 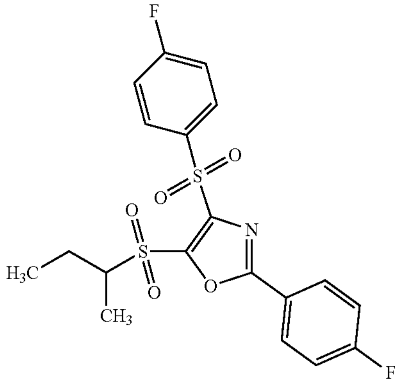 [SMILES: CCC(C)S(=O)(=O)c1oc(-c2ccc(F)cc2)nc1S(=O)(=O)c1ccc(F)cc1] | ++++ |
| BC18577 | 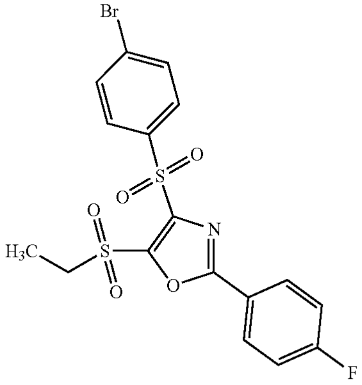 [SMILES: CCS(=O)(=O)c1oc(-c2ccc(F)cc2)nc1S(=O)(=O)c1ccc(Br)cc1] | ++++ |
| BC18578 | 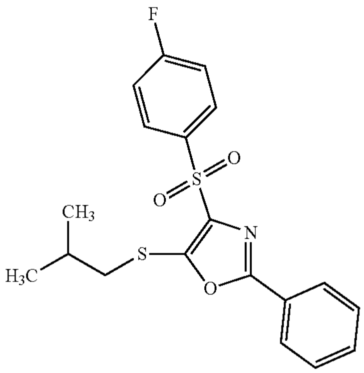 [SMILES: CC(C)CSc1oc(-c2ccccc2)nc1S(=O)(=O)c1ccc(F)cc1] | ++ |
| BC18579 | 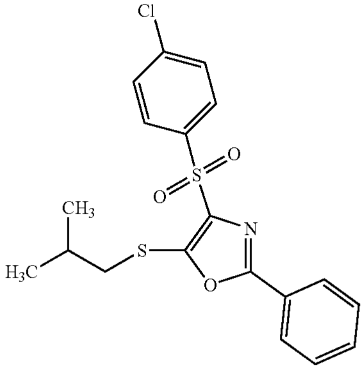 [SMILES: CC(C)CSc1oc(-c2ccccc2)nc1S(=O)(=O)c1ccc(Cl)cc1] | ++ |

TABLE 3a-continued
| BC No. | Compound | $IC_{50}$ (NF-κB assay) |
|---|---|---|
| BC18580 | 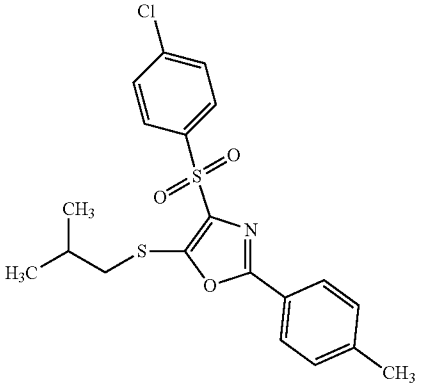 [SMILES: Cc1ccc(-c2nc(S(=O)(=O)c3ccc(Cl)cc3)c(SCC(C)C)o2)cc1] | + |
| BC18581 | 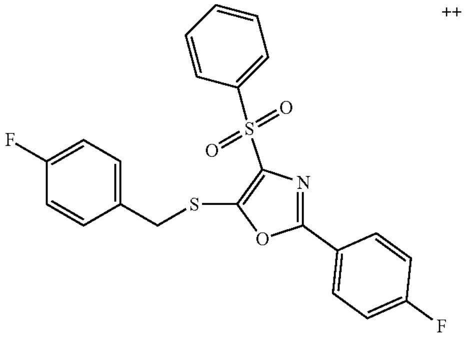 | ++ |
| BC18582 | 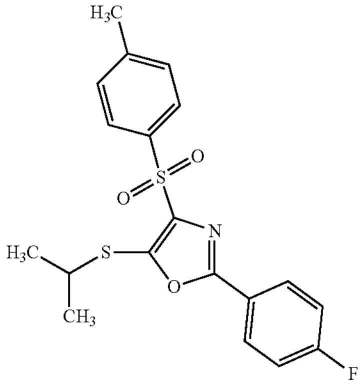 [SMILES: Cc1ccc(S(=O)(=O)c2nc(-c3ccc(F)cc3)oc2SC(C)C)cc1] | ++ |
| BC18583 | 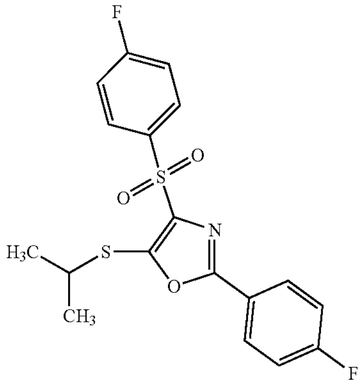 [SMILES: CC(C)Sc1oc(-c2ccc(F)cc2)nc1S(=O)(=O)c1ccc(F)cc1] | ++ |
TABLE 3a-continued
| BC No. | Compound | $IC_{50}$ (NF-κB assay) |
|---|---|---|
| BC18584 | 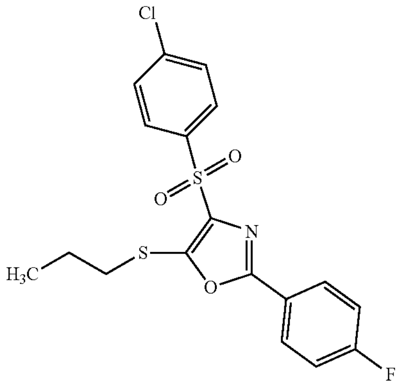 [SMILES: CCCSc1oc(-c2ccc(F)cc2)nc1S(=O)(=O)c1ccc(Cl)cc1] | + |
| BC18585 | 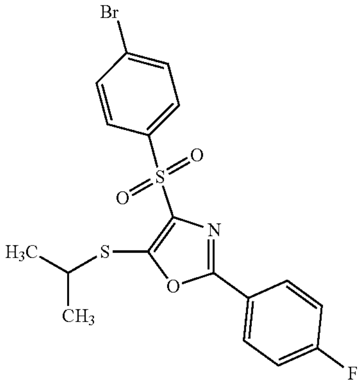 [SMILES: CC(C)Sc1oc(-c2ccc(F)cc2)nc1S(=O)(=O)c1ccc(Br)cc1] | ++ |
| BC18586 | 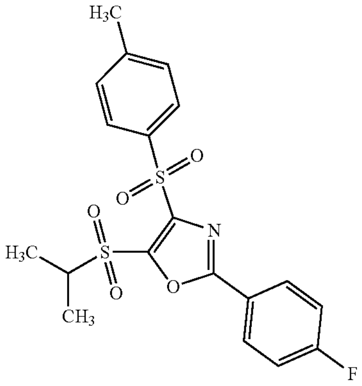 [SMILES: Cc1ccc(S(=O)(=O)c2nc(-c3ccc(F)cc3)oc2S(=O)(=O)C(C)C)cc1] | ++++ |
| BC18587 | 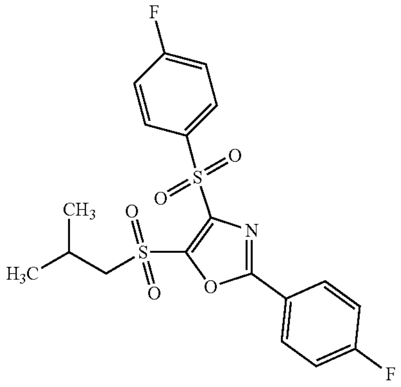 [SMILES: CC(C)CS(=O)(=O)c1oc(-c2ccc(F)cc2)nc1S(=O)(=O)c1ccc(F)cc1] | ++++ |

TABLE 3a-continued
| BC No. | Compound | $IC_{50}$ (NF-κB assay) |
|---|---|---|
| BC18588 | 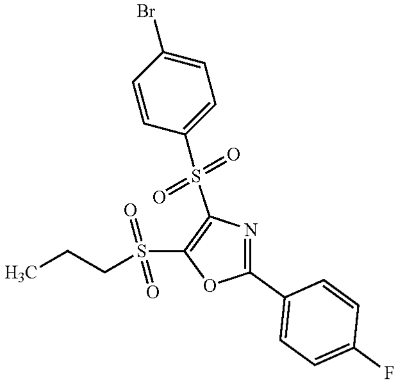 [SMILES: CCCS(=O)(=O)c1oc(-c2ccc(F)cc2)nc1S(=O)(=O)c1ccc(Br)cc1] | ++++ |
TABLE 3b
| BC No. | ZE No. | Structure | $IC_{50}$ (NF-κB assay) | $IC_{50}$ (TNF assay) |
|---|---|---|---|---|
| BC19125 | ZE23-0008 | 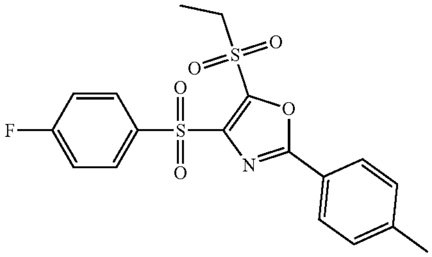 [SMILES: CCS(=O)(=O)c1oc(-c2ccc(C)cc2)nc1S(=O)(=O)c1ccc(F)cc1] | ++++ | ++++ |
| BC19126 | ZE23-0009 | 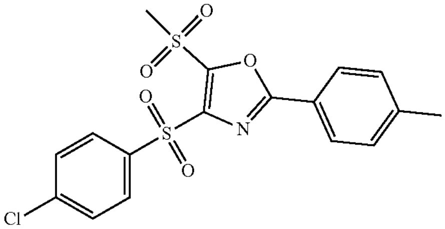 [SMILES: Cc1ccc(-c2nc(S(=O)(=O)c3ccc(Cl)cc3)c(S(C)(=O)=O)o2)cc1] | ++ | +++ |
| BC19127 | ZE23-0010 | 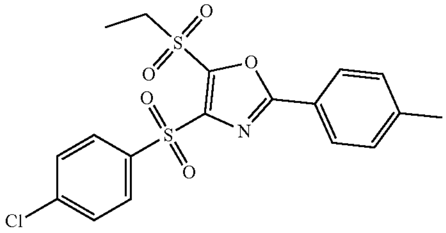 [SMILES: CCS(=O)(=O)c1oc(-c2ccc(C)cc2)nc1S(=O)(=O)c1ccc(Cl)cc1] | ++++ | ++ |
| BC19128 | ZE23-0012 | 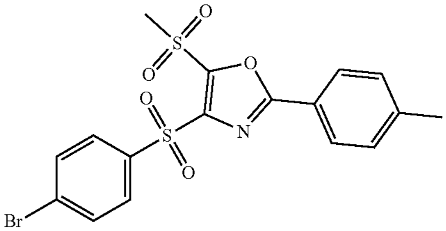 [SMILES: Cc1ccc(-c2nc(S(=O)(=O)c3ccc(Br)cc3)c(S(C)(=O)=O)o2)cc1] | ++ | +++ |

TABLE 3b-continued
| BC No. | ZE No. | Structure | $IC_{50}$ (NF-κB assay) | $IC_{50}$ (TNF assay) |
|---|---|---|---|---|
| BC19129 | ZE23-0013 | 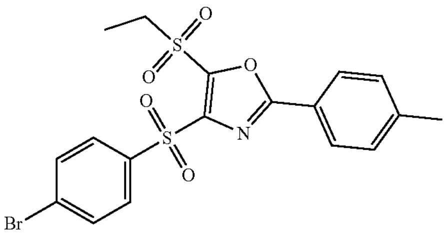 | ++++ | +++ |
| BC19130 | ZE23-0014 | 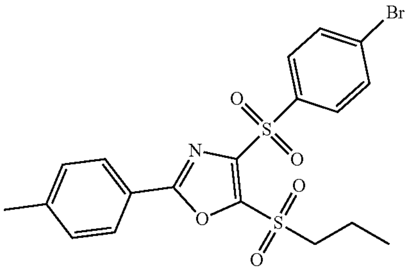 [SMILES: CCCS(=O)(=O)c1oc(-c2ccc(C)cc2)nc1S(=O)(=O)c1ccc(Br)cc1] | +++ | +++ |
| BC19146 | ZE23-0004 | 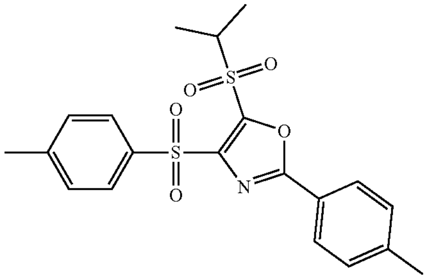 | ++++ | +++ |
| BC19147 | ZE23-0007 | 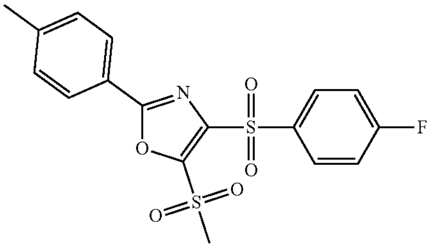 [SMILES: Cc1ccc(-c2nc(S(=O)(=O)c3ccc(F)cc3)c(S(C)(=O)=O)o2)cc1] | +++ | +++ |
| BC19260 | ZE23-0016 | 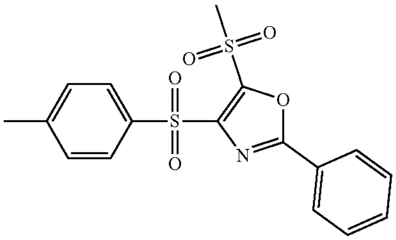 [SMILES: Cc1ccc(S(=O)(=O)c2nc(-c3ccccc3)oc2S(C)(=O)=O)cc1] | ++++ | ++++ |

TABLE 3b-continued
| BC No. | ZE No. | Structure | IC50 (NF-κB assay) | IC50 (TNF assay) |
|---|---|---|---|---|
| BC19261 | ZE23-0018 | 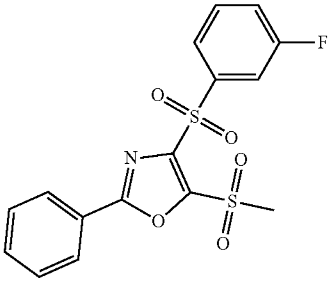 [SMILES: CS(=O)(=O)c1oc(-c2ccccc2)nc1S(=O)(=O)c1cccc(F)c1] | ++++ | + |
| BC19262 | ZE23-0019 | 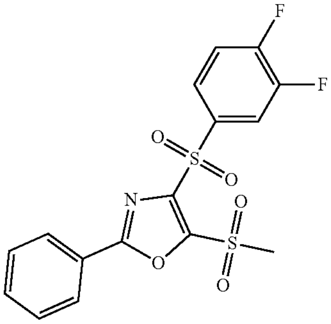 [SMILES: CS(=O)(=O)c1oc(-c2ccccc2)nc1S(=O)(=O)c1ccc(F)c(F)c1] | +++ | ++++ |
| BC19263 | ZE23-0022 | 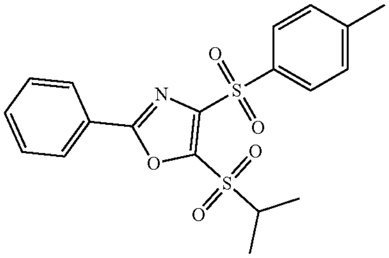 [SMILES: Cc1ccc(S(=O)(=O)c2nc(-c3ccccc3)oc2S(=O)(=O)C(C)C)cc1] | +++ | +++ |
| BC19264 | ZE23-0023 | 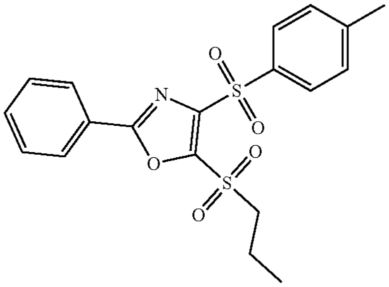 [SMILES: CCCS(=O)(=O)c1oc(-c2ccccc2)nc1S(=O)(=O)c1ccc(C)cc1] | ++++ | +++ |
| BC19265 | ZE23-0024 | 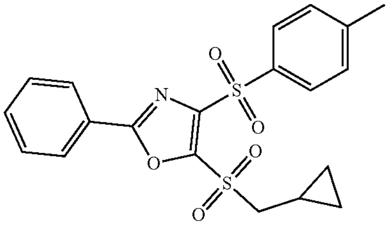 [SMILES: Cc1ccc(S(=O)(=O)c2nc(-c3ccccc3)oc2S(=O)(=O)CC2CC2)cc1] | ++++ | +++ |

TABLE 3b-continued
| BC No. | ZE No. | Structure | IC50 (NF-κB assay) | IC50 (TNF assay) |
|---|---|---|---|---|
| BC19266 | ZE23-0025 | 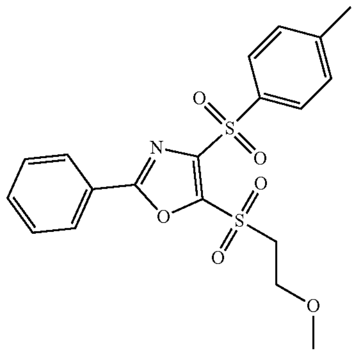 [SMILES: COCCS(=O)(=O)c1oc(-c2ccccc2)nc1S(=O)(=O)c1ccc(C)cc1] | ++++ | ++++ |
| BC19267 | ZE23-0026 | 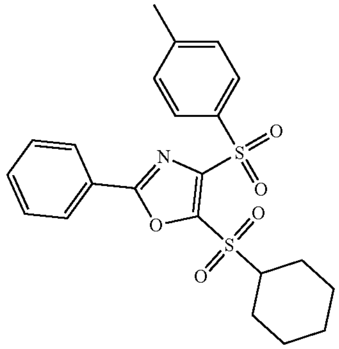 [SMILES: Cc1ccc(S(=O)(=O)c2nc(-c3ccccc3)oc2S(=O)(=O)C2CCCCC2)cc1] | ++++ | +++ |
| BC19268 | ZE23-0028 | 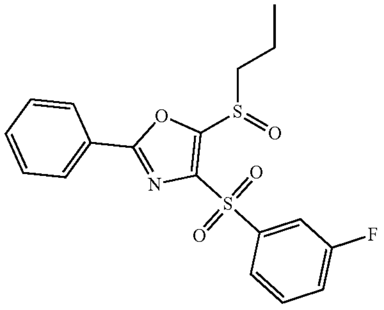 [SMILES: CCCS(=O)c1oc(-c2ccccc2)nc1S(=O)(=O)c1cccc(F)c1] | +++ | ++++ |
| BC19269 | ZE23-0030 | 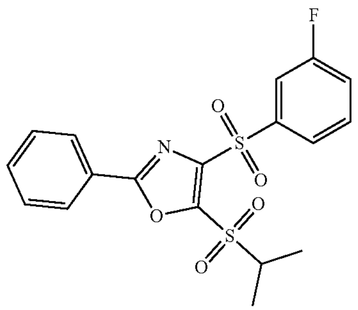 [SMILES: CC(C)S(=O)(=O)c1oc(-c2ccccc2)nc1S(=O)(=O)c1cccc(F)c1] | +++ | ++++ |

TABLE 3b-continued
| BC No. | ZE No. | Structure | $IC_{50}$ (NF-κB assay) | $IC_{50}$ (TNF assay) |
|---|---|---|---|---|
| BC19270 | ZE23-0031 | 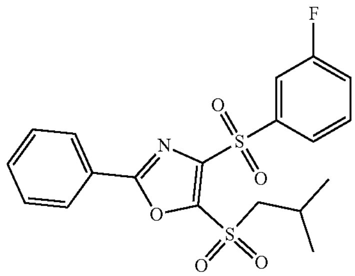 [SMILES: CC(C)CS(=O)(=O)c1oc(-c2ccccc2)nc1S(=O)(=O)c1cccc(F)c1] | ++++ | ++++ |
| BC19271 | ZE23-0032 | 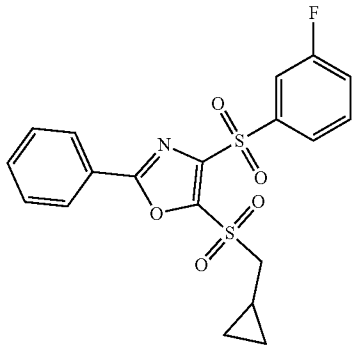 [SMILES: O=S(=O)(CC1CC1)c1oc(-c2ccccc2)nc1S(=O)(=O)c1cccc(F)c1] | +++ | ++++ |
| BC19272 | ZE23-0033 | 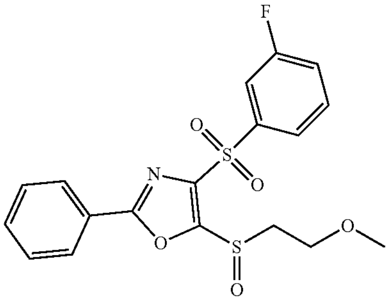 [SMILES: COCCS(=O)c1oc(-c2ccccc2)nc1S(=O)(=O)c1cccc(F)c1] | ++++ | ++++ |
| BC19273 | ZE23-0039 | 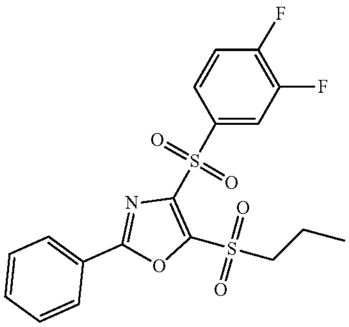 [SMILES: CCCS(=O)(=O)c1oc(-c2ccccc2)nc1S(=O)(=O)c1ccc(F)c(F)c1] | +++ | +++ |

TABLE 3b-continued
| BC No. | ZE No. | Structure | $IC_{50}$ (NF-κB assay) | $IC_{50}$ (TNF assay) |
|---|---|---|---|---|
| BC19274 | ZE23-0040 | 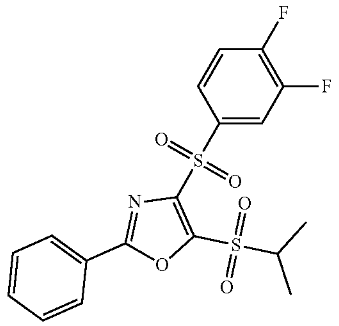 [SMILES: CC(C)S(=O)(=O)c1oc(-c2ccccc2)nc1S(=O)(=O)c1ccc(F)c(F)c1] | ++++ | +++ |
| BC19275 | ZE23-0041 | 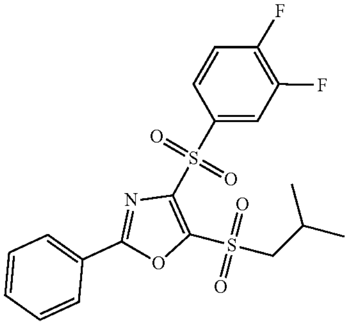 [SMILES: CC(C)CS(=O)(=O)c1oc(-c2ccccc2)nc1S(=O)(=O)c1ccc(F)c(F)c1] | ++++ | ++++ |
| BC19276 | ZE23-0044 | 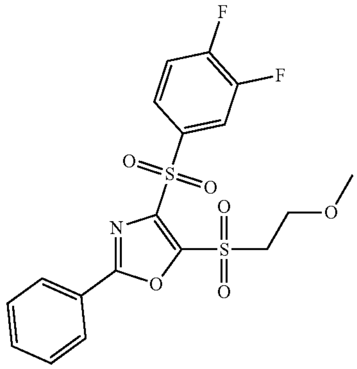 [SMILES: COCCS(=O)(=O)c1oc(-c2ccccc2)nc1S(=O)(=O)c1ccc(F)c(F)c1] | +++ | ++++ |
| BC19277 | ZE23-0045 | 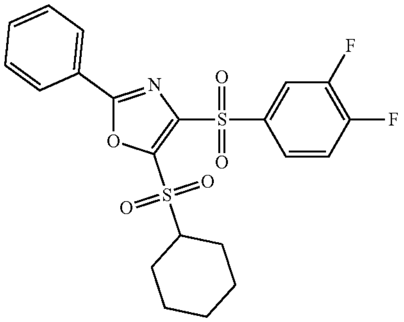 [SMILES: O=S(=O)(c1ccc(F)c(F)c1)c1nc(-c2ccccc2)oc1S(=O)(=O)C1CCCCC1] | ++++ | +++ |

TABLE 3b-continued
| BC No. | ZE No. | Structure | $IC_{50}$ (NF-κB assay) | $IC_{50}$ (TNF assay) |
|---|---|---|---|---|
| BC19278 | ZE23-0051 | 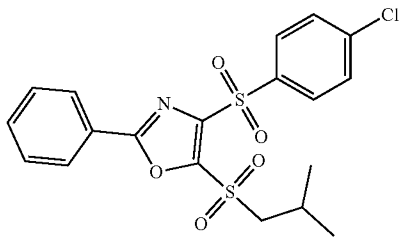 [SMILES: CC(C)CS(=O)(=O)c1oc(-c2ccccc2)nc1S(=O)(=O)c1ccc(Cl)cc1] | ++++ | ++++ |
| BC19279 | ZE23-0065 | 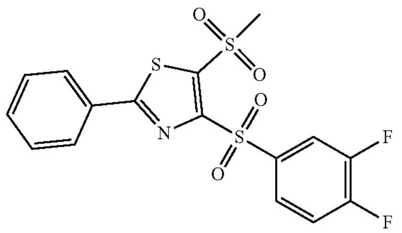 [SMILES: CS(=O)(=O)c1sc(-c2ccccc2)nc1S(=O)(=O)c1ccc(F)c(F)c1] | +++ | +++ |
| BC19327 | ZE23-0037 | 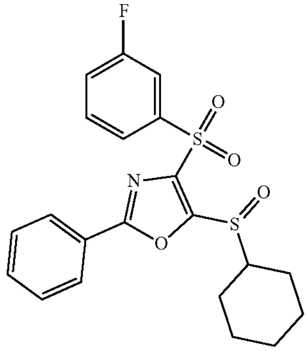 [SMILES: O=S(c1oc(-c2ccccc2)nc1S(=O)(=O)c1cccc(F)c1)C1CCCCC1] | ++ | ++ |
| BC19328 | ZE23-0038 | 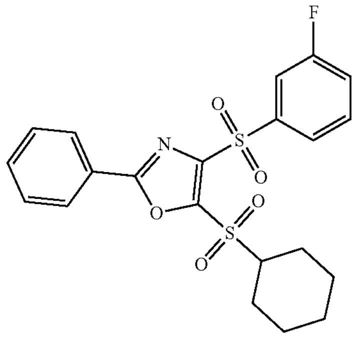 [SMILES: O=S(=O)(c1cccc(F)c1)c1nc(-c2ccccc2)oc1S(=O)(=O)C1CCCCC1] | ++++ | +++ |
| BC19329 | ZE23-0047 | 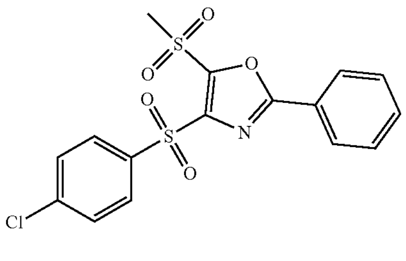 [SMILES: CS(=O)(=O)c1oc(-c2ccccc2)nc1S(=O)(=O)c1ccc(Cl)cc1] | ++++ | ++++ |

TABLE 3b-continued
| BC No. | ZE No. | Structure | $IC_{50}$ (NF-κB assay) | $IC_{50}$ (TNF assay) |
|---|---|---|---|---|
| BC19330 | ZE23-0052 | 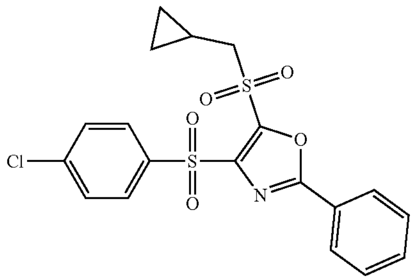 [SMILES: O=S(=O)(CC1CC1)c1oc(-c2ccccc2)nc1S(=O)(=O)c1ccc(Cl)cc1] | +++ | +++ |
| BC19331 | ZE23-0055 | 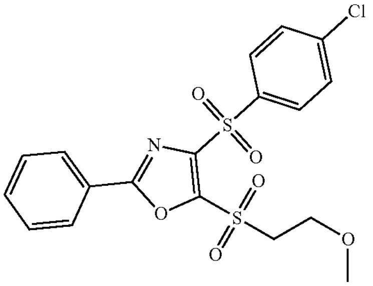 [SMILES: COCCS(=O)(=O)c1oc(-c2ccccc2)nc1S(=O)(=O)c1ccc(Cl)cc1] | ++++ | ++++ |
| BC19332 | ZE23-0057 | 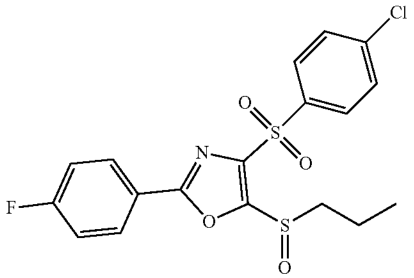 [SMILES: CCCS(=O)c1oc(-c2ccc(F)cc2)nc1S(=O)(=O)c1ccc(Cl)cc1] | +++ | ++++ |
| BC19333 | ZE23-0058 | 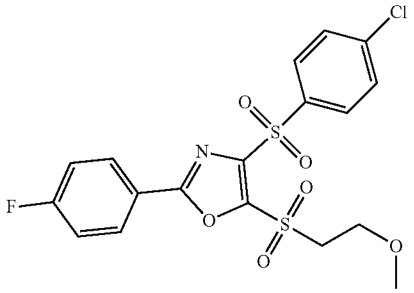 [SMILES: COCCS(=O)(=O)c1oc(-c2ccc(F)cc2)nc1S(=O)(=O)c1ccc(Cl)cc1] | ++++ | ++++ |
| BC19334 | ZE23-0064 | 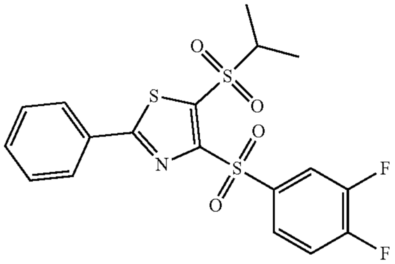 [SMILES: CC(C)S(=O)(=O)c1sc(-c2ccccc2)nc1S(=O)(=O)c1ccc(F)c(F)c1] | + | ++ |

TABLE 3b-continued
| BC No. | ZE No. | Structure | $IC_{50}$ (NF-κB assay) | $IC_{50}$ (TNF assay) |
|---|---|---|---|---|
| BC19335 | ZE23-0066 | 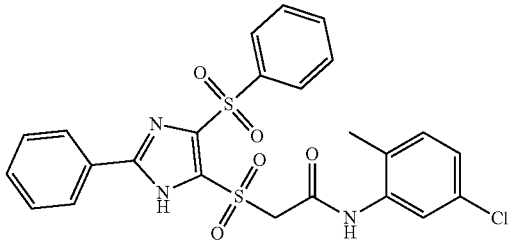 [SMILES: Cc1ccc(Cl)cc1NC(=O)CS(=O)(=O)c1[nH]c(-c2ccccc2)nc1S(=O)(=O)c1ccccc1] | + | + |
| BC19336 | ZE23-0083 | 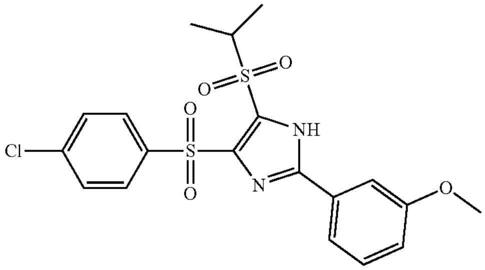 [SMILES: COc1cccc(-c2nc(S(=O)(=O)c3ccc(Cl)cc3)c(S(=O)(=O)C(C)C)[nH]2)c1] | + | + |
| BC19337 | ZE23-0087 | 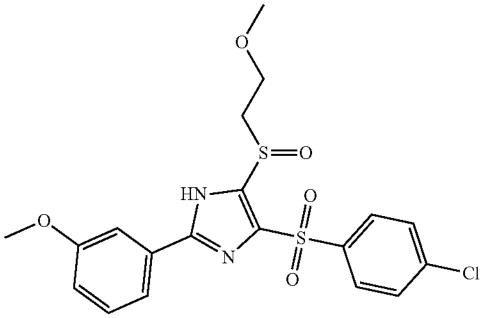 [SMILES: COCCS(=O)c1[nH]c(-c2cccc(OC)c2)nc1S(=O)(=O)c1ccc(Cl)cc1] | + | + |
| BC19342 | ZE23-0102 | 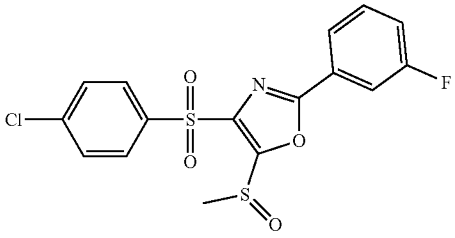 [SMILES: CS(=O)c1oc(-c2cccc(F)c2)nc1S(=O)(=O)c1ccc(Cl)cc1] | ++++ | ++++ |
| BC19343 | ZE23-0103 | 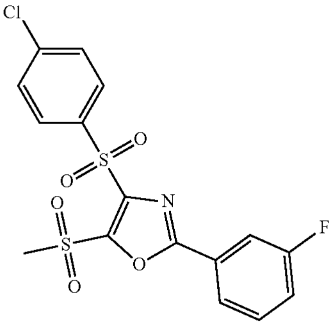 [SMILES: CS(=O)(=O)c1oc(-c2cccc(F)c2)nc1S(=O)(=O)c1ccc(Cl)cc1] | ++ | ++++ |

TABLE 3b-continued
| BC No. | ZE No. | Structure | $IC_{50}$ (NF-κB assay) | $IC_{50}$ (TNF assay) |
|---|---|---|---|---|
| BC19344 | ZE23-0104 | 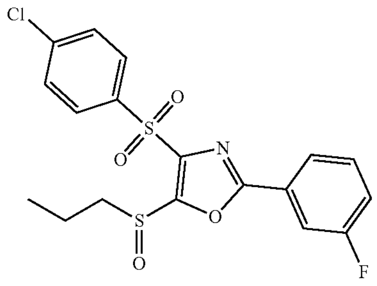 [SMILES: CCCS(=O)c1oc(-c2cccc(F)c2)nc1S(=O)(=O)c1ccc(Cl)cc1] | +++ | +++ |
| BC19345 | ZE23-0105 | 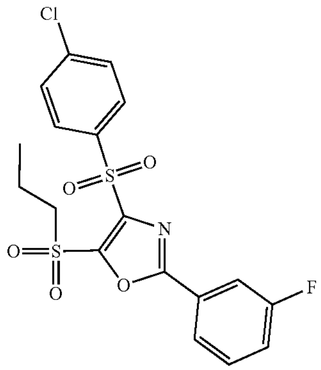 [SMILES: CCCS(=O)(=O)c1oc(-c2cccc(F)c2)nc1S(=O)(=O)c1ccc(Cl)cc1] | +++ | +++ |
| BC19346 | ZE23-0106 | 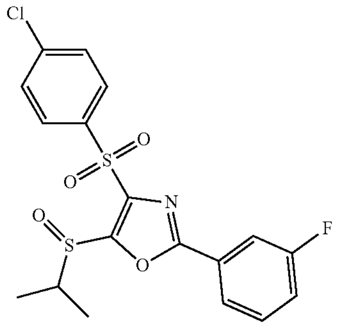 [SMILES: CC(C)S(=O)c1oc(-c2cccc(F)c2)nc1S(=O)(=O)c1ccc(Cl)cc1] | ++++ | ++++ |
| BC19347 | ZE23-0108 | 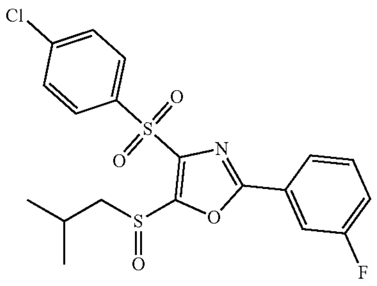 [SMILES: CC(C)CS(=O)c1oc(-c2cccc(F)c2)nc1S(=O)(=O)c1ccc(Cl)cc1] | ++++ | ++++ |

TABLE 3b-continued
| BC No. | ZE No. | Structure | $IC_{50}$ (NF-κB assay) | $IC_{50}$ (TNF assay) |
|---|---|---|---|---|
| BC19348 | ZE23-0109 | 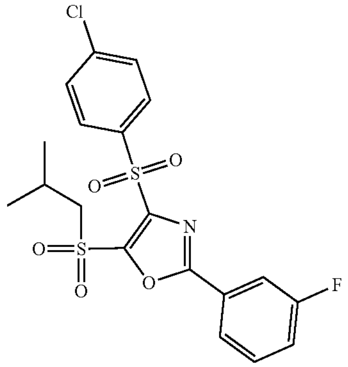 [SMILES: CC(C)CS(=O)(=O)c1oc(-c2cccc(F)c2)nc1S(=O)(=O)c1ccc(Cl)cc1] | ++++ | +++ |
| BC19349 | ZE23-0110 | 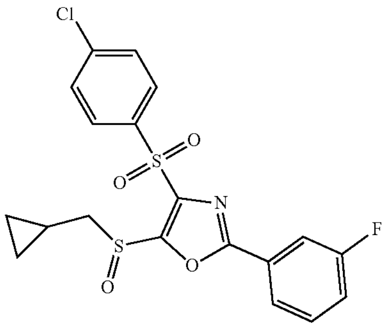 [SMILES: O=S(CC1CC1)c1oc(-c2cccc(F)c2)nc1S(=O)(=O)c1ccc(Cl)cc1] | +++ | ++++ |
| BC19350 | ZE23-0111 | 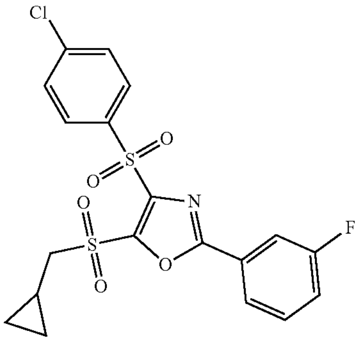 [SMILES: O=S(=O)(CC1CC1)c1oc(-c2cccc(F)c2)nc1S(=O)(=O)c1ccc(Cl)cc1] | ++ | ++ |
| BC19351 | ZE23-0112 | 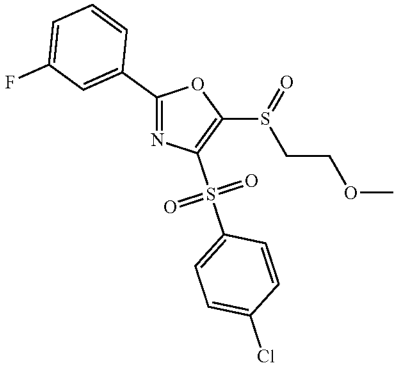 [SMILES: COCCS(=O)c1oc(-c2cccc(F)c2)nc1S(=O)(=O)c1ccc(Cl)cc1] | +++ | ++++ |

TABLE 3b-continued
| BC No. | ZE No. | Structure | $IC_{50}$ (NF-κB assay) | $IC_{50}$ (TNF assay) |
|---|---|---|---|---|
| BC19352 | ZE23-0113 | 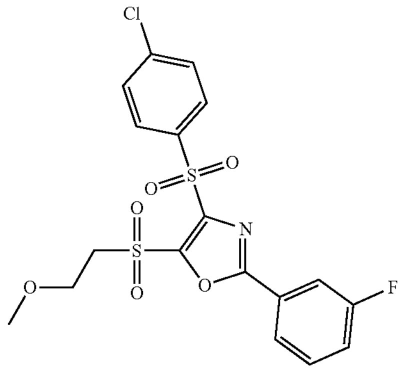 [SMILES: COCCS(=O)(=O)c1oc(-c2cccc(F)c2)nc1S(=O)(=O)c1ccc(Cl)cc1] | +++ | ++++ |
| BC19353 | ZE23-0116 | 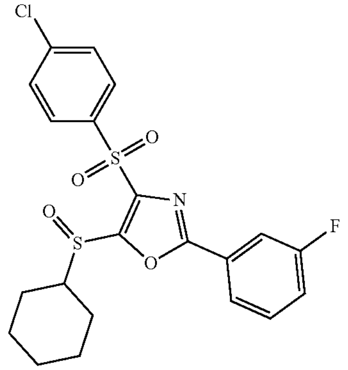 [SMILES: O=S(c1oc(-c2cccc(F)c2)nc1S(=O)(=O)c1ccc(Cl)cc1)C1CCCCC1] | +++ | +++ |
| BC19410 | ZE23-0082 | 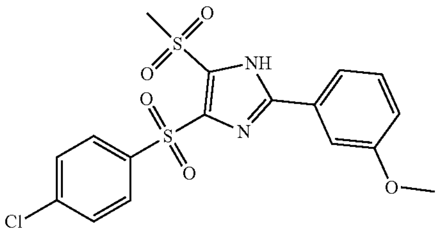 [SMILES: COc1cccc(-c2nc(S(=O)(=O)c3ccc(Cl)cc3)c(S(C)(=O)=O)[nH]2)c1] | +++ | + |
| BC19411 | ZE23-0107 | 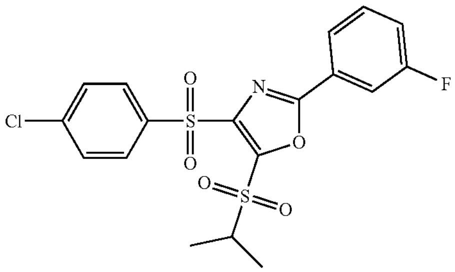 [SMILES: CC(C)S(=O)(=O)c1oc(-c2cccc(F)c2)nc1S(=O)(=O)c1ccc(Cl)cc1] | ++++ | ++++ |

TABLE 3b-continued
| BC No. | ZE No. | Structure | $IC_{50}$ (NF-κB assay) | $IC_{50}$ (TNF assay) |
|---|---|---|---|---|
| BC19412 | ZE23-0117 | 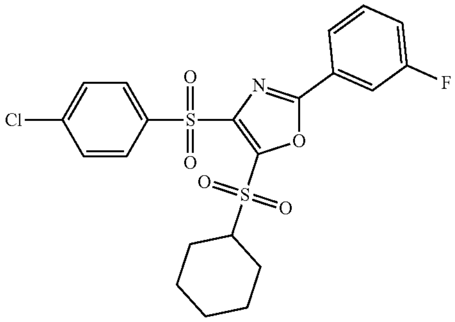 [SMILES: O=S(=O)(c1ccc(Cl)cc1)c1nc(-c2cccc(F)c2)oc1S(=O)(=O)C1CCCCC1] | +++ | +++ |
| BC19413 | ZE23-0127 | 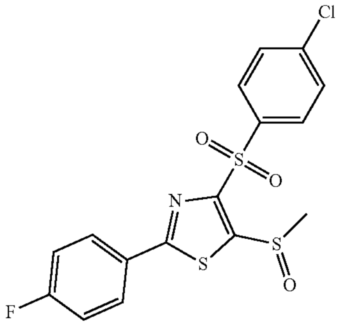 [SMILES: CS(=O)c1sc(-c2ccc(F)cc2)nc1S(=O)(=O)c1ccc(Cl)cc1] | + | ++ |
| BC19414 | ZE23-0128 | 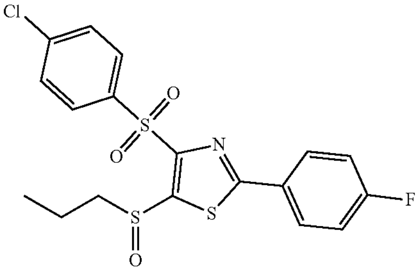 [SMILES: CCCS(=O)c1sc(-c2ccc(F)cc2)nc1S(=O)(=O)c1ccc(Cl)cc1] | + | + |
| BC19415 | ZE23-0129 | 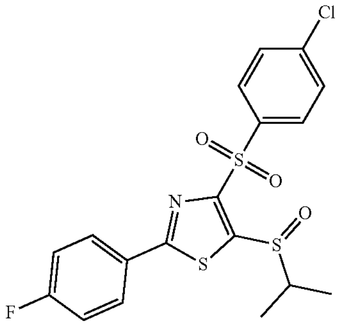 [SMILES: CC(C)S(=O)c1sc(-c2ccc(F)cc2)nc1S(=O)(=O)c1ccc(Cl)cc1] | + | ++ |

TABLE 3b-continued
| BC No. | ZE No. | Structure | $IC_{50}$ (NF-κB assay) | $IC_{50}$ (TNF assay) |
| --- | --- | --- | --- | --- |
| BC19416 | ZE23-0131 | 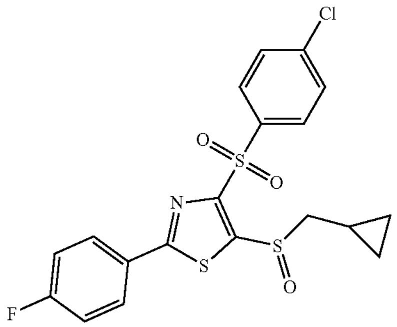 [SMILES: O=S(CC1CC1)c1sc(-c2ccc(F)cc2)nc1S(=O)(=O)c1ccc(Cl)cc1] | + | + |
| BC19417 | ZE23-0133 | 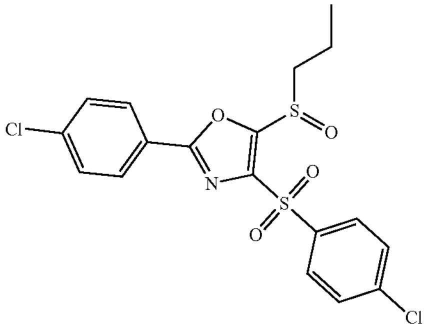 [SMILES: CCCS(=O)c1oc(-c2ccc(Cl)cc2)nc1S(=O)(=O)c1ccc(Cl)cc1] | +++ | ++ |
| BC19418 | ZE23-0134 | 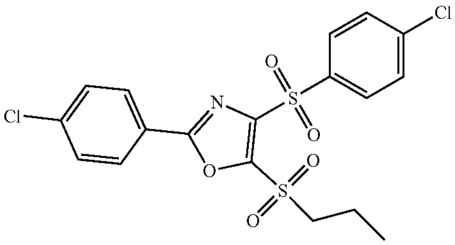 [SMILES: CCCS(=O)(=O)c1oc(-c2ccc(Cl)cc2)nc1S(=O)(=O)c1ccc(Cl)cc1] | ++ | ++ |
| BC19419 | ZE23-0136 | 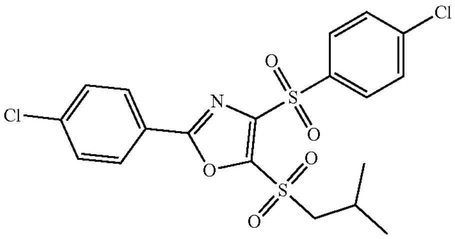 [SMILES: CC(C)CS(=O)(=O)c1oc(-c2ccc(Cl)cc2)nc1S(=O)(=O)c1ccc(Cl)cc1] | ++ | +++ |
| BC19420 | ZE23-0145 | 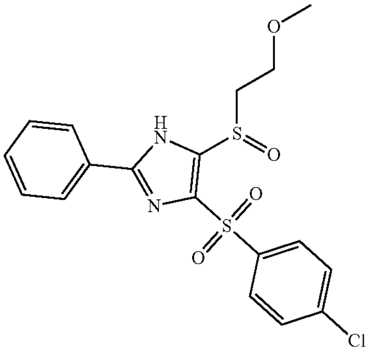 [SMILES: COCCS(=O)c1[nH]c(-c2ccccc2)nc1S(=O)(=O)c1ccc(Cl)cc1] | + | + |

TABLE 3b-2
| BC No. | Structure | $IC_{50}$ (NF-κB assay) | $IC_{50}$ (TNF assay) |
|---|---|---|---|
| BC19463 | 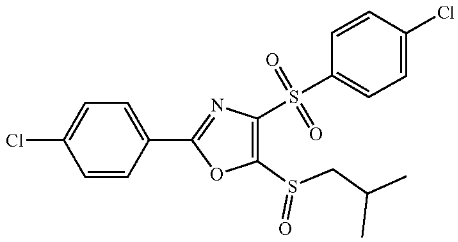 [SMILES: CC(C)CS(=O)c1oc(-c2ccc(Cl)cc2)nc1S(=O)(=O)c1ccc(Cl)cc1] | ++++ | +++ |
| BC19464 | 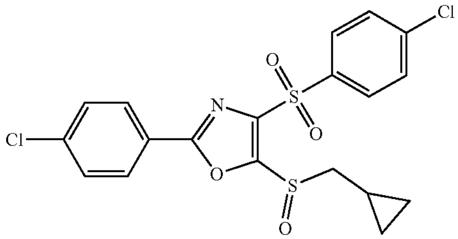 [SMILES: O=S(CC1CC1)c1oc(-c2ccc(Cl)cc2)nc1S(=O)(=O)c1ccc(Cl)cc1] | +++ | ++++ |
| BC19521 | 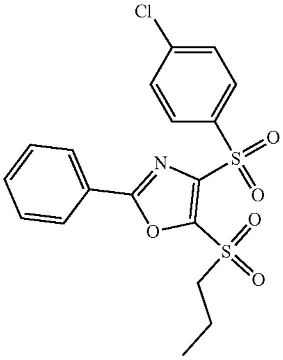 [SMILES: CCCS(=O)(=O)c1oc(-c2ccccc2)nc1S(=O)(=O)c1ccc(Cl)cc1] | ++++ | +++ |
TABLE 3c
| BC No. | ZE No. | Structure | $IC_{50}$ (NF-κB assay) | $IC_{50}$ (TNF assay) |
|---|---|---|---|---|
| BC19204 | ZE23-0020 | 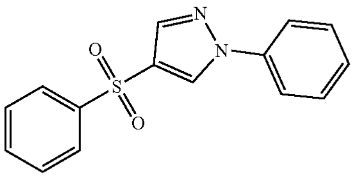 [SMILES: O=S(=O)(c1ccccc1)c1cnn(-c2ccccc2)c1] | + | + |
| BC19205 | ZE23-0021 | 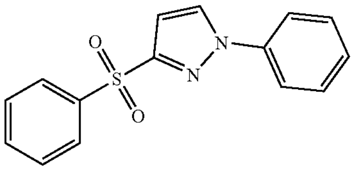 [SMILES: O=S(=O)(c1ccccc1)c1ccn(-c2ccccc2)n1] | ++ | + |

TABLE 3c-continued
| BC No. | ZE No. | Structure | IC50 (NF-κB assay) | IC50 (TNF assay) |
|---|---|---|---|---|
| BC19338 | ZE23-0091 | 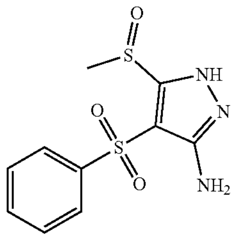 [SMILES: CS(=O)c1[nH]nc(N)c1S(=O)(=O)c1ccccc1] | + | + |
| BC19339 | ZE23-0092 | 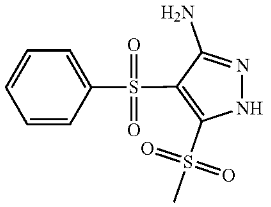 [SMILES: CS(=O)(=O)c1[nH]nc(N)c1S(=O)(=O)c1ccccc1] | + | + |
| BC19340 | ZE23-0096 | 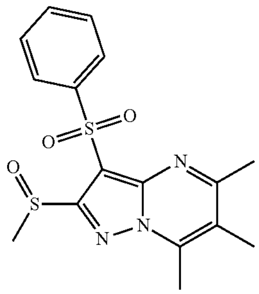 [SMILES: Cc1nc2c(S(=O)(=O)c3ccccc3)c(S(C)=O)nn2c(C)c1C] | + | + |
| BC19341 | ZE23-0098 | 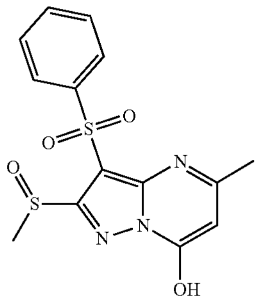 [SMILES: Cc1cc(O)n2nc(S(C)=O)c(S(=O)(=O)c3ccccc3)c2n1] | + | + |
TABLE 8
| BC No. | Structure | IC50 (NF-κB assay) | IC50 (TNF assay) |
|---|---|---|---|
| BC19543 | 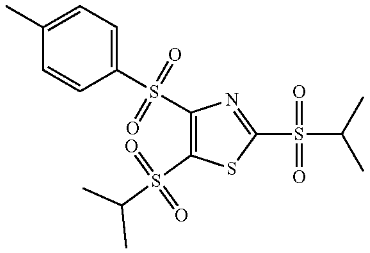 [SMILES: Cc1ccc(S(=O)(=O)c2nc(S(=O)(=O)C(C)C)sc2S(=O)(=O)C(C)C)cc1] | +++ | ++++ |

TABLE 8-continued
| BC No. | Structure | $IC_{50}$ (NF-κB assay) | $IC_{50}$ (TNF assay) |
|---|---|---|---|
| BC19635 | 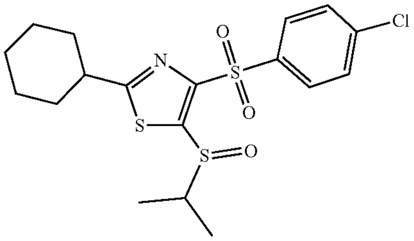 [SMILES: CC(C)S(=O)c1sc(C2CCCCC2)nc1S(=O)(=O)c1ccc(Cl)cc1] | + | + |
| BC19636 | 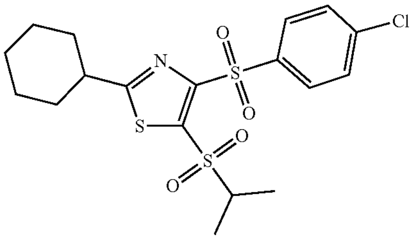 [SMILES: CC(C)S(=O)(=O)c1sc(C2CCCCC2)nc1S(=O)(=O)c1ccc(Cl)cc1] | + | + |
| BC19637 | 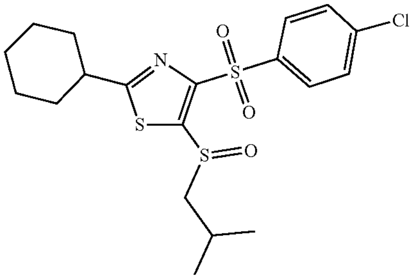 [SMILES: CC(C)CS(=O)c1sc(C2CCCCC2)nc1S(=O)(=O)c1ccc(Cl)cc1] | + | + |
| BC19638 | 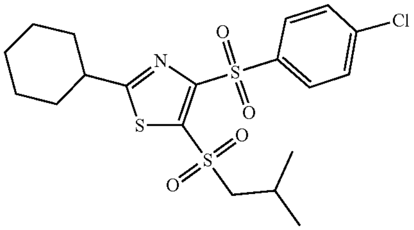 | + | + |
| BC19639 | 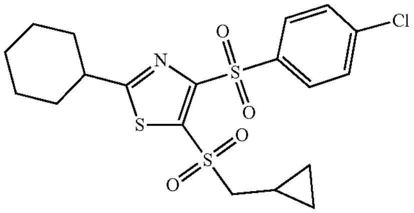 [SMILES: O=S(=O)(CC1CC1)c1sc(C2CCCCC2)nc1S(=O)(=O)c1ccc(Cl)cc1] | + | + |
| BC19640 | 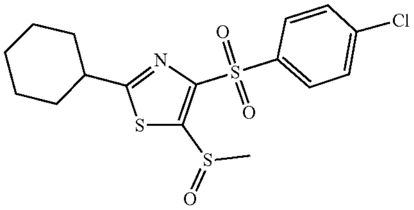 [SMILES: CS(=O)c1sc(C2CCCCC2)nc1S(=O)(=O)c1ccc(Cl)cc1] | + | + |

TABLE 8-continued
| BC No. | Structure | IC50 (NF-κB assay) | IC50 (TNF assay) |
|---|---|---|---|
| BC19641 | 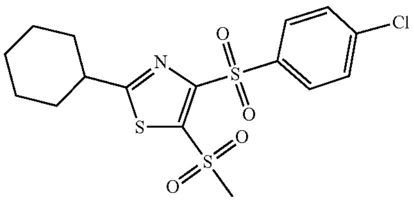 [SMILES: CS(=O)(=O)c1sc(C2CCCCC2)nc1S(=O)(=O)c1ccc(Cl)cc1] | + | + |
| BC19642 | 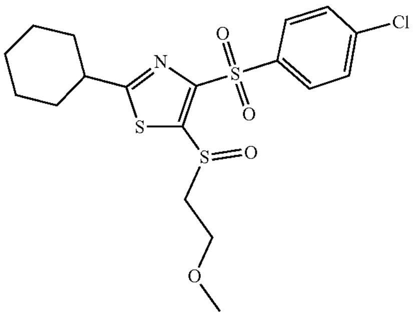 [SMILES: COCCS(=O)c1sc(C2CCCCC2)nc1S(=O)(=O)c1ccc(Cl)cc1] | + | + |
| BC19645 | 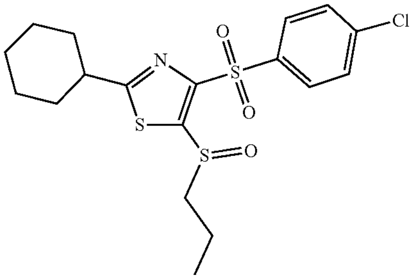 [SMILES: CCCS(=O)c1sc(C2CCCCC2)nc1S(=O)(=O)c1ccc(Cl)cc1] | + | + |
| BC19646 | 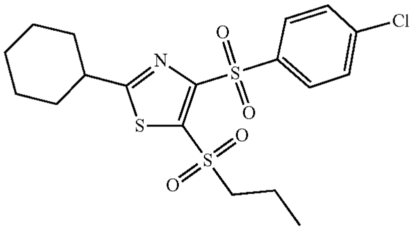 [SMILES: CCCS(=O)(=O)c1sc(C2CCCCC2)nc1S(=O)(=O)c1ccc(Cl)cc1] | + | + |
| BC19679 | 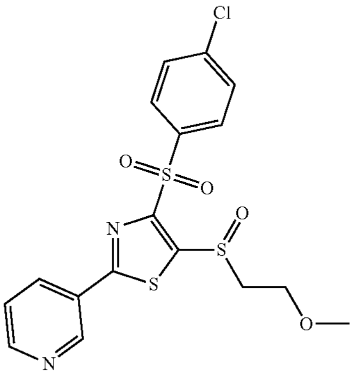 [SMILES: COCCS(=O)c1sc(-c2cccnc2)nc1S(=O)(=O)c1ccc(Cl)cc1] | ++ | +++ |

TABLE 8-continued
| BC No. | Structure | $IC_{50}$ (NF-κB assay) | $IC_{50}$ (TNF assay) |
|---|---|---|---|
| BC19724 | 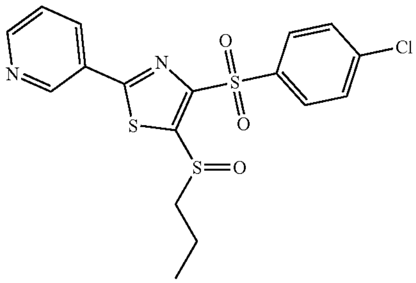 [SMILES: CCCS(=O)c1sc(-c2cccnc2)nc1S(=O)(=O)c1ccc(Cl)cc1] | ++ | ++ |
| BC19725 | 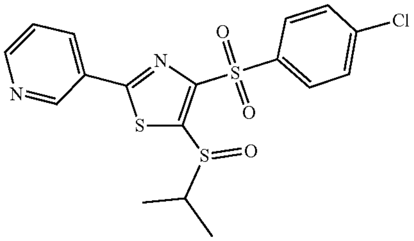 [SMILES: CC(C)S(=O)c1sc(-c2cccnc2)nc1S(=O)(=O)c1ccc(Cl)cc1] | + | + |
TABLE 9
| BC No. | Structure | $IC_{50}$ (NF-κB assay) | $IC_{50}$ (TNF assay) |
|---|---|---|---|
| BC19542 | 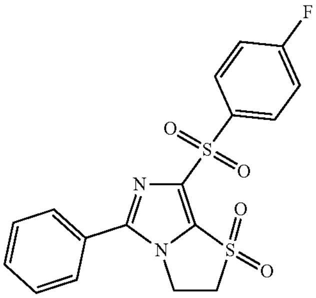 [SMILES: O=S1(=O)CCn2c(-c3ccccc3)nc(S(=O)(=O)c3ccc(F)cc3)c21] | + | + |
| BC19647 | 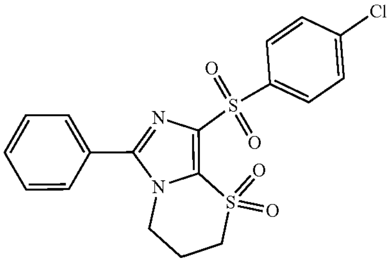 [SMILES: O=S1(=O)CCCn2c(-c3ccccc3)nc(S(=O)(=O)c3ccc(Cl)cc3)c21] | + | ++ |

TABLE 10
| BC No. | Structure | IC50 (NF-κB assay) | IC50 (TNF assay) |
|---|---|---|---|
| BC19279 | 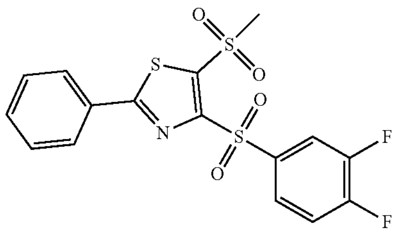 [SMILES: CS(=O)(=O)c1sc(-c2ccccc2)nc1S(=O)(=O)c1ccc(F)c(F)c1] | +++ | +++ |
| BC19334 | 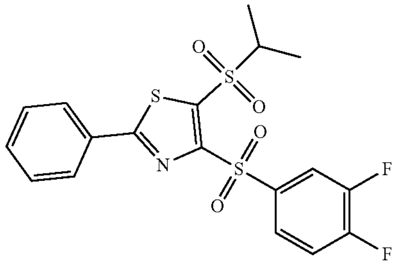 [SMILES: CC(C)S(=O)(=O)c1sc(-c2ccccc2)nc1S(=O)(=O)c1ccc(F)c(F)c1] | + | ++ |
| BC19413 | 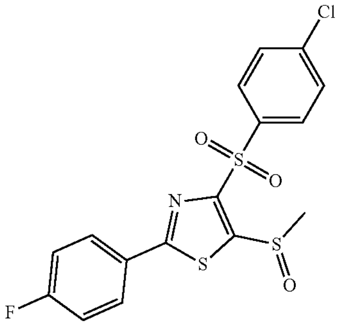 [SMILES: CS(=O)c1sc(-c2ccc(F)cc2)nc1S(=O)(=O)c1ccc(Cl)cc1] | + | ++ |
| BC19414 | 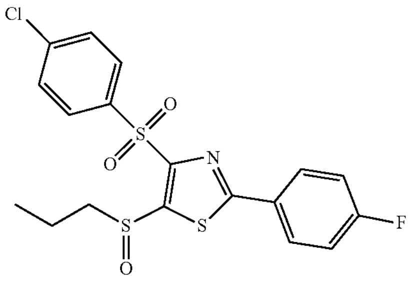 [SMILES: CCCS(=O)c1sc(-c2ccc(F)cc2)nc1S(=O)(=O)c1ccc(Cl)cc1] | + | + |
| BC19415 | 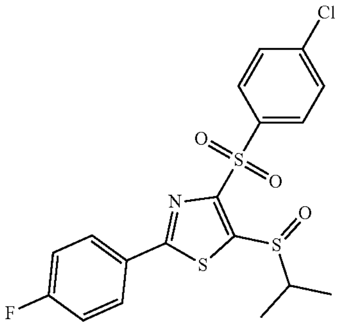 [SMILES: CC(C)S(=O)c1sc(-c2ccc(F)cc2)nc1S(=O)(=O)c1ccc(Cl)cc1] | + | ++ |

TABLE 10-continued
| BC No. | Structure | $IC_{50}$ (NF-κB assay) | $IC_{50}$ (TNF assay) |
|---|---|---|---|
| BC19416 | 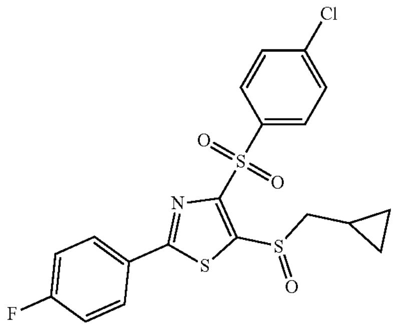 [SMILES: O=S(CC1CC1)c1sc(-c2ccc(F)cc2)nc1S(=O)(=O)c1ccc(Cl)cc1] | + | + |
| BC19471 | 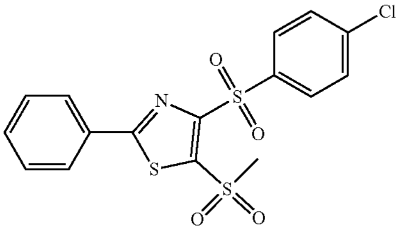 [SMILES: CS(=O)(=O)c1sc(-c2ccccc2)nc1S(=O)(=O)c1ccc(Cl)cc1] | ++ | ++ |
| BC19472 | 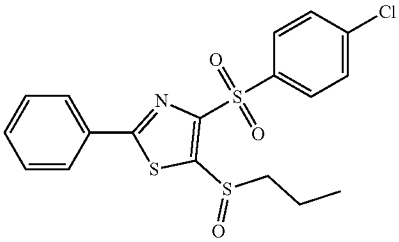 [SMILES: CCCS(=O)c1sc(-c2ccccc2)nc1S(=O)(=O)c1ccc(Cl)cc1] | + | + |
| BC19473 | 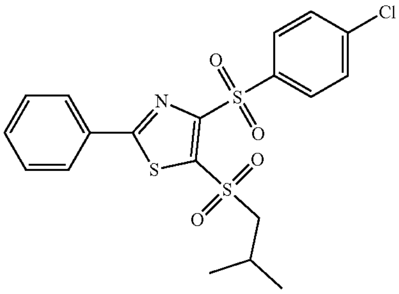 [SMILES: CC(C)CS(=O)(=O)c1sc(-c2ccccc2)nc1S(=O)(=O)c1ccc(Cl)cc1] | + | + |
| BC19474 | 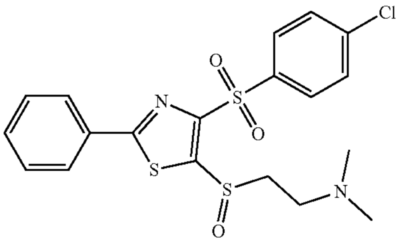 [SMILES: CN(C)CCS(=O)c1sc(-c2ccccc2)nc1S(=O)(=O)c1ccc(Cl)cc1] | ++ | + |

TABLE 10-continued
| BC No. | Structure | $IC_{50}$ (NF-κB assay) | $IC_{50}$ (TNF assay) |
|---|---|---|---|
| BC19475 | 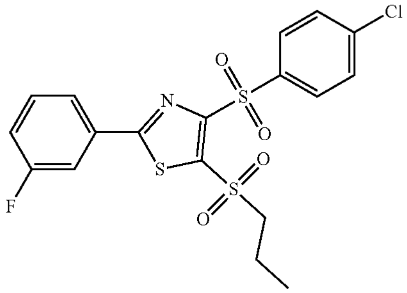 [SMILES: CCCS(=O)(=O)c1sc(-c2cccc(F)c2)nc1S(=O)(=O)c1ccc(Cl)cc1] | ++ | ++ |
| BC19476 | 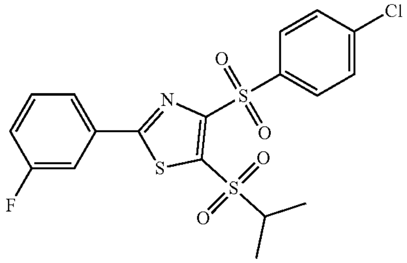 [SMILES: CC(C)S(=O)(=O)c1sc(-c2cccc(F)c2)nc1S(=O)(=O)c1ccc(Cl)cc1] | + | + |
| BC19477 | 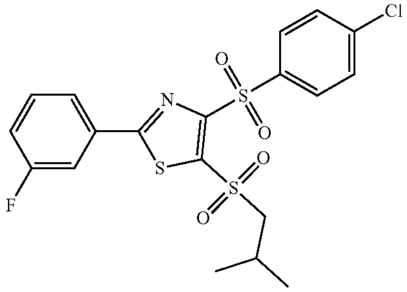 [SMILES: CC(C)CS(=O)(=O)c1sc(-c2cccc(F)c2)nc1S(=O)(=O)c1ccc(Cl)cc1] | + | + |
| BC19478 | 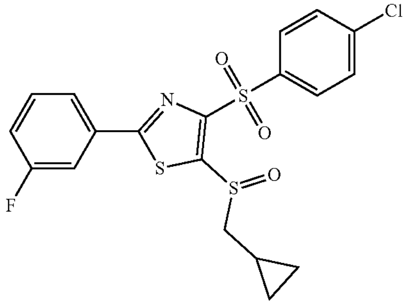 [SMILES: O=S(CC1CC1)c1sc(-c2cccc(F)c2)nc1S(=O)(=O)c1ccc(Cl)cc1] | + | ++ |
| BC19479 | 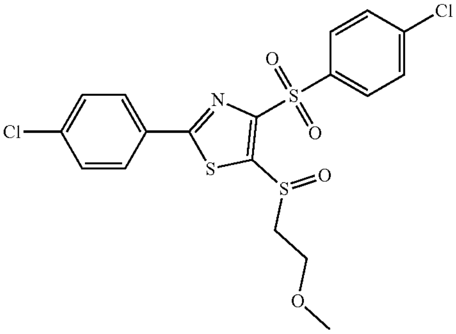 [SMILES: COCCS(=O)c1sc(-c2ccc(Cl)cc2)nc1S(=O)(=O)c1ccc(Cl)cc1] | + | + |

TABLE 10-continued
| BC No. | Structure | $IC_{50}$ (NF-κB assay) | $IC_{50}$ (TNF assay) |
|---|---|---|---|
| BC19480 | 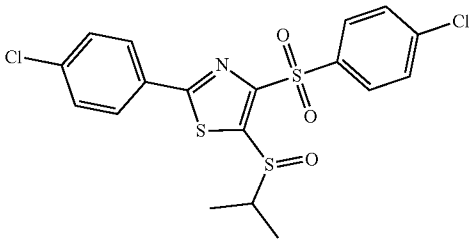 [SMILES: CC(C)S(=O)c1sc(-c2ccc(Cl)cc2)nc1S(=O)(=O)c1ccc(Cl)cc1] | + | + |
| BC19525 | 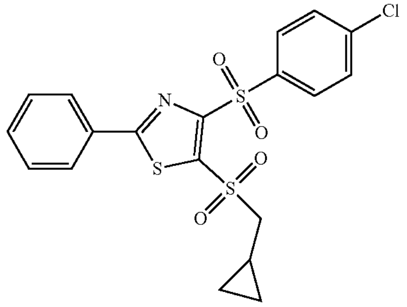 [SMILES: O=S(=O)(CC1CC1)c1sc(-c2ccccc2)nc1S(=O)(=O)c1ccc(Cl)cc1] | ++ | ++ |
| BC19526 | 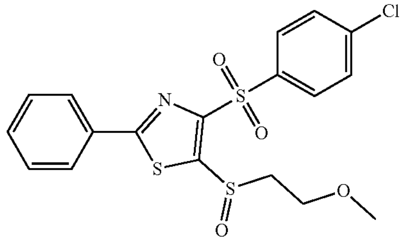 [SMILES: COCCS(=O)c1sc(-c2ccccc2)nc1S(=O)(=O)c1ccc(Cl)cc1] | ++ | ++ |
| BC19527 | 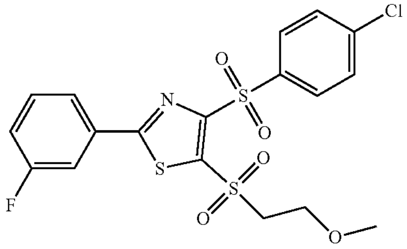 [SMILES: COCCS(=O)(=O)c1sc(-c2cccc(F)c2)nc1S(=O)(=O)c1ccc(Cl)cc1] | ++ | ++ |
| BC19528 | 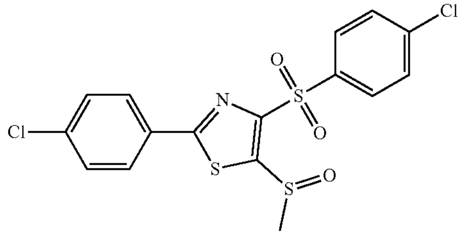 [SMILES: CS(=O)c1sc(-c2ccc(Cl)cc2)nc1S(=O)(=O)c1ccc(Cl)cc1] | ++ | +++ |

TABLE 10-continued
| BC No. | Structure | IC50 (NF-κB assay) | IC50 (TNF assay) |
|---|---|---|---|
| BC19529 | 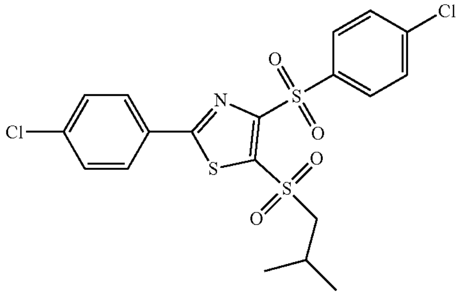 [SMILES: CC(C)CS(=O)(=O)c1sc(-c2ccc(Cl)cc2)nc1S(=O)(=O)c1ccc(Cl)cc1] | + | ++ |
| BC19530 | 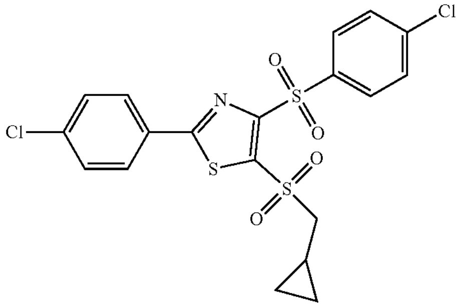 [SMILES: O=S(=O)(CC1CC1)c1sc(-c2ccc(Cl)cc2)nc1S(=O)(=O)c1ccc(Cl)cc1] | ++ | ++ |
| BC19531 | 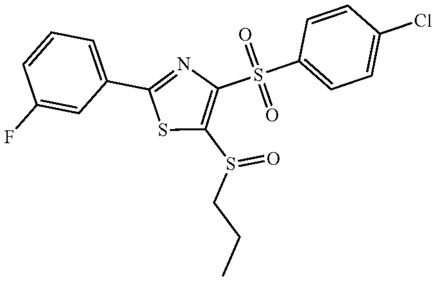 [SMILES: CCCS(=O)c1sc(-c2cccc(F)c2)nc1S(=O)(=O)c1ccc(Cl)cc1] | ++ | +++ |
| BC19532 | 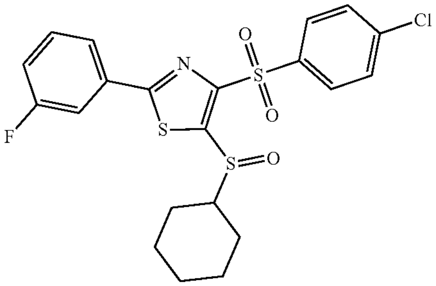 [SMILES: O=S(c1sc(-c2cccc(F)c2)nc1S(=O)(=O)c1ccc(Cl)cc1)C1CCCCC1] | + | + |
| BC19533 | 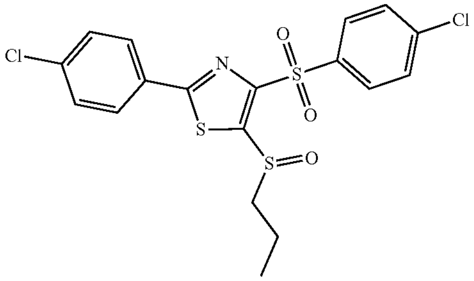 [SMILES: CCCS(=O)c1sc(-c2ccc(Cl)cc2)nc1S(=O)(=O)c1ccc(Cl)cc1] | ++ | ++ |

TABLE 10-continued
| BC No. | Structure | $IC_{50}$ (NF-κB assay) | $IC_{50}$ (TNF assay) |
|---|---|---|---|
| BC19534 | 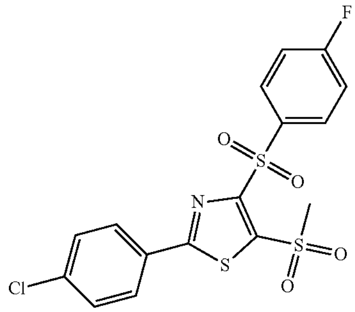 [SMILES: CS(=O)(=O)c1sc(-c2ccc(Cl)cc2)nc1S(=O)(=O)c1ccc(F)cc1] | ++ | ++ |
| BC19535 | 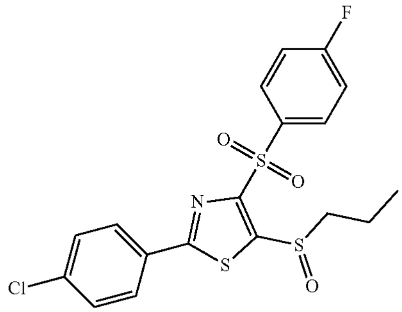 [SMILES: CCCS(=O)c1sc(-c2ccc(Cl)cc2)nc1S(=O)(=O)c1ccc(F)cc1] | ++ | ++ |
| BC19536 | 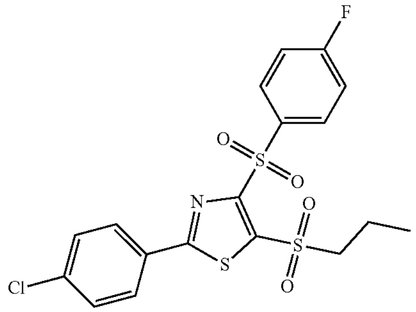 [SMILES: CCCS(=O)(=O)c1sc(-c2ccc(Cl)cc2)nc1S(=O)(=O)c1ccc(F)cc1] | ++ | +++ |
| BC19537 | 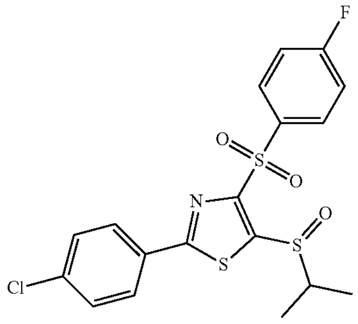 [SMILES: CC(C)S(=O)c1sc(-c2ccc(Cl)cc2)nc1S(=O)(=O)c1ccc(F)cc1] | + | + |

TABLE 10-continued
| BC No. | Structure | IC$_{50}$ (NF-κB assay) | IC$_{50}$ (TNF assay) |
|---|---|---|---|
| BC19538 | 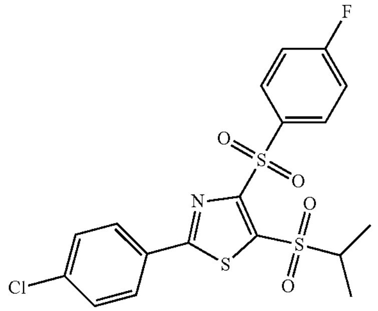 [SMILES: CC(C)S(=O)(=O)c1sc(-c2ccc(Cl)cc2)nc1S(=O)(=O)c1ccc(F)cc1] | ++ | ++ |
| BC19539 | 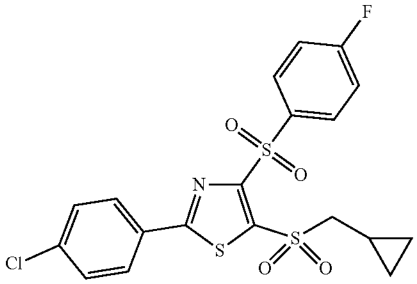 [SMILES: O=S(=O)(CC1CC1)c1sc(-c2ccc(Cl)cc2)nc1S(=O)(=O)c1ccc(F)cc1] | ++ | ++ |
| BC19540 | 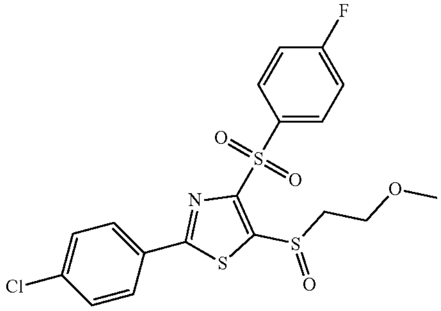 [SMILES: COCCS(=O)c1sc(-c2ccc(Cl)cc2)nc1S(=O)(=O)c1ccc(F)cc1] | ++ | ++ |
| BC19541 | 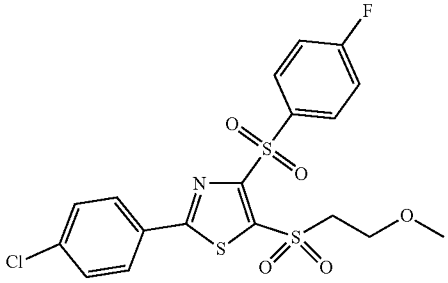 [SMILES: COCCS(=O)(=O)c1sc(-c2ccc(Cl)cc2)nc1S(=O)(=O)c1ccc(F)cc1] | ++ | ++ |
| BC19583 | 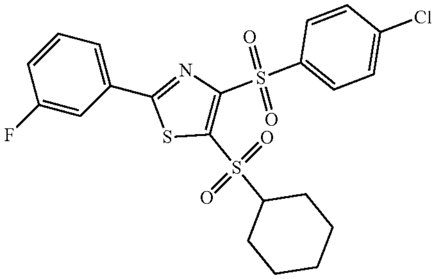 [SMILES: O=S(=O)(c1ccc(Cl)cc1)c1nc(-c2cccc(F)c2)sc1S(=O)(=O)C1CCCCC1] | + | + |

TABLE 10-continued
| BC No. | Structure | $IC_{50}$ (NF-κB assay) | $IC_{50}$ (TNF assay) |
|---|---|---|---|
| BC19587 | 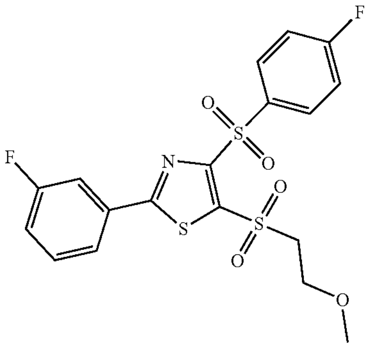 [SMILES: COCCS(=O)(=O)c1sc(-c2cccc(F)c2)nc1S(=O)(=O)c1ccc(F)cc1] | ++ | ++ |
| BC19588 | 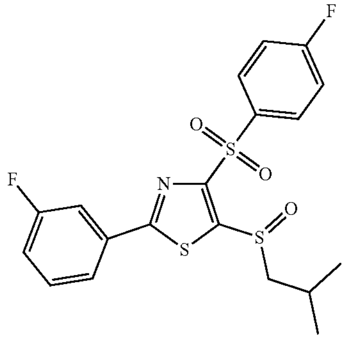 [SMILES: CC(C)CS(=O)c1sc(-c2cccc(F)c2)nc1S(=O)(=O)c1ccc(F)cc1] | ++ | + |
| BC19589 | 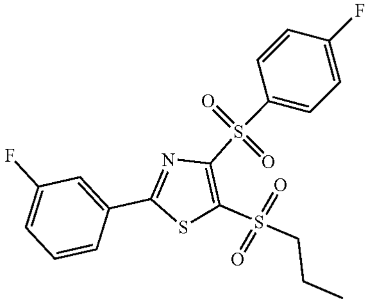 [SMILES: CCCS(=O)(=O)c1sc(-c2cccc(F)c2)nc1S(=O)(=O)c1ccc(F)cc1] | ++ | ++ |
| BC19590 | 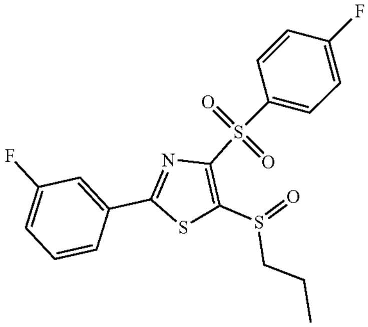 [SMILES: CCCS(=O)c1sc(-c2cccc(F)c2)nc1S(=O)(=O)c1ccc(F)cc1] | ++ | ++ |

TABLE 10-continued
| BC No. | Structure | $IC_{50}$ (NF-κB assay) | $IC_{50}$ (TNF assay) |
|---|---|---|---|
| BC19591 | 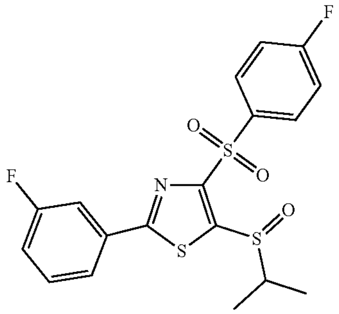 [SMILES: CC(C)S(=O)c1sc(-c2cccc(F)c2)nc1S(=O)(=O)c1ccc(F)cc1] | ++ | ++ |
| BC19592 | 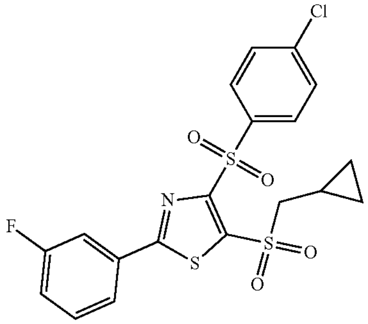 [SMILES: O=S(=O)(CC1CC1)c1sc(-c2cccc(F)c2)nc1S(=O)(=O)c1ccc(Cl)cc1] | ++ | ++ |
| BC19593 | 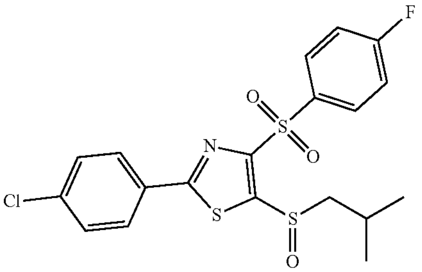 [SMILES: CC(C)CS(=O)c1sc(-c2ccc(Cl)cc2)nc1S(=O)(=O)c1ccc(F)cc1] | +++ | ++ |
| BC19594 | 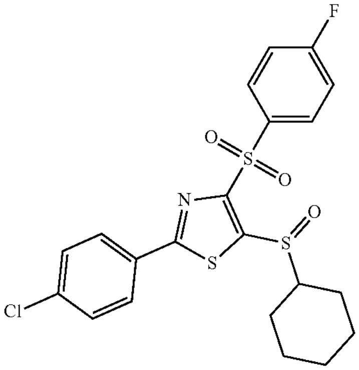 [SMILES: O=S(c1sc(-c2ccc(Cl)cc2)nc1S(=O)(=O)c1ccc(F)cc1)C1CCCCC1] | + | + |
| BC19595 | 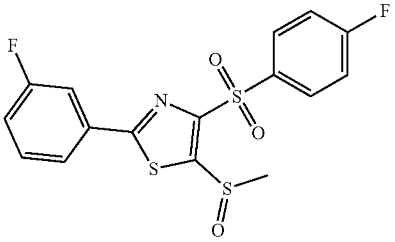 [SMILES: CS(=O)c1sc(-c2cccc(F)c2)nc1S(=O)(=O)c1ccc(F)cc1] | +++ | +++ |

TABLE 10-continued
| BC No. | Structure | $IC_{50}$ (NF-κB assay) | $IC_{50}$ (TNF assay) |
|---|---|---|---|
| BC19596 | 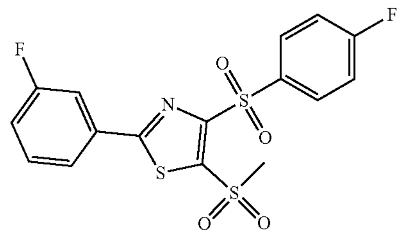 [SMILES: CS(=O)(=O)c1sc(-c2cccc(F)c2)nc1S(=O)(=O)c1ccc(F)cc1] | +++ | ++ |
| BC19597 | 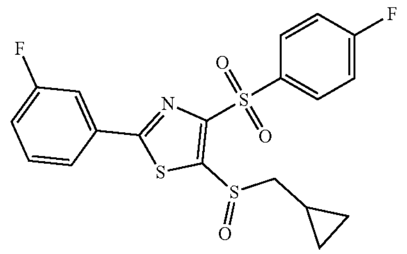 [SMILES: O=S(CC1CC1)c1sc(-c2cccc(F)c2)nc1S(=O)(=O)c1ccc(F)cc1] | ++ | + |
| BC19598 | 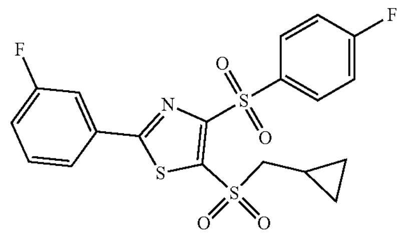 [SMILES: O=S(=O)(CC1CC1)c1sc(-c2cccc(F)c2)nc1S(=O)(=O)c1ccc(F)cc1] | ++ | ++ |
| BC19599 | 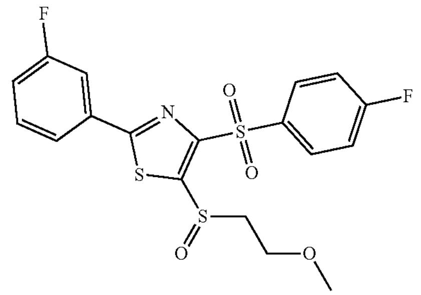 [SMILES: COCCS(=O)c1sc(-c2cccc(F)c2)nc1S(=O)(=O)c1ccc(F)cc1] | ++ | ++ |
| BC19620 | 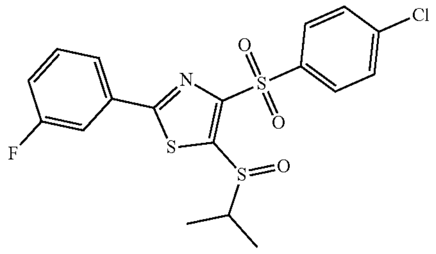 [SMILES: CC(C)S(=O)c1sc(-c2cccc(F)c2)nc1S(=O)(=O)c1ccc(Cl)cc1] | + | + |
| BC19621 | 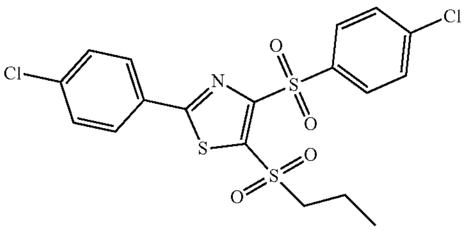 [SMILES: CCCS(=O)(=O)c1sc(-c2ccc(Cl)cc2)nc1S(=O)(=O)c1ccc(Cl)cc1] | ++ | ++ |

TABLE 10-continued
| BC No. | Structure | $IC_{50}$ (NF-κB assay) | $IC_{50}$ (TNF assay) |
|---|---|---|---|
| BC19622 | 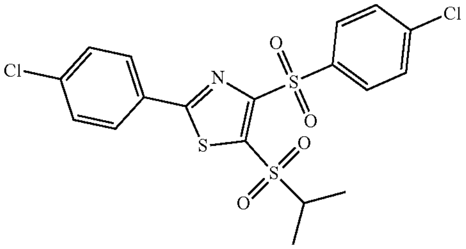 [SMILES: CC(C)S(=O)(=O)c1sc(-c2ccc(Cl)cc2)nc1S(=O)(=O)c1ccc(Cl)cc1] | ++ | ++ |
| BC19623 | 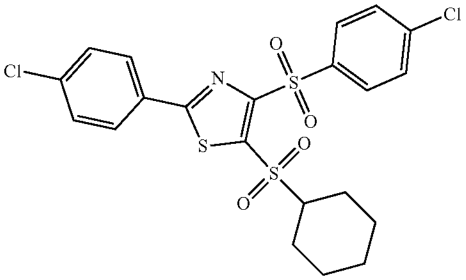 [SMILES: O=S(=O)(c1ccc(Cl)cc1)c1nc(-c2ccc(Cl)cc2)sc1S(=O)(=O)C1CCCCC1] | + | + |
| BC19624 | 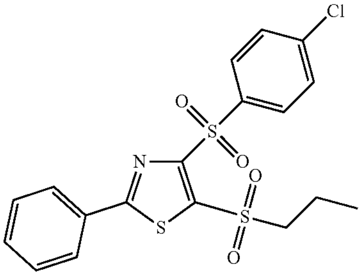 [SMILES: CCCS(=O)(=O)c1sc(-c2ccccc2)nc1S(=O)(=O)c1ccc(Cl)cc1] | ++ | ++ |
| BC19625 | 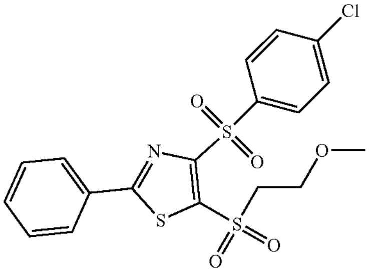 [SMILES: COCCS(=O)(=O)c1sc(-c2ccccc2)nc1S(=O)(=O)c1ccc(Cl)cc1] | ++ | ++ |
| BC19626 | 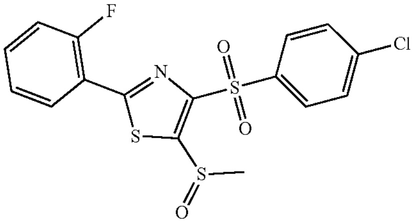 [SMILES: CS(=O)c1sc(-c2ccccc2F)nc1S(=O)(=O)c1ccc(Cl)cc1] | ++ | ++ |
| BC19627 | 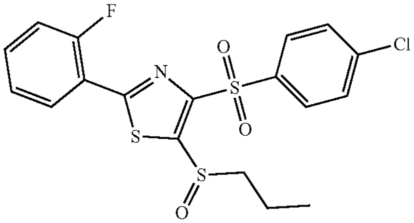 [SMILES: CCCS(=O)c1sc(-c2ccccc2F)nc1S(=O)(=O)c1ccc(Cl)cc1] | ++ | + |

TABLE 10-continued
| BC No. | Structure | $IC_{50}$ (NF-κB assay) | $IC_{50}$ (TNF assay) |
|---|---|---|---|
| BC19628 | 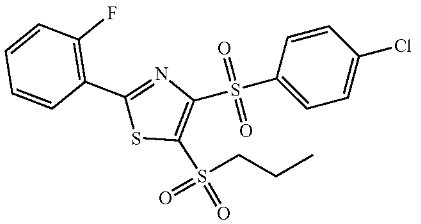 [SMILES: CCCS(=O)(=O)c1sc(-c2ccccc2F)nc1S(=O)(=O)c1ccc(Cl)cc1] | + | + |
| BC19629 | 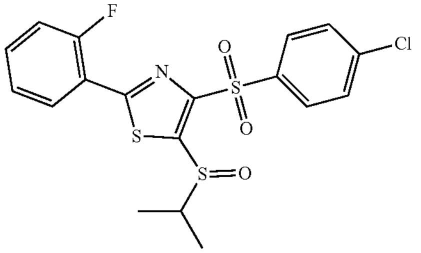 [SMILES: CC(C)S(=O)c1sc(-c2ccccc2F)nc1S(=O)(=O)c1ccc(Cl)cc1] | + | + |
| BC19630 | 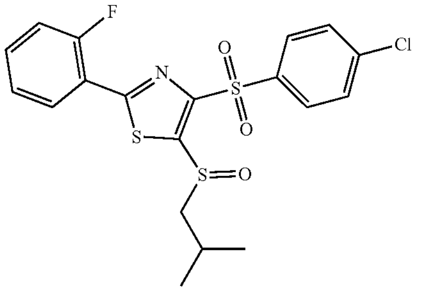 [SMILES: CC(C)CS(=O)c1sc(-c2ccccc2F)nc1S(=O)(=O)c1ccc(Cl)cc1] | + | ++ |
| BC19631 | 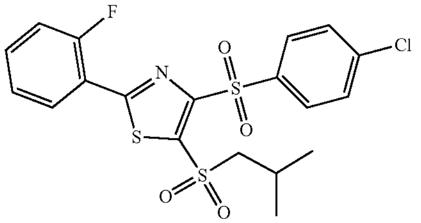 [SMILES: CC(C)CS(=O)(=O)c1sc(-c2ccccc2F)nc1S(=O)(=O)c1ccc(Cl)cc1] | ++ | + |
| BC19632 | 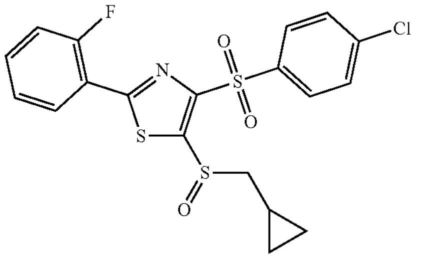 [SMILES: O=S(CC1CC1)c1sc(-c2ccccc2F)nc1S(=O)(=O)c1ccc(Cl)cc1] | + | + |
| BC19633 | 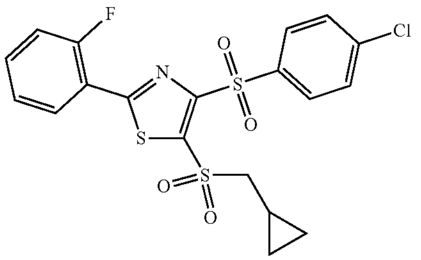 [SMILES: O=S(=O)(CC1CC1)c1sc(-c2ccccc2F)nc1S(=O)(=O)c1ccc(Cl)cc1] | ++ | ++ |

TABLE 10-continued
| BC No. | Structure | $IC_{50}$ (NF-κB assay) | $IC_{50}$ (TNF assay) |
|---|---|---|---|
| BC19671 | 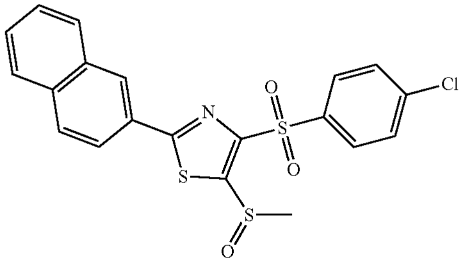 [SMILES: CS(=O)c1sc(-c2ccc3ccccc3c2)nc1S(=O)(=O)c1ccc(Cl)cc1] | ++ | ++++ |
| BC19672 | 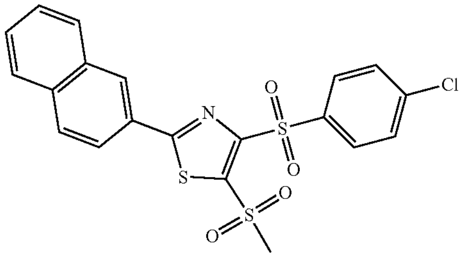 [SMILES: CS(=O)(=O)c1sc(-c2ccc3ccccc3c2)nc1S(=O)(=O)c1ccc(Cl)cc1] | ++ | +++ |
| BC19673 | 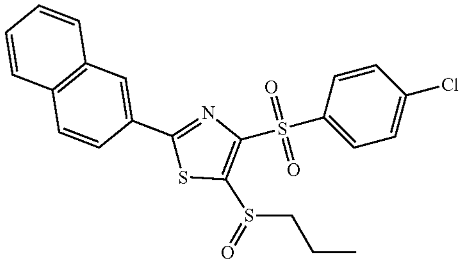 [SMILES: CCCS(=O)c1sc(-c2ccc3ccccc3c2)nc1S(=O)(=O)c1ccc(Cl)cc1] | ++ | + |
| BC19674 | 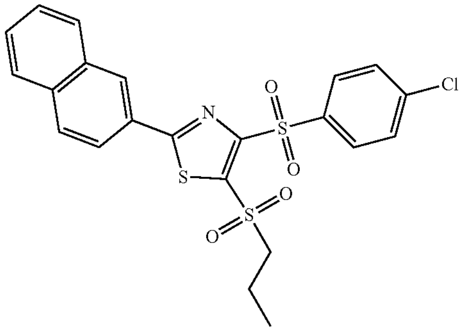 [SMILES: CCCS(=O)(=O)c1sc(-c2ccc3ccccc3c2)nc1S(=O)(=O)c1ccc(Cl)cc1] | ++ | + |
| BC19675 | 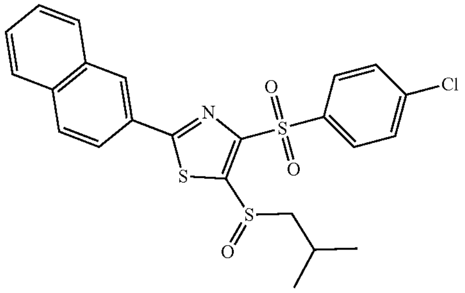 [SMILES: CC(C)CS(=O)c1sc(-c2ccc3ccccc3c2)nc1S(=O)(=O)c1ccc(Cl)cc1] | ++ | ++ |

TABLE 10-continued
| BC No. | Structure | $IC_{50}$ (NF-κB assay) | $IC_{50}$ (TNF assay) |
|---|---|---|---|
| BC19676 | 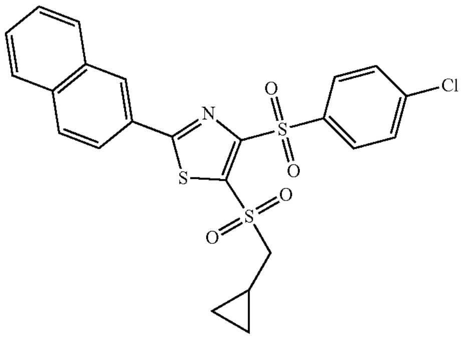 [SMILES: O=S(=O)(CC1CC1)c1sc(-c2ccc3ccccc3c2)nc1S(=O)(=O)c1ccc(Cl)cc1] | ++ | + |
| BC19677 | 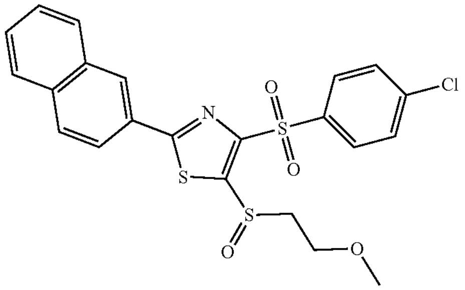 [SMILES: COCCS(=O)c1sc(-c2ccc3ccccc3c2)nc1S(=O)(=O)c1ccc(Cl)cc1] | ++ | ++ |
| BC19678 | 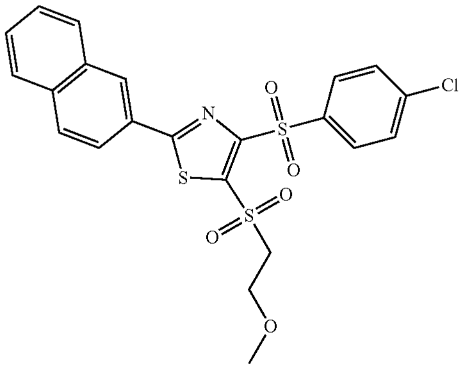 [SMILES: COCCS(=O)(=O)c1sc(-c2ccc3ccccc3c2)nc1S(=O)(=O)c1ccc(Cl)cc1] | ++ | ++ |
TABLE 11
| BC No. | Structure | $IC_{50}$ (NF-κB assay) | $IC_{50}$ (TNF assay) |
|---|---|---|---|
| BC19335 | 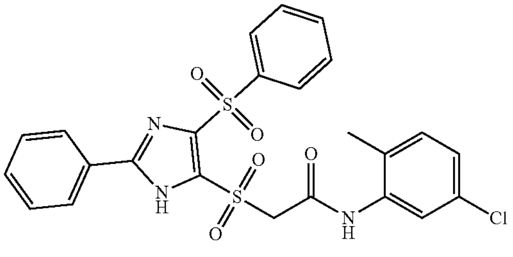 [SMILES: Cc1ccc(Cl)cc1NC(=O)CS(=O)(=O)c1[nH]c(-c2ccccc2)nc1S(=O)(=O)c1ccccc1] | + | + |

TABLE 11-continued
| BC No. | Structure | $IC_{50}$ (NF-κB assay) | $IC_{50}$ (TNF assay) |
|---|---|---|---|
| BC19336 | 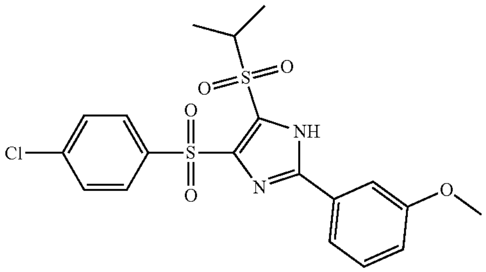 [SMILES: COc1cccc(-c2nc(S(=O)(=O)c3ccc(Cl)cc3)c(S(=O)(=O)C(C)C)[nH]2)c1] | + | + |
| BC19337 | 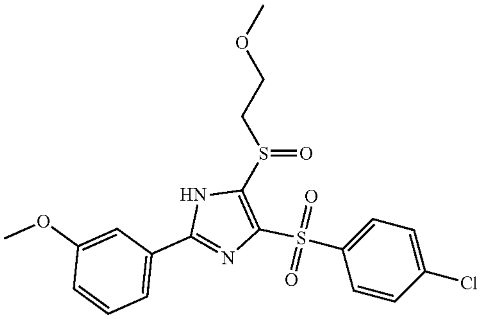 [SMILES: COCCS(=O)c1[nH]c(-c2cccc(OC)c2)nc1S(=O)(=O)c1ccc(Cl)cc1] | + | + |
| BC19410 | 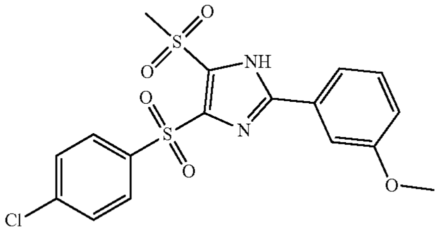 [SMILES: COc1cccc(-c2nc(S(=O)(=O)c3ccc(Cl)cc3)c(S(C)(=O)=O)[nH]2)c1] | +++ | + |
| BC19420 | 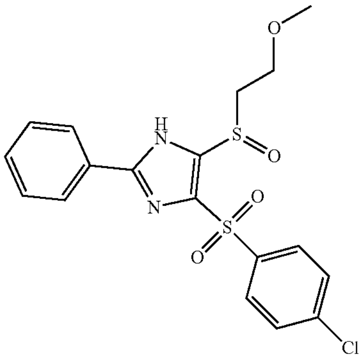 [SMILES: COCCS(=O)c1[nH]c(-c2ccccc2)nc1S(=O)(=O)c1ccc(Cl)cc1] | + | + |

TABLE 11-continued
| BC No. | Structure | $IC_{50}$ (NF-κB assay) | $IC_{50}$ (TNF assay) |
|---|---|---|---|
| BC19462 | 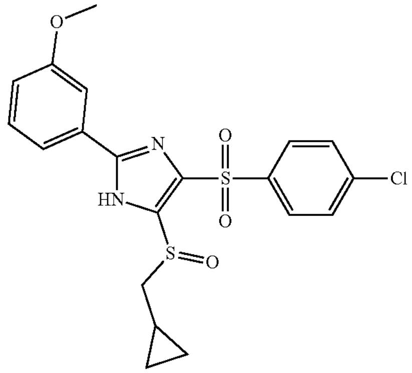 [SMILES: COc1cccc(-c2nc(S(=O)(=O)c3ccc(Cl)cc3)c(S(=O)CC3CC3)[nH]2)c1] | ++ | + |
| BC19465 | 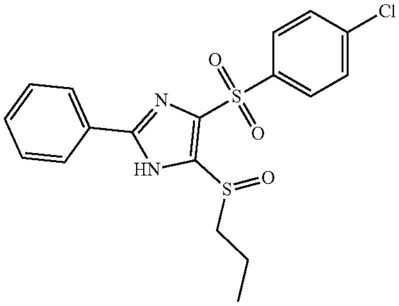 [SMILES: CCCS(=O)c1[nH]c(-c2ccccc2)nc1S(=O)(=O)c1ccc(Cl)cc1] | ++ | + |
| BC19466 | 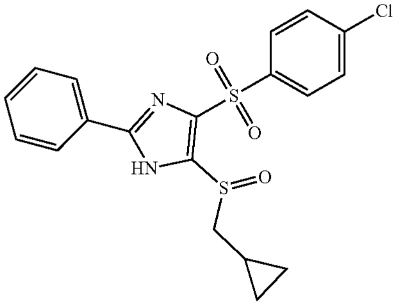 [SMILES: O=S(CC1CC1)c1[nH]c(-c2ccccc2)nc1S(=O)(=O)c1ccc(Cl)cc1] | ++ | + |
| BC19467 | 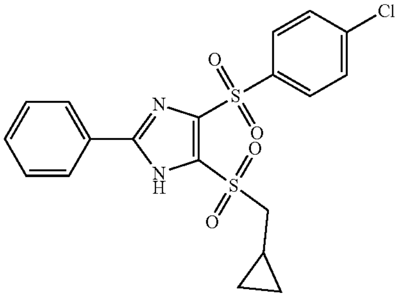 [SMILES: O=S(=O)(CC1CC1)c1[nH]c(-c2ccccc2)nc1S(=O)(=O)c1ccc(Cl)cc1] | ++ | ++ |

TABLE 11-continued
| BC No. | Structure | $IC_{50}$ (NF-κB assay) | $IC_{50}$ (TNF assay) |
|---|---|---|---|
| BC19468 | 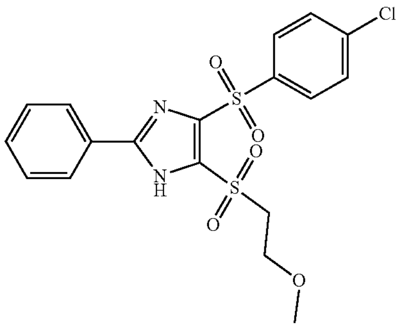 [SMILES: COCCS(=O)(=O)c1[nH]c(-c2ccccc2)nc1S(=O)(=O)c1ccc(Cl)cc1] | ++ | + |
| BC19469 | 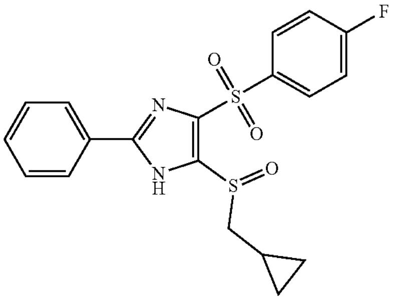 [SMILES: O=S(CC1CC1)c1[nH]c(-c2ccccc2)nc1S(=O)(=O)c1ccc(F)cc1] | ++ | + |
| BC19470 | 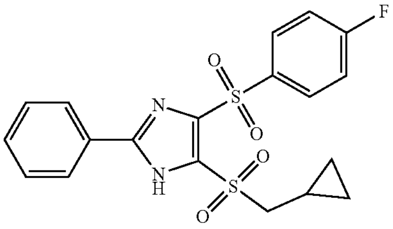 [SMILES: O=S(=O)(CC1CC1)c1[nH]c(-c2ccccc2)nc1S(=O)(=O)c1ccc(F)cc1] | + | + |
| BC19522 | 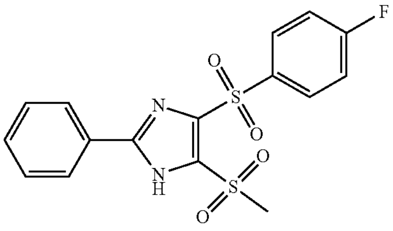 [SMILES: CS(=O)(=O)c1[nH]c(-c2ccccc2)nc1S(=O)(=O)c1ccc(F)cc1] | ++ | + |
| BC19523 | 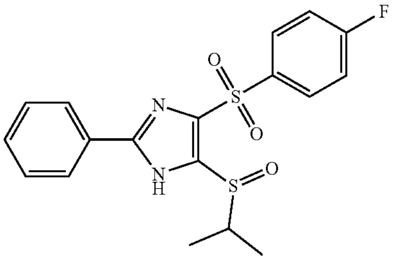 [SMILES: CC(C)S(=O)c1[nH]c(-c2ccccc2)nc1S(=O)(=O)c1ccc(F)cc1] | ++ | + |

TABLE 11-continued
| BC No. | Structure | $IC_{50}$ (NF-κB assay) | $IC_{50}$ (TNF assay) |
|---|---|---|---|
| BC19524 | 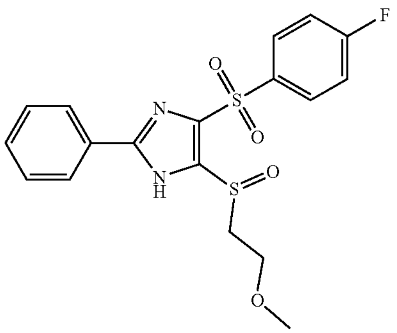 [SMILES: COCCS(=O)c1[nH]c(-c2ccccc2)nc1S(=O)(=O)c1ccc(F)cc1] | + | + |
| BC19581 | 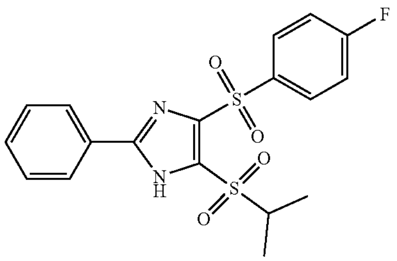 [SMILES: CC(C)S(=O)(=O)c1[nH]c(-c2ccccc2)nc1S(=O)(=O)c1ccc(F)cc1] | + | + |
| BC19582 | 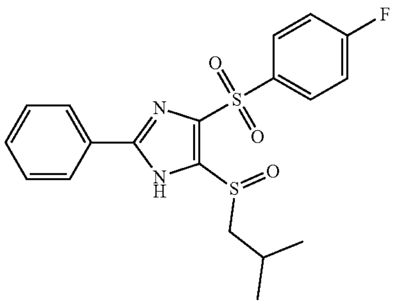 [SMILES: CC(C)CS(=O)c1[nH]c(-c2ccccc2)nc1S(=O)(=O)c1ccc(F)cc1] | ++ | + |
| BC19584 | 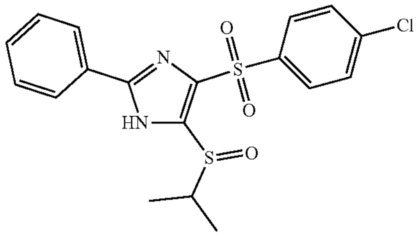 [SMILES: CC(C)S(=O)c1[nH]c(-c2ccccc2)nc1S(=O)(=O)c1ccc(Cl)cc1] | ++ | + |
| BC19585 | 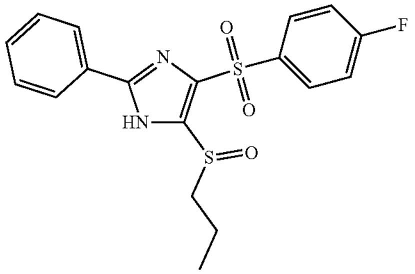 [SMILES: CCCS(=O)c1[nH]c(-c2ccccc2)nc1S(=O)(=O)c1ccc(F)cc1] | ++ | + |

TABLE 11-continued
| BC No. | Structure | $IC_{50}$ (NF-κB assay) | $IC_{50}$ (TNF assay) |
|---|---|---|---|
| BC19586 | 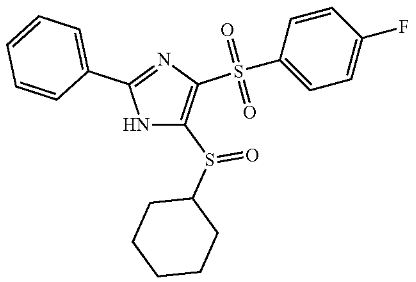 [SMILES: O=S(c1[nH]c(-c2ccccc2)nc1S(=O)(=O)c1ccc(F)cc1)C1CCCCC1] | ++ | + |
| BC19600 | 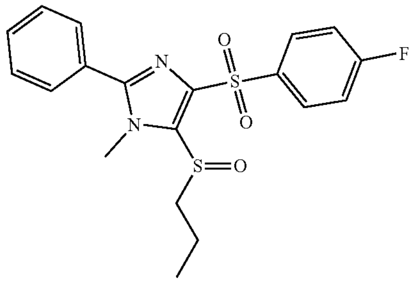 [SMILES: CCCS(=O)c1c(S(=O)(=O)c2ccc(F)cc2)nc(-c2ccccc2)n1C] | + | + |
| BC19601 | 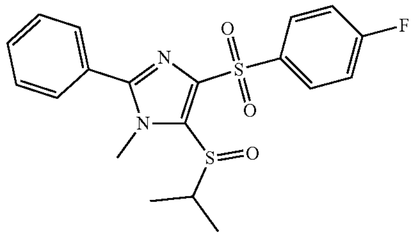 [SMILES: CC(C)S(=O)c1c(S(=O)(=O)c2ccc(F)cc2)nc(-c2ccccc2)n1C] | + | + |
| BC19602 | 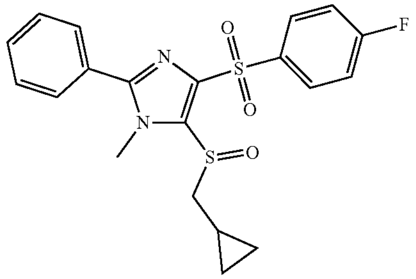 [SMILES: Cn1c(-c2ccccc2)nc(S(=O)(=O)c2ccc(F)cc2)c1S(=O)CC1CC1] | + | + |
| BC19634 | 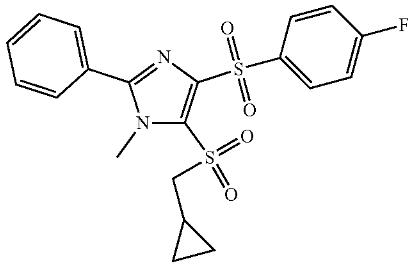 [SMILES: Cn1c(-c2ccccc2)nc(S(=O)(=O)c2ccc(F)cc2)c1S(=O)(=O)CC1CC1] | + | + |

TABLE 11-continued
| BC No. | Structure | $IC_{50}$ (NF-κB assay) | $IC_{50}$ (TNF assay) |
|---|---|---|---|
| BC19644 | 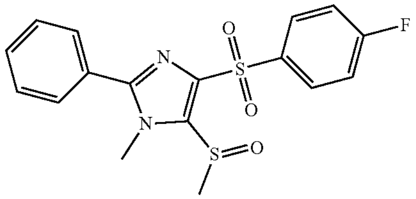 [SMILES: Cn1c(-c2ccccc2)nc(S(=O)(=O)c2ccc(F)cc2)c1S(C)=O] | + | + |
TABLE 12
| BC No. | Structure | $IC_{50}$ (NF-κB assay) | $IC_{50}$ (TNF assay) |
|---|---|---|---|
| BC19643 | 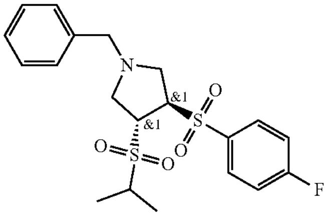 [SMILES: CC(C)S(=O)(=O)[C@@H]1CN(Cc2ccccc2)C[C@H]1S(=O)(=O)c1ccc(F)cc1] | + | + |
| BC19670 | 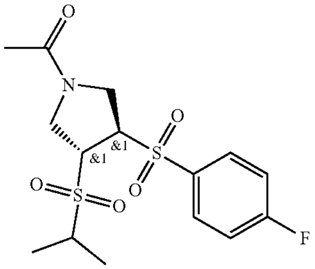 [SMILES: CC(=O)N1C[C@@H](S(=O)(=O)c2ccc(F)cc2)[C@H](S(=O)(=O)C(C)C)C1] | ++ | ++ |
| BC19683 | 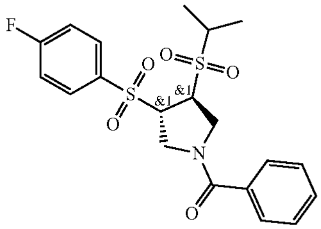 [SMILES: CC(C)S(=O)(=O)[C@H]1CN(C(=O)c2ccccc2)C[C@@H]1S(=O)(=O)c1ccc(F)cc1] | + | ++ |
| BC19684 | 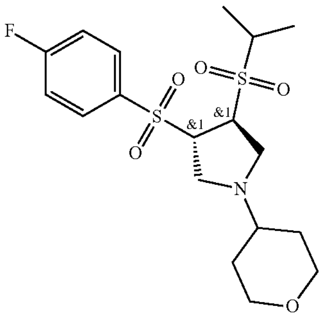 [SMILES: CC(C)S(=O)(=O)[C@H]1CN(C2CCOCC2)C[C@@H]1S(=O)(=O)c1ccc(F)cc1] | + | + |
TABLE 15
| BC No. | Structure | $IC_{50}$ (NF-κB assay) | $IC_{50}$ (TNF assay) |
|---|---|---|---|
| BC19680 | 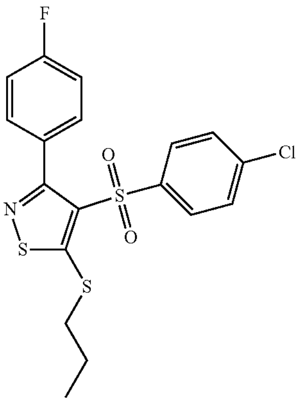 [SMILES: CCCSc1snc(-c2ccc(F)cc2)c1S(=O)(=O)c1ccc(Cl)cc1] | + | + |
| BC19681 | 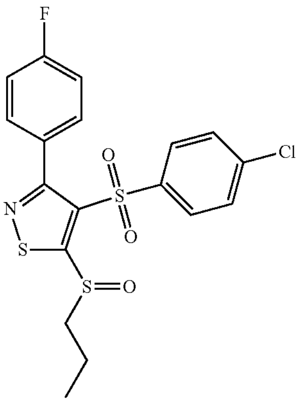 [SMILES: CCCS(=O)c1snc(-c2ccc(F)cc2)c1S(=O)(=O)c1ccc(Cl)cc1] | +++ | ++++ |

TABLE 15-continued
| BC No. | Structure | $IC_{50}$ (NF-κB assay) | $IC_{50}$ (TNF assay) |
|---|---|---|---|
| BC19682 | 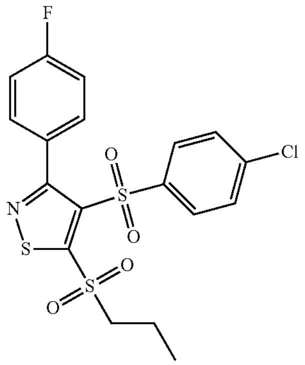 [SMILES: CCCS(=O)(=O)c1snc(-c2ccc(F)cc2)c1S(=O)(=O)c1ccc(Cl)cc1] | +++ | ++++ |
| BC19726 | 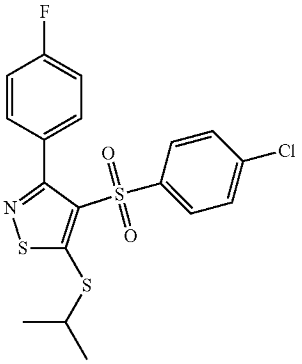 [SMILES: CC(C)Sc1snc(-c2ccc(F)cc2)c1S(=O)(=O)c1ccc(Cl)cc1] | + | + |
| BC19727 | 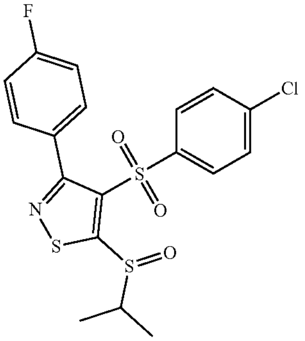 [SMILES: CC(C)S(=O)c1snc(-c2ccc(F)cc2)c1S(=O)(=O)c1ccc(Cl)cc1] | ++ | ++ |
| BC19728 | 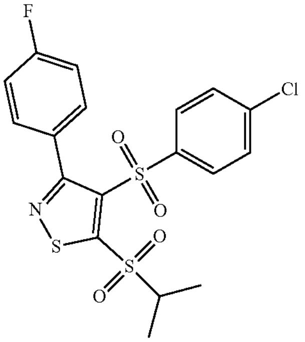 [SMILES: CC(C)S(=O)(=O)c1snc(-c2ccc(F)cc2)c1S(=O)(=O)c1ccc(Cl)cc1] | + | ++ |
Example 4—Bioassay Data for Tested Compounds
TABLE 4a
| BC No. | Compound | $IC_{50}$ (NF-κB assay) |
|---|---|---|
| BC18400 | 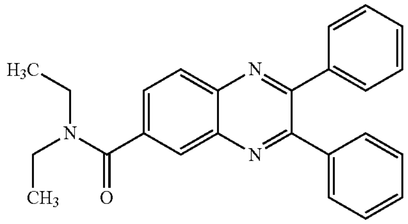 [SMILES: CCN(CC)C(=O)c1ccc2nc(-c3ccccc3)c(-c3ccccc3)nc2c1] | ++++ |
| BC18401 | 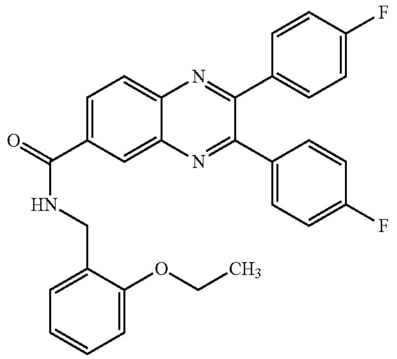 [SMILES: CCOc1ccccc1CNC(=O)c1ccc2nc(-c3ccc(F)cc3)c(-c3ccc(F)cc3)nc2c1] | +++ |

TABLE 4a-continued
| BC No. | Compound | IC50 (NF-κB assay) |
|---|---|---|
| BC18402 | 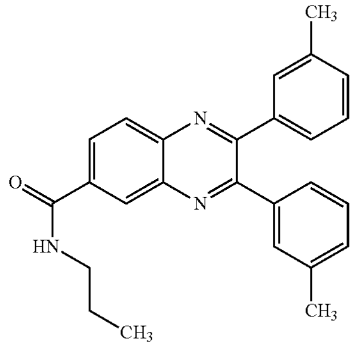 [SMILES: CCCNC(=O)c1ccc2nc(-c3cccc(C)c3)c(-c3cccc(C)c3)nc2c1] | ++ |
| BC18403 | 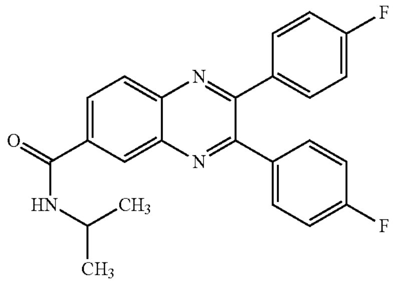 [SMILES: CC(C)NC(=O)c1ccc2nc(-c3ccc(F)cc3)c(-c3ccc(F)cc3)nc2c1] | ++++ |
| BC18404 | 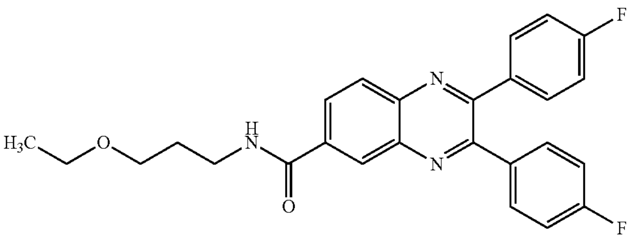 [SMILES: CCOCCCNC(=O)c1ccc2nc(-c3ccc(F)cc3)c(-c3ccc(F)cc3)nc2c1] | ++++ |
| BC18405 | 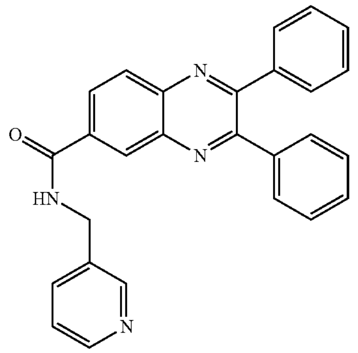 [SMILES: O=C(NCc1cccnc1)c1ccc2nc(-c3ccccc3)c(-c3ccccc3)nc2c1] | ++++ |
| BC18406 | 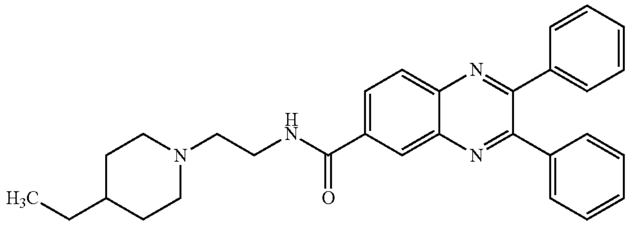 [SMILES: CCC1CCN(CCNC(=O)c2ccc3nc(-c4ccccc4)c(-c4ccccc4)nc3c2)CC1] | ++++ |

TABLE 4a-continued
| BC No. | Compound | $IC_{50}$ (NF-κB assay) |
|---|---|---|
| BC18407 | 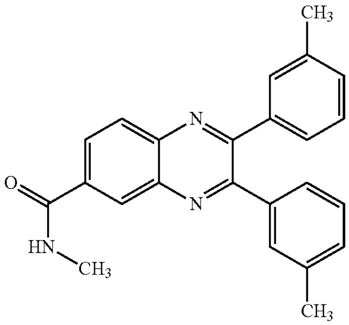 [SMILES: CNC(=O)c1ccc2nc(-c3cccc(C)c3)c(-c3cccc(C)c3)nc2c1] | ++ |
| BC18408 | 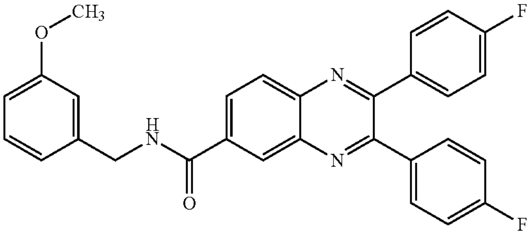 [SMILES: COc1cccc(CNC(=O)c2ccc3nc(-c4ccc(F)cc4)c(-c4ccc(F)cc4)nc3c2)c1] | +++ |
| BC18409 | 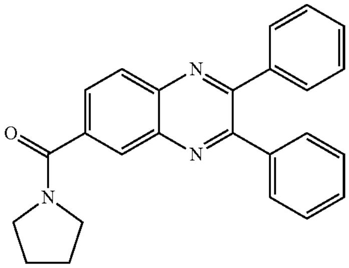 [SMILES: O=C(c1ccc2nc(-c3ccccc3)c(-c3ccccc3)nc2c1)N1CCCC1] | ++++ |
| BC18410 | 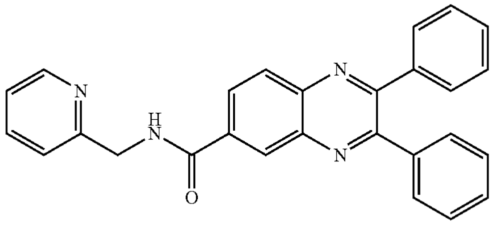 [SMILES: O=C(NCc1ccccn1)c1ccc2nc(-c3ccccc3)c(-c3ccccc3)nc2c1] | ++++ |
| BC18411 | 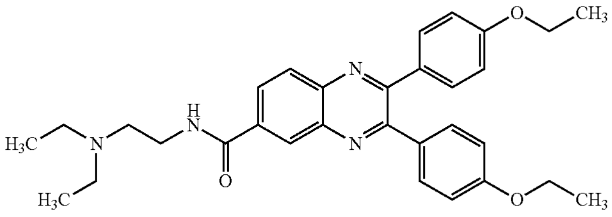 [SMILES: CCOc1ccc(-c2nc3ccc(C(=O)NCCN(CC)CC)cc3nc2-c2ccc(OCC)cc2)cc1] | ++ |
| BC18412 | 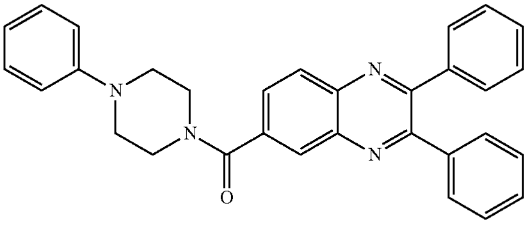 [SMILES: O=C(c1ccc2nc(-c3ccccc3)c(-c3ccccc3)nc2c1)N1CCN(c2ccccc2)CC1] | ++ |

TABLE 4a-continued
| BC No. | Compound | $IC_{50}$ (NF-κB assay) |
|---|---|---|
| BC18413 | 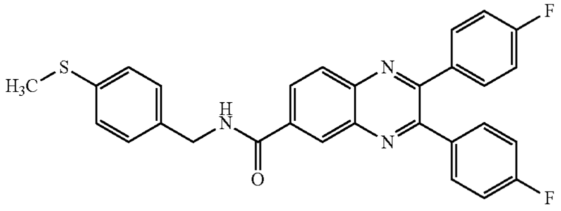 [SMILES: CSc1ccc(CNC(=O)c2ccc3nc(-c4ccc(F)cc4)c(-c4ccc(F)cc4)nc3c2)cc1] | +++ |
| BC18414 | 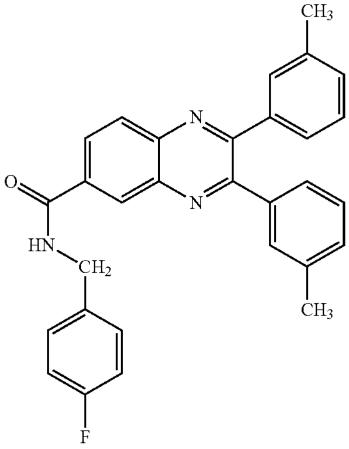 [SMILES: Cc1cccc(-c2nc3ccc(C(=O)NCc4ccc(F)cc4)cc3nc2-c2cccc(C)c2)c1] | + |
| BC18415 | 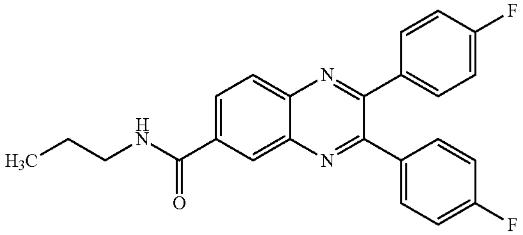 [SMILES: CCCNC(=O)c1ccc2nc(-c3ccc(F)cc3)c(-c3ccc(F)cc3)nc2c1] | ++++ |
| BC18416 | 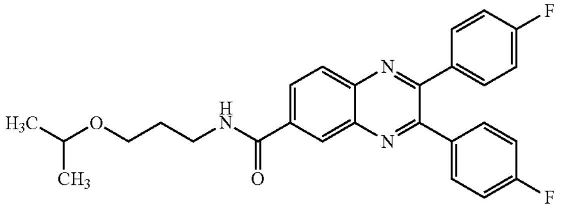 [SMILES: CC(C)OCCCNC(=O)c1ccc2nc(-c3ccc(F)cc3)c(-c3ccc(F)cc3)nc2c1] | ++++ |
| BC18417 | 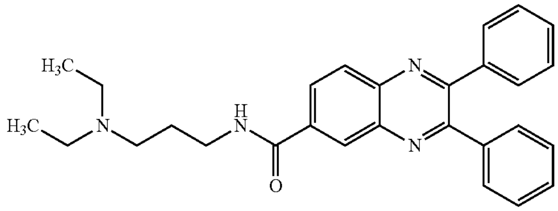 [SMILES: CCN(CC)CCCNC(=O)c1ccc2nc(-c3ccccc3)c(-c3ccccc3)nc2c1] | ++++ |
| BC18418 | 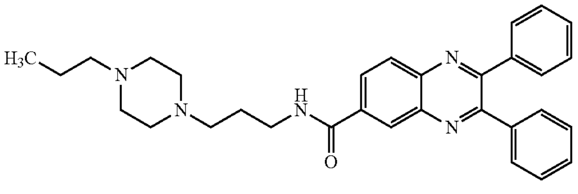 [SMILES: CCCN1CCN(CCCNC(=O)c2ccc3nc(-c4ccccc4)c(-c4ccccc4)nc3c2)CC1] | +++ |

TABLE 4a-continued
| BC No. | Compound | $IC_{50}$ (NF-κB assay) |
|---|---|---|
| BC18419 | 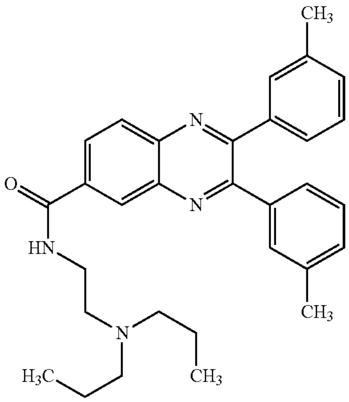 [SMILES: CCCN(CCC)CCNC(=O)c1ccc2nc(-c3cccc(C)c3)c(-c3cccc(C)c3)nc2c1] | ++ |
| BC18420 | 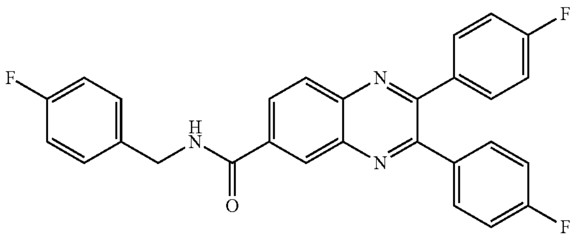 [SMILES: O=C(NCc1ccc(F)cc1)c1ccc2nc(-c3ccc(F)cc3)c(-c3ccc(F)cc3)nc2c1] | +++ |
| BC18421 | 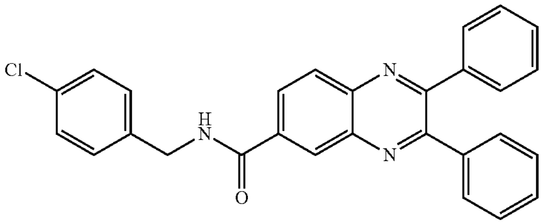 [SMILES: O=C(NCc1ccc(Cl)cc1)c1ccc2nc(-c3ccccc3)c(-c3ccccc3)nc2c1] | + |
| BC18422 | 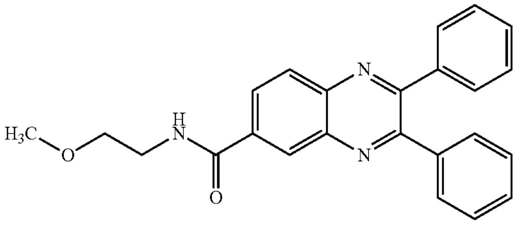 [SMILES: COCCNC(=O)c1ccc2nc(-c3ccccc3)c(-c3ccccc3)nc2c1] | ++++ |
| BC18423 | 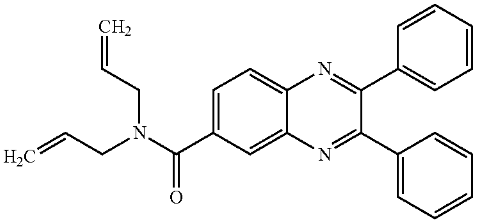 [SMILES: C=CCN(CC=C)C(=O)c1ccc2nc(-c3ccccc3)c(-c3ccccc3)nc2c1] | ++++ |

TABLE 4a-continued
| BC No. | Compound | $IC_{50}$ (NF-κB assay) |
| --- | --- | --- |
| BC18424 | 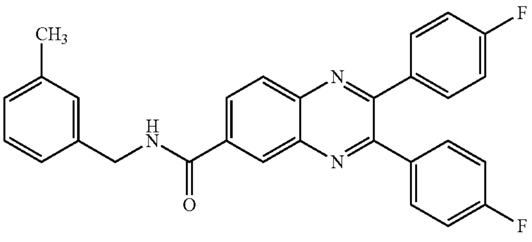 [SMILES: Cc1cccc(CNC(=O)c2ccc3nc(-c4ccc(F)cc4)c(-c4ccc(F)cc4)nc3c2)c1] | +++ |
| BC18425 | 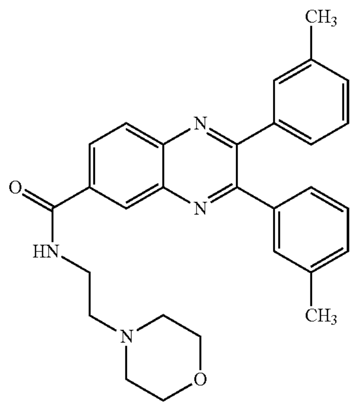 [SMILES: Cc1cccc(-c2nc3ccc(C(=O)NCCN4CCOCC4)cc3nc2-c2cccc(C)c2)c1] | ++ |
| BC18426 | 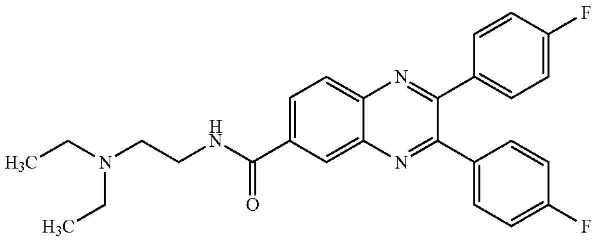 [SMILES: CCN(CC)CCNC(=O)c1ccc2nc(-c3ccc(F)cc3)c(-c3ccc(F)cc3)nc2c1] | ++++ |
| BC18427 | 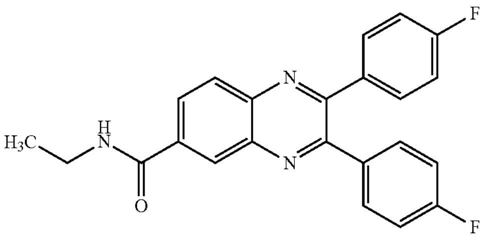 [SMILES: CCNC(=O)c1ccc2nc(-c3ccc(F)cc3)c(-c3ccc(F)cc3)nc2c1] | ++++ |
| BC18428 | 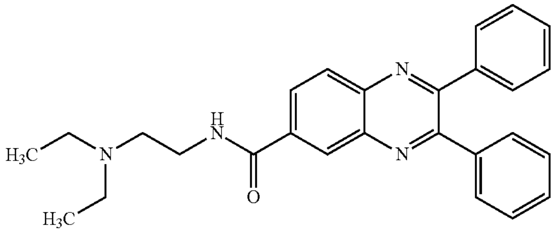 [SMILES: CCN(CC)CCNC(=O)c1ccc2nc(-c3ccccc3)c(-c3ccccc3)nc2c1] | ++++ |

TABLE 4a-continued
| BC No. | Compound | IC50 (NF-κB assay) |
|---|---|---|
| BC18429 | 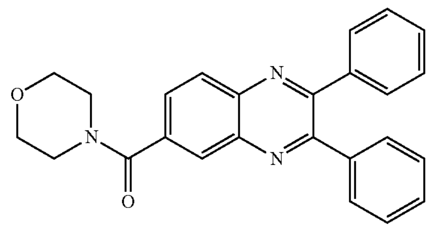 [SMILES: O=C(c1ccc2nc(-c3ccccc3)c(-c3ccccc3)nc2c1)N1CCOCC1] | ++++ |
| BC18430 | 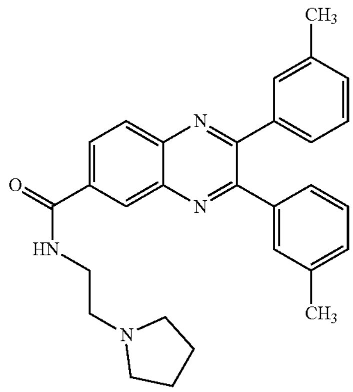 [SMILES: Cc1cccc(-c2nc3ccc(C(=O)NCCN4CCCC4)cc3nc2-c2cccc(C)c2)c1] | ++ |
| BC18431 | 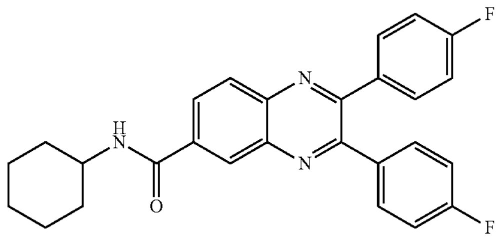 [SMILES: O=C(NC1CCCCC1)c1ccc2nc(-c3ccc(F)cc3)c(-c3ccc(F)cc3)nc2c1] | +++ |
| BC18432 | 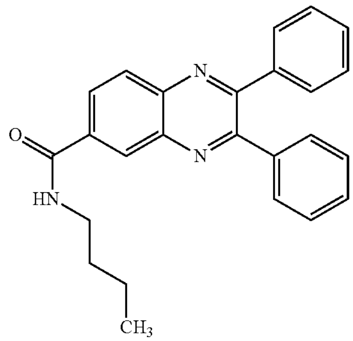 [SMILES: CCCCNC(=O)c1ccc2nc(-c3ccccc3)c(-c3ccccc3)nc2c1] | +++ |
| BC18433 | 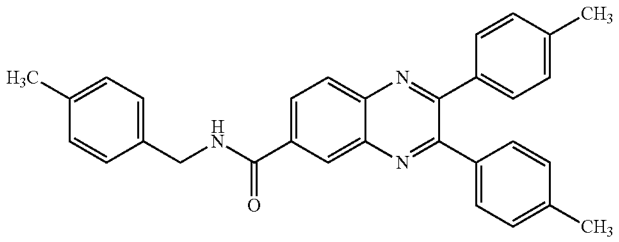 | + |

TABLE 4a-continued
| BC No. | Compound | $IC_{50}$ (NF-κB assay) |
|---|---|---|
| BC18434 | 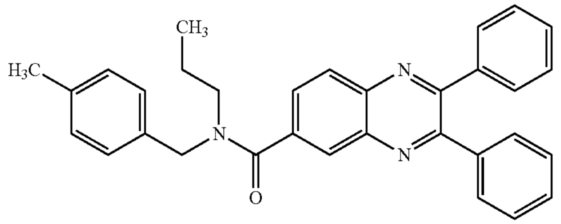 [SMILES: CCCN(Cc1ccc(C)cc1)C(=O)c1ccc2nc(-c3ccccc3)c(-c3ccccc3)nc2c1] | +++ |
| BC18435 | 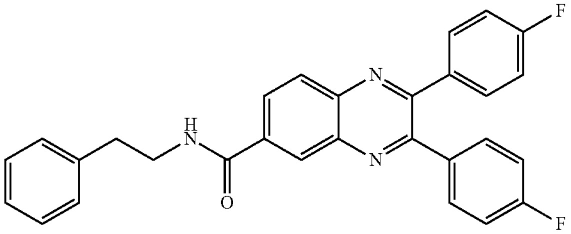 [SMILES: O=C(NCCc1ccccc1)c1ccc2nc(-c3ccc(F)cc3)c(-c3ccc(F)cc3)nc2c1] | +++ |
| BC18436 | 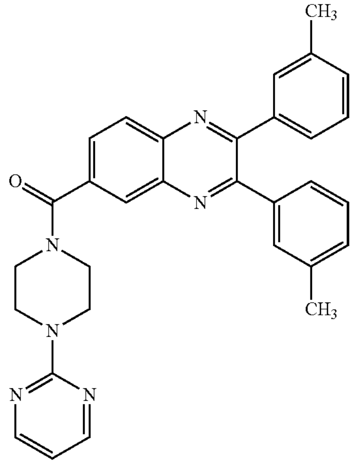 [SMILES: Cc1cccc(-c2nc3ccc(C(=O)N4CCN(c5ncccn5)CC4)cc3nc2-c2cccc(C)c2)c1] | ++ |
| BC18437 | 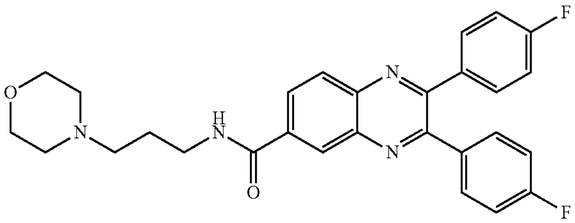 [SMILES: O=C(NCCCN1CCOCC1)c1ccc2nc(-c3ccc(F)cc3)c(-c3ccc(F)cc3)nc2c1] | ++++ |
| BC18438 | 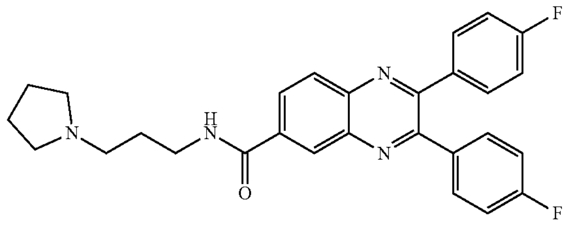 [SMILES: O=C(NCCCN1CCCC1)c1ccc2nc(-c3ccc(F)cc3)c(-c3ccc(F)cc3)nc2c1] | ++++ |

TABLE 4a-continued
| BC No. | Compound | IC50 (NF-κB assay) |
|---|---|---|
| BC18439 | 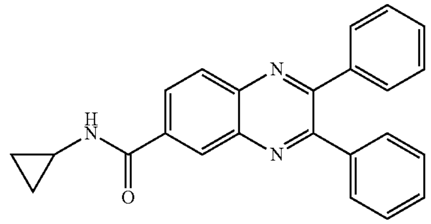 [SMILES: O=C(NC1CC1)c1ccc2nc(-c3ccccc3)c(-c3ccccc3)nc2c1] | ++++ |
| BC18440 | 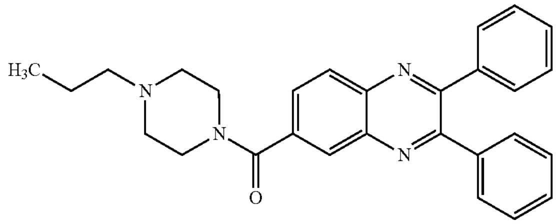 [SMILES: CCCN1CCN(C(=O)c2ccc3nc(-c4ccccc4)c(-c4ccccc4)nc3c2)CC1] | ++++ |
| BC18441 | 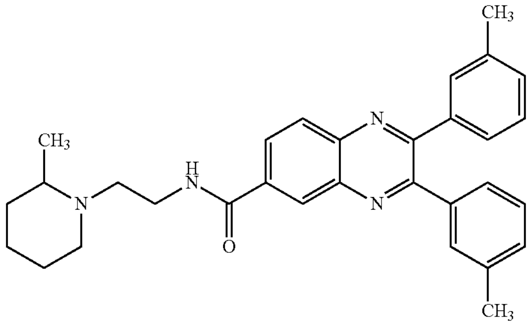 [SMILES: Cc1cccc(-c2nc3ccc(C(=O)NCCN4CCCCC4C)cc3nc2-c2cccc(C)c2)c1] | ++ |
| BC18442 | 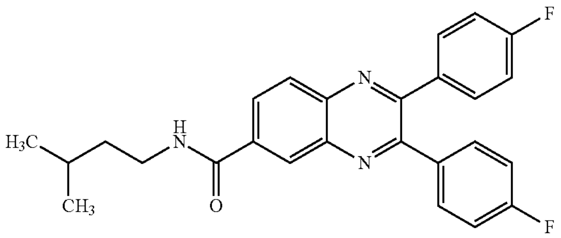 [SMILES: CC(C)CCNC(=O)c1ccc2nc(-c3ccc(F)cc3)c(-c3ccc(F)cc3)nc2c1] | ++++ |
| BC18443 | 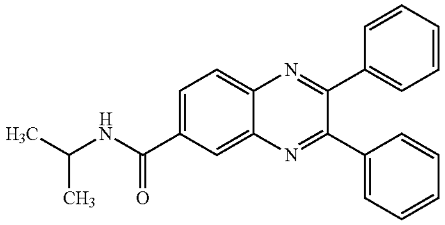 [SMILES: CC(C)NC(=O)c1ccc2nc(-c3ccccc3)c(-c3ccccc3)nc2c1] | ++++ |
| BC18444 | 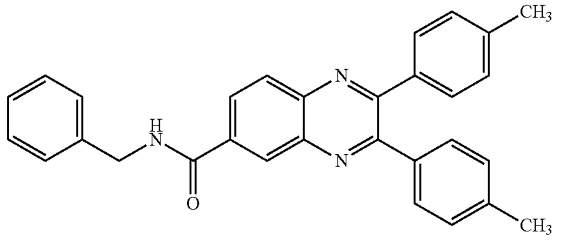 [SMILES: Cc1ccc(-c2nc3ccc(C(=O)NCc4ccccc4)cc3nc2-c2ccc(C)cc2)cc1] | + |

TABLE 4a-continued
| BC No. | Compound | $IC_{50}$ (NF-κB assay) |
|---|---|---|
| BC18445 | 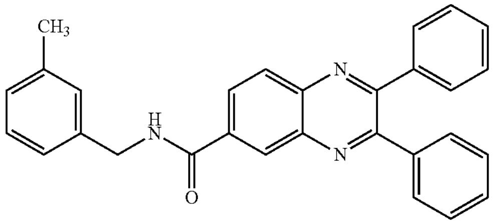 [SMILES: Cc1cccc(CNC(=O)c2ccc3nc(-c4ccccc4)c(-c4ccccc4)nc3c2)c1] | +++ |
| BC18446 | 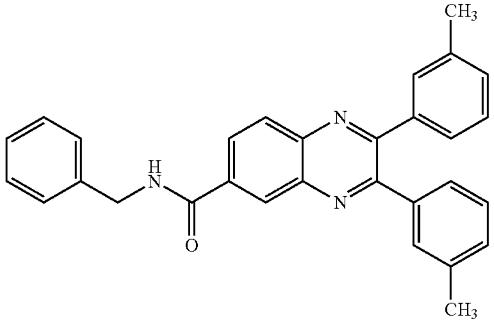 [SMILES: Cc1cccc(-c2nc3ccc(C(=O)NCc4ccccc4)cc3nc2-c2cccc(C)c2)c1] | + |
| BC18447 | 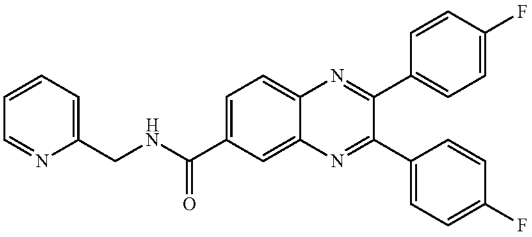 [SMILES: O=C(NCc1ccccn1)c1ccc2nc(-c3ccc(F)cc3)c(-c3ccc(F)cc3)nc2c1] | ++++ |
| BC18448 | 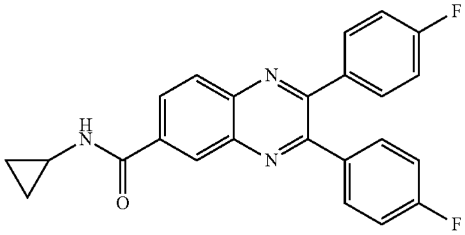 [SMILES: O=C(NC1CC1)c1ccc2nc(-c3ccc(F)cc3)c(-c3ccc(F)cc3)nc2c1] | ++++ |
| BC18449 | 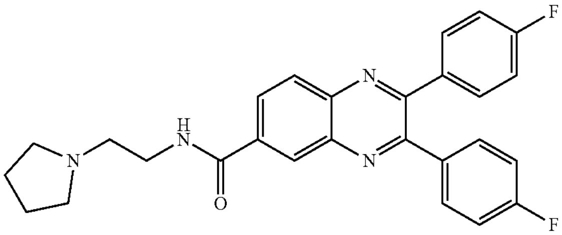 [SMILES: O=C(NCCN1CCCC1)c1ccc2nc(-c3ccc(F)cc3)c(-c3ccc(F)cc3)nc2c1] | ++++ |
| BC18450 | 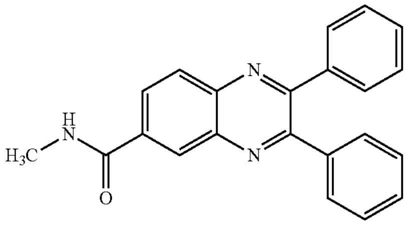 [SMILES: CNC(=O)c1ccc2nc(-c3ccccc3)c(-c3ccccc3)nc2c1] | ++++ |

TABLE 4a-continued
| BC No. | Compound | IC50 (NF-κB assay) |
|---|---|---|
| BC18451 | 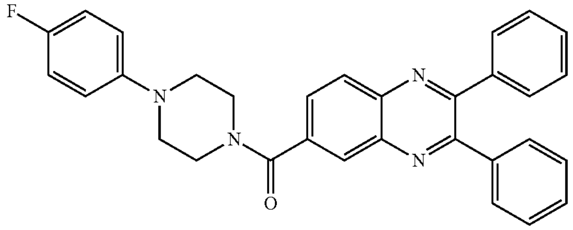 [SMILES: O=C(c1ccc2nc(-c3ccccc3)c(-c3ccccc3)nc2c1)N1CCN(c2ccc(F)cc2)CC1] | +++ |
| BC18452 | 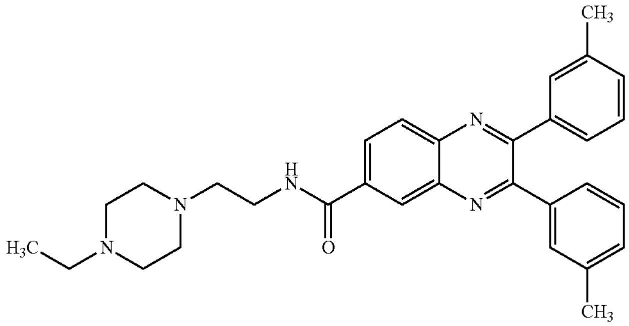 [SMILES: CCN1CCN(CCNC(=O)c2ccc3nc(-c4cccc(C)c4)c(-c4cccc(C)c4)nc3c2)CC1] | ++ |
| BC18453 | 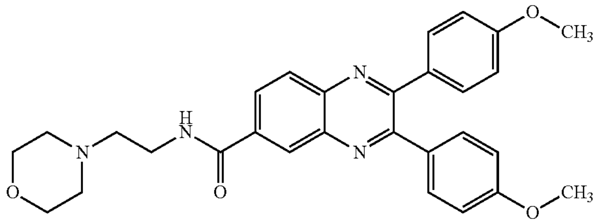 [SMILES: COc1ccc(-c2nc3ccc(C(=O)NCCN4CCOCC4)cc3nc2-c2ccc(OC)cc2)cc1] | ++ |
| BC18454 | 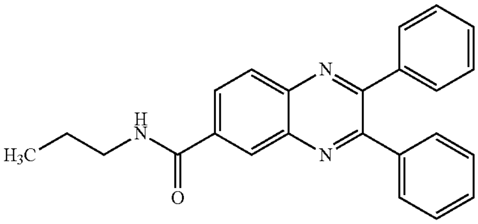 [SMILES: CCCNC(=O)c1ccc2nc(-c3ccccc3)c(-c3ccccc3)nc2c1] | +++ |
| BC18455 | 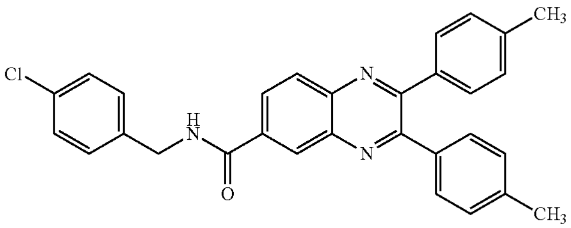 [SMILES: Cc1ccc(-c2nc3ccc(C(=O)NCc4ccc(Cl)cc4)cc3nc2-c2ccc(C)cc2)cc1] | + |
| BC18456 | 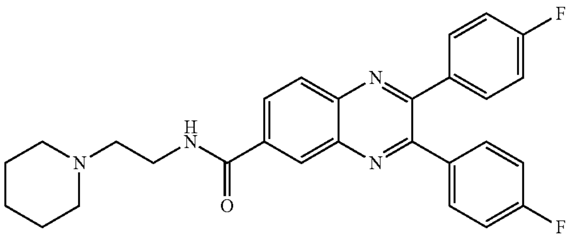 [SMILES: O=C(NCCN1CCCCC1)c1ccc2nc(-c3ccc(F)cc3)c(-c3ccc(F)cc3)nc2c1] | ++++ |

TABLE 4a-continued
| BC No. | Compound | IC$_{50}$ (NF-κB assay) |
|---|---|---|
| BC18457 | 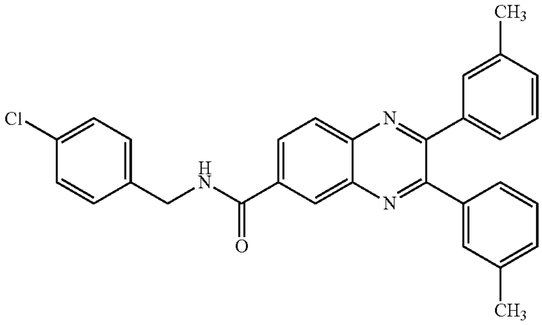 [SMILES: Cc1cccc(-c2nc3ccc(C(=O)NCc4ccc(Cl)cc4)cc3nc2-c2cccc(C)c2)c1] | + |
| BC18458 | 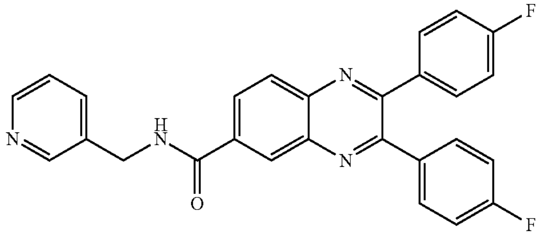 [SMILES: O=C(NCc1cccnc1)c1ccc2nc(-c3ccc(F)cc3)c(-c3ccc(F)cc3)nc2c1] | ++++ |
| BC18459 | 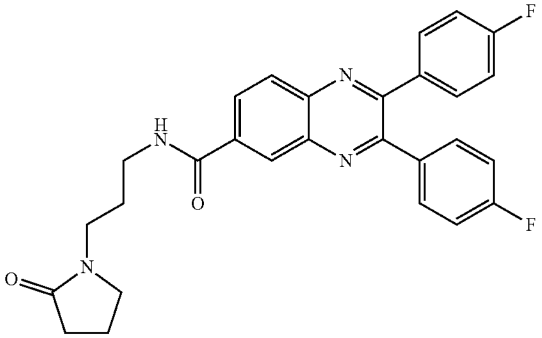 [SMILES: O=C(NCCCN1CCCC1=O)c1ccc2nc(-c3ccc(F)cc3)c(-c3ccc(F)cc3)nc2c1] | ++++ |
| BC18460 | 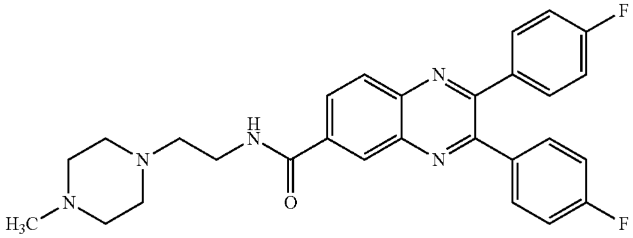 [SMILES: CN1CCN(CCNC(=O)c2ccc3nc(-c4ccc(F)cc4)c(-c4ccc(F)cc4)nc3c2)CC1] | ++++ |
| BC18461 | 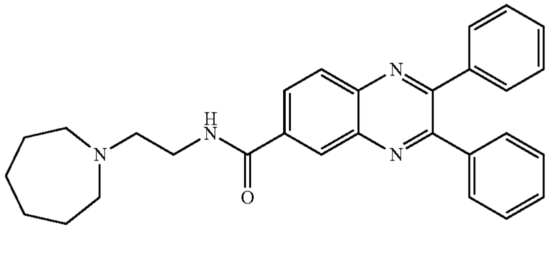 [SMILES: O=C(NCCN1CCCCCC1)c1ccc2nc(-c3ccccc3)c(-c3ccccc3)nc2c1] | ++++ |

TABLE 4a-continued
| BC No. | Compound | IC50 (NF-κB assay) |
|---|---|---|
| BC18462 | 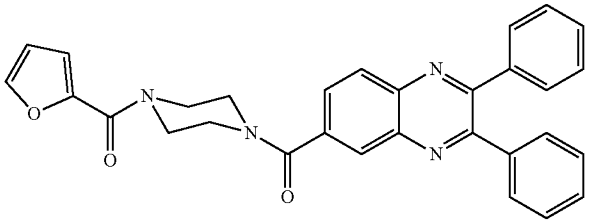 [SMILES: O=C(c1ccc2nc(-c3ccccc3)c(-c3ccccc3)nc2c1)N1CCN(C(=O)c2ccco2)CC1] | ++++ |
| BC18463 | 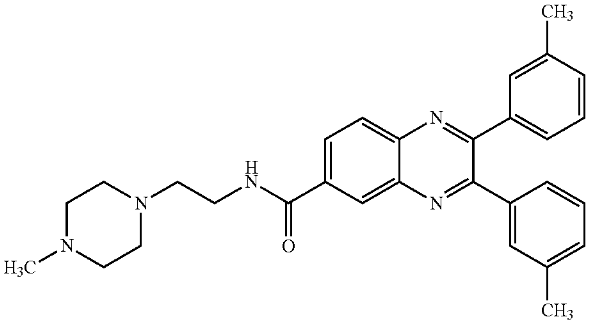 [SMILES: Cc1cccc(-c2nc3ccc(C(=O)NCCN4CCN(C)CC4)cc3nc2-c2cccc(C)c2)c1] | ++ |
| BC18464 | 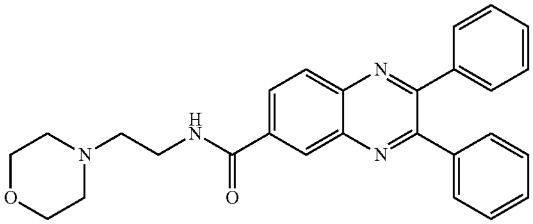 [SMILES: O=C(NCCN1CCOCC1)c1ccc2nc(-c3ccccc3)c(-c3ccccc3)nc2c1] | ++++ |
| BC18465 | 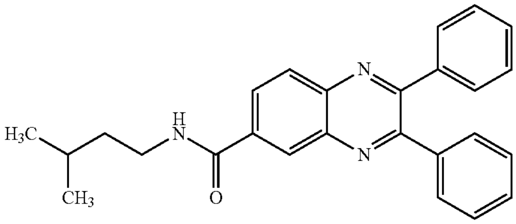 [SMILES: CC(C)CCNC(=O)c1ccc2nc(-c3ccccc3)c(-c3ccccc3)nc2c1] | +++ |
| BC18466 | 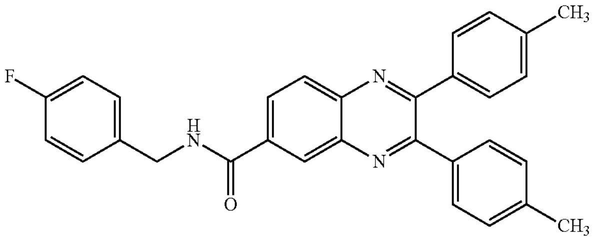 [SMILES: Cc1ccc(-c2nc3ccc(C(=O)NCc4ccc(F)cc4)cc3nc2-c2ccc(C)cc2)cc1] | + |

TABLE 4a-continued
| BC No. | Compound | $IC_{50}$ (NF-κB assay) |
|---|---|---|
| BC18467 | 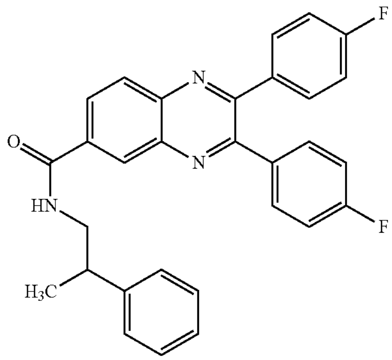 [SMILES: CC(CNC(=O)c1ccc2nc(-c3ccc(F)cc3)c(-c3ccc(F)cc3)nc2c1)c1ccccc1] | +++ |
| BC18468 | 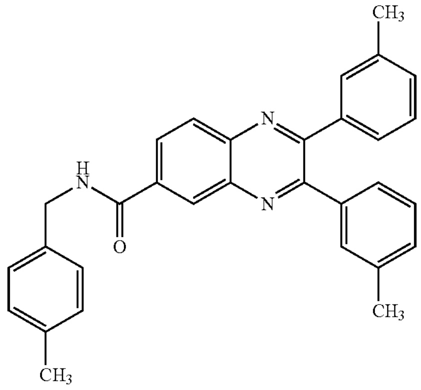 [SMILES: Cc1ccc(CNC(=O)c2ccc3nc(-c4cccc(C)c4)c(-c4cccc(C)c4)nc3c2)cc1] | + |
| BC18469 | 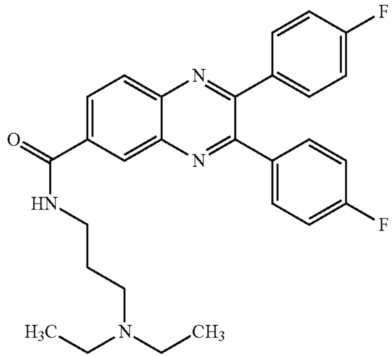 [SMILES: CCN(CC)CCCNC(=O)c1ccc2nc(-c3ccc(F)cc3)c(-c3ccc(F)cc3)nc2c1] | ++++ |
| BC18470 | 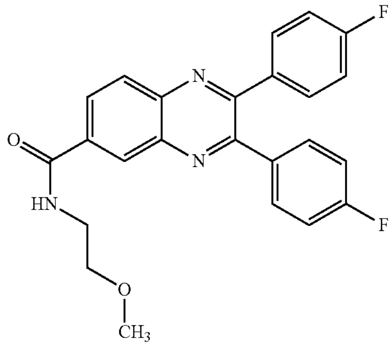 [SMILES: COCCNC(=O)c1ccc2nc(-c3ccc(F)cc3)c(-c3ccc(F)cc3)nc2c1] | ++++ |

TABLE 4a-continued
| BC No. | Compound | $IC_{50}$ (NF-κB assay) |
|---|---|---|
| BC18471 | 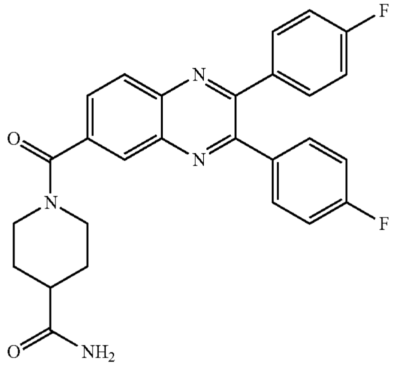 [SMILES: NC(=O)C1CCN(C(=O)c2ccc3nc(-c4ccc(F)cc4)c(-c4ccc(F)cc4)nc3c2)CC1] | ++++ |
| BC18472 | 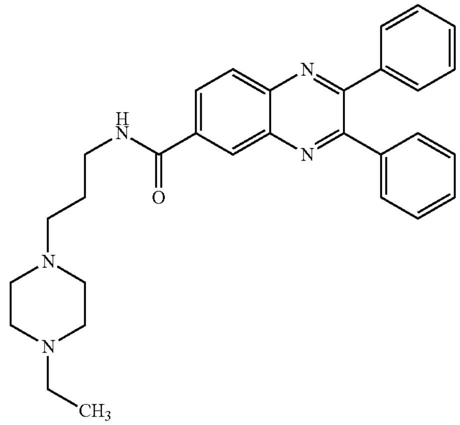 [SMILES: CCN1CCN(CCCNC(=O)c2ccc3nc(-c4ccccc4)c(-c4ccccc4)nc3c2)CC1] | +++ |
| BC18473 | 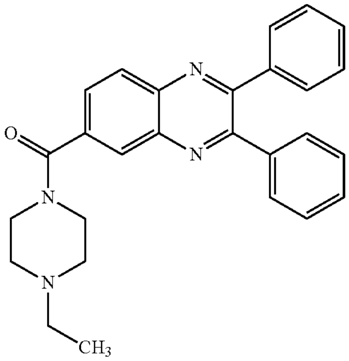 [SMILES: CCN1CCN(C(=O)c2ccc3nc(-c4ccccc4)c(-c4ccccc4)nc3c2)CC1] | ++++ |
| BC18474 | 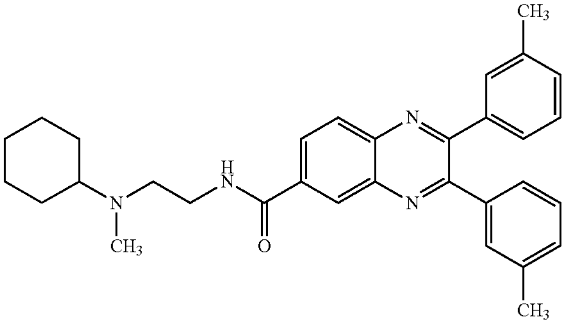 [SMILES: Cc1cccc(-c2nc3ccc(C(=O)NCCN(C)C4CCCCC4)cc3nc2-c2cccc(C)c2)c1] | ++ |

TABLE 4a-continued
| BC No. | Compound | $IC_{50}$ (NF-κB assay) |
|---|---|---|
| BC18475 | 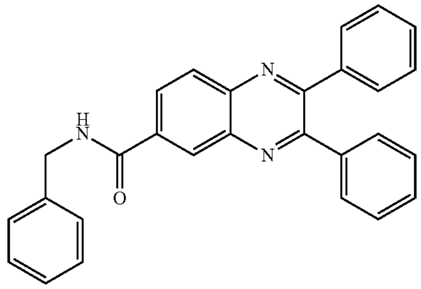 [SMILES: O=C(NCc1ccccc1)c1ccc2nc(-c3ccccc3)c(-c3ccccc3)nc2c1] | + |
| BC18476 | 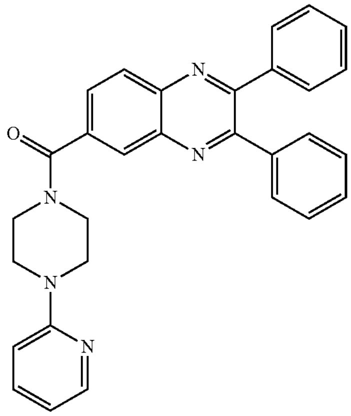 [SMILES: O=C(c1ccc2nc(-c3ccccc3)c(-c3ccccc3)nc2c1)N1CCN(c2ccccn2)CC1] | +++ |
| BC18477 | 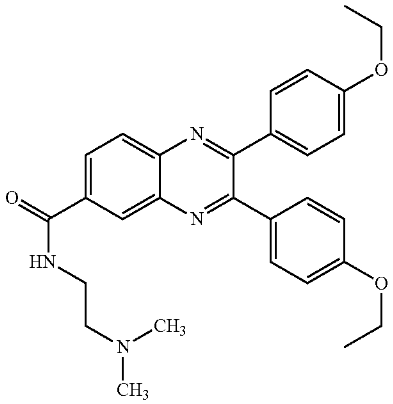 [SMILES: CCOc1ccc(-c2nc3ccc(C(=O)NCCN(C)C)cc3nc2-c2ccc(OCC)cc2)cc1] | ++ |
| BC18478 | 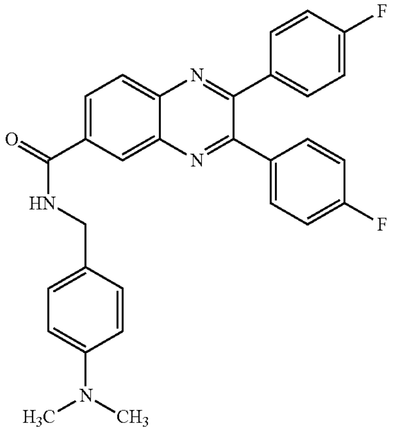 [SMILES: CN(C)c1ccc(CNC(=O)c2ccc3nc(-c4ccc(F)cc4)c(-c4ccc(F)cc4)nc3c2)cc1] | +++ |

TABLE 4a-continued
| BC No. | Compound | $IC_{50}$ (NF-κB assay) |
| --- | --- | --- |
| BC18479 | 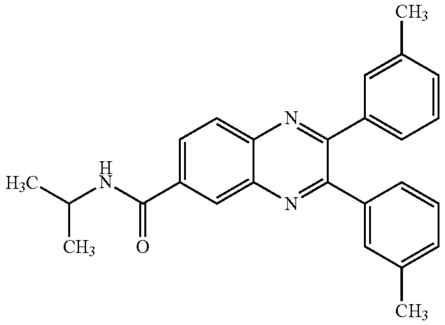 [SMILES: Cc1cccc(-c2nc3ccc(C(=O)NC(C)C)cc3nc2-c2cccc(C)c2)c1] | ++ |
| BC18480 | 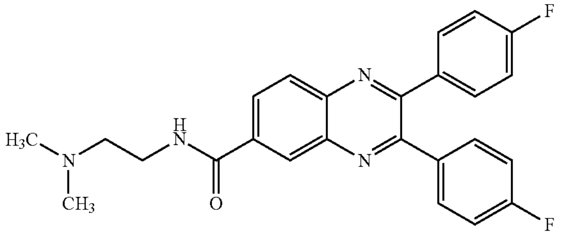 [SMILES: CN(C)CCNC(=O)c1ccc2nc(-c3ccc(F)cc3)c(-c3ccc(F)cc3)nc2c1] | ++++ |
| BC18481 | 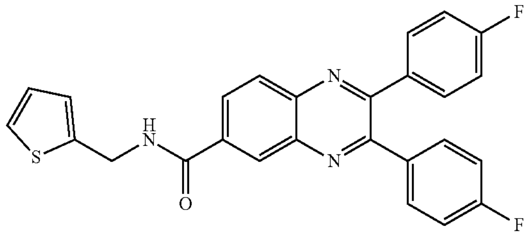 [SMILES: O=C(NCc1cccs1)c1ccc2nc(-c3ccc(F)cc3)c(-c3ccc(F)cc3)nc2c1] | ++++ |
| BC18482 | 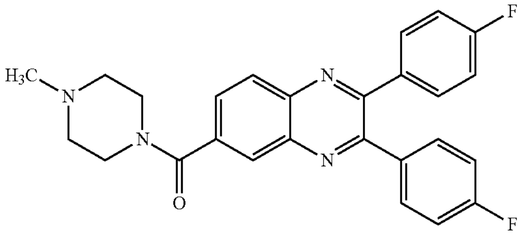 [SMILES: CN1CCN(C(=O)c2ccc3nc(-c4ccc(F)cc4)c(-c4ccc(F)cc4)nc3c2)CC1] | ++++ |
| BC18483 | 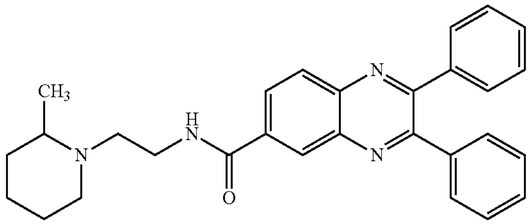 [SMILES: CC1CCCCN1CCNC(=O)c1ccc2nc(-c3ccccc3)c(-c3ccccc3)nc2c1] | ++++ |

TABLE 4a-continued
| BC No. | Compound | IC$_{50}$ (NF-κB assay) |
|---|---|---|
| BC18484 | 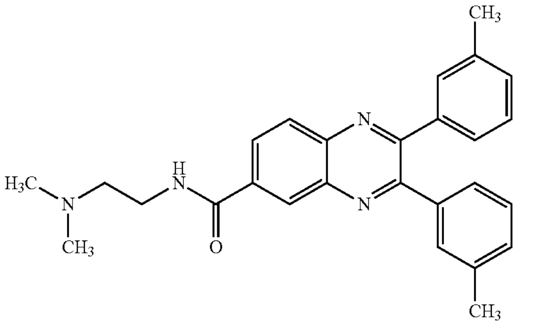 [SMILES: Cc1cccc(-c2nc3ccc(C(=O)NCCN(C)C)cc3nc2-c2cccc(C)c2)c1] | ++ |
| BC18485 | 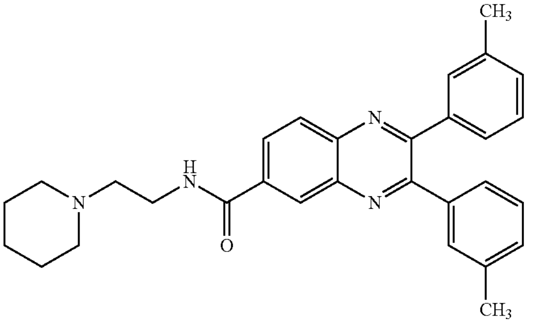 [SMILES: Cc1cccc(-c2nc3ccc(C(=O)NCCN4CCCCC4)cc3nc2-c2cccc(C)c2)c1] | ++ |
| BC18486 | 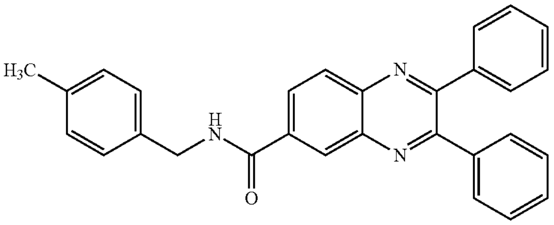 [SMILES: Cc1ccc(CNC(=O)c2ccc3nc(-c4ccccc4)c(-c4ccccc4)nc3c2)cc1] | + |
| BC18487 | 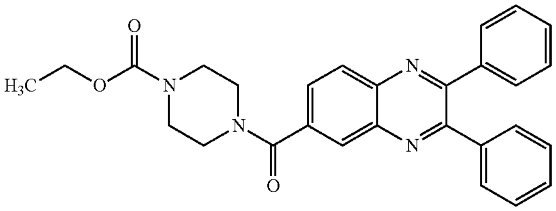 [SMILES: CCOC(=O)N1CCN(C(=O)c2ccc3nc(-c4ccccc4)c(-c4ccccc4)nc3c2)CC1] | ++++ |
| BC18488 | 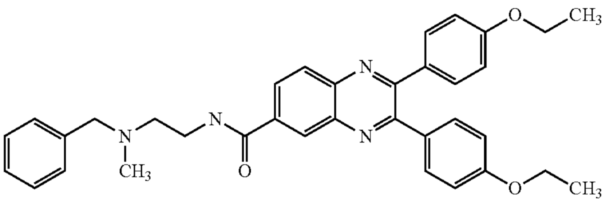 [SMILES: CCOc1ccc(-c2nc3ccc(C(=O)NCCN(C)Cc4ccccc4)cc3nc2-c2ccc(OCC)cc2)cc1] | ++ |

TABLE 4b
| BC No. | ZE No. | Structure | $IC_{50}$ (NF-κB assay) | $IC_{50}$ (TNF assay) |
|---|---|---|---|---|
| BC19118 | ZE18-0085 | 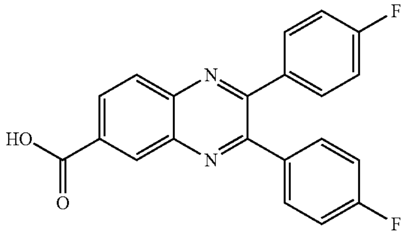 [SMILES: O=C(O)c1ccc2nc(-c3ccc(F)cc3)c(-c3ccc(F)cc3)nc2c1] | ++ | + |
| BC19154 | ZE18-0097 | 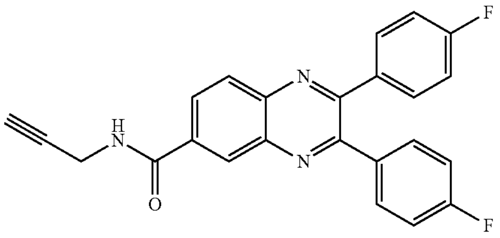 [SMILES: C#CCNC(=O)c1ccc2nc(-c3ccc(F)cc3)c(-c3ccc(F)cc3)nc2c1] | ++++ | + |
| BC19192 | ZE18-0147 | 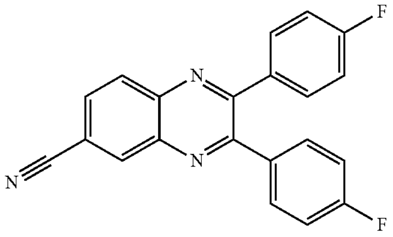 [SMILES: N#Cc1ccc2nc(-c3ccc(F)cc3)c(-c3ccc(F)cc3)nc2c1] | +++ | + |
| BC19194 | ZE18-0149 | 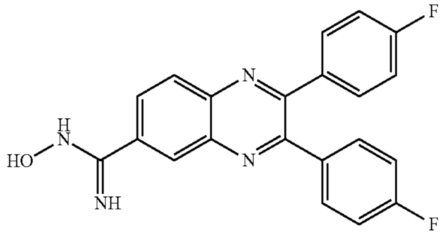 [SMILES: N=C(NO)c1ccc2nc(-c3ccc(F)cc3)c(-c3ccc(F)cc3)nc2c1] | ++++ | + |
| BC19237 | ZE18-0150 | 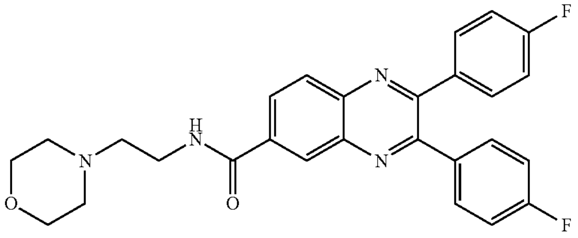 [SMILES: O=C(NCCN1CCOCC1)c1ccc2nc(-c3ccc(F)cc3)c(-c3ccc(F)cc3)nc2c1] | ++++ | + |
| BC19316 | ZE18-0198 | 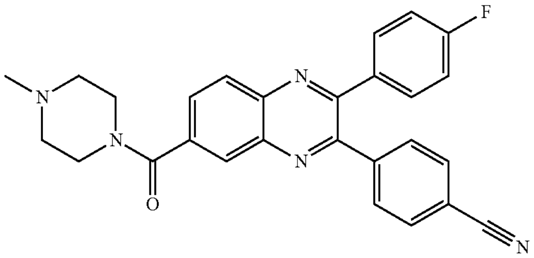 [SMILES: CN1CCN(C(=O)c2ccc3nc(-c4ccc(F)cc4)c(-c4ccc(C#N)cc4)nc3c2)CC1] | +++ | + |

TABLE 4b-continued
| BC No. | ZE No. | Structure | $IC_{50}$ (NF-κB assay) | $IC_{50}$ (TNF assay) |
|---|---|---|---|---|
| BC19317 | ZE18-0199 | 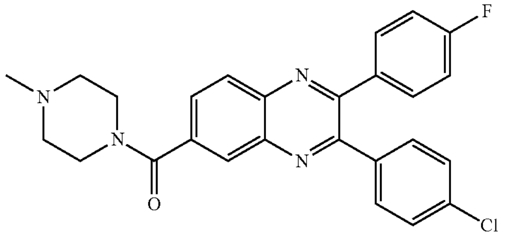 [SMILES: CN1CCN(C(=O)c2ccc3nc(-c4ccc(F)cc4)c(-c4ccc(Cl)cc4)nc3c2)CC1] | ++++ | + |
| BC19318 | ZE18-0200 | 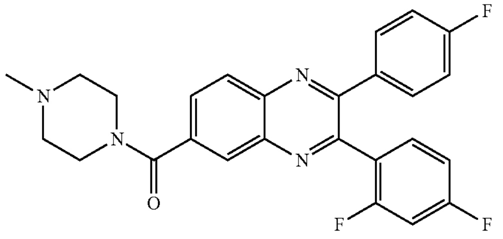 [SMILES: CN1CCN(C(=O)c2ccc3nc(-c4ccc(F)cc4)c(-c4ccc(F)cc4F)nc3c2)CC1] | ++++ | + |
| BC19319 | ZE18-0204 | 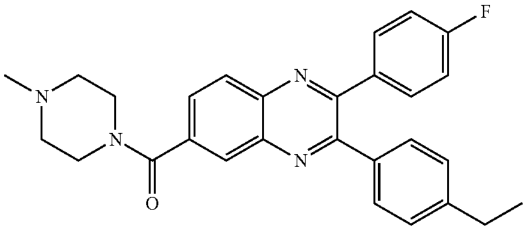 [SMILES: CCc1ccc(-c2nc3cc(C(=O)N4CCN(C)CC4)ccc3nc2-c2ccc(F)cc2)cc1] | ++ | + |
| BC19398 | ZE18-0203 | 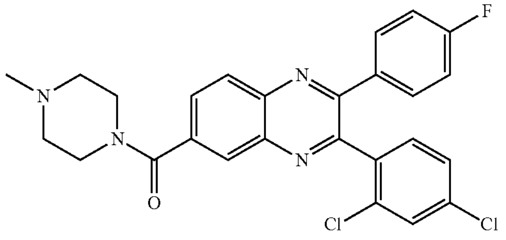 [SMILES: CN1CCN(C(=O)c2ccc3nc(-c4ccc(F)cc4)c(-c4ccc(Cl)cc4Cl)nc3c2)CC1] | +++ | + |
| BC19399 | ZE18-0205 | 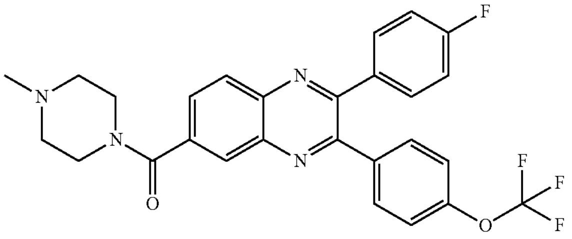 [SMILES: CN1CCN(C(=O)c2ccc3nc(-c4ccc(F)cc4)c(-c4ccc(OC(F)(F)F)cc4)nc3c2)CC1] | + | + |
| BC19405 | ZE18-0216 | 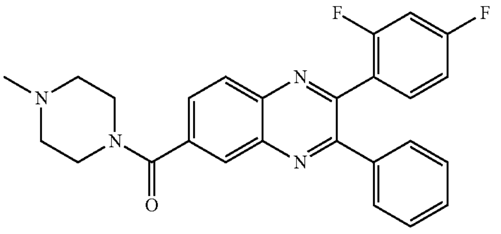 [SMILES: CN1CCN(C(=O)c2ccc3nc(-c4ccc(F)cc4F)c(-c4ccccc4)nc3c2)CC1] | +++ | + |

TABLE 4b-continued
| BC No. | ZE No. | Structure | $IC_{50}$ (NF-κB assay) | $IC_{50}$ (TNF assay) |
|---|---|---|---|---|
| BC19406 | ZE18-0217 | 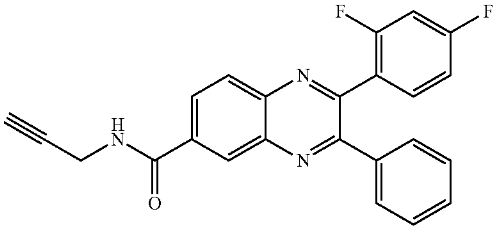 [SMILES: C#CCNC(=O)c1ccc2nc(-c3ccc(F)cc3F)c(-c3ccccc3)nc2c1] | +++ | + |
| BC19403 | ZE18-0214 | 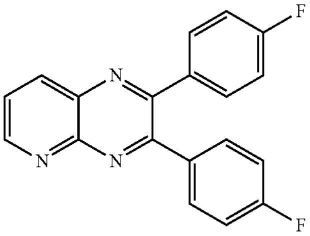 [SMILES: Fc1ccc(-c2nc3cccnc3nc2-c2ccc(F)cc2)cc1] | +++ | + |
| BC19407 | ZE18-0224 | 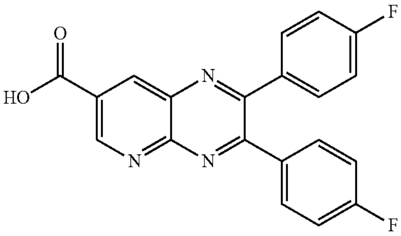 [SMILES: O=C(O)c1cnc2nc(-c3ccc(F)cc3)c(-c3ccc(F)cc3)nc2c1] | +++ | + |
| BC19408 | ZE18-0225 | 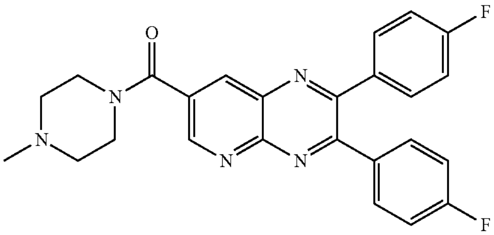 [SMILES: CN1CCN(C(=O)c2cnc3nc(-c4ccc(F)cc4)c(-c4ccc(F)cc4)nc3c2)CC1] | +++ | + |
TABLE 4b-2
| BC No. | Structure | $IC_{50}$ (NF-κB assay) | $IC_{50}$ (TNF assay) |
|---|---|---|---|
| BC19445 | 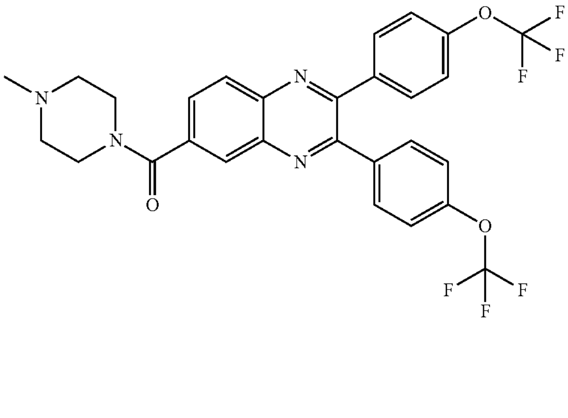 [SMILES: CN1CCN(C(=O)c2ccc3nc(-c4ccc(OC(F)(F)F)cc4)c(-c4ccc(OC(F)(F)F)cc4)nc3c2)CC1] | + | + |

TABLE 4b-2-continued
| BC No. | Structure | $IC_{50}$ (NF-κB assay) | $IC_{50}$ (TNF assay) |
|---|---|---|---|
| BC19446 | 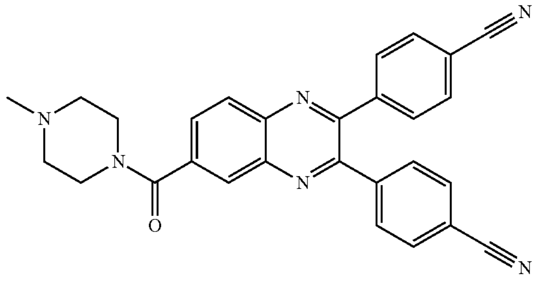 [SMILES: CN1CCN(C(=O)c2ccc3nc(-c4ccc(C#N)cc4)c(-c4ccc(C#N)cc4)nc3c2)CC1] | + | + |
| BC19447 | 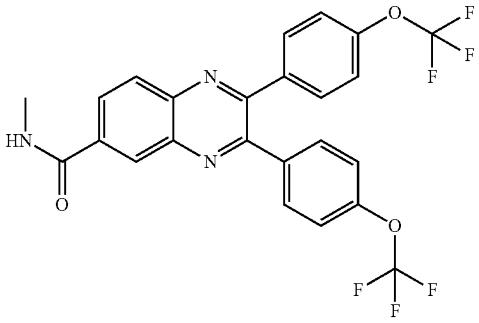 [SMILES: CNC(=O)c1ccc2nc(-c3ccc(OC(F)(F)F)cc3)c(-c3ccc(OC(F)(F)F)cc3)nc2c1] | + | + |
| BC19449 | 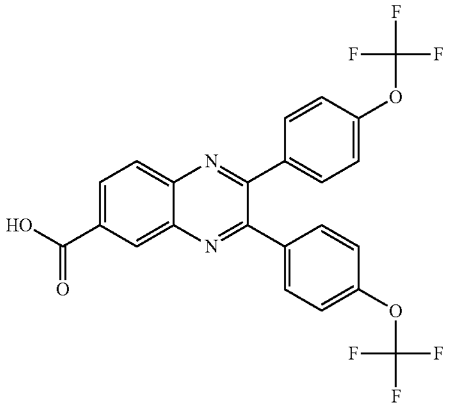 [SMILES: O=C(O)c1ccc2nc(-c3ccc(OC(F)(F)F)cc3)c(-c3ccc(OC(F)(F)F)cc3)nc2c1] | + | + |
| BC19450 | 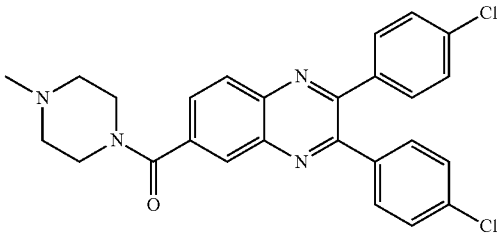 | ++ | + |
| BC19451 | 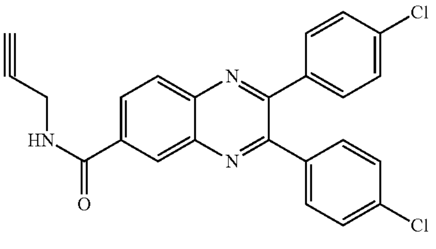 [SMILES: C#CCNC(=O)c1ccc2nc(-c3ccc(Cl)cc3)c(-c3ccc(Cl)cc3)nc2c1] | +++ | + |

TABLE 4b-2-continued
| BC No. | Structure | $IC_{50}$ (NF-κB assay) | $IC_{50}$ (TNF assay) |
|---|---|---|---|
| BC19452 | 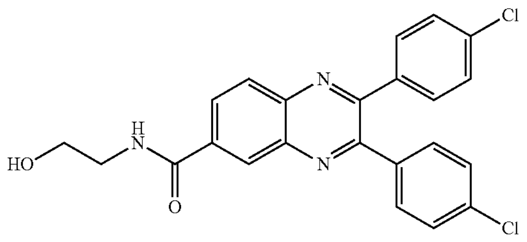 [SMILES: O=C(NCCO)c1ccc2nc(-c3ccc(Cl)cc3)c(-c3ccc(Cl)cc3)nc2c1] | +++ | + |
| BC19453 | 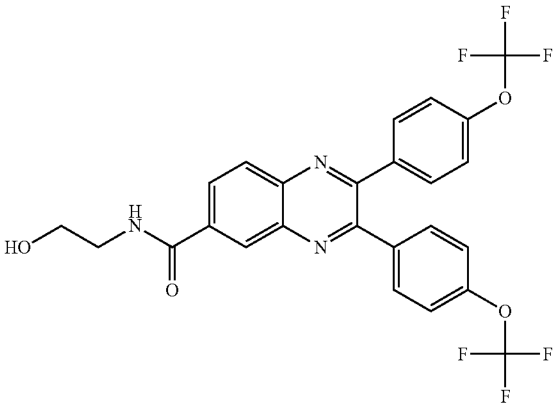 [SMILES: O=C(NCCO)c1ccc2nc(-c3ccc(OC(F)(F)F)cc3)c(-c3ccc(OC(F)(F)F)cc3)nc2c1] | + | + |
| BC19495 | 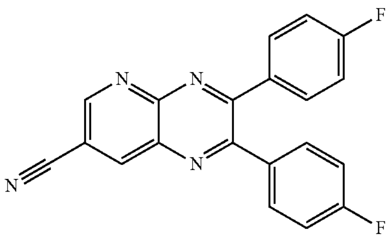 [SMILES: N#Cc1cnc2nc(-c3ccc(F)cc3)c(-c3ccc(F)cc3)nc2c1] | +++ | + |
| BC19497 | 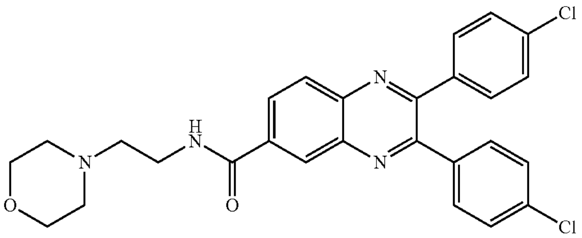 [SMILES: O=C(NCCN1CCOCC1)c1ccc2nc(-c3ccc(Cl)cc3)c(-c3ccc(Cl)cc3)nc2c1] | ++++ | + |
| BC19498 | 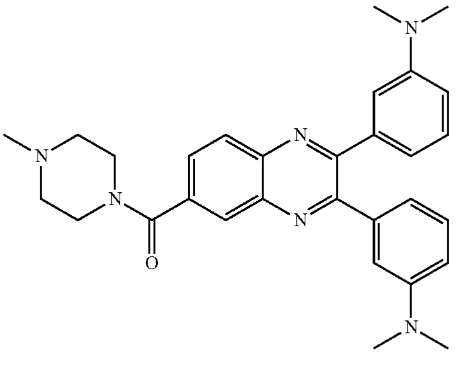 | + | + |

TABLE 4b-2-continued
| BC No. | Structure | IC$_{50}$ (NF-κB assay) | IC$_{50}$ (TNF assay) |
|---|---|---|---|
| BC19499 | 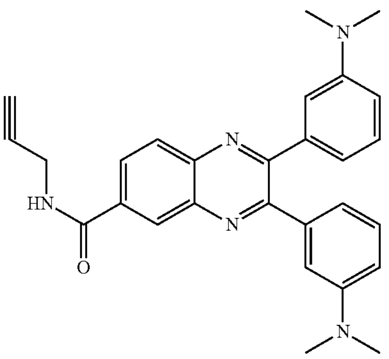 [SMILES: C#CCNC(=O)c1ccc2nc(-c3cccc(N(C)C)c3)c(-c3cccc(N(C)C)c3)nc2c1] | ++ | + |
| BC19500 | 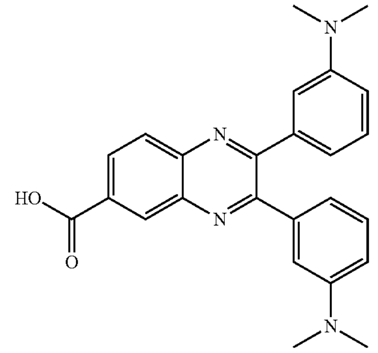 [SMILES: CN(C)c1cccc(-c2nc3ccc(C(=O)O)cc3nc2-c2cccc(N(C)C)c2)c1] | + | + |
| BC19501 | 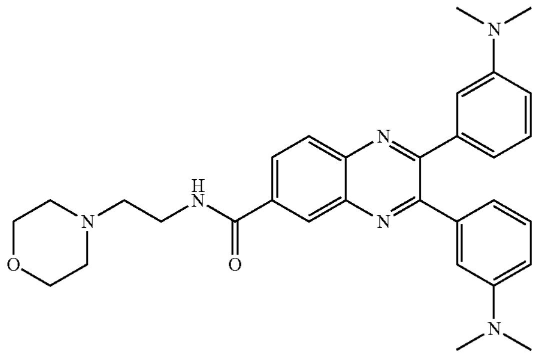 [SMILES: CN(C)c1cccc(-c2nc3ccc(C(=O)NCCN4CCOCC4)cc3nc2-c2cccc(N(C)C)c2)c1] | + | + |
| BC19502 | 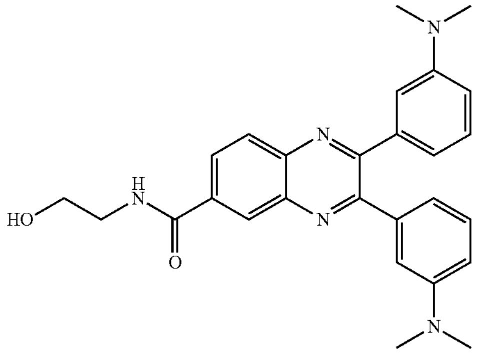 [SMILES: CN(C)c1cccc(-c2nc3ccc(C(=O)NCCO)cc3nc2-c2cccc(N(C)C)c2)c1] | + | + |

TABLE 4b-2-continued
| BC No. | Structure | IC$_{50}$ (NF-κB assay) | IC$_{50}$ (TNF assay) |
|---|---|---|---|
| BC19503 | 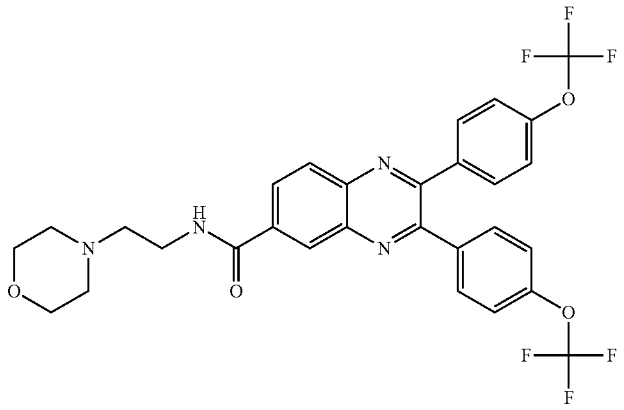 [SMILES: O=C(NCCN1CCOCC1)c1ccc2nc(-c3ccc(OC(F)(F)F)cc3)c(-c3ccc(OC(F)(F)F)cc3)nc2c1] | ++ | ++ |
| BC19513 | 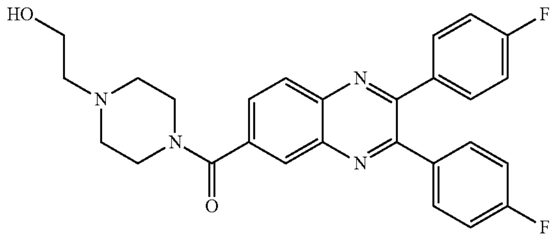 [SMILES: O=C(c1ccc2nc(-c3ccc(F)cc3)c(-c3ccc(F)cc3)nc2c1)N1CCN(CCO)CC1] | ++++ | + |
| BC19514 | 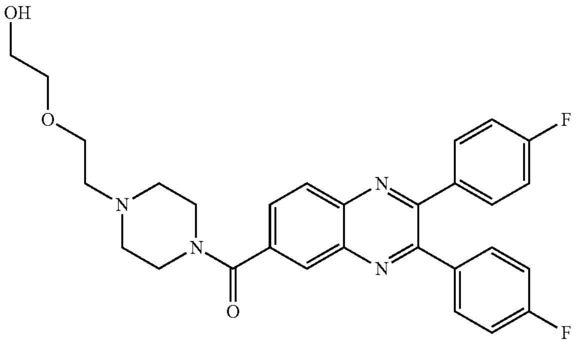 [SMILES: O=C(c1ccc2nc(-c3ccc(F)cc3)c(-c3ccc(F)cc3)nc2c1)N1CCN(CCOCCO)CC1] | +++ | ++ |
| BC19577 | 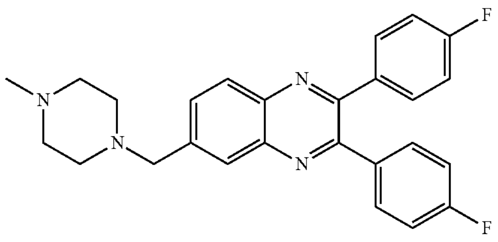 [SMILES: CN1CCN(Cc2ccc3nc(-c4ccc(F)cc4)c(-c4ccc(F)cc4)nc3c2)CC1] | +++ | + |

TABLE 4b-2-continued
| BC No. | Structure | $IC_{50}$ (NF-κB assay) | $IC_{50}$ (TNF assay) |
|---|---|---|---|
| BC19578 | 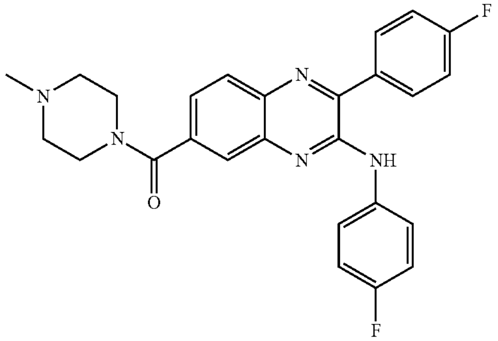 [SMILES: CN1CCN(C(=O)c2ccc3nc(-c4ccc(F)cc4)c(Nc4ccc(F)cc4)nc3c2)CC1] | + | + |
| BC19512 | 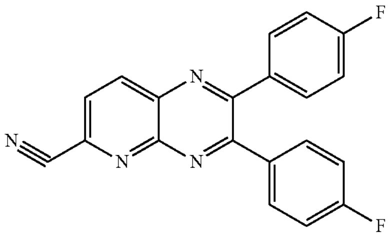 [SMILES: N#Cc1ccc2nc(-c3ccc(F)cc3)c(-c3ccc(F)cc3)nc2n1] | +++ | + |
| BC19448 | 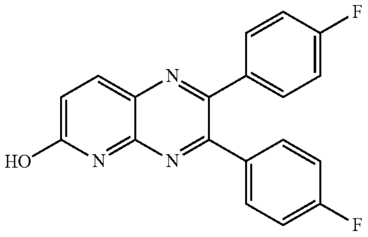 [SMILES: Oc1ccc2nc(-c3ccc(F)cc3)c(-c3ccc(F)cc3)nc2n1] | +++ | + |
| BC19618 | 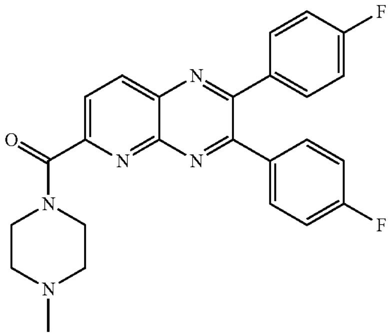 [SMILES: CN1CCN(C(=O)c2ccc3nc(-c4ccc(F)cc4)c(-c4ccc(F)cc4)nc3n2)CC1] | +++ | + |
| BC19666 | 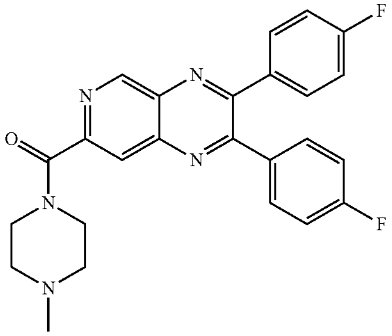 [SMILES: CN1CCN(C(=O)c2cc3nc(-c4ccc(F)cc4)c(-c4ccc(F)cc4)nc3cn2)CC1] | +++ | + |

TABLE 4b-2-continued
| BC No. | Structure | $IC_{50}$ (NF-κB assay) | $IC_{50}$ (TNF assay) |
|---|---|---|---|
| BC19668 | 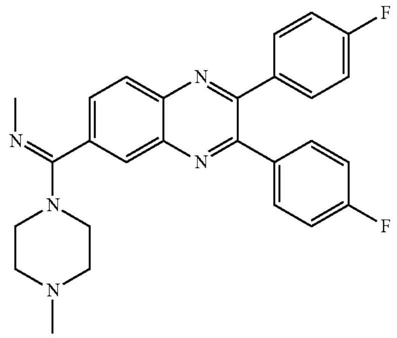 [SMILES: C/N=C(\c1ccc2nc(-c3ccc(F)cc3)c(-c3ccc(F)cc3)nc2c1)N1CCN(C)CC1] | +++ | + |
TABLE 4c
| BC No. | ZE No. | Structure | $IC_{50}$ (NF-κB assay) | $IC_{50}$ (TNF assay) |
|---|---|---|---|---|
| BC19101 | ZE18-0001 | 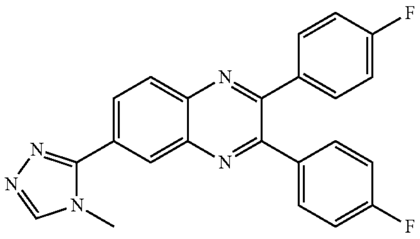 [SMILES: Cn1cnnc1-c1ccc2nc(-c3ccc(F)cc3)c(-c3ccc(F)cc3)nc2c1] | ++++ | + |
| BC19102 | ZE18-0006 | 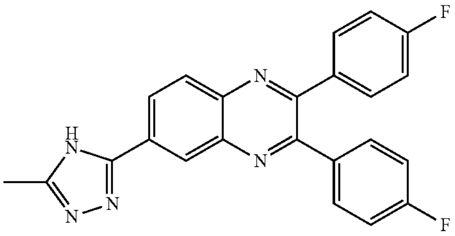 [SMILES: Cc1nnc(-c2ccc3nc(-c4ccc(F)cc4)c(-c4ccc(F)cc4)nc3c2)[nH]1] | +++ | + |
| BC19139 | ZE18-0003 | 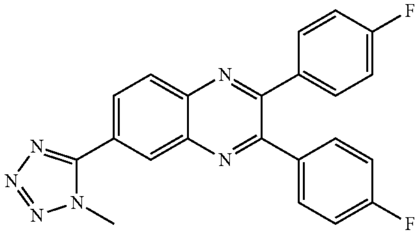 [SMILES: Cn1nnnc1-c1ccc2nc(-c3ccc(F)cc3)c(-c3ccc(F)cc3)nc2c1] | ++++ | + |
| BC19140 | ZE18-0004 | 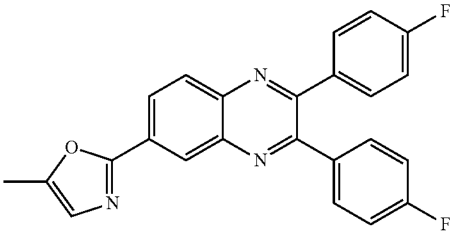 [SMILES: Cc1cnc(-c2ccc3nc(-c4ccc(F)cc4)c(-c4ccc(F)cc4)nc3c2)o1] | ++ | + |

TABLE 4c-continued
| BC No. | ZE No. | Structure | $IC_{50}$ (NF-κB assay) | $IC_{50}$ (TNF assay) |
| --- | --- | --- | --- | --- |
| BC19141 | ZE18-0005 | 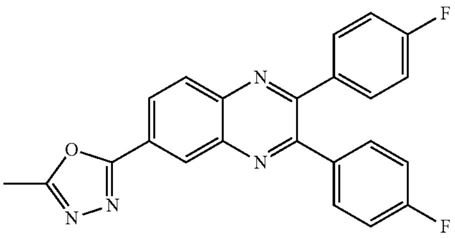 [SMILES: Cc1nnc(-c2ccc3nc(-c4ccc(F)cc4)c(-c4ccc(F)cc4)nc3c2)o1] | +++ | + |
| BC19143 | ZE18-0031 | 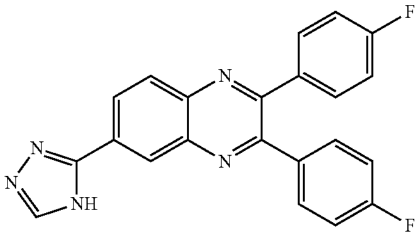 [SMILES: Fc1ccc(-c2nc3ccc(-c4nnc[nH]4)cc3nc2-c2ccc(F)cc2)cc1] | +++ | + |
| BC19144 | ZE18-0033 | 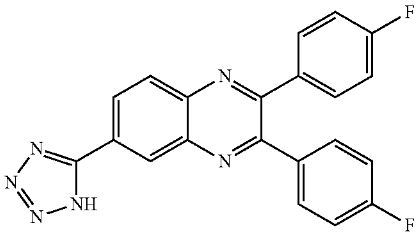 | ++ | + |
| BC19145 | ZE18-0046 | 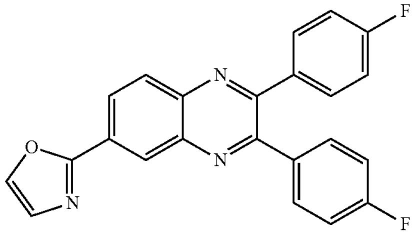 [SMILES: Fc1ccc(-c2nc3ccc(-c4ncco4)cc3nc2-c2ccc(F)cc2)cc1] | ++ | + |
| BC19148 | ZE18-0002 | 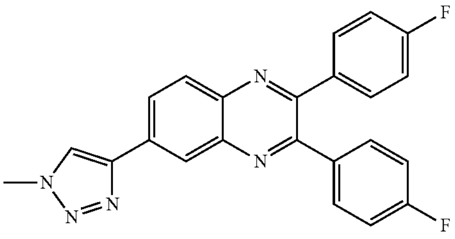 [SMILES: Cn1cc(-c2ccc3nc(-c4ccc(F)cc4)c(-c4ccc(F)cc4)nc3c2)nn1] | ++++ | + |
| BC19150 | ZE18-0032 | 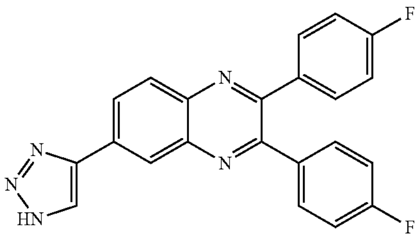 [SMILES: Fc1ccc(-c2nc3ccc(-c4c[nH]nn4)cc3nc2-c2ccc(F)cc2)cc1] | +++ | ++ |

TABLE 4c-continued
| BC No. | ZE No. | Structure | $IC_{50}$ (NF-κB assay) | $IC_{50}$ (TNF assay) |
|---|---|---|---|---|
| BC19190 | ZE18-0119 | 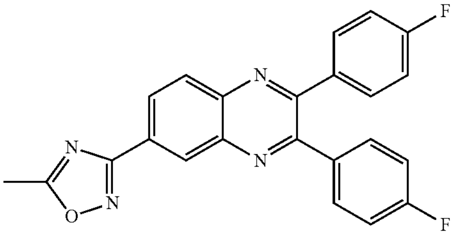 [SMILES: Cc1nc(-c2ccc3nc(-c4ccc(F)cc4)c(-c4ccc(F)cc4)nc3c2)no1] | +++ | + |
| BC19193 | ZE18-0148 | 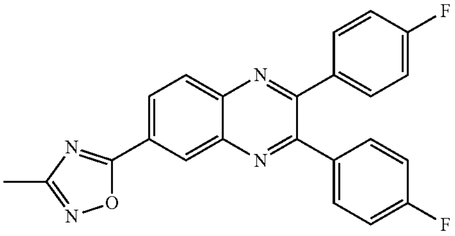 [SMILES: Cc1noc(-c2ccc3nc(-c4ccc(F)cc4)c(-c4ccc(F)cc4)nc3c2)n1] | +++ | + |
| BC19238 | ZE18-0151 | 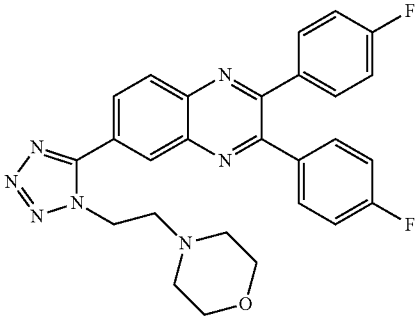 [SMILES: Fc1ccc(-c2nc3ccc(-c4nnnn4CCN4CCOCC4)cc3nc2-c2ccc(F)cc2)cc1] | ++++ | + |
| BC19240 | ZE18-0156 | 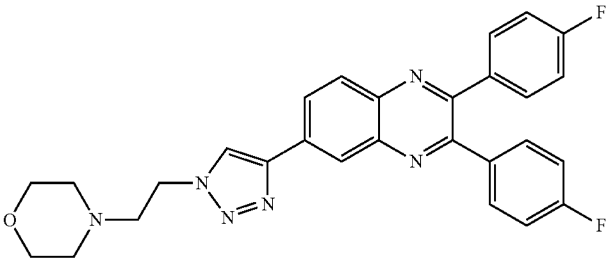 [SMILES: Fc1ccc(-c2nc3ccc(-c4cn(CCN5CCOCC5)nn4)cc3nc2-c2ccc(F)cc2)cc1] | ++++ | + |
| BC19241 | ZE18-0157 | 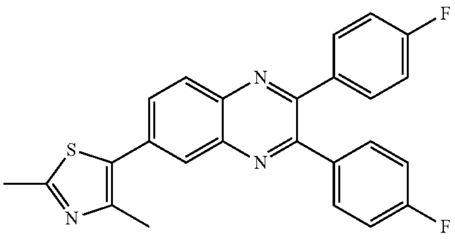 [SMILES: Cc1nc(C)c(-c2ccc3nc(-c4ccc(F)cc4)c(-c4ccc(F)cc4)nc3c2)s1] | ++ | + |

TABLE 4c-continued
| BC No. | ZE No. | Structure | $IC_{50}$ (NF-κB assay) | $IC_{50}$ (TNF assay) |
|---|---|---|---|---|
| BC19242 | ZE18-0163 | 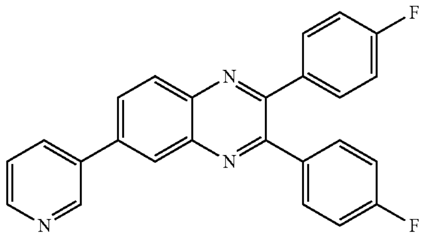 [SMILES: Fc1ccc(-c2nc3ccc(-c4cccnc4)cc3nc2-c2ccc(F)cc2)cc1] | +++ | + |
| BC19243 | ZE18-0165 | 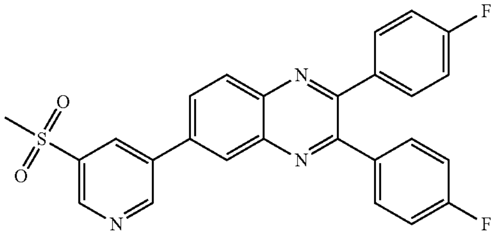 [SMILES: CS(=O)(=O)c1cncc(-c2ccc3nc(-c4ccc(F)cc4)c(-c4ccc(F)cc4)nc3c2)c1] | +++ | + |
| BC19244 | ZE18-0169 | 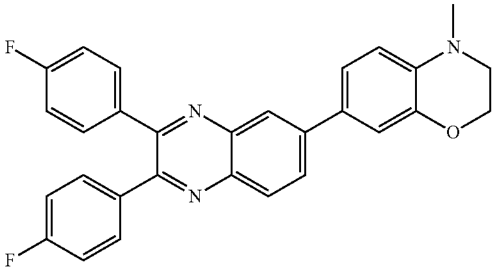 [SMILES: CN1CCOc2cc(-c3ccc4nc(-c5ccc(F)cc5)c(-c5ccc(F)cc5)nc4c3)ccc21] | + | + |
| BC19245 | ZE18-0171 | 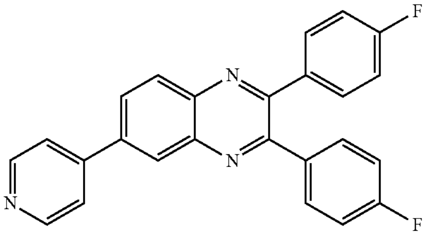 [SMILES: Fc1ccc(-c2nc3ccc(-c4ccncc4)cc3nc2-c2ccc(F)cc2)cc1] | ++ | + |
| BC19246 | ZE18-0177 | 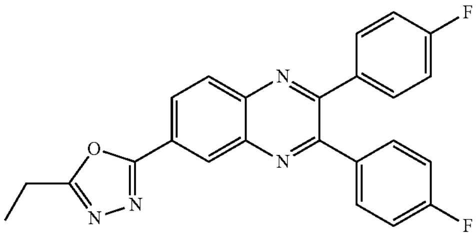 [SMILES: CCc1nnc(-c2ccc3nc(-c4ccc(F)cc4)c(-c4ccc(F)cc4)nc3c2)o1] | ++ | + |
| BC19247 | ZE18-0178 | 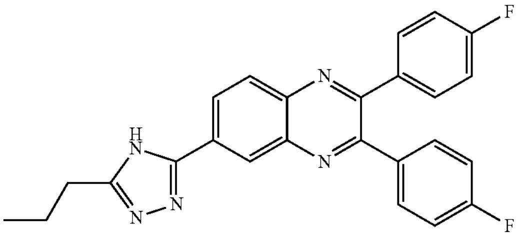 [SMILES: CCCc1nnc(-c2ccc3nc(-c4ccc(F)cc4)c(-c4ccc(F)cc4)nc3c2)[nH]1] | ++ | + |

TABLE 4c-continued
| BC No. | ZE No. | Structure | $IC_{50}$ (NF-κB assay) | $IC_{50}$ (TNF assay) |
|---|---|---|---|---|
| BC19250 | ZE18-0182 | 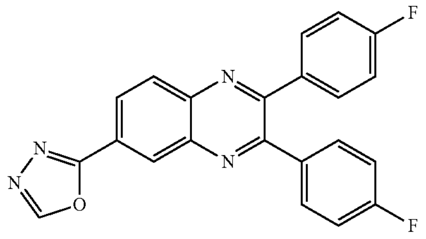 [SMILES: Fc1ccc(-c2nc3ccc(-c4nnco4)cc3nc2-c2ccc(F)cc2)cc1] | ++++ | + |
| BC19301 | ZE18-0155 | 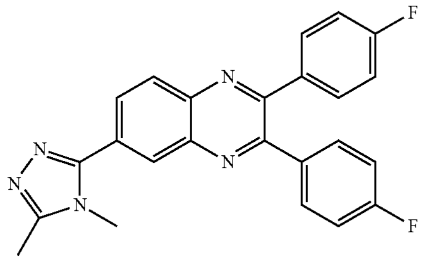 [SMILES: Cc1nnc(-c2ccc3nc(-c4ccc(F)cc4)c(-c4ccc(F)cc4)nc3c2)n1C] | ++++ | + |
| BC19302 | ZE18-0162 | 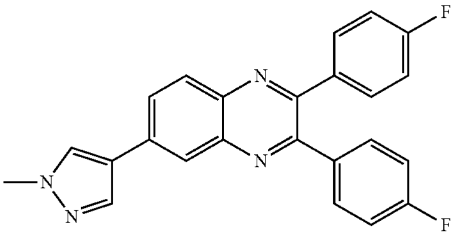 [SMILES: Cn1cc(-c2ccc3nc(-c4ccc(F)cc4)c(-c4ccc(F)cc4)nc3c2)cn1] | ++ | + |
| BC19303 | ZE18-0164 | 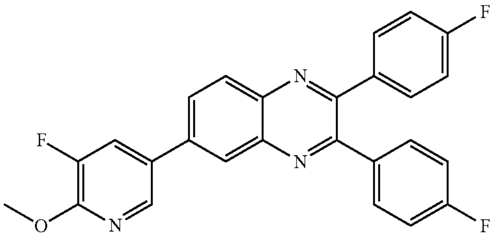 [SMILES: COc1ncc(-c2ccc3nc(-c4ccc(F)cc4)c(-c4ccc(F)cc4)nc3c2)cc1F] | + | + |
| BC19304 | ZE18-0167 | 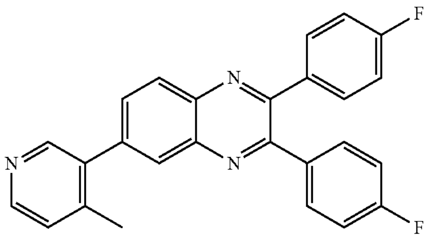 [SMILES: Cc1ccncc1-c1ccc2nc(-c3ccc(F)cc3)c(-c3ccc(F)cc3)nc2c1] | ++ | + |
| BC19305 | ZE18-0170 | 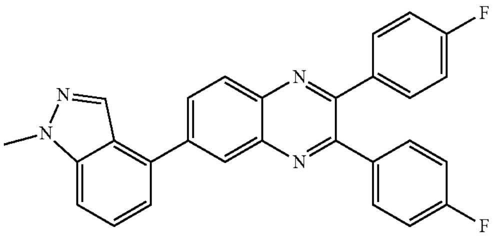 [SMILES: Cn1ncc2c(-c3ccc4nc(-c5ccc(F)cc5)c(-c5ccc(F)cc5)nc4c3)cccc21] | + | + |

TABLE 4c-continued
| BC No. | ZE No. | Structure | $IC_{50}$ (NF-κB assay) | $IC_{50}$ (TNF assay) |
|---|---|---|---|---|
| BC19306 | ZE18-0180 | 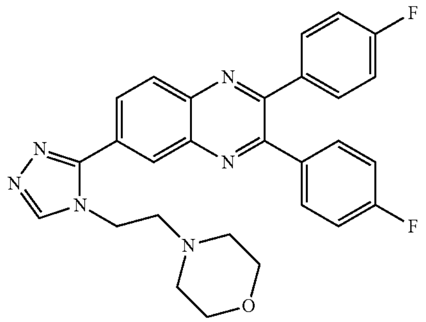 [SMILES: Fc1ccc(-c2nc3ccc(-c4nncn4CCN4CCOCC4)cc3nc2-c2ccc(F)cc2)cc1] | +++ | + |
| BC19396 | ZE18-0188 | 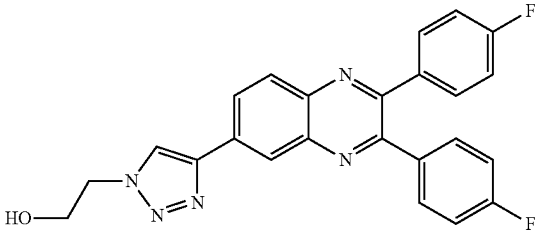 [SMILES: OCCn1cc(-c2ccc3nc(-c4ccc(F)cc4)c(-c4ccc(F)cc4)nc3c2)nn1] | ++++ | + |
| BC19401 | ZE18-0212 | 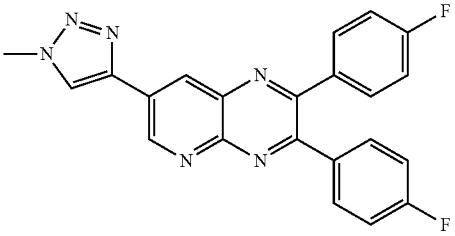 [SMILES: Cn1cc(-c2cnc3nc(-c4ccc(F)cc4)c(-c4ccc(F)cc4)nc3c2)nn1] | ++++ | + |
| BC19402 | ZE18-0213 | 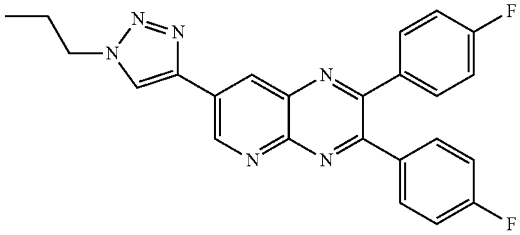 [SMILES: CCCn1cc(-c2cnc3nc(-c4ccc(F)cc4)c(-c4ccc(F)cc4)nc3c2)nn1] | ++++ | + |
| BC19404 | ZE18-0215 | 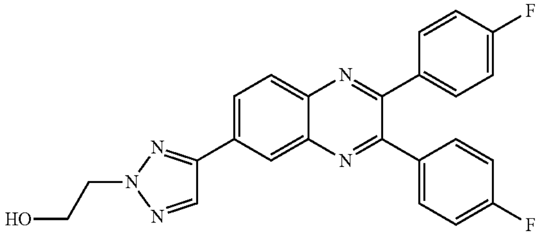 [SMILES: OCCn1ncc(-c2ccc3nc(-c4ccc(F)cc4)c(-c4ccc(F)cc4)nc3c2)n1] | ++ | + |
| BC19111 | ZE18-0061 | 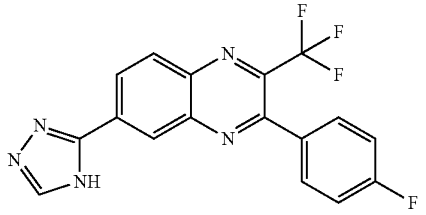 [SMILES: Fc1ccc(-c2nc3cc(-c4nnc[nH]4)ccc3nc2C(F)(F)F)cc1] | + | + |

TABLE 4c-continued
| BC No. | ZE No. | Structure | $IC_{50}$ (NF-κB assay) | $IC_{50}$ (TNF assay) |
|---|---|---|---|---|
| BC19112 | ZE18-0062 | 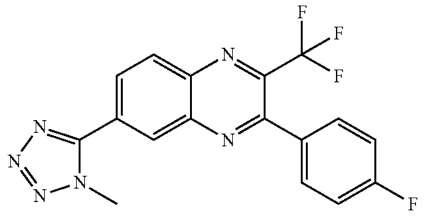 [SMILES: Cn1nnnc1-c1ccc2nc(C(F)(F)F)c(-c3ccc(F)cc3)nc2c1] | + | + |
| BC19113 | ZE18-0063 | 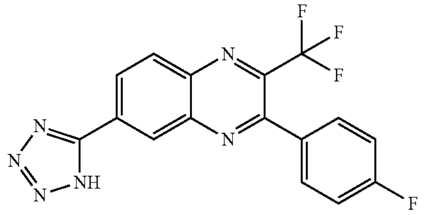 [SMILES: Fc1ccc(-c2nc3cc(-c4nnn[nH]4)ccc3nc2C(F)(F)F)cc1] | + | + |
| BC19114 | ZE18-0064 | 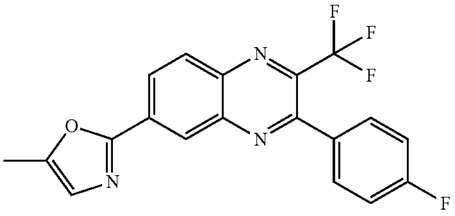 [SMILES: Cc1cnc(-c2ccc3nc(C(F)(F)F)c(-c4ccc(F)cc4)nc3c2)o1] | + | + |
| BC19115 | ZE18-0065 | 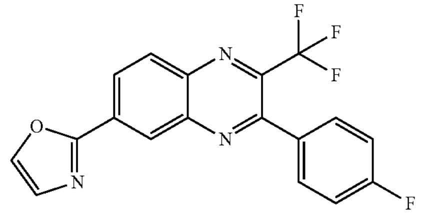 [SMILES: Fc1ccc(-c2nc3cc(-c4ncco4)ccc3nc2C(F)(F)F)cc1] | + | + |
| BC19116 | ZE18-0067 | 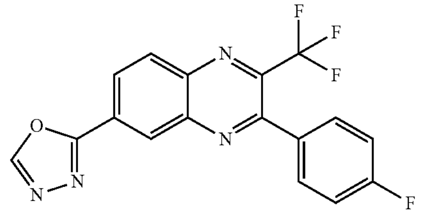 [SMILES: Fc1ccc(-c2nc3cc(-c4nnco4)ccc3nc2C(F)(F)F)cc1] | + | + |
| BC19151 | ZE18-0066 | 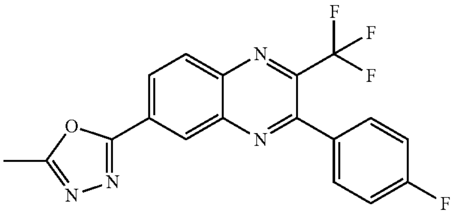 [SMILES: Cc1nnc(-c2ccc3nc(C(F)(F)F)c(-c4ccc(F)cc4)nc3c2)o1] | + | + |

TABLE 4c-continued
| BC No. | ZE No. | Structure | $IC_{50}$ (NF-κB assay) | $IC_{50}$ (TNF assay) |
|---|---|---|---|---|
| BC19152 | ZE18-0079 | 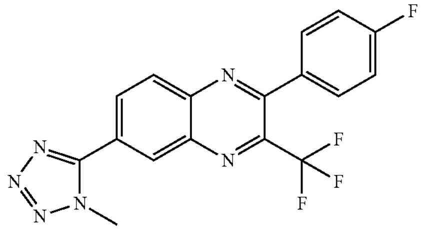 [SMILES: Cn1nnnc1-c1ccc2nc(-c3ccc(F)cc3)c(C(F)(F)F)nc2c1] | + | + |
| BC19153 | ZE18-0080 | 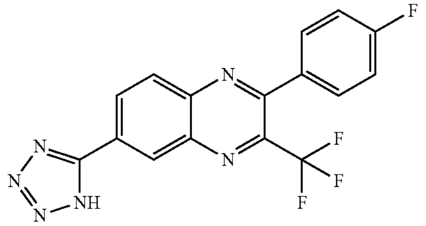 [SMILES: Fc1ccc(-c2nc3ccc(-c4nnn[nH]4)cc3nc2C(F)(F)F)cc1] | + | + |
| BC19159 | ZE18-0144 | 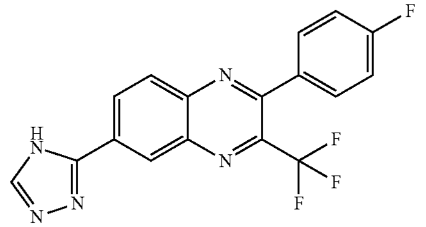 [SMILES: Fc1ccc(-c2nc3ccc(-c4nnc[nH]4)cc3nc2C(F)(F)F)cc1] | + | + |
| BC19186 | ZE18-0071 | 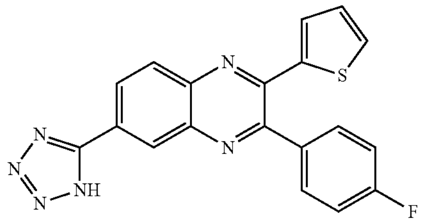 [SMILES: Fc1ccc(-c2nc3cc(-c4nnn[nH]4)ccc3nc2-c2cccs2)cc1] | ++ | + |
| BC19248 | ZE18-0179 | 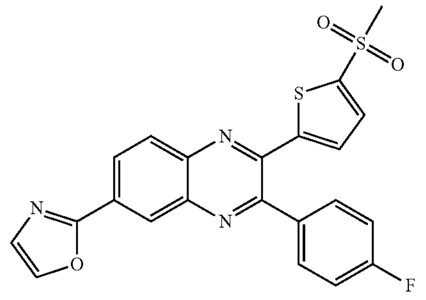 [SMILES: CS(=O)(=O)c1ccc(-c2nc3ccc(-c4ncco4)cc3nc2-c2ccc(F)cc2)s1] | + | + |
| BC19249 | ZE18-0181 | 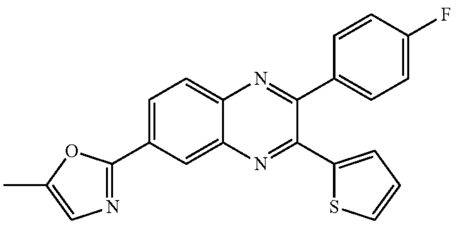 [SMILES: Cc1cnc(-c2ccc3nc(-c4ccc(F)cc4)c(-c4cccs4)nc3c2)o1] | ++ | + |

TABLE 4c-continued
| BC No. | ZE No. | Structure | IC50 (NF-κB assay) | IC50 (TNF assay) |
|---|---|---|---|---|
| | ZE18-0075 | 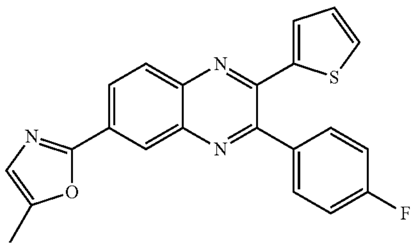 [SMILES: Cc1cnc(-c2ccc3nc(-c4cccs4)c(-c4ccc(F)cc4)nc3c2)o1] | | |
| | ZE18-0591 | 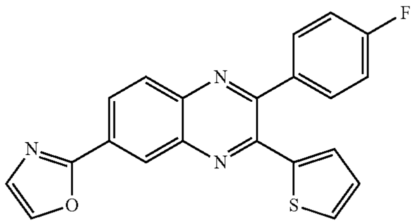 [SMILES: Fc1ccc(-c2nc3ccc(-c4ncco4)cc3nc2-c2cccs2)cc1] | | |
| | ZE18-0592 | 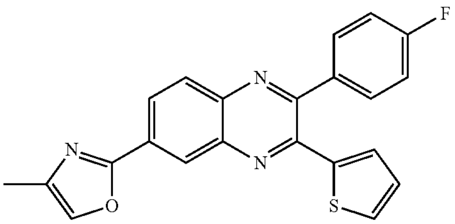 [SMILES: Cc1coc(-c2ccc3nc(-c4ccc(F)cc4)c(-c4cccs4)nc3c2)n1] | | |
| | ZE18-0593 | 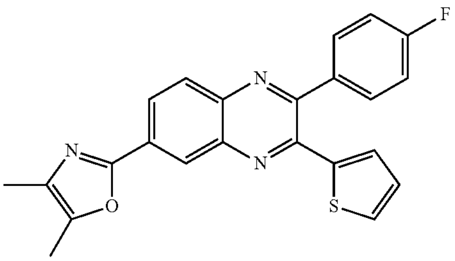 [SMILES: Cc1nc(-c2ccc3nc(-c4ccc(F)cc4)c(-c4cccs4)nc3c2)oc1C] | | |
| | ZE18-0594 | 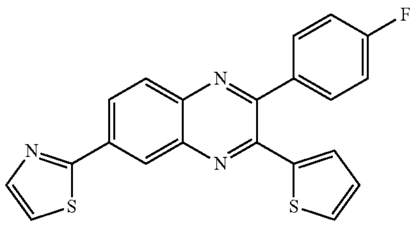 | | |
| | ZE18-0595 | 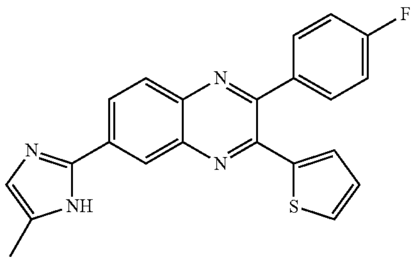 [SMILES: Cc1cnc(-c2ccc3nc(-c4ccc(F)cc4)c(-c4cccs4)nc3c2)[nH]1] | | |

TABLE 4c-continued
| BC No. | ZE No. | Structure | $IC_{50}$ (NF-κB assay) | $IC_{50}$ (TNF assay) |
|---|---|---|---|---|
| | ZE18-0596 | 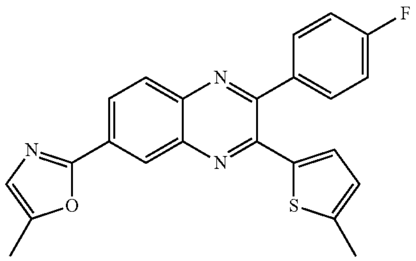 [SMILES: Cc1cnc(-c2ccc3nc(-c4ccc(F)cc4)c(-c4ccc(C)s4)nc3c2)o1] | | |
| | ZE18-0597 | 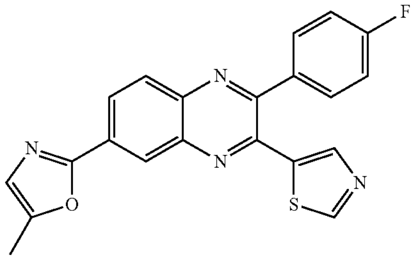 [SMILES: Cc1cnc(-c2ccc3nc(-c4ccc(F)cc4)c(-c4cncs4)nc3c2)o1] | | |
| | ZE18-0598 | 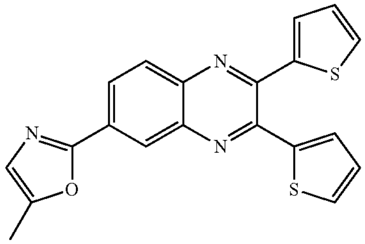 [SMILES: Cc1cnc(-c2ccc3nc(-c4cccs4)c(-c4cccs4)nc3c2)o1] | | |
| | ZE18-0600 | 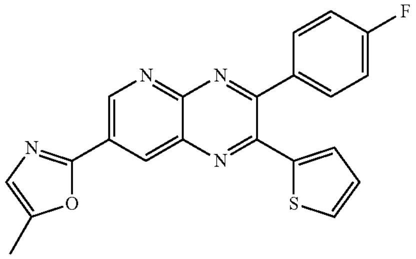 | | |
| | ZE18-0601 | 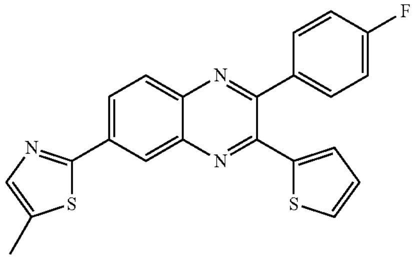 [SMILES: Cc1cnc(-c2ccc3nc(-c4ccc(F)cc4)c(-c4cccs4)nc3c2)s1] | | |

TABLE 4c-2
| BC No. | Structure | $IC_{50}$ (NF-κB assay) | $IC_{50}$ (TNF assay) |
|---|---|---|---|
| BC19444 | 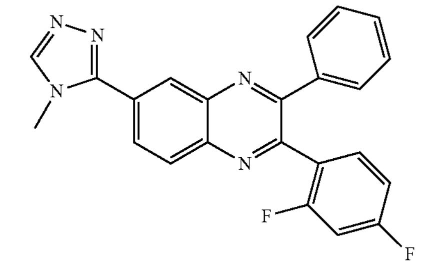 [SMILES: Cn1cnnc1-c1ccc2nc(-c3ccc(F)cc3F)c(-c3ccccc3)nc2c1] | +++ | + |
| BC19496 | 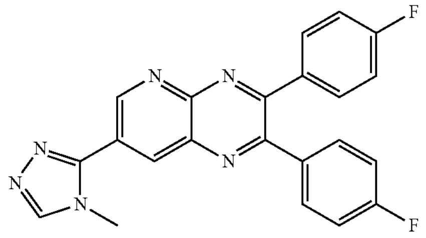 [SMILES: Cn1cnnc1-c1cnc2nc(-c3ccc(F)cc3)c(-c3ccc(F)cc3)nc2c1] | ++++ | + |
| BC19619 | 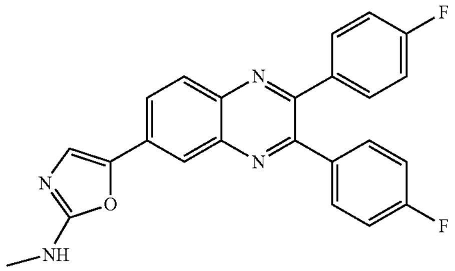 [SMILES: CNc1ncc(-c2ccc3nc(-c4ccc(F)cc4)c(-c4ccc(F)cc4)nc3c2)o1] | ++ | + |
| BC19664 | 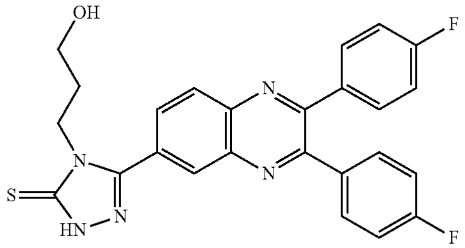 [SMILES: OCCCn1c(-c2ccc3nc(-c4ccc(F)cc4)c(-c4ccc(F)cc4)nc3c2)n[nH]c1=S] | +++ | +++ |
| BC19665 | 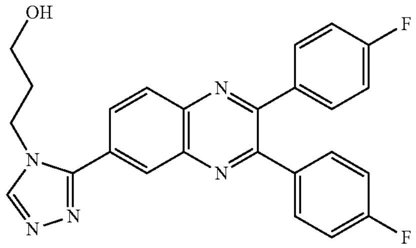 [SMILES: OCCCn1cnnc1-c1ccc2nc(-c3ccc(F)cc3)c(-c3ccc(F)cc3)nc2c1] | ++++ | ++ |

TABLE 4c-2-continued
| BC No. | Structure | $IC_{50}$ (NF-κB assay) | $IC_{50}$ (TNF assay) |
|---|---|---|---|
| BC19667 | 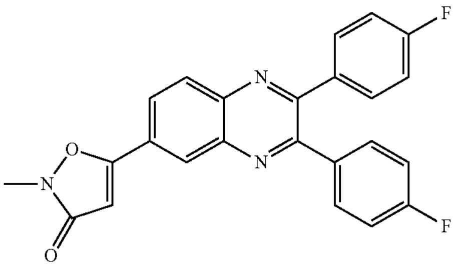 [SMILES: Cn1oc(-c2ccc3nc(-c4ccc(F)cc4)c(-c4ccc(F)cc4)nc3c2)cc1=O] | + | + |
TABLE 4d
| BC No. | ZE No. | Structure | $IC_{50}$ (NF-κB assay) | $IC_{50}$ (TNF assay) |
|---|---|---|---|---|
| BC19103 | ZE18-0007 | 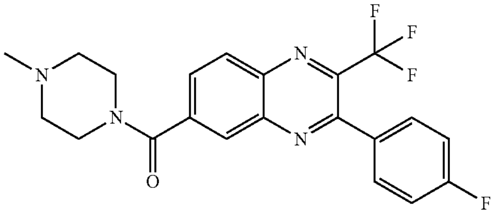 [SMILES: CN1CCN(C(=O)c2ccc3nc(C(F)(F)F)c(-c4ccc(F)cc4)nc3c2)CC1] | + | + |
| BC19104 | ZE18-0008 | 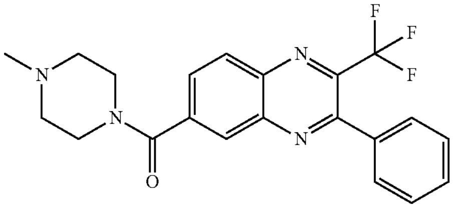 [SMILES: CN1CCN(C(=O)c2ccc3nc(C(F)(F)F)c(-c4ccccc4)nc3c2)CC1] | + | + |
| BC19105 | ZE18-0010 | 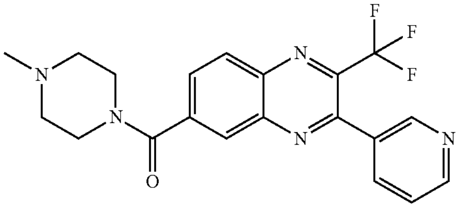 [SMILES: CN1CCN(C(=O)c2ccc3nc(C(F)(F)F)c(-c4cccnc4)nc3c2)CC1] | + | + |
| BC19106 | ZE18-0012 | 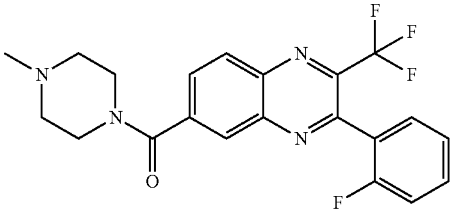 [SMILES: CN1CCN(C(=O)c2ccc3nc(C(F)(F)F)c(-c4ccccc4F)nc3c2)CC1] | + | + |
| BC19107 | ZE18-0013 | 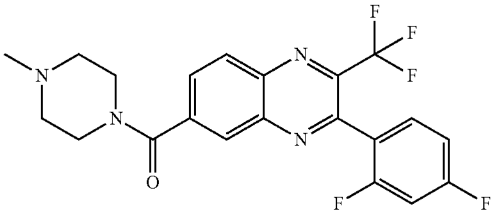 [SMILES: CN1CCN(C(=O)c2ccc3nc(C(F)(F)F)c(-c4ccc(F)cc4F)nc3c2)CC1] | + | + |

TABLE 4d-continued
| BC No. | ZE No. | Structure | $IC_{50}$ (NF-κB assay) | $IC_{50}$ (TNF assay) |
|---|---|---|---|---|
| BC19108 | ZE18-0014 | 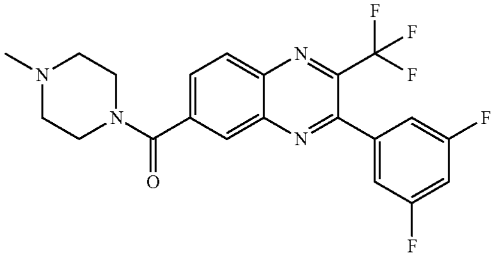 [SMILES: CN1CCN(C(=O)c2ccc3nc(C(F)(F)F)c(-c4cc(F)cc(F)c4)nc3c2)CC1] | + | + |
| BC19142 | ZE18-0011 | 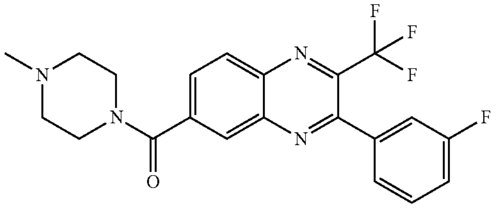 [SMILES: CN1CCN(C(=O)c2ccc3nc(C(F)(F)F)c(-c4cccc(F)c4)nc3c2)CC1] | + | + |
| BC19149 | ZE18-0009 | 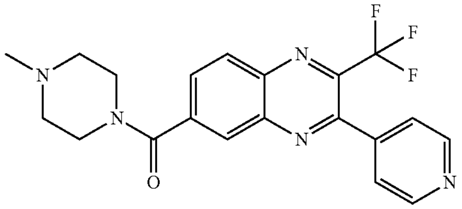 [SMILES: CN1CCN(C(=O)c2ccc3nc(C(F)(F)F)c(-c4ccncc4)nc3c2)CC1] | + | + |
| BC19110 | ZE18-0034 | 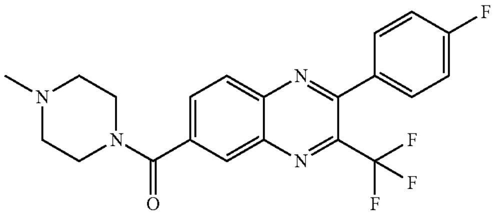 [SMILES: CN1CCN(C(=O)c2ccc3nc(-c4ccc(F)cc4)c(C(F)(F)F)nc3c2)CC1] | + | + |
| BC19109 | ZE18-0017 | 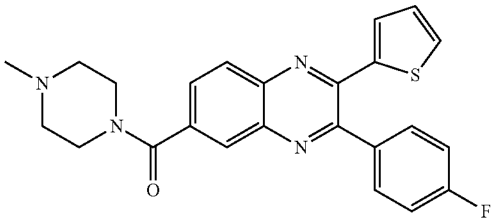 [SMILES: CN1CCN(C(=O)c2ccc3nc(-c4cccs4)c(-c4ccc(F)cc4)nc3c2)CC1] | +++ | + |
| BC19191 | ZE18-0125 | 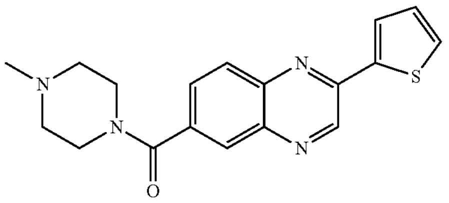 [SMILES: CN1CCN(C(=O)c2ccc3nc(-c4cccs4)cnc3c2)CC1] | + | + |

TABLE 4d-continued
| BC No. | ZE No. | Structure | $IC_{50}$ (NF-κB assay) | $IC_{50}$ (TNF assay) |
|---|---|---|---|---|
| BC19185 | ZE18-0026 | 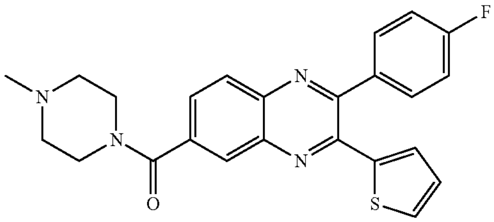 [SMILES: CN1CCN(C(=O)c2ccc3nc(-c4ccc(F)cc4)c(-c4cccs4)nc3c2)CC1] | ++++ | + |
| BC19307 | ZE18-0185 | 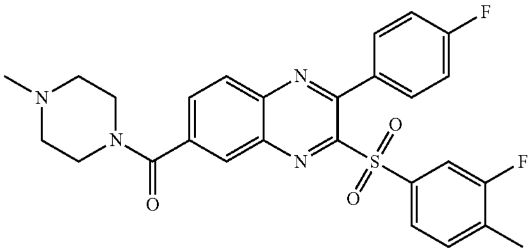 | +++ | ++++ |
| BC19308 | ZE18-0155 | 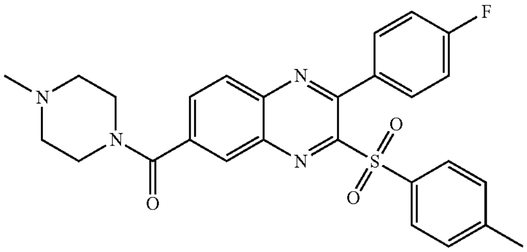 | +++ | ++++ |
| BC19395 | ZE18-0184 | 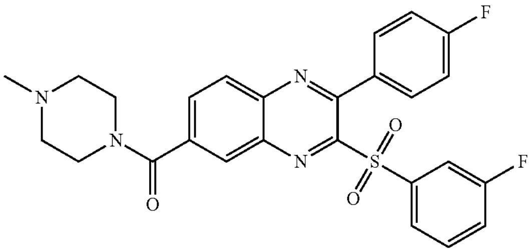 [SMILES: CN1CCN(C(=O)c2ccc3nc(-c4ccc(F)cc4)c(S(=O)(=O)c4cccc(F)c4)nc3c2)CC1] | +++ | ++++ |
| BC19117 | ZE18-0083 | 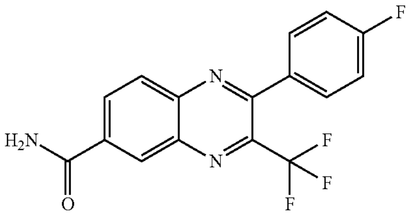 [SMILES: NC(=O)c1ccc2nc(-c3ccc(F)cc3)c(C(F)(F)F)nc2c1] | + | + |
| BC19158 | ZE18-0124 | 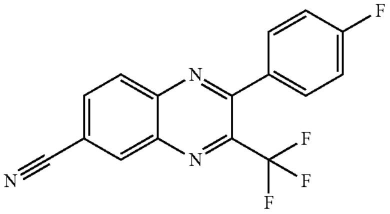 [SMILES: N#Cc1ccc2nc(-c3ccc(F)cc3)c(C(F)(F)F)nc2c1] | + | + |

TABLE 4d-continued
| BC No. | ZE No. | Structure | $IC_{50}$ (NF-κB assay) | $IC_{50}$ (TNF assay) |
|---|---|---|---|---|
| BC19119 | ZE18-0103 | 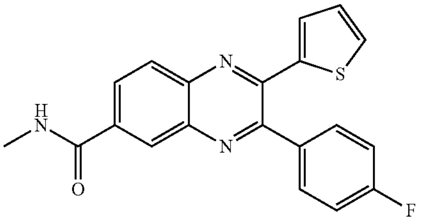 [SMILES: CNC(=O)c1ccc2nc(-c3cccs3)c(-c3ccc(F)cc3)nc2c1] | ++++ | ++++ |
| BC19120 | ZE18-0105 | 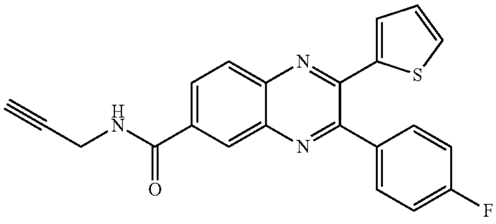 [SMILES: C#CCNC(=O)c1ccc2nc(-c3cccs3)c(-c3ccc(F)cc3)nc2c1] | ++++ | ++++ |
| BC19155 | ZE18-0099 | 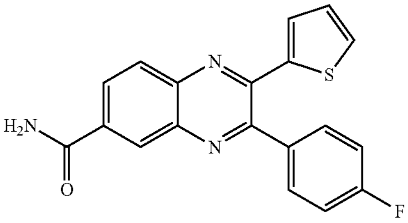 [SMILES: NC(=O)c1ccc2nc(-c3cccs3)c(-c3ccc(F)cc3)nc2c1] | +++ | ++ |
| BC19157 | ZE18-0104 | 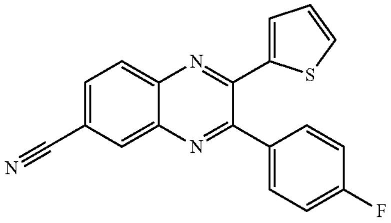 [SMILES: N#Cc1ccc2nc(-c3cccs3)c(-c3ccc(F)cc3)nc2c1] | + | + |
| BC19156 | ZE18-0101 | 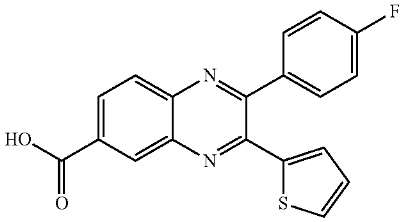 [SMILES: O=C(O)c1ccc2nc(-c3ccc(F)cc3)c(-c3cccs3)nc2c1] | ++ | + |
| BC19187 | ZE18-0114 | 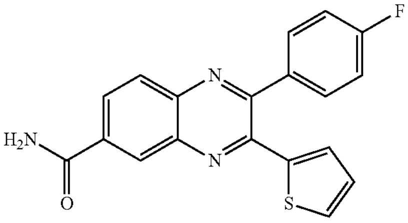 [SMILES: NC(=O)c1ccc2nc(-c3ccc(F)cc3)c(-c3cccs3)nc2c1] | +++ | + |

TABLE 4d-continued
| BC No. | ZE No. | Structure | IC50 (NF-κB assay) | IC50 (TNF assay) |
|---|---|---|---|---|
| BC19188 | ZE18-0115 | 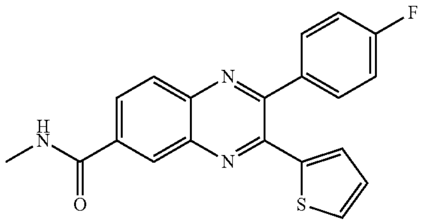 [SMILES: CNC(=O)c1ccc2nc(-c3ccc(F)cc3)c(-c3cccs3)nc2c1] | +++ | + |
| BC19189 | ZE18-0116 | 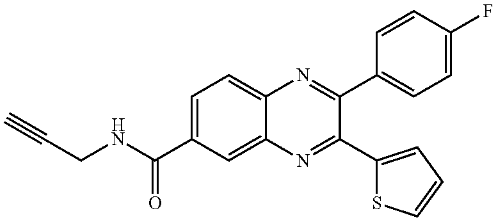 [SMILES: C#CCNC(=O)c1ccc2nc(-c3ccc(F)cc3)c(-c3cccs3)nc2c1] | +++ | + |
TABLE 4e
| BC No. | ZE No. | Structure | IC50 (NF-κB assay) | IC50 (TNF assay) |
|---|---|---|---|---|
| BC19320 | ZE18-0209 | 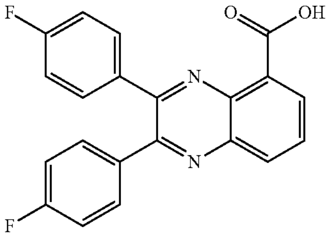 [SMILES: O=C(O)c1cccc2nc(-c3ccc(F)cc3)c(-c3ccc(F)cc3)nc12] | + | + |
| BC19321 | ZE18-0211 | 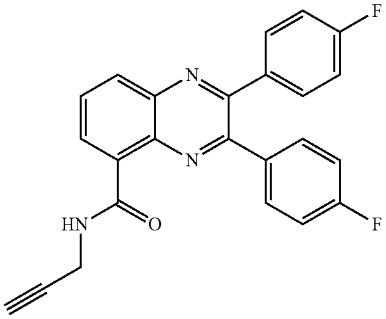 [SMILES: C#CCNC(=O)c1cccc2nc(-c3ccc(F)cc3)c(-c3ccc(F)cc3)nc12] | ++ | + |
| BC19400 | ZE18-0210 | 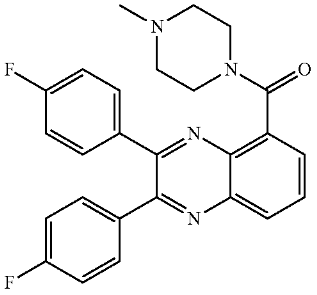 [SMILES: CN1CCN(C(=O)c2cccc3nc(-c4ccc(F)cc4)c(-c4ccc(F)cc4)nc23)CC1] | + | + |

TABLE 4f
| BC No. | ZE No. | Structure | IC50 (NF-κB assay) | IC50 (TNF assay) |
|---|---|---|---|---|
| BC19195 | ZE18-0152 | 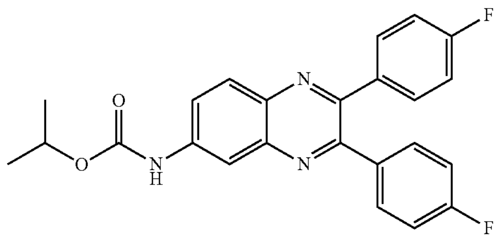 [SMILES: CC(C)OC(=O)Nc1ccc2nc(-c3ccc(F)cc3)c(-c3ccc(F)cc3)nc2c1] | ++ | + |
| BC19239 | ZE18-0154 | 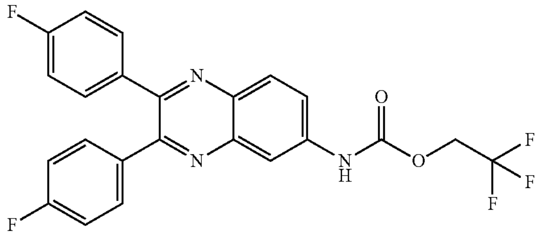 [SMILES: O=C(Nc1ccc2nc(-c3ccc(F)cc3)c(-c3ccc(F)cc3)nc2c1)OCC(F)(F)F] | +++ | + |
| BC19251 | ZE18-0187 | 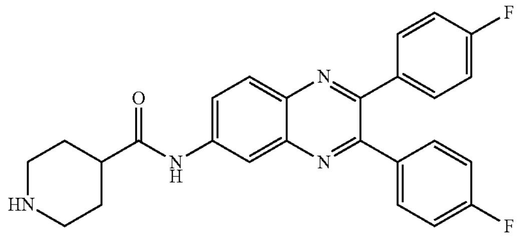 [SMILES: O=C(Nc1ccc2nc(-c3ccc(F)cc3)c(-c3ccc(F)cc3)nc2c1)C1CCNCC1] | ++++ | ++ |
| BC19309 | ZE18-0189 | 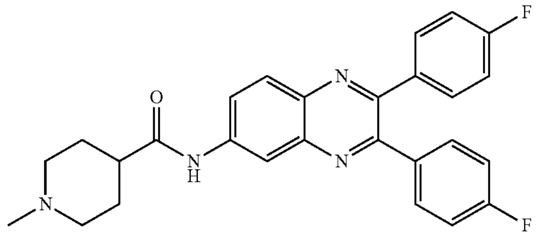 [SMILES: CN1CCC(C(=O)Nc2ccc3nc(-c4ccc(F)cc4)c(-c4ccc(F)cc4)nc3c2)CC1] | +++ | ++ |
| BC19310 | ZE18-0190 | 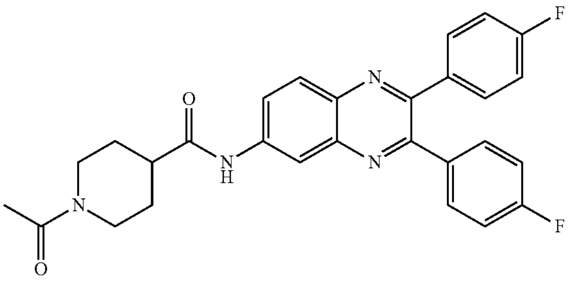 [SMILES: CC(=O)N1CCC(C(=O)Nc2ccc3nc(-c4ccc(F)cc4)c(-c4ccc(F)cc4)nc3c2)CC1] | ++++ | + |

TABLE 4f-continued
| BC No. | ZE No. | Structure | $IC_{50}$ (NF-κB assay) | $IC_{50}$ (TNF assay) |
|---|---|---|---|---|
| BC19311 | ZE18-0192 | 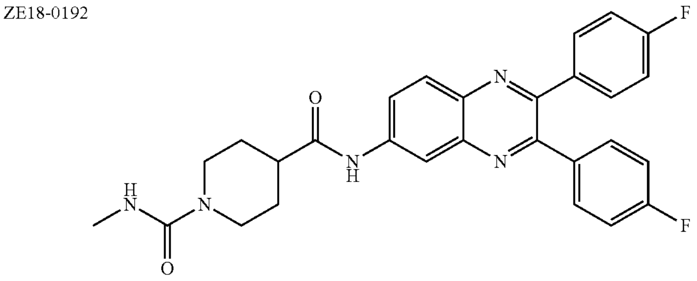 | ++++ | + |
| BC19312 | ZE18-0193 | 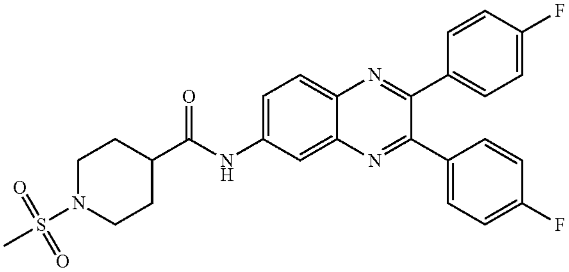 [SMILES: CS(=O)(=O)N1CCC(C(=O)Nc2ccc3nc(-c4ccc(F)cc4)c(-c4ccc(F)cc4)nc3c2)CC1] | ++++ | ++ |
| BC19313 | ZE18-0194 | 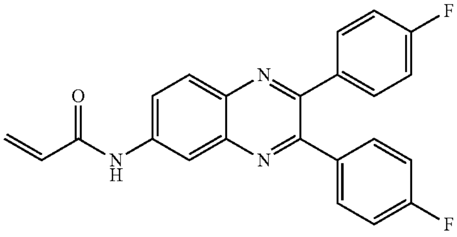 [SMILES: C=CC(=O)Nc1ccc2nc(-c3ccc(F)cc3)c(-c3ccc(F)cc3)nc2c1] | +++ | ++ |
| BC19314 | ZE18-0196 | 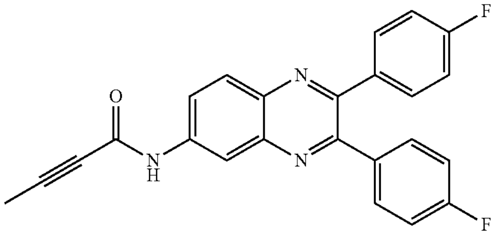 [SMILES: CC#CC(=O)Nc1ccc2nc(-c3ccc(F)cc3)c(-c3ccc(F)cc3)nc2c1] | ++++ | ++ |
| BC19315 | ZE18-0197 | 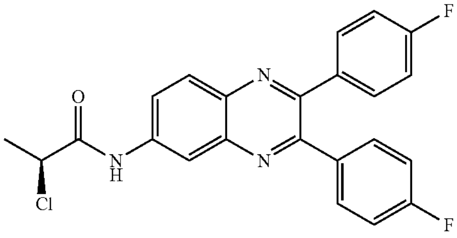 [SMILES: C[C@H](Cl)C(=O)Nc1ccc2nc(-c3ccc(F)cc3)c(-c3ccc(F)cc3)nc2c1] | +++ | + |
| BC19397 | ZE18-0195 | 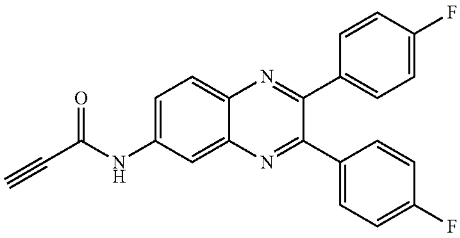 [SMILES: C#CC(=O)Nc1ccc2nc(-c3ccc(F)cc3)c(-c3ccc(F)cc3)nc2c1] | ++++ | +++ |

TABLE 4f-continued
| BC No. | ZE No. | Structure | $IC_{50}$ (NF-κB assay) | $IC_{50}$ (TNF assay) |
|---|---|---|---|---|
| | ZE18-0568 | 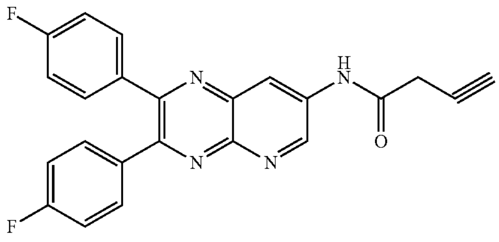 [SMILES: C#CCC(=O)Nc1cnc2nc(-c3ccc(F)cc3)c(-c3ccc(F)cc3)nc2c1] | | |
| | ZE18-0569 | 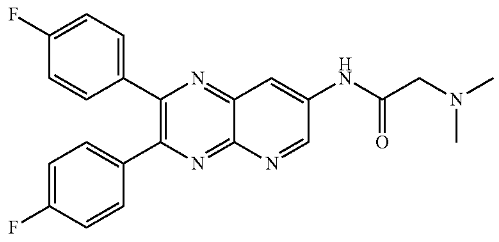 [SMILES: CN(C)CC(=O)Nc1cnc2nc(-c3ccc(F)cc3)c(-c3ccc(F)cc3)nc2c1] | | |
| | ZE18-0570 | 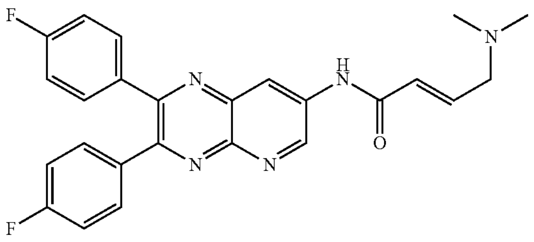 [SMILES: CN(C)C/C=C/C(=O)Nc1cnc2nc(-c3ccc(F)cc3)c(-c3ccc(F)cc3)nc2c1] | | |
| | ZE18-0571 | 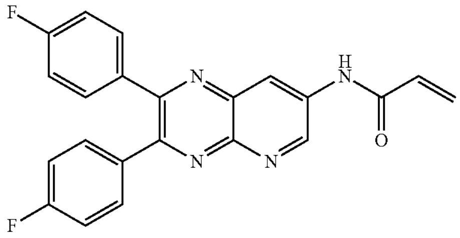 [SMILES: C=CC(=O)Nc1cnc2nc(-c3ccc(F)cc3)c(-c3ccc(F)cc3)nc2c1] | | |
| | ZE18-0581 | 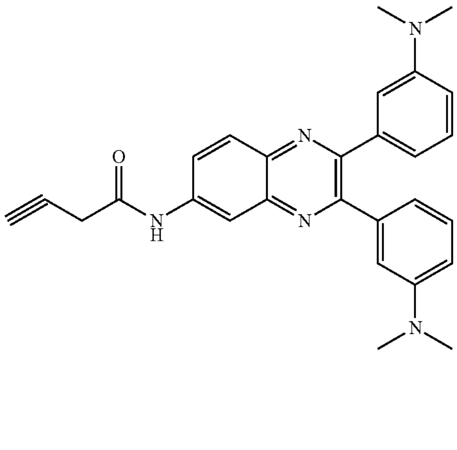 [SMILES: C#CCC(=O)Nc1ccc2nc(-c3cccc(N(C)C)c3)c(-c3cccc(N(C)C)c3)nc2c1] | | |

TABLE 4f-continued
| BC No. | ZE No. | Structure | $IC_{50}$ (NF-κB assay) | $IC_{50}$ (TNF assay) |
|---|---|---|---|---|
| | ZE18-0586 | 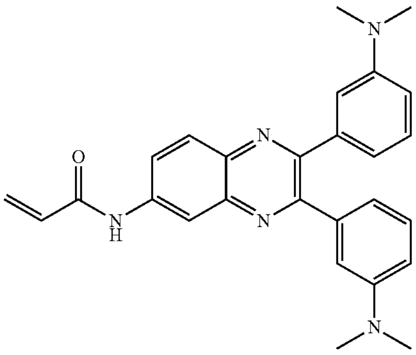 [SMILES: C=CC(=O)Nc1ccc2nc(-c3cccc(N(C)C)c3)c(-c3cccc(N(C)C)c3)nc2c1] | | |
| | ZE18-0588 | 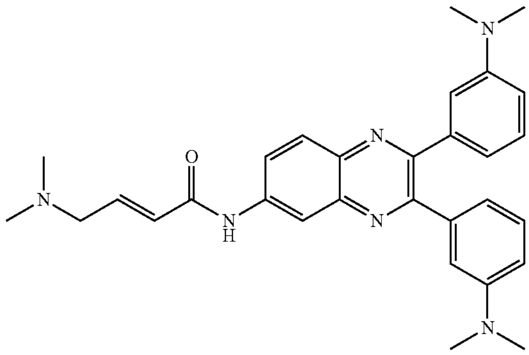 | | |
TABLE 4f-2
| BC No. | Structure | $IC_{50}$ (NF-κB assay) | $IC_{50}$ (TNF assay) |
|---|---|---|---|
| BC19494 | 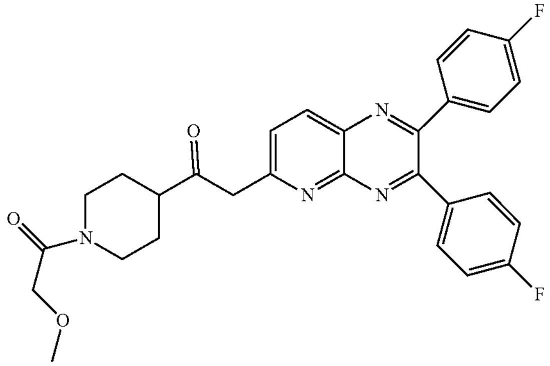 [SMILES: COCC(=O)N1CCC(C(=O)Cc2ccc3nc(-c4ccc(F)cc4)c(-c4ccc(F)cc4)nc3n2)CC1] | +++ | + |
| BC20317 | 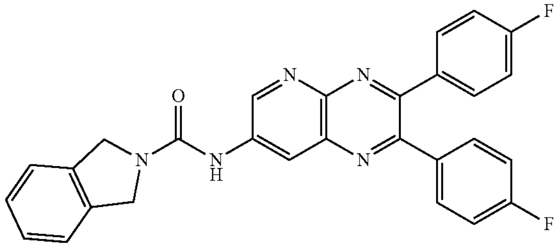 [SMILES: O=C(Nc1cnc2nc(-c3ccc(F)cc3)c(-c3ccc(F)cc3)nc2c1)N1Cc2ccccc2C1] | | |

TABLE 4f-2-continued
| BC No. | Structure | IC50 (NF-κB assay) | IC50 (TNF assay) |
|---|---|---|---|
| BC20321 | 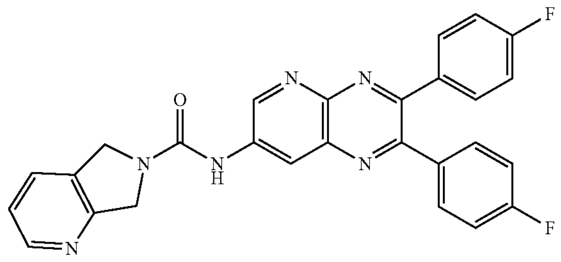 [SMILES: O=C(Nc1cnc2nc(-c3ccc(F)cc3)c(-c3ccc(F)cc3)nc2c1)N1Cc2cccnc2C1] | | |
| BC20330 | 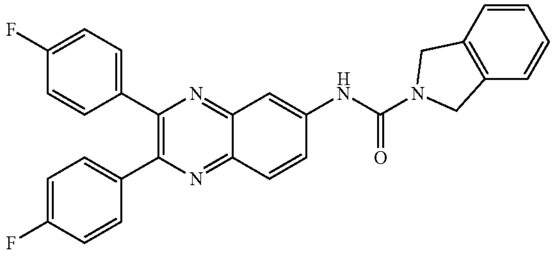 [SMILES: O=C(Nc1ccc2nc(-c3ccc(F)cc3)c(-c3ccc(F)cc3)nc2c1)N1Cc2ccccc2C1] | | |
| BC20333 | 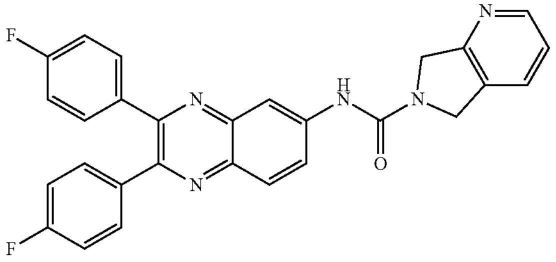 [SMILES: O=C(Nc1ccc2nc(-c3ccc(F)cc3)c(-c3ccc(F)cc3)nc2c1)N1Cc2cccnc2C1] | | |
| BC20334 | 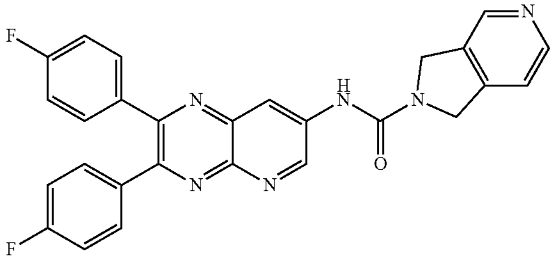 [SMILES: O=C(Nc1cnc2nc(-c3ccc(F)cc3)c(-c3ccc(F)cc3)nc2c1)N1Cc2ccncc2C1] | | |
| ZEIS-0567 | 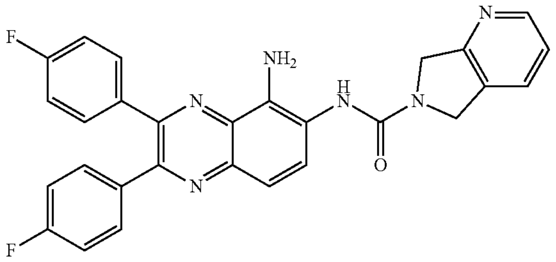 [SMILES: Nc1c(NC(=O)N2Cc3cccnc3C2)ccc2nc(-c3ccc(F)cc3)c(-c3ccc(F)cc3)nc12] | | |

TABLE 4f-2-continued
| BC No. | Structure | IC50 (NF-κB assay) | IC50 (TNF assay) |
|---|---|---|---|
| BC19510 | 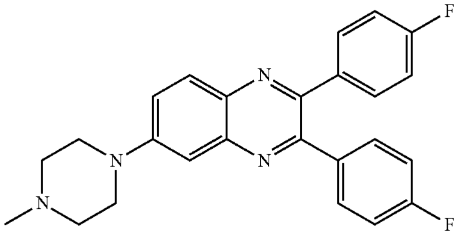 [SMILES: CN1CCN(c2ccc3nc(-c4ccc(F)cc4)c(-c4ccc(F)cc4)nc3c2)CC1] | +++ | + |
| BC19511 | 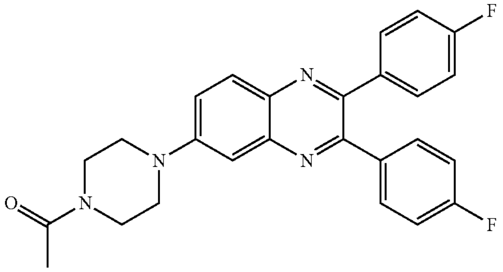 [SMILES: CC(=O)N1CCN(c2ccc3nc(-c4ccc(F)cc4)c(-c4ccc(F)cc4)nc3c2)CC1] | ++++ | + |
| BC20218 | 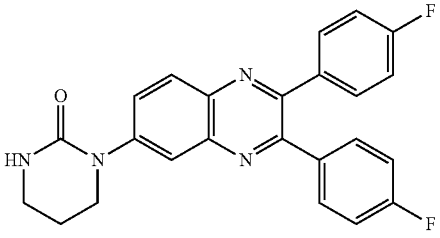 [SMILES: O=C1NCCCN1c1ccc2nc(-c3ccc(F)cc3)c(-c3ccc(F)cc3)nc2c1] | | |
| BC20219 | 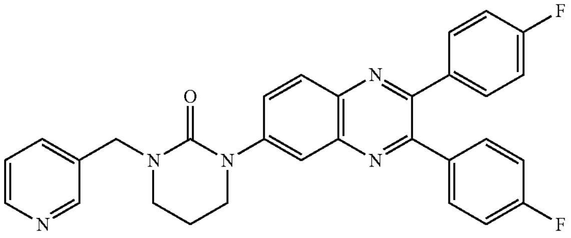 [SMILES: O=C1N(Cc2cccnc2)CCCN1c1ccc2nc(-c3ccc(F)cc3)c(-c3ccc(F)cc3)nc2c1] | | |
| BC20226 | 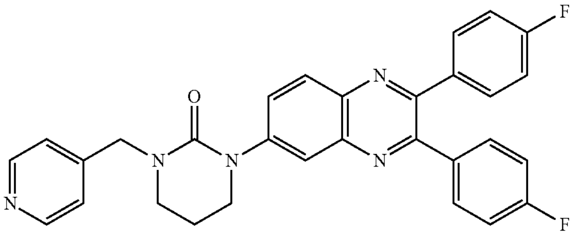 [SMILES: O=C1N(Cc2ccncc2)CCCN1c1ccc2nc(-c3ccc(F)cc3)c(-c3ccc(F)cc3)nc2c1] | | |

TABLE 4f-2-continued
| BC No. | Structure | $IC_{50}$ (NF-κB assay) | $IC_{50}$ (TNF assay) |
|---|---|---|---|
| BC20277 | 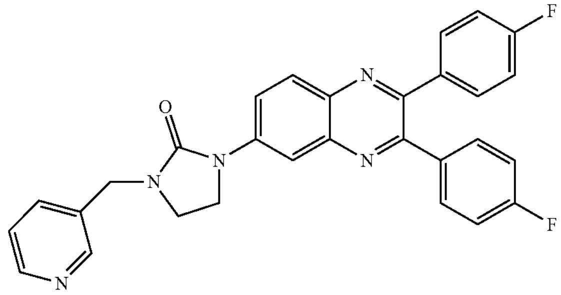 [SMILES: O=C1N(Cc2cccnc2)CCN1c1ccc2nc(-c3ccc(F)cc3)c(-c3ccc(F)cc3)nc2c1] | | |
| BC20291 | 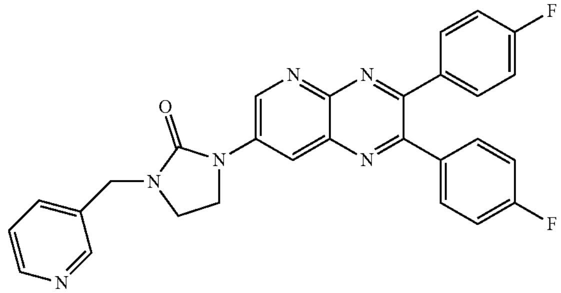 [SMILES: O=C1N(Cc2cccnc2)CCN1c1cnc2nc(-c3ccc(F)cc3)c(-c3ccc(F)cc3)nc2c1] | | |
| BC19563 | 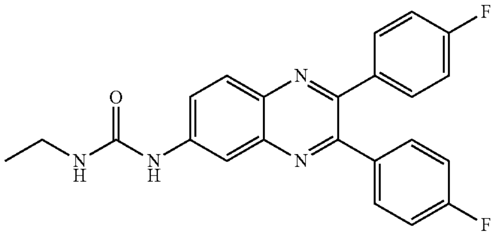 [SMILES: CCNC(=O)Nc1ccc2nc(-c3ccc(F)cc3)c(-c3ccc(F)cc3)nc2c1] | ++++ | + |
| BC20297 | 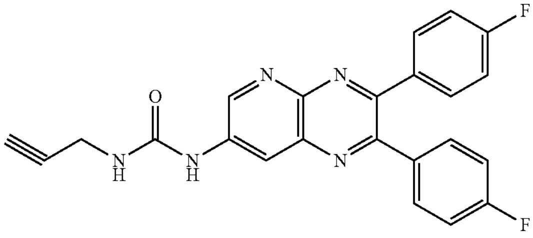 [SMILES: C#CCNC(=O)Nc1cnc2nc(-c3ccc(F)cc3)c(-c3ccc(F)cc3)nc2c1] | | |
| BC19564 | 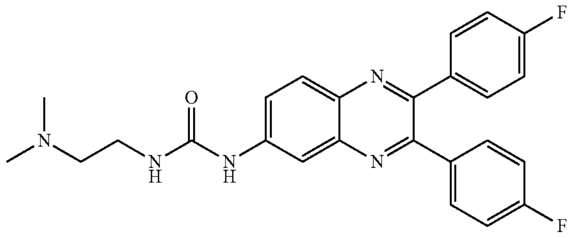 [SMILES: CN(C)CCNC(=O)Nc1ccc2nc(-c3ccc(F)cc3)c(-c3ccc(F)cc3)nc2c1] | ++++ | ++ |

TABLE 4f-2-continued
| BC No. | Structure | $IC_{50}$ (NF-κB assay) | $IC_{50}$ (TNF assay) |
|---|---|---|---|
| BC20312 | 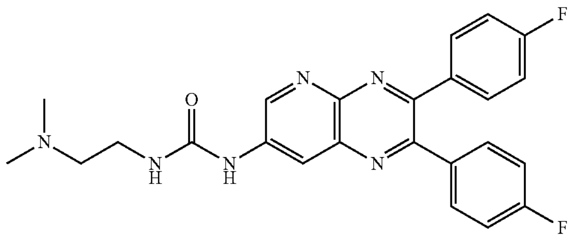 [SMILES: CN(C)CCNC(=O)Nc1cnc2nc(-c3ccc(F)cc3)c(-c3ccc(F)cc3)nc2c1] | | |
| BC19565 | 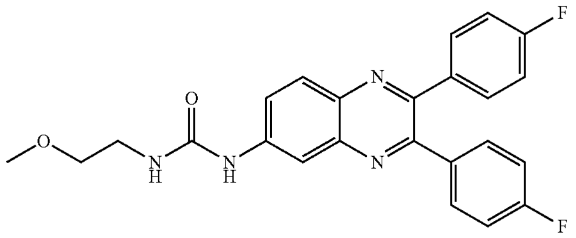 [SMILES: COCCNC(=O)Nc1ccc2nc(-c3ccc(F)cc3)c(-c3ccc(F)cc3)nc2c1] | ++++ | + |
| BC20298 | 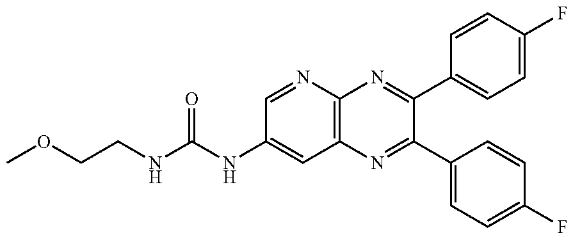 [SMILES: COCCNC(=O)Nc1cnc2nc(-c3ccc(F)cc3)c(-c3ccc(F)cc3)nc2c1] | | |
| BC19566 | 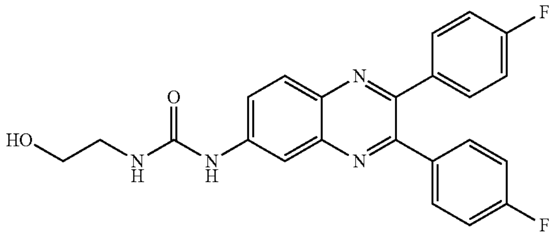 [SMILES: O=C(NCCO)Nc1ccc2nc(-c3ccc(F)cc3)c(-c3ccc(F)cc3)nc2c1] | ++++ | + |
| BC19567 | 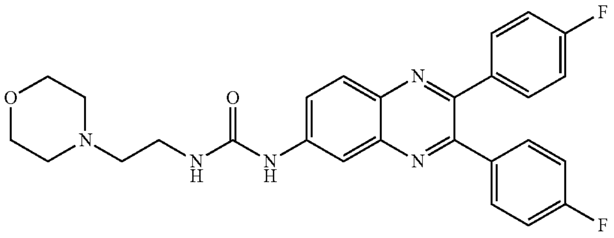 [SMILES: O=C(NCCN1CCOCC1)Nc1ccc2nc(-c3ccc(F)cc3)c(-c3ccc(F)cc3)nc2c1] | +++ | ++ |

TABLE 4f-2-continued
| BC No. | Structure | $IC_{50}$ (NF-κB assay) | $IC_{50}$ (TNF assay) |
|---|---|---|---|
| BC20299 | 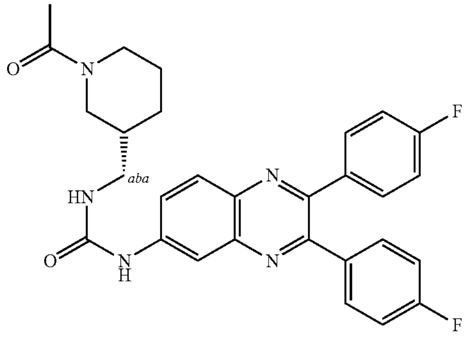 | | |
| BC20300 | 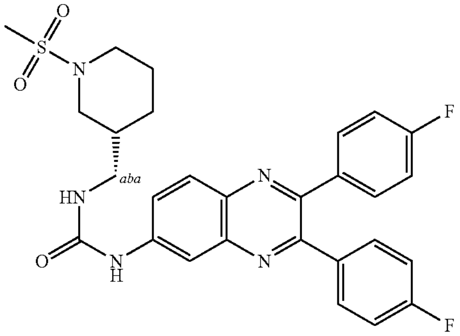 | | |
| BC20217 | 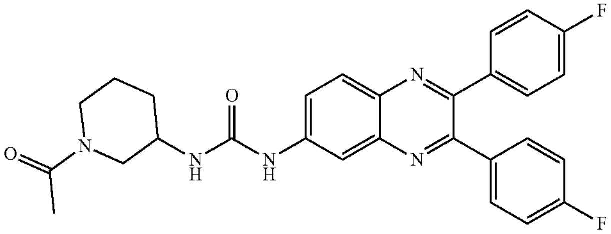 [SMILES: CC(=O)N1CCCC(NC(=O)Nc2ccc3nc(-c4ccc(F)cc4)c(-c4ccc(F)cc4)nc3c2)C1] | | |
| BC20225 | 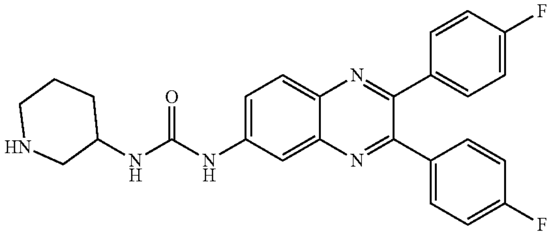 [SMILES: O=C(Nc1ccc2nc(-c3ccc(F)cc3)c(-c3ccc(F)cc3)nc2c1)NC1CCCNC1] | | |
| BC20237 | 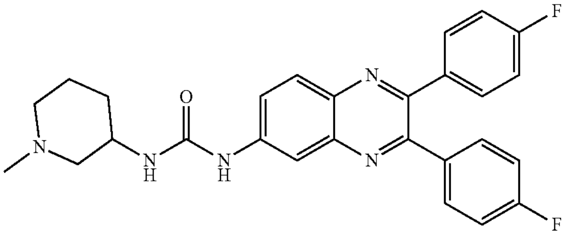 [SMILES: CN1CCCC(NC(=O)Nc2ccc3nc(-c4ccc(F)cc4)c(-c4ccc(F)cc4)nc3c2)C1] | | |

TABLE 4f-2-continued
| BC No. | Structure | $IC_{50}$ (NF-κB assay) | $IC_{50}$ (TNF assay) |
|---|---|---|---|
| BC20238 | 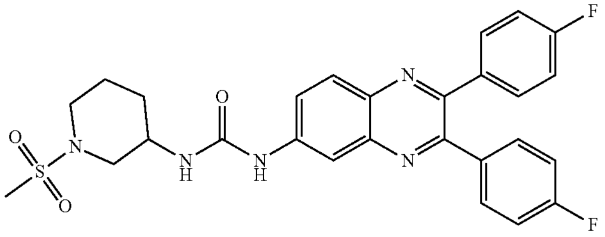 [SMILES: CS(=O)(=O)N1CCCC(NC(=O)Nc2ccc3nc(-c4ccc(F)cc4)c(-c4ccc(F)cc4)nc3c2)C1] | | |
| BC20239 | 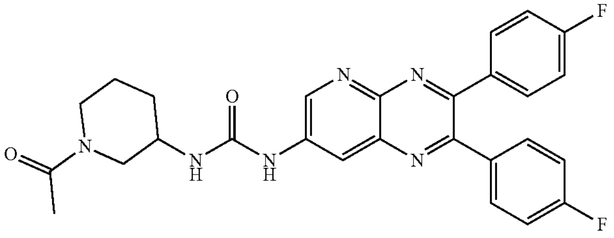 [SMILES: CC(=O)N1CCCC(NC(=O)Nc2cnc3nc(-c4ccc(F)cc4)c(-c4ccc(F)cc4)nc3c2)C1] | | |
| BC20255 | 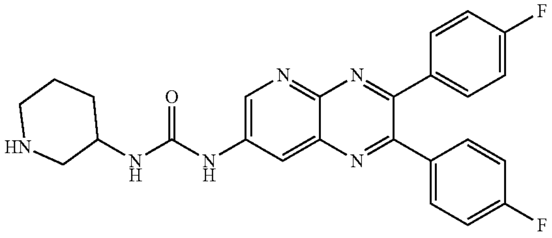 [SMILES: O=C(Nc1cnc2nc(-c3ccc(F)cc3)c(-c3ccc(F)cc3)nc2c1)NC1CCCNC1] | | |
| BC20256 | 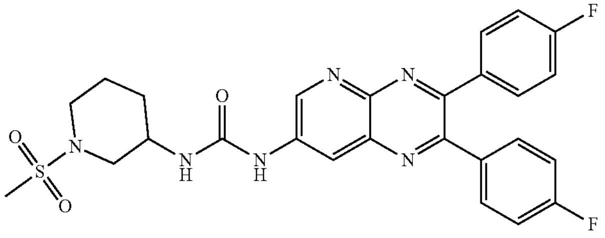 [SMILES: CS(=O)(=O)N1CCCC(NC(=O)Nc2cnc3nc(-c4ccc(F)cc4)c(-c4ccc(F)cc4)nc3c2)C1] | | |
| BC20269 | 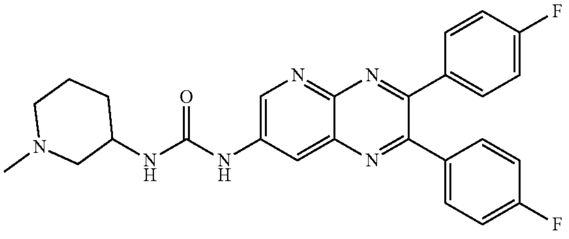 [SMILES: CN1CCCC(NC(=O)Nc2cnc3nc(-c4ccc(F)cc4)c(-c4ccc(F)cc4)nc3c2)C1] | | |

TABLE 4f-2-continued
| BC No. | Structure | $IC_{50}$ (NF-κB assay) | $IC_{50}$ (TNF assay) |
|---|---|---|---|
| BC20293 | 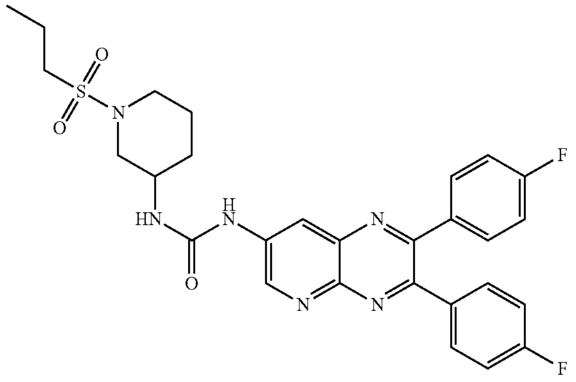 [SMILES: CCCS(=O)(=O)N1CCCC(NC(=O)Nc2cnc3nc(-c4ccc(F)cc4)c(-c4ccc(F)cc4)nc3c2)C1] | | |
| BC19568 | 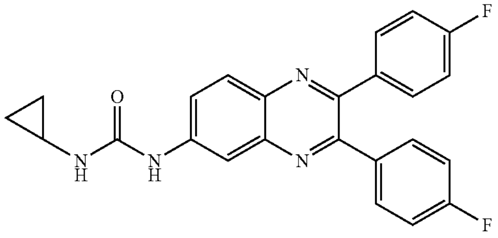 [SMILES: O=C(Nc1ccc2nc(-c3ccc(F)cc3)c(-c3ccc(F)cc3)nc2c1)NC1CC1] | +++ | + |
| BC19569 | 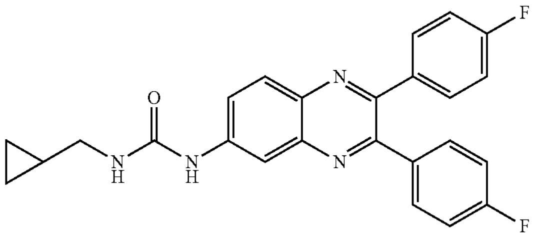 [SMILES: O=C(NCC1CC1)Nc1ccc2nc(-c3ccc(F)cc3)c(-c3ccc(F)cc3)nc2c1] | +++ | + |
| BC19570 | 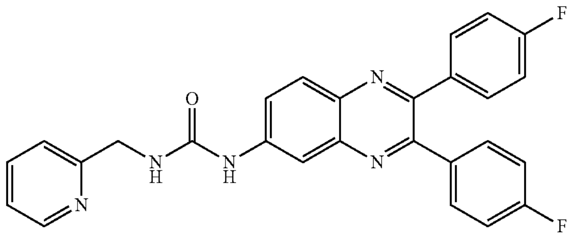 [SMILES: O=C(NCc1ccccn1)Nc1ccc2nc(-c3ccc(F)cc3)c(-c3ccc(F)cc3)nc2c1] | +++ | + |
| BC20207 | 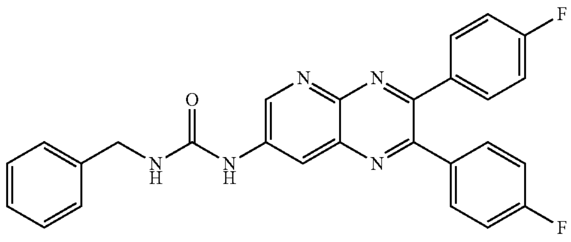 [SMILES: O=C(NCc1ccccc1)Nc1cnc2nc(-c3ccc(F)cc3)c(-c3ccc(F)cc3)nc2c1] | | |

TABLE 4f-2-continued
| BC No. | Structure | IC$_{50}$ (NF-κB assay) | IC$_{50}$ (TNF assay) |
|---|---|---|---|
| BC19571 | 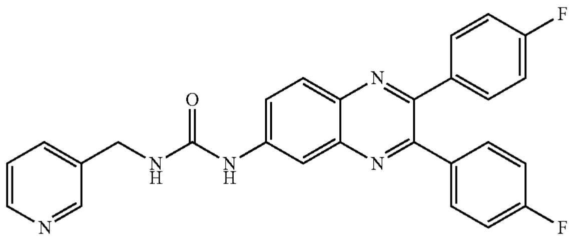 [SMILES: O=C(NCc1cccnc1)Nc1ccc2nc(-c3ccc(F)cc3)c(-c3ccc(F)cc3)nc2c1] | +++ | ++ |
| BC20310 | 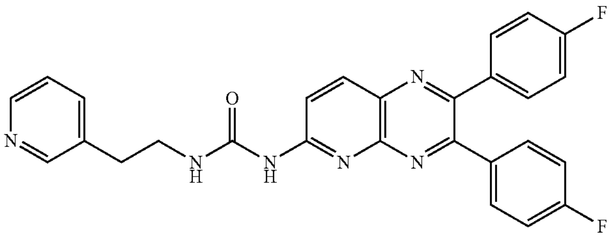 [SMILES: O=C(NCCc1cccnc1)Nc1ccc2nc(-c3ccc(F)cc3)c(-c3ccc(F)cc3)nc2n1] | | |
| BC20311 | 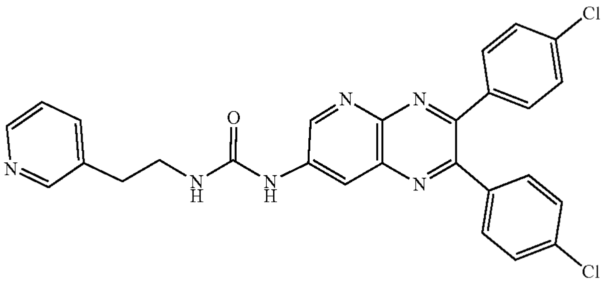 [SMILES: O=C(NCCc1cccnc1)Nc1cnc2nc(-c3ccc(Cl)cc3)c(-c3ccc(Cl)cc3)nc2c1] | | |
| BC20224 | 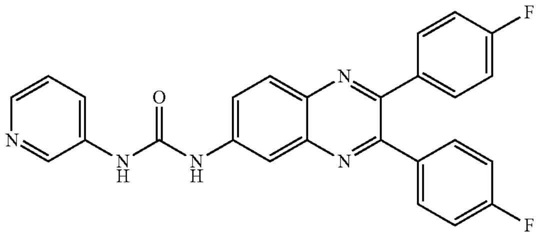 [SMILES: O=C(Nc1cccnc1)Nc1ccc2nc(-c3ccc(F)cc3)c(-c3ccc(F)cc3)nc2c1] | | |
| BC20254 | 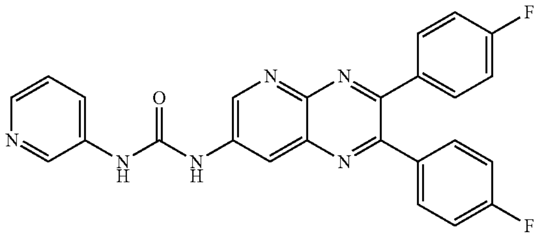 [SMILES: O=C(Nc1cccnc1)Nc1cnc2nc(-c3ccc(F)cc3)c(-c3ccc(F)cc3)nc2c1] | | |

TABLE 4f-2-continued
| BC No. | Structure | $IC_{50}$ (NF-κB assay) | $IC_{50}$ (TNF assay) |
|---|---|---|---|
| BC20213 | 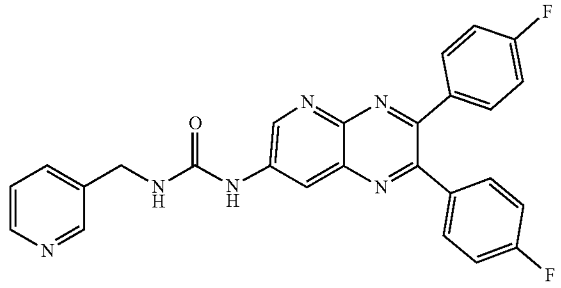 [SMILES: O=C(NCc1cccnc1)Nc1cnc2nc(-c3ccc(F)cc3)c(-c3ccc(F)cc3)nc2c1] | | |
| BC20316 | 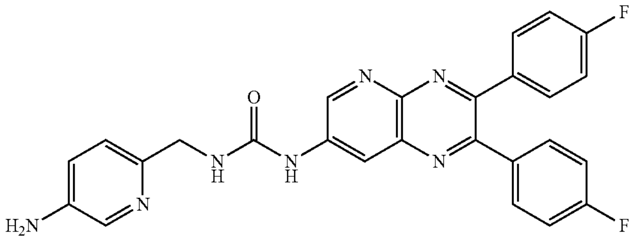 [SMILES: Nc1ccc(CNC(=O)Nc2cnc3nc(-c4ccc(F)cc4)c(-c4ccc(F)cc4)nc3c2)nc1] | | |
| BC20216 | 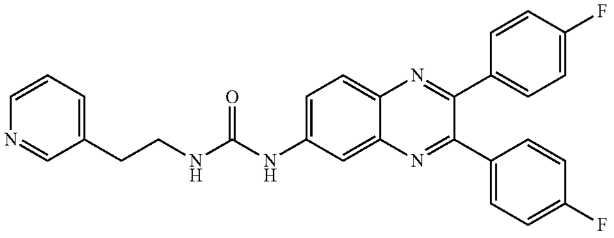 [SMILES: O=C(NCCc1cccnc1)Nc1ccc2nc(-c3ccc(F)cc3)c(-c3ccc(F)cc3)nc2c1] | | |
| BC20268 | 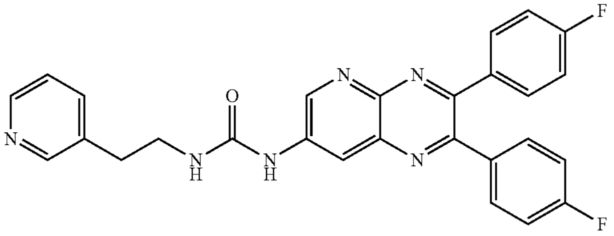 [SMILES: O=C(NCCc1cccnc1)Nc1cnc2nc(-c3ccc(F)cc3)c(-c3ccc(F)cc3)nc2c1] | | |
| BC20314 | 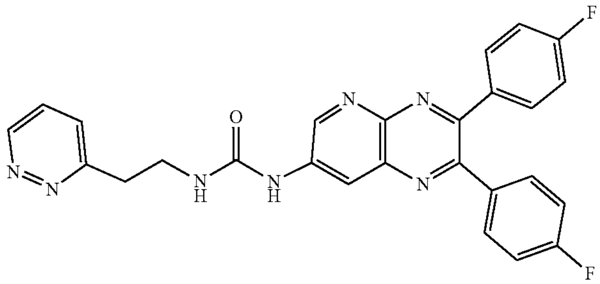 [SMILES: O=C(NCCc1cccnn1)Nc1cnc2nc(-c3ccc(F)cc3)c(-c3ccc(F)cc3)nc2c1] | | |

TABLE 4f-2-continued
| BC No. | Structure | IC50 (NF-κB assay) | IC50 (TNF assay) |
|---|---|---|---|
| BC20315 | 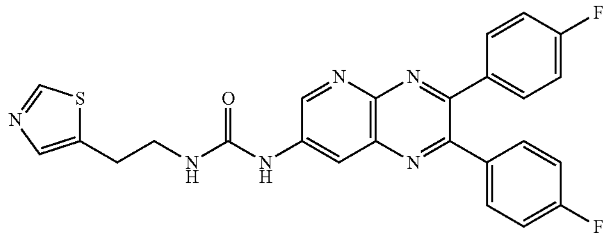 [SMILES: O=C(NCCc1cncs1)Nc1cnc2nc(-c3ccc(F)cc3)c(-c3ccc(F)cc3)nc2c1] | | |
| BC20318 | 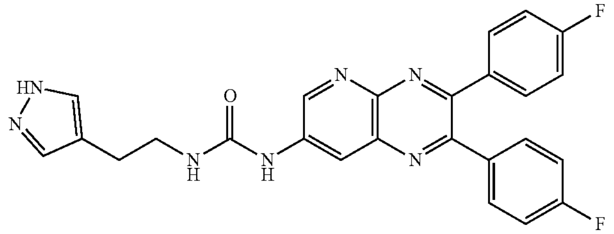 [SMILES: O=C(NCCc1cn[nH]c1)Nc1cnc2nc(-c3ccc(F)cc3)c(-c3ccc(F)cc3)nc2c1] | | |
| BC20320 | 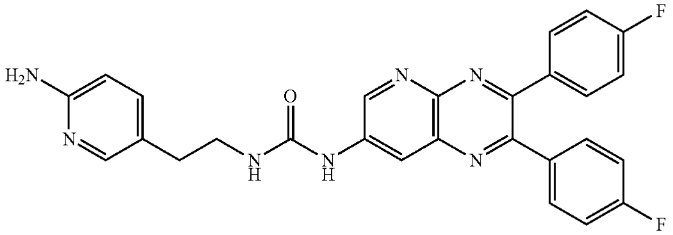 [SMILES: Nc1ccc(CCNC(=O)Nc2cnc3nc(-c4ccc(F)cc4)c(-c4ccc(F)cc4)nc3c2)cn1] | | |
| BC20331 | 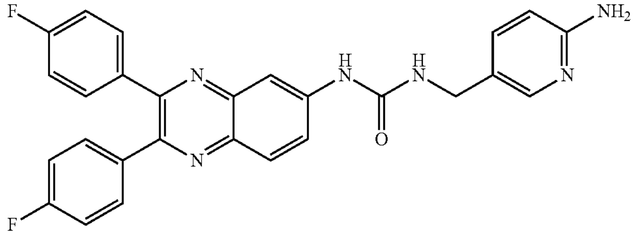 [SMILES: Nc1ccc(CNC(=O)Nc2ccc3nc(-c4ccc(F)cc4)c(-c4ccc(F)cc4)nc3c2)cn1] | | |
| BC20319 | 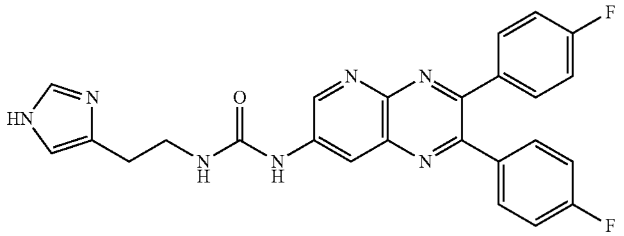 [SMILES: O=C(NCCc1c[nH]cn1)Nc1cnc2nc(-c3ccc(F)cc3)c(-c3ccc(F)cc3)nc2c1] | | |
| BC19572 | 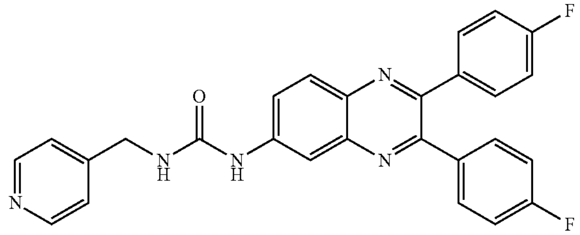 [SMILES: O=C(NCc1ccncc1)Nc1ccc2nc(-c3ccc(F)cc3)c(-c3ccc(F)cc3)nc2c1] | +++ | + |

TABLE 4f-2-continued
| BC No. | Structure | $IC_{50}$ (NF-κB assay) | $IC_{50}$ (TNF assay) |
|---|---|---|---|
| BC19573 | 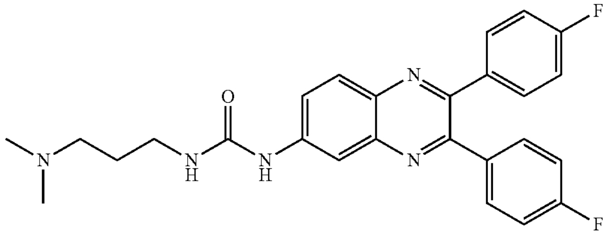 [SMILES: CN(C)CCCNC(=O)Nc1ccc2nc(-c3ccc(F)cc3)c(-c3ccc(F)cc3)nc2c1] | +++ | +++ |
| BC19574 | 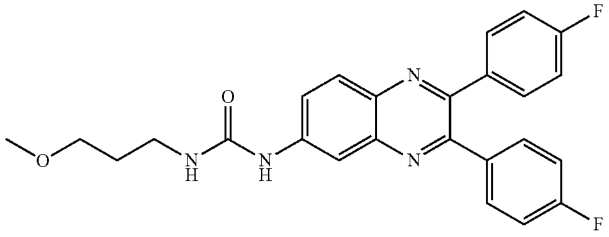 [SMILES: COCCCNC(=O)Nc1ccc2nc(-c3ccc(F)cc3)c(-c3ccc(F)cc3)nc2c1] | +++ | + |
| BC19575 | 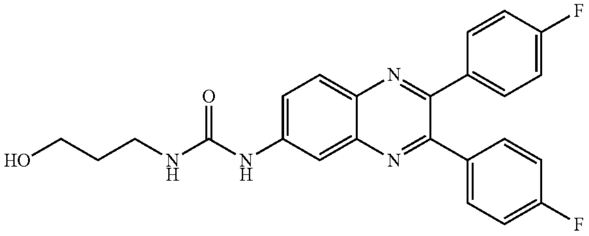 [SMILES: O=C(NCCCO)Nc1ccc2nc(-c3ccc(F)cc3)c(-c3ccc(F)cc3)nc2c1] | +++ | + |
| BC19576 | 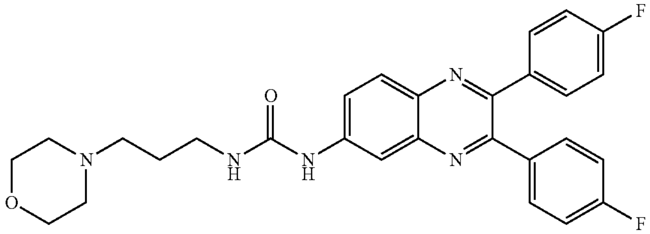 [SMILES: O=C(NCCCN1CCOCC1)Nc1ccc2nc(-c3ccc(F)cc3)c(-c3ccc(F)cc3)nc2c1] | +++ | + |
| BC19616 | 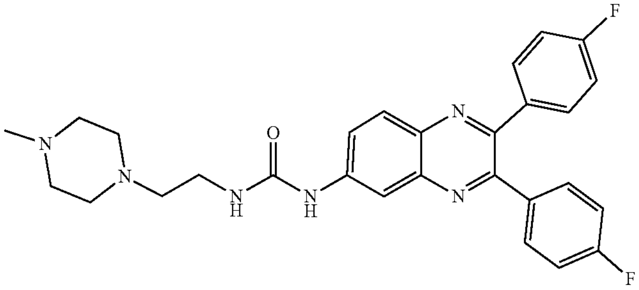 [SMILES: CN1CCN(CCNC(=O)Nc2ccc3nc(-c4ccc(F)cc4)c(-c4ccc(F)cc4)nc3c2)CC1] | +++ | ++ |
| BC19617 | 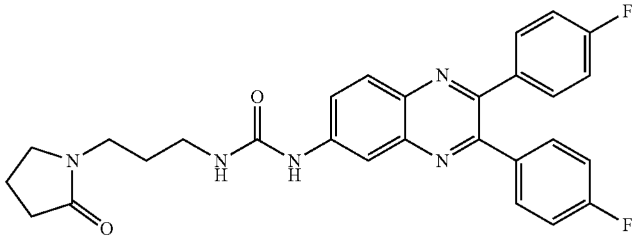 [SMILES: O=C(NCCCN1CCCC1=O)Nc1ccc2nc(-c3ccc(F)cc3)c(-c3ccc(F)cc3)nc2c1] | +++ | + |

TABLE 4g
| BC No. | Structure | IC50 (NF-κB assay) | IC50 (TNF assay) |
|---|---|---|---|
| BC19504 | 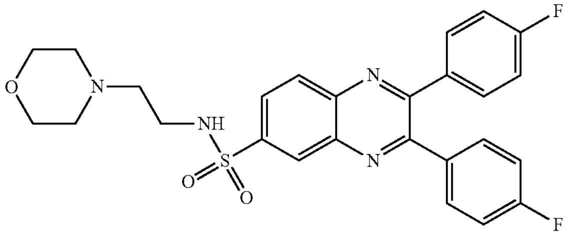 [SMILES: O=S(=O)(NCCN1CCOCC1)c1ccc2nc(-c3ccc(F)cc3)c(-c3ccc(F)cc3)nc2c1] | +++ | + |
| BC19505 | 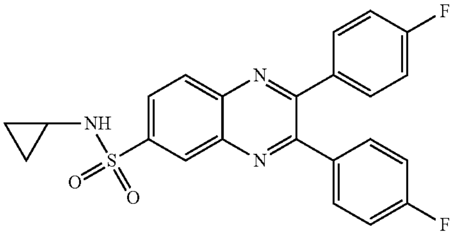 [SMILES: O=S(=O)(NC1CC1)c1ccc2nc(-c3ccc(F)cc3)c(-c3ccc(F)cc3)nc2c1] | +++ | + |
| BC19506 | 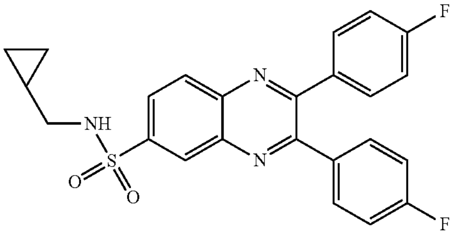 [SMILES: O=S(=O)(NCC1CC1)c1ccc2nc(-c3ccc(F)cc3)c(-c3ccc(F)cc3)nc2c1] | +++ | + |
| BC19507 | 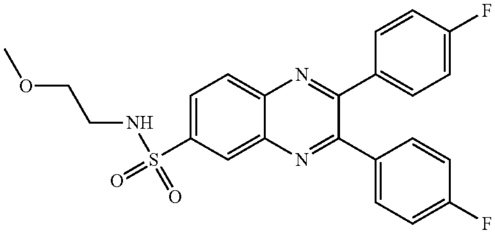 [SMILES: COCCNS(=O)(=O)c1ccc2nc(-c3ccc(F)cc3)c(-c3ccc(F)cc3)nc2c1] | ++++ | + |
| BC19508 | 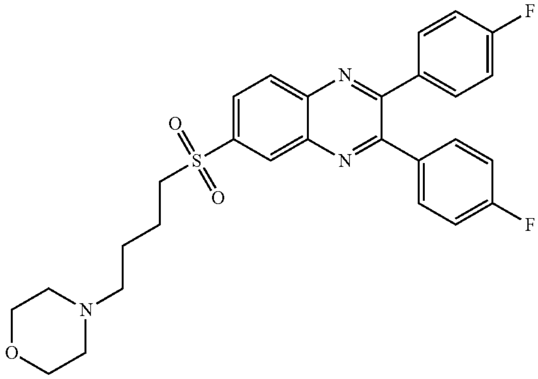 [SMILES: O=S(=O)(CCCCN1CCOCC1)c1ccc2nc(-c3ccc(F)cc3)c(-c3ccc(F)cc3)nc2c1] | +++ | ++ |

TABLE 4g-continued
| BC No. | Structure | $IC_{50}$ (NF-κB assay) | $IC_{50}$ (TNF assay) |
|---|---|---|---|
| BC19509 | 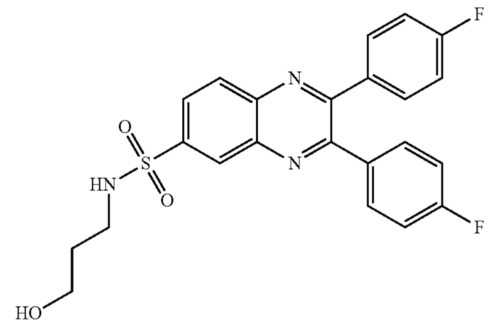 [SMILES: O=S(=O)(NCCCO)c1ccc2nc(-c3ccc(F)cc3)c(-c3ccc(F)cc3)nc2c1] | ++++ | + |
| BC19554 | 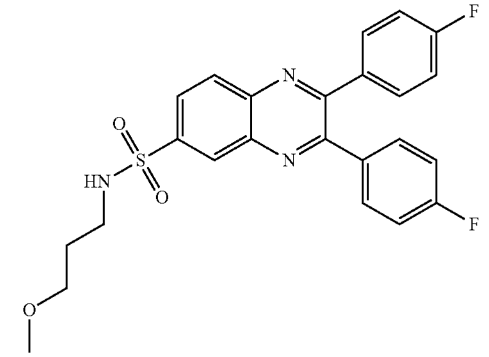 [SMILES: COCCCNS(=O)(=O)c1ccc2nc(-c3ccc(F)cc3)c(-c3ccc(F)cc3)nc2c1] | ++++ | + |
| BC19555 | 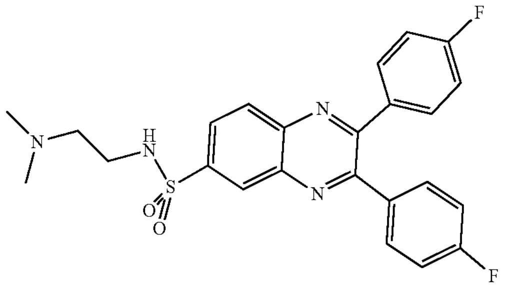 [SMILES: CN(C)CCNS(=O)(=O)c1ccc2nc(-c3ccc(F)cc3)c(-c3ccc(F)cc3)nc2c1] | ++++ | ++ |
| BC19556 | 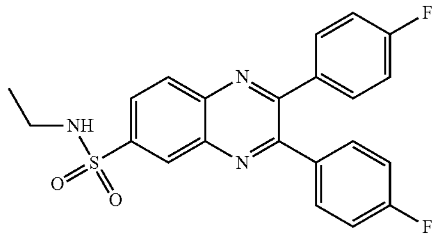 [SMILES: CCNS(=O)(=O)c1ccc2nc(-c3ccc(F)cc3)c(-c3ccc(F)cc3)nc2c1] | +++ | + |
| BC19557 | 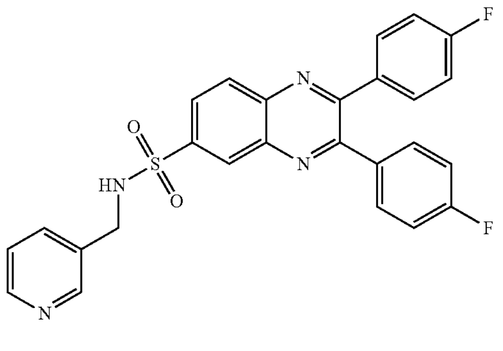 [SMILES: O=S(=O)(NCc1cccnc1)c1ccc2nc(-c3ccc(F)cc3)c(-c3ccc(F)cc3)nc2c1] | ++++ | + |

TABLE 4g-continued
| BC No. | Structure | $IC_{50}$ (NF-κB assay) | $IC_{50}$ (TNF assay) |
|---|---|---|---|
| BC19558 | 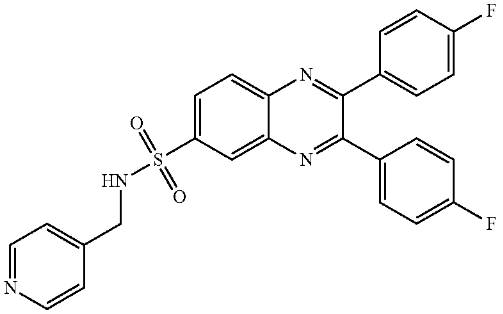 [SMILES: O=S(=O)(NCc1ccncc1)c1ccc2nc(-c3ccc(F)cc3)c(-c3ccc(F)cc3)nc2c1] | +++ | + |
| BC19559 | 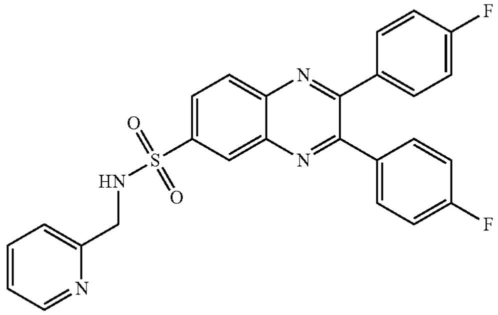 [SMILES: O=S(=O)(NCc1ccccn1)c1ccc2nc(-c3ccc(F)cc3)c(-c3ccc(F)cc3)nc2c1] | ++++ | + |
| BC19560 | 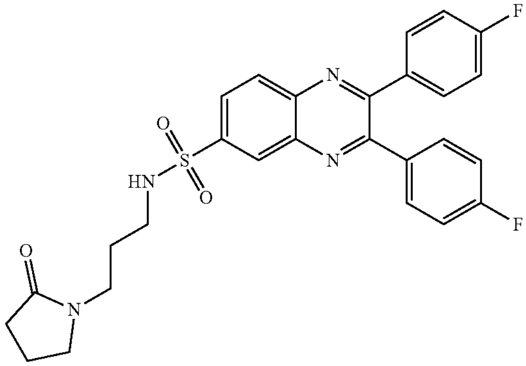 [SMILES: O=C1CCCN1CCCNS(=O)(=O)c1ccc2nc(-c3ccc(F)cc3)c(-c3ccc(F)cc3)nc2c1] | ++++ | + |
| BC19561 | 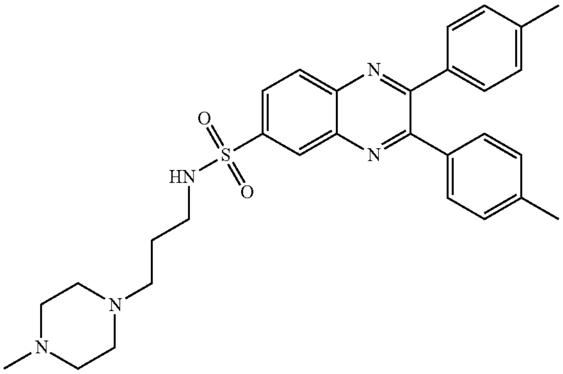 | +++ | + |

TABLE 4g-continued
| BC No. | Structure | IC50 (NF-κB assay) | IC50 (TNF assay) |
|---|---|---|---|
| BC19562 | 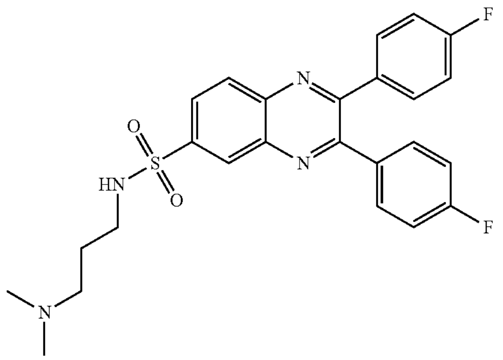 [SMILES: CN(C)CCCNS(=O)(=O)c1ccc2nc(-c3ccc(F)cc3)c(-c3ccc(F)cc3)nc2c1] | +++ | ++ |
TABLE 17
| BC No. | Structure | IC50 (NF-κB assay) | IC50 (TNF assay) |
|---|---|---|---|
| BC19663 | 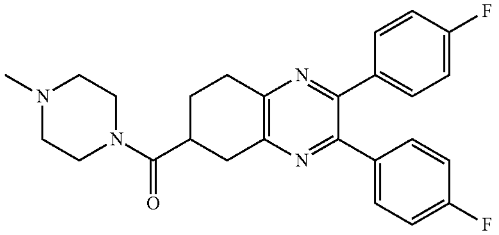 [SMILES: CN1CCN(C(=O)C2CCc3nc(-c4ccc(F)cc4)c(-c4ccc(F)cc4)nc3C2)CC1] | +++ | + |
| BC19723 | 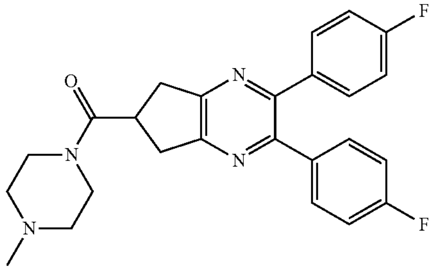 [SMILES: CN1CCN(C(=O)C2Cc3nc(-c4ccc(F)cc4)c(-c4ccc(F)cc4)nc3C2)CC1] | +++ | + |
NUMBERED PARAGRAPHS
1. A method for inhibiting NF-κB activity within a cell within a mammal, wherein said method comprises administering, to said mammal, an effective amount of a compound of Formula (Ia):

(Ia)

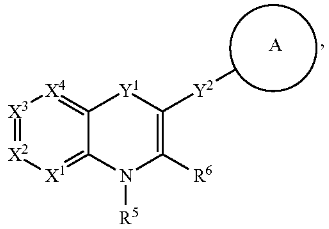

or a pharmaceutically acceptable salt thereof, wherein:

$Y^1$ is selected from C(O) and $S(O)_2$;

$Y^2$ is selected from C(O) and $S(O)_2$;

$X^1$ is selected from N and $CR^1$;

$X^2$ is selected from N and $CR^2$;

$X^3$ is selected from N and $CR^3$;

$X^4$ is selected from N and $CR^4$;

provided that no more than two of $X^1$, $X^2$, $X^3$, and $X^4$ are N;

each of $R^1$, $R^2$, $R^3$, $R^4$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^5$ is selected from H, $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $R^8$;

each $R^8$ is independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$.

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of paragraph 1, wherein $Y^1$ is C(O).

3. The method of paragraph 1, wherein $Y^1$ is $S(O)_2$.

4. The method of any one of paragraphs 1-3, wherein $Y^2$ is C(O).

5. The method of any one of paragraphs 1-3, wherein $Y^2$ is $S(O)_2$.

6. The method of paragraph 1, wherein the compound of Formula (Ia) has formula:

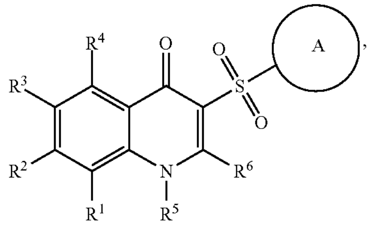

or a pharmaceutically acceptable salt thereof.

7. The method of paragraph 1, wherein the compound of Formula (Ia) has formula:

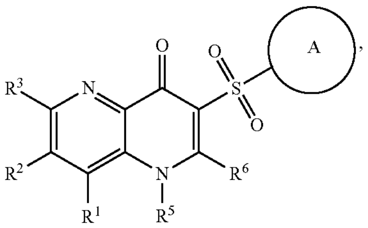

or a pharmaceutically acceptable salt thereof.

8. The method of paragraph 1, wherein the compound of Formula (Ia) has formula:

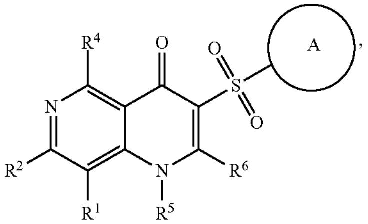

or a pharmaceutically acceptable salt thereof.

9. The method of paragraph 1, wherein the compound of Formula (Ia) has formula:

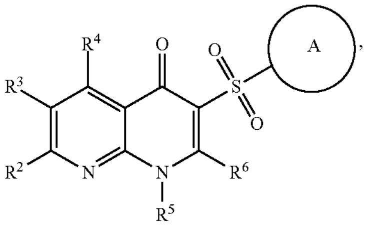

or a pharmaceutically acceptable salt thereof.

10. The method of any one of paragraphs 1-9, wherein ring A is selected from $C_{6-10}$ aryl and 5-10 membered heteroaryl, each of which is optionally substituted with 1-6 substituents independently selected from $R^A$.

11. The method of any one of paragraphs 1-9, wherein ring A is $C_{6-10}$ aryl, optionally substituted with 1-5 substituents independently selected from $R^A$.

12. The method of any one of paragraphs 1-9, wherein ring A is 5-10 membered heteroaryl, optionally substituted with 1-6 substituents independently selected from $R^A$.

13. The method of any one of paragraphs 1-9, wherein ring A is selected from any one of the following moieties:

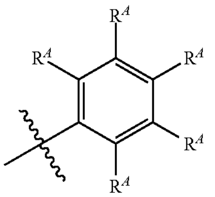

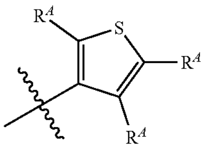

-continued

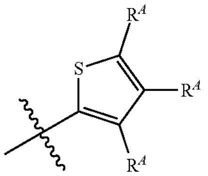

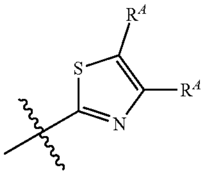

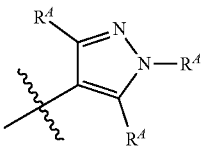

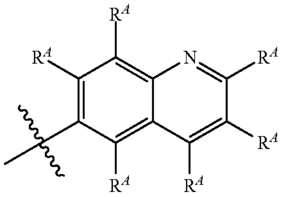

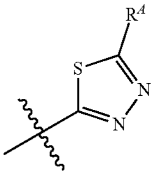

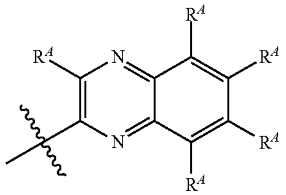

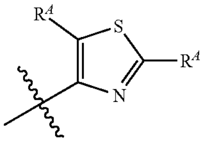

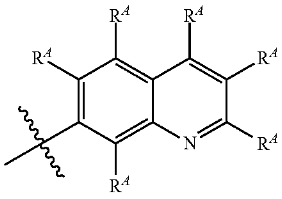

14. The method of paragraph 1, wherein the compound of Formula (Ia) is selected from any one of the following compounds:

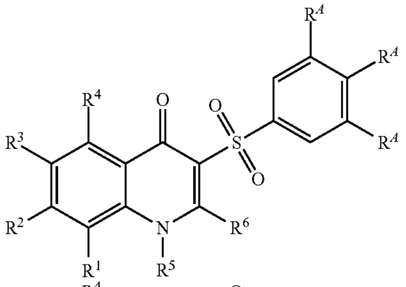

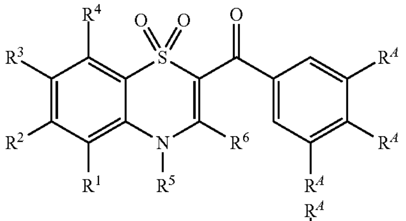

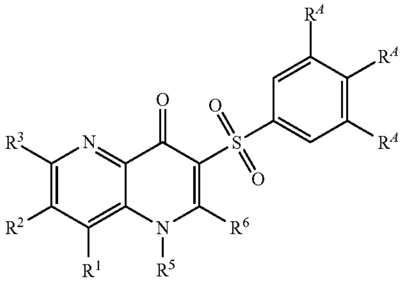

-continued

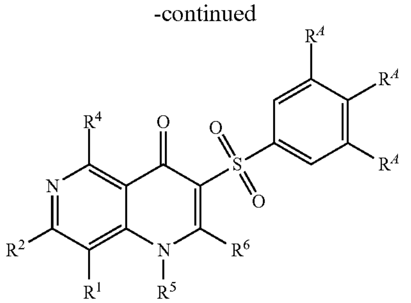

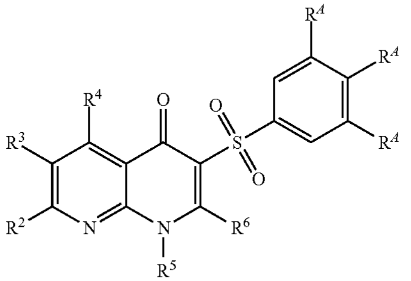

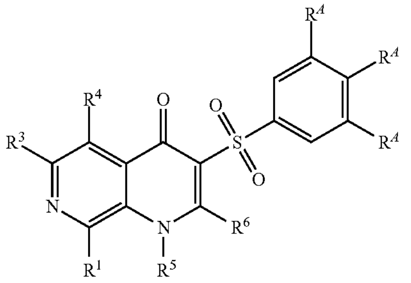

or a pharmaceutically acceptable salt thereof.

15. The method of any one of paragraphs 1-14, wherein each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^9$.

16. The method of any one of paragraphs 1-15, wherein each $R^9$ is independently selected from CN, $NO_2$, OH, $C_{1-6}$ alkoxy, $C(O)NH_2$, C(O)OH, $NH_2$, and $S(O)_2NH_2$.

17. The method of any one of paragraphs 1-15, wherein each $R^A$ is independently selected from H, halo, CN, $C_{1-6}$ alkyl, and $C_{1-6}$ alkoxy.

18. The method of any one of paragraphs 1-17, wherein each of $R^1$, $R^2$, $R^3$, $R^4$, and $R^6$, if present in the compound of Formula (Ia), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^7$.

19. The method of any one of paragraphs 1-17, wherein each of $R^1$, $R^2$, $R^3$, $R^4$, and $R^6$, if present in the compound of Formula (Ia), is independently selected from H, halo, CN, $C_{1-6}$ alkyl, and $OR^{a1}$.

20. The method of any one of paragraphs 1-17, wherein:

$R^1$, if present in the compound of Formula (Ia), is selected from H, halo, $C_{1-6}$ alkyl, and $C_{1-6}$ alkoxy;

$R^2$, if present in the compound of Formula (Ia), is selected from H, CN, halo, $C_{1-6}$ alkoxy, and $C_{1-6}$ alkyl;

$R^3$, if present in the compound of Formula (Ia), is selected from H, CN, halo, $C_{1-6}$ alkoxy, and $C_{1-6}$ alkyl;

$R^4$, if present in the compound of Formula (Ia), is selected from H, halo, $C_{1-6}$ alkyl, and $C_{1-6}$ alkoxy; and $R^6$, if present in the compound of Formula (Ia), is selected from H and OH.

21. The method of any one of paragraphs 1-18, wherein $R^7$ is selected from CN, $NO_2$, OH, $C_{1-6}$ alkoxy, $C(O)NH_2$, C(O)OH, $NH_2$, and $S(O)_2NH_2$.

22. The method of any one of paragraphs 1-21, wherein $R^5$ is selected from H, $C_{1-6}$ alkyl, and $Cy^1$, wherein said $C_{1-6}$ alkyl is optionally substituted with 1, 2, or 3 substituents independently selected from $R^8$.

23. The method of any one of paragraphs 1-22, wherein $R^8$ is selected from $Cy^1$, CN, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$.

24. The method of paragraph 23, wherein $R^8$ is selected from $Cy^1$ and $C(O)NR^{c1}R^{d1}$.

25. The method of any one of paragraphs 1-21, wherein $R^5$ is $Cy^1$.

26. The method of any one of paragraphs 1-21, wherein $R^5$ is $C_{1-6}$ alkyl, optionally substituted with $Cy^1$.

27. The method of any one of paragraphs 1-26, wherein $Cy^1$ is selected from $C_{6-10}$ aryl and 5-10 membered heteroaryl, each of which is optionally substituted with 1, 2, or 3 substituents independently selected from $R^{Cy1}$.

28. The method of any one of paragraphs 1-26, wherein $Cy^1$ is $C_{6-10}$ aryl, optionally substituted with $R^{Cy1}$.

29. The method of any one of paragraphs 1-28, wherein $R^{Cy1}$ is selected from halo, CN, $NO_2$, $C_{1-6}$ alkyl, $C_{1-6}$ alkoxy, and $C_{1-6}$ haloalkyl.

30. The method of any one of paragraphs 1-28, wherein $Cy^1$ is $C_{6-10}$ aryl, optionally substituted with halo.

31. The method of any one of paragraphs 1-21, wherein $R^5$ is H.

32. The method of any one of paragraphs 1-21, wherein $R^5$ is $C_{1-6}$ alkyl, optionally substituted with $C(O)NR^{c1}R^{d1}$.

33. The method of any one of paragraphs 1-32, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$.

34. The method of any one of paragraphs 1-32, wherein each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^g$.

35. The method of any one of paragraphs 1-34, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

36. The method of any one of paragraphs 1-34, wherein each $R^g$ is independently selected from halo and $C_{1-6}$ alkyl.

37. The method of any one of paragraphs 1-14, wherein:

each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

each $R^9$ is independently selected from CN, $NO_2$, OH, $C_{1-6}$ alkoxy, $C(O)NH_2$, C(O)OH, $NH_2$, and $S(O)_2NH_2$;

each of $R^1$, $R^2$, $R^3$, $R^4$, and $R^6$, if present in the compound of Formula (Ia), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^7$;

$R^7$ is selected from CN, $NO_2$, OH, $C_{1-6}$ alkoxy, $C(O)NH_2$, C(O)OH, $NH_2$, and $S(O)_2NH_2$;

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$, CN, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$;

each $Cy^1$ is independently selected from $C_{6-10}$ aryl and 5-10 membered heteroaryl, each of which is optionally substituted with 1, 2, or 3 substituents independently selected from $R^{Cy1}$;

each $R^{Cy1}$ is independently selected from halo, CN, $NO_2$, $C_{1-6}$ alkyl, $C_{1-6}$ alkoxy, and $C_{1-6}$ haloalkyl;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

38. The method of any one of paragraphs 1-14, wherein:

each $R^A$ is independently selected from H, halo, CN, $C_{1-6}$ alkyl, and $C_{1-6}$ alkoxy;

each of $R^1$, $R^2$, $R^3$, $R^4$, and $R^6$, if present in the compound of Formula (Ia), is independently selected from H, halo, CN, $C_{1-6}$ alkyl, and $OR^{a1}$;

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$ and $C(O)NR^{c1}R^{d1}$, $Cy^1$ is $C_{6-10}$ aryl, optionally substituted with $R^{Cy1}$;

$R^{Cy1}$ is selected from halo, CN, $NO_2$, $C_{1-6}$ alkyl, $C_{1-6}$ alkoxy, and $C_{1-6}$ haloalkyl;

each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$; and wherein each $R^g$ is independently selected from halo and $C_{1-6}$ alkyl.

39. The method of any one of paragraphs 1-14, wherein:

each $R^A$ is independently selected from H, halo, CN, $C_{1-6}$ alkyl, and $C_{1-6}$ alkoxy;

$R^1$, if present in the compound of Formula (Ia), is selected from H, halo, $C_{1-6}$ alkyl, and $C_{1-6}$ alkoxy;

$R^2$, if present in the compound of Formula (Ia), is selected from H, CN, halo, $C_{1-6}$ alkoxy, and $C_{1-6}$ alkyl;

$R^3$, if present in the compound of Formula (Ia), is selected from H, CN, halo, $C_{1-6}$ alkoxy, and $C_{1-6}$ alkyl;

$R^4$, if present in the compound of Formula (Ia), is selected from H, halo, $C_{1-6}$ alkyl, and $C_{1-6}$ alkoxy; and $R^6$, if present in the compound of Formula (Ia), is selected from H and OH.

$R^5$ is selected from H, $C_{1-6}$ alkyl, and $Cy^1$, wherein said $C_{1-6}$ alkyl is optionally substituted with 1, 2, or 3 substituents independently selected from $R^8$;

each $R^8$ is independently selected from $Cy^1$ and $C(O)NR^{c1}R^{d1}$;

$Cy^1$ is $C_{6-10}$ aryl, optionally substituted with halo;

each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$; and wherein each $R^g$ is independently selected from halo and $C_{1-6}$ alkyl.

40. The method of any one of paragraphs 1-39, wherein the compound of Formula (Ia) is selected from any one of the compounds of Table 1a, Table 1d, or Table 1e, or a pharmaceutically acceptable salt thereof. 41. A compound of Formula (Ib):

(Ib)

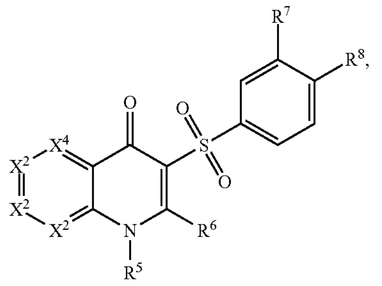

or a pharmaceutically acceptable salt thereof, wherein:

$X^1$ is selected from N and $CR^1$;

$X^2$ is selected from N and $CR^2$;

$X^3$ is selected from N and $CR^3$;

$X^4$ is selected from N and $CR^4$;

provided that at least one of $X^1$, $X^2$, $X^3$, and $X^4$ is N;

each of $R^1$, $R^2$, $R^3$, $R^4$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^5$ is selected from H, $C_{1-6}$ alkyl, $C_{1-6}$ haloalkyl, $C_{2-6}$ alkenyl, $C_{2-6}$ alkynyl, and $Cy^1$, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from $Cy^1$, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

42. The compound of paragraph 41, wherein the compound of Formula (Ib) has formula:

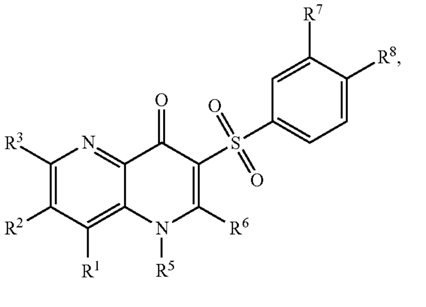

or a pharmaceutically acceptable salt thereof.

43. The compound of paragraph 41, wherein the compound of Formula (Ib) is selected from:

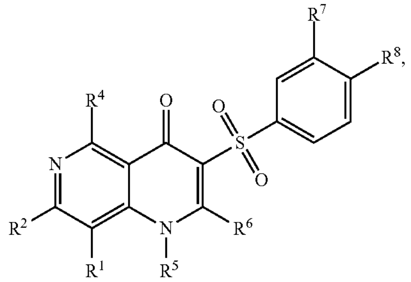

and

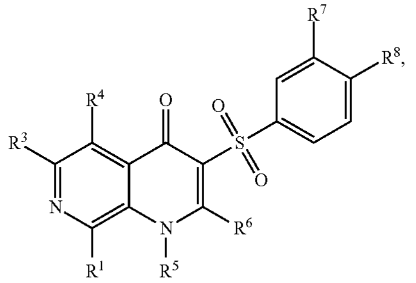

or a pharmaceutically acceptable salt thereof.

44. The compound of paragraph 41, wherein the compound of Formula (Ib) has formula:

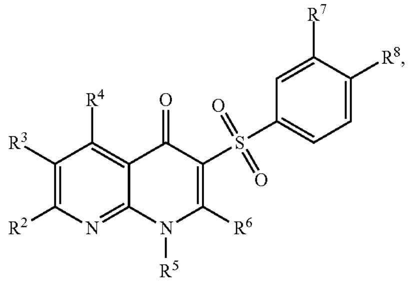

or a pharmaceutically acceptable salt thereof.

45. The compound of any one of paragraphs 41-44, wherein $R^7$ and $R^8$ are each independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$.

46. The compound of any one of paragraphs 41-44, wherein $R^7$ and $R^8$ are each independently selected from H, halo, and $C_{1-6}$ alkyl.

47. The compound of any one of paragraphs 41-46, wherein each of $R^1$, $R^2$, $R^3$, $R^4$, and $R^6$, if present in the compound of Formula (Ib), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$.

48. The compound of any one of paragraphs 41-46, wherein each of $R^1$, $R^2$, $R^3$, $R^4$, and $R^6$, if present in the compound of Formula (Ib), is independently selected from H, halo, and $OR^{a1}$.

49. The compound of any one of paragraphs 41-46, wherein:

each of $R^1$, $R^2$, $R^3$, and $R^4$, if present in the compound of Formula (Ib), is independently selected from H, halo, and $C_{1-6}$ alkoxy; and $R^6$ is selected from H and OH.

50. The compound of any one of paragraphs 41-49, wherein $R^5$ is selected from H, $C_{1-6}$ alkyl, and $Cy^1$, wherein said $C_{1-6}$ alkyl is optionally substituted with 1, 2, or 3 substituents independently selected from $R^{10}$.

51. The compound of any one of paragraphs 41-49, wherein $R^5$ is selected from H and $C_{1-6}$ alkyl.

52. The compound of any one of paragraphs 41-49, wherein $R^5$ is H.

53. The compound of any one of paragraphs 41-52, wherein each $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^g$.

54. The compound of any one of paragraphs 41-52, wherein each $R^{a1}$, $R^{b1}$, $R^{c1}$, and $R^{d1}$ is independently selected from H and $C_{1-6}$ alkyl.

55. The compound of paragraph 41, wherein:

$R^7$ and $R^8$ are each independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{11}$;

each of $R^1$, $R^2$, $R^3$, $R^4$, and $R^6$, if present in the compound of Formula (Ib), is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

$R^5$ is selected from H, $C_{1-6}$ alkyl, and $Cy^1$, wherein said $C_{1-6}$ alkyl is optionally substituted with 1, 2, or 3 substituents independently selected from $R^{10}$; and $R^{a1}$, $R^{b1}$, $R^{c1}$, and $R^{d1}$ is independently selected from H, $C_{1-6}$ alkyl, and $C_{6-10}$ aryl, wherein said $C_{1-6}$ alkyl and $C_{6-10}$ aryl are optionally substituted with 1, 2, or 3 substituents independently selected from $R^8$.

56. The compound of paragraph 41, wherein:

$R^7$ and $R^8$ are each independently selected from H, halo, and $C_{1-6}$ alkyl; each of $R^1$, $R^2$, $R^3$, and $R^4$, if present in the compound of Formula (Ib), is independently selected from H, halo, and $C_{1-6}$ alkoxy;

$R^6$ is selected from H and OH;

$R^5$ is selected from H and $C_{1-6}$ alkyl; and each $R^{a1}$, $R^{b1}$, $R^{c1}$, and $R^{d1}$ is independently selected from H and $C_{1-6}$ alkyl.

57. The compound of paragraph 41, wherein the compound of Formula (Ib) is selected from any one of the compounds of Table 1d, or a pharmaceutically acceptable salt thereof.

58. A compound selected from any one of the compounds of Table 1e, or a pharmaceutically acceptable salt thereof.

59. A pharmaceutical composition comprising a compound of any one of paragraphs 41-58, or a pharmaceutically acceptable salt thereof, and a pharmaceutically available carrier.

60. A method for inhibiting NF-κB activity within a cell within a mammal, wherein said method comprises administering, to said mammal, an effective amount of a compound of Formula (Ic):

(Ic)

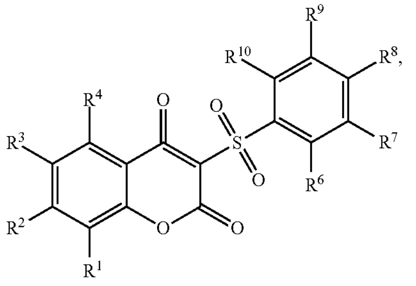

or a pharmaceutically acceptable salt thereof, wherein:

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^B$;

each $R^B$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

61. The method of paragraph 60, wherein each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^B$.

62. The method of paragraph 60 or 61, wherein each $R^B$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$.

63. The method of paragraph 60, wherein each of $R^1$, $R^2$, $R^3$, $R^4$, and $R^5$ is independently selected from H, halo, and $C_{1-6}$ alkoxy.

64. The method of any one of paragraphs 60-63, wherein each of $R^6$, $R^7$, $R^8$, $R^9$, and $R^{10}$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$; wherein said $C_{1-6}$ alkyl is optionally substituted with 1, 2, or 3 substituents independently selected from $R^C$.

65. The method of paragraph 64, wherein each $R^C$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$.

66. The method of any one of paragraphs 60-63, wherein each of $R^6$, $R^7$, $R^8$, $R^9$, and $R^{10}$ is independently selected from H, halo, CN, and $C_{1-6}$ alkyl.

67. The method of any one of paragraphs 60-66, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, each of which is optionally substituted with 1, 2, 3, 4, or 5 substituents independently selected from $R^g$.

68. The method of any one of paragraphs 60-66, wherein each $R^{a1}$, $R^{b1}$, $R^{c1}$, and $R^{d1}$ is independently selected from H and $C_{1-6}$ alkyl.

69. The method of any one of paragraphs 60-67, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

70. The method of paragraph 60, wherein:

each of $R^1$, $R^2$, $R^3$, $R^4$, and $R^5$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^B$;

each $R^B$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$;

each of $R^6$, $R^7$, $R^8$, $R^9$, and $R^{10}$ is independently selected from H, halo, CN, $NO_2$, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^C$;

each $R^C$ is independently selected from $OR^{a1}$, $C(O)NR^{c1}R^{d1}$, $C(O)OR^{a1}$, $NR^{c1}R^{d1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, each of which is optionally substituted with 1, 2, 3, 4, or 5 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, and di($C_{1-6}$ alkyl)amino.

71. The method of paragraph 60, wherein:

each of $R^1$, $R^2$, $R^3$, $R^4$, and $R^5$ is independently selected from H, halo, and $C_{1-6}$ alkoxy; and each of $R^6$, $R^7$, $R^8$, $R^9$, and $R^{10}$ is independently selected from H, halo, CN, and $C_{1-6}$ alkyl.

72. The method of paragraph 60, wherein the compound of Formula (Ic) is selected from any one of the compound of Table 1b, or a pharmaceutically acceptable salt thereof.

73. A method for inhibiting NF-κB activity within a cell within a mammal, wherein said method comprises administering, to said mammal, an effective amount of a compound of Formula (Id):

(Id)

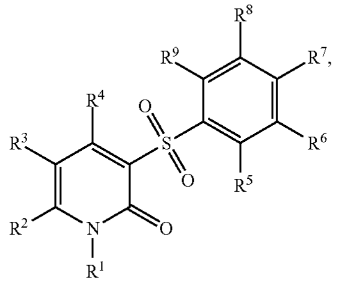

or a pharmaceutically acceptable salt thereof, wherein:

$R^1$ is selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^2$, $R^3$, and $R^4$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^B$;

each $R^B$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^5$, $R^6$, $R^7$, $R^8$, and $R^9$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

74. The method of paragraph 73, wherein $R^1$ is H.

75. The method of paragraph 73 or 74, wherein each of $R^2$, $R^3$, and $R^4$ is independently selected from H and $C_{1-6}$ alkyl.

76. The method of any one of paragraphs 73-75, wherein each of $R^5$, $R^6$, $R^7$, $R^8$, and $R^9$ is independently selected from H and halo.

77. The method of paragraph 73, wherein:

$R^1$ is H;

each of $R^2$, $R^3$, and $R^4$ is independently selected from H and $C_{1-6}$ alkyl; and each of $R^5$, $R^6$, $R^7$, $R^8$, and $R^9$ is independently selected from H and halo.

78. The method of paragraph 73, wherein the compound of Formula (Id) is selected from any one of the compounds of Table 1c, or a pharmaceutically acceptable salt thereof.

79. A compound of Formula (Ie):

(Ie)

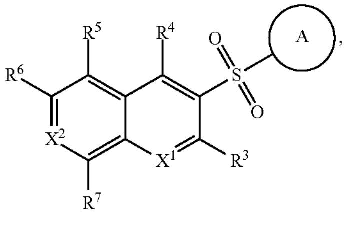

or a pharmaceutically acceptable salt thereof, wherein:

$X^1$ is selected from N and $CR^1$;

$X^2$ is selected from N and $CR^2$;

each $R^1$, $R^2$, $R^3$, $R^4$, $R^5$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^8$;

each $R^8$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^7$ is selected from $OR^{a2}$ and $NR^{c2}R^{d2}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$;

or any $R^{c2}$ and $R^{d2}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

80. The compound of paragraph 79, wherein the compound of Formula (Ie) has formula:

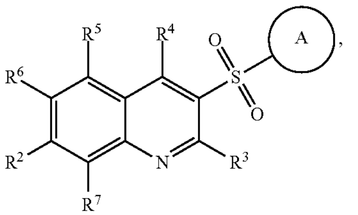

or a pharmaceutically acceptable salt thereof.

81. The compound of paragraph 79, wherein the compound of Formula (Ie) has formula:

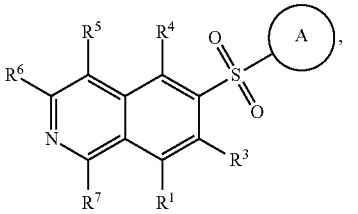

or a pharmaceutically acceptable salt thereof.

82. The compound of paragraph 79, wherein the compound of Formula (Ie) has formula:

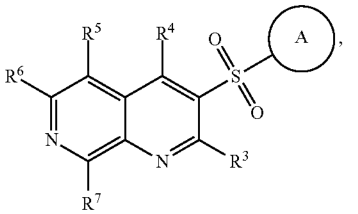

or a pharmaceutically acceptable salt thereof.

83. The compound of any one of paragraphs 79-82, wherein each of $R^1$, $R^2$, $R^3$, $R^4$, and $R^6$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$, wherein said $C_{1-6}$ alkyl is optionally substituted with 1, 2, or 3 substituents independently selected from $R^8$.

84. The compound of any one of paragraphs 79-83, wherein each $R^8$ is independently selected from CN, $NO_2$, OH, $C_{1-6}$ alkoxy, $C(O)NH_2$, C(O)OH, $NH_2$, and $S(O)_2NH_2$.

85. The compound of any one of paragraphs 79-82, wherein each of $R^1$, $R^2$, $R^3$, $R^4$, and $R^6$, if present in the compound of Formula (Ia), is independently selected from H, halo, CN, OH, $C_{1-6}$ alkyl, and $C_{1-6}$ alkoxy.

86 The compound of any one of paragraphs 79-85, wherein $R^7$ is $OR^{a2}$.

87. The compound of any one of paragraphs 79-85, wherein $R^7$ is $NR^{c2}R^{d2}$.

88. The compound of any one of paragraphs 79-87, wherein ring A is selected from $C_{6-10}$ aryl and 5-10 membered heteroaryl, each of which is optionally substituted with 1-6 substituents independently selected from $R^A$.

89. The compound of any one of paragraphs 79-87, wherein ring A is $C_{6-10}$ aryl, optionally substituted with 1-5 substituents independently selected from $R^A$.

90. The compound of any one of paragraphs 79-87, wherein ring A is 5-10 membered heteroaryl, optionally substituted with 1-6 substituents independently selected from $R^A$.

91. The compound of any one of paragraphs 79-87, wherein ring A is selected from any one of the following moieties:

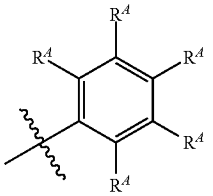

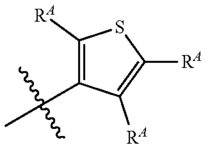

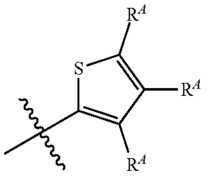

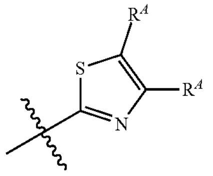

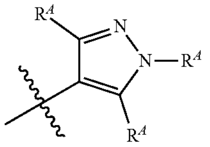

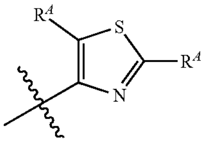

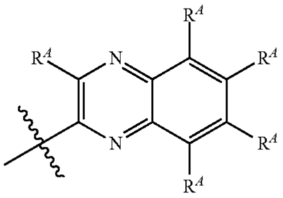

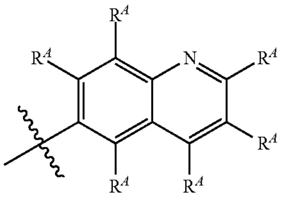

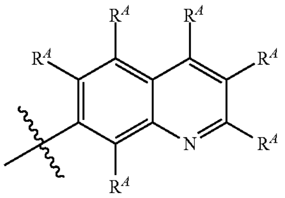

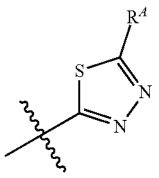

92. The compound of paragraph 79, wherein the compound of Formula (Ie) has formula:

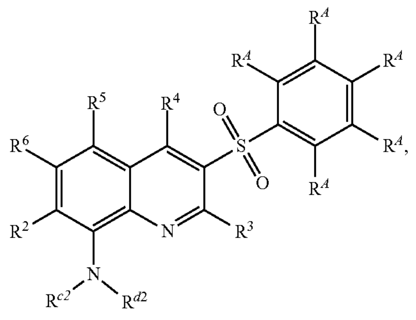

or a pharmaceutically acceptable salt thereof.

93. The compound of paragraph 79, wherein the compound of Formula (Ie) has formula:

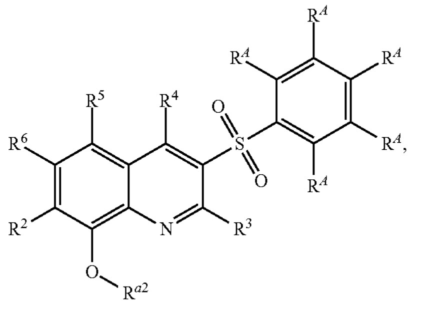

or a pharmaceutically acceptable salt thereof.

94. The compound of any one of paragraphs 79-93, wherein each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$.

95. The compound of any one of paragraphs 79-94, wherein each $R^9$ is independently selected from CN, $NO_2$, OH, $C_{1-6}$ alkoxy, $C(O)NH_2$, C(O)OH, $NH_2$, and $S(O)_2NH_2$.

96. The compound of any one of paragraphs 79-93, wherein each $R^A$ is independently selected from H, halo, CN, $C_{1-6}$ alkyl, and $C_{1-6}$ alkoxy.

97. The compound of any one of paragraphs 79-96, wherein each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$.

98. The compound of any one of paragraphs 79-97, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

99. The compound of any one of paragraphs 79-96, wherein each $R^{a1}$, $R^{a2}$, $R^{b1}$, $R^{c1}$, $R^{c2}$, $R^{d1}$, and $R^{d2}$ is independently selected from H and $C_{1-6}$ alkyl.

100. The compound of paragraph 79, wherein $R^1$, $R^2$, $R^3$, $R^4$, and $R^6$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; wherein said $C_{1-6}$ alkyl is optionally substituted with 1, 2, or 3 substituents independently selected from $R^8$;

each $R^8$ is independently selected from CN, $NO_2$, OH, $C_{1-6}$ alkoxy, $C(O)NH_2$, C(O)OH, $NH_2$, and $S(O)_2NH_2$;

ring A is selected from $C_{6-10}$ aryl and 5-10 membered heteroaryl, each of which is optionally substituted with 1-6 substituents independently selected from $R^A$, each $R^A$ is independently selected from H, halo, CN, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $NR^{c1}C(O)OR^{a1}$ $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^9$;

each $R^9$ is independently selected from CN, $NO_2$, OH, $C_{1-6}$ alkoxy, $C(O)NH_2$, C(O)OH, $NH_2$, and $S(O)_2NH_2$;

each $R^{a1}$, $R^{a2}$, $R^{b1}$, $R^{c1}$, $R^{c2}$, $R^{d1}$, and $R^{d2}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

101. The compound of paragraph 79, wherein:

each of $R^1$, $R^2$, $R^3$, $R^4$, and $R^6$, if present in the compound of Formula (Ia), is independently selected from H, halo, CN, OH, $C_{1-6}$ alkyl, and $C_{1-6}$ alkoxy;

ring A is selected from $C_{6-10}$ aryl and 5-10 membered heteroaryl, each of which is optionally substituted with 1-6 substituents independently selected from $R^A$;

each $R^A$ is independently selected from H, halo, CN, $C_{1-6}$ alkyl, and $C_{1-6}$ alkoxy; and each $R^{a1}$, $R^{a2}$, $R^{b1}$, $R^{c1}$, $R^{c2}$, $R^{d1}$, and $R^{d2}$ is independently selected from H and $C_{1-6}$ alkyl.

102. The compound of paragraph 79, wherein the compound of Formula (Ie) is selected from any one of the compounds of Table If, or a pharmaceutically acceptable salt thereof.

103. A pharmaceutical composition comprising a compound of any one of paragraphs 79-102, or a pharmaceutically acceptable salt thereof, and a pharmaceutically acceptable carrier.

104. A compound of Formula (If):

(If)

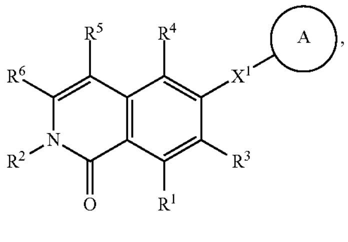

or a pharmaceutically acceptable salt thereof, wherein:

$X^1$ is selected from S, S(O), and $S(O)_2$;

$R^1$, $R^3$, $R^4$, $R^5$, and $R^6$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

$R^2$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2$ $R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

105. The compound of paragraph 104, wherein $X^1$ is S.

106. The compound of paragraph 104, wherein $X^1$ is S(O).

107. The compound of paragraph 104, wherein $X^1$ is $S(O)_2$.

108. The compound of any one of paragraphs 104-107, wherein $R^1$, $R^3$, $R^4$, $R^5$, and $R^6$ is independently selected from H, halo, OH, CN, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

109. The compound of any one of paragraphs 104-107, wherein $R^1$, $R^3$, $R^4$, $R^5$, and $R^6$ are each H.

110. The compound of any one of paragraphs 104-109, wherein $R^2$ is selected from H, $C_{1-6}$ alkyl, and $C_{1-6}$ haloalkyl.

111. The compound of any one of paragraphs 104-110, wherein ring A is $C_{6-10}$ aryl, optionally substituted with 1 or 2 substituents independently selected from halo and $C_{1-6}$ alkyl.

112. The compound of paragraph 104, wherein:

$R^1$, $R^3$, $R^4$, $R^5$, and $R^6$ is independently selected from H, halo, OH, CN, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$R^2$ is selected from H, $C_{1-6}$ alkyl, and $C_{1-6}$ haloalkyl; and ring A is $C_{6-10}$ aryl, optionally substituted with 1 or 2 substituents independently selected from halo and $C_{1-6}$ alkyl.

113. The compound of paragraph 104, wherein the compound is selected from any one of the compound of Table 1g, or a pharmaceutically acceptable salt thereof.

114. A pharmaceutical composition of comprising a compound of any one of paragraphs 104-113, or a pharmaceutically acceptable salt thereof, and a pharmaceutically acceptable carrier.

115. A compound of Formula (Ig):

(Ig)

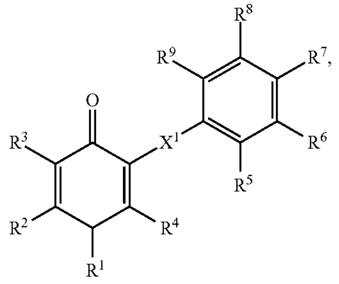

or a pharmaceutically acceptable salt thereof, wherein:

$X^1$ is selected from S, S(O), and $S(O)_2$;

$R^1$ is selected from H, $C_{1-6}$ alkyl, $C_{1-6}$ haloalkyl, $C_{2-6}$ alkenyl, and $C_{2-6}$ alkynyl, wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^2$, $R^3$, and $R^4$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^B$;

each $R^B$ independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each of $R^5$, $R^6$, $R^7$, $R^8$, and $R^9$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^C$;

each $R^C$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

116. The compound of paragraph 115, wherein $X^1$ is selected from S(O) and $S(O)_2$.

117. The compound of paragraph 115, wherein $R^1$ is H.

118. The compound of any one of paragraphs 115-117, wherein each of $R^2$, $R^3$, and $R^4$ is independently selected from H and $C_{1-6}$ alkyl.

119. The compound of any one of paragraphs 115-118, wherein each of $R^5$, $R^6$, $R^7$, $R^8$, and $R^9$ is independently selected from H, halo, and $C_{1-6}$ alkyl.

120. The compound of paragraph 115, wherein:

$X^1$ is S(O) or $S(O)_2$;

$R^1$ is H;

each of $R^2$, $R^3$, and $R^4$ is independently selected from H and $C_{1-6}$ alkyl; and each of $R^5$, $R^6$, $R^7$, $R^8$, and $R^9$ is independently selected from H, $C_{1-6}$ alkyl and halo.

121. The compound of paragraph 115, wherein the compound of Formula (Ig) is selected from any one of the compounds of Table 1h, or a pharmaceutically acceptable salt thereof.

122. A pharmaceutical composition comprising a compound of any one of paragraphs 115-121, or a pharmaceutically acceptable salt thereof, and a pharmaceutically acceptable carrier.

123. A method of inhibiting activation of an NF-κB pathway within a cell within a mammal, wherein said method comprises administering, to said mammal, an effective amount of a compound of Formula (IIa):

(IIa)

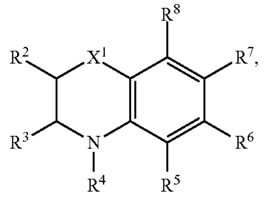

or a pharmaceutically acceptable salt thereof, wherein:

$X^1$ is selected from O and $NR^1$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^3$ is selected from H, $C_{1-6}$ alkyl, $C_{1-6}$ haloalkyl, $C_{2-6}$ alkenyl, $C_{2-6}$ alkynyl, and oxo, wherein said $C_{1-6}$ alkyl, $C_{2-6}$ alkenyl, and $C_{2-6}$ alkynyl are each optionally substituted with 1, 2, or 3 substituents independently selected from $R^9$;

$R^1$ and $R^4$ are each independently selected from H, $C_{1-6}$ alkyl, $C_{1-6}$ haloalkyl, $C_{2-6}$ alkenyl, $C_{2-6}$ alkynyl, C(O)$R^{b1}$, C(O)$NR^{c1}R^{d1}$, C(O)$OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^5$ and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, C(O)$R^{b1}$, C(O)$NR^{c1}R^{d1}$, C(O)$OR^{a1}$, $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, $S(O)_2NR^{c1}R^{d1}$, and a group of formula (i):

(i)

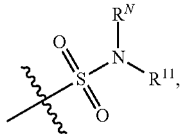

wherein said $C_{1-6}$ alkyl, $C_{2-6}$ alkenyl, and $C_{2-6}$ alkynyl are each optionally substituted with 1, 2, or 3 substituents independently selected from $R^9$;

provided that at least one of $R^7$ and $R^8$ is a group of formula (i);

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, C(O)$R^{b1}$, C(O)$NR^{c1}R^{d1}$, C(O)$OR^{a1}$ $NR^{c1}R^{d1}$, $NR^{c1}$C(O)$R^{b1}$, $NR^{c1}$C(O)$OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10-}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

124. The method of paragraph 123, wherein the compound of Formula (IIa) has formula:

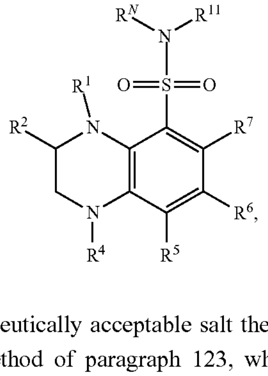

or a pharmaceutically acceptable salt thereof.

125. The method of paragraph 123, wherein the compound of Formula (IIa) has formula:

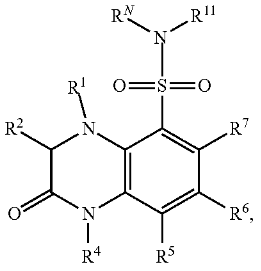

or a pharmaceutically acceptable salt thereof.

126. The method of paragraph 123, wherein the compound of Formula (Ia) has formula:

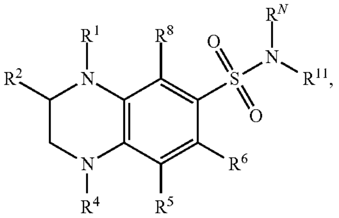

or a pharmaceutically acceptable salt thereof.

127. The method of paragraph 123, wherein the compound of Formula (IIa) has formula:

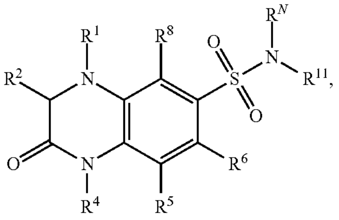

or a pharmaceutically acceptable salt thereof.

128. The method of any one of paragraphs 123-127, wherein:

$R^2$ is selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$.

129. The method of paragraph 128, wherein $R^1$ is selected from $C_{1-6}$ alkyl, $C(O)R^{b1}$, and $C(O)NR^{c1}R^{d1}$.

130. The method of paragraph 123, wherein the compound of Formula (IIa) is selected from:

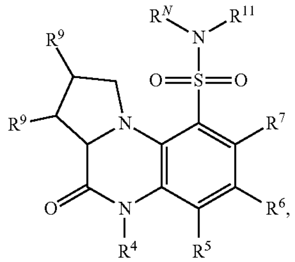

-continued

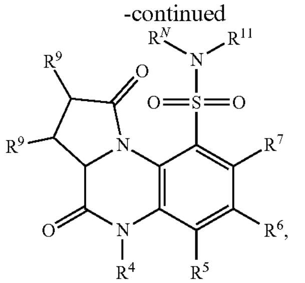

and

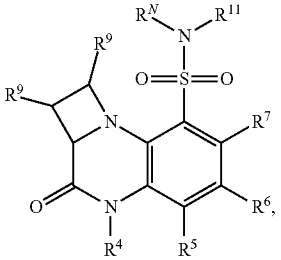

or a pharmaceutically acceptable salt thereof.

131. The method of paragraph 123, wherein the compound of Formula (IIa) is selected from:

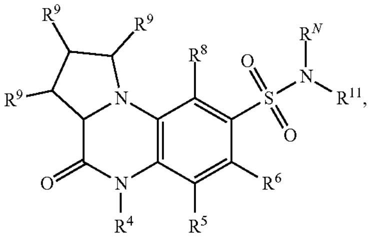

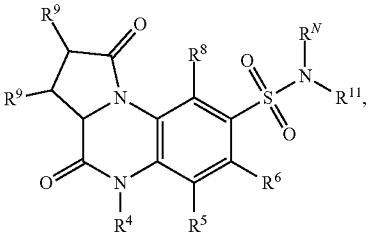

and

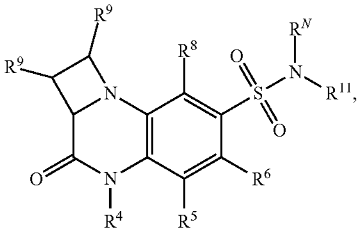

or a pharmaceutically acceptable salt thereof.

132. The method of paragraph 123, wherein the compound of Formula (IIa) has formula:

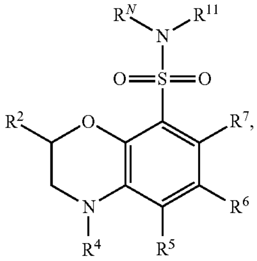

or a pharmaceutically acceptable salt thereof.

133. The method of paragraph 123, wherein the compound of Formula (IIa) has formula:

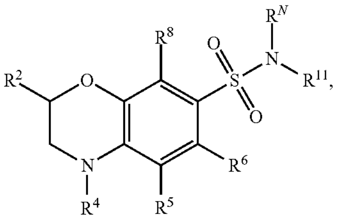

or a pharmaceutically acceptable salt thereof.

134. The method of paragraph 123, wherein the compound of Formula (Ia) has formula:

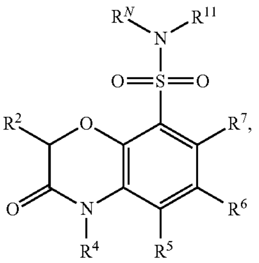

or a pharmaceutically acceptable salt thereof.

135. The method of paragraph 123, wherein the compound of Formula (IIa) has formula:

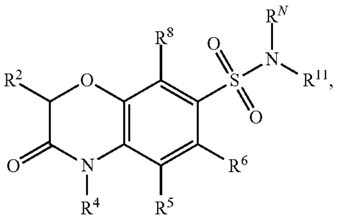

or a pharmaceutically acceptable salt thereof.

136. The method of any one of paragraphs 132-135, wherein $R^2$ is selected from H and $C_{1-6}$ alkyl.

137. The method of any one of paragraphs 123-136, wherein $R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$.

138. The method of any one of paragraphs 123-136, wherein $R^4$ is H.

139. The method of any one of paragraphs 123-138, wherein $R^5$ and $R^6$ are each independently selected from H, halo, $C_{1-6}$ alkyl, $C_{1-6}$ haloalkyl, $OR^{a1}$, $C(O)NR^{c1}R^{d1}$, C(O) $OR^{a1}$, $NR^{c1}R^{d1}$, $NR^{c1}S(O)_2R^{b1}$, $S(O)_2R^{b1}$, and $S(O)_2$ $NR^{c1}R^{d1}$; wherein said $C_{1-6}$ alkyl is optionally substituted with 1, 2, or 3 substituents independently selected from $R^9$.

140. The method of any one of paragraphs 123-138, wherein $R^5$ and $R^6$ are each independently selected from H, halo, $C_{1-6}$ alkyl, and $S(O)_2R^{b1}$, wherein said $C_{1-6}$ alkyl is optionally substituted with $R^9$.

141. The method of paragraph 140, wherein $R^5$ is H and $R^6$ is $C_{1-6}$ alkyl, optionally substituted with $NR^{c1}R^{d1}$.

142. The method of paragraph 140, wherein $R^5$ is H and $R^6$ is halo.

143. The method of paragraph 140, wherein $R^5$ is H and $R^6$ is $S(O)_2R^{b1}$.

144. The method of any one of paragraphs 123-143, wherein $R^7$ is selected from H and $C_{1-6}$ alkyl.

145. The method of any one of paragraphs 123-144, wherein $R^8$ is selected from H and $C_{1-6}$ alkyl.

146. The method of any one of paragraphs 123-145, wherein $R^N$ is selected from H and $C_{1-6}$ alkyl.

147. The method of any one of paragraphs 123-146, wherein $R^{11}$ is ring A.

148. The method of any one of paragraphs 123-146, wherein $R^{11}$ is $C_{1-6}$ alkyl, optionally substituted with ring A.

149. The method of any one of paragraphs 123-145, wherein $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$.

150. The method of any one of paragraphs 123-148, wherein ring A is selected from any one of the following moieties:

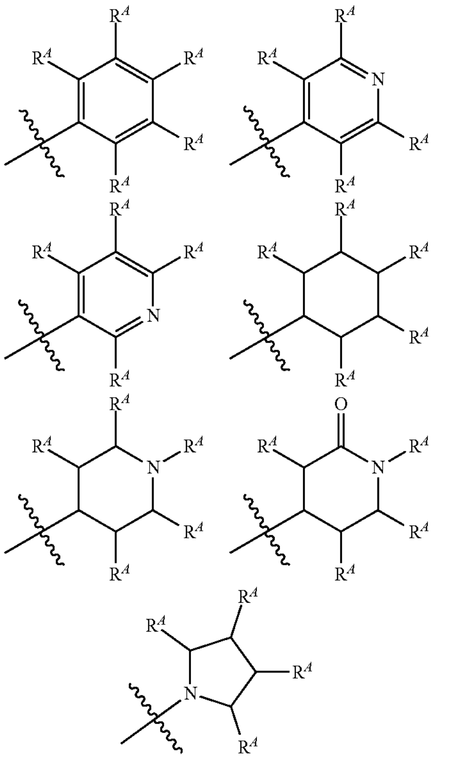

151. The method of any one of paragraphs 123-150, wherein each $R^A$ is independently selected from H, halo, CN, $C_{1-6}$ alkyl, $C_{1-6}$ haloalkyl, $OR^{a1}$, $SR^{a1}$, $C(O)R^{b1}$, C(O) $NR^{c1}R^{d1}$, $C(O)OR^{a1}$, $NR^{c1}R^{d1}$, $NR^{c1}C(O)R^{b1}$, $NR^{c1}C(O)$ $OR^{a1}$, $NR^{c1}S(O)_2R^{b1}$, $S(O)_2R^{b1}$, and $S(O)_2NR^{c1}R^{d1}$, wherein said $C_{1-6}$ alkyl is optionally substituted with 1, 2, or 3 substituents independently selected from $R^{10}$.

152. The method of any one of paragraphs 123-150, wherein each $R^A$ is independently selected from H, halo, CN, $C_{1-6}$ alkyl, $C_{1-6}$ haloalkyl, $OR^{a1}$, $SR^{a1}$, $C(O)R^{b1}$, C(O) $OR^{a1}$, $NR^{c1}R^{d1}$, and $NR^{c1}C(O)R^{b1}$, wherein said $C_{1-6}$ alkyl is optionally substituted with 1, 2, or 3 substituents independently selected from $R^{10}$.

153. The method of any one of paragraphs 123-152, wherein each $R^{10}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S$ $(O)_2R^{b1}$, and $S(O)_2NR^{c1}R^{d1}$ 154. The method of any one of paragraphs 123-150, wherein each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with C(O) $OR^{a1}$.

155. The method of any one of paragraphs 123-154, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$.

156. The method of any one of paragraph 123-155, wherein each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

157. The method of paragraph 123, wherein:

$R^2$ is selected from H and $C_{1-6}$ alkyl;

$R^1$ is selected from H, $C_{1-6}$ alkyl, $C_{1-6}$ haloalkyl, $C(O)R^{b1}$, and $C(O)NR^{c1}R^{d1}$; wherein said $C_{1-6}$ alkyl is optionally substituted with 1, 2, or 3 substituents independently selected from $R^9$; or $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^3$ is selected from H and oxo;

$R^4$ is selected from H, $C_{1-6}$ alkyl, and $C_{1-6}$ haloalkyl, wherein said $C_{1-6}$ alkyl is optionally substituted with 1, 2, or 3 substituents independently selected from $R^9$;

$R^5$ and $R^6$ are each independently selected from H, halo, $C_{1-6}$ alkyl, $C_{1-6}$ haloalkyl, $OR^{a1}$, $C(O)NR^{c1}R^{d1}$, C(O) $OR^{a1}$, $NR^{c1}R^{d1}$, $NR^{c1}S(O)_2R^{b1}$, $S(O)_2R^{b1}$, and S(O) $_2NR^{c1}R^{d1}$, wherein said $C_{1-6}$ alkyl is optionally substituted with 1, 2, or 3 substituents independently selected from $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, C(O) $NR^{c1}R^{d1}$, $C(O)OR^{a1}$, $NR^{c1}R^{d1}$, $NR^{c1}C(O)R^{b1}$, $NR^{c1}C$ $(O)OR^{a1}$, $NR^{c1}S(O)_2R^{b1}$, $S(O)_2R^{b1}$, and $S(O)_2$ $NR^{c1}R^{d1}$; wherein said $C_{1-6}$ alkyl is optionally substituted with 1, 2, or 3 substituents independently selected from $R^{10}$;

$R^{10}$ is independently selected from $OR^{a1}$, $C(O)NR^{c1}R^{d1}$, $C(O)OR^{a1}$, $NR^{c1}R^{d1}$, $NR^{c1}C(O)R^{b1}$, $NR^{c1}S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^8$; and each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

158. The method of paragraph 123, wherein:

$R^2$ is selected from H and $C_{1-6}$ alkyl;

$R^1$ is selected from $C_{1-6}$ alkyl, $C(O)R^{b1}$, and $C(O)NR^{c1}R^{d1}$, $R^1$ and $R^2$, together with N atom to which $R^1$ is attached and C atom to which $R^2$ is attached, form a 4-10 membered heterocycloalkyl ring, which is substituted with 1, 2, or 3 substituents independently selected from $R^9$;

$R^3$ is selected from H and oxo;

$R^4$ is H;

$R^5$ and $R^6$ are each independently selected from H, halo, $C_{1-6}$ alkyl, and $S(O)_2R^{b1}$, wherein said $C_{1-6}$ alkyl is optionally substituted with $R^9$;

$R^7$ and $R^8$ are independently selected from H, $C_{1-6}$ alkyl, and a moiety of formula (i);

$R^N$ is selected from H and $C_{1-6}$ alkyl; or $R^N$ and $R^{11}$, together with the N atom to which they are attached, form a ring selected from morpholinyl, piperidinyl, and piperazinyl, each of which is optionally substituted with 1, 2, or 3 substituents independently selected from $R^9$;

each $R^A$ is independently selected from H, halo, CN, $C_{1-6}$ alkyl, $C_{1-6}$ haloalkyl, $OR^{a1}$, $SR^{a1}$, $C(O)R^{b1}$, $C(O)OR^{a1}$, $NR^{c1}R^{d1}$, and $NR^{c1}C(O)R^{b1}$, wherein said $C_{1-6}$ alkyl is optionally substituted with $C(O)OR^{a1}$;

each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, or 3 substituents independently selected from $R^8$; and each $R^8$ is independently selected from OH, $NO_2$, CN, halo, $C_{1-6}$ alkyl, $C_{1-6}$ alkoxy, $C_{1-6}$ haloalkoxy, amino, $C_{1-6}$ alkylamino, di($C_{1-6}$ alkyl)amino, and carboxy.

159. The method of paragraph 123, wherein the compound of Formula (IIa) is selected from any one of the compounds of Table 2a, Table 2c, Table 2c-2, Table 2d, Table 2d-2, Table 2e, or Table 16, or a pharmaceutically acceptable salt thereof.

160. The method of paragraph 123, wherein the compound of Formula (IIa) is selected from any one of the compounds of Table 2a, Table 2c, Table 2d, or Table 2e, or a pharmaceutically acceptable salt thereof.

161. A compound selected from any one of the compounds of Table 16, or a pharmaceutically acceptable salt thereof.

162. A pharmaceutical composition comprising a compound of any one of paragraphs 123-161, or a pharmaceutically acceptable salt thereof, and a pharmaceutically acceptable carrier.

163. A compound of Formula (IIb):

(IIb)

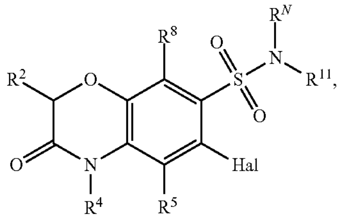

or a pharmaceutically acceptable salt thereof, wherein:

Hal is a halogen;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, for a -10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

164. The compound of paragraph 163, wherein $R^2$ is selected from H and $C_{1-6}$ alkyl.

165. The compound of paragraph 163 or 164, wherein $R^4$, $R^5$, and $R^8$ are each H.

166. The compound of any one of paragraphs 163-165, wherein $R^N$ is H.

167. The compound of any one of paragraphs 163-165, wherein $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$.

168. The compound of any one of paragraphs 163-166, wherein ring A is selected from $C_{6-10}$ aryl and $C_{3-10}$ cycloalkyl, each of which is optionally substituted with 1-10 substituents independently selected from $R^A$.

169. The compound of any one of paragraphs 163-168, wherein each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{11}$.

170. The compound of any one of paragraphs 163-168, wherein each $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

171. The compound of paragraphs 163, wherein:

$R^2$ is selected from H and $C_{1-6}$ alkyl;

$R^4$, $R^5$, and $R^8$ are each H;

$R^N$ is H; or $R^N$ and $R^{11}$, together with the N atom to which they are attached, form a ring selected from pyrrolidinyl, morpholinyl, and piperazinyl, each of which is optionally substituted with 1, 2, or 3 substituents independently selected from $R^9$;

ring A is selected from $C_{6-10}$ aryl and $C_{3-10}$ cycloalkyl, each of which is optionally substituted with 1-10 substituents independently selected from $R^4$; and each $R^A$ is independently selected from H, halo, CN, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

172. The compound of paragraph 171, wherein $R^A$ is independently selected from H, halo, $C_{1-6}$ alkyl, $C_{1-6}$ haloalkyl, $OR^{a1}$, $SR^{a1}$, and $C(O)R^{b1}$, wherein said $C_{1-6}$ alkyl is optionally substituted with 1, 2, or 3 substituents independently selected from $R^{10}$.

173. The compound of any one of paragraphs 163-172, wherein the compound of Formula (IIb) is selected from any one of the compounds of Table 2c or Table 2c-2, or a pharmaceutically acceptable salt thereof.

174. The compound of paragraph 163, wherein the compound of Formula (IIb) is selected from any one of the compounds of Table 2c, or a pharmaceutically acceptable salt thereof.

175. A pharmaceutical composition comprising a compound of any one of paragraphs 163-174, or a pharmaceutically acceptable salt thereof, and a pharmaceutically acceptable carrier.

176. A compound of Formula (IIc):

(IIc)

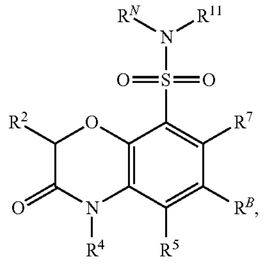

or a pharmaceutically acceptable salt thereof, wherein:

$R^B$ is selected from halogen and $S(O)_2R^{b1}$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

177. The compound of paragraph 176, wherein $R^B$ is a halogen.

178. The compound of paragraph 176, wherein $R^B$ is $S(O)_2R^{b1}$.

179. The compound of any one of paragraphs 176-178, wherein $R^2$ is selected H and $C_{1-6}$ alkyl.

180. The compound of any one of paragraphs 176-179, wherein $R^4$ is H.

181. The compound of any one of paragraphs 176-180, wherein $R^5$ is H.

182. The compound of any one of paragraphs 176-181, wherein $R^7$ is selected H and $C_{1-6}$ alkyl.

183. The compound of any one of paragraphs 176-182, wherein $R^N$ is H.

184. The compound of any one of paragraphs 176-182, wherein $R^N$ and $R^{11}$, together with the N atom to which they are attached, form a ring selected from morpholinyl and piperazinyl, each of which is optionally substituted with 1, 2, or 3 substituents independently selected from $R^9$.

185. The compound of any one of paragraphs 176-183, wherein ring A is selected from $C_{6-10}$ aryl and $C_{3-10}$ cycloalkyl, optionally substituted with 1-10 substituents independently selected from $R^A$.

186. The compound of any one of paragraphs 176-185, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

187. The compound of any one of paragraphs 176-179, wherein:

$R^2$ is selected H and $C_{1-6}$ alkyl;

$R^4$ is H;

$R^5$ is H;

$R^7$ is selected H and $C_{1-6}$ alkyl;

$R^N$ is H; or $R^N$ and $R^{11}$, together with the N atom to which they are attached, form a ring selected from morpholinyl and piperazinyl, each of which is optionally substituted with 1, 2, or 3 substituents independently selected from $R^9$;

ring A is selected from $C_{6-10}$ aryl and $C_{3-10}$ cycloalkyl, optionally substituted with 1-10 substituents independently selected from $R^A$; and each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

188. The compound of paragraph 176, wherein the compound of Formula (IIc) is selected from any one of the compounds of Table 2d or Table 2d-2, or a pharmaceutically acceptable salt thereof.

189. The compound of paragraph 176, wherein the compound of Formula (IIc) is selected from any one of the compounds of Table 2d, or a pharmaceutically acceptable salt thereof.

190. A pharmaceutical composition comprising a compound of any one of paragraphs 176-189, or a pharmaceutically acceptable salt thereof, and a pharmaceutically acceptable carrier.

191. A compound of Formula (IId):

(IId)

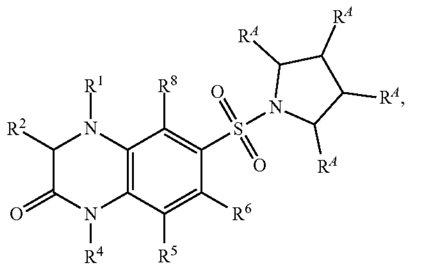

or a pharmaceutically acceptable salt thereof, wherein:

$R^1$ and $R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^2$ is selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^5$, $R^6$, and $R^8$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

192. The compound of paragraph 191, wherein $R^2$ is selected from H and $C_{1-6}$ alkyl.

193. The compound of paragraph 191 or paragraph 192, wherein $R^4$ is H.

194. The compound of any one of paragraphs 191-193, wherein $R^5$, $R^6$, and $R^8$ are each H.

195. The compound of any one of paragraphs 191-194, wherein $R^1$ is selected from H, $C_{1-6}$ alkyl, $C(O)R^{b1}$, and $C(O)NR^{c1}R^{d1}$, wherein said $C_{1-6}$ alkyl is optionally substituted with 1, 2, or 3 substituents independently selected from $R^9$.

196. The compound of any one of paragraphs 191-195, wherein each $R^A$ is H.

197. The compound of paragraph 191, wherein:

$R^2$ is selected from H and $C_{1-6}$ alkyl;

$R^4$ is H;

$R^5$, $R^6$, and $R^8$ are each H;

$R^1$ is selected from H, $C_{1-6}$ alkyl, $C(O)R^{b1}$, and $C(O)NR^{c1}R^{d1}$, wherein said $C_{1-6}$ alkyl is optionally substituted with 1, 2, or 3 substituents independently selected from $R^9$;

each $R^9$ is independently selected from OH, $C_{1-6}$ alkoxy, carboxy, $C(O)NH_2$, amino, $C_{1-6}$ alkylamino, and di($C_{1-6}$ alkyl)amino; and each $R^A$ is H.

198. The compound of paragraph 191, wherein the compound of Formula (IId) is selected from any one of the compounds of Table 2e, or a pharmaceutically acceptable salt thereof.

199. A pharmaceutical composition comprising a compound of any one of paragraphs 191-198, or a pharmaceutically acceptable salt thereof, and a pharmaceutically acceptable carrier.

200. A compound of Formula (IIe)

(IIe)

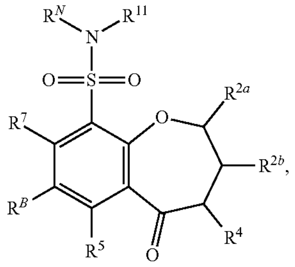

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

201. The compound of paragraph 200, wherein $R^B$ is a halogen.

202. The compound of paragraph 200, wherein $R^B$ is $S(O)_2R^{b1}$.

203. The compound of any one of paragraphs 200-202, wherein $R^{2a}$ and $R^{2b}$ are each independently selected from H and $C_{1-6}$ alkyl.

204. The compound of any one of paragraphs 200-203 wherein $R^4$ is H.

205. The compound of any one of paragraphs 200-204, wherein $R^5$ is H.

206. The compound of any one of paragraphs 200-205, wherein $R^7$ is selected H and $C_{1-6}$ alkyl.

207. The compound of any one of paragraphs 200-206, wherein $R^N$ is H.

208. The compound of any one of paragraphs 200-207, wherein ring A is $C_{6-10}$ aryl, optionally substituted with 1-5 substituents independently selected from $R^A$.

209. The compound of any one of paragraphs 200-208, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

210. The compound of paragraph 200, wherein:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

211. The compound of paragraph 200, wherein the compound of Formula (IIe) is selected from any one of the compounds of Table 2f, or a pharmaceutically acceptable salt thereof.

212. A pharmaceutical composition comprising a compound of any one of paragraphs 200-211, or a pharmaceutically acceptable salt thereof, and a pharmaceutically acceptable carrier.

213. A compound of Formula (IIf):

(IIf)

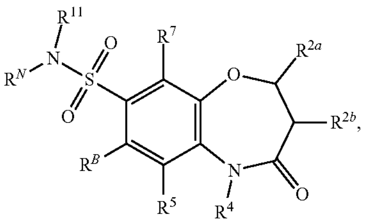

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

214. The compound of paragraph 213, wherein $R^B$ is a halogen.

215. The compound of paragraph 213, wherein $R^B$ is $S(O)_2R^{b1}$.

216. The compound of any one of paragraphs 213-215, wherein $R^{2a}$ and $R^{2b}$ are each independently selected from H and $C_{1-6}$ alkyl.

217. The compound of any one of paragraphs 213-216, wherein $R^4$ is H.

218. The compound of any one of paragraphs 213-217, wherein $R^5$ is H.

219. The compound of any one of paragraphs 213-218, wherein $R^7$ is selected H and $C_{1-6}$ alkyl.

220. The compound of any one of paragraphs 213-219, wherein $R^N$ is H.

221. The compound of any one of paragraphs 213-220, wherein ring A is $C_{6-10}$ aryl, optionally substituted with 1-5 substituents independently selected from $R^A$.

222. The compound of any one of paragraphs 213-221, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

223. The compound of paragraph 213, wherein:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$, and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

224. The compound of paragraph 213, wherein the compound of Formula (IIf) is selected from any one of the compounds of Table 2g, or a pharmaceutically acceptable salt thereof.

225. A pharmaceutical composition comprising a compound of any one of paragraphs 213-224, or a pharmaceutically acceptable salt thereof, and a pharmaceutically acceptable carrier.

226. A compound of Formula (IIg):

(IIg)

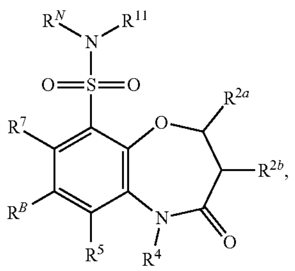

or a pharmaceutically acceptable salt thereof, wherein:

$R^B$ is selected from halogen and $S(O)_2R^{b1}$;

$R^{2a}$ and $R^{2b}$ are each independently selected from H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^4$ are each independently selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^5$ and $R^7$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^{11}$ is selected from $C_{1-6}$ alkyl and ring A, wherein said $C_{1-6}$ alkyl is optionally substituted with ring A;

$R^N$ is selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{2-6}$ alkenyl, and $C_{2-6}$ alkynyl are each optionally substituted with 1, 2, or 3 substituents independently selected from $R^9$; or $R^{11}$ and $R^N$, together with the N atom to which they are attached, form a 4-10 membered heterocycloalkyl, optionally substituted with 1, 2, or 3 substituents independently selected from $R^9$;

each $R^9$ is independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

ring A is selected from $C_{6-10}$ aryl, $C_{3-10}$ cycloalkyl, 5-10 membered heteroaryl, and 4-10 membered heterocycloalkyl, each of which is substituted with 1-10 substituents independently selected from $R^A$;

each $R^A$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

each $R^{10}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

227. The compound of paragraph 226, wherein $R^B$ is a halogen.

228. The compound of paragraph 226, wherein $R^B$ is $S(O)_2R^{b1}$.

229. The compound of any one of paragraphs 226-228, wherein $R^{2a}$ and $R^{2b}$ are each independently selected from H and $C_{1-6}$ alkyl.

230. The compound of any one of paragraphs 226-229, wherein $R^4$ is H.

231. The compound of any one of paragraphs 226-230, wherein $R^5$ is H.

232. The compound of any one of paragraphs 226-231, wherein $R^7$ is selected H and $C_{1-6}$ alkyl.

233. The compound of any one of paragraphs 226-232, wherein $R^N$ is H.

234. The compound of any one of paragraphs 226-233, wherein ring A is $C_{6-10}$ aryl, optionally substituted with 1-5 substituents independently selected from $R^A$.

235. The compound of any one of paragraphs 226-234, wherein each $R^A$ is independently selected from H, halo, CN, $C_{1-6}$ alkyl, $C_{1-6}$ haloalkyl, and $OR^{a1}$; wherein said $C_{1-6}$ alkyl is optionally substituted with 1, 2, or 3 substituents independently selected from $R^{10}$.

236. The compound of paragraph 226, wherein:

$R^{2a}$ and $R^{2b}$ are each independently selected H and $C_{1-6}$ alkyl;

$R^4$ is H;

$R^5$ is H;

$R^7$ is selected H and $C_{1-6}$ alkyl;

$R^N$ is H;

$R^{11}$ is $C_{6-10}$ aryl, optionally substituted with 1-5 substituents independently selected from $R^A$; and each $R^A$ is independently selected from H, halo, CN, $C_{1-6}$ alkyl, $C_{1-6}$ haloalkyl, $C_{1-6}$ alkoxy, and $C_{1-6}$ haloalkoxy.

237. The compound of paragraph 226, wherein the compound of Formula (IIg) is selected from any one of the compounds of Table 2h, or a pharmaceutically acceptable salt thereof.

238. A pharmaceutical composition comprising a compound of any one of paragraphs 226-237, or a pharmaceutically acceptable salt thereof, and a pharmaceutically acceptable carrier.

239. A method for inhibiting NF-κB activity within a cell within a mammal, wherein said method comprises administering, to said mammal, an effective amount of a compound of Formula (IIIa):

(IIIa)

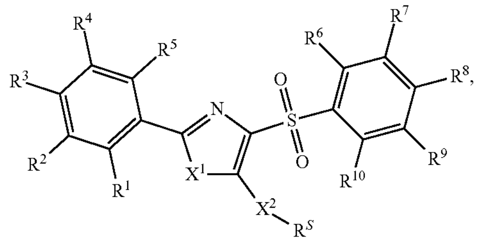

or a pharmaceutically acceptable salt thereof, wherein:

$X^1$ is selected from O, S, and NRN;

$R^N$ is selected from H and $C_{1-6}$ alkyl;

$X^2$ is selected from S, S(O), and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

or any two adjacent $R^1$, $R^2$, $R^3$, $R^4$, and $R^5$ groups, together with the carbon atoms to which they are attached, form a $C_{6-10}$ aryl ring, which is optionally substituted with 1, 2, or 3 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$.

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$, each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

240. The method of paragraph 239, wherein:

$X^1$ is selected from O, S, and $NR^N$, $R^N$ is selected from H and $C_{1-6}$ alkyl;

$X^2$ is selected from S, S(O), and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-

$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

241. The method of paragraph 239 or 240, wherein $X^1$ is O.

242. The method of paragraph 239 or 240, wherein $X^1$ is S.

243. The method of paragraph 239 or 240, wherein $X^1$ is $NR^N$.

244. The method of any one of paragraphs 239-243, wherein $X^2$ is S.

245. The method of any one of paragraphs 239-243, wherein $X^2$ is S(O).

246. The method of any one of paragraphs 239-243, wherein $X^2$ is $S(O)_2$.

247. The method of any one of paragraphs 239-246, wherein $R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$.

248. The method of paragraph 247, wherein $R^S$ is $C_{1-6}$ alkyl, optionally substituted with $Cy^1$, $OR^{a1}$, $C(O)R^{b1}$, $NR^{c1}R^{d1}$, and $C(O)NR^{c1}R^{d1}$ 249. The method of paragraph 247, wherein $R^S$ is $C_{1-6}$ alkyl, optionally substituted with $Cy^1$, $OR^{a1}$, $C(O)R^{b1}$, and $C(O)NR^{c1}R^{d1}$ 250. The method of paragraph 247, wherein $R^S$ is selected from $C_{6-10}$ aryl and $C_{3-10}$ cycloalkyl, each of which is optionally substituted with 1, 2, or 3 substituents independently selected from halo and $C_{1-6}$ alkyl.

251. The method of any one of paragraphs 239-250, wherein each $R^{11}$ independently selected from $Cy^1$, halo, $C_{1-6}$ alkyl, $OR^{a1}$, $C(O)R^{b1}$, and $C(O)NR^{c1}R^{d1}$ 252. The method of any one of paragraphs 239-251, wherein each $Cy^1$ is independently selected from $C_{6-10}$ aryl and $C_{3-10}$ cycloalkyl, each of which is optionally substituted with 1, 2, or 3 substituents independently selected from 253. The method of any one of paragraphs 239-252, wherein each $R^{Cy1}$ is independently selected from halo, $C_{1-6}$ alkyl, $C_{1-6}$ haloalkyl, $OR^{a1}$, $C(O)R^{b1}$, $(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$.

254. The method of any one of paragraphs 239-252, wherein each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$.

255. The method of any one of paragraphs 239-254, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$.

256. The method of any one of paragraphs 239-254, wherein each $R^{a1}$, $R^{b1}$, $R^{c1}$, and $R^{d1}$ is independently selected from H, $C_{1-6}$ alkyl, and $C_{6-10}$ aryl, each of which is optionally substituted with 1, 2, or 3 substituents independently selected from $R^g$.

257. The method of any one of paragraphs 239-256, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

258. The method of paragraph 239, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, $C_{1-6}$ alkyl, $C_{1-6}$ haloalkyl, $OR^{a1}$, $C(O)R^{b1}$, $(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$;

each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

259. The method of paragraph 258, wherein $R^{11}$ independently selected from $Cy^1$, halo, $C_{1-6}$ alkyl, $OR^{a1}$, $C(O)R^{b1}$, and $C(O)NR^{c1}R^{d1}$.

260. The method of paragraph 239, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$;

each $R^{a1}$, $R^{b1}$, $R^{c1}$, and $R^{d1}$ is independently selected from H, $C_{1-6}$ alkyl, and $C_{6-10}$ aryl, each of which is optionally substituted with 1, 2, or 3 substituents independently selected from $R^g$; and $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

261. The method of paragraph 260, wherein $R^{11}$ independently selected from $Cy^1$, halo, $C_{1-6}$ alkyl, $OR^{a1}$, $C(O)R^{b1}$, and $C(O)NR^{c1}R^{d1}$;

262. The method of paragraph 239, wherein the compound of Formula (IIIa) is selected from any one of the compounds of Table 3a, Table 3b, Table 3b-2, Table 10, or Table 11.

263. The method of paragraph 239, wherein the compound of Formula (IIIa) is selected from any one of the compounds of Table 3a or Table 3b, or a pharmaceutically acceptable salt thereof.

264. A compound selected from any one of the compounds of Table 3b or Table 3b-2, or a pharmaceutically acceptable salt thereof.

265. A compound selected from any one of the compounds of Table 3b, or a pharmaceutically acceptable salt thereof.

266. A pharmaceutical composition comprising a compound of paragraph 264 or 265, or a pharmaceutically acceptable salt thereof, and a pharmaceutically acceptable carrier.

267. A compound of Formula (IIIc):

(IIIc)

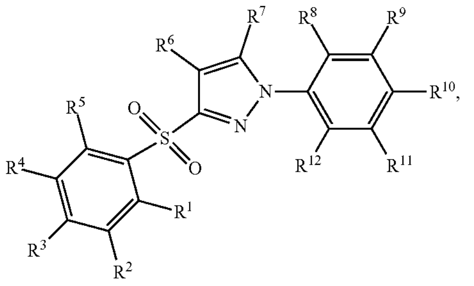

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{13}$;

each $R^{13}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

268. The compound of paragraph 267, wherein each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, OH, $C_{1-6}$ alkyl, $C_{1-6}$ haloalkyl, $C_{1-6}$ alkoxy, $C_{1-6}$ haloalkoxy.

269. The compound of paragraph 267, wherein each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, OH, $C_{1-6}$ alkyl, and $C_{1-6}$ alkoxy.

270. The compound of paragraph 267, wherein the compound of Formula (IIIc) is:

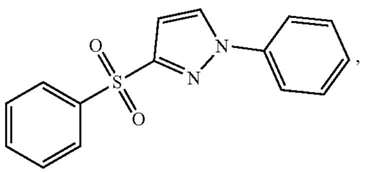 [SMILES: O=S(=O)(c1ccccc1)c1ccn(-c2ccccc2)n1]

or a pharmaceutically acceptable salt thereof.

271. A pharmaceutical composition comprising a compound of any one of paragraphs 267-270, or a pharmaceutically acceptable salt thereof, and a pharmaceutically acceptable carrier.

272. A compound of Formula (IIId):

(IIId)

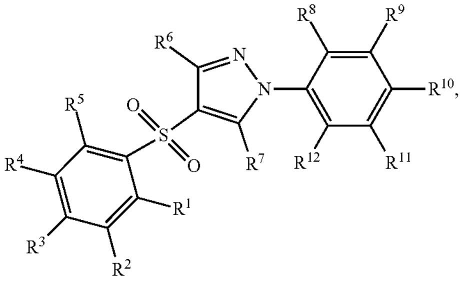

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{13}$;

each $R^{13}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^8$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

273. The compound of paragraph 272, wherein each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

274. The compound of paragraph 272, wherein each of $R^1$, $R^2$, $R^3$, $R^4$, $R^5$, $R^6$, $R^7$, $R^8$, $R^9$, $R^{10}$, $R^{11}$, and $R^{12}$ is independently selected from H, halo, OH, $C_{1-6}$ alkyl, and $C_{1-6}$ alkoxy.

275. The compound of paragraph 272, wherein the compound of Formula (IIId) is:

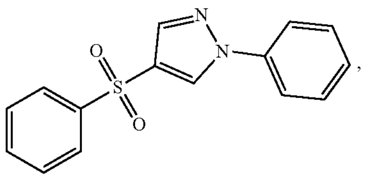 [SMILES: O=S(=O)(c1ccccc1)c1cnn(-c2ccccc2)c1]

or a pharmaceutically acceptable salt thereof.

276. A pharmaceutical composition comprising a compound of any one of paragraphs 272-275, or a pharmaceutically acceptable salt thereof, and a pharmaceutically acceptable carrier.

277. A compound of Formula (IIIe):

(IIIe)

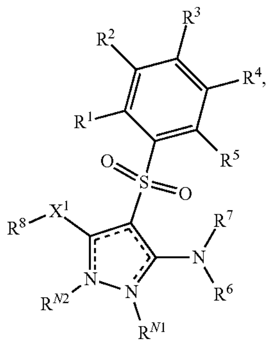

or a pharmaceutically acceptable salt thereof, wherein:

$X^1$ is selected from S, S(O), and $S(O)_2$;

each  represents a single bond or a double bond, provided that not more than two of  are double bonds;

$R^{N2}$ is absent if  between the N atom to which $R^{N2}$ is attached and the C atom to which $X^1$ is attached is a double bond; or $R^{N2}$ is selected from the group consisting of H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

$R^{N1}$ is absent if  between the N atom to which $R^{N1}$ is attached and the C atom to which $NR^6R^7$ is attached is a double bond; or $R^{N1}$ is selected from the group consisting of H, $C_{1-6}$ alkyl, $C_{1-6}$ haloalkyl, $C_{2-6}$ alkenyl, and $C_{2-6}$ alkynyl, each of which is optionally substituted with 1, 2, or 3 substituents independently selected from $R^9$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^{N1}$ together with the N atoms to which they are attached from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

278. The compound of paragraph 277, wherein $X^1$ is selected from S(O) and $S(O)_2$.

279. The compound of paragraph 277, wherein $X^1$ is S(O).

280. The compound of paragraph 277, wherein $X^1$ is $S(O)_2$.

281. The compound of any one of paragraphs 277-280, wherein the compound of Formula (IIIe) has formula:

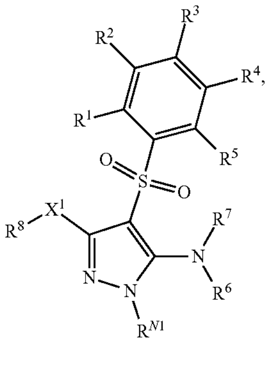

or a pharmaceutically acceptable salt thereof.

282. The compound of paragraph 281, wherein $R^{N1}$ is selected from H and $C_{1-6}$ alkyl.

283. The compound of paragraph 282, wherein $R^{N1}$ is H.

284. The compound of any one of paragraphs 281-283, wherein the compound of Formula (IIIe) has formula:

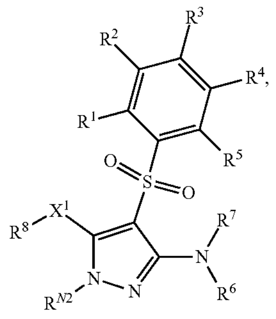

or a pharmaceutically acceptable salt thereof.

285. The compound of any one of paragraphs 277-284, wherein $R^6$ and $R^7$ are each independently selected from H and $C_{1-6}$ alkyl.

286. The compound of paragraph 285, wherein $R^6$ and $R^7$ are both H.

287. The compound of any one of paragraphs 277-281, wherein $R^6$ and $R^{N1}$ together with the N atoms to which they are attached from a 5-10 membered heteroaryl, substituted with 1, 2, or 3 substituents independently selected from $R^{10}$.

288. The compound of paragraph 287, wherein the compound of Formula (IIIe) has formula:

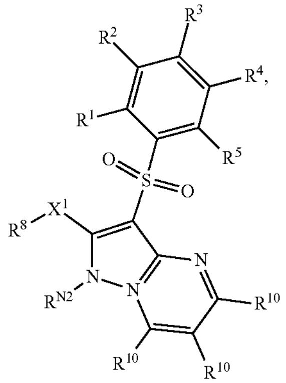

or a pharmaceutically acceptable salt thereof.

289. The compound of any one of paragraphs 277-288, wherein each $R^{10}$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

290. The compound of any one of paragraphs 277-288, wherein each $R^{10}$ is independently selected from H, halo, OH, $C_{1-6}$ alkyl, and $C_{1-6}$ alkoxy.

291. The compound of any one of paragraphs 277-288, wherein each $R^{10}$ is independently selected from H, OH, and $C_{1-6}$ alkyl.

292. The compound of any one of paragraphs 284-291, wherein $R^{N2}$ is selected from H and $C_{1-6}$ alkyl.

293. The compound of paragraph 292, wherein $R^{N2}$ is H.

294. The compound of any one of paragraphs 277-293, wherein each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

295. The compound of paragraph 294, wherein each of $R^1$, $R^2$, $R^3$, $R^4$, and $R^5$ is independently selected from H, halo, $C_{1-6}$ alkyl, and $C_{1-6}$ alkoxy.

296. The compound of any one of paragraphs 277-295, wherein $R^8$ is $C_{1-6}$ alkyl.

297. The compound of paragraph 288, wherein:

$X^1$ is selected from S(O) and $S(O)_2$;

each $R^{10}$ is independently selected from H, halo, CN, $NO_2$, OH, $C_{1-6}$ alkyl, $C_{1-6}$ haloalkyl, $C_{1-6}$ alkoxy, $C_{1-6}$ haloalkoxy;

$R^{N2}$ is selected from H and $C_{1-6}$ alkyl;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy; and $R^8$ is $C_{1-6}$ alkyl.

298. The compound of paragraph 288, wherein:

$X^1$ is selected from S(O) and $S(O)_2$;

each $R^{10}$ is independently selected from H, OH, and $C_{1-6}$ alkyl;

$R^{N2}$ is H;

$R^1$, $R^2$, $R^3$, $R^4$, and $R^5$ are each independently selected from H, halo, $C_{1-6}$ alkyl, and $C_{1-6}$ alkoxy; and $R^8$ is $C_{1-6}$ alkyl.

299. The compound of paragraph 281, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl;

$R^{N1}$ is selected from H and $C_{1-6}$ alkyl; and $R^6$ and $R^7$ are each independently selected from H and $C_{1-6}$ alkyl.

300. The compound of paragraph 299, wherein the compound of Formula (IIIe) has formula:

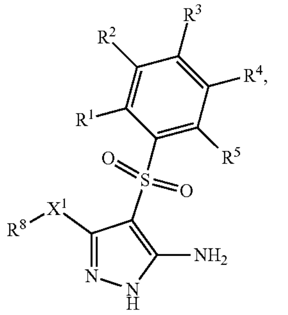

or a pharmaceutically acceptable salt thereof.

301. The compound of paragraph 284, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl;

$R^{N2}$ is selected from H and $C_{1-6}$ alkyl; and $R^6$ and $R^7$ are each independently selected from H and $C_{1-6}$ alkyl.

302. The compound of paragraph 301, wherein the compound of Formula (IIIe) has formula:

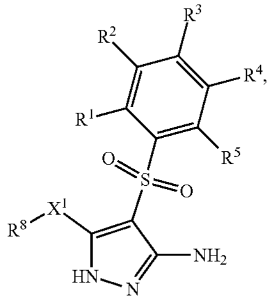

or a pharmaceutically acceptable salt thereof.

303. The compound of paragraph 277, wherein the compound of Formula (IIIe) is selected from any one of the following compounds:

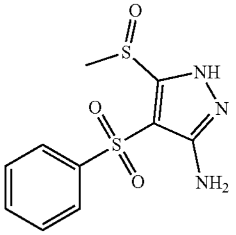

BC19338
ZE23-0091

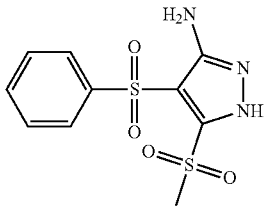

BC19339
ZE23-0092

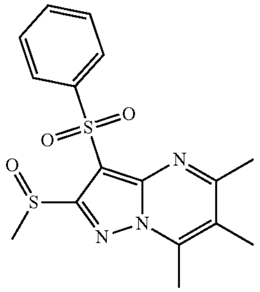

BC19340
ZE23-0096

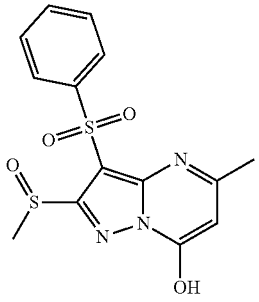

BC19341
ZE23-0098 or a pharmaceutically acceptable salt thereof.

304. A pharmaceutical composition comprising a compound of any one of paragraphs 277-303, or a pharmaceutically acceptable salt thereof, and a pharmaceutically acceptable carrier.

305. A compound of Formula (IIIf):

(IIIf)

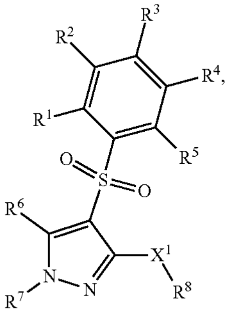

or a pharmaceutically acceptable salt thereof, wherein:

$X^1$ is selected from S, S(O), and $S(O)_2$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

provided that at least one of $R^6$ and $R^7$ is selected from $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^7$, together with the C atom to which $R^6$ is attached and N atom to which $R^7$ is attached, from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

306. The compound of paragraph 305, wherein $X^1$ is selected from S(O) and $S(O)_2$.

307. The compound of paragraph 305, wherein $X^1$ is S(O).

308. The compound of paragraph 305, wherein $X^1$ is $S(O)_2$.

309. The compound of any one of paragraphs 305-308, wherein each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

310. The compound of any one of paragraphs 305-308, wherein each of $R^1$, $R^2$, $R^3$, $R^4$, and $R^5$ is independently selected from H, halo, $C_{1-6}$ alkyl, and $C_{1-6}$ alkoxy.

311. The compound of any one of paragraphs 305-310, wherein $R^8$ is $C_{1-6}$ alkyl, optionally substituted with $OR^{a1}$ or $NR^{c1}R^{d1}$.

312. The compound of any one of paragraphs 305-308, wherein $R^8$ is selected from $C_{3-10}$ cycloalkyl and 4-10 membered heterocycloalkyl, each of which is optionally substituted with 1, 2, or 3 substituents independently selected from $R^9$.

313. The compound of any one of paragraphs 305-312, wherein:

$R^6$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$; and $R^7$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$.

314. The compound of any one of paragraphs 305-312, wherein:

$R^6$ is selected from H, $C_{1-6}$ alkyl, and $C_{1-6}$ haloalkyl; and $R^7$ is selected from phenyl, naphthyl, pyridinyl, cyclohexyl, tetrahydropyranyl, and piperidinyl, each of which is optionally substituted with 1, 2, or 3 substituents independently selected from $R^9$.

315. The compound of any one of paragraphs 305-312, wherein:

$R^7$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$; and $R^6$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$.

316. The compound of any one of paragraphs 305-312, wherein:

$R^7$ is selected from H, $C_{1-6}$ alkyl, and $C_{1-6}$ haloalkyl; and $R^6$ is selected from phenyl, naphthyl, pyridinyl, cyclohexyl, tetrahydropyranyl, and piperidinyl, each of which is optionally substituted with 1, 2, or 3 substituents independently selected from $R^9$.

317. The compound of any one of paragraphs 305-312, wherein the compound of Formula (IIIf) has formula:

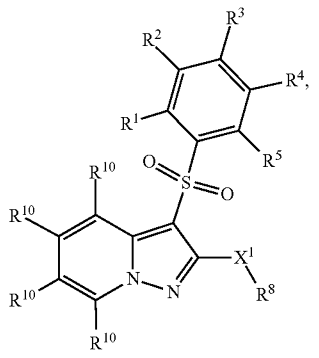

or a pharmaceutically acceptable salt thereof.

318. The compound of any one of paragraphs 305-312, wherein the compound of Formula (IIIf) has formula:

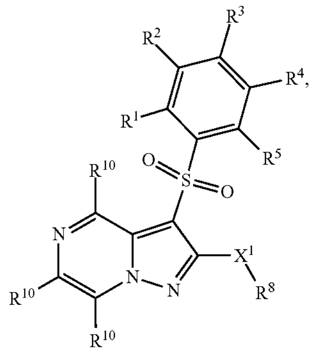

or a pharmaceutically acceptable salt thereof.

319. The compound of any one of paragraphs 305-312, wherein the compound of Formula (IIIf) has formula:

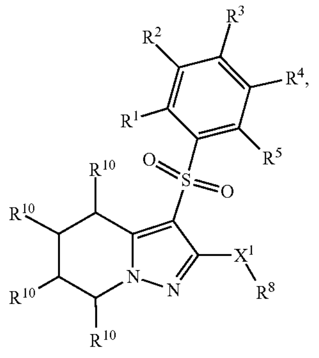

or a pharmaceutically acceptable salt thereof.

320. The compound of any one of paragraphs 305-312, wherein the compound of Formula (IIIf) has formula:

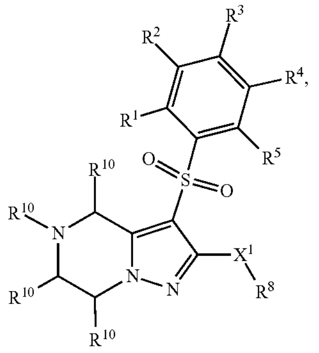

or a pharmaceutically acceptable salt thereof.

321. The compound of any one of paragraphs 305-320, wherein each $R^9$ is independently selected from halo, OH, $C_{1-6}$ alkyl, $C_{1-6}$ haloalkyl, $C_{1-6}$ alkoxy, and $C_{1-6}$ haloalkoxy.

322. The compound of any one of paragraphs 305-321, wherein each $R^{10}$ is independently selected from H, halo, OH, $C_{1-6}$ alkyl, $C_{1-6}$ haloalkyl, $C_{1-6}$ alkoxy, and $C_{1-6}$ haloalkoxy.

323. The compound of paragraph 305, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^6$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$;

$R^7$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

324. The compound of paragraph 305, wherein:

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^6$ is selected from H, $C_{1-6}$ alkyl, and $C_{1-6}$ haloalkyl; and $R^7$ is selected from phenyl, naphthyl, pyridinyl, cyclohexyl, tetrahydropyranyl, and piperidinyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

325. The compound of paragraph 305, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^7$ is selected from H, $C_{1-6}$ alkyl, $C_{1-6}$ haloalkyl, $C_{2-6}$ alkenyl and $C_{2-6}$ alkynyl, each of which is optionally substituted with 1, 2, or 3 substituents independently selected from $R^9$;

$R^6$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

326. The compound of paragraph 305, wherein:

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

$R^7$ is selected from H, $C_{1-6}$ alkyl, and $C_{1-6}$ haloalkyl; and $R^6$ is selected from phenyl, naphthyl, pyridinyl, cyclohexyl, tetrahydropyranyl, and piperidinyl, each of which is optionally substituted with 1, 2, or 3 substituents independently selected from $R^9$; and each $R^9$ is independently selected from halo, OH, $C_{1-6}$ alkyl, $C_{1-6}$ haloalkyl, $C_{1-6}$ alkoxy, and $C_{1-6}$ haloalkoxy.

327. The compound of any one of paragraphs 305 and 319-321, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^9$;

each $R^9$ is independently selected from halo, OH, $C_{1-6}$ alkyl, $C_{1-6}$ haloalkyl, $C_{1-6}$ alkoxy, and $C_{1-6}$ haloalkoxy; and each $R^{10}$ is independently selected from H, halo, OH, $C_{1-6}$ alkyl, $C_{1-6}$ haloalkyl, $C_{1-6}$ alkoxy, and $C_{1-6}$ haloalkoxy.

328. A pharmaceutical composition comprising a compound of any one of paragraphs 305-327, or a pharmaceutically acceptable salt thereof, and a pharmaceutically acceptable carrier.

329. A compound of Formula (IIIg-2):

(IIIg-2)

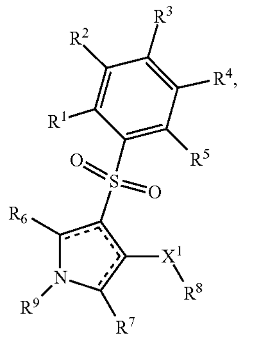

or a pharmaceutically acceptable salt thereof, wherein:

$X^1$ is selected from S, S(O), and $S(O)_2$;

each  represents a single bond or a double bond, provided that not more than two of  are double bonds;

each of $R^1$, $R^2$, $R^3$, $R^4$, $R^5$, $R^6$, and $R^7$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$R^9$ is selected from $C(O)R^{b1}$, $C(O)NR^{c1}R^{d1}$, $S(O)_2R^{b1}$, $S(O)_2NR^{c1}R^{d1}$, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, wherein each of said $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl is optionally substituted with 1, 2, 3, 4, or 5 substituents independently selected from $R^{10}$; or $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^9$, together with the N atom to which $R^9$ is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$;

each $R^{10}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{11}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^8$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

330. The compound of paragraph 329, wherein the compound has formula:

(IIIg)

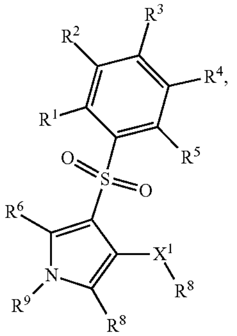

or a pharmaceutically acceptable salt thereof, wherein:

$X^1$ is selected from S, S(O), and $S(O)_2$;

each of $R^1$, $R^2$, $R^3$, $R^4$, $R^5$, $R^6$, and $R^7$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$R^9$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^9$, together with the N atom to which $R^9$ is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$;

each $R^{10}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^8$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylamino-sulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

331. The compound of paragraph 329, having formula:

(IIIg)

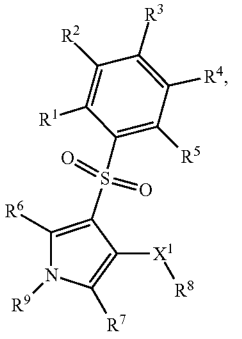

or a pharmaceutically acceptable salt thereof.

332. The compound of paragraph 329, having formula:

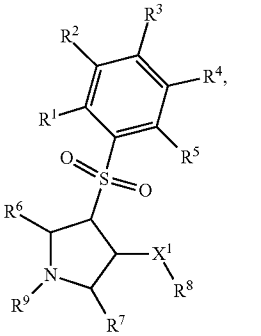

or a pharmaceutically acceptable salt thereof.

333. The compound of any one of paragraphs 329-332, wherein $X^1$ is selected from S(O) and $S(O)_2$.

334. The compound of any one of paragraphs 329-332, wherein $X^1$ is S(O).

335. The compound of any one of paragraphs 329-332, wherein $X^1$ is $S(O)_2$.

336. The compound of any one of paragraphs 329-335, wherein each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

337. The compound of any one of paragraphs 329-335, wherein each of $R^1$, $R^2$, $R^3$, $R^4$, and $R^5$ is independently selected from H, halo, $C_{1-6}$ alkyl, and $C_{1-6}$ alkoxy.

338. The compound of any one of paragraphs 329-337, wherein $R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

339. The compound of any one of paragraphs 329-337, wherein:

$R^6$ is H or $C_{1-6}$ alkyl; and $R^7$ is H or $C_{1-6}$ alkyl.

340. The compound of any one of paragraphs 329-337, wherein:

$R^6$ is H or $C_{1-6}$ alkyl; and $R^7$ is selected from halo, CN, $NO_2$, OH, $C_{1-6}$ alkyl, $C_{1-6}$ haloalkyl, $C_{1-6}$ alkoxy, and $C_{1-6}$ haloalkoxy.

341. The compound of any one of paragraphs 329-337, wherein:

$R^7$ is H or $C_{1-6}$ alkyl; and $R^6$ is selected from halo, CN, $NO_2$, OH, $C_{1-6}$ alkyl, $C_{1-6}$ haloalkyl, $C_{1-6}$ alkoxy, and $C_{1-6}$ haloalkoxy.

342. The compound of any one of paragraphs 329-337, wherein:

$R^6$ is H or $C_{1-6}$ alkyl; and $R^7$ and $R^9$, together with the N atom to which $R^9$ is attached and C atom to which $R^7$ is attached, form a 5-10 membered heteroaryl or 4-10 membered heterocycloalkyl, each of which is substituted with 1, 2, 3, 4, or 5 substituents independently selected from $R^{11}$.

343. The compound of paragraph 342, wherein the compound of Formula (IIIg) has formula:

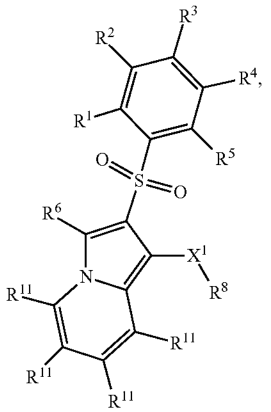

or a pharmaceutically acceptable salt thereof.

344. The compound of paragraph 342, wherein the compound has formula:

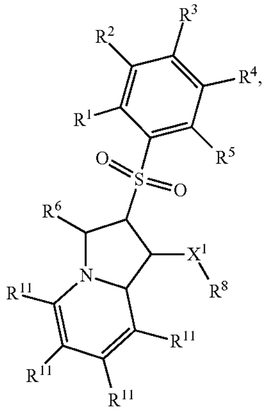

or a pharmaceutically acceptable salt thereof.

345. The compound of paragraph 342, wherein the compound of Formula (IIIg) has formula:

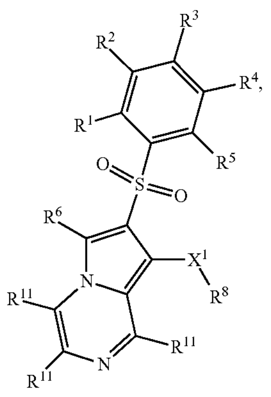

or a pharmaceutically acceptable salt thereof.

346. The compound of paragraph 342, having formula:

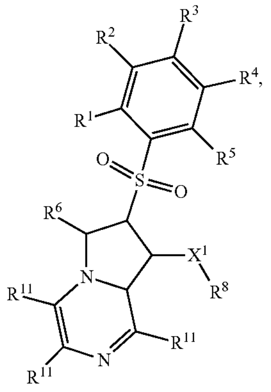

or a pharmaceutically acceptable salt thereof.

347. The compound of paragraph 342, wherein the compound of Formula (IIIg) has formula:

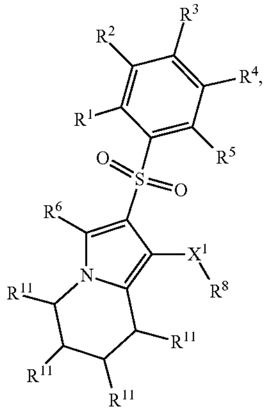

or a pharmaceutically acceptable salt thereof.

348. The compound of paragraph 342, wherein the compound has formula:

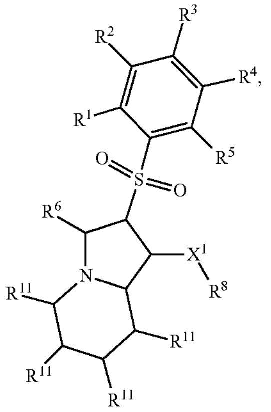

or a pharmaceutically acceptable salt thereof.

349. The compound of paragraph 342, wherein the compound of Formula (IIIg) has formula:

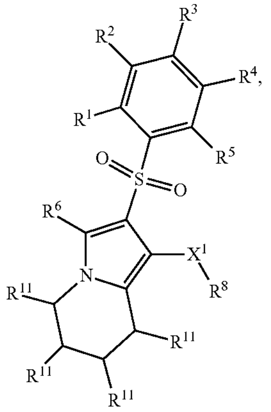

or a pharmaceutically acceptable salt thereof.

350. The compound of paragraph 342, having the formula:

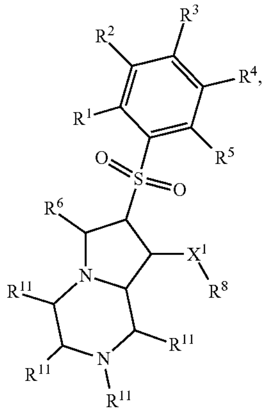

or a pharmaceutically acceptable salt thereof.

351. The compound of any one of paragraphs 329-337, wherein:

$R^7$ is H or $C_{1-6}$ alkyl; and $R^6$ and $R^9$, together with the N atom to which $R^9$ is attached and C atom to which $R^6$ is attached, form a 5-10 membered heteroaryl or 4-10 membered heterocycloalkyl, each of which is substituted with 1, 2, 3, 4, or 5 substituents independently selected from $R^{11}$.

352. The compound of paragraph 351, wherein the compound of Formula (IIIg) has formula:

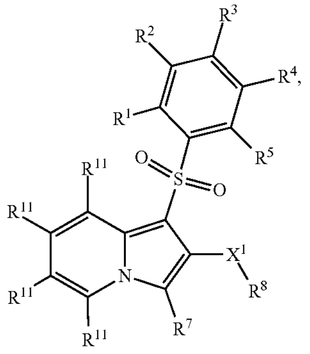

or a pharmaceutically acceptable salt thereof.

353. The compound of paragraph 351, having the formula:

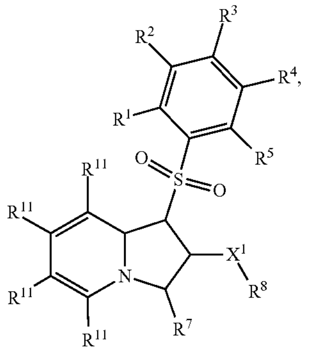

or a pharmaceutically acceptable salt thereof.

354. The compound of paragraph 351, wherein the compound of Formula (IIIg) has formula:

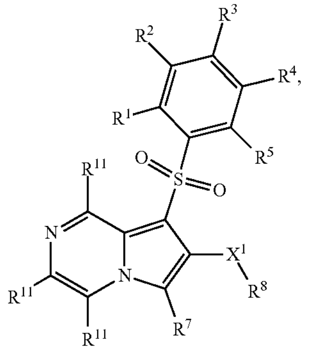

or a pharmaceutically acceptable salt thereof.

355. The compound of paragraph 351, having the formula:

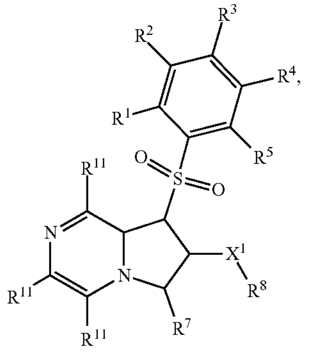

or a pharmaceutically acceptable salt thereof.

356. The compound of paragraph 351, wherein the compound of Formula (IIIg) has formula:

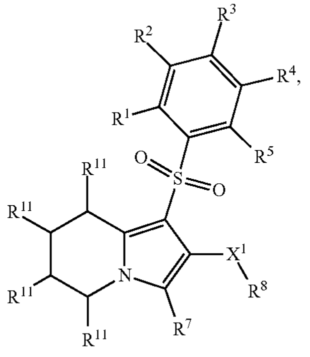

or a pharmaceutically acceptable salt thereof.

357. The compound of paragraph 351, having the formula:

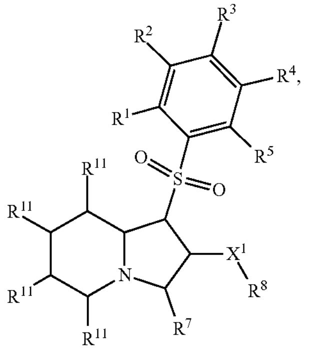

or a pharmaceutically acceptable salt thereof.

358. The compound of paragraph 351, wherein the compound of Formula (IIIg) has formula:

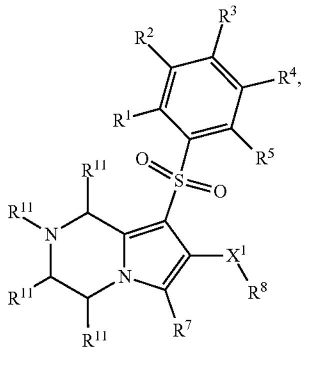

or a pharmaceutically acceptable salt thereof.

359. The compound of paragraph 351, wherein the compound has the formula:

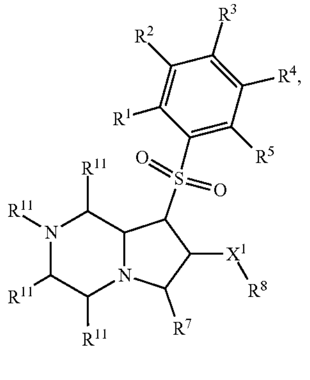

or a pharmaceutically acceptable salt thereof.

360. The compound of any one of paragraphs 329-341, wherein $R^9$ is $C_{1-6}$ alkyl, optionally substituted with 1, 2, or 3 substituents independently selected from $R^{10}$.

361. The compound of any one of paragraphs 329-341, wherein $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

362. The compound of any one of paragraphs 329-341, wherein $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$.

363. The compound of any one of paragraphs 329-341, wherein $R^9$ is $C(O)R^{b1}$.

364. The compound of any one of paragraphs 329-341, wherein $R^9$ is 4-10 membered heterocycloalkyl, which is optionally substituted with 1, 2, or 3 substituents independently selected from $R^{10}$.

365. The compound of any one of paragraphs 329-364, wherein $R^8$ is $C_{1-6}$ alkyl, optionally substituted with $OR^{a1}$ or $NR^{c1}R^{d1}$.

366. The compound of any one of paragraphs 329-365, wherein $R^8$ is selected from $C_{3-10}$ cycloalkyl and 4-10 membered heterocycloalkyl, each of which is optionally substituted with 1, 2, or 3 substituents independently selected from $R^{10}$.

367. The compound of any one of paragraphs 329-366, wherein $R^{10}$ is independently selected from $C_{6-12}$ aryl, halo, OH, $C_{1-6}$ alkyl, $C_{1-6}$ haloalkyl, $C_{1-6}$ alkoxy, and $C_{1-6}$ haloalkoxy.

368. The compound of any one of paragraphs 329-366, wherein $R^{10}$ is independently selected from halo, OH, $C_{1-6}$ alkyl, $C_{1-6}$ haloalkyl, $C_{1-6}$ alkoxy, and $C_{1-6}$ haloalkoxy.

369. The compound of any one of paragraphs 329-368, wherein $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

370. The compound of paragraph 329, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

$R^9$ is selected from $C(O)R^{b1}$, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^{10}$; and each $R^{10}$ is independently selected from $C_{6-12}$ aryl, halo, OH, $C_{1-6}$ alkyl, $C_{1-6}$ haloalkyl, $C_{1-6}$ alkoxy, and $C_{1-6}$ haloalkoxy.

371. The compound of paragraph 329, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ and $R^7$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$; and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

372. The compound of paragraph 329, wherein:

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^6$ is H or $C_{1-6}$ alkyl;

$R^7$ is selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$; and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

373. The compound of paragraph 329, wherein:

$X^1$ is selected from S(O) and $S(O)_2$;

each of $R^1$, $R^2$, $R^3$, $R^4$, and $R^5$ is independently selected from H, halo, $C_{1-6}$ alkyl, and $C_{1-6}$ alkoxy;

$R^7$ is H or $C_{1-6}$ alkyl;

$R^6$ is selected from halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$; and each $R^{10}$ is independently selected from halo, OH, $C_{1-6}$ alkyl, $C_{1-6}$ haloalkyl, $C_{1-6}$ alkoxy, and $C_{1-6}$ haloalkoxy.

374. The compound of paragraph 329, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is H or $C_{1-6}$ alkyl;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

375. The compound of paragraph 329, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is H or $C_{1-6}$ alkyl;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

376. The compound of paragraph 329, wherein the compound is selected from any one of the compounds of Table 12, or a pharmaceutically acceptable salt thereof.

377. A pharmaceutical composition comprising a compound of any one of paragraphs 329-376, or a pharmaceutically acceptable salt thereof, and a pharmaceutically acceptable carrier.

378. A compound of Formula (IIIh):

(IIIh)

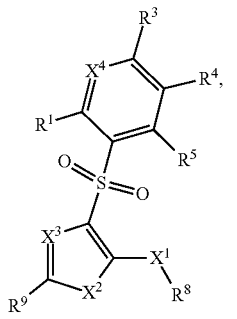

or a pharmaceutically acceptable salt thereof, wherein:

$X^1$ is selected from S, S(O), and $S(O)_2$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$X^4$ is selected from N and $CR^2$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^2$ is selected from O, S, and $NR^6$;

$R^6$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^3$ is selected from N and $CR^7$;

$R^7$ is selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^9$ is selected from $S(O)_2R^{b1}$, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^9$ and $R^6$, together with the carbon atom to which $R^9$ is attached and the N atom to which $R^6$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^8$, together with N atom to which $R^6$ is attached and S atom to which $R^8$ is attached, form 4-10 membered heterocycloalkyl substituted with 1, 2, 3, 4, or 5 substituents independently selected from $R^{11}$;

each $R^{10}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{11}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

provided that if $X^3$ is N and $X^2$ is O, then $R^9$ is selected from $S(O)_2R^{b1}$, $C_{1-6}$ alkyl, $C_{1-6}$ haloalkyl, $C_{2-6}$ alkenyl, $C_{2-6}$ alkynyl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$.

379. A compound of Formula (IIIh):

(IIIh)

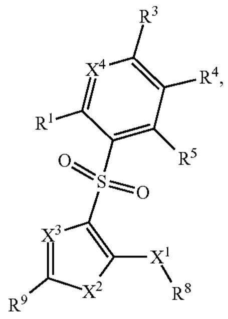

or a pharmaceutically acceptable salt thereof, wherein:

$X^1$ is selected from S, S(O), and $S(O)_2$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$;

$X^4$ is selected from N and $CR^2$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^2$ is selected from O, S, and $NR^6$;

$R^6$ is selected from H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$X^3$ is selected from N and $CR^7$;

$R^7$ is selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{10}$;

$R^9$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{10}$; or $R^9$ and $R^6$, together with the carbon atom to which $R^9$ is attached and the N atom to which $R^6$ is attached, form a 5-10 membered heteroaryl or 4-10 membered heterocycloalkyl, each of which is substituted with 1, 2, 3, 4, or 5 substituents independently selected from $R^{11}$; or $R^6$ and $R^8$, together with N atom to which $R^6$ is attached and S atom to which $R^8$ is attached, form 4-10 membered heterocycloalkyl substituted with 1, 2, 3, 4, or 5 substituents independently selected from $R^{11}$;

each $R^{10}$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$ $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{11}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

380. The compound of paragraph 378 or 379, wherein $X^1$ is selected from S(O) and $S(O)_2$.

381. The compound of paragraph 378 or 379, wherein $X^1$ is S(O).

382. The compound of paragraph 378 or 379, wherein $X^1$ is $S(O)_2$.

383. The compound of any one of paragraphs 378-382, wherein $X^4$ is $CR^2$.

384. The compound of any one of paragraphs 378-383, wherein each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

385. The compound of any one of paragraphs 378-383, wherein each of $R^1$, $R^2$, $R^3$, $R^4$, and $R^5$ is independently selected from H, halo, $C_{1-6}$ alkyl, and $C_{1-6}$ alkoxy.

386. The compound of any one of paragraphs 378-385, wherein $X^4$ is N.

387. The compound of any one of paragraphs 378-386, wherein $R^8$ is $C_{1-6}$ alkyl, optionally substituted with $OR^{a1}$ or $NR^{c1}R^{d1}$.

388. The compound of any one of paragraphs 378-387, wherein $R^8$ is selected from $C_{3-10}$ cycloalkyl and 4-10 membered heterocycloalkyl, each of which is optionally substituted with 1, 2, or 3 substituents independently selected from $R^{10}$.

389. The compound of any one of paragraphs 378-388, wherein the compound of Formula (IIIh) has formula:

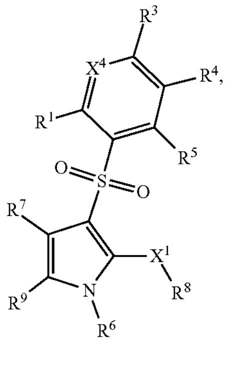

or a pharmaceutically acceptable salt thereof.

390. The compound of any one of paragraphs 378-389, wherein $R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy.

391. The compound of any one of paragraphs 378-389, wherein $R^7$ is selected from H, halo, $C_{1-6}$ alkyl, and $C_{1-6}$ alkoxy.

392. The compound of any one of paragraphs 378-388, wherein the compound of Formula (IIIh) has formula:

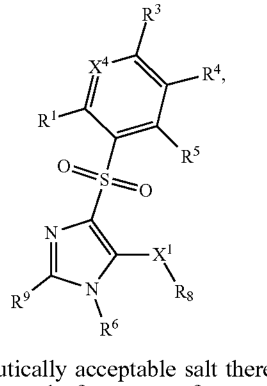

or a pharmaceutically acceptable salt thereof.

393. The compound of any one of paragraphs 378-392, wherein $R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$.

394. The compound of any one of paragraphs 378-393, wherein $R^6$ is selected from H and $C_{1-6}$ alkyl.

395. The compound of any one of paragraphs 378-388, wherein the compound of Formula (IIIh) has formula:

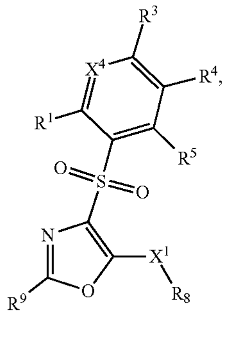

or a pharmaceutically acceptable salt thereof.

396. The compound of any one of paragraphs 378-388, wherein the compound of Formula (IIIh) has formula:

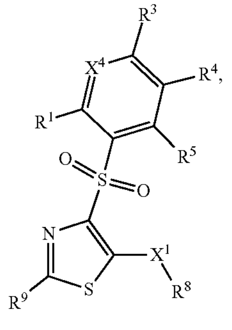

or a pharmaceutically acceptable salt thereof.

397. The compound of any one of paragraphs 378-396, wherein $R^9$ is $C_{1-6}$ alkyl, optionally substituted with 1, 2, or 3 substituents independently selected from $R^{10}$.

398. The compound of any one of paragraphs 378-396, wherein $R^9$ is $S(O)_2R^{b1}$.

399. The compound of any one of paragraphs 378-396, wherein $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$.

400. The compound of any one of paragraphs 378-396, wherein $R^9$ is selected from $C_{3-10}$ cycloalkyl and 5-10 membered heteroaryl, each of which is optionally substituted with 1, 2, or 3 substituents independently selected from $R^{10}$.

401. The compound of paragraph 399, wherein $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$.

402. The compound of any one of paragraphs 378-392, wherein the compound of Formula (IIIh) has formula:

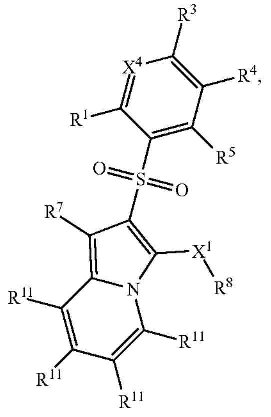

or a pharmaceutically acceptable salt thereof.

403. The compound of any one of paragraphs 378-388, wherein the compound of Formula (IIIh) has formula:

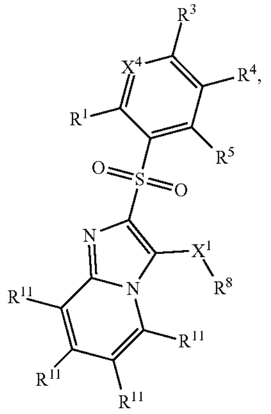

or a pharmaceutically acceptable salt thereof.

404. The compound of any one of paragraphs 378-392, wherein the compound of Formula (IIIh) has formula:

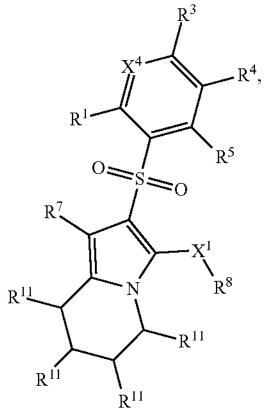

or a pharmaceutically acceptable salt thereof.

405. The compound of any one of paragraphs 378-388, wherein the compound of Formula (IIIh) has formula:

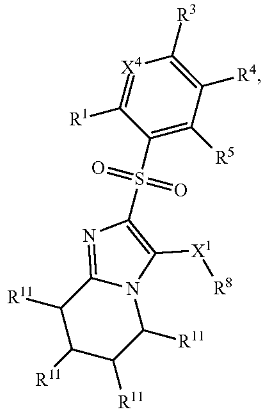

or a pharmaceutically acceptable salt thereof.

406. The compound of any one of paragraphs 378-392, wherein the compound of Formula (IIIh) has formula:

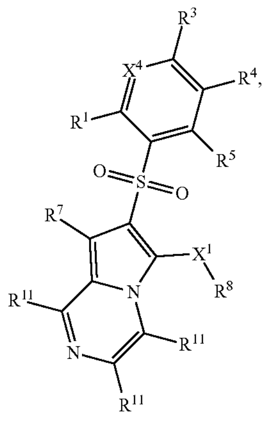

or a pharmaceutically acceptable salt thereof.

407. The compound of any one of paragraphs 378-388, wherein the compound of Formula (IIIh) has formula:

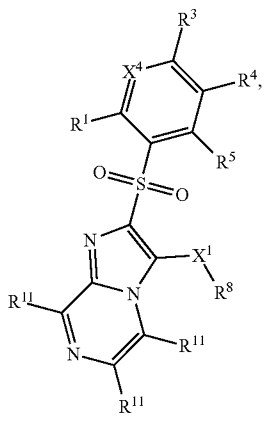

or a pharmaceutically acceptable salt thereof.

408. The compound of any one of paragraphs 378-392, wherein the compound of Formula (IIIh) has formula:

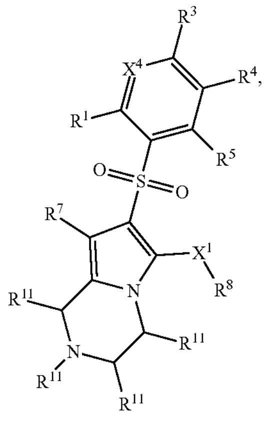

or a pharmaceutically acceptable salt thereof.

409. The compound of any one of paragraphs 378-388, wherein the compound of Formula (IIIh) has formula:

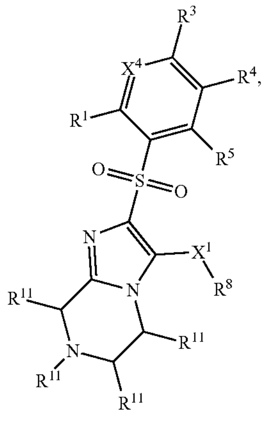

or a pharmaceutically acceptable salt thereof.

410. The compound of any one of paragraphs 378-401, wherein the compound of Formula (IIIh) has formula:

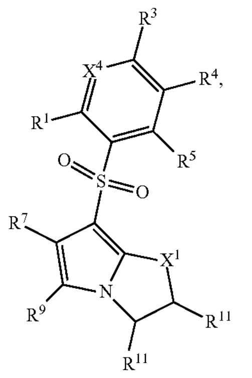

or a pharmaceutically acceptable salt thereof.

411. The compound of any one of paragraphs 378-401, wherein the compound of Formula (IIIh) has formula:

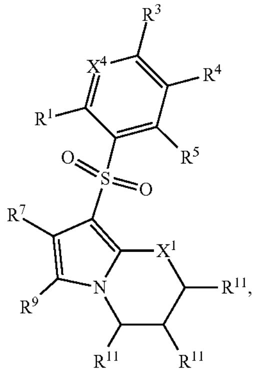

or a pharmaceutically acceptable salt thereof.

412. The compound of any one of paragraphs 378-401, wherein the compound of Formula (IIIh) has formula:

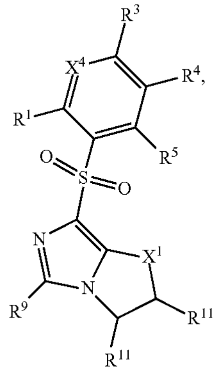

or a pharmaceutically acceptable salt thereof.

413. The compound of any one of paragraphs 378-401, wherein the compound of Formula (IIIh) has formula:

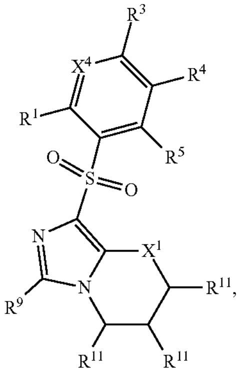

or a pharmaceutically acceptable salt thereof.

414. The compound of any one of paragraphs 378-409, wherein each $R^{10}$ is independently selected from $Cy^1$, halo, $C_{1-6}$ alkyl, $C_{1-6}$ haloalkyl, $OR^{a1}$, $C(O)NR^{c1}R^{d1}$, and $NR^{c1}R^{d1}$.

415. The compound of any one of paragraphs 378-409, wherein $Cy^1$ is $C_{3-10}$ cycloalkyl, optionally substituted with 1, 2, or 3 substituents independently selected from $R^{11}$.

416. The compound of any one of paragraphs 378-409, wherein each $R^{10}$ is independently selected from halo, OH, $C_{1-6}$ alkyl, $C_{1-6}$ haloalkyl, $C_{1-6}$ alkoxy, and $C_{1-6}$ haloalkoxy.

417. The compound of any one of paragraphs 378-409, wherein each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

418. The compound of paragraph 378, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$, or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$.

$R^9$ is selected from $S(O)_2R^{b1}$ and $C_{1-6}$ alkyl, optionally substituted with 1, 2, or 3 substituents independently selected from $R^{10}$; or $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

each $R^{10}$ is independently selected from $Cy^1$, halo, $C_{1-6}$ alkyl, $C_{1-6}$ haloalkyl, $OR^{a1}$, $C(O)NR^{c1}R^{d1}$, and $NR^{c1}R^{d1}$, and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

419. The compound of paragraph 378, wherein:

$X^1$ is selected from S(O) and $S(O)_2$;

each of $R^1$, $R^2$, $R^3$, $R^4$, and $R^5$ is independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^6$ is selected from H, $C_{1-6}$ alkyl, and $C_{1-6}$ haloalkyl, wherein said $C_{1-6}$ alkyl is optionally substituted with 1, 2, or 3 substituents independently selected from $R^{10}$;

$R^9$ is $C_{1-6}$ alkyl, optionally substituted with 1, 2, or 3 substituents independently selected from $R^{10}$; or $R^9$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

420. The compound of paragraph 378, wherein:

$X^1$ is selected from S(O) and $S(O)_2$;

$R^1$, $R^2$, $R^3$, $R^4$, and $R^5$ is independently selected from H, halo, $C_{1-6}$ alkyl, and $C_{1-6}$ alkoxy;

$R^8$ is $C_{1-6}$ alkyl, optionally substituted with $OR^{a1}$ or $NR^{c1}R^{d1}$; or $R^8$ is selected from $C_{3-10}$ cycloalkyl and 4-10 membered heterocycloalkyl, each of which is optionally substituted with 1, 2, or 3 substituents independently selected from $R^{10}$;

$R^7$ is selected from H, halo, $C_{1-6}$ alkyl, and $C_{1-6}$ alkoxy;

$R^6$ is selected from H and $C_{1-6}$ alkyl;

$R^9$ is $C_{1-6}$ alkyl, optionally substituted with 1, 2, or 3 substituents independently selected from $R^{10}$, or $R^9$ is selected from phenyl, naphthyl, pyridinyl, cyclohexyl, tetrahydropyranyl, and piperidinyl, each of which is optionally substituted with 1, 2, or 3 substituents independently selected from $R^{10}$;

each $R^{10}$ is independently selected from halo, OH, $C_{1-6}$ alkyl, $C_{1-6}$ haloalkyl, $C_{1-6}$ alkoxy, and $C_{1-6}$ haloalkoxy; and each $R^{11}$ is independently selected from H, halo, OH, $C_{1-6}$ alkyl, $C_{1-6}$ haloalkyl, $C_{1-6}$ alkoxy, and $C_{1-6}$ haloalkoxy.

421. The compound of paragraph 378, wherein the compound of Formula (IIIh) is selected from any one of the compounds of Table 8, Table 9, Table 10, and Table 11, or a pharmaceutically acceptable salt thereof.

422. A pharmaceutical composition comprising a compound of any one of paragraphs 378-421, or a pharmaceutically acceptable salt thereof, and a pharmaceutically acceptable carrier.

423. A compound of Formula (IIIi):

(IIIi)

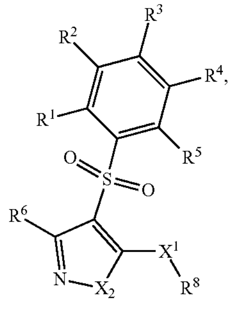

or a pharmaceutically acceptable salt thereof, wherein:

$X^1$ is selected from S, S(O), and $S(O)_2$;

$X^2$ is selected from S and $NR^7$;

each of $R^1$, $R^2$, $R^3$, $R^4$, and $R^5$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^8$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^9$;

$R^6$ and $R^7$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

provided that at least one of $R^6$ and $R^7$ is selected from $C_{6-10}$ aryl, $C_{3-10}$ cycloalkyl, 5-10 membered heteroaryl, and 4-10 membered heterocycloalkyl; each of which is optionally substituted with 1, 2, or 3 substituents independently selected from $R^9$;

or $R^6$ and $R^7$, together with the C atom to which $R^6$ is attached and N atom to which $R^7$ is attached, from a 5-10 membered heteroaryl or 4-10 membered heterocycloalkyl, each of which is substituted with 1, 2, 3, 4, or 5 substituents independently selected from $R^{10}$;

each $R^9$ independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{10}$ independently selected from H, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

424. The compound of paragraph 423, having the formula:

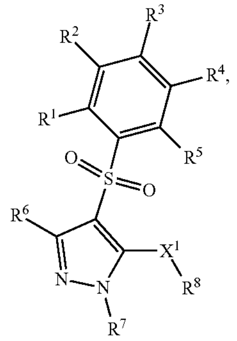

or a pharmaceutically acceptable salt thereof.

425. The compound of paragraph 423, having the formula:

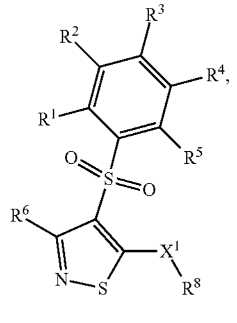

or a pharmaceutically acceptable salt thereof.

426. The compound of any one of paragraphs 423-425, wherein each of $R^1$, $R^2$, $R^3$, $R^4$, and $R^5$ is independently selected from H and halo.

427. The compound of any one of paragraphs 423-426, wherein $R^6$ is $C_{6-10}$ aryl, optionally substituted with 1, 2, or 3 substituents independently selected from $R^9$.

428. The compound of any one of paragraphs 423-427, wherein $R^8$ is $C_{1-6}$ alkyl, optionally substituted with 1, 2, or 3 substituents independently selected from $R^9$.

429. The compound of paragraph 423, wherein:

each of $R^1$, $R^2$, $R^3$, $R^4$, and $R^5$ is independently selected from H and halo;

$R^6$ is $C_{6-10}$ aryl, optionally substituted with 1, 2, or 3 substituents independently selected from $R^9$; and $R^8$ is $C_{1-6}$ alkyl, optionally substituted with 1, 2, or 3 substituents independently selected from $R^9$.

430. The compound of paragraph 423, wherein the compound is selected from any one of the compounds of Table 15, or a pharmaceutically acceptable salt thereof.

431. A pharmaceutical composition comprising a compound of any one of paragraphs 423-430, or a pharmaceutically acceptable salt thereof, and a pharmaceutically acceptable carrier.

432. A method for inhibiting NF-κB activity within a cell within a mammal, wherein said method comprises administering, to said mammal, an effective amount of a compound of Formula (IVa):

(IVa)

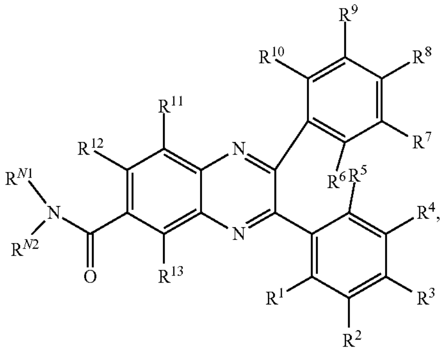

or a pharmaceutically acceptable salt thereof, wherein:

each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{14}$;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$;

or $R^{N1}$ and $R^{N2}$ together with the N atom to which they are attached from a 4-10 membered heterocycloalkyl, each of which is optionally substituted with 1, 2, 3, 4, or 5 substituents independently selected from $R^{14}$;

each $R^{14}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

433. The method of paragraph 432, wherein each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, $C_{1-6}$ haloalkyl, $OR^{a1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{14}$.

434. The method of paragraph 432, wherein each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, and $C_{1-6}$ alkoxy.

435. The method of any one of paragraphs 432-434, wherein $R^{N1}$ is selected from H, $C_{1-6}$ alkyl, and $C_{2-6}$ alkenyl.

436. The method of any one of paragraphs 432-435, wherein $R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$.

437. The method of any one of paragraphs 432-436, wherein $R^{N1}$ and $R^{N2}$ together with the N atom to which they are attached from a 4-10 membered heterocycloalkyl, each of which is optionally substituted with 1, 2, or 3 substituents independently selected from $R^{14}$.

438. The method of paragraph 437, wherein the 4-10 membered heterocycloalkyl is selected from pyrrolidine, piperazine, morpholine, and piperidine.

439. The method of any one of paragraphs 432-438, wherein each $R^{14}$ independently selected from $Cy^1$, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$.

440. The method of any one of paragraphs 432-438, wherein each $R^{14}$ independently selected from $Cy^1$, $C_{1-6}$ alkyl, $OR^{a1}$, $C(O)R^{b1}$, $C(O)NR^{c1}R^{d1}$, $C(O)OR^{a1}$, and $NR^{c1}R^{d1}$.

441. The method of any one of paragraphs 432-440, wherein each $Cy^1$ is independently selected from $C_{6-10}$ aryl, 5-10 membered heteroaryl, and 4-10 membered heterocycloalkyl, each of which is optionally substituted with 1, 2, or 3, substituents independently selected from $R^{Cy1}$.

442. The method of any one of paragraphs 432-440, wherein each $Cy^1$ is independently selected from phenyl, piperidine, thiophene, pyridine, piperazine, morpholine, azepane, pyrrolidone, pyrrolidine, and pyrimidine, each of which is optionally substituted with 1, 2, or 3, substituents independently selected from $R^{Cy1}$.

443. The method of any one of paragraphs 432-442, wherein each $R^{Cy1}$ is independently selected from halo, $C_{1-6}$ alkyl, $C_{1-6}$ haloalkyl, $OR^{a1}$, $SR^{a1}$, $C(O)NR^{c1}R^{d1}$, $C(O)OR^{a1}$, and $NR^{c1}R^{d1}$.

444. The method of any one of paragraphs 432-442, wherein each $R^{Cy1}$ is independently selected from halo, $C_{1-6}$ alkyl, $OR^{a1}$, $SR^{a1}$, and $NR^{c1}R^{d1}$.

445. The method of any one of paragraphs 432-444, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^8$.

446. The method of any one of paragraphs 432-444, wherein each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^8$.

447. The method of any one of paragraphs 432-446, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

448. The method of paragraph 432, wherein each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, $C_{1-6}$ haloalkyl, $OR^{a1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{14}$;

$R^{N1}$ is selected from H, $C_{1-6}$ alkyl, and $C_{2-6}$ alkenyl;

$R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$; or $R^{N1}$ and $R^{N2}$ together with the N atom to which they are attached from a 4-10 membered heterocycloalkyl, each of which is optionally substituted with 1, 2, or 3 substituents independently selected from $R^{14}$;

$R^{14}$ independently selected from $Cy^1$, halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$;

$Cy^1$ is independently selected from $C_{6-10}$ aryl, 5-10 membered heteroaryl, and 4-10 membered heterocycloalkyl, each of which is optionally substituted with 1, 2, or 3, substituents independently selected from $R^{Cy1}$;

$R^{Cy1}$ is independently selected from halo, $C_{1-6}$ alkyl, $C_{1-6}$ haloalkyl, $OR^{a1}$ $SR^{a1}$, $C(O)NR^{c1}R^{d1}$, $C(O)OR^{a1}$, and $NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

449. The method of paragraph 432, wherein:

each of $R^1$, $R^2$, $R^3$, $R^4$, $R^5$, $R^6$, $R^7$, $R^8$, $R^9$, $R^{10}$, $R^{11}$, $R^{12}$, and $R^{13}$ is independently selected from H, halo, $C_{1-6}$ alkyl, and $C_{1-6}$ alkoxy;

$R^{N1}$ is selected from H, $C_{1-6}$ alkyl, and $C_{2-6}$ alkenyl;

$R^{N2}$ is selected from H, $C_{1-6}$ alkyl, $C_{2-6}$ alkenyl, and $C_{3-10}$ cycloalkyl, wherein said $C_{1-6}$ alkyl is optionally substituted with 1, 2, or 3 substituents independently selected from $R^{14}$; or $R^{N1}$ and $R^{N2}$ together with the N atom to which they are attached from pyrrolidine, piperazine, morpholine, or piperidine, each of which is optionally substituted with 1, 2, or 3 substituents independently selected from $R^{14}$;

each $R^{14}$ independently selected from $Cy^1$, $C_{1-6}$ alkyl, $OR^{a1}$, $C(O)R^{b1}$, $C(O)NR^{c1}R^{d1}$, $C(O)OR^{a1}$, and $NR^{c1}R^{d1}$;

each $Cy^1$ is independently selected from phenyl, piperidine, thiophene, pyridine, piperazine, morpholine, azepane, pyrrolidone, pyrrolidine, and pyrimidine, each of which is optionally substituted with 1, 2, or 3, substituents independently selected from $R^{Cy1}$;

each $R^{Cy1}$ is independently selected from halo, $C_{1-6}$ alkyl, $OR^{a1}$, $SR^{a1}$, and $NR^{c1}R^{d1}$;

each $R^{a1}$, $R^{b1}$, $R^{c1}$, and $R^{d1}$ is independently selected from H, $C_{1-6}$ alkyl, $C_{3-10}$ cycloalkyl, 5-10 membered heteroaryl, and $C_{6-10}$ aryl-$C_{1-4}$ alkylene, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

450. The method of paragraph 432, wherein the compound of Formula (IVa) is selected from any one of the compounds of Table 4a, or a pharmaceutically acceptable salt thereof.

451. A compound selected from any one of the compounds of Table 4b or Table 4b-2, or a pharmaceutically acceptable salt thereof.

452. A compound selected from any one of the compounds of Table 4b, or a pharmaceutically acceptable salt thereof.

453. A pharmaceutical composition comprising a compound of paragraph 451 or 452, or a pharmaceutically acceptable salt thereof, and a pharmaceutically acceptable carrier.

454. A compound of Formula (IVb):

(IVb)

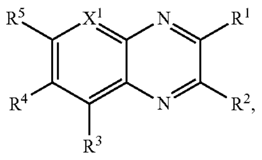

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$ and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$ $NR^{c1}S(O)_2R^{b1}$, $S(O)_2R^{b1}$, and $S(O)_2NR^{c1}R^{d1}$;

$R^4$ is 5-10 membered heteroaryl, optionally substituted with 1, 2, 3, 4, or 5 substituents independently selected from $R^8$;

each $R^8$ is independently selected from halo, CN, $NO_2$, $C_{1-6}$ alkyl, $C_{1-6}$ haloalkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, or 3 substituents independently selected from $R^9$;

each $R^9$ is independently selected from $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, 4-10 membered heterocycloalkyl, halo, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, and 4-10 membered heterocycloalkyl are each optionally substituted with 1, 2, 3, 4, or 5 substituents independently selected from $R^8$;

$R^1$ and $R^2$ are each independently selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

455. The compound of paragraph 454, wherein $X^1$ is $CR^6$.

456. The compound of any one of paragraphs 454-455, wherein $R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

457. The compound of any one of paragraphs 454-455, wherein $R^3$, $R^5$, and $R^6$ are each independently selected from H, halo, $C_{1-6}$ alkyl, and $C_{1-6}$ alkoxy.

458. The compound of paragraphs 454, wherein $X^1$ is N.

459. The compound of any one of paragraphs 454-458, wherein $R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$.

460. The compound of any one of paragraphs 454-459, wherein each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$.

461. The compound of any one of paragraphs 454-460, wherein each $R^9$ is independently selected from $OR^{a1}$ and $NR^{c1}R^{d1}$.

462. The compound of any one of paragraphs 454-461, wherein:

$R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

463. The compound of any one of paragraphs 454-461, wherein:

$R^1$ is $C_{1-6}$ haloalkyl; and $R^2$ is $C_{6-10}$ aryl, optionally substituted with 1, 2, or 3 substituents independently selected from $R^{10}$.

464. The compound of any one of paragraphs 454-461, wherein:

$R^1$ is $C_{6-10}$ aryl, optionally substituted with 1, 2, or 3 substituents independently selected from $R^{10}$; and $R^2$ is $C_{1-6}$ haloalkyl.

465. The compound of any one of paragraphs 454-461, wherein:

$R^1$ is 5-10 membered heteroaryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

466. The compound of any one of paragraphs 454-461, wherein $R^1$ is $C_{6-10}$ aryl, optionally substituted with 1, 2, or 3 substituents independently selected from $R^{10}$; and $R^2$ is 5-10 membered heteroaryl, optionally substituted with 1, 2, or 3 substituents independently selected from $R^{10}$.

467. The compound of any one of paragraphs 465-466, wherein the 5-10 membered heteroaryl is thiophene.

468. The compound of any one of paragraphs 462-466, wherein the $C_{6-10}$ aryl is phenyl.

469. The compound of any one of paragraphs 454-468, wherein each $R^{10}$ is independently selected from halo and $S(O)_2R^{b1}$.

470. The compound of paragraph 454, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

471. The compound of paragraph 454, wherein:

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$ wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$, $R^1$ is phenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

472. The compound of paragraph 454, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is $C_{1-6}$ haloalkyl;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

473. The compound of paragraph 454, wherein:

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is trifluoromethyl;

$R^2$ is phenyl, optionally substituted with 1, 2, or 3 substituents independently selected from $R^{10}$; and each $R^{10}$ is independently selected from halo and $S(O)_2R^{b1}$.

474. The compound of paragraph 454, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is $C_{6-10}$ aryl, optionally substituted with 1, 2, or 3 substituents independently selected from $R^{10}$; and $R^2$ is $C_{1-6}$ haloalkyl;

each $R^{10}$ is independently selected from halo and $S(O)_2R^{b1}$.

475. The compound of paragraph 454, wherein:

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is phenyl, optionally substituted with 1, 2, or 3 substituents independently selected from $R^{10}$, and $R^2$ is trifluoromethyl;

each $R^{10}$ is independently selected from halo and $S(O)_2R^{b1}$.

476. The compound of paragraph 454, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is 5-10 membered heteroaryl, optionally substituted with 1, 2, or 3 substituents independently selected from $R^{10}$;

$R^2$ is $C_{6-10}$ aryl, optionally substituted with 1, 2, or 3 substituents independently selected from $R^{10}$; and each $R^{10}$ is independently selected from halo and $S(O)_2R^{b1}$.

477. The compound of paragraph 454, wherein:

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is thiophenyl, optionally substituted with 1, 2, or 3 substituents independently selected from $R^{10}$;

$R^2$ is phenyl, optionally substituted with 1, 2, or 3 substituents independently selected from $R^{10}$; and each $R^{10}$ is independently selected from halo and $S(O)_2R^{b1}$.

478. The compound of paragraph 454, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^4$ is 5-10 membered heteroaryl, optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is $C_{6-10}$ aryl, optionally substituted with 1, 2, or 3 substituents independently selected from $R^{10}$;

$R^2$ is 5-10 membered heteroaryl, optionally substituted with 1, 2, or 3 substituents independently selected from $R^{10}$; and each $R^{10}$ is independently selected from halo and $S(O)_2R^{b1}$.

479. The compound of paragraph 454, wherein:

$R^3$, $R^5$, and $R^6$ are each independently selected from H, halo, $C_{1-6}$ alkyl, and $C_{1-6}$ alkoxy;

$R^4$ is selected from 1,2,4-triazolyl, tetrazolyl, oxazolyl, isoxazolyl, thiophenyl, indolyl, pyrimidinyl, pyrrolopyridinyl, benzoxadiazolyl, 1,3,4-oxadiazolyl, 1,2,3-triazolyl, 1,2,4-oxadiazolyl, thiazolyl, pyridinyl, benzoxazinyl, pyrazolyl, and indazolyl, each of which is optionally substituted with 1, 2, or 3 substituents independently selected from $R^8$;

each $R^8$ is independently selected from halo, $C_{1-6}$ alkyl, $OR^{a1}$, and $S(O)_2R^{b1}$, wherein said $C_{1-6}$ alkyl is optionally substituted with 1, 2, or 3 substituents independently selected from $R^9$;

each $R^9$ is independently selected from $OR^{a1}$ and $NR^{c1}R^{d1}$;

$R^1$ is phenyl, optionally substituted with 1, 2, or 3 substituents independently selected from $R^{10}$;

$R^2$ is thiophenyl, optionally substituted with 1, 2, or 3 substituents independently selected from $R^{10}$; and each $R^{10}$ is independently selected from halo and $S(O)_2R^{b1}$.

480. The compound of paragraph 454, wherein the compound of Formula (IVb) is selected from any one of the compounds of Table 4c or Table 4c-2, or a pharmaceutically acceptable salt thereof.

481. The compound of paragraph 454, wherein the compound of Formula (IVb) is selected from any one of the compounds of Table 4c, or a pharmaceutically acceptable salt thereof.

482. A pharmaceutical composition comprising a compound of any one of paragraphs 454-481, or a pharmaceutically acceptable salt thereof, and a pharmaceutically acceptable carrier.

483. A compound of Formula (IVc):

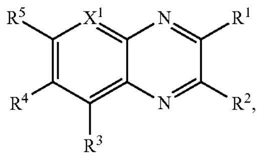

(IVc)

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^4$ is selected from $C(O)NR^{N1}R^{N2}$, $C(O)OR^{a1}$, and CN;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-10 membered heterocycloalkyl, which is substituted with 1, 2, or 3 substituents independently selected from $R^{14}$;

each $R^{14}$ independently selected from H, $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^8$ and $S(O)_2R^8$;

$R^8$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

provided that $R^1$ and $R^2$ are not both $C_{6-10}$ aryl;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

484. The compound of paragraph 483, wherein $X^1$ is $CR^6$.

485. The compound of any one of paragraphs 483-484, wherein $R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

486. The compound of any one of paragraphs 483-484, wherein $R^3$, $R^5$, and $R^6$ are each independently selected from H, halo, $C_{1-6}$ alkyl, and $C_{1-6}$ alkoxy.

487. The compound of any one of paragraphs 483-486, wherein $R^4$ is $C(O)NR^{N1}R^{N2}$.

488. The compound of any one of paragraphs 483-486, wherein $R^4$ is $C(O)OR^{a1}$.

489. The compound of any one of paragraphs 483-486, wherein $R^4$ is CN.

490. The compound of any one of paragraphs 483-489, wherein each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

491. The compound of any one of paragraphs 483-489, wherein $R^{N1}$ and $R^{N2}$, together with the N atom to which they are attached, form a 4-6 membered heterocycloalkyl, which is substituted with 1, 2, or 3 substituents independently selected from $R^{14}$.

492. The compound of any one of paragraphs 483-491, wherein each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$.

493. The compound of any one of paragraphs 483-491, wherein each $R^{14}$ is independently selected from $C_{1-6}$ alkyl and $NR^{c1}R^{d1}$.

494. The compound of paragraph 483, wherein the compound of Formula (IVc) has formula:

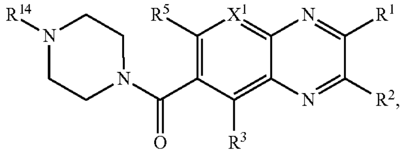

or a pharmaceutically acceptable salt thereof.

495. The compound of any one of paragraphs 483-494, wherein:

$R^1$ is $C_{1-6}$ haloalkyl; and $R^2$ is selected from $C_{6-10}$ aryl and 5-10 membered heteroaryl, each of which is optionally substituted with 1, 2, or 3 independently selected $R^{10}$.

496. The compound of any one of paragraphs 483-494, wherein:

$R^1$ is selected from $C_{6-10}$ aryl and 5-10 membered heteroaryl, each of which is optionally substituted with 1, 2, or 3 independently selected $R^{10}$; and $R^2$ is $C_{1-6}$ haloalkyl.

497. The compound of any one of paragraphs 483-494, wherein:

$R^1$ is $C_{6-10}$ aryl, optionally substituted with 1, 2, or 3 independently selected $R^{10}$; and $R^2$ is 5-10 membered heteroaryl, optionally substituted with 1, 2, or 3 independently selected $R^{10}$.

498. The compound of any one of paragraphs 483-494, wherein:

$R^1$ is 5-10 membered heteroaryl, optionally substituted with 1, 2, or 3 independently selected $R^{10}$; and $R^1$ is $C_{6-10}$ aryl, optionally substituted with 1, 2, or 3 independently selected $R^{10}$.

499. The compound of paragraph 483, wherein the compound of Formula (IVc) has formula:

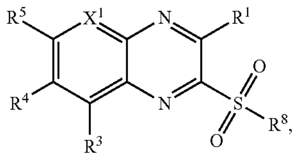

or a pharmaceutically acceptable salt thereof.

500. The compound of paragraph 499, wherein the compound of Formula (IVc) has formula:

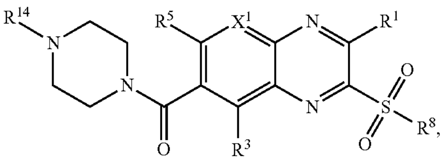

or a pharmaceutically acceptable salt thereof.

501. The compound of any one of paragraphs 499-500, wherein:

$R^1$ is $C_{1-6}$ haloalkyl; and $R^8$ is selected from $C_{6-10}$ aryl and 5-10 membered heteroaryl, each of which is optionally substituted with 1, 2, or 3 independently selected $R^{10}$.

502. The compound of any one of paragraphs 499-500, wherein:

$R^1$ is selected from $C_{6-10}$ aryl and 5-10 membered heteroaryl, each of which is optionally substituted with 1, 2, or 3 independently selected $R^{10}$; and $R^8$ is $C_{1-6}$ haloalkyl.

503. The compound of any one of paragraphs 499-500, wherein:

$R^1$ is $C_{6-10}$ aryl, optionally substituted with 1, 2, or 3 independently selected $R^{10}$; and $R^8$ is 5-10 membered heteroaryl, optionally substituted with 1, 2, or 3 independently selected $R^{10}$.

504. The compound of any one of paragraphs 499-500, wherein:

$R^1$ is 5-10 membered heteroaryl, optionally substituted with 1, 2, or 3 independently selected $R^{10}$; and $R^8$ is $C_{6-10}$ aryl, optionally substituted with 1, 2, or 3 independently selected $R^{10}$.

505. The compound of any one of paragraphs 499-500, wherein:

$R^1$ is $C_{6-10}$ aryl, optionally substituted with 1, 2, or 3 independently selected $R^{10}$; and $R^8$ is $C_{6-10}$ aryl, optionally substituted with 1, 2, or 3 independently selected $R^{10}$.

506. The compound of any one of paragraphs 499-500, wherein:

$R^1$ is 5-10 membered heteroaryl, optionally substituted with 1, 2, or 3 independently selected $R^{10}$; and $R^8$ is 5-10 membered heteroaryl, optionally substituted with 1, 2, or 3 independently selected $R^{10}$.

507. The compound of any one of paragraphs 499-500, wherein:

the 5-10 membered heteroaryl is selected from thiophenyl and pyridinyl; and the $C_{6-10}$ aryl is phenyl.

508. The compound of any one of paragraphs 499-500, wherein:

$R^1$ is $C_{1-6}$ haloalkyl; and $R^8$ is $C_{1-6}$ haloalkyl.

509. The compound of any one of paragraphs 483-508, wherein each $R^{10}$ is independently selected from halo and $C_{1-6}$ alkyl.

510. The compound of paragraph 483, wherein:

$R^3$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-6 membered heterocycloalkyl, which is substituted with 1, 2, or 3 substituents independently selected from $R^{14}$;

each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; and each $R^{10}$ is independently selected from halo and $C_{1-6}$ alkyl.

511. The compound of paragraph 510, wherein:

$R^3$, $R^5$, and $R^6$ are each independently selected from H, halo, $C_{1-6}$ alkyl, and $C_{1-6}$ alkoxy; and $R^{14}$ is independently selected from $C_{1-6}$ alkyl and $NR^{c1}R^{d1}$.

512. The compound of paragraph 483, wherein the compound of Formula (IVc) is selected from any one of the compounds of Table 4d, or a pharmaceutically acceptable salt thereof.

513. A pharmaceutical composition comprising a compound of any one of paragraphs 483-512, or a pharmaceutically acceptable salt thereof, and a pharmaceutically acceptable carrier.

514. A compound of Formula (IVd):

(IVd)

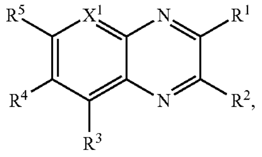

or a pharmaceutically acceptable salt thereof, wherein:

$X^1$ is selected from N and $CR^6$;

$R^4$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^7$;

each $R^7$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^3$ is selected from $C(O)NR^{N1}R^{N2}$ and $C(O)OR^{a1}$;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-10 membered heterocycloalkyl, which is substituted with 1, 2, or 3 substituents independently selected from $R^{14}$;

each $R^{14}$ independently selected from H, $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$ and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^8$ and $S(O)_2R^8$;

$R^8$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$ $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylamino-sulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

515. The compound of paragraph 514, wherein $X^1$ is $CR^6$.

516. The compound of any one of paragraphs 514-515, wherein $R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

517. The compound of any one of paragraphs 514-515, wherein $R^4$, $R^5$, and $R^6$ are each independently selected from H, halo, $C_{1-6}$ alkyl, and $C_{1-6}$ alkoxy.

518. The compound of any one of paragraphs 514-517, wherein $R^3$ is $C(O)NR^{N1}R^{N2}$.

519. The compound of any one of paragraphs 514-517, wherein $R^3$ is $C(O)OR^{a1}$.

520. The compound of any one of paragraphs 514-519, wherein each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$.

521. The compound of any one of paragraphs 514-519, wherein $R^{N1}$ and $R^{N2}$ together with the N atom to which they are attached, form a 4-6 membered heterocycloalkyl, which is substituted with 1, 2, or 3 substituents independently selected from $R^{14}$.

522. The compound of any one of paragraph 521, wherein the compound of Formula (IVd) has formula:

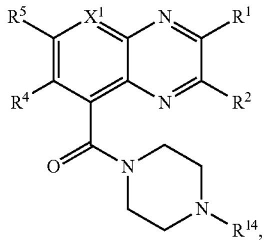

or a pharmaceutically acceptable salt thereof.

523. The compound of any one of paragraphs 514-522, wherein each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$ 524. The compound of any one of paragraphs 514-522, wherein each $R^{14}$ is independently selected from $C_{1-6}$ alkyl and $NR^{c1}R^{d1}$.

525. The compound of any one of paragraphs 514-524, wherein:

$R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

526. The compound of any one of paragraphs 514-525, wherein each $R^{10}$ is independently selected from halo and $C_{1-6}$ alkyl.

527. The compound of paragraph 514, wherein:

$R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

each of $R^{N1}$ and $R^{N2}$ is independently selected from H, $C_{1-6}$ alkyl, $C_{2-6}$ alkynyl, and 4-10 membered heterocycloalkyl, each of which is optionally substituted with 1, 2, or 3 substituents independently selected from $R^{14}$; or $R^{N1}$ and $R^{N2}$, together with the N atom to which they are attached, form a 4-6 membered heterocycloalkyl, which is substituted with 1, 2, or 3 substituents independently selected from $R^{14}$;

wherein each $R^{14}$ is independently selected from halo, $C_{1-6}$ alkyl, $C_{1-6}$ haloalkyl, $OR^{a1}$, $C(O)NR^{c1}R^{d1}$, $C(O)OR^{a1}$, $NR^{c1}R^{d1}$, $S(O)_2R^{b1}$, and $S(O)_2NR^{c1}R^{d1}$; and each $R^{10}$ is independently selected from halo and $C_{1-6}$ alkyl.

528. The compound of paragraph 527, wherein:

$R^4$, $R^5$, and $R^6$ are each independently selected from H, halo, $C_{1-6}$ alkyl, and $C_{1-6}$ alkoxy;

each $R^{14}$ is independently selected from $C_{1-6}$ alkyl and $NR^{c1}R^{d1}$.

529. The compound of paragraph 514, wherein the compound of Formula (IVd) is selected from any one of the compound of Table 4e, or a pharmaceutically acceptable salt thereof.

530. A pharmaceutical composition comprising a compound of any one of paragraphs 514-529, or a pharmaceutically acceptable salt thereof, and a pharmaceutically acceptable carrier.

531. A compound of Formula (IVe):

(IVe)

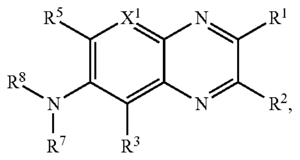

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

or $R^7$ and $R^8$ together with the N atom to which they are attached form a 4-10 membered heterocycloalkyl ring, which is optionally substituted with 1, 2, or 3 substituents independently selected from $R^g$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^{8a}$ and $S(O)_2R^{8a}$, $R^{8a}$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

532. The compound of paragraph 531, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $R^{8a}$ and $S(O)_2R^{8a}$;

$R^{8a}$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

533. The compound of paragraph 531 or 532, wherein $X^1$ is $CR^6$.

534. The compound of any one of paragraphs 531-533, wherein $R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy.

535. The compound of any one of paragraphs 531-534, wherein $R^4$, $R^5$, and $R^6$ are each independently selected from H, halo, $C_{1-6}$ alkyl, and $C_{1-6}$ alkoxy.

536. The compound of any one of paragraphs 531-535, wherein:

$R^7$ is selected from H and $C_{1-6}$ alkyl; and $R^8$ is selected from $C(O)R^{b1}$ and $C(O)OR^{a1}$.

537. The compound of any one of paragraphs 531-535, wherein:

$R^7$ is selected from H and $C_{1-6}$ alkyl;

$R^8$ is $C(O)NR^{c1}R^{d1}$.

538. The compound of any one of paragraphs 531-537, wherein:

each $R^{c1}$ and $R^{d1}$ is independently selected from H, $C_{1-6}$ alkyl, and $C_{3-10}$ cycloalkyl, wherein said $C_{1-6}$ alkyl and $C_{3-10}$ cycloalkyl are each optionally substituted with 1 or 2 independently selected $R^g$.

539. The compound of any one of paragraphs 531-538, wherein each $R^{a1}$ and $R^{b1}$ is independently selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1, 2, or 3 substituents independently selected from $R^g$.

540. The compound of any one of paragraphs 531-539, wherein each $R^g$ is independently selected from OH, halo, $C_{1-6}$ alkyl, $C_{1-6}$ alkoxy, 4-10 membered heterocycloalkyl, amino, $C_{1-6}$ alkylamino, di($C_{1-6}$ alkyl)amino, $C_{1-6}$ alkylsulfonyl, $C_{1-6}$ alkylcarbamyl, and $C_{1-6}$ alkylcarbonyl, and any $C_{1-6}$ alkyl, $C_{1-6}$ alkoxy, or 4-10 membered heterocycloalkyl of $R^g$ is optionally substituted with 1 or 2 substituents independently selected from $C_{1-6}$ alkyl and $C_{1-6}$ alkoxy.

541. The compound of any one of paragraphs 531-539, wherein each $R^g$ is independently selected from halo, $C_{1-6}$ alkyl, 4-10 membered heterocycloalkyl, amino, $C_{1-6}$ alkylsulfonyl, $C_{1-6}$ alkylcarbamyl, and $C_{1-6}$ alkylcarbonyl.

542. The compound of any one of paragraphs 531-541, wherein:

$R^1$ is $C_{6-10}$ aryl, optionally substituted with 1, 2, or 3 independently selected $R^{10}$; and $R^2$ is $C_{6-10}$ aryl, optionally substituted with 1, 2, or 3 independently selected $R^{10}$.

543. The compound of any one of paragraphs 531-542, wherein each $R^{10}$ is independently selected from halo and $C_{1-6}$ alkyl.

544. The compound of paragraph 531, wherein:

$R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is selected from H and $C_{1-6}$ alkyl;

$R^8$ is selected from $C(O)R^{b1}$ and $C(O)OR^{a1}$;

each $R^{a1}$ and $R^{b1}$ is independently selected from $C_{1-6}$ alkyl, $C_{1-4}$ haloalkyl, $C_{2-6}$ alkenyl, $C_{2-6}$ alkynyl, and 4-10 membered heterocycloalkyl, each of which is optionally substituted with 1, 2, or 3 substituents independently selected from $R^g$;

each $R^g$ is independently selected from halo, $C_{1-6}$ alkyl, 4-10 membered heterocycloalkyl, amino, $C_{1-6}$ alkylsulfonyl, $C_{1-6}$ alkylcarbamyl, and $C_{1-6}$ alkylcarbonyl;

$R^1$ is $C_{6-10}$ aryl, optionally substituted with 1, 2, or 3 independently selected $R^{10}$;

$R^2$ is $C_{6-10}$ aryl, optionally substituted with 1, 2, or 3 independently selected $R^{10}$; and each $R^{10}$ is independently selected from halo and $C_{1-6}$ alkyl.

545. The compound of paragraph 531, wherein:

$R^4$, $R^5$, and $R^6$ are each independently selected from H, halo, CN, $NO_2$, OH, $C_{1-6}$ alkyl, $C_{1-6}$ haloalkyl, $C_{1-6}$ alkoxy, and $C_{1-6}$ haloalkoxy;

$R^7$ is selected from H and $C_{1-6}$ alkyl;

$R^8$ is $C(O)NR^{c1}R^{d1}$;

each $R^{c1}$ and $R^{d1}$ is independently selected from H, $C_{1-6}$ alkyl, and $C_{3-10}$ cycloalkyl, wherein said $C_{1-6}$ alkyl and $C_{3-10}$ cycloalkyl are each optionally substituted with 1 or 2 independently selected $R^g$;

each $R^g$ is independently selected from OH, halo, $C_{1-6}$ alkyl, $C_{1-6}$ alkoxy, 4-10 membered heterocycloalkyl, amino, $C_{1-6}$ alkylamino, di($C_{1-6}$ alkyl)amino, $C_{1-6}$ alkylsulfonyl, $C_{1-6}$ alkylcarbamyl, and $C_{1-6}$ alkylcarbonyl, and any $C_{1-6}$ alkyl, $C_{1-6}$ alkoxy, or 4-10 membered heterocycloalkyl of $R^g$ is optionally substituted with 1 or 2 substituents independently selected from $C_{1-6}$ alkyl and $C_{1-6}$ alkoxy;

$R^1$ is $C_{6-10}$ aryl, optionally substituted with 1, 2, or 3 independently selected $R^{10}$;

$R^2$ is $C_{6-10}$ aryl, optionally substituted with 1, 2, or 3 independently selected $R^{10}$; and each $R^{10}$ is independently selected from halo and $C_{1-6}$ alkyl.

546. The compound of paragraph 531, wherein the compound of Formula (IVe) is selected from any one of the compounds of Table 4f or Table 4f-2, or a pharmaceutically acceptable salt thereof.

547. The compound of paragraph 531, wherein the compound of Formula (IVe) is selected from any one of the compounds of Table 4f, or a pharmaceutically acceptable salt thereof.

548. A pharmaceutical composition comprising a compound of any one of paragraphs 531-547, or a pharmaceutically acceptable salt thereof, and a pharmaceutically acceptable carrier.

549. A compound of Formula (IVf):

(IVf)

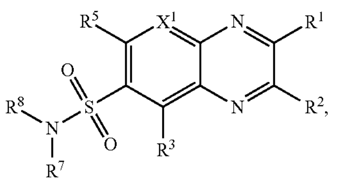

or a pharmaceutically acceptable salt thereof, wherein:

$X^1$ is selected from N and $CR^6$;

$R^3$, $R^5$, and $R^6$ are each independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^9$;

$R^7$ and $R^8$ are each independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, or 3 substituents independently selected from $R^9$;

each $R^9$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is selected from $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{10}$;

or $R^7$ and $R^8$ together with the N atom to which they are attached form a 4-10 membered heterocycloalkyl ring, which is optionally substituted with 1, 2, or 3 substituents independently selected from $R^g$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$ $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R_g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^8$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

550. The compound of paragraph 549, wherein X is N.

551. The compound of paragraph 549, wherein X is $CR^6$.

552. The compound of any one of paragraphs 549-551, wherein $R^3$, $R^5$, and $R^6$ are each independently selected from H, halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

553. The compound of paragraph 552, wherein $R^3$, $R^5$, and $R^6$ are each H.

554. The compound of any one of paragraphs 549-553, wherein:

$R^7$ is H; and $R^8$ is selected from $C_{1-6}$ alkyl and $C_{3-10}$ cycloalkyl, each of which is independently selected from 1 or 2 substituents independently selected from $R^9$.

555. The compound of any one of paragraphs 549-554, wherein $R^9$ is independently selected from $C_{3-10}$ cycloalkyl, 5-10 membered heteroaryl, 4-10 membered heterocycloalkyl, halo, $C_{1-6}$ alkyl, $C_{1-6}$ haloalkyl, CN, $OR^{a1}$, $C(O)NR^{c1}R^{d1}$, $C(O)OR^{a1}$, and $NR^{c1}R^{d1}$, wherein said $C_{3-10}$ cycloalkyl, 5-10 membered heteroaryl, and 4-10 membered heterocycloalkyl are each optionally substituted with 1 or 2 substituents independently selected from $R^{10}$.

556. The compound of any one of paragraphs 549-555, wherein $R^1$ is $C_{6-10}$ aryl, optionally substituted with 1 or 2 independently selected $R^{10}$; and $R^2$ is $C_{6-10}$ aryl, optionally substituted with 1 or 2 independently selected $R^{10}$.

557. The compound of any one of paragraphs 549-556, wherein each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl) amino.

558. The compound of paragraph 549, wherein:

$R^1$ is $C_{6-10}$ aryl, optionally substituted with 1 or 2 independently selected $R^{10}$;

$R^2$ is $C_{6-10}$ aryl, optionally substituted with 1 or 2 independently selected $R^{10}$;

X is $CR^6$;

$R^3$, $R^5$, and $R^6$ are each independently selected from H, halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

$R^7$ is H;

$R^8$ is selected from $C_{1-6}$ alkyl and $C_{3-10}$ cycloalkyl, each of which is independently selected from 1 or 2 substituents independently selected from $R^9$;

each $R^9$ is independently selected from $C_{3-10}$ cycloalkyl, 5-10 membered heteroaryl, 4-10 membered heterocycloalkyl, halo, $C_{1-6}$ alkyl, $C_{1-6}$ haloalkyl, CN, $OR^{a1}$, $C(O)NR^{c1}R^{d1}$, $C(O)OR^{a1}$, and $NR^{c1}R^{d1}$; wherein said $C_{3-10}$ cycloalkyl, 5-10 membered heteroaryl, and 4-10 membered heterocycloalkyl are each optionally substituted with 1 or 2 substituents independently selected from $R^{10}$; and each $R^{10}$ is independently selected from halo, OH, CN, $NO_2$, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

559. The compound of paragraph 549, wherein the compound is selected from any one of the compounds of Table 4g, or a pharmaceutically acceptable salt thereof.

560. A pharmaceutical composition comprising a compound of any one of paragraphs 549-559, or a pharmaceutically acceptable salt thereof, and a pharmaceutically acceptable carrier.

561. A compound of Formula (IVg)

(IVg)

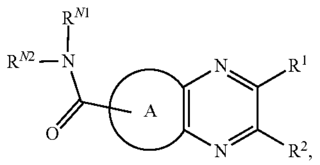

or a pharmaceutically acceptable salt thereof, wherein:

ring A is $C_{3-8}$ cycloalkyl, which is optionally substituted with 1, 2, or 3 substituents independently selected from $R^{14}$;

each of $R^{N1}$ and $R^{N2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^{14}$;

or $R^{N1}$ and $R^{N2}$ together with the N atom to which they are attached from a 4-10 membered heterocycloalkyl, each of which is optionally substituted with 1, 2, 3, 4, or 5 substituents independently selected from $R^{14}$;

each $R^{14}$ independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$ $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{15}$;

each $R^{15}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

$R^1$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

$R^2$ is selected from $C_{1-6}$ haloalkyl, $C_{6-10}$ aryl, 5-10 membered heteroaryl, and 4-10 membered heterocycloalkyl, each of which is optionally substituted with 1, 2, 3, 4, or 5 substituents independently selected from $R^{10}$;

each $R^{10}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino, and any $C_{1-6}$ alkyl, $C_{1-6}$ alkoxy, $C_{6-10}$ aryl, $C_{3-10}$ cycloalkyl, 5-10 membered heteroaryl, or 4-10 membered heterocycloalkyl of $R^g$ is optionally substituted with 1, 2, or 3 substituents independently selected from OH, $NO_2$, CN, halo, $C_{1-6}$ alkyl, $C_{1-4}$ haloalkyl, $C_{1-6}$ alkoxy, and $C_{1-6}$ haloalkoxy.

562. The compound of paragraph 561, having a formula:

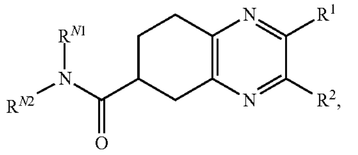

or a pharmaceutically acceptable salt thereof.

563. The compound of paragraph 561, having a formula:

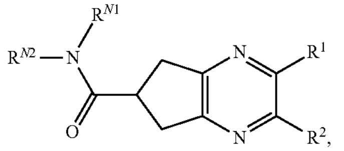

or a pharmaceutically acceptable salt thereof.

564. The compound of paragraph 561, wherein:

$R^{N1}$ and $R^{N2}$ together with the N atom to which they are attached from a 4-10 membered heterocycloalkyl, which is optionally substituted with 1, 2, or 3 substituents independently selected from $R^{14}$;

$R^1$ is $C_{6-10}$ aryl, optionally substituted with 1, 2, or 3 substituents independently selected from $R^{10}$; and $R^2$ is $C_{6-10}$ aryl, optionally substituted with 1, 2, or 3 substituents independently selected from $R^{10}$.

565. The compound of paragraph 561, wherein the compound is selected from any one of the compounds of Table 17, or a pharmaceutically acceptable salt thereof.

566. A pharmaceutical composition comprising a compound of any one of paragraphs 561-565, or a pharmaceutically acceptable salt thereof, and a pharmaceutically acceptable carrier.

567. A method of treating a mammal having a disease, disorder, or condition responsive to inhibiting NF-κB activity within a cell, wherein said method comprises administering, to said mammal, a compound selected from (i) a compound of any one of paragraphs 41-58, 79-102, 104-113, 115-121, 161, 163-174, 176-189, 191-198, 200-211, 213-224, 226-237, 264, 265, 267-270, 272-275, 277-303, 305-327, 329-376, 378-421, 423-430, 451, 452, 454-481, 483-512, 514-529, 531-547, 549-559, and 561-565, or a pharmaceutically acceptable salt thereof; and (ii) a compound as recited in any one of paragraphs 1-40, 60-72, 73-78, 123-160, 239-263, and 432-450, or a pharmaceutically acceptable salt thereof; or a pharmaceutical composition of any one of paragraphs 59, 103, 114, 122, 162, 175, 190, 199, 212, 225, 238, 266, 271, 276, 304, 328, 377, 422, 431, 453, 482, 513, 530, 548, 560, and 566.

568. The method of paragraph 567, wherein the mammal is human.

569. The method of any one of paragraphs 567-568, wherein said method comprises treating a mammal having a cancer.

570. The method of any one of paragraphs 567-569, wherein said method comprises treating a mammal having an inflammation.

571. The method of paragraph 570, wherein the inflammation is an autoimmune disease.

572. A method for inhibiting NF-κB activity within cells of a mammal, wherein said method comprises administering, to said mammal, a compound selected from (i) a compound of any one of paragraphs 41-58, 79-102, 104-113, 115-121, 161, 163-174, 176-189, 191-198, 200-211, 213-224, 226-237, 264, 265, 267-270, 272-275, 277-303, 305-327, 329-376, 378-421, 423-430, 451, 452, 454-481, 483-512, 514-529, 531-547, 549-559, and 561-565, or a pharmaceutically acceptable salt thereof; and (ii) a compound as recited in any one of paragraphs 1-40, 60-72, 73-78, 123-160, 239-263, and 432-450, or a pharmaceutically acceptable salt thereof; or a pharmaceutical composition of any one of paragraphs 59, 103, 114, 122, 162, 175, 190, 199, 212, 225, 238, 266, 271, 276, 304, 328, 377, 422, 431, 453, 482, 513, 530, 548, 560, and 566.

573. The method of paragraph 572, wherein the mammal is human.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method for inhibiting NF-κB activity within a cell within a mammal, wherein said method comprises administering, to said mammal, an effective amount of a compound of Formula (IIIa):

(IIIa)

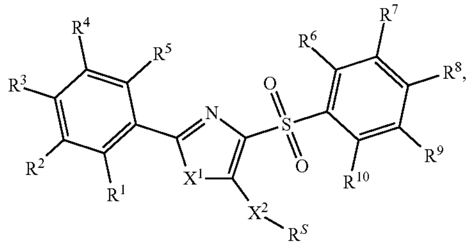

or a pharmaceutically acceptable salt thereof, wherein:

$X^1$ is selected from O, S, and $NR^N$;

$R^N$ is selected from H and $C_{1-6}$ alkyl;

$X^2$ is selected from S(O) and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C$ (O)$R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$ $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R_g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The method of claim 1, wherein:

$X^1$ is selected from O, S, and $NR^N$;

$R^N$ is selected from H and $C_{1-6}$ alkyl;

$X^2$ is selected from S(O) and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl) aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

3. The method of claim 1, wherein $X^1$ is O.

4. The method of claim 1, wherein $X^1$ is S.

5. The method of claim 1, wherein $X^1$ is NH.

6. The method of claim 1, wherein $X^2$ is S(O).

7. The method of claim 1, wherein $X^2$ is $S(O)_2$.

8. The method of claim 1, wherein $R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$.

9. The method of claim 1, wherein each $R^{11}$ is independently selected from $Cy^1$, halo, $C_{1-6}$ alkyl, $OR^{a1}$, $C(O)R^{b1}$, and $C(O)NR^{c1}R^{d1}$.

10. The method of claim 1, wherein each $Cy^1$ is independently selected from $C_{6-10}$ aryl and $C_{3-10}$ cycloalkyl, each of which is optionally substituted with 1, 2, or 3 substituents independently selected from $R^{Cy1}$.

11. The method of claim 1, wherein each $R^{Cy1}$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$.

12. The method of claim 1, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, wherein each of $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl is optionally substituted with 1, 2, or 3 substituents independently selected from $R^g$.

13. The method of claim 1, wherein each $R^{a1}$, $R^{b1}$, $R^{c1}$, and $R^{d1}$ is independently selected from H, $C_{1-6}$ alkyl, and $C_{6-10}$ aryl, wherein each of $C_{1-6}$ alkyl and $C_{6-10}$ aryl is optionally substituted with 1, 2, or 3 substituents independently selected from $R^g$.

14. The method of claim 1, wherein each $R^8$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

15. The method of claim 1, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ is independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl) amino, and carboxy.

16. The method of claim 1, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ is independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$;

each $R^{a1}$, $R^{b1}$, $R^{c1}$, and $R^{d1}$ is independently selected from H, $C_{1-6}$ alkyl, and $C_{6-10}$ aryl, wherein each of $C_{1-6}$ alkyl and $C_{6-10}$ aryl is optionally substituted with 1, 2, or 3 substituents independently selected from $R^g$; and $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

17. A method for inhibiting NF-κB activity within a cell within a mammal, wherein said method comprises administering, to said mammal, an effective amount of a compound selected from any one of the following compounds, or a pharmaceutically acceptable salt thereof:

BC18500

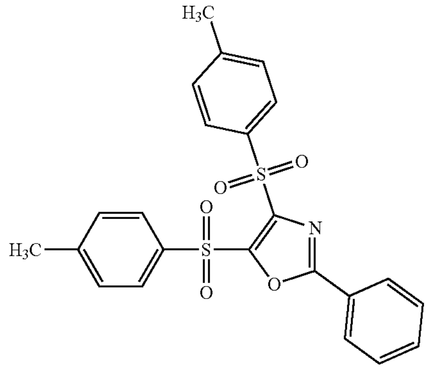

BC18508

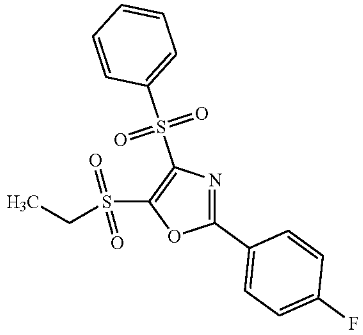

-continued
BC18509
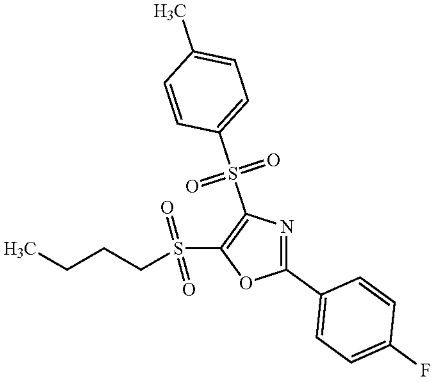
BC18510
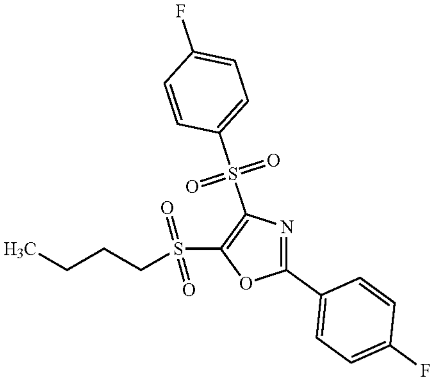
BC18511
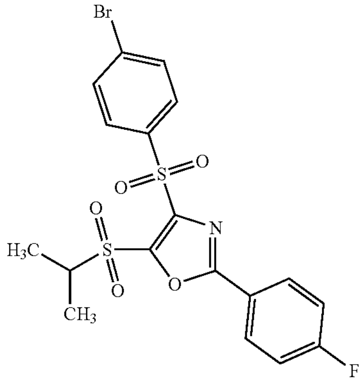
BC18520
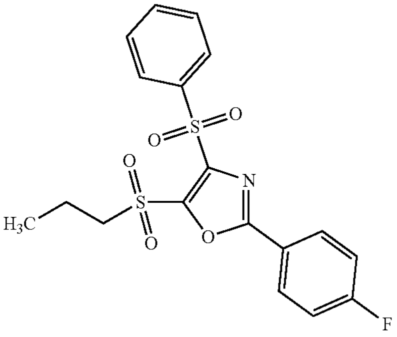
-continued
BC18521
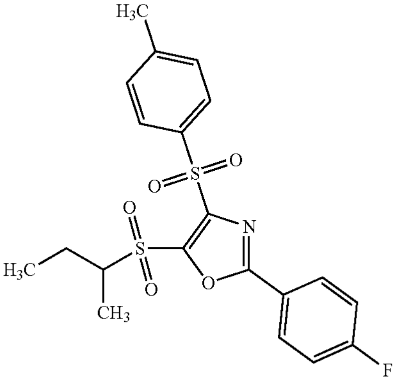
BC18522
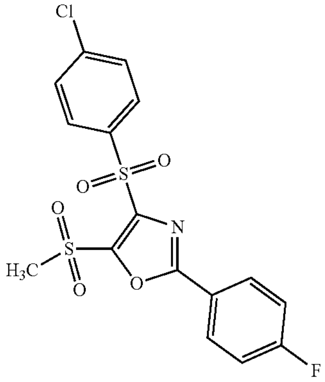
BC18531
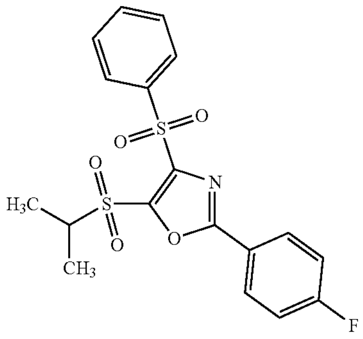
BC18532
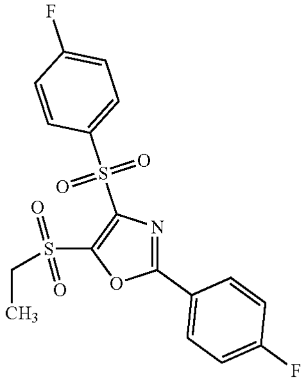

-continued
BC18533
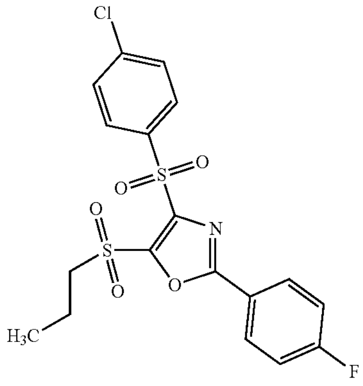
BC18542
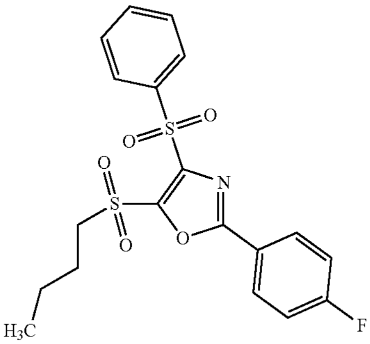
BC18543
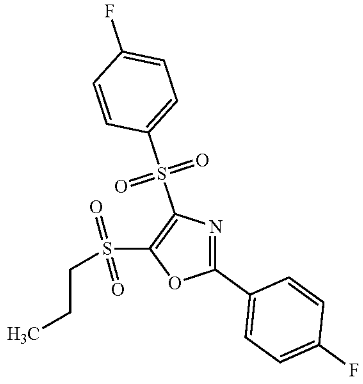
BC18544
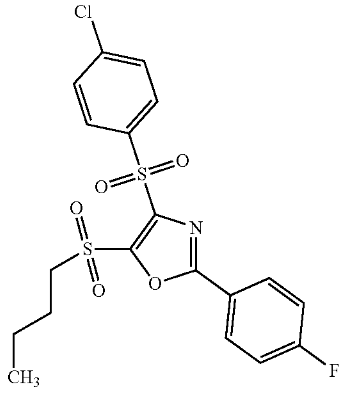
-continued
BC18553
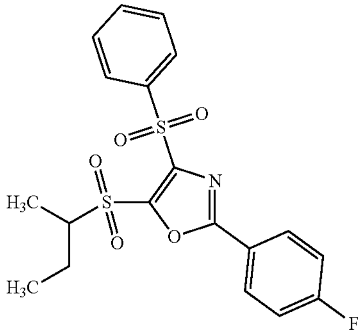
BC18554
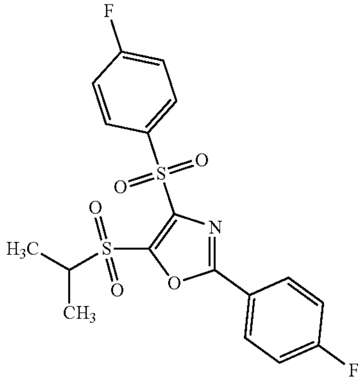
BC18555
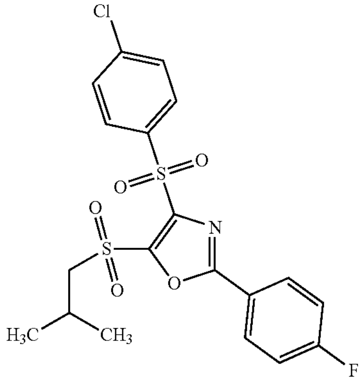
BC18564
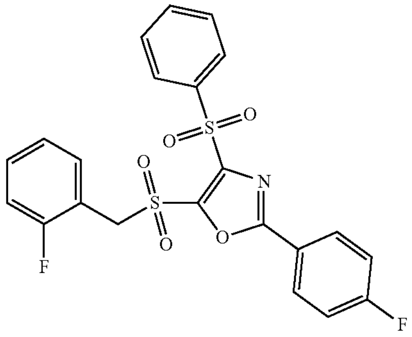

-continued
BC18565
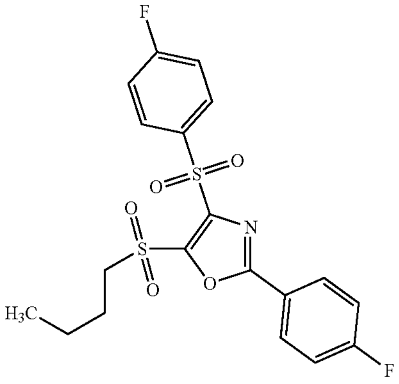
BC18566
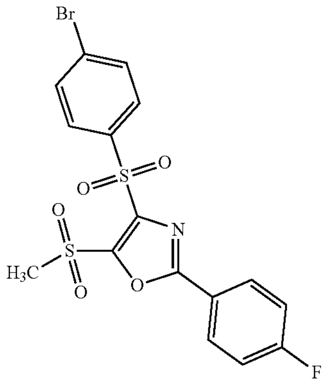
BC18575
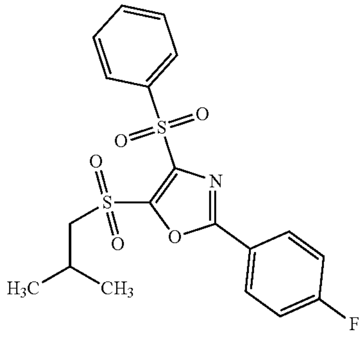
BC18576
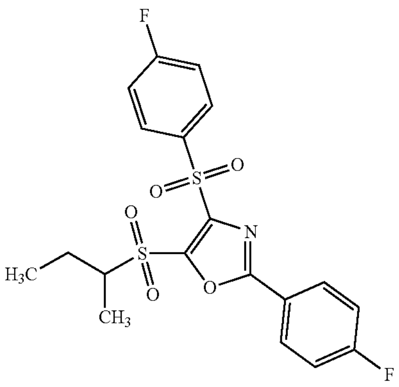
-continued
BC18577
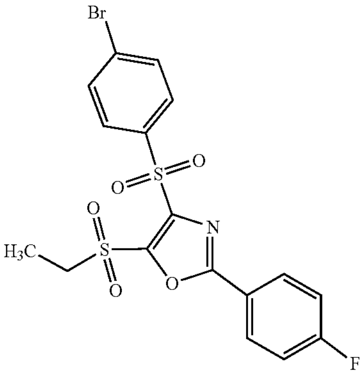
BC18586
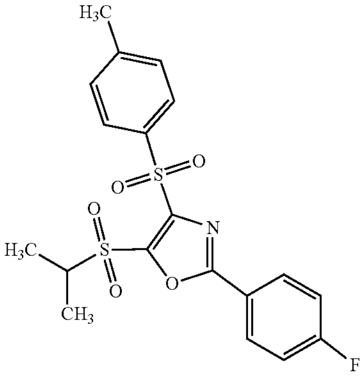
BC18587
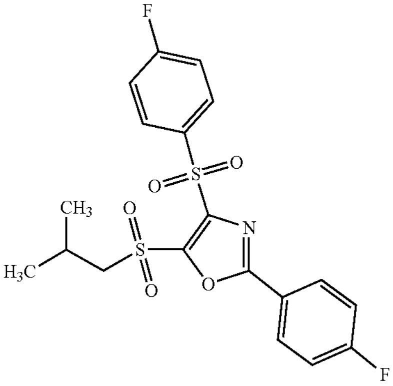
BC18588
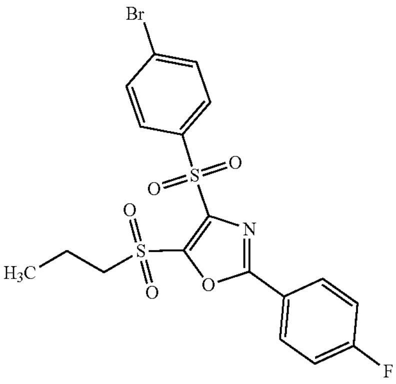

-continued
BC19125
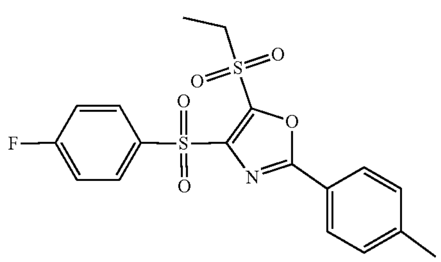
BC19126
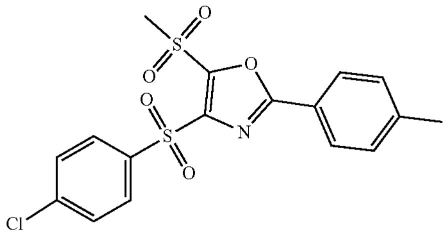
BC19127
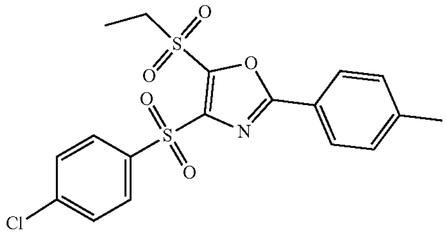
BC19128
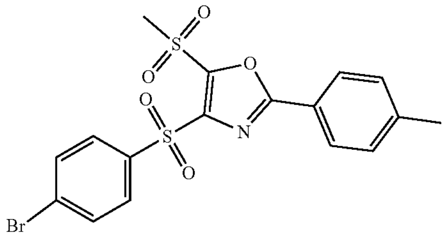
BC19129
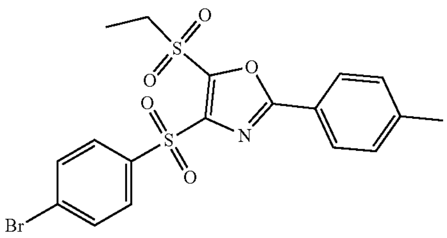
BC19130
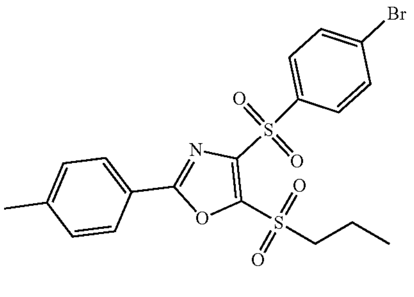
-continued
BC19146
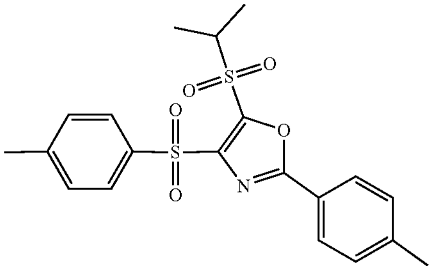
BC19147
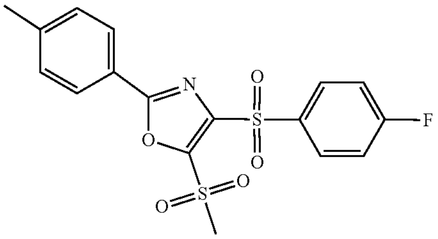
BC19260
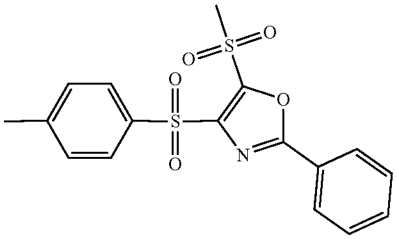
BC19261
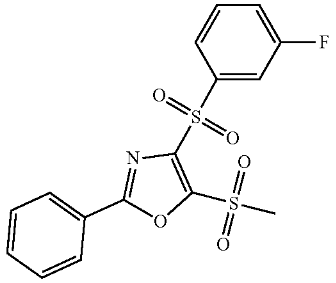
BC19262
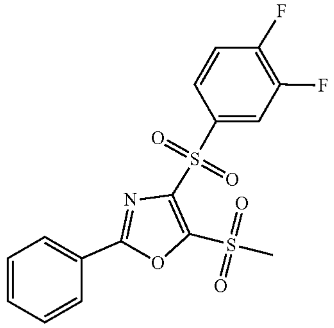

-continued
BC19263
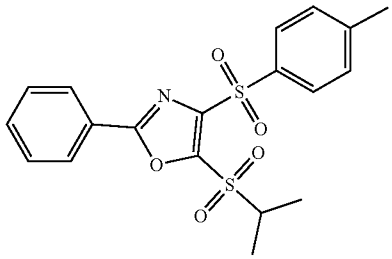
BC19264
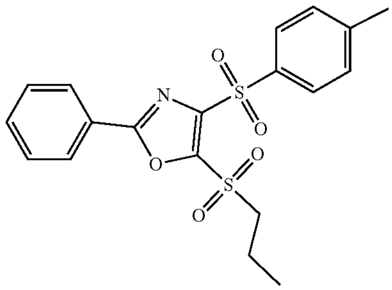
BC19265
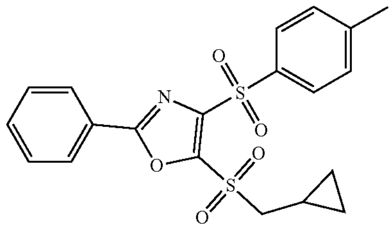
BC19266
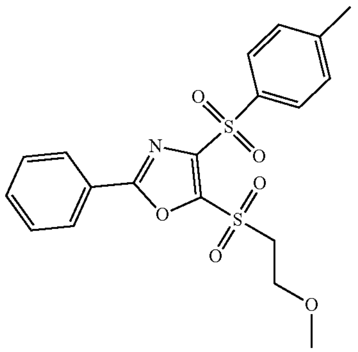
BC19267
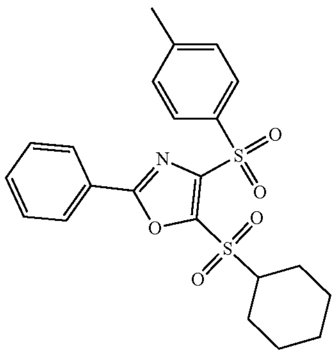
BC19268
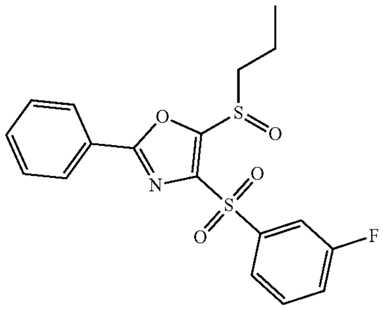
BC19269
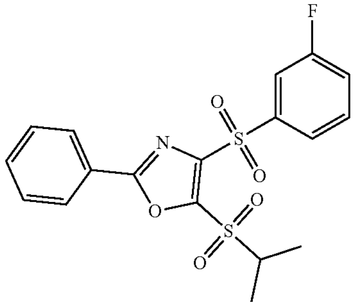
BC19270
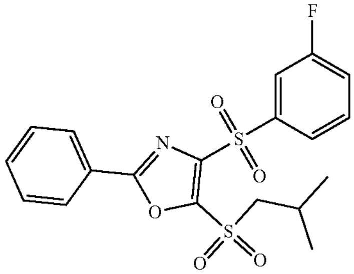
BC19271
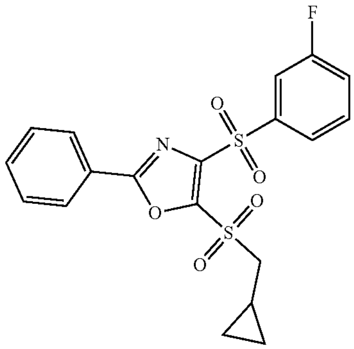
BC19272
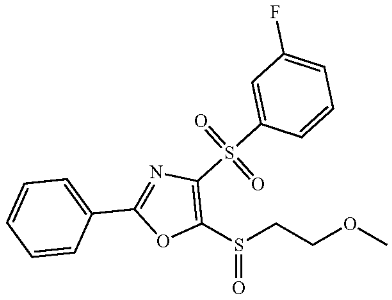

-continued
BC19273
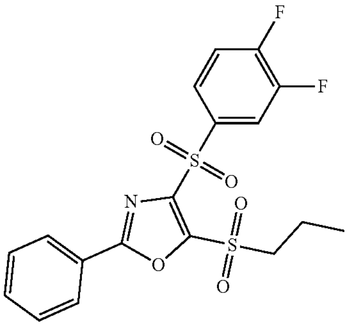
BC19274
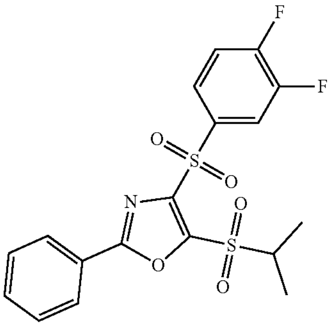
BC19275
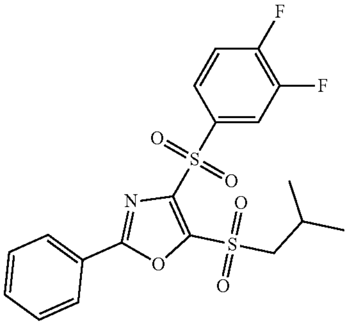
BC19276
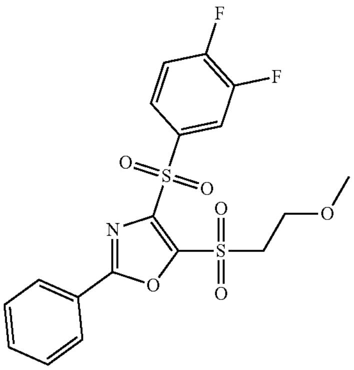
-continued
BC19277
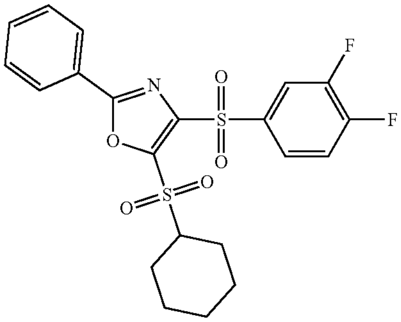
BC19278
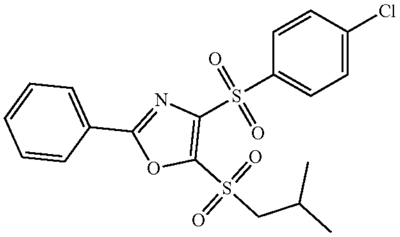
BC19279
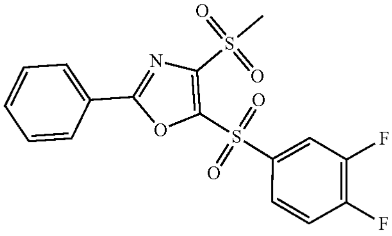
BC19327
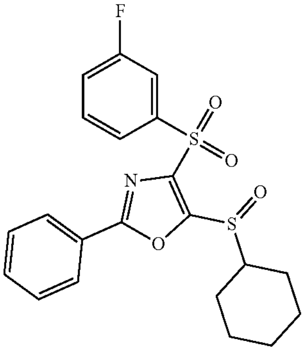
BC19328
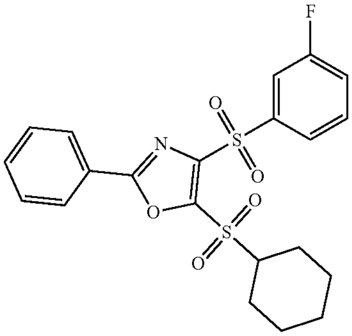

-continued
BC19329
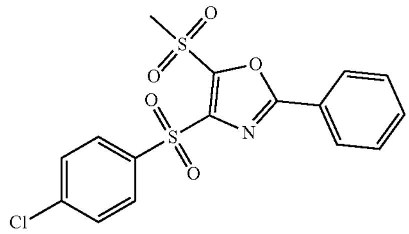
BC19330
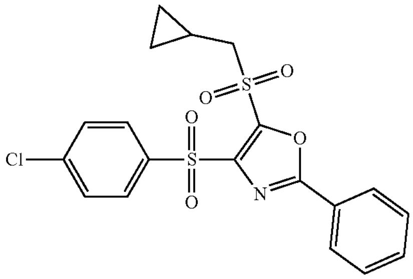
BC19331
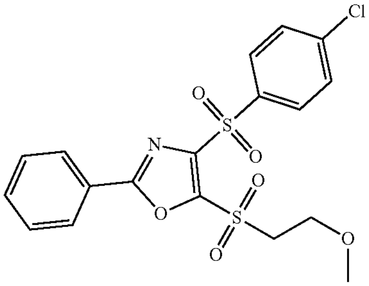
BC19332
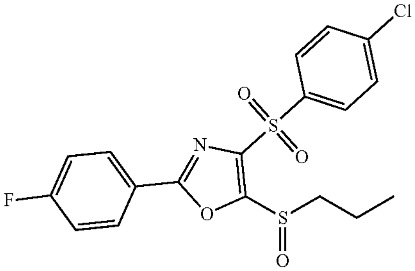
BC19333
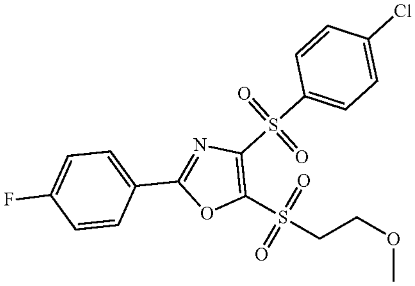
-continued
BC19334
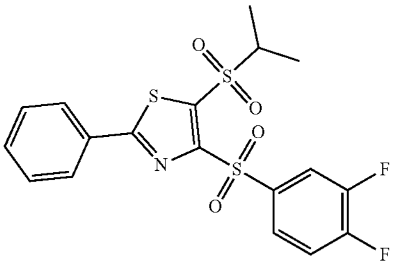
BC19335
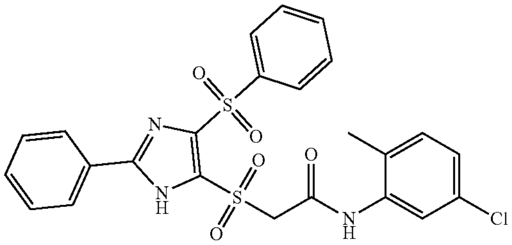
BC19336
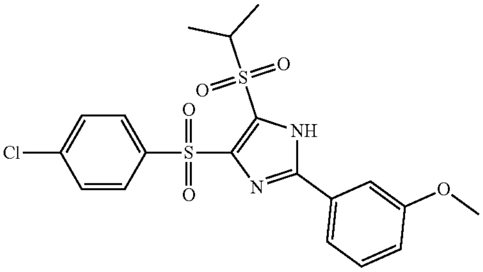
BC19337
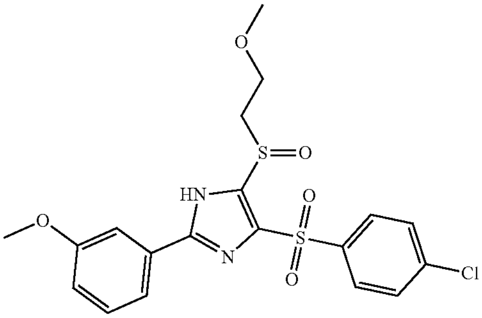
BC19342
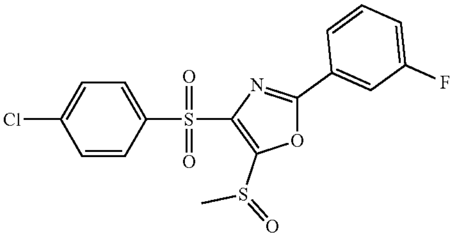

BC19343
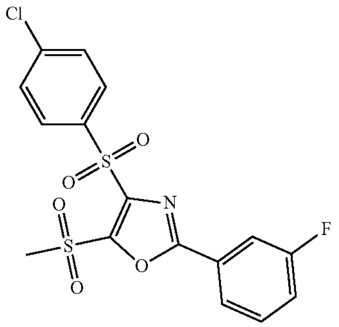
BC19344
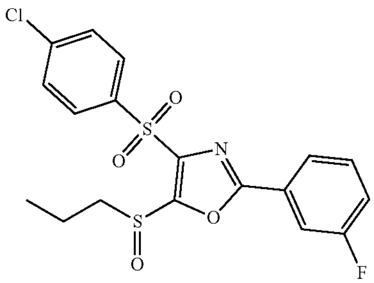
BC19345
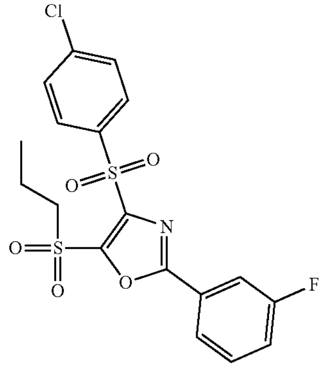
BC19346
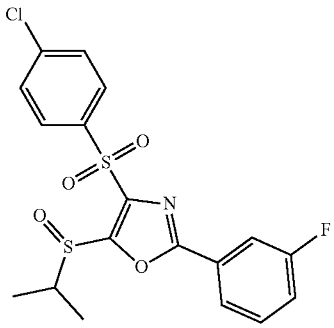
BC19347
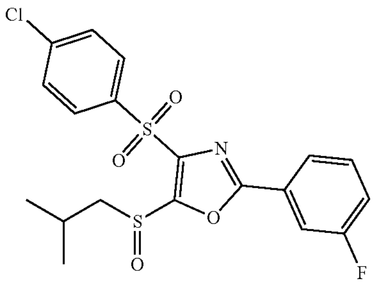
BC19348
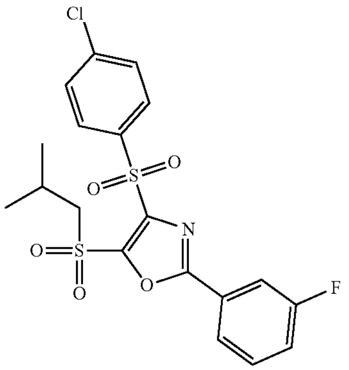
BC19349
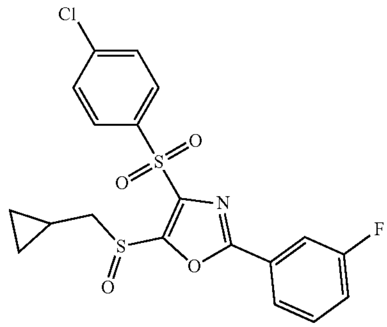
BC19350
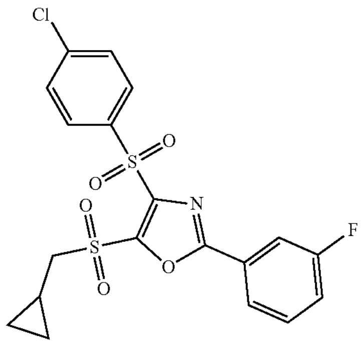
BC19351
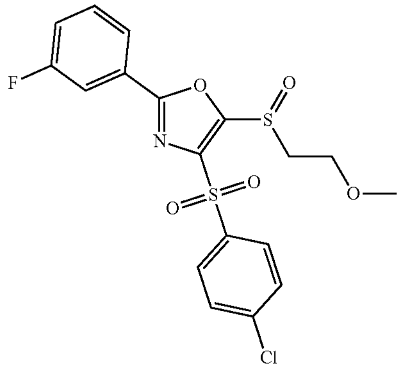

-continued
BC19352
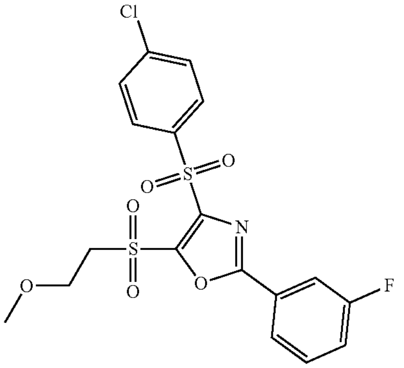
BC19353
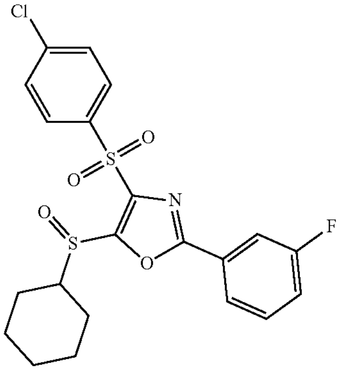
BC19410
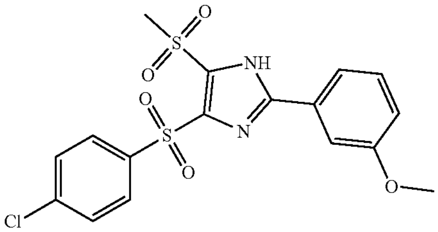
BC19411
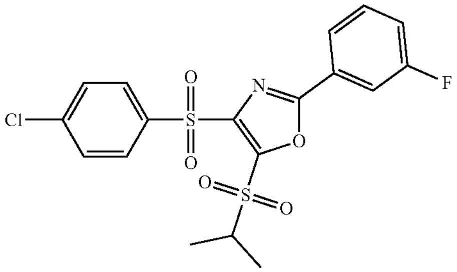
BC19412
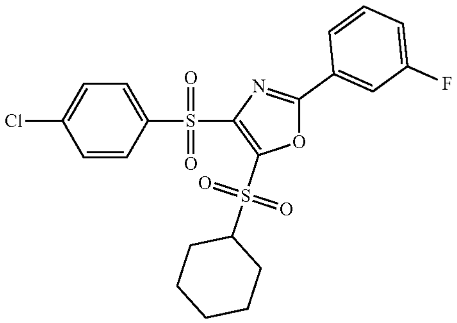
-continued
BC19413
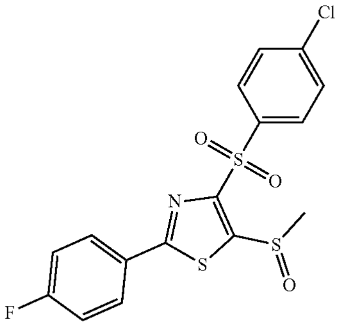
BC19414
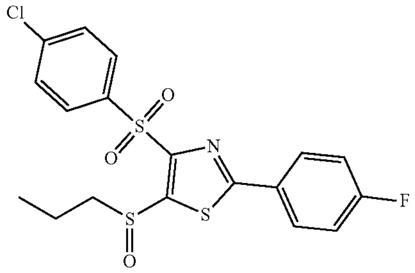
BC19415
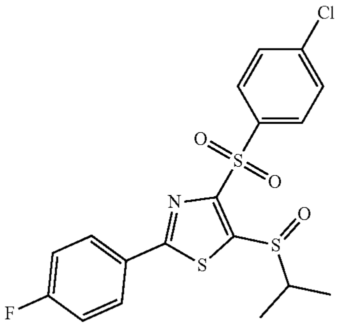
BC19416
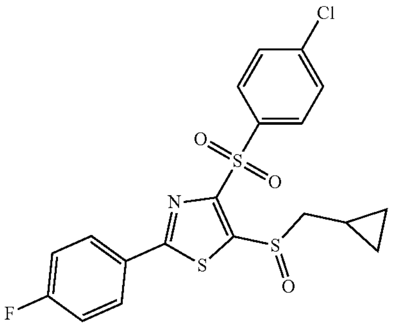
BC19417
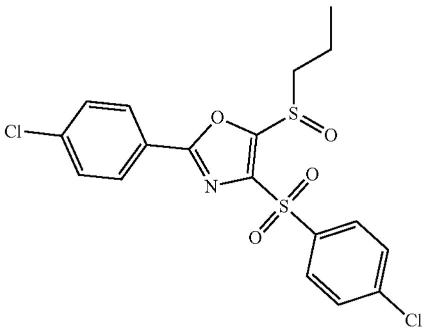

BC19418
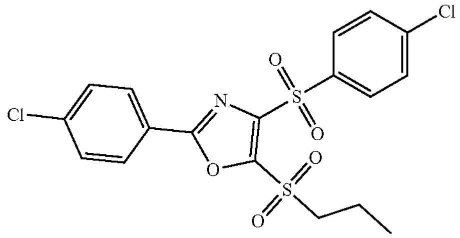
BC19419
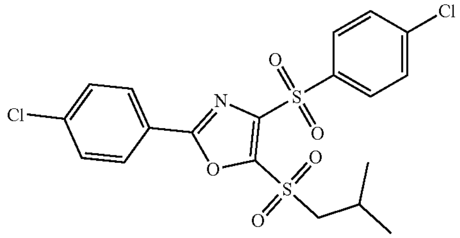
BC19420
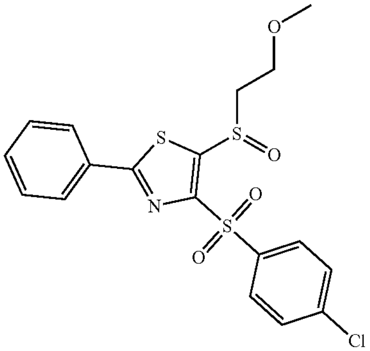
BC19463
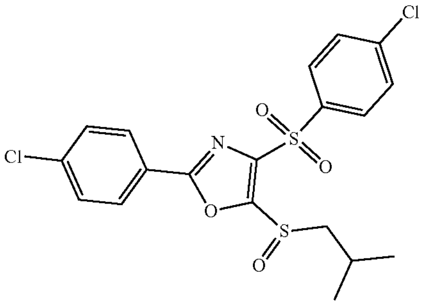
BC19464
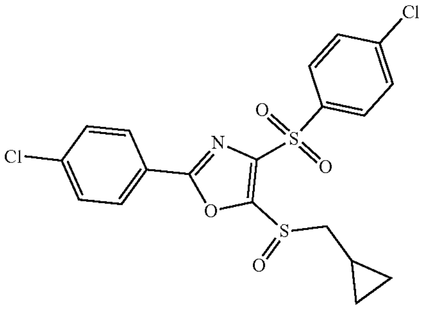
BC19521
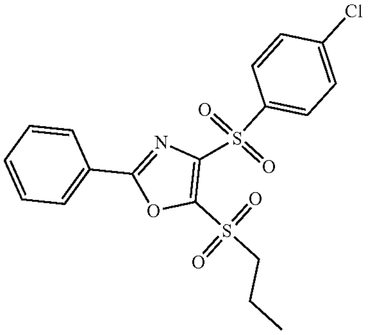
BC19279
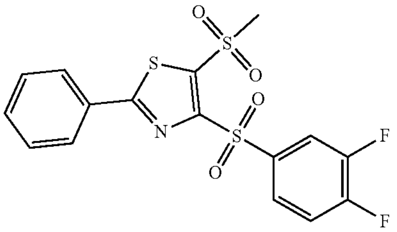
BC19334
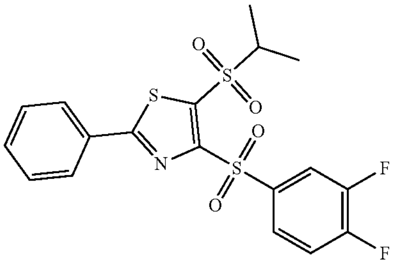
BC19413
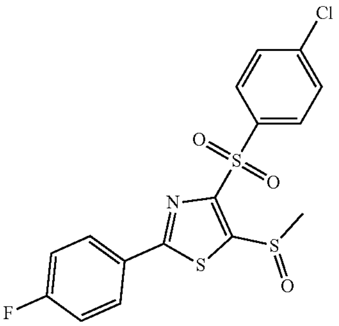
BC19414
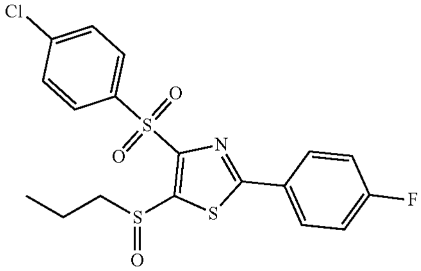

-continued
BC19415
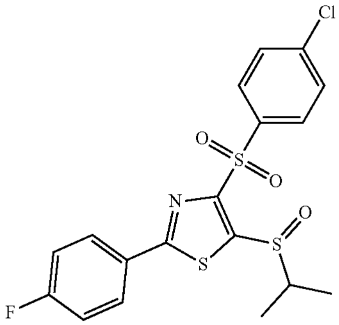
BC19416
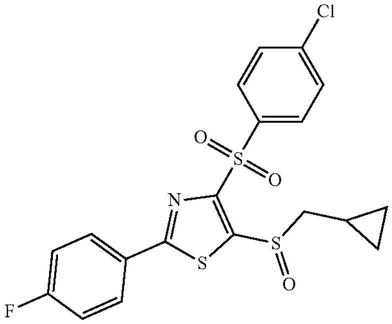
BC19471
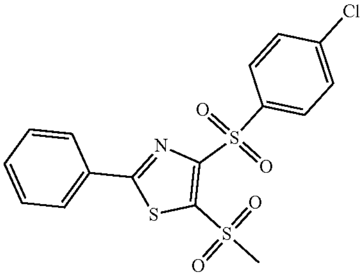
BC19472
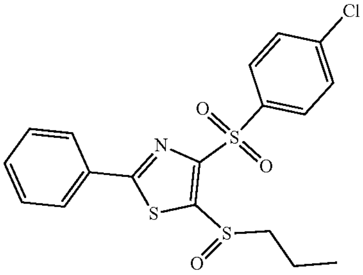
BC19473
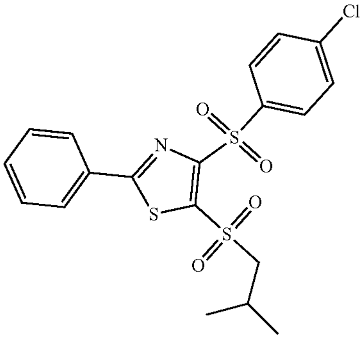
-continued
BC19474
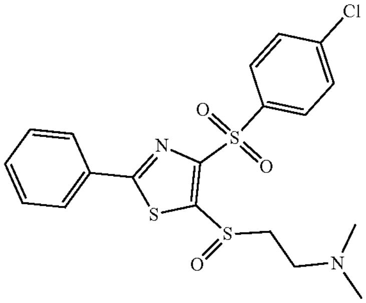
BC19475
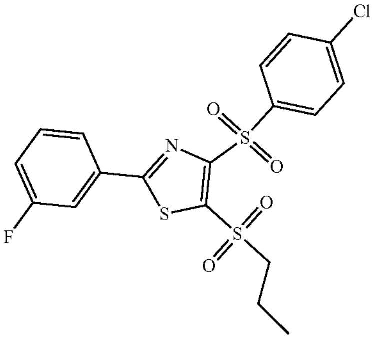
BC19476
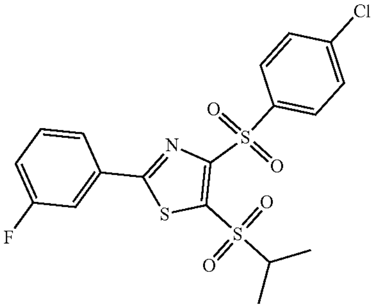
BC19477
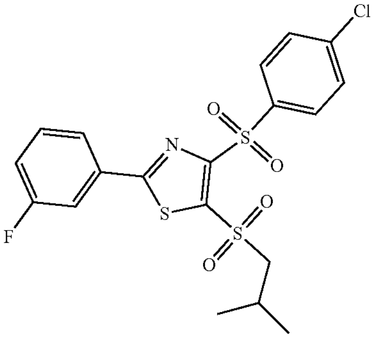
BC19478
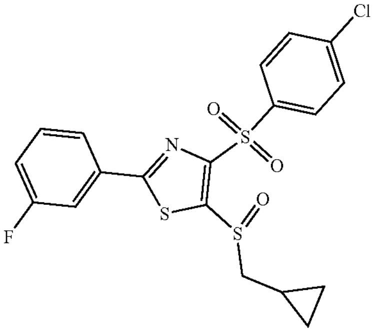

-continued
BC19479
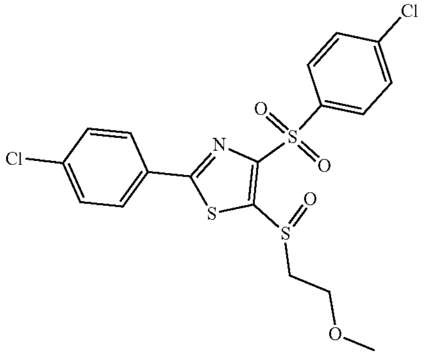
BC19480
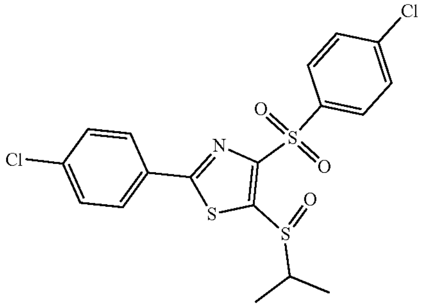
BC19525
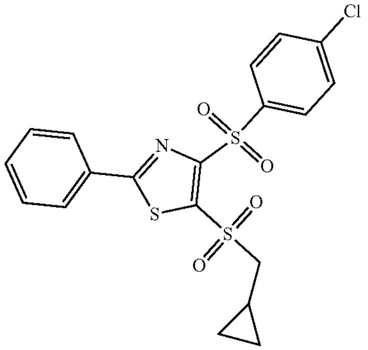
BC19526
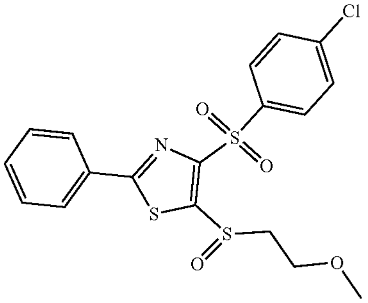
BC19527
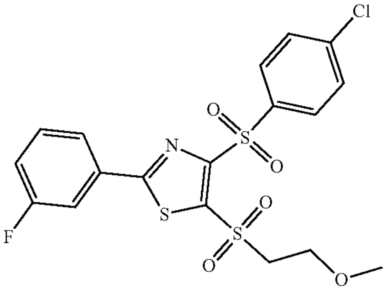
-continued
BC19528
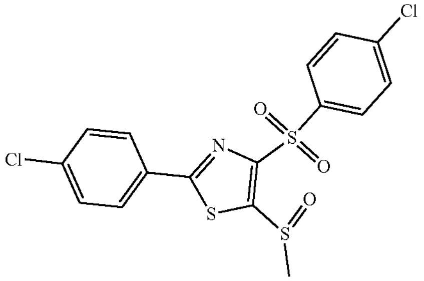
BC19529
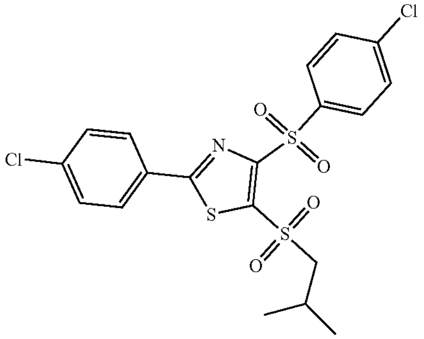
BC19530
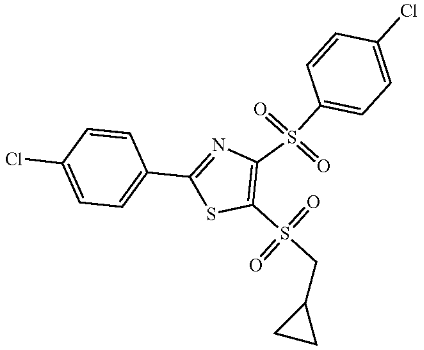
BC19531
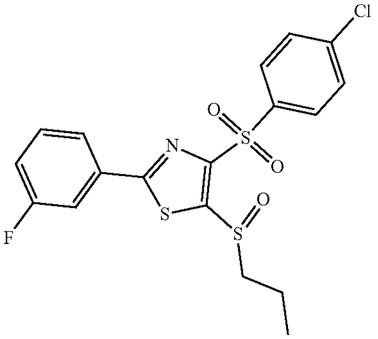

-continued
BC19532
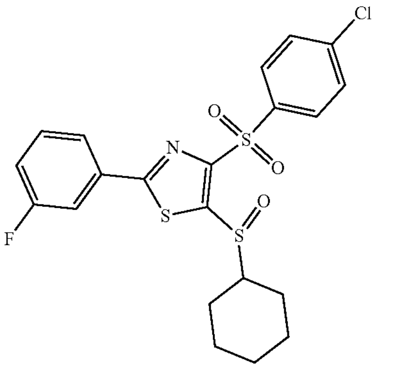
BC19533
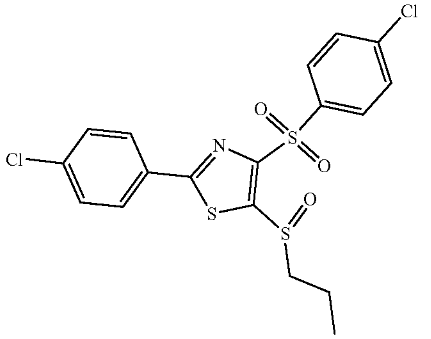
BC19534
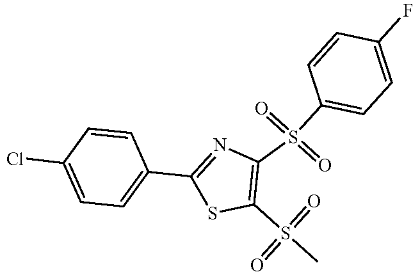
BC19535
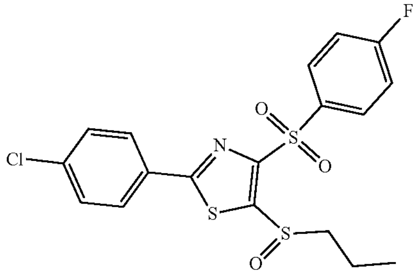
BC19536
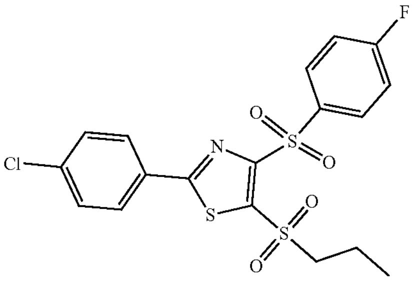
BC19537
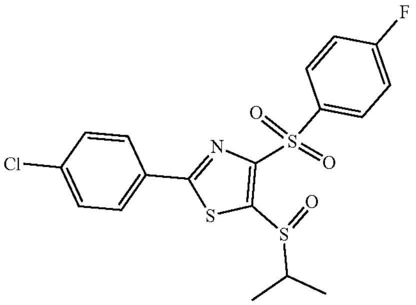
BC19538
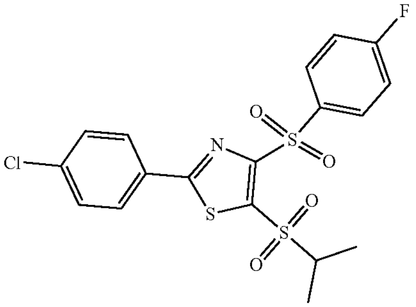
BC19539
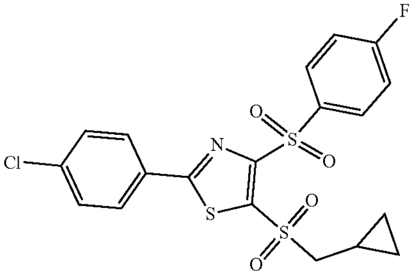
BC19540
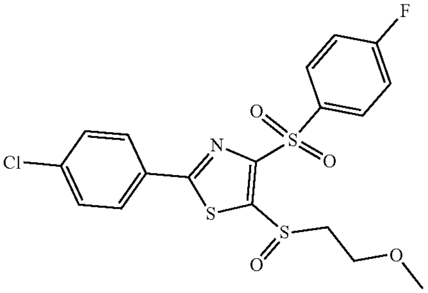

-continued
BC19541
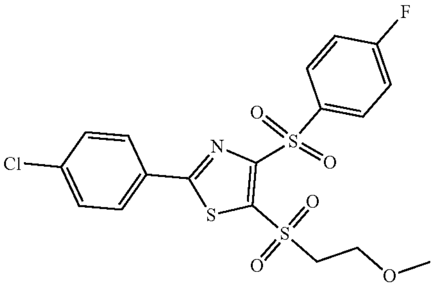
BC19583
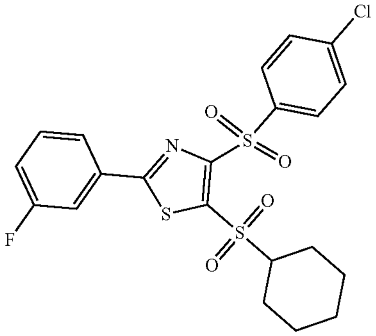
BC19587
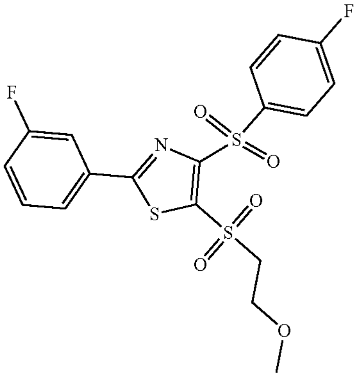
BC19588
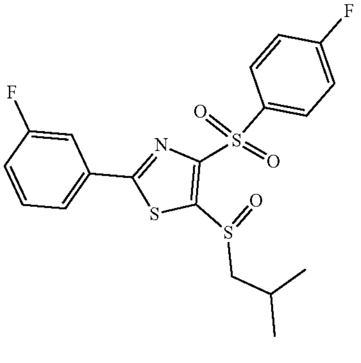
-continued
BC19589
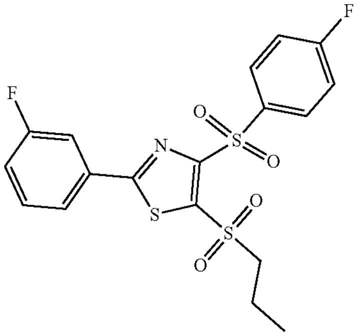
BC19590
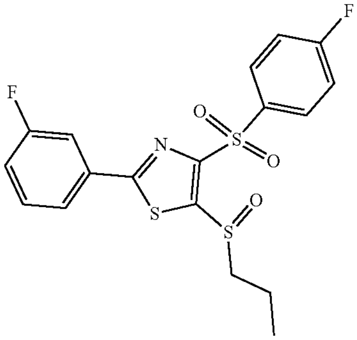
BC19591
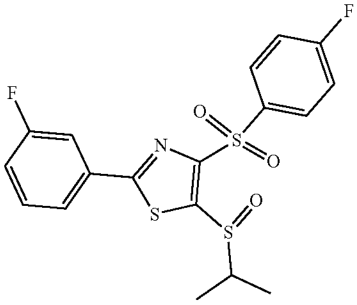
BC19592
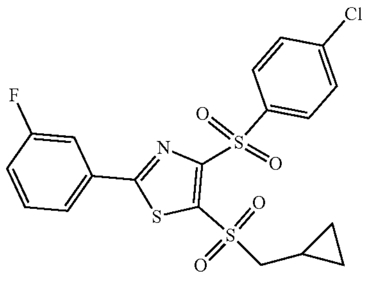
BC19593
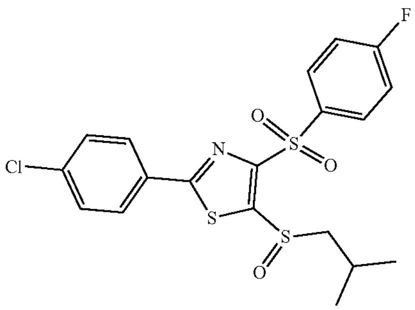

BC19594
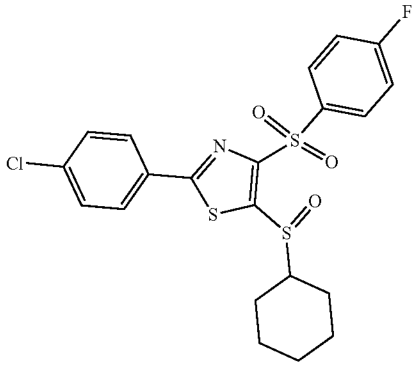
BC19595
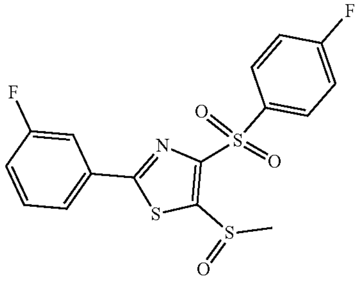
BC19596
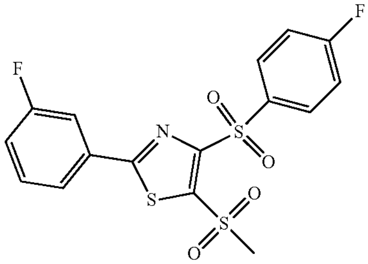
BC19597
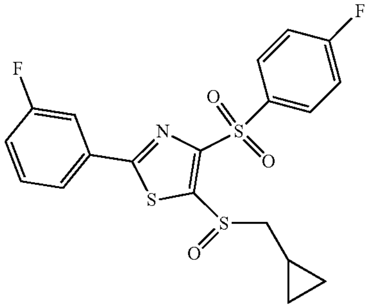
BC19598
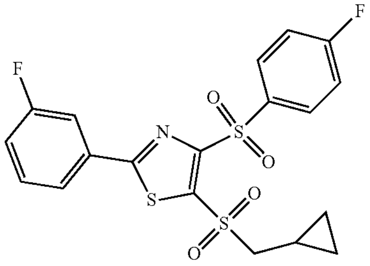
BC19599
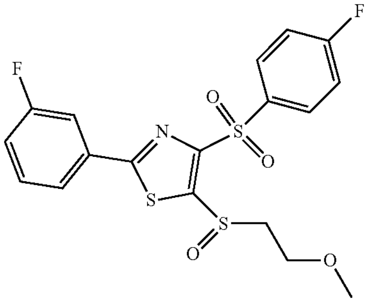
BC19620
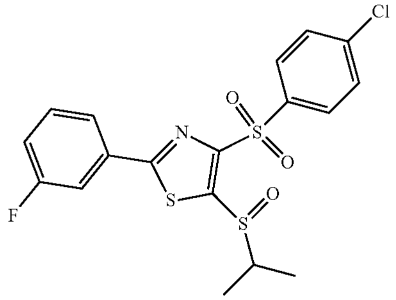
BC19621
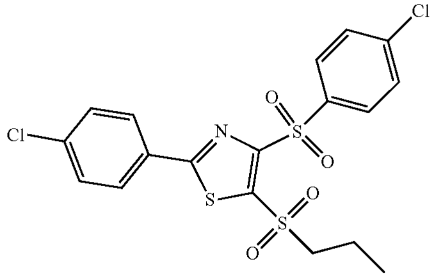
BC19622
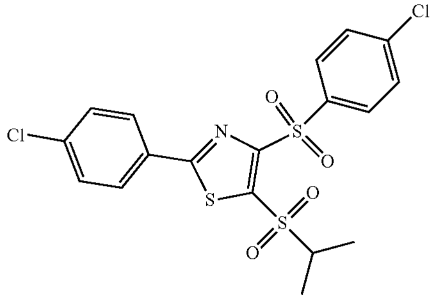
BC19623
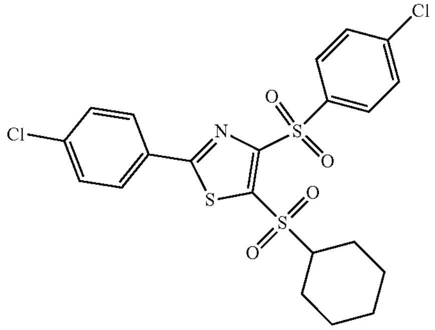

-continued
BC19624
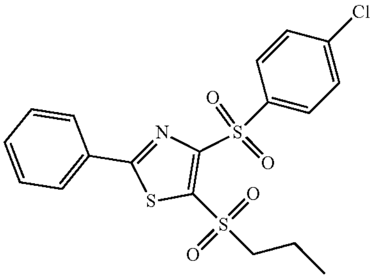
BC19625
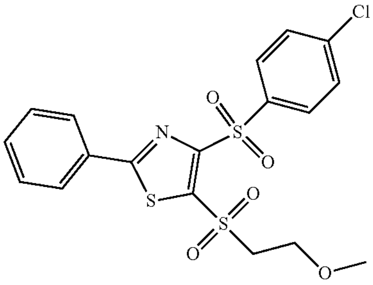
BC19626
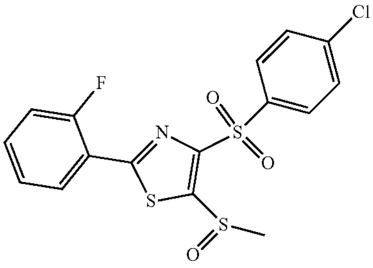
BC19627
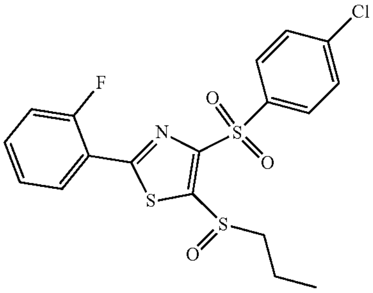
BC19628
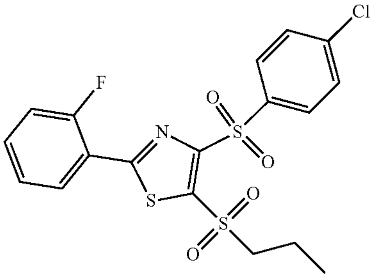
-continued
BC19629
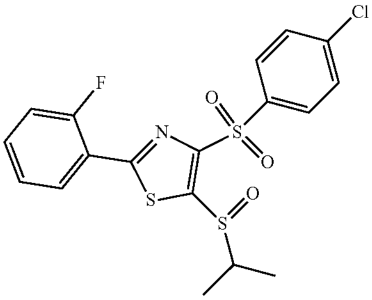
BC19630
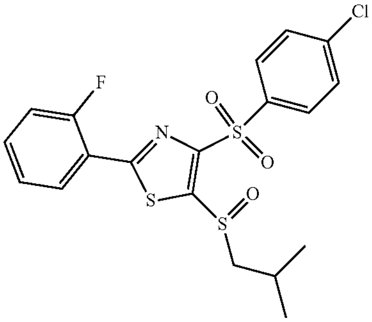
BC19631
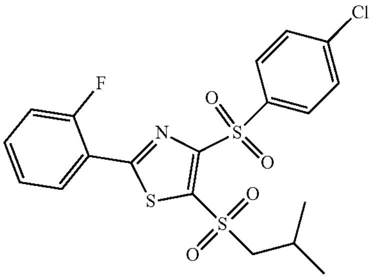
BC19632
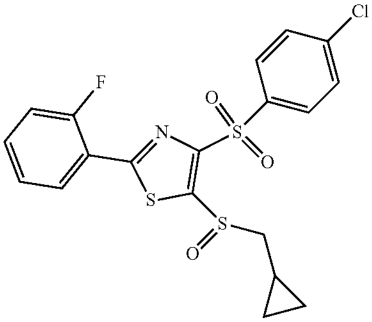
BC19633
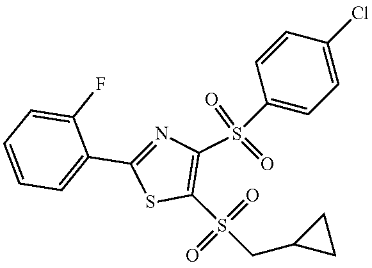

-continued
BC19671
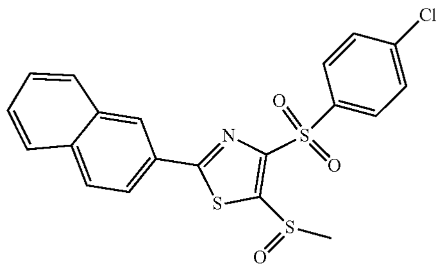
BC19672
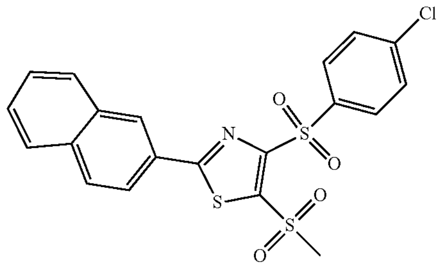
BC19673
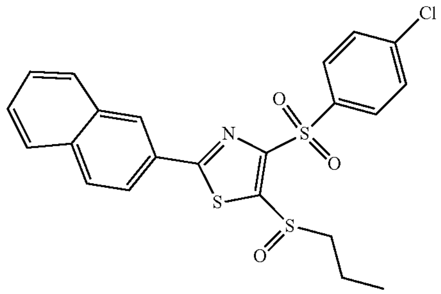
BC19674
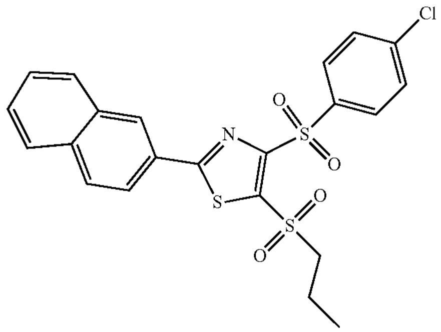
BC19675
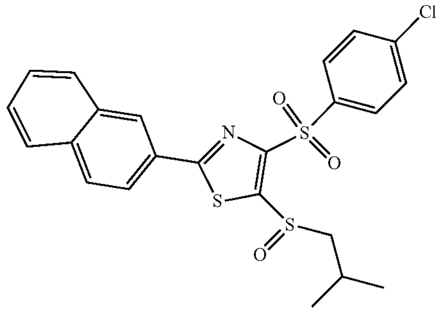
-continued
BC19676
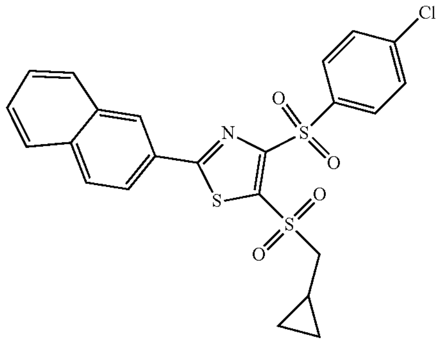
BC19677
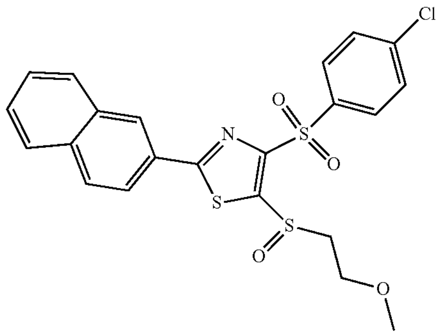
BC19678
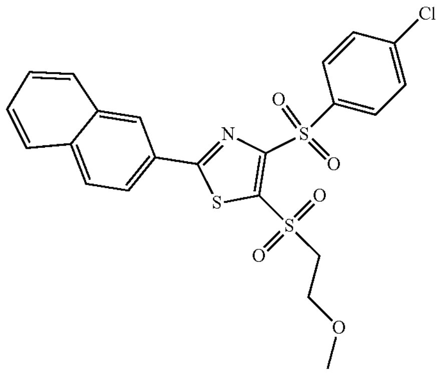
BC19335
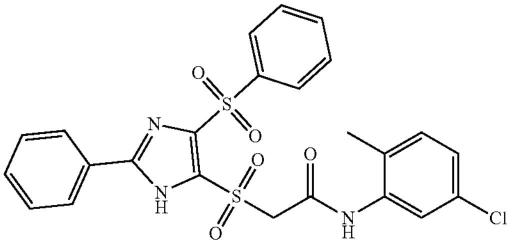

-continued
BC19336
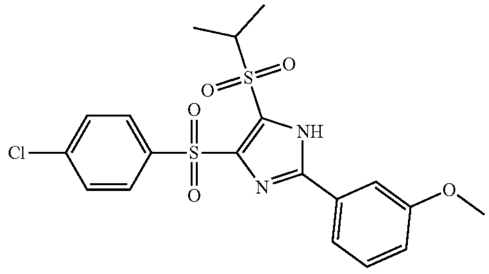
BC19337
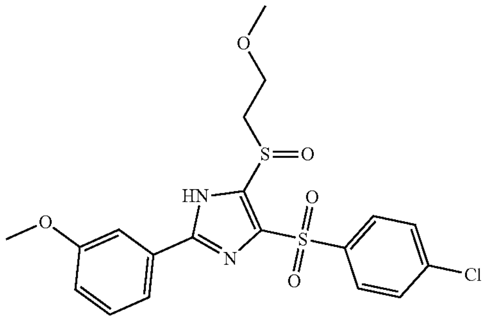
BC19410
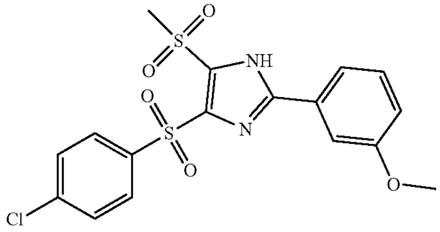
BC19420
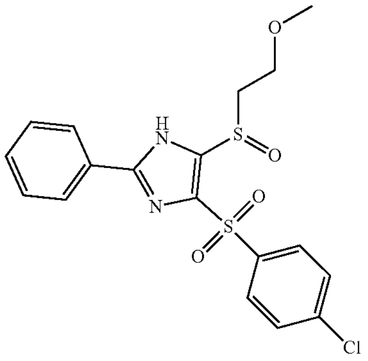
-continued
BC19462
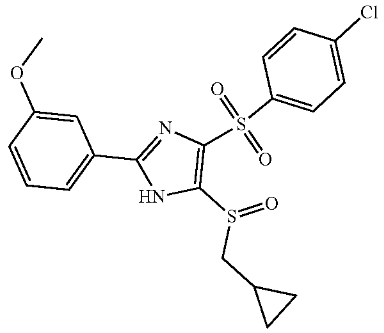
[[
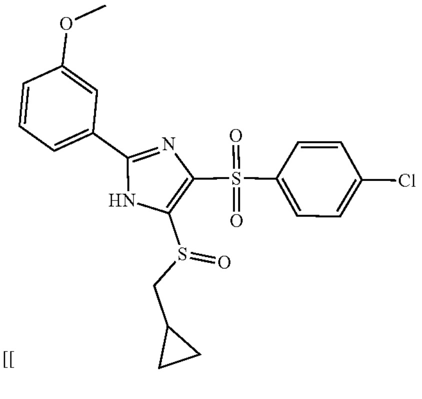
]]
BC19465
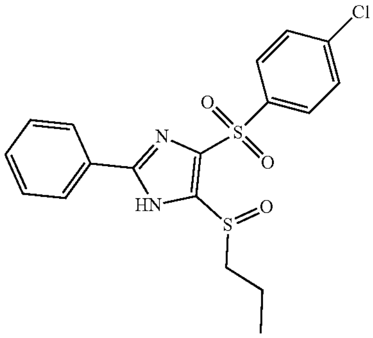
[[
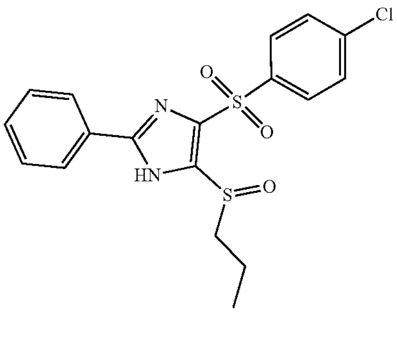
]]

-continued
BC19466
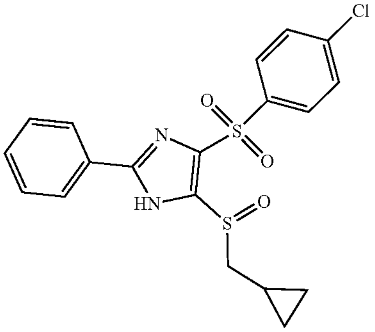
[[ 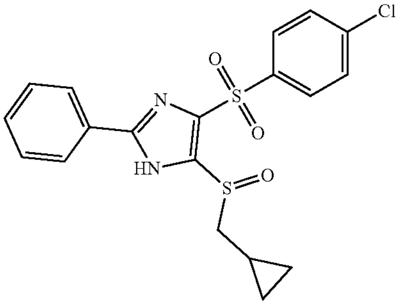 ]]
BC19467
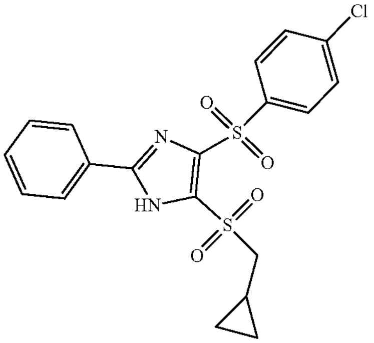
[[ 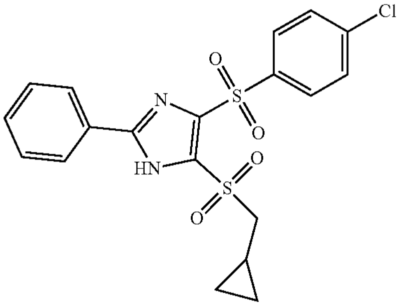 ]]
BC19468
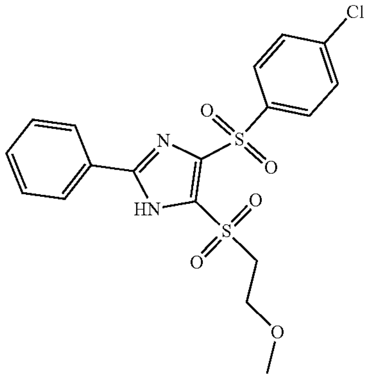
-continued
[[ 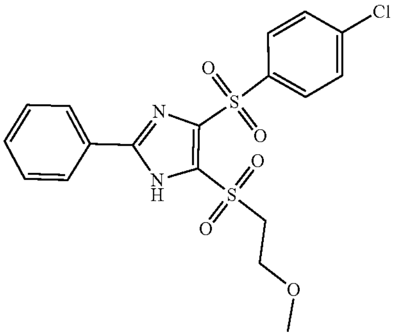 ]]
BC19469
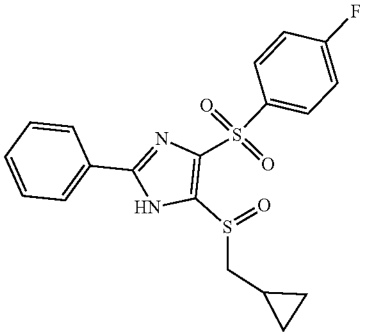
[[ 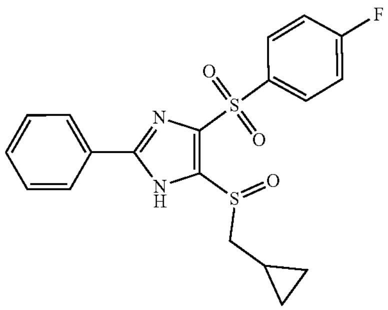 ]]
BC19470
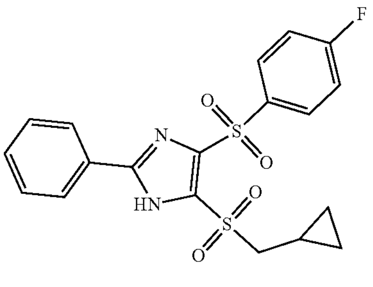
[[ 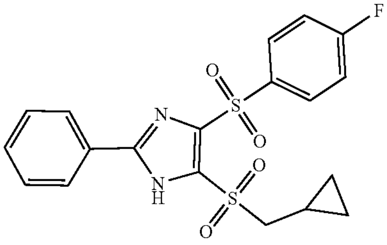 ]]

-continued
BC19522
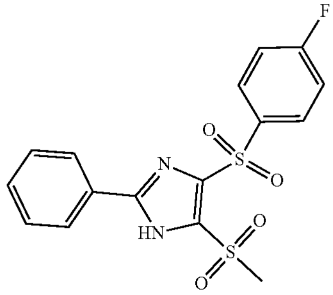
[[
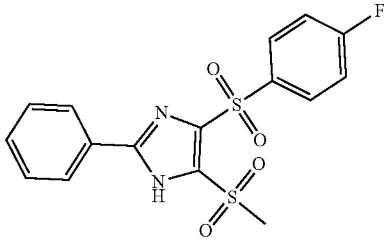
]]
BC19523
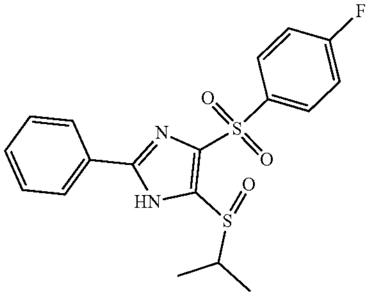
[[
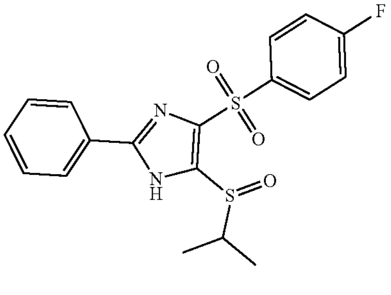
]]
BC19524
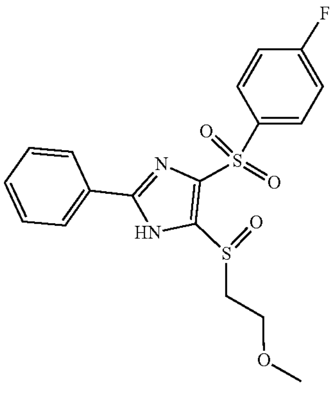
-continued
[[
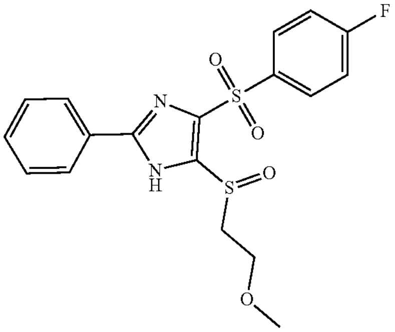
]]
BC19581
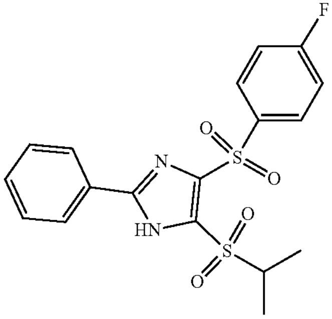
[[
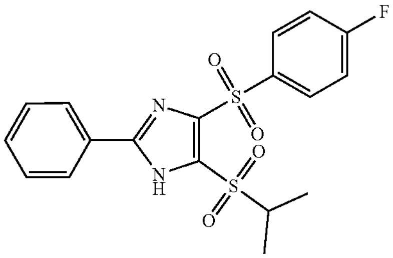
]]
BC19582
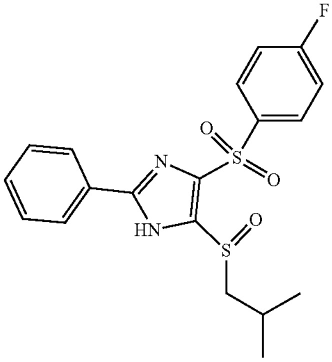
[[
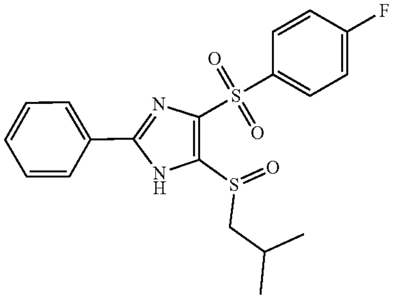
]]

-continued
BC19584
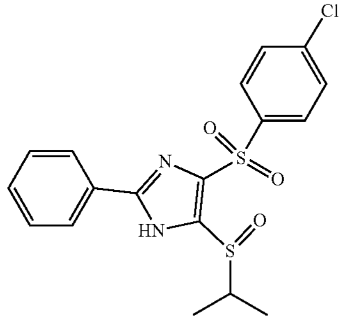
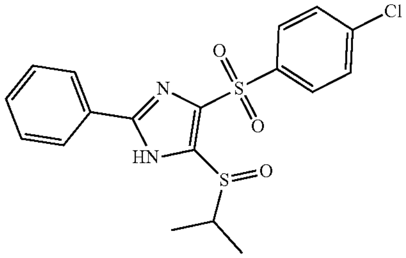
BC19585
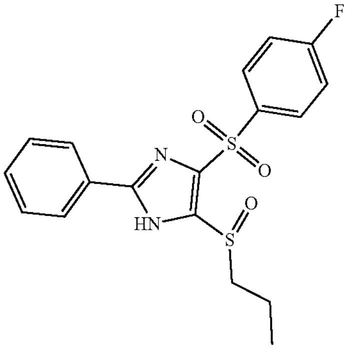
BC19586
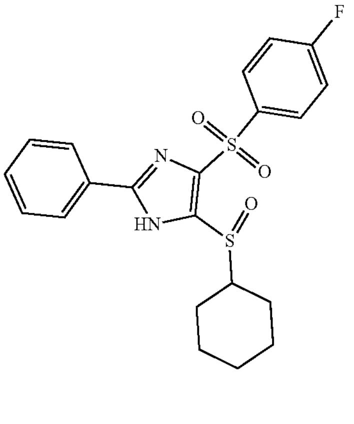
-continued
BC19600
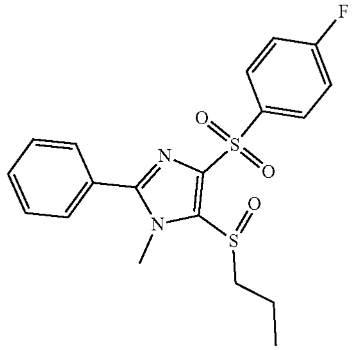
BC19601
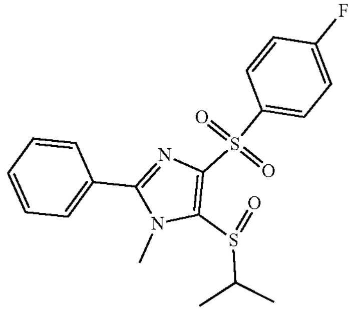
BC19602
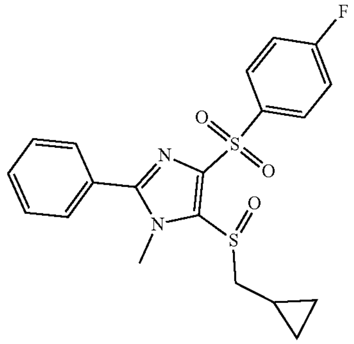
BC19634
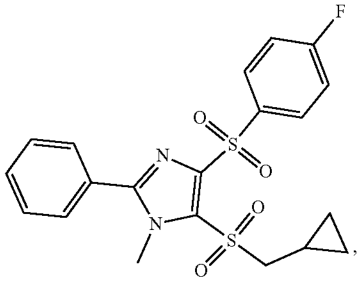
, and
BC19644
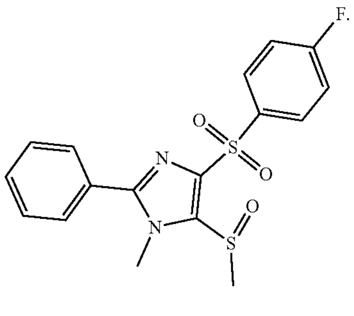

18. The method of claim 1, wherein the method comprises treating a mammal having a disease, disorder, or condition responsive to inhibiting NF-κB activity within a cell.

19. The method of claim 18, wherein said method comprises treating a mammal having a disease, disorder, or condition selected from cancer, inflammation, and an autoimmune disease.

20. A method for inhibiting NF-κB activity within a cell within a mammal, wherein said method comprises administering, to said mammal, an effective amount of a compound of Formula (IIIa):

(IIIa)

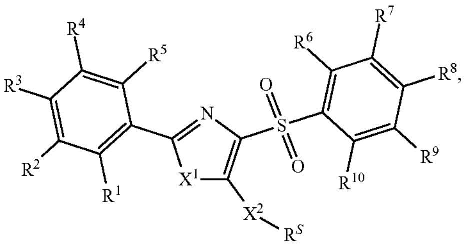

or a pharmaceutically acceptable salt thereof, wherein:

$X^1$ is S;

$X^2$ is selected from S, S(O), and $S(O)_2$;

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

or any two adjacent $R^1$, $R^2$, $R^3$, $R^4$, and $R^5$ groups, together with the carbon atoms to which they are attached, form a $C_{6-10}$ aryl ring, which is optionally substituted with 1, 2, or 3 substituents independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$, each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

21. The method of claim 20, wherein:

$R^S$ is selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{11}$;

each of $R^1$, $R^2$, $R^3$, $R^4$, $R^5$, $R^6$, $R^7$, $R^8$, $R^9$, and $R^{10}$ is independently selected from H, halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, or 3 substituents independently selected from $R^{11}$;

each $R^{11}$ is independently selected from $Cy^1$, halo, $C_{1-6}$ alkyl, $C_{1-6}$ haloalkyl, $C_{2-6}$ alkenyl, $C_{2-6}$ alkynyl, CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $Cy^1$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, 4, or 5 substituents independently selected from $R^{Cy1}$;

each $R^{Cy1}$ is independently selected from halo, CN, $NO_2$, $C_{1-6}$ alkyl, $C_{1-6}$ haloalkyl, $C_{2-6}$ alkenyl, $C_{2-6}$ alkynyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are each optionally substituted with 1, 2, or 3 substituents independently selected from $R^{12}$;

each $R^{12}$ is independently selected from CN, $NO_2$, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}S(O)_2R^{b1}$, $S(O)_2R^{b1}$, and $S(O)_2NR^{c1}R^{d1}$;

each $R^{a1}$, $R^{b1}$, $R^{c1}$, and $R^{d1}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-10 membered heterocycloalkyl)-$C_{1-4}$ alkylene are each optionally substituted with 1, 2, 3, 4, or 5 substituents independently selected from $R^g$;

or any $R^{c1}$ and $R^{d1}$ together with the N atom to which they are attached form a 4-7 membered heterocycloalkyl, which is optionally substituted with 1, 2, or 3 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-10 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-10 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

22. The method of claim 20, wherein $X^2$ is S.

23. The method of claim 20, wherein $X^2$ is S(O).

24. The method of claim 20, wherein $X^2$ is $S(O)_2$.

25. The method of claim 20, wherein $R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$.

26. The method of claim 20, wherein each $R^{11}$ is independently selected from $Cy^1$, halo, $C_{1-6}$ alkyl, $OR^{a1}$, $C(O)R^{b1}$, and $C(O)NR^{c1}R^{d1}$.

27. The method of claim 20, wherein each $Cy^1$ is independently selected from $C_{6-10}$ aryl and $C_{3-10}$ cycloalkyl, each of which is optionally substituted with 1, 2, or 3 substituents independently selected from $R^{Cy1}$.

28. The method of claim 20, wherein each $R^{Cy1}$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$.

29. The method of claim 20, wherein each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, wherein each of $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl is optionally substituted with 1, 2, or 3 substituents independently selected from $R^g$.

30. The method of claim 20, wherein each $R^{a1}$, $R^{b1}$, $R^{c1}$, and $R^{d1}$ is independently selected from H, $C_{1-6}$ alkyl, and $C_{6-10}$ aryl, wherein each of $C_{1-6}$ alkyl and $C_{6-10}$ aryl is optionally substituted with 1, 2, or 3 substituents independently selected from $R^g$.

31. The method of claim 20, wherein each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

32. The method of claim 20, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ is independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, $C_{1-6}$ alkyl, $C_{1-6}$ haloalkyl, $OR^{a1}$, $C(O)R^{b1}$, $C(O)NR^{c1}R^{d1}$, $C(O)OR^{a1}$, and $NR^{c1}R^{d1}$, wherein said $C_{1-6}$ alkyl is optionally substituted with 1, 2, or 3 substituents independently selected from $R^{12}$;

each $R^{a1}$, $R^{b1}$, $R^{c1}$, and $R^{d1}$ is independently selected from H, $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl, wherein each of $C_{1-6}$ alkyl, $C_{1-4}$ haloalkyl, $C_{6-10}$ aryl, $C_{3-10}$ cycloalkyl, 5-10 membered heteroaryl, and 4-10 membered heterocycloalkyl is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

33. The method of claim 20, wherein:

$R^S$ is selected from $C_{1-6}$ alkyl, $C_{6-10}$ aryl, and $C_{3-10}$ cycloalkyl, each of which is optionally substituted with 1, 2, 3, 4, or 5 substituents independently selected from $R^{11}$;

$R^{11}$ is independently selected from $Cy^1$, halo, $C_{1-6}$ alkyl, $OR^{a1}$, $C(O)R^{b1}$, $NR^{c1}R^{d1}$, and $C(O)NR^{c1}R^{d1}$;

$Cy^1$ is independently selected from $C_{6-10}$ aryl and $C_{3-10}$ cycloalkyl, each of which is optionally substituted with 1, 2, or 3 substituents independently selected from $R^{Cy1}$;

each $R^{Cy1}$ is independently selected from halo, CN, $NO_2$, OH, $C_{1-6}$ alkoxy, $C(O)NH_2$, C(O)OH, amino, $C_{1-6}$ alkylamino, di($C_{1-6}$ alkyl)amino, and $S(O)_2NH_2$;

each $R^{a1}$, $R^{b1}$, $R^{c1}$, and $R^{d1}$ is independently selected from H, $C_{1-6}$ alkyl, and $C_{6-10}$ aryl, wherein each of $C_{1-6}$ alkyl and $C_{6-10}$ aryl is optionally substituted with 1, 2, or 3 substituents independently selected from $R^g$; and $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, amino, $C_{1-6}$ alkylamino, di($C_{1-6}$ alkyl)amino, and carboxy.

* * * * *